(12) United States Patent
Wong et al.

(10) Patent No.: US 10,336,784 B2
(45) Date of Patent: Jul. 2, 2019

(54) METHODS FOR MODULAR SYNTHESIS OF N-GLYCANS AND ARRAYS THEREOF

(71) Applicant: Academia Sinica, Taipei (TW)

(72) Inventors: Chi-Huey Wong, Rancho Santa Fe, CA (US); Chung-Yi Wu, New Taipei (TW); Sachin S. Shivatare, Taipei (TW)

(73) Assignee: ACADEMIA SINICA, Taipei (TW)

( * ) Notice: Subject to any disclaimer, the term of this patent is extended or adjusted under 35 U.S.C. 154(b) by 0 days.

(21) Appl. No.: 15/453,836

(22) Filed: Mar. 8, 2017

(65) Prior Publication Data

US 2017/0362265 A1 Dec. 21, 2017

Related U.S. Application Data

(60) Provisional application No. 62/305,441, filed on Mar. 8, 2016.

(51) Int. Cl.
| | |
|---|---|
| *C07H 5/06* | (2006.01) |
| *A61K 31/702* | (2006.01) |
| *C12N 9/10* | (2006.01) |
| *C07K 16/10* | (2006.01) |
| *C12P 19/04* | (2006.01) |
| *G01N 33/50* | (2006.01) |
| *G01N 33/532* | (2006.01) |
| *G01N 33/68* | (2006.01) |
| *C08B 37/00* | (2006.01) |
| *G01N 33/569* | (2006.01) |
| *C12P 19/28* | (2006.01) |

(52) U.S. Cl.
CPC ............ *C07H 5/06* (2013.01); *A61K 31/702* (2013.01); *C07K 16/1045* (2013.01); *C08B 37/006* (2013.01); *C12N 9/107* (2013.01); *C12P 19/04* (2013.01); *G01N 33/50* (2013.01); *G01N 33/532* (2013.01); *G01N 33/56988* (2013.01); *G01N 33/68* (2013.01); *G01N 33/6893* (2013.01); *C12N 2740/16063* (2013.01); *C12P 19/28* (2013.01)

(58) Field of Classification Search
CPC ............ C07H 6/06; C12N 2740/16063; C12N 9/107; C12N 9/28; C07K 16/1045; A61K 31/702
USPC ........................................................ 536/55.1
See application file for complete search history.

(56) References Cited

U.S. PATENT DOCUMENTS

| | | | |
|---|---|---|---|
| 3,773,919 A | 11/1973 | Boswell et al. | |
| 3,896,111 A | 7/1975 | Kupchan et al. | |
| 4,137,230 A | 1/1979 | Hashimoto et al. | |
| 4,151,042 A | 4/1979 | Higashide et al. | |
| 4,248,870 A | 2/1981 | Miyashita et al. | |
| 4,256,746 A | 3/1981 | Miyashita et al. | |
| 4,260,608 A | 4/1981 | Miyashita et al. | |
| 4,265,814 A | 5/1981 | Hashimoto et al. | |
| 4,270,537 A | 6/1981 | Romaine | |
| 4,294,757 A | 10/1981 | Asai | |
| 4,307,016 A | 12/1981 | Asai et al. | |
| 4,308,268 A | 12/1981 | Miyashita et al. | |
| 4,308,269 A | 12/1981 | Miyashita et al. | |
| 4,309,428 A | 1/1982 | Miyashita et al. | |
| 4,313,946 A | 2/1982 | Powell et al. | |
| 4,315,929 A | 2/1982 | Freedman et al. | |
| 4,317,821 A | 3/1982 | Miyashita et al. | |
| 4,322,348 A | 3/1982 | Asai et al. | |
| 4,331,598 A | 5/1982 | Hasegawa et al. | |
| RE30,985 E | 6/1982 | Cartaya | |
| 4,361,650 A | 11/1982 | Asai et al. | |
| 4,362,663 A | 12/1982 | Kida et al. | |
| 4,364,866 A | 12/1982 | Asai et al. | |
| 4,371,533 A | 2/1983 | Akimoto et al. | |
| 4,376,110 A | 3/1983 | David et al. | |
| 4,419,446 A | 12/1983 | Howley et al. | |
| 4,424,219 A | 1/1984 | Hashimoto et al. | |
| 4,450,254 A | 5/1984 | Isley et al. | |
| 4,560,655 A | 12/1985 | Baker | |
| 4,596,556 A | 6/1986 | Morrow et al. | |
| 4,596,792 A | 6/1986 | Vyas | |
| 4,599,230 A | 7/1986 | Milich et al. | |
| 4,599,231 A | 7/1986 | Milich et al. | |
| 4,601,903 A | 7/1986 | Frasch | |

(Continued)

FOREIGN PATENT DOCUMENTS

| | | |
|---|---|---|
| EP | 0404097 A2 | 12/1990 |
| EP | 0341735 B1 | 9/1992 |

(Continued)

OTHER PUBLICATIONS

Unverzagt et al, Chem. Eur. J. 2008, 14, 1304-1311.*

(Continued)

*Primary Examiner* — Ganapathy Krishnan
(74) *Attorney, Agent, or Firm* — Duane Morris LLP

(57) ABSTRACT

The present disclosure relates to novel modular methods for generating a diversity of N-glycans of high mannose, hybrid and complex types. The present disclosure also relates to exemplary arrays of the synthesized N-glycans spotted onto aluminium oxide coated slides. These arrays can be used to detect and analyze binding interactions between the synthesized N-glycans and glycan binding molecules, such as HIV-1 neutralizing antibodies. The present disclosure also relates to methods for identifying agents that bind to various types of molecules on the arrays and to defining the structural elements of the molecules on the arrays that bind to those agents. The arrays and methods provided herein may be used for general epitope identification, drug discovery and as analytical tools. The present disclosure also provides useful glycans and epitope determinants that are useful in detecting, diagnosing, recurrence monitoring and preventing pathological diseases such as HIV.

6 Claims, 237 Drawing Sheets
(47 of 237 Drawing Sheet(s) Filed in Color)

(56) References Cited

U.S. PATENT DOCUMENTS

| | | |
|---|---|---|
| 4,601,978 A | 7/1986 | Karin |
| 4,657,866 A | 4/1987 | Kumar |
| 4,676,980 A | 6/1987 | Segal et al. |
| 4,741,900 A | 5/1988 | Alvarez et al. |
| 4,767,704 A | 8/1988 | Cleveland et al. |
| 4,790,824 A | 12/1988 | Morrow et al. |
| 4,816,567 A | 3/1989 | Cabilly et al. |
| 4,849,222 A | 7/1989 | Broaddus |
| 4,886,499 A | 12/1989 | Cirelli et al. |
| 4,927,762 A | 5/1990 | Darfler |
| 4,940,460 A | 7/1990 | Casey et al. |
| 4,941,880 A | 7/1990 | Burns |
| 4,965,199 A | 10/1990 | Capon et al. |
| 4,970,198 A | 11/1990 | Lee et al. |
| 4,975,278 A | 12/1990 | Senter et al. |
| 5,004,697 A | 4/1991 | Pardridge |
| 5,015,235 A | 5/1991 | Crossman |
| 5,053,394 A | 10/1991 | Ellestad et al. |
| 5,061,620 A | 10/1991 | Tsukamoto et al. |
| 5,064,413 A | 11/1991 | McKinnon et al. |
| 5,075,109 A | 12/1991 | Tice et al. |
| 5,079,233 A | 1/1992 | Lee |
| 5,100,669 A | 3/1992 | Hyon et al. |
| 5,112,596 A | 5/1992 | Malfroy-Camine |
| 5,122,469 A | 6/1992 | Mather et al. |
| 5,141,496 A | 8/1992 | Dalto et al. |
| 5,190,521 A | 3/1993 | Hubbard et al. |
| 5,208,020 A | 5/1993 | Chari et al. |
| 5,229,275 A | 7/1993 | Goroff |
| 5,264,365 A | 11/1993 | Georgiou et al. |
| 5,268,164 A | 12/1993 | Kozarich et al. |
| 5,312,335 A | 5/1994 | McKinnon et al. |
| 5,326,856 A | 7/1994 | Coughlin et al. |
| 5,328,483 A | 7/1994 | Jacoby |
| 5,334,144 A | 8/1994 | Alchas et al. |
| 5,339,163 A | 8/1994 | Homma et al. |
| 5,362,852 A | 11/1994 | Geoghegan |
| 5,369,017 A | 11/1994 | Wong et al. |
| 5,374,541 A | 12/1994 | Wong et al. |
| 5,383,851 A | 1/1995 | McKinnon, Jr. et al. |
| 5,395,541 A | 3/1995 | Carpenter et al. |
| 5,416,064 A | 5/1995 | Chari et al. |
| 5,417,662 A | 5/1995 | Hjertman et al. |
| 5,466,220 A | 11/1995 | Brenneman |
| 5,480,381 A | 1/1996 | Weston |
| 5,500,362 A | 3/1996 | Robinson et al. |
| 5,503,627 A | 4/1996 | McKinnon et al. |
| 5,506,206 A | 4/1996 | Kozarich et al. |
| 5,508,192 A | 4/1996 | Georgiou et al. |
| 5,518,725 A | 5/1996 | Daynes et al. |
| 5,520,639 A | 5/1996 | Peterson et al. |
| 5,527,288 A | 6/1996 | Gross et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,569,189 A | 10/1996 | Parsons |
| 5,569,825 A | 10/1996 | Lonberg et al. |
| 5,571,894 A | 11/1996 | Wels et al. |
| 5,580,717 A | 12/1996 | Dower et al. |
| 5,585,089 A | 12/1996 | Queen et al. |
| 5,587,458 A | 12/1996 | King et al. |
| 5,591,669 A | 1/1997 | Krimpenfort et al. |
| 5,591,828 A | 1/1997 | Bosslet et al. |
| 5,599,302 A | 2/1997 | Lilley et al. |
| 5,606,040 A | 2/1997 | McGahren et al. |
| 5,624,821 A | 4/1997 | Winter et al. |
| 5,625,126 A | 4/1997 | Lonberg et al. |
| 5,633,425 A | 5/1997 | Lonberg et al. |
| 5,635,483 A | 6/1997 | Pettit et al. |
| 5,639,635 A | 6/1997 | Joly et al. |
| 5,641,870 A | 6/1997 | Rinderknecht et al. |
| 5,643,577 A | 7/1997 | Pang et al. |
| 5,648,237 A | 7/1997 | Carter |
| 5,648,260 A | 7/1997 | Winter et al. |
| 5,649,912 A | 7/1997 | Peterson |
| 5,661,016 A | 8/1997 | Lonberg et al. |
| 5,663,149 A | 9/1997 | Pettit et al. |
| 5,674,988 A | 10/1997 | Sabesan |
| 5,677,180 A | 10/1997 | Robinson et al. |
| 5,686,416 A | 11/1997 | Kozarich et al. |
| 5,690,938 A | 11/1997 | Ermak et al. |
| 5,693,762 A | 12/1997 | Queen et al. |
| 5,704,911 A | 1/1998 | Parsons |
| 5,712,374 A | 1/1998 | Kuntsman et al. |
| 5,714,374 A | 2/1998 | Arnold et al. |
| 5,714,586 A | 2/1998 | Kunstman et al. |
| 5,731,168 A | 3/1998 | Cater et al. |
| 5,733,743 A | 3/1998 | Johnson et al. |
| 5,736,137 A | 4/1998 | Anderson et al. |
| 5,739,116 A | 4/1998 | Hamann et al. |
| 5,767,285 A | 6/1998 | Hamann et al. |
| 5,770,701 A | 6/1998 | McGahren et al. |
| 5,773,001 A | 6/1998 | Hamann et al. |
| 5,780,588 A | 7/1998 | Pettit et al. |
| 5,814,344 A | 9/1998 | Tice et al. |
| 5,820,883 A | 10/1998 | Tice et al. |
| 5,821,337 A | 10/1998 | Carter et al. |
| 5,837,234 A | 11/1998 | Gentile et al. |
| 5,840,523 A | 11/1998 | Simmons et al. |
| 5,849,716 A | 12/1998 | Akimoto |
| 5,853,763 A | 12/1998 | Tice et al. |
| 5,869,046 A | 2/1999 | Presta et al. |
| 5,877,296 A | 3/1999 | Hamann et al. |
| 5,893,397 A | 4/1999 | Peterson et al. |
| 5,993,412 A | 11/1999 | Deily et al. |
| 6,004,940 A | 12/1999 | Marasco et al. |
| 6,027,888 A | 2/2000 | Georgiou et al. |
| 6,083,715 A | 7/2000 | Georgiou et al. |
| 6,111,132 A | 8/2000 | Kim et al. |
| 6,143,724 A | 11/2000 | Ohira et al. |
| 6,210,670 B1 | 4/2001 | Berg |
| 6,265,150 B1 | 7/2001 | Terstappen et al. |
| 6,329,173 B1 | 12/2001 | Marasco et al. |
| 6,340,702 B1 | 1/2002 | Honda et al. |
| 6,399,071 B1 | 6/2002 | Duthaler |
| 6,455,571 B1 | 9/2002 | Maring et al. |
| 6,506,564 B1 | 1/2003 | Mirkin et al. |
| 6,528,286 B1 | 3/2003 | Ryll |
| 6,548,476 B1 | 4/2003 | Wu et al. |
| 6,680,054 B1 | 1/2004 | Reece et al. |
| 6,696,304 B1 | 2/2004 | Davies |
| 6,703,019 B1 | 3/2004 | Malfroy-Camine |
| 6,824,780 B1 | 11/2004 | Devaux et al. |
| 6,855,551 B2 | 2/2005 | Bawendi et al. |
| 6,873,914 B2 | 3/2005 | Winfield et al. |
| 6,984,630 B1 | 1/2006 | Descamps et al. |
| 6,994,966 B2 | 2/2006 | Dukler |
| 7,019,288 B2 | 3/2006 | Becker |
| 7,090,973 B1 | 8/2006 | Breton |
| 7,151,164 B2 | 12/2006 | Hansen et al. |
| 7,157,433 B2 | 1/2007 | Mercep et al. |
| 7,205,333 B2 | 4/2007 | Wu et al. |
| 7,488,491 B2 | 2/2009 | Tsjui et al. |
| 7,498,298 B2 | 3/2009 | Doronina et al. |
| 7,854,934 B2 | 12/2010 | Danishefsky |
| 7,888,337 B2 | 2/2011 | Wong et al. |
| 7,923,013 B2 | 4/2011 | Tsuji et al. |
| 7,928,077 B2 | 4/2011 | Wong et al. |
| 7,943,330 B2 | 5/2011 | Wong et al. |
| 7,960,139 B2 | 6/2011 | Sawa et al. |
| 7,977,097 B1 | 7/2011 | Gay et al. |
| 8,022,043 B2 | 9/2011 | Porcelli |
| 8,088,387 B2 | 1/2012 | Steeves et al. |
| 8,101,179 B2 | 1/2012 | Numazaki et al. |
| 8,268,969 B2 | 9/2012 | Wong et al. |
| 8,383,554 B2 | 2/2013 | Wong et al. |
| 8,507,660 B2 | 8/2013 | Wong et al. |
| 8,680,020 B2 | 3/2014 | Wong et al. |
| 8,716,465 B2 | 5/2014 | Rossi et al. |
| 8,802,438 B2 | 8/2014 | Rossi et al. |
| 8,815,941 B2 | 8/2014 | Withers |
| 8,883,506 B2 | 11/2014 | Rossi et al. |
| 8,906,832 B2 | 12/2014 | Wong et al. |

(56) References Cited

U.S. PATENT DOCUMENTS

| | | |
|---|---|---|
| 8,907,111 B2 | 12/2014 | Withers |
| 9,187,552 B2 | 11/2015 | Stadheim |
| 9,221,859 B2 | 12/2015 | Withers |
| 9,382,284 B2 | 7/2016 | Withers |
| 9,434,786 B2 | 9/2016 | Wang |
| 9,759,726 B2 | 9/2017 | Wong et al. |
| 9,803,177 B2 | 10/2017 | Rossi et al. |
| 9,914,956 B2 | 3/2018 | Wong et al. |
| 2002/0025313 A1 | 2/2002 | Micklus et al. |
| 2002/0038086 A1 | 3/2002 | Hynynen et al. |
| 2002/0065259 A1 | 5/2002 | Schatzberg et al. |
| 2003/0073713 A1 | 4/2003 | Schoenhard |
| 2003/0083299 A1 | 5/2003 | Ferguson |
| 2003/0104402 A1 | 6/2003 | Zauderer et al. |
| 2003/0118592 A1 | 6/2003 | Ledbetter et al. |
| 2003/0129186 A1 | 7/2003 | Beliveau et al. |
| 2003/0162695 A1 | 8/2003 | Schatzberg et al. |
| 2003/0175884 A1 | 9/2003 | Umana et al. |
| 2003/0219433 A1 | 11/2003 | Hansen et al. |
| 2004/0072290 A1 | 4/2004 | Umana |
| 2004/0086423 A1 | 5/2004 | Wohlstadter |
| 2004/0131692 A1 | 7/2004 | Kreuter et al. |
| 2004/0137557 A1 | 7/2004 | DeFrees et al. |
| 2004/0204354 A1 | 10/2004 | Nelson et al. |
| 2004/0259142 A1 | 12/2004 | Chai et al. |
| 2005/0085413 A1 | 4/2005 | Jin et al. |
| 2005/0089473 A1 | 4/2005 | Black et al. |
| 2005/0106108 A1 | 5/2005 | Hansen et al. |
| 2005/0123546 A1 | 6/2005 | Umana et al. |
| 2005/0124533 A1 | 6/2005 | Schatzberg et al. |
| 2005/0221337 A1 | 10/2005 | Seeberger et al. |
| 2005/0221397 A1 | 10/2005 | Saito |
| 2005/0255491 A1 | 11/2005 | Lee |
| 2006/0019256 A1 | 1/2006 | Clarke et al. |
| 2006/0073122 A1 | 4/2006 | Koezuka et al. |
| 2006/0073161 A1 | 4/2006 | Breton |
| 2006/0211856 A1 | 9/2006 | Tsuji et al. |
| 2006/0286140 A1 | 12/2006 | Wickstrom et al. |
| 2006/0286637 A1 | 12/2006 | Hamilton |
| 2007/0059769 A1 | 3/2007 | Blixt et al. |
| 2007/0065949 A1 | 3/2007 | Hutchens |
| 2007/0207090 A1 | 9/2007 | Giudice |
| 2007/0213278 A1 | 9/2007 | Wong et al. |
| 2007/0219351 A1 | 9/2007 | Fiume et al. |
| 2007/0224189 A1 | 9/2007 | Lazar et al. |
| 2007/0238871 A1 | 10/2007 | Tsuji et al. |
| 2008/0070324 A1 | 3/2008 | Floyd |
| 2008/0220988 A1 | 9/2008 | Zhou |
| 2008/0260774 A1 | 10/2008 | Wong et al. |
| 2009/0035179 A1 | 2/2009 | Rakow et al. |
| 2009/0081255 A1 | 3/2009 | Bublot et al. |
| 2009/0123439 A1 | 5/2009 | Yun et al. |
| 2009/0285837 A1 | 11/2009 | Kao et al. |
| 2009/0298797 A1 | 12/2009 | Zheng et al. |
| 2009/0317837 A1 | 12/2009 | Wong et al. |
| 2010/0009339 A1 | 1/2010 | Bovin et al. |
| 2010/0022026 A1 | 1/2010 | Rump et al. |
| 2010/0047827 A1 | 2/2010 | Laine et al. |
| 2010/0047828 A1 | 2/2010 | Sorenson et al. |
| 2010/0068806 A1 | 3/2010 | Laine et al. |
| 2010/0112195 A1 | 5/2010 | Kodas et al. |
| 2010/0113397 A1 | 5/2010 | Wong et al. |
| 2010/0136009 A1 | 6/2010 | Papkoff et al. |
| 2010/0136042 A1 | 6/2010 | Wong et al. |
| 2010/0173323 A1 | 7/2010 | Strome |
| 2011/0086408 A1 | 4/2011 | Power |
| 2011/0104188 A1 | 5/2011 | Tashiro et al. |
| 2011/0124116 A1 | 5/2011 | Wohlstadter et al. |
| 2011/0137570 A1 | 6/2011 | Lapadula et al. |
| 2011/0237459 A1 | 9/2011 | Nova et al. |
| 2011/0263828 A1 | 10/2011 | Wong et al. |
| 2012/0046346 A1 | 2/2012 | Rossi et al. |
| 2012/0171201 A1 | 7/2012 | Sapra |
| 2012/0178705 A1 | 7/2012 | Liang et al. |
| 2012/0178802 A1 | 7/2012 | Withers et al. |
| 2012/0226024 A1 | 9/2012 | Wang et al. |
| 2012/0294859 A1 | 11/2012 | Goletz et al. |
| 2012/0322864 A1 | 12/2012 | Rossi et al. |
| 2012/0322865 A1 | 12/2012 | Rossi et al. |
| 2012/0328646 A1 | 12/2012 | Wong et al. |
| 2013/0189258 A1 | 7/2013 | Rother et al. |
| 2013/0196356 A1 | 8/2013 | Jackson et al. |
| 2013/0230886 A1 | 9/2013 | Votsmeier et al. |
| 2013/0295104 A1 | 11/2013 | Deckert et al. |
| 2013/0337018 A1 | 12/2013 | Fox |
| 2014/0051127 A1 | 2/2014 | Wong et al. |
| 2014/0086916 A1 | 3/2014 | Zha |
| 2014/0127241 A1 | 5/2014 | Leuschner et al. |
| 2014/0178365 A1 | 6/2014 | Ghaderi et al. |
| 2014/0302028 A1 | 10/2014 | Zha |
| 2014/0308746 A1 | 10/2014 | Rossi et al. |
| 2015/0087814 A1 | 3/2015 | Wang et al. |
| 2015/0160217 A1 | 6/2015 | Wong et al. |
| 2015/0225766 A1 | 8/2015 | Wong et al. |
| 2015/0309041 A1 | 10/2015 | Wong et al. |
| 2015/0344544 A1 | 12/2015 | Wong et al. |
| 2015/0344551 A1 | 12/2015 | Wong et al. |
| 2015/0344559 A1 | 12/2015 | Wong et al. |
| 2015/0344585 A1 | 12/2015 | Wong et al. |
| 2015/0344587 A1 | 12/2015 | Wong et al. |
| 2016/0009803 A1 | 1/2016 | Rother et al. |
| 2016/0102151 A1 | 4/2016 | Wong et al. |
| 2016/0215061 A1 | 7/2016 | Shaheen |
| 2016/0274121 A1 | 9/2016 | Wong et al. |
| 2016/0280794 A1 | 9/2016 | Wong et al. |
| 2016/0289340 A1 | 10/2016 | Wong et al. |
| 2017/0275389 A1 | 9/2017 | Wong et al. |
| 2017/0283878 A1 | 10/2017 | Wong et al. |

FOREIGN PATENT DOCUMENTS

| | | |
|---|---|---|
| EP | 0425235 B1 | 9/1996 |
| EP | 1208909 A2 | 5/2002 |
| EP | 1391213 A1 | 2/2004 |
| EP | 2123271 | 11/2009 |
| EP | 2187217 A1 | 5/2010 |
| JP | 05-222085 | 8/1993 |
| JP | 05-507068 | 10/1993 |
| JP | 05-339283 A | 12/1993 |
| JP | 11-343295 A | 12/1999 |
| JP | 2005-06008 | 5/2000 |
| WO | WO 87/00195 A1 | 1/1987 |
| WO | WO 90/03430 A1 | 4/1990 |
| WO | WO 91/00360 A1 | 1/1991 |
| WO | WO 91/10741 A1 | 7/1991 |
| WO | WO 92/00373 A1 | 1/1992 |
| WO | WO 92/006691 | 4/1992 |
| WO | WO 92/09690 A2 | 6/1992 |
| WO | WO 93/01161 A1 | 1/1993 |
| WO | WO 93/06213 A1 | 4/1993 |
| WO | WO 93/07861 A1 | 4/1993 |
| WO | WO 93/08829 A1 | 5/1993 |
| WO | WO 93/09764 | 5/1993 |
| WO | WO 93/16185 A2 | 8/1993 |
| WO | WO 93/021232 A1 | 10/1993 |
| WO | WO 94/04690 A1 | 3/1994 |
| WO | WO 94/11026 | 5/1994 |
| WO | WO 94/29351 | 12/1994 |
| WO | WO 95/11010 A1 | 4/1995 |
| WO | WO 96/07754 A1 | 3/1996 |
| WO | WO 96/16673 A1 | 6/1996 |
| WO | WO 96/33735 A1 | 10/1996 |
| WO | WO 96/34096 A1 | 10/1996 |
| WO | WO 97/05267 A2 | 2/1997 |
| WO | WO 97/013537 | 4/1997 |
| WO | WO 97/17852 A1 | 5/1997 |
| WO | WO 97/037705 | 10/1997 |
| WO | WO 98/00558 A1 | 1/1998 |
| WO | WO 98/02463 A1 | 1/1998 |
| WO | WO 98/24893 A2 | 6/1998 |
| WO | WO 99/034850 | 7/1999 |
| WO | WO 99/49019 A2 | 9/1999 |
| WO | WO 99/051642 | 10/1999 |
| WO | WO 99/057134 A1 | 11/1999 |

(56) References Cited

FOREIGN PATENT DOCUMENTS

| WO | WO 01/42505 A2 | 6/2001 |
|---|---|---|
| WO | WO 01/86001 A1 | 11/2001 |
| WO | WO 02/088172 | 11/2002 |
| WO | WO 03/040104 A1 | 5/2003 |
| WO | WO 03/68821 A2 | 8/2003 |
| WO | WO 03/077945 A1 | 9/2003 |
| WO | WO 2004/035607 A2 | 4/2004 |
| WO | WO 2004/056312 A2 | 7/2004 |
| WO | WO 2004/063351 | 7/2004 |
| WO | WO 2004/103404 A1 | 12/2004 |
| WO | WO 2005/030258 A2 | 4/2005 |
| WO | WO 2005/044859 | 5/2005 |
| WO | WO 2005/088310 A2 | 9/2005 |
| WO | WO 2005/103081 A2 | 11/2005 |
| WO | WO 2006/055925 A2 | 5/2006 |
| WO | WO 2006/064983 A1 | 6/2006 |
| WO | WO 2006/106959 | 10/2006 |
| WO | WO 2006/126069 A2 | 11/2006 |
| WO | WO 2006/130458 A2 | 12/2006 |
| WO | WO 2007/078873 A1 | 7/2007 |
| WO | WO 2007/0133855 | 11/2007 |
| WO | WO 2007/146847 A2 | 12/2007 |
| WO | WO 2008-020596 A2 | 2/2008 |
| WO | WO 2008/087260 A1 | 7/2008 |
| WO | WO 2008/118013 | 10/2008 |
| WO | WO 2008/133801 A1 | 11/2008 |
| WO | WO 2008/133857 A1 | 11/2008 |
| WO | WO 2009/029888 A3 | 3/2009 |
| WO | WO 2010/006315 A2 | 1/2010 |
| WO | WO 2010/009271 A1 | 1/2010 |
| WO | WO 2010/011703 | 1/2010 |
| WO | WO 2011/005756 A1 | 1/2011 |
| WO | WO 2011/006237 A1 | 1/2011 |
| WO | WO 2011/031236 A1 | 3/2011 |
| WO | WO 2011/074621 A1 | 6/2011 |
| WO | WO 2011/089004 A1 | 7/2011 |
| WO | WO 2011/130332 | 10/2011 |
| WO | WO 2011/143262 A2 | 11/2011 |
| WO | WO 2011/145957 A1 | 11/2011 |
| WO | WO 2012/082635 A1 | 6/2012 |
| WO | WO 2012/094540 A2 | 7/2012 |
| WO | WO 2013/011347 A1 | 1/2013 |
| WO | WO 2013/024895 A1 | 2/2013 |
| WO | WO 2013/088395 A1 | 6/2013 |
| WO | WO 2013/120066 A1 | 8/2013 |
| WO | WO 2013/130603 A1 | 9/2013 |
| WO | WO 2013/152034 A1 | 10/2013 |
| WO | WO 2013/155375 A1 | 10/2013 |
| WO | WO 2013/181585 A2 | 12/2013 |
| WO | WO 2014/031498 | 2/2014 |
| WO | WO 2014/078373 A1 | 5/2014 |
| WO | WO 2014/210397 A1 | 12/2014 |
| WO | WO 2014/210564 | 12/2014 |
| WO | WO 2015/026484 A1 | 2/2015 |
| WO | WO 2015/035337 A1 | 3/2015 |
| WO | WO 2015/038963 A1 | 3/2015 |
| WO | WO 2015/184008 | 12/2015 |
| WO | WO 2016/040369 A2 | 3/2016 |
| WO | WO 2016-118090 A1 | 7/2016 |
| WO | WO 2014/031762 A1 | 2/2017 |

OTHER PUBLICATIONS

Shivatare et al, Nature Chemistry, 2016, 8(4), 338-346.*
Serna et al, Chem. Eur. J. 2010, 16, 13163-13175.*
Greene et al, Protective Groups in Organic Synthesis, second ed., John Wiley, 1991, pp. 42-51 and 96-100.*
Schelhaas et al, Angew. Chem. Int. Ed., 1996, 35, 2056-2083.*
Shivatare et al, J. Am. Chem. Soc., 2013, 135, 15282-15391.*
U.S. Appl. No. 15/005,930, filed Jan. 25, 2016, Wong et al.
U.S. Appl. No. 15/011,543, filed Jan. 30, 2016, Wong et al.
U.S. Appl. No. 15/011,544, filed Jan. 30, 2016, Wong et al.
U.S. Appl. No. 15/173,496, filed Jun. 3, 2016, Wong et al.

Abbas et al., "Functional diversity of helper T lymphocytes," *Nature*, Oct. 31, 1996, 383(6603):787-793.
Abrahmsén et al, "Analysis of signals for secretion in the *staphylococcal* protein A gene," *EMBO J.*, Dec. 30, 1985, 4(13B):3901-3906.
Achtman, M., Epidemic Spread and Antigenic Variability of Neisseria Meningitidis, Trends Microbial 1995, 3, 186-192.
Adam et al., "Proteomic profiling of mechanistically distinct enzyme classes using a common chemotype," *Nat. Biotechnol.*, Aug. 2002, 20(8):805-809.
Agard, N. et al., A Strain-Promoted [3+2]Azide-Alkyne Cycloaddition for Covalent Modification of Biomolecules in Living Systems, J. Am. Chem. Soc. 2004, 126, 15046-15047.
Ahmadi, T. S. et al., Shape-Controlled Synthesis of Colloidal Platinum Nanoparticles, Science, 272, 1924 (1996).
Ahmed et al.,Structural Characterization of Anti-Inflammatory Immunoglobulin G Fc Proteins, K Mol Biol (2014) 426, 3166-3179.
Altevogt, Peter et al., Different Patterns of Lectin Binding and Cell Surface Sialylation Detected on Related High- and Low-Metastatic Tumor Lines, Cancer Res. 43, 5138-5144, 1983.
Altschul SF et al., "Basic local alignment search tool", *J Mol Biol.* Oct. 5, 1990;215(3):403-10.
Altschul SF, et al., "Gapped BLAST and PSI-BLAST: a new generation of protein database search programs", Nucleic Acids Res. Sep. 1, 1997;25(17):3389-402.
Amin, M. N. et al. Synthetic glycopeptides reveal the glycan specificity of HIV-neutralizing antibodies. Nat. Chem. Biol. 9, 521-526, (2013.
Anderson et al., "Stimulation of Natural Killer T Cells by Glycolipids", *Molecules*, May 2013, 18(12), 15662-15688.
Andrews et al., Synthesis and influenza virus sialidase inhibitory activity of analogues of 4-Guanidino-Neu5Ac2en (Zanamivir modified in the glycerol side-chain. Eur J Med Chem Jul.-Aug. 1999;34(7-8):563-74.
Angata et al., "Chemical diversity in the sialic acids and related α-keto acids: an evolutionary perspective," *Chem. Rev.*, Feb. 2002, 102(2):439-469.
Anthony, Robert et al., Recapitulation of IVIG Anti-Inflammatory Activity with a Recombinant IgG Fc, Science Apr. 18, 2008. 320:373-376.
Arase et al., "NK1.1⁺CD4⁺CD8- thymocytes with specific lymphokine secretion," *Eur. J. Immunol.*, Jan. 1993, 23(1):307-310.
Arié et al., "Chaperone function of FkpA, a heat shock prolyl isomerase, in the periplasm of *Escherichia coli,*" *Mol. Microbiol.*, Jan. 2001, 39(1):199-210.
Aspeslagh et al., "Galactose-modified iNKT cell agonists stabilized by an induced fit of CD1d prevent tumour metastasis," *EMBO J.*, Jun. 1, 2011, 30(11):2294-2305.
Astronomo, R. D. & Burton, D.R. Carbohydrate vaccines: developing sweet solutions to sticky situations? Nat. Rev. Drug. Discov. 9, 308-324, (2010.
Bachmann, Cellular and Molecular Biology, vol. 2, Chapter 72: Derivations and Genotypes of Some Mutant Derivatives of *Escherichia coli* K-12, Neidhardt et al., eds., 1987, pp. 1190-1219, American Society for Microbiology, Washington, D.C.
Bacilieri, Magdalena et al., Ligand-Based Drug Design Methodologies in Drug Discovery Process: An Overview, Current Drug Discovery Technologies, vol. 3 (3), Sep. 2006, p. 155-165.
Bai, Dan et al., Exploring Forster Electronic Energy Transfer in a Decoupled Anthracenyl-based Borondipyrromethene (Bodipy) Dyad, Physical Chemistry Chemical Physics (2012), 14(13), 4447-4456.
Bailey, Ryan et al., Real-Time Multicolor DNA Detection with Chemoresponsive Diffraction Gratings and Nanoparticle Probes, J. Am Chem. Soc., 2003, 125, 13541-13547.
Baldwin et al., "Monoclonal antibodies in cancer treatment," *Lancet*, Mar. 15, 1986, 327(8481):603-605.
Banchereau et al., "Dendritic cells and the control of immunity," *Nature*, Mar. 19, 1998, 392(6673):245-252.
Barbas et al., "Assembly of combinatorial antibody libraries on phage surfaces: the gene III site," *Proc. Natl. Acad. Sci. U.S.A.*, Sep. 15, 1991, 88(18):7978-7982.

(56) References Cited

OTHER PUBLICATIONS

Barbas et al., "In vitro evolution of a neutralizing human antibody to human immunodeficiency virus type 1 to enhance affinity and broaden strain cross-reactivity," *Proc. Nat. Acad. Sci. U.S.A.*, Apr. 26, 1994, 91(9):3809-3813.

Barbas et al., "Semisynthetic combinatorial antibody libraries: a chemical solution to the diversity problem," *Proc. Natl. Acad. Sci. U.S.A.*, May 15, 1992, 89(10):4457-4461.

Bardotti, Angela et al., Size Determination of Bacterial Capsular Oligosaccharides Used to Prepare Conjugated Vaccines Against Neisseria Meningitidis Groups Y and W135, Vaccine 2005, 23, 1887-1899.

Barnes et al., "Methods for growth of cultured cells in serum-free medium," *Anal. Biochem.*, Mar. 1, 1980, 102(2):255-270.

Barouch, D. H. Challenges in the development of an HIV-I vaccine. Nature 455, 613-619, (2008).

Barry, C.S. et al., 'Naked' and Hydrated Confirmers of the Conserved Core Pentasaccharide of N-Linked Glycoproteins and Its Building Blocks, Journal of the American Chemical Society, 2013, vol. 135(45), p. 16895-16903.

Basak et al., In Vitro Elucidation of Substrate Specificity and Bioassay of Proprotein Convertase 4 Using Intramolecularly Quenched Fluorogenic Peptides, Biochem. J. Jun. 1, 2004, 380(pt 2): 505-514.

Baselga J, et al., "Phase II study of weekly intravenous recombinant humanized anti-p185HER2 monoclonal antibody in patients with HER2/neu-overexpressing metastatic breast cancer", *J Clin Oncol.* Mar. 1996;14(3):737-44.

Baskin, J.M.; Amacher, S. L.; Bertozzi, C.R." In vivo imaging of membraneassociated glycans in developing zebrafish." Science 2008, 320, 664-667.

Bass et al., "Hormone phage: an enrichment method for variant proteins with altered binding properties," *Proteins*, 1990, 8(4):309-314.

Bassell, G.J. et al., Single mRNAs Visualized by Ultrastructural in Situ Hybridization are Principally Localized at Actin Filament Intersections in Fibroblasts, J. Cell Biol., 126, 863-876 (1994.

Baz et al., Emergence of oseltamivir-resistant pandemic H1N1 virus during prophylaxis. N Engl J Med. Dec. 3, 2009;361(23):2296-7. doi: 10.1056/NEJMc0910060. Epub Nov. 11, 2009.

Beck A., "Biosimilar, biobetter and next generation therapeutic antibodies" *MAbs.* Mar.-Apr. 2011;3(2):107-10. Epub Mar. 1, 2011.

Beckman et al., Antibody constructs in cancer therapy: protein engineering strategies to improve exposure in solid tumors, cancer, 109(2): 170-179 (2007).

Bendayan, Moise, Possibilities of False Immunocytochemical Results Generated by the Use of Momoclonal Antibodies: The Example of the Anti-Proinsulin Antibody, J. Histochem. Cytochem, 43: 881-886, (1995).

Bennett, Clay et al., Chemoenzymatic Approaches to Glycoprotein Synthesis, Chem. Soc. Rev. 2007, 36:1227-1238.

Berge, Steven et al. J. Pharmaceutical Sciences (1977) 66: 1-19.

Berra et al., "Correlation between ganglioside distribution and histological grading of human astrocytomas," *Int. J. Cancer*, Sep. 15, 1985, 36(3):363-366.

Best, M. D. " Click chemistry and bioorthogonal reactions: unprecedented selectivity in the labeling of biological molecules." Biochemistry 2009, 48, 6571-6584.

Bertozzi, CR et al., Glycans in Cancer and Inflammation—Potential for Therapeutics and Diagnostics, Nat Rev Drug Discovery, 2005, 4, 477-488.

Bigi et al., "Human sialidase NEU4 long and short are extrinsic proteins bound to outer mitochondrial membrane and the endoplasmic reticulum, respectively," *Glycobiology*, Feb. 2010, 20(2):148-157.

Birklé et al., "Role of tumor-associated gangliosides in cancer progression," *Biochimie*, Mar.-Apr. 2003, 85(3-4):455-463.

Blixt, O. et al. Printed covalent glycan array for ligand profiling of diverse glycan binding proteins. Proc. Natl. Acad. Sci. U.S. A. 101, 17033-17038, (2004.

Bobo et al., "Convection-enhanced delivery of macromolecules in the brain," *Proc. Natl. Acad. Sci. U.S.A.*, Mar. 15, 1994, 91(6) 2076-2080.

Boens, N. et al., "Fluorescent indicators based on BODIPY." Chem. Soc. Rev. 2012, 41, 1130-1172.

Boerner et al., "Production of antigen-specific human monoclonal antibodies from in vitro-primed human splenocytes," *J. Immunol.*, Jul. 1, 1991, 147(1):86-95.

Borg et al., "CD1d-lipid-antigen recognition by the semi-invariant NKT T-cell receptor," *Nature*, Jul. 5, 2007, 448(7149):44-49.

Bosmann et al., "Enzyme activity in invasive tumors of human breast and colon," Proc. Natl. Acad. Sci. *USA*, May 1974, 71(5):1833-1837.

Bost, Kenneth et al., Antibodies Against A Peptide Sequence Within the HIV Envelope Protein Crossreacts With Human Interleukin-2, Immunol. Invest., 17: 577-586 (1988).

Bothmann et al., "The periplasmic *Escherichia coli* peptidylprolyl cis,trans-isomerase FkpA. I. Increased functional expression of antibody fragments with and without cis-prolines," *J. Biol. Chem.*, Jun. 2, 2000, 275(22):17100-17105.

Boyer, David et al., Photothermal Imaging of Nanometer-Sized Metal Particles Among Scatterers, Science, 2002, 297, 1160-116 3.

Braun-Howland et al., Development of a Rapid Method for Detecting Bacterial Cell in Situ Using 16S rRNA-Targeted Probes, Biotechniques, 13, 928-931 (1992).

Brennan et al., "Preparation of bispecific antibodies by chemical recombination of monoclonal immunoglobulin $G_1$ fragments," *Science*, Jul. 5, 1985, 229(4708):81-83.

Bricard et al., "Enrichment of human CD4+ Vα24/Vβ11 invariant NKT cells in intrahepatic malignant tumors," *J. Immunol.*, Apr. 15, 2009, 182(2):5140-5151.

Brimble et al., "The cell surface glycosphingolipids SSEA-3 and SSEA-4 are not essential for human ESC pluripotency," *Stem Cells*, Jan. 2007, 25(1):54-62.

Brodeur et al., Monoclonal Antibody Production Techniques and Applications, Chapter 4: Mouse-Human Myeloma Partners for the Production of Heterohybridomas, Schook, ed., 1987, pp. 51-63, Marcel Dekker, Inc., New York.

Bruchez, Marcel et al. Semiconductor Nanocrystals as Fluorescent Biological Labels, Science 281:2013-2016, 1998.

Brüggemann et al., "Designer mice: the production of human antibody repertoires in transgenic animals," *Year in Immunol.*, 1993, 7:33-40.

Buchini et al., "Towards a new generation of specific *Trypanosoma cruzi* trans-sialidase inhibitors," *Angew. Chem. Int. Ed. Engl.*, 2008, 47(14):2700-2703.

Burton, D.R., Mascola, J. R. Antibody responses to envelope glycoproteins in HIV-I infection. Nature Immunol. 16, 571-6, (2015).

Calarese, D. A. et al. Antibody domain exchange is an immunological solution to carbohydrate cluster recognition. Science 300, 2065-2071, (2003).

Cao, Y. C. et al., Nanoparticles with Raman Spectroscopic Fingerprints for DNA and RNA Detection, Science, 2002, 289, 1757-60.

Capel PJ et al., "Heterogeneity of human IgG Fc receptors" *Immunomethods*. Feb. 1994;4(1):25-34.

Carlsson, Jan et al., Protein Thiolation and Reversible Protein-Protein Conjugation, Biochem J 173: 723-737 (1978).

Carter et al., "High level *Escherichia coli* expression and production of a bivalent humanized antibody fragment," *Nature Biotechnology*, Feb. 1992, 10(2):163-167.

Carter et al., "Humanization of an anti-p185$^{HER2}$ antibody for human cancer therapy," *Proc. Natl. Acari. Sci. U.S.A.*, May 15, 1992, 89(10):4285-4289.

Carter PJ. "Potent antibody therapeutics by design" *Nat Rev Immunol.* May 2006;6(5):343-357.

Carter, A rationale for using steroids in the treatment of severe cases of H5N1 avian influenza. J Med Microbiol. Jul. 2007;56(Pt 7):875-83.

Centers for Disease Control and Prevention (CDC), "Influenza activity—United States and worldwide, 2007-08 season" *MMWR*, Jun. 27, 2008, 57(25):692-697.

(56) References Cited

OTHER PUBLICATIONS

Cespedes et al., Mouse models in oncogenesis and cancer therapy, Clin Transl Oncl., 8(5): 318-329 (2006).

Chan, Warren et al., Quantum Dot Bioconjugates for Ultrasensitive Nonisotopic Detection, Science 281:2016-2018 (1998).

Chandler et al., Synthesis of the potent influenza neuraminidase inhibitor 5-guanidino Neu5Ac2en. X-Ray molecular structure of 5-acetaminido-4amino-2,6-anahydro-3,4,5-tryoxy-D-erythoro-L-gluco-nononic acid. J Chem Soc Perkin Trans 1. 1995; 1173-1180.

Chang et at, "Expression of Globo H and SSEA3 in breast cancer stem cells and the involvement of fucosyl transferases 1 and 2 in Globo H synthesis," *Proc. Natl. Acad. Sci. U.S.A.*, Aug. 19, 2008, 105(33):11667-11672.

Chang, S. H. et al. Glycan array on aluminum oxide-coated glass slides through phosphonate chemistry. J. Am. Chem. Soc. 132, 13371-13380, (2010).

Chang et al., "Potent immune-modulating and anticancer effects of NKT cell stimulatory glycolipids," *Proc. Natl. Acad. Sci. USA*, Jun. 19, 2007, 104(25):10299-10304.

Chao, W.; Fang, X.; Nisaraporn, S.; Jian, S.; Qian, W. "Tuning the optical properties of BODIPY dye through Cu(I) catalyzed azide-alkyne cycloaddition (CuAAC) reaction." Sci. China Chemistry 2012, 55, 125-130.

Chari, Ravi et al., Immunoconjuates Containing Novel Maytansinoids: Promising Anticancer Drugs Cancer Research 52: 127-131 (1992).

Chauhan, D. P.; Saha, T.; Lahiri, M.; Talukdar, P. "BODIPY based 'click on' fluorogenic dyes: application in live cell imaging." Tetrahedron Lett. 2014, 55, 244-247.

Chen et al., "Chaperone activity of DsbC," *J. Bio. Chem.*, Jul. 9, 1999, 274(28): 19601-19605.

Chen et al., "Selection and analysis of an optimized anti-VEGF antibody: crystal structure of an affinity-matured Fab in complex with antigen," *J. Mol. Biol.*, Nov. 5, 1999, 293(4):865-881.

Chen et al., "Selective killing of transformed cells by cyclin/cyclin-dependent kinase 2 antagonists," *Proc. Natl. Acad. Sci. U.S.A.*, Apr. 13, 1999, 96(8):4325-4329.

Cheng, Peter et al., Oseltamivir-and Amandtadine-resistant Influenza Viruses A (H1N1), Emerg. Infect. Dis., Jun. 2009, 15(6): 966-968.

Cheung et al., Stage-specific embryonic antigen-3 (SSEA-3) and beta3GalT5 are cancer specific and significant markers for breast cancer stem cells, PNAS, Jan. 26, 2016, vol. 113, No. 4, pp. 960-965.

Chiang et al., Ethyl caffeate suppresses NF-kappaB activation and its downstream inflammatory mediators, iNOS, COX-2, and PGE2 in vitro or in mouse skin. Br J Pharmacol. Oct. 2005; 146(3):352-63.

Chiari, M. et al., Advanced Polymers for Molecular Recognition and Sensing at the Interface. J Chromatography B, Apr. 15, 2008, 866(1-2):89-103.

Childs et al., Receptor-Binding Specificity of Pandemic Influenza A (H1N1) 2009 Virus Determined by Carbohydrate Microarray. Nat. Biotechnol. 2009, 27(9): 797-799.

Cho, Se-Heon et al., Sialyl-Tn Antigen Expression Occurs Early During Human Mammary Carcinogenesis and is Associated with High Nuclear Grade and Aneuploidy, Cancer Res. 54, 6302-6305, 1994.

Chong et al., Influenza Virus Sialidase: Effect of Calcium on Steady-State Kinetic Parameters, Biochim. Biophys. Acta, Mar. 8, 1991, 1077(1): 65-71.

Chothia et al., "Canonical structures for the hypervariable regions of immunoglobulins," *J. Mol. Biol.*, Aug. 20, 1987, 196(4):901-917.

Chothia et al., "Domain association in immunoglobulin molecules. The packing of variable domains," *J. Mol. Biol.*, Dec. 5, 1985, 186(3):651-663.

Clackson et al., "Making antibody fragments using phage display libraries," Nature, Aug. 15, 1991, 352(6336):624-628.

Clark EA et al., "Structure, function, and genetics of human B cell-associated surface molecules" Adv Cancer Res. 1989;52:81-149.

Clynes R, et al., "Fc receptors are required in passive and active immunity to melanoma" *Proc Natl Acad Sci U S A*. Jan. 20, 1998;95(2):652-6.

Codelli, J. A. et al., Second-Generation Difluorinated Cycloctynes for Copper-Free Click Chemistry, J. Am. Chem. Soc. 2008, 130, 11486-11493.

Cohen-Daniel et al., Emergance of Oseltamivir-Resistant Influenza A/H3N2 Virus with Altered Hemagglutination Pattern in Hematopoietic Stem Cell Transplant Recipient, J Clin Virol., Feb. 2009, 44(2):138-140.

Coligan et al., Current Protocols in Immunology, sections 2.5.1-2.6.7, 1991.

Collins et al., Crystal Structures of Oseltamivir-Resistant Influenza Virus Neuraminidase Mutants, Nature, Jun. 26, 2008, 453(7199):1258-1261.

Connor, Robert et al., Receptor Specifcity in Human, Avian, and Equine H2 and H3 Influenza Virus Isolates, Virology, 205: 17, 1994.

Cox et al., New Options for the Prevention of Influenza, N. Engl. J. Med. Oct. 28, 1999, 341(18): 1387-1388.

Cragg, M.S. et al., Complement-Mediated Lysis by Anti-CD20 mAb Correlates with Segregation into Lipid Rafts, Blood 101 (2003) 1045-1052.

Cragg, M.S. et al., Antibody Specificity Controls in Vivo Effector Mechanism of Anti-CD20 Reagents, Blood, 103 (2004) 2738-2743.

Craigo, J. K., Montelaro, R. C. Lessons in AIDs vaccine development learned from studies of equine infectious, anemia virus infection and immunity. Viruses 5, 2963-76, (2013).

Crispin et al., "Carbohydrate and domain architecture of an immature antibody glycoform exhibiting enhanced effector functions," J. Mol. Biol., Apr. 17, 2009, 387(5):1061-1066.

Cunningham et al., "High-resolution epitope mapping of hGH-receptor interactions by alanine-scanning mutagenesis," *Science*, Jun. 2, 1989, 244(4908):1081-1085.

Cyranoski, Threat of Pandemic Brings Flu Drug Back to Life, Nat. Med. Sep. 2005, 11(9): 909.

Daëron, "Fc receptor biology," *Annu. Rev. Immunol.*, 1997, 15:203-234.

Davies, JW et al., Streamlining Lead Discovery by Aligning in Silico and High-Throughput Screening, Curr Opin Chem Biol. Aug. 2006; 10(4):343-51.

Davodeau et al., "Close phenotypic and functional similarities between human and murine αβ T cells expressing invariant TCR alpha-chains," *J. Immunol.*, Jun. 15, 1997, 158(12):5603-5611.

De Almeida et al., "Thiacycloalkynes for copper-free click chemistry," *Angew. Chem. Int. Ed. Engl.*, Mar. 5, 2012, 51(10):2443-2447.

Debets, M. F. et al., Bioconjugation with Strained Alkenes and Alkynes, Acc. Chem. Res. 2011, 44, 805-815.

De Haas et al., "Fcγ receptors of phagocytes," *J. Lab. Clin. Med.*, Oct. 1995, 126(4):330-341.

Dejong et al., Fatal outcome of human influenza A (H5N1) is associated with high viral load and hypercytokinemia. Nat Med Oct. 2006;12(10):1203-7. Epub Sep. 10, 2006.

Delente, Jacqubs, Glycosylation Revisited, Trends in Biotechnology 3, letters to editor, No. 9 (1985).

Dellabona et al., "An invariant Vα24-JαQ/Vβ11 T cell receptor is expressed in all individuals by clonally expanded CD4-8- T cells," J. Exp. Med., Sep. 1, 1994, 180(3):1171-1176.

Demchenko, A.V., Ed., Hanbook of Chemical Glycosylation: Advances in Stereoselectivity and Therapeutic Relevance (2008) WILEY-VCH. Chapter 1. General Aspects of the Glycosidic Bond Formation, in 28 pages.

Dennis, Carina, Cancer: Off by a whisker, Nature 442: 739-741 (2006).

De Paz, J. L., Horlacher, T. & Seeberger, P.H. Oligosaccharide microarrays to map interactions of carbohydrates in biological systems. Methods Enzymol. 415, 269-292, (2006).

Dhodapkar et al., "α-Galactosyl ceramide-loaded dendritic cells for expansion of natural killer T cells" CAPLUS 145:354715 (2006).

Dhodapkar et al., "A reversible defect in natural killer T cell function characterizes the progression of premalignant to malignant multiple myeloma," *J. Exp. Med.*, Jun. 16, 2003, 197(12):1667-1676.

(56) References Cited

OTHER PUBLICATIONS

Dohi, Taeko et al., Fucosyltransferase-Producing Sialyl Lea and Sialyl Lex Carbohydrate Antigen in Benign and Malignant Gastrointestinal Mucosa, Cancer 73, 1552, 1994.

Dohi, H. et al., Stereoselective Glycal Fluorophosphorlation: Synthesis of ADP-2-Fluoroheptose, an Inhibitor of the LPS Biosynthesis, Chem-Eur J 2008, 14, 9530-9539.

Dommerholt, Jan, Readily Accessible Bicyclononynes for Bioorthogonal Labeling and Three-Dimensional Imaging of Living Cells, Angew. Chem. Int. Ed. 2010, 49, 9422-9425.

Doores KJ, et al. A nonself sugar mimic of the HIV glycan shield shows enhanced antigenicity. Proc. Natl. Acad Sci. US.A. 107(40), 17107-17112, (2010).

Doores, K. J. & Burton, D.R. Variable Loop Glycan Dependency of the Broad and Potent HIV-I-Neutralizing Antibodies PG9 and PG16. J. Virol. 84, 10510-10521, (2010).

Doores, K. J. et al. Envelope glycans of immunodeficiency virions are almost entirely oligomannose antigens. Proc. Natl. Acad. Sci. U.S. A 107, 13800-13805, (2010).

Doronina, Svetlana et al., Development of Potent Monoclonal Antibody Auristatin Conjugates for Cancer Therapy, Nat Biotechnol 21(7): 778-784 (2003).

Dougan, Michael et al., Immune Therapy for Cancer, Annual Review of Immunology, 2009, 27, pp. 83-117.

Drugs of the future 25(7): 686 (2000).

Dubertret. Benoit et al., In Vivo Imaging of Quantum Dots Encapsulated in Phospholipid Micelles, Science 298:759-1762, 2002.

Duncan, AR; Winter, G, The binding Site for C1q on lgG, Nature 322:738-40 (1988).

Dunn et al., Zanamivir: A Review of Its Use in Influenza, Drugs, Oct. 1999, 58(4):761-784.

Durrant et al., "Immunology in the clinic review series; focus on cancer: glycolipids as targets for tumour immunotherapy," Clin. Exp. Immunol., Feb. 2012, 167(2):206-215.

Eberl et al., "Selective bystander proliferation of memory CD4+ and CD8+ T cells upon NK T or T cell activation," J. Immunol., Oct. 15, 2000, 165(8):4305-4311.

Eberl et al., "Selective induction of NK cell proliferation and cytotoxicity by activated NKT cells," Eur. J. Immunol., Apr. 2000, 30(4):985-992.

Eggink, D. et al. Lack of complex N-glycans on HIV-I envelope glycoproteins preserves protein conformation and entry function. Virology 401, 236-247, (2010).

Eisen, Michael et al., Binding of the Influenza A Virus to Cell-Surface Receptors: Structures of Five Hemagglutinin-Sialyloligosaccharide Complexes Determined by X-Ray Crystallography, Virology, 232:19, 1997.

Ellis J., et al., Evaluation of Four Real-Time PCR Assays for Detection of Influenza A9H1N1)v Viruses, Euro Surveill. 2009; 14(22), p. 1-3.

Embleton et al., "In-cell PCR from mRNA: amplifying and linking the rearranged immunoglobulin heavy and light chain V-genes within single cells," Nucl. Acids Res., Aug. 11, 1992, 20(15):3831-3837.

Engels et al., "Gene synthesis [new synthetic methods (77)],"Angew. Chem. Int. Ed. Engl., Jun. 1989, 28(6):716-734.

European Search Report issued in connection with corresponding European Patent Application No. 15181446.4, dated Dec. 7, 2015, 10 pages.

Evans, Michael et al., "Mechanism-based profiling of enzyme families," Chem. Rev., Aug. 2006, 106(8):3279-3301.

Evans, "The rise of azide-alkyne 1,3-dipolar 'click' cycloaddition and its application to polymer science and surface modification," Australian J. Chem., Jun. 2007, 60(6):384-395.

Extended European Search Report dated Jan. 5, 2016 in European Patent Application No. 13830785.5, in 10 pages.

Falkowska, E. et al. Broadly neutralizing HIV antibodies define a glycan-dependent epitope on the prefusion conformation of gp41 on cleaved envelope trimers. Immunity 40, 657-68, 2014.

Fan, Shu-Quan et al., Remarkable Transglycosylation Activity of Glycosynthase Mutants of Endo-D, an Endo-β-N-acetylglucosaminidase from Streptococcus pneumoniae, JBC Vol. 287, No. 14, pp. 11272-11281, Mar. 30, 2012.

Fazio, F. et al., Synthesis of sugar arrays in microtiter plate. J. Am. Chem. Soc. 124, 14397-14402, (2002).

FDA Guidance for Industry for Container Closure Systems for Packaging Human Drugs and Biologics, May 1999.

Fedson, Confronting the next influenza pandemic with anti-inflammatory and immunomodulatory agents: why they are needed and how they might work. Influenza Other Respi Viruts. Jul. 2009;3(4):129-42.

Feizi, Ten, Carbohydrate Differentiation Antigens: Probable Ligands for Cell Adhesion Molecules,Trends Biochem. Sci. 16, 84-86.

Fellouse et al., "Synthetic antibodies from a four-amino-acid code: a dominant role for tyrosine in antigen recognition," Proc. Natl. Acad. Sci. U.S.A., Aug. 24, 2004, 101(34):12467-12472.

Fernandez-Tejada, Alberto et al., Designing synthetic vaccines for HIV. Expert Rev. Vaccines 14, 815-31, 2015.

Fernandez-Megia et al., A Click Approach to Unprotected Glycodendrimers. Macromolecules 2006, vol. 39, pp. 2113-2120.

Fessner et al., Enzymes in Organic Synthesis, Short Enzymatic Synthesis of L-Fucose Analogs. Eur. J. Org. Chem 2000, p. 125-132.

Fiehn, Oliver, Combining Genomics, Metabolome Analysis, and Biochemical Modelling to Understand Metabolic Networks, Comparative and Functional Genomics 2:155-168, 2001.

Fishwild et al., "High-avidity human IgGκ monoclonal antibodies from a novel strain of minilocus transgenic mice," Nature Biotechnol., Jul. 1996, 14(7):845-851.

Fraker, PJ et al., Protein and Cell Membrane Iodinations with a Sparingly Soluble Chloroamide, 1,3,4,6-tetrachloro-3a,6a-diphrenylglycoluril, Biochem. Biophys. Res. Commun. 80: 49-57 (1978).

Fredman et al., "Expression of gangliosides GD3 and 3'-isoLM1 in autopsy brains from patients with malignant tumors," J. Neurochem., Jan. 1993, 60(1):99-105.

Fredman et al., "Potential ganglioside antigens associated with human gliomas," Neurol. Res., Jun. 1986, 8(2):123-126.

Fredman et al., "Sialyllactotetraosylceramide, a ganglioside marker for human malignant gliomas," J. Neurochem., Mar. 1988, 50(3):912-919.

Friscourt, F. et al., A Fluorogenic Probe for the Catalyst-Free Detection of Azide-Tagged Molecules, J. Am. Chem. Soc. 2012, 134, 18809-18815.

Friscourt et al., "Polar Dibenzocyclooctynes for Selective Labeling of Extracellular Glycoconjugates of Living Cells," J. Am. Chem. Soc., Mar. 21, 2012, 134(11):5381-5389.

Fujimore, Kenji et al., A Modeling Analysis of Monoclonal Antibody Percolation Through Tumors: A Binding-Site Barrier, J Nuc Med. 31: 1191-1198 (1990).

Fujio, M. et al. "Structure-Based Discovery of Glycolipids for CD1d-Mediated NKT Cell Activation: Turning the Adjuvant versus Immunosuppression Activity." CAPLUS 145:240945 (2006).

Fujio, M. et al. "Structure-Based Discovery of Glycolipids for CD1d-Mediated NKT Cell Activation: Turning the Adjuvant versus Immunosuppression Activity." J. Am. Chem. Soc. (2006), vol. 128, pp. 9022-9023.

Fujita M et al., "A novel disaccharide substrate having 1,2-oxazoline moiety for detection of transglycosylating activity of endoglycosidases" Biochim Biophys Acta. Sep. 3, 2001;1528(1):9-14.

Fukui, S et al., Oligosaccharide microarrays for high-throughput detection and specificity assignments of carbohydrate-protein interactions. Nat. Biotechnol. 20, 1011-1017, (2002).

Gabius, HJ. Tumor Lectinology: at the intersection of carbohydrate chemistry, biochemistry, cell biology and oncology. Angew. Chem. Int. Ed. Engl. 27, 1267-1276.

Galfrè et al., "Preparation of monoclonal antibodies: strategies and procedures," Methods Enzymol., 1981, 73(Pt B):3-46.

Gamblin, SJ et al., The Structure and Receptor Binding Properties of the 1918 Influenza Hemagglutinin, Science, 303:1838, 2004.

(56) References Cited

OTHER PUBLICATIONS

Garces, F. et al. Structural evolution of glycan recognition by a family of potent HIV antibodies. Cell 159, 69-79, (2014).
Gaschen, B. et al. AIDS—Diversity Considerations in HIV-I vaccine selection. Science 296, 2354-2360, (2002).
Gazzano-Santoro et al., "A non-radioactive complement-dependent cytotoxicity assay for anti-CD20 nonclonal antibody," *J. Immunol. Methods*, Mar. 28, 1997, 202(2):163-171.
Geiler et al., Comparison of pro-inflammatory cytokine expression and cellular signal transduction in human macrophages infected with different influenza A viruses. Med Microbiol Immunol. Feb. 2011;200(1):53-60.
GenBank accession No. AAA24922.1, "endoglycosidase F [Elizabethkingia meningoseptica]," May 27, 2008.
GenBank accession No. AAA24923.1, "endoglycosidase, partial [Elizabethkingia meningoseptica]," Jun. 8, 1993.
GenBank accession No. AAA24924.1.1, "endoglycosidase, partial [Elizabethkingia meningoseptica]," Jun. 7, 1993.
GenBank accession No. AAA26738.1, "endo-beta-N-acetylglucosaminidase H [Streptomyces plicates]," Apr. 26, 1993.
GenBank accession No. J05449.1, "F.meningosepticum peptide-N-4-(N-acetyl-beta-D-glucosaminyl) asparagine amidase (PNGase F) mRNA, complete cds," Jan. 16, 1996.
GenBank accession No. YP_212855.1, "Putative exported alpha-L-fucosidase protein [Bacteroides fragilis NCTC 9343]," Mar. 2, 2014.
GenBank accession No. WP_0080769537.1, published May 10, 2013.
GenBank accession No. WP_008767711.1, published May 10, 2013.
Geoghegan, Kieran et al., Site-Directed Conjugation of Nonpeptide Groups to Peptides and Proteins Via Periodate Oxidation of a 2-amino Alcohol. Applications to Modification at N-Terminal Serine, Bioconjugate chem. 3:138-146 (1992).
Gerson et al., "ESR. Spectra and Structures of Radical Anions in the Dibenzo[a, e]cyclooxtene Series," *Helvetica Chinica Acta*, Jan. 1, 1976, 59(6): 2038-2048.
Giaccone, Giuseppe et al., "A phase I study of the natural killer T-cell ligand α-galactosylceramide (KRN7000) in patients with solid tumors," *Clin. Cancer Res.*, Dec. 2002, 8(12):3702-3709.
Gill et al., "Direct brain infusion of glial cell line-derived neurotrophic factor in Parkinson disease," *Nature Med.*, May 2003, 9(5):589-595 and Addendum from Apr. 2006, 12(4):479.
Go, E. P. et al. Characterization of glycosylation profiles of HIV-I transmitted/founder envelopes by mass spectrometry. J. Virol. 85, 8270-8284, (2011).
Go, E. P. et al. Comparative Analysis of the Glycosylation Profiles of Membrane-Anchored HIV-I Envelope Glycoprotein Trimers and Soluble gp140. J. Virol. 89, 8245-57, (2015).
Godefroy, S. et al., Effect of Skin Barrier Disruption on Immune Responses to Topically Applied Cross-Reacting Material, CRM197 of Diphtheria Toxin, Infect. Immun. 2005, 73, 4803.
Goding, *Monoclonal Antibodies: Principles and Practice 2nd ed.*, Chapter 3: Production of Monoclonal Antibodies, 1986, pp. 59-103, Academic Press, London.
Goldenthal et al., "Safety Evaluation of Vaccine Adjuvants: National Cooperative Vaccine Development Working Group," *AIDS Res. Hum. Retroviruses*, 1993, 9(Supp.1):S47-S51.
Golkowski et al., "Strategy for catch and release of azide-tagged biomolecules utilizing a photolabile strained alkyne construct," *Organic and Biomolecular Chemistry*, Jan. 1, 2012, 10(23):4496.
Goochee CF et al., "The oligosaccharides of glycoproteins: bioprocess factors affecting oligosaccharide structure and their effect on glycoprotein properties", *Biotechnology* (N Y). Dec. 1991;9(12):1347-55.
Gordon et al., "Reactivity of biarylazacyclooctynones in copper-free click chemistry," *J. Am. Chem. Soc.*, Jun. 6, 2012, 134(22): 9199-9208.
Gottschling et al., "Stage-specific embryonic antigen-4 is expressed in basaloid lung cancer and associated with poor prognosis," *Eur. Respir. J.*, Mar. 2013, 41(3):656-663.

Govorkova et al, Combination chemotherapy for influenza. Viruses. Aug. 2010;2(8):1510-29.
Graham et al., "Characteristics of a human cell line transformed by DNA from human adenovirus type 5," *J. Gen. Virol.*, Jul. 1977, 36(1):59-72.
Graham, Duncan et al., Surface-Enhanced Resonance Raman Scattering as a Novel Method of DNA Discrimination, Angew. Chem., 2000, 112(6), 1103-1105.
Gram et al., "In vitro selection and affinity maturation of antibodies from a naive combinatorial immunoglobulin library," *Proc. Natl. Acari. Sci. U.S.A.*, Apr. 15, 1992, 89(8):3576-3580.
Grandjean, C. et al., On the Preparation of Carbohydrate-Protein Conjugates Using the Traceless Staudinger Ligation, J Org Chem 2005, 70, 7123-7132.
Green, "Targeting targeted therapy," *N. Engl. J. Med.*, May 20, 2004, 350(21):2191-2193.
Greenbaum et al., "Chemical approaches for functionally probing the proteome," *Mol. Cell. Proteomics*, 2002, 1:60-68.
Griffiths et al., "Human anti-self antibodies with high specificity from phage display libraries," *EMBO J.*, Feb. 1993, 12(2):725-734.
Gruber et al., "Efficient tumor cell lysis mediated by a bispecific single chain antibody expressed in *Escherichia coli*," *J. Immunol.*, Jun. 1, 1994, 152(11):5368-5374.
Grubisha, D. S. et al., Femtomolar Detection of Prostate-Specific Antigen: An Immunoassay Based on Surface-Enhanced Raman Scattering and Immunogold labels, Anal. Chem. (2003), 75, 5936-5943.
Gulati et al., Deletions of Neuraminidase and Resistance to Oseltamivir May Be a Consequence of Restricted Receptor Specificity in Recent H3N2 Influenza Viruses. Virol. J. 2009, 6(22)L 1-15.
Gulland, Fire Cases of Spread of Oseltamivir Resistant Swine Flu Between Patients are Reported in Wales, BMJ, Nov. 23, 2009:339:b4975.
Guss et al., "Structure of the IgG-binding regions of streptococcal protein G," *EMBO J.*, Jul. 1986, 5(7):1567-1575.
Guyer et al., "Immunoglobulin binding by mouse intestinal epithelial cell receptors," *J. Immunol.*, Aug. 1976, 117(2):587-593.
Ha, Ya et al., X-Ray Structures of H5 Avian and H9 Swine Influenza Virus Hemagglutinins Bound to Avian and Human Receptor Analogs, Proc Natl Acad Sci USA, 98:11181-11186, 2001.
Ha, YA et al., X-Ray Structure of the Hemagglutinin of a Potential H3 Avian Progenitor of the 1968 Hong Kong Pandemic Influenza Virus, Virology, 309:209-218, 2003.
Hajishengallis, "Mucosal immunization with a bacterial protein antigen genetically coupled to cholera toxin A2/B subunits," *J. Immuol.*, May 1, 1995, 154(9):4322-4332.
Hakomori et al., "Glycosphingolipid antigens and cancer therapy," *Chem. Biol.*, Feb. 1997, 4(2):97-104.
Hakomori, "Glycosylation defining cancer malignancy: new wine in an old bottle," *Proc. Natl. Acad. Sci. U.S.A.*, Aug. 6, 2002, 99(16):10231-10233.
Ham, Richard et al., Media and Growth Requirements, Meth. Enz 58, 44 (1979).
Hammerling et al., in: Monoclonal Antibodies and T-Cell Hybridomas 563-587, 1981.
Han, Junyan et al., 3- and 5-Functionalized BODIPYs via the Liebeskind-Srogl Reaction, Organic & Biomolecular Chemistry (2009), 7(1), 34-36.
Hanski, Christoph et al., Altered Glycosylation of the MUC-1 Protein Core Contributes to the Colon Carcinoma-Associated Increase of Mucin-Bound Sialyl-Lewis Expression, Cancer Res. 53, 4082-4088 (1993).
Hanski, C. et al., Characterization of the Major Sialyl-Lex-Poristive Mucins Present in Colon, Colon Carcinoma, and Sera of Patients with Colorectal Cancer, Cancer Res. 55, 928-933 (1995).
Hara et al., "Overproduction of penicillin-binding protein 7 suppresses thermosensitive growth defect at low osmolarity due to an spr mutation of *Escherichia coli*," *Microbial Drug Resistance*, Spring 1996, 2(1):63-72.
Harris, "Production of humanized monoclonal antibodies for in vivo imaging and therapy," *Biochem. Soc. Transactions*, Nov. 1995, 23(4):1035-1038.

(56) References Cited

OTHER PUBLICATIONS

Hasegawa, Akira, et al., Synthesis of Sialyl Lewis X Ganglioside Analogues Containing Modified L-Fucose Residues, Carbohydr. Res. 1995, 274, 165-181.
Hata, K. et al., Limited Inhibitory Effects of Oseltamivir and Zanamivir on Human Sialidases, Antimicrobial Agents and Chemotherapy, vol. 52, No. 10, Oct. 2008, in 8 pages.
Hawkins et al., "Selection of phage antibodies by binding affinity. Mimicking affinity maturation," J. Mol. Biol., 1992, 226(3):889-896.
Healthy Living, "10 Simple and Natural Ways to Boost Your Immune System," Published Jan. 31, 2014, downloaded from online, http://www.everydayhealth.com/columns/white-seeber-grogan-the-remedy-chicks/ten-simple-natural-ways-to-b . . . on Aug. 19, 2016.
Henglein, A. et al., Absorption Spectrum and Some Chemical Reactions of Colloidal Platinum in Aqueous Solution, J. Phys. Chem., 99, 14129 (1995).
Herner, A et al., A new family of bioorthogonally applicable fluorogenic labelst, Org. Biomol. Chem. 2013, 11, 3297-3306.
Hey, Thomas et al., Artificial, non-antibody binding proteins for pharmaceutical and industrial application, Trends in Biotechnology 23(10) 514-522 (2005).
Heyman, "Complement and Fc-receptors in regulation of the antibody response," Immunol. Lett., Dec. 1996, 54(2-3):195-199.
Hinman et al., "Preparation and characterization of monoclonal antibody conjugates of the calicheamicins: a novel and potent family of antitumor antibiotics," Cancer Res., Jul. 15, 1993, 53(14):3336-3342.
Hirabayashi, J. et al., Oligosaccharide Microarrays for Glycomics, Trends in Biotechnology 21 (4): 141-143, 2003.
Hogrefe et al., "A bacteriophage lambda vector for the cloning and expression of immunoglobulin Fab fragments on the surface of filamentous phage," Gene, Jun. 15, 1993, 128(1):119-126.
Holliger et al., "'Diabodies': small bivalent and bispecific antibody fragments," Proc. Natl. Acad. Sci. U.S.A., Jul. 15, 1993, 90(14):6444-6448.
Holmskov, Uffe et al., Collectins: Collagenous C-Type Lectins of the Innate Immune Defense System, 1994, Immunol. Today, 15: 67.
Honda et al., Synthesis and anti-influenza virus activity of 7-0-alkylated derivatives related to zanamivir. Bioorg Med Chem Lett. Aug. 5, 2002;12(15):1925-8.
Honegger et al., "Yet another numbering scheme for immunoglobulin variable domains: an automatic modeling and analysis tool," J. Mol. Biol., Jun. 8, 2001, 309:657-670.
Hoogenboom et al., "By-passing immunisation: Human antibodies from synthetic repertoires of germline $V_h$ gene segments rearranged in vitro," J. Mol. Biol., Sep. 20, 1992, 227(2):381-388.
Hoogenboom et al., "Multi-subunit proteins on the surface of filamentous phage: methodologies for displaying antibody (Fab) heavy and light chains," Nucl. Acids Res., Aug. 11, 1991 19(15):4133-4137.
Hotha, Srinivas et al., "Click Chemistry" Inspired Synthesis of Pseudo-Oligosaccharides and Amino Acid Glycoconjugates, J Org Chem 2006, 71, 364-367.
Horiya, S. et al., Recent strategies targeting HIV glycans in vaccine design. Nat. Chem. Biol. 10, 990-999, (2014).
Horn et al., Investigation into an Efficient Synthesis of 2,3-dehydro-N-acetyl Neuraminic Acid Leads to Three Decarboxylated Sialic Acid Dimers, Carbohdr. Res., Apr. 7, 2008, 343(5):936-940.
Howard et al., "Biological properties of interleukin 10," Immunol. Today, Jun. 1992, 13(6):198-200.
Hsu et al., "Alkynyl sugar analogs for the labeling and visualization of glycoconjugates in cells," Proc. Natl. Acad. Sci. USA, Feb. 20, 2007, 104(8), 2614-2619.
Huang et al., "Carbohydrate-based vaccines with a glycolipid adjuvant for breast cancer," Proc. Natl. Acad. Sci. U.S.A., Feb. 12, 2013, 110(7):2517-2522.
Huang, Lijun et al., Iterative One-Pot Syntheses of Chitotetroses, Carbohydr. Res. 2006, 341, 1669-1679.
Huang et al., Recombinant immunotherpaeutics: current state and perspectives regarding the feasibility and market, Appl Microbiol Biotechnol, 87: 401-410. 2010.
Hung et al., "Investigation of SSEA-4 binding protein in breast cancer cells," J. Am. Chem. Soc., Apr. 24, 2013, 135(16):5934-5937.
Hurle et al., "Protein engineering techniques for antibody humanization," Curr. Opin. Biotechnol., Aug. 1994, 5(4):428-433.
Immunogenicity, Wikipedia p. 1-3. Downloaded on Aug. 16, 2016 from https://en.wikipedia.org/wiki/Immunogenicity. (2016).
Inouye et al., "Single-step purification of $F(ab')_{2\mu}$ fragments of mouse monoclonal antibodies (immunoglobulins M) by hydrophobic interaction high-performance liquid chromatography using TSKgel Ether-5PW," J. Biochem. Biophys. Methods, Feb. 1993, 26(1):27-39.
International Search Report and Written Opinion issued for International application No. PCT/US2015/011748, dated Aug. 21, 2015, 17 pages.
International Search Report and Written Opinion issued for International application No. PCT/US2015/032737, dated Oct. 1, 2015, 13 pages.
International Search Report and Written Opinion issued for International application No. PCT/US2015/032738, dated Oct. 20, 2015, 15 pages.
International Search Report and Written Opinion issued for International application No. PCT/US2015/032740, dated Oct. 26, 2015, 13 pages.
International Search Report and Written Opinion issued for International application No. PCT/US2015/032744, dated Oct. 2, 2015, 12 pages.
International Search Report and Written Opinion issued for International application No. PCT/US2015/032745, dated Oct. 8, 2015, 13 pages.
International Search Report dated Jan. 13, 2012, from corresponding International Patent Application No. PCT/US2011/035982, 17 pages.
International Search Report dated Nov. 13, 2014, from corresponding International Patent Application No. PCT/US2014/054617, 10 pages.
International Search Report issued for International application No. PCT/US2015/049014, dated Dec. 14, 2015, 3 pages.
International Search Report and Written Opinion in International Application No. PCT/US16/15858, dated Jun. 27, 2016, in 8 pages.
International Search Report issued for International application No. PCT/US15/22977, dated Jun. 22, 2015, 3 pages.
International Search Report issued for International application No. PCT/US15/40199, dated Mar. 2, 2016, 6 pages.
International Search Report issued for International application No. PCT/US2009/050754, dated Feb. 24, 2010, 10 pages.
International Search Report and Written Opinion in International Application No. PCT/US2017/021454, dated Jul. 31, 2017, 8 pages.
Isshiki et al., Cloning, Expression, and Characterization of a Novel UDP-galactose:b-N-Acetylglucosamine b1,3-Galactosyltransferase (b3Gal-T5) Responsible for Synthesis of Type 1 Chain in Colorectal and Pancreatic Epithelia and Tumor Cells Derived Therefrom, The Journal of Biological Chemistry, Apr. 30, 1999, vol. 274, No. 18, pp. 12499-12507.
Ito, Akihiro et al., A Novel Ganglioside Isolated From Renal Cell Carcinoma, Biol Chem 2001, 276, 16695.
Jackson et al., "In vitro antibody maturation: Improvement of a high affinity, neutralizing antibody against IL-1β," J. Immunol., Apr. 1, 1995, 154(7):3310-3319.
Jacobs et al., "Metabolic labeling of glycoproteins with chemical tags through unnatural sialic acid biosynthesis," Methods Enzymol., 2000, 327:260-275.
Jakobovits et al., "Analysis of homozygous mutant chimeric mice: deletion of the immunoglobulin heavy-chain joining region blocks B-cell development and antibody production," Proc. Natl. Acad. Sci. U.S.A., Mar. 15, 1993, 90(6):2551-2555.
Jakobovits et al., "Germ-line transmission and expression of a human-derived yeast artificial chromosome," Nature, Mar. 18, 1993, 362(6417):255-258.
Japanese Office Action dated Apr. 21, 2015, from Related Japanese Patent Application No. 2013-510261, 6 Pages.

(56) References Cited

OTHER PUBLICATIONS

Jayasena, Sumedha, Aptamers: An Emerging Class of Molecules That Rival Antibodies in Diagnostics, Clin. Chem. (1999), 45, 1628-1650.

Jenkins N, Curling EM., "Glycosylation of recombinant proteins: problems and prospects", *Enzyme Microb Technol.* May 1994;16(5):354-64.

Jewett, J.C.; Bertozzi, C.R., Cu-Free Click Cycloaddition Reactions in Chemical Biology, Chem. Soc. Rev. 2010, 39, 1272-1279.

Jewett, J.C.; Sletten, E. M.; Bertozzi, C.R., Rapid Cu-Free Click Chemistry with Readily Synthesized Biarylazacyclooctynones, J. Am. Chem. Soc. 2010, 132, 3688-3690.

Jewett et al., "Synthesis of a fluorogenic cyclooctyne activate by Cu-free click chemistry," *Org. Lett.*, Nov. 18, 2011, 13(22):5937-5939.

Jin, R. C. et al., Photoinduced Conversion of Silver Nanospheres to Nanoprisms, Science (2001), 294, 1901-1903.

Jobling, Michael et al., Fusion Proteins Containing the A2 Domain of Cholera Toxin Assemble With B Polypeptides of Cholera Toxin to Form Immunoreactive and Functional Holotoxin-Like Chimeras, Infect Immun., 60: 4915-24, 1992.

John, F. & Hendrickson, T. L. Synthesis of Truncated Analogues for Studying the Process of Glycosyl Phosphatidylinositol Modification. Org. Lett. 12, 2080-2083, (2010).

Jones et al., "Rapid PCR-cloning of full-length mouse immunoglobulin variable regions," *Nature Biotechnol.*, Jan. 1991, 9(1):88-89.

Jones et al., "Replacing the complementarity-determining regions in a human antibody with those from a mouse," *Nature*, May 29-Jun. 4, 1986, 321(6069):522-525.

Jones, "Analysis of polypeptides and proteins," *Adv. Drug Delivery Rev.*, Jan.-Apr. 1993, 10(1):29-90.

Jonges, M. et al., Dynamics of Antiviral-Resistant Influenza Viruses in the Netherlands, 2005-2008, Antiviral Res., Sep. 2009, 83(3): 290-297.

Jorgensen, Trond et al., Up-Regulation of the Oligosaccharide Sialyl Lewisx: A New Prognostic Parameter in Metastatic Prostate Cancer, Cancer Res. 55, 1817-1819, 1995.

Jose, Jiney et al., Energy transfer dyads based on Nile Red, Tetrahedron Letters (2009), 50(47), 6442-6445.

Joshi, Shantaran et al., Cell Surface Properties Associated with Malignancy of Metastatic Large Cell Lymphoma Cells, (1987) Cancer Res. 47, 3551-3557.

Joyce, J. G. et al. An oligosaccharide-based HIV-I 2G12 mimotope vaccine induces carbohydrate-specific antibodies that fail to neutralize HIV-I virions. Proc. Natl. Acad. Sci. U. S. A 105, 15684-15689, (2008).

Kakeji, Y. et al., Correlation Between Sialyl Tn Antigen and Lymphatic Metastasis in Patients with Borrmann Type IV Gastric Carcinoma, Brit. J. Cancer 71, 191-195, 1995.

Kale et al., Detection of intact influenza viruses using biotinylated biantennary S-sialosides. J Am Chem Soc. Jul. 2, 2008;130(26):8169-71.

Kalesh et al., "Peptide-based activity-based probes (ABPs) for target-specific profiling of protein tyrosine phosphatases (PTPs)," *Chem. Commun.*, Jan. 28, 2010, 46(4):589-591.

Kamkaew, A. et al., "BODIPY dyes in photodynamic therapy." Chem. Soc. Rev. 2013, 42, 77-88.

Kam et al., "Carbon nanotubes as multifunctional biological transporters and near-infrared agents for selective cancer cell destruction," *Proc. Natl. Acad. Sci. U.S.A.*, Aug. 16, 2005, 102(33):11600-11605.

Kaneko et al., "Anti-inflammatory activity of immunoglobulin G resulting from Fc sialylation," *Science*, Aug. 4, 2006, 313(5787):670-673.

Kawakami et al., "Critical role of Vα14+ natural killer T cells in the innate phase of host protection against *Streptococcus pneumoniae* infection," *Eur. J. Immunol.*, Dec. 2003, 33(12):3322-3330.

Kawano et al., "CD1d-restricted and TCR-mediated activation of $v_\alpha$ 14 NKT cells by glycosylceramides," *Science*, Nov. 28, 1997, 278(5343):1626-1629.

Kanie, Osmau et al., Orthogonal glycosylation strategy in synthesis of extended blood group B determinant. Tetrahedron Lett. 37, 4551-4554 (1996).

Kannagi et al., "New globoseries glycosphingolipids in human teratocarcinoma reactive with the monoclonal antibody directed to a developmentally regulated antigen, stage-specific embryonic antigen 3," *J. Biol. Chem.*, Jul. 25, 1983, 258(14):8934-8942.

Kannagi et al., "Stage-specific embryonic antigens (SSEA-3 and -4) are epitopes of a unique globo-series ganglioside isolated from human teratocarcinoma cells, "*EMBO J.*, 1983, 2(12):2355-2361.

Kannappan, Ramaswamy et al., "Photoaffinity labeling of sialidase with a biotin-conjugated phenylaminodizairine derivative of 2,3-didehydro-2-deoxy-N-acetylneuraminic acid," *Biol. Pharm. Bull.*, Mar. 2008, 31(3):352-356.

Karlin, Samuel et al., Applications and Statistics for Multiple High-Scoring Segments in Molecular Sequences, Proc. Natl. Acad Sci. USA 90:5873-77, 1993.

Karlin S. et al., "Methods for assessing the statistical significance of molecular sequence features by using general scoring schemes", *Proc Nall Acad Sci USA*. Mar. 1990;87(6):2264-8.

Karmakar, M. et al., Current Trends in Research and Application of Microbial Cellulases, Research Journal of Microbiology, (2001) 6(1): 41-53.

Kato et al., "GMab-1, a high-affinity anti-3'-isoLM1/3'6'-isoLD1 IgG monoclonal antibody, raised in lacto-series ganglioside-defective knockout mice," *Biochem. Biophys. Res. Commun.*, Jan. 1, 2010, 391(1):750-755.

Kermani, Pouneh et al., Production of ScFv Antibody Fragments Following Immunization with a Phage-Displayed Fusion Protein and Analysis of Reactivity to Surface-Exposed Epitopes of the Protein F of Pseudomonas Aeruginosa by Cytofluorometry, Hybridoma, 14(4):323-328 (1995).

Kidd et al., "Profiling serine hydrolase activities in complex proteomes," *Biochemistry*, Apr. 3, 2001, 40(13):4005-4015.

Kiick, K.L. et al., Identification of an Expanded Set of Translationally Active Methionine Analogues in *Escherichia coli*, tetrahedron 56:9487, 2001.

Kim et al., "Localization of the site of the murine IgG1 molecule that is involved in binding to the murine intestinal Fc receptor," *Eur. J. Immunol.*, 1994, 24:2429-2434.

Kim et al., High-Throughput Screening of Glycan-Binding Proteins Using Miniature Pig Kidney N-Glycan-Immobilized Beads, Chemistry & biology 15.3, p. 215-223 (2008).

Kim, Gap-Sue et al., AB Initio Study of Excited Electronic States and Vibronic Spectra of Phenyl Radical, Chem Phys. Lett., 2002, 3 5 2, 421.

Kimura et al., Design and Synthesis of Immobilized Tamiflu Analog on Resin for Affinity Chromatography, Tetrahedron Lett., Jul. 1, 2009, 50(26):3205-3208.

King, M. et al., New Tetramethlthiepinium (TMTI) for Copper-Free Click Chemistry, Chem. Commun. 2012, 48, 9308-9309.

Kitamura et al., "α-galactosylceramide induces early B-cell activation through IL-4 production by NKT cells," *Cell. Immunol.*, Jan. 10, 2000, 199(1):37-42.

Klein, J. et al., "Isomaltines and their N-acyl derivatives, their preparation, and use of some acyl derivatives as surfactants or for preparation of hydrophilic polymers," CAPLUS 110:95711 (1989).

Köhler et al., "Continuous cultures of fused cells secreting antibody of predefined specificity," *Nature*, Aug. 7, 1975, 256(5517):495-497.

Kolb et al., "Click chemistry: diverse chemical function from a few good reactions," *Angew. Chem. Int. Ed. Engl.*, Jun. 1, 2001, 40(11):2004-2021.

Kolb et al., "The growing impact of click chemistry on drug discovery," *Drug Discov. Today*, Dec. 15, 2003, 8(24):1128-1137.

Komba S, et al. Synthesis and Bioloical Activities of Three Sulfated Sialyl Lex Ganglioside Analogues for Clarifying the Real Carbohydrate Ligand Structure of L-Selectin, Bioorg. Med. Chem. 1996, 4, 1833-1847.

(56) References Cited

OTHER PUBLICATIONS

Komori, Tatsuya et al., Study on Systematizing the Synthesis of the A-Series Ganglioside Glycans GT1a, GD1a, and GM1 Using the Newly Developed N-Troc-Protected GM3 and GaIN Intermediates, Carbohydr. Res. 2009, 344, 1453.
Kong, L. et al. Expression-system-dependent modulation of HIV-I envelope glycoprotein antigenicity and immunogenicity. J. Mol. Biol. 403, 131-147, (2010).
Kontermann, "Intrabodies as therapeutic agents," *Methods*, Oct. 2004, 34(2): 163-170.
Kos, "Regulation of adaptive immunity by natural killer cells," *Immunol. Res.*, 1998, 17(3):303-312.
Koshihara et al., 1984, Biochmica et biophysica acta, 792(1), pp. 92-97.
Kostelny et al., "Formation of a bispecific antibody by the use of leucine zippers," *J. Immunol.*, Mar. 1, 1992, 148(5):1547-1553.
Kotteas et al., Immunotherapy for pancreatic cancer, J cancer Res Clin Oncol, 142(8): 1795-1805, 2016.
Kozbor, "A human hybrid myeloma for production of human monoclonal antibodies," *J. Immunol.*, Dec. 1984, 133(6):3001-3005.
Kriegler M et al., "A novel form of NF/cachectin is a cell surface cytotoxic transmembrane protein: ramifications for the complex physiology of TNF" *Cell.* Apr. 8, 1998;53(1):45-53.
Krise, Jeffrey et al., Prodrugs of Phosphates, Phosphonates, and Phosphinates, Adv. Drug Deliv. Rev. 1996, 19(2), 287-310.
Kruis et al., Low dose balsalazide (1.5 g twice daily) and mesalazine (0.5 g three times daily) maintained remission of ulcerative colitis but high dose alsalazide (3.0 g twice daily) was superior in preventing relapses. Gut. Dec. 2001;49(6):783-9.
Kubin, R. F. et al., Fluorescence Quantum Yields of Some Rhodamine Dyes, Luminescence 1982, 27, 455-462.
Kubler-Kielb, J. et al., A New Method for Conjugation of Carbohydrates to Proteins Using an Aminooxy-Thiol Heterbifunctional Linker, J Org Chem 2005, 70, 6987-6990.
Kudo et al., "Up-regulation of a set of glycosyltransferase genes in human colorectal cancer," *Lab. Invest.*, Jul. 1998, 78(7):797-811.
Kwong, Peter et al., Rational Design of Vaccines to Elicit Broadly Neutralizing Antibodies to HIV-I. Cold Spring Harb.Perspect. Med. 1, 2011, 1-16.
Lantz et al., "An invariant T cell receptor α chain is used by a unique subset of major histocompatibility complex class I-specific CD4$^+$ and CD4$^-$8$^-$T cells in mice and humans," *J. Exp. Med.*, Sep. 1, 1994, 180(3):1097-1106.
Lau et al., "N-Glycans in cancer progression," *Glycobiology*, Oct. 2008, 18(10):750-760.
Lau, K. et al. Highly efficient chemoenzymatic synthesis of β1-4-linked galactosides with promiscuous bacterial β1-4-galactosyltransferases. Chem. Commun. 46, 6066-6068, (2010).
Le, Mai et al., Avian flu: Isolation of Drug-Resistant H5N1 Virus, Nature, Oct. 20, 2005, 437(7062):1108.
Lebens et al., Mucosal vaccines based on the use of cholera toxin B as immunogen and antigen carrier, *Dev. Biol. Stand.*, 1994, 82:215-227.
Le Droumaguet, C. et al., Fluorogenic Click Reaction., Chem. Soc. Rev. 2010, 39, 1233-1239.
Lederman et al., A single amino acid substitution in a common African allele of the CD4 molecule ablates binding of the monoclonal antibody, OKT4, Molecular Immunology, 28, 1171-1181 (1991).
Lee et al., Analogs of Cell Surface Carbohydrates. Synthesis of D-Galactose Derivatives Having an Ethynyl, Vinyl or Epoxy Residue at c-5. Carbohydrate Research 1988, vol. 176, pp. 59-72.
Lee et al., "Bivalent antibody phage display mimics natural immunoglobulin," *J. Immunol. Methods*, Jan. 2004, 284(1-2):119-132.
Lee et al., "High-affinity human antibodies from phage-displayed synthetic Fab libraries with a single framework scaffold," *J. Mol. Biol.*, Jul. 23, 2004, 340(5):1073-1093.
Lee et al., A new Solvent System for Efficient Synthesis of 1,2,3-Triazoles, Tetrahedron Lett., Jul. 17, 2006, 47(29):5105-5109.
Lee et al., An Efficient and Practical Method for the Synthesis of Mono-N-Protected α,ω-diaminoalkanes, Tetrahedron Lett., Apr. 2, 2001, 42(14):2709-2711.
Lee, H.K. et al. Reactivity-based one-pot synthesis of oligomannoses: defining antigens recognized by 2G12, a broadly neutralizing anti-HIV-I antibody. Angew. Chem. Int. Ed. 43, 1000-1003, (2004).
Lee et al., Immunogenicity Study of Globo H Analogues with Modification at the Reducing or Nonreducing end of the tumor antigen, J Am Chem Soc, 136: 16844-16853 (2014).
LeFranc et al., "IMGT, the international ImMunoGeneTics database," *Nucleic Acids Res.*, Jan. 1, 1999, 27(1):209-212.
Lehninger, *Biochemistry: The Molecular Basis of Cell Structure and Function*, 2$^{nd}$ ed., 1975, pp. 73-75, Worth Publishers, New York.
Lemieux, R. U. et al., Halide ion catalyzed glycosidation reactions. Syntheses of a-linked disaccharides. J Am. Chem. Soc. 97(14), 4056-62, (1975).
Leung et al., "A method for random mutagenesis of a defined DNA segment using a modified polymerase chain reaction," *Technique—A Journal of Methods in Cell and Molecular Biology*, Aug. 1989, 1(1):11-15.
Lew et al., Discovery and Development of GS 4104 (oseltamivir): an Orally Active Influenza Neuraminidase Inhibitor, Gun Med Chem, Jun. 2000, 7(6):663-672.
Li et al., β-endorphin omission analogs: Dissociation of Immunoreactivity from other biological activities, Proc Natl Avad Sci USA, 77:3211-3214 (1980).
Li, Y. L. et al., Crystallization and Melting Behaviors of PPC-BS/PVA Blends, 19, 1557-1566, 2003.
Li, Henghui et al., MALDI-MS Analysis of Sialylated N-Glycan Linkage Isomers Using Solid-Phase Two Step Derivatization Method, Analytica Chimica Acta 924 (2016) 77-85.
Li et al., "Design of a potent CD1d-binding NKT cell ligand as a vaccine adjuvant," *Proc. Natl. Acad. Sci. USA*, Jul. 20, 2010, 107:13010-13015.
Li, J.; Hu, M.; Yao, S. Q. "Rapid synthesis, screening, and identification ofxanthone and xanthene-based fluorophores using click chemistry." Org. Lett. 2009, 11, 3008-3011.
Li, Lingling, et al., "Syntheses and spectral properties of functionalized, water-soluble BODIPY derivatives." J. Org. Chem. 2008, 73, 1963-1970.
Li, L. et al. Efficient chemoenzymatic synthesis of an N-glycan isomer library. Chem. Sci. 6, 5652-5661 (2015).
Liang et al., "Quantitative microarray analysis of intact glycolipid-CD1d interaction and correlation with cell-based cytokine production," *J. Am. Chem. Soc.*, Sep. 17, 2008, 130(37):12348-12354.
Liang, P. H., Wang, S. K. & Wong, C. -H. Quantitative analysis of carbohydrate-protein interactions using glycan microarrays: Determination of surface and solution dissociation constants. J. Am. Chem. Soc. 129, 11177-11184, (2007).
Liang, Chi-Hui et al., Iron Oxide/Gold Core/Shell Nanoparticles for Ultrasensitive Detection of Carbohydrate-Protein Interactions, Anal. Chem. 2009; 81, 7750-7756.
Liang, P.H. et al., Quantitative Analysis of Carbohydrate-Protein Interactions Using Glycan Microarrays: Determination of Surface and Solution Dissociation Constants, J. Amer. Chem. Sci. 2007, 129, 11177-11184.
Lin et al., A common glycan structure on immunoglobulin G for enhancement of effector functions, PNAS, Aug. 25, 2015, vol. 112, No. 34, p. 10611-10616.
Lindmark et al., "Binding of immunoglobulins to protein A and immunoglobulin levels in mammalian sera," *J. Immunol. Meth.*, Aug. 12, 1983, 62(1):1-13.
Liu C, et al., "Expansion of spleen myeloid suppressor cells represses NK cell cytotoxicity in tumor-bearing host" *Blood.* May 15, 2007;109(10):4336-42. Epub Jan. 23, 2007.
Liu et al., "Activity-based protein profiling: the serine hydrolases," *Proc. Natl. Acad. Sci. USA*, Dec. 21, 1999, 96(26):14694-14699.
Liu et al., "Eradication of large colon tumor xenografts by targeted delivery of maytansinoids," *Proc. Natl., Acad. Sci. U.S.A.*, Aug. 6, 1996, 93(16):8618-8623.
Liu et al., Enhanced anti-influenza agents conjugated with anti-inflammatory activity. J Med Chem. Oct. 11, 2012;55(19):8493-501.

(56) References Cited

OTHER PUBLICATIONS

Liu et al., Intramolecular ion-pair prodrugs of znamivir nad guanidino-oseltamivir. Bioorganic & Medicinal Chemistry. Jun. 2011; 19(16):4796-4802.

Liu et al., Synthesis and anti-influenza activities of carboxyl alkoxyalkyl esters of 4-guanidino-Neu5Ac2en (zanamivir). Bioorg Med Chem Lett. Sep. 1, 2007;17(17):4851-4. Epub Jun. 20, 2007.

LoBuglio et al., "Mouse/human chimeric monoclonal antibody in man: kinetics and immune response," *Proc. Natl. Acad. Sci. U.S.A.*, Jun. 1989, 86(11):4220-4224.

Lode et al., "Targeted therapy with a novel enediyene antibiotic calicheamicin $\Theta^I{}_1$ effectively suppresses growth and dissemination of liver metastases in a syngeneic model of murine neuroblastoma," *Cancer Res.*, Jul. 15, 1998, 58(14):2925-2928.

Lonberg et al., "Antigen-specific human antibodies from mice comprising four distinct genetic modifications," *Nature*, Apr. 28, 1994, 368(6474):856-859.

Lonberg et al., "Human antibodies from transgenic mice," *Int. Rev. Immunol.*, 1995, 13(1):65-93.

Lopes, J.F. et al., Simulataneous Chromatographic Separation of Enantiomers, Anomers and Structural Isomers of Some Biologically Relevant Monsaccharides. J. Chomatogr. A, (2008) 1188:34-42.

Lou, et al., Stage-specific embryonic antigent-4 as a potential therapeutic target in glioblastoma multiforms and other cancers. Proc Natl Acad Sci USA 2014, 111(7):2482-7.

Loudet, A.; Burgess, K. "BODIPY dyes and their derivatives: syntheses and spectroscopic properties." Chem. Rev. 2007, 107, 4891-4932.

Louis et al., "The 2007 WHO classification of tumours of the central nervous system," *Acta. Neuropathol.*, Aug. 2007, 114(2):97-109.

Lu et al., "Design of a mechanism-based probe for neuraminidase to capture influenza viruses," *Angew. Chem. Int. Ed. Engl.*, Oct. 28, 2005, 44(42):6888-6892.

Lu, Guokai et al., Reactivity-Based One-Pot Synthesis of Immunosuppressive Glycolipids From the Caribbean Sponge Plakortis Simplex, J. Chem. 2009, 27, 2217-2222.

Lu et al., "Single chain anti-c-Met antibody conjugated nanoparticles for in vivo tumor-targeted imaging and drug delivery," *Biomaterials*, Apr. 2011, 32(12):3265-3274.

MacBeath, G. And Schreiber, S. L., Printing Proteins as Microarrays for High-Throughput Function Determination, Science, 289, 1760-1763, 2000.

MacFarlane GT, et al., "Formation of glycoprotein degrading enzymes by Bacteroides fragilis" *FEMS Microbiol Lett.* Jan. 15, 1991;61(2-3):289-93.

Makino et al., Predominant expression of invariant $V_\alpha 14^{30}$ TCR α chain in NK1.1$^+$ T cell populations, *Int. Immunol.*, Jul. 1995, 7(7):1157-1161.

Mandler et al., "Immunoconjugates of geldanamycin and anti-HER2 monoclonal antibodies: antiproliferative activity on human breast carcinoma cell lines," *J. Nat. Cancer Inst.*, Oct. 4, 2000, 92(19):1573-1581.

Mandler et al., "Modifications in synthesis strategy improve the yield and efficacy of geldanamycin-herceptin immunoconjugates," *Bioconjugate Chem.*, Jul.-Aug. 2002, 13(4):786-791.

Mandler et al., "Synthesis and evaluation of antiproliferative activity of a geldanamycin-Herceptin™ immunoconjugate," *Bioorganic & Med. Chem. Letters*, May 15, 2000, 10(10):1025-1028.

Mandal, M., Dudkin, V. Y., Geng, X. & Danishefsky, S. J. In pursuit of carbohydrate-based HIV vaccines, part I: The total synthesis of hybrid-type gp 120 fragments. Angew. Chem. Int. Ed. 43, 2557-2561, (2004).

Månsson et al., "Characterization of new gangliosides of the lactotetraose series in murine xenografts of a human glioma cell line," *FEBS Lett.*, May 26, 1986, 201(1):109-113.

Marasco et al., "Design, intracellular expression, and activity of a human anti-human immunodeficiency virus type 1 gp120 single-chain antibody," *Proc. Natl. Acad. Sci. U.S.A.*, Aug. 15, 1993, 90(16):7889-7893.

Marasco, "Intrabodies: turning the humoral immune system outside in for intracellular immunization," *Gene Therapy*, Jan. 1997, 4(1):11-15.

Marcato et al., "Chapter 17: The Rocky Road from Cancer Stem Cell Discovery to Diagnostic Applicability," Cancer Stem Cells Theories and Practice, pp. 335-360, Mar. 22, 2011.

Marks et al., "By-passing immunization. Human antibodies from V-gene libraries displayed on phage," *J. Mol. Biol.*, Dec. 5, 1991, 222(3):581-597.

Marks et al., "By-passing immunization: Building high affinity human antibodies by chain shuffling," *Nature Biotechnology*, Jul. 1992, 10(7):779-783.

Massart, R., IEEE Transactions on Magnetics, 17, 1247 (1981).

Masuko, T. et al., Thiolation of Chitosan. Attachment of Proteins Via Thioether Formation, Biomacromolecules 2005, 6, 880-884.

Mather et al., "Culture of testicular cells in hormone-supplemented serum-free medium," *Annals N.Y. Acad. Sci.*, 1982, 383:44-68.

Mather, "Establishment and characterization of two distinct mouse testicular epithelial cell lines," *Biol. Reprod.*, Aug. 1980, 23(1):243-252.

Matrosovich M, et al., The Surface Glycoproteins of H5 Influenza Viruses Isolated From Humans, Chickens, and Wild Aquatic Birds Have Distinguishable Properties, J. Virol. 1999, 73, 1146-1155.

Matsuda et al., "Structure and physical map of 64 variable segments in the 3' 0.8-megabase region of the human immunoglobulin heavy-chain locus," *Nature Genet.*, Jan. 1993, 3(1):88-94.

Matz et al., "Fluorescent proteins from nonbioluminescent Anthozoa species," *Nat. Biotechnol.*, Oct. 1999, 17(10):969-973.

McCafferty et al., "Phage antibodies: Filamentous phage displaying antibody variable domains," *Nature*, Dec. 6, 1990, 348:552-554.

McKimm-Breschkin et al., "Tethered neuraminidase inhibitors that bind an influenza virus: a first step towards a diagnostic method for influenza," Angew. Chem. Int. Ed Engl., Jul. 14, 2003, 42(27):3118-3121.

McKimm-Breschkin, "Resistance of influenza viruses to neuraminidase inhibitors—a review," Antiviral Res., Jul. 2000, 47(1): 1-17.

McKimm-Breschkin, J. et al., "Neuraminidase Sequence Analysis and Susceptibilities of Influenza Virus Clinical Isolates to Zanamivir and Oseltamivir," Antimicrobial Agents and Chemotherapy, vol. 47, No. 7, Jul. 2003, in 10 pages.

Meezan et al., "Comparative studies on the carbohydrate-containing membrane components of normal and virus-transformed mouse fibroblasts: II: Separation of glycoproteins and glycopeptides by Sephadex chromatography," *Biochemistry*, Jun. 1969, 8(6):2518-2524.

Medelson et al., NKp46 O-glycan Sequences that are involved in the interaction with Hemagglutinin Type 1 of Influenza Virus. J. Virol. Feb. 10, 2010, 84(8):3789-3797.
McLellan, J. S. et al. Structure of HIV-I gp120 V1/V2 domain with broadly neutralizing antibody PG9. Nature 480, 336-343, 2011.
Meyer, "Malignant gliomas in adults," *N. Engl. J. Med.*, Oct. 23, 2008, 359(17):1850.
Milstein, C & Cuello, AC, Hybrid Hydridomas and their use in immunohistochemistry, Nature 305, 537-540, Oct. 1993.
Mimura et al., "Role of oligosaccharide residues of IgG1-Fc in FcγRIIb binding," *J. Biol. Chem.*, Dec. 7, 2001, 276(49):45539-45547.
Mishima et al., "Growth suppression of intracranial xenografted glioblastomas overexpressing mutant epidermal growth factor receptors by systemic administration of monoclonal antibody (mAb) 806, a novel monoclonal antibody directed to the receptor," *Cancer Res.*, Jul. 15, 2001, 61(14):5349-5354.
Miyagi et al., "Mammalian sialidases: Physiological and pathological roles in cellular functions," *Glycobiology*, Jul. 2012, 22(7):880-896.
Miyagi et al., "Plasma membrane-associated sialidase as a crucial regulator of transmembrane signalling," *J. Biochem.*, Sep. 2008, 144(3):279-285.
Miyagi et al., "Sialidase and malignancy: a minireview," *Glycoconj. J.*, 2004, 20(3):189-198.
Miyagi, "Aberrant expression of sialidase and cancer progression," *Proc. Jpn. Acad. Ser. B. Phys. Biol. Sci.*, 2008(10), 84:407-418.

(56) References Cited

OTHER PUBLICATIONS

Miyaji, E. N. et al., Induction of Neutralizing Antibodies Against Diphtheria Toxin by Priming with Recombinant Mycobacterium Bovis BCG Expressing CRM197, a Mutant Diphtheria Toxin, Infect. Immun. 2001, 69, 869.
Miyamoto et al., "A synthetic glycolipid prevents autoimmune encephalomyelitis by inducing $T_H2$ bias of natural killer T cells," *Nature*, Oct. 4, 2001, 413(6855):531-534.
Monti et al., "Sialidases in vertebrates: a family of enzymes tailored for several cell functions," *Adv. Carbohydr. Chem. Biochem.*, 2010, 64:403-479.
Moody, M. D. et al., Array-based ELISAs for High-Throughput Analysis of Human Cytokines. Biotechniques (2001), 31, 186-194.
Morelle, W. et al., "The Mass Spectrometric Analysis of Glycoproteins and their Glycan Structures", *Review in Current Analytical Chemistry*, vol. 1, No. 1 (2005), pp. 29-57.
Mori K, et al., "Non-fucosylated therapeutic antibodies: the next generation of therapeutic antibodies" *Cytotechnology*. Dec. 2007;55(2-3):109-14. Epub Oct. 31, 2007.
Morimoto et al., "Single-step purification of F(ab')$_2$ fragments of mouse monoclonal antibodies (immunoglobulins G1) by hydrophobic interaction high performance liquid chromatography using TSKgel Phenyl-5PW," *J. Biochem. Biophys. Meth.*, Mar. 1992, 24(1-2):107-117.
Morphy et al., Designed multiple ligands. An emerging drug discovery paradigm. J Med Chem. Oct. 20, 2005;48(21):6523-43.
Morphy et al., From magic bullets to designed multiple ligands. Drug Discov Today. Aug. 1, 2004;9(15):641-51.
Morrison et al., "Chimeric human antibody molecules: mouse antigen-binding domains with human constant region domains," *Proc. Natl. Acad. Sci. U.S.A.*, Nov. 1984, 81(21):6851-6855.
Morrison, "Immunology. Success in specification," *Nature*, Apr. 28, 1994, 368(6474):812-813.
Moscona, "Global transmission of oseltamivir-resistant influenza," N Engl. J Med, Mar. 5, 2009, 360(10):953-956.
Moscona, Oseltamivir Resistance—Disabling Our Influenza Defenses, The New England Journal of Medicine, 2005, vol. 353, pp. 2633-2636.
Mosmann et al., "The expanding universe of T-cell subsets: Th1, Th2 and more," *Immunol. Today*, Mar. 1996, 17(3):138-146.
Mossong et al., "Emergence of oseltamivir-resistant influenza A H1N1 virus during the 2007-2008 winter season in Luxembourg: clinical characteristics and epidemiology," Antiviral Res., Oct. 2009, 84(1):91-94.
Mouquet, H. et al. Complex-type N-glycan recognition by potent broadly neutralizing HIV antibodies. Proc. Natl. Acad. Sci. U. S. A 109, E3268-E3277, (2012).
Munson et al., "Ligand: a versatile computerized approach for characterization of ligand-binding systems," *Anal. Biochem.*, Sep. 1, 1980, 107(1):220-239.
Murphy, C. I. et al. Enhanced expression, secretion, and large-scale purification of recombinant HIV-I gp 120 in insect cell using the baculovirus egt and p67 signal peptides. Protein Expres. Purif. 4, 349-357 (1993).
Muthana, S., Yu, H., Huang, S., and Chen, X. Chemoenzymatic synthesis of size-defined polysaccharides by sialyltransferase-catalyzed block transfer of oligosaccharides. J. Am. Chem. Soc. 129, 11918-11919, (2007).
Natarajan et al, Caffeic acid phenethyl ester is a potent and specific inhibitor of activation of nuclear transcription factor NF-kappa B. Proc Nat! Acad Sci USA Aug. 20, 1996;93(17):9090-5.
Neuberger et al., "Recombinant antibodies possessing novel effector functions," *Nature*, Dec. 13-19, 1984, 312(5995):604-608.
Neuberger, "Generating high-avidity human Mabs in mice," *Nature Biotechnol.*, Jul. 1996, 14(7):826.
Ni, Jing et al., Immunoassay Readout Method Using Extrinsic Raman Labels Adsorbed on Immunogold Colloids, Anal. Chem., 1999, 71(21), pp. 4903-4908.
Nicolaou et al., "Calicheamicin $\Theta^I_1$," *Angew. Chem. Intl. Ed. Engl.*, Feb. 1, 1994, 33(2):183-186.
Niculescu-Duvaz et al., "Antibody-directed enzyme prodrug therapy (ADEPT): A review," *Adv. Drg. Del. Rev.*, Jul. 7, 1997, 26(2-3):151-172.
Nieuwenhuis et al., "CD1d-dependent macrophage-mediated clearance of *Pseudomonas aeruginosa* from lung," *Nat. Med.*, Jun. 2002, 8(6):588-593.
Nielsen, U. B. et al., Multiplexed Sandwich Assays in Microarray Format, Journal Immunol. Meth. (2004), 290, 107-120.
Ning, X. et al., Visualizing Metabolically-Labeled Glycoconjugates of Living Cells by Copper-Free and Fast Huisgen Cycloadditions, J. Angew. Chem. Int. Ed. 2008, 47, 2253-2255.
Noto et al., "CD44 and SSEA-4 positive cells in an oral cancer cell line HSC-4 possess cancer stem-like cell characteristics," *Oral Oncol.*, Aug. 2013, 49(8):787-795.
Nowak, MW et al., Nicotinic Receptor Binding Site Probed With Unnatural Amino Acid Incorporation in Intact Cells, Science 268:439, 1995.
Novotný et al., "Structural invariants of antigen binding: comparison of immunoglobulin $V_L$—$V_H$ and $V_L$—$V_L$ domain dimers," *Proc. Natl. Acad. Sci. USA*, Jul. 1985, 82(14):4592-4596.
Office Action dated Dec. 3, 2013, from corresponding Chinese Patent Application No. 201180034218.3, 15 total pages.
Office Action dated Oct. 22, 2014, from corresponding Chinese Patent Application No. 201180034218.3, 16 total pages.
O'Garra, "Cytokines induce the development of functionally heterogeneous T helper cell subsets," *Immunity*, Mar. 1998, 8(3):275-283.
Okada, Yoshio et al. Changes in the Expression of Sialyl-Lewisx, a Hepatic Necroinflammation-Associated Carbohydrate Neoantigen, in Human Depatocellular Carcinomas, (1994) Cancer 73, 1811-1816.
Okamura et al., "Interleukin-18: a novel cytokine that augments both innate and acquired immunity," *Adv. Immunol.*, 1998, 70:281-312.
Olden, Kenneth et al., Carbohydrate Moieties of Glycoproteins: A Re-Evaluation of Their Function, Biochem et Biophys Acta 650:209-232 (1982).
Orlandi et al., "Cloning immunoglobulin variable domains for expression by the polymerase chain reaction," *Proc. Natl. Acad. Sci. U.S.A.*, May 1989, 86(10):3833-3837.
Ørum et al., "Efficient method for constructing comprehensive murine Fab antibody libraries displayed on phage." *Nucleic Acids Res.*, Sep. 25, 1993, 21(19):4491-4498.
Otsubo N, et al., An Efficient and Straightforward Synthesis of Sialyl Lex Glycolipid as a Potent Selectin Blocker[[1]], Carbohydr. Res. 1998, 306, 517-530.
Ottolini et al., Combination anti-inflammatory and antiviral therapy of influenza in a cotton rat model. Pediatr. Pulmonol. 2003:36;290-4.
Oyelaran, 0. & Gildersleeve, J. C. Glycan arrays: recent advances and future challenges. Curr. Opin. Chem. Biol. 13, 406-413, (2009).
Pabst, M. et al., Glycan profiles of the 27 Nglycosylation sites of the HIV envelope protein CN54gp140. Biol. Chem. 393, 719-730, (2012).
Pacino, G. et al., Purification and Characterization of a Breast-Cancer-Associated Glycoprotein Not Expressed in Normal Breast and Identified by Monoclonal Antibody 83D4, Br. J. Cancer, 1991, 63, 390-398.
Pancera, M. et al. Crystal structure of PG16 and chimeric dissection with somatically related PG9: structure-function analysis of two quaternary-specific antibodies that effectively neutralize HIV-I. J. Virol. 84, 8098-8110, (2010).
Pancera, M. et al. Structural basis for diverse N-glycan recognition by HIV-I-neutralizing V1-V2-directed antibody PG16. Nat. Struct. Mol. Biol. 20, 804-813, (2013).
Papanastassiou et al., "The potential for efficacy of the modified (ICP 34.5$^-$) herpes simplex virus HSV1716 following intratumoural injection into human malignant glioma: a proof of principle study," *Gene Therapy*, Mar. 2002, 9(6):398-406.

(56) References Cited

OTHER PUBLICATIONS

Parker, C. A.; Rees, W. T., Correction of Fluorescence Spectra and Measurement of Fluorescence Quantum Efficiency, Analyst 1960, 85, 587-600.
Parrish, M. L. et al., A Microarray Platform Comparison for Neuroscience Applications, J. Neurosci. Methods, 2004, 132, 57-68.
Patricelli et al., "Functional interrogation of the kinome using nucleotide acyl phosphates," *Biochemistry*, Jan. 16, 2007, 46(2):350-358.
Paulson, J. C., Blixt, 0. & Collins, B. E. Sweet spots in functional glycomics. Nat. Chem. Biol. 2, 238-248, (2006).
Pearlman et al., *Peptide and Protein Drug Delivery*, Chapter 6: Analysis of Protein Drugs, Lee, ed., 1991, pp. 247-301, Marcel Dekker Publishing, New York.
Peelle et al., "Characterization and use of green fluorescent proteins from *Renilla mulleri* and *Ptilosancus guennyi* for the human cell display of functional peptides," J. Protein Chem., Aug. 2001, 20(6):507-519.
Peipp et al., "Antibody fucosylation differentially impacts cytotoxicity mediated by NK and PMN effector cells," *Blood*, 2008, 112(6):2390-2399.
Peiris et al., Re-emergence of fatal human influenza A subtype H5N1disease. Lancet. Feb. 21, 2004 ;363(9409):617-9.
Pejchal, R. et al. A potent and broad neutralizing antibody recognizes and penetrates the HIV glycan shield. Science 334, 1097-1103, (2011).
Pellicci et al., "Differential recognition of CD1d-α-galactosyl ceramide by the Vβ8.2 and Vβ7 semi-invariant NKT T-cell receptors," *Immunity*, Jul. 17, 2009, 31(1):47-59.
Perlmutter, R.M. et al., Subclass Restriction of Murine Anti-Carbohydrate Antibodies, Journal of immunology 1978, 121, 566-572.
Pettit, George et al., Antineoplastic Agents. Part 189. The Absolute Configuration and Synthesis of Natural (−)-Dolastatin 10, J Am Chem Soc. 111:5463-5465 (1989).
Pettit, George et al., Dolastatins 23: Stereospecific Synthesis of Dolaisoleuine, J Chem Soc Perkin Trans. 15:853-858 (1996).
Pettit, George et al., Antineoplastic Agents 365. Dolastatin 10 SAR Probes, Anti-Cancer Drug Design 13:243-277 (1998).
Pettit, Robin et al., Specific Activities of Dolastatin 10 and Peptide Derivatives Against Cryptococcus Neoformans, Antimicrob Agents Chemother. 42:2961-2965 (1998).
Pettit, George et al., The Dolastatins; 18: Stereospecific Synthesis of Dolaproine, Synthesis, 719-725 (1996).
Piizi, G. and Hardinger, S., Stereochemistry: an Introduction, UCLA Chemistry 30A Presentation, Fall 2002, in 40 pages.
Plückthun, "Mono- and bivalent antibody fragments produced in *Escherichia coli*: Engineering, folding and antigen binding," *Immunol. Rev.*, Dec. 1992, 130:151-188.
Plückthun, *Handbook of Experimental Pharmacology, vol. 113: The Pharacology of Monoclonal Antibodies*, Chapter 11: Antibodies from *Escherichia coli*, Rosenberg et al., eds., 1994, pp. 269-315, Springer-Verlag, Berlin.
Poloukhtine et al., "Selective labeling of living cells by a photo-triggered click reaction, " *J. Am. Chem. Soc.*, Nov. 4, 2009, 131(43):15769-15776.
Porcelli, S.A., "Preparation of α-galactosylceramide derivatives as modulators of immunity and autoimmunity," CAPLUS 147:440317 (2007).
Potier et al., "Fluorometric assay of neuraminidase with a sodium ( 4-methylumbelliferyl-alpha-D-N-acetylneuraminate) substrate," Anal. Biochem., Apr. 15, 1979, 94(2):287-296.
Pratt, M. R. & Bertozzi, C. R. Chemoselective ligation applied to the synthesis of a biantennary N-linked glycoform of CD52. J Am. Chem. Soc. 125, 6149-6159, (2003).
Prescher, J. A.; Bertozzi, C.R. "Chemistry in living systems." Nat. Chem. Biol. 2005, 1, 13-21.
Presta et al., "Humanization of an antibody directed against IgE," *J. Immunol.*, Sep. 1, 1993, 151(5):2623-2632.
Presta et al., "Humanization of an anti-vascular endothelial growth factor monoclonal antibody for the therapy of solid tumors and other disorders," *Cancer Res.*, Oct. 15, 1997, 57(20):4593-4599.
Presta, "Antibody engineering," *Curr. Opin. Biotechnol.*, Aug. 1992, 3(4):394-398.
Presta, "Antibody engineering," *Curr. Opin. Struct. Biol.*, Aug. 1992, 2(4):593-596.
Pritchard, L. K. et al. Structural Constraints Determine the Glycosylation of HIV-I Envelope Trimers. Cell Rep. 11, 1604-13, (2015).
Pritchard, Laura et al., Cell- and Protein-Directed Glycosylation of Native Cleaved HIV-I Envelope. J. Virol. 89, 8932-44, (2015).
Proba et al., "Functional antibody single-chain fragments from the cytoplasm of *Escherichia coli*: influence of thioredoxin reductase (TrxB)," *Gene*, Jul. 4, 1995, 159(2):203-207.
Pshezhetsky, M. Potier, J. Biol. Chem. 1996, 271, 28359-28365. Association of N-acetylgalactosamine-6-sulfate sulfatase with the multienzyme lysosomal complex of betagalactosidase, cathepsin A, and neuraminidase. Possible implication for intralysosomal catabolism of keratan sulfate.
Puigbò P, Guzmán E, Romeu A, Garcia-Vallvé S. Optimizer: a web server for optimizing the codon usage of DNA sequences. *Nucleic Acids Res*. Jul. 2007;35(Web Server issue):W126-31. Epub Apr. 16, 2007.
Qi, Jianjun et al., Developing visible fluorogenic 'clickon' dyes for cellular imaging, Bioconjugate Chem. 2011, 22, 1758-1762.
Rabbani, Said et al., Glycosyltransferases: An efficient tool for the enzymatic synthesis of oligosaccharides and derivatives as well as mimetics thereof Chimia 60, 23-27, (2006).
Raju et al., "Synthesis and evaluation of 3" - and 4"-deoxy and -fluoro analogs of the immunostimulatory glycolipid, KRN7000," Bioorg. Med. Chem. Lett., 2009, 19:4122-4125.
Ramm et al., "The periplasmic *Escherichia coli* peptidylprolyl cis, trans-isomerase FkpA. II. Isomerase-independent chaperone activity in vitro," *J. Biol. Chem.*, Jun. 2, 2000, 275(22):17106-17113.
Rana, G. Kucukayan-Dogu, E. Bengu "Growth of vertically aligned carbon nanotubes over self-ordered nano-porous alumina films and their surface properties" Applied Surface Science, 2012, 258 7112-7117.
Raska, M. et al. Glycosylation patterns of HIV-I gp120 depend on the type of expressing cells and affect antibody recognition. J. Biol. Chem. 285, 20860-20869, (2010).
Ravetch et al., "Divergent roles for Fc receptors and complement in vivo," *Ann. Rev. Immunol.*, 1998, 16:421-432.
Ravetch et al., "Fc receptors," *Annu. Rev. Immunol.*, 1991, 9:457-492.
Reyes et al., "Expression of human β-interferon cDNA under the control of a thymidine kinase promoter from herpes simplex virus," *Nature*, Jun. 17, 1982, 297(5867):598-601.
Riechmann et al., "Reshaping human antibodies for therapy," *Nature*, Mar. 24, 1988, 332(6162):323-327.
Rillahan, C. D. & Paulson, J. C. Glycan microarrays for decoding the glycome. Annu. Rev. Biochem. 80, 797-823, (2011).
Ritamo, Ilja al., Comparison of the Glycosylation of in Vitro Generated Polyclonal Human IgG and Therapeutic Immunoglins, Mol Immunol. Feb. 2014; 57(2): 255-62.
Rogers, GN et al., Single Amino Acid Substitutions in Influenza Haemagglutinin Change Receptor Binding Specificity. Nature, 304:76, 1983.
Rogers, GN et al., Receptor Determinants of Human and Animal Influenza Virus Isolates: Differences in Receptor Specificity of the H3 Hemagglutinin Based on Species of Origin. Virology, 127:361, 1983.
Roguska et al., "Humanization of murine monoclonal antibodies through variable domain resurfacing," *Proc. Natl. Acad. Sci. U.S.A.*, Feb. 1, 1994, 91(3):969-973.
Romagnani, "Induction of $T_H1$ and $T_H2$ responses: a key role for the 'natural' immune response?" *Immunol. Today*, Oct. 1992, 13(10):379-381.
Roos et al., "Specific inhibition of the classical complement pathway by C1q-binding peptides," *J. Immunol.*, Dec. 15, 2001, 167(12):7052-7059.
Rosenstein, N.E. et al, Meningococcal Disease, n. Engl J Med 2001, 344, 1378-1388.

(56) References Cited

OTHER PUBLICATIONS

Rostovtsev et al., "A stepwise Huisgen cycloaddition process catalyzed by copper(I) regioselective ligation of azides and terminal alkynes," *Angew. Chem. Int. Ed. Engl.*, Jul. 15, 2002, 41(41):2596-2599.
Roth, Jurgen et al., Reexpression of Poly(sialic Acid) Units of the Neural Cell Adhesion Molecule in Wilms Tumor, Proc. Natl. Acad. Sci. 85, 2999-3000, 1988.
Rowland et al, "Drug localisation and growth inhibition studies of vindesine-monoclonal anti-CEA conjugates in a human tumour xenograft," *Cancer Immunol. Immunother.*, 1986, 21(3):183-187.
Rudnick et al., Affinity and Avidity in Antibody-Based Tumor Targeting, Can Biotherp & Radoipharm, 24, 155-162 (2009).
Ruiz et al., "IMGT, the international ImMunoGeneTics database," *Nucl. Acids Res.*, Jan. 1, 2000, 28(1):219-221.
Russell et al., "The structure of H5N1 avian influenza neuraminidase suggests new opportunities for drug design," Nature, Sep. 7, 2006, 443(7107):45-49.
Saito, Seiichi et al., Haptoglobin-β Chain Defined by Monoclonal Antibody RM2 as a Novel Serum Marker for Prostate Cancer, Int. J Cancer, 2008, 123(3), 633-640.
Saito et al., "Expression of globo-series gangliosides in human renal cell carcinoma," *Jpn. J. Cancer Res.*, Jul. 1997, 88(7):652-659.
Saito et al., "Human α2,3-sialyltransferase (ST3Gal II) is a stage-specific embryonic antigen-4 synthase," *J. Biol. Chem.*, Jul. 18, 2003, 278(29):26474-26479.
Saitoh, Osamu et al., Differential Glycosylation and Cell Surface Expression of Lysosomal Membrane Glycoproteins in Sublines of a Human Colon Cancer Exhibiting Distinct Metastatic Potentials*, J. Biol. Chem. 267, 5700-5711, 1992.
Salisbury et al., "Activity-based probes for proteomic profiling of histone deacetylase complexes," *Proc. Natl. Acad. Sci. USA*, Jan. 23, 2007, 104(4):1171-1176.
Salomon et al., Inhibition of the cytokine response does not protect against lethal H5N1 nfluenza infection. Proc Natl Acad Sci U S A Jul. 24, 2007;104(30): 12479-81.
Sanna, Peitro et al., Directed Selection of Recombinant Human Monoclonal Antibodies to Herpes Simplex Virus Glycoproteins From Phage Display Libraries, Proc. Natl. Acad. Sci., 92:6439 (1995).
Sarkar et al., "Disaccharide uptake and priming in animal cells: inhibition of sialyl Lewis X by acetylated Galβ1→4G1cNAcβ-O-naphthalenemethanol," *Proc. Natl. Acad. Sci. USA*, Apr. 11, 1995, 92(8):3323-3327.
Sastry et al., "Cloning of the immunological repertoire in *Escherichia coli* for generation of monoclonal catalytic antibodies: construction of a heavy chain variable region-specific cDNA library," *Proc. Natl. Acari. Sci. U.S.A.*, Aug. 1989, 86(15):5728-5732.
Sauter, NK et al., Binding of Influenza Virus Hemagglutinin to Analogs of Its Cell-Surface Receptor, Sialic Acid: Analysis by Proton Nuclear Magnetic Resonance Spectroscopy and X-Ray Crystallography. Biochemistry, 31 :9609, 1992.
Sawa, M.; Hsu, T.-L.; Itoh,T.; Sugiyama, M. ; Hanson, S. R. ; Vogt, P. K.; Wong, C.-H. "Glycoproteomic probes for fluorescent imaging of fucosylated glycans in vivo." Proc. Nat. Acad. Sci. US.A., 2006, 103, 12371-12376.
Sawada, Tetsuji et al., E-Selectin Binding by Pancreatic Tumor Cells is Inhibited by Cancer Sera, Int. J. Cancer 57, 901-907, 1994.
Sawada, Ritsuko et al., Differential E-Selectin-Dependent Adhesion Efficiency in Sublines of a Human Colon Cancer Exhibiting Distinct Metastatic Potentials, J. Biol. Chem. 269, 1425-1431, 1994.
Scanlan, C. N. et al., Exploiting the defensive sugars of HIV-I for drug and vaccine design. Nature 446, 1038-1045, (2007).
Schena, M. et al., Quantitative Monitoring of Gene Expression Patterns with a Complementary DNA Microarray, Science, 1995, 270:467-70.
Schengrund et al., "Localization of sialidase in the plasma membrane of rat liver cells," *J. Biol. Chem.*, May 10, 1972, 247(9):2742-2746.

Schenkel-Brunner, *Human Blood Groups*, Chapter 8: P System, 1995, pp. 211-234, Springer-Verlag, Vienna.
Schier et al., "Identification of functional and structural amino-acid residues by parsimonious mutagenesis," *Gene*, Mar. 9, 1996, 169(2):147-155.
Schmitz, U. et al., Phage Display: A Molecular Tool for the Generation of Antibodies—A Review, Placenta, 21 Suppl. A:S 106 (2000).
Schneider, M.C. et al., Interactions Between Neisseria Meningitidis and the Complement System, Trends Microbial 2007, 15, 233-240.
Schroder et al., The Peptides, vol. 1, p. 76-136, 1965.
Schug, Kevin et al., "Noncovalent binding between guanidinium and anionic groups: focus on biological- and synthetic-based arginine/guanidinium interactions with phosph[on]ate and sulf[on]ate residues," Chem. Rev., Jan. 2005, 105(1):67-113.
Schweitzer, Barry et al., Multiplexed Protein Profiling on Microarrays by Rolling-Circle Amplification, Nat. Biotechnol. (2002), 20, 359-365.
Scurr, D. J. et al. Surface characterization of carbohydrate microarrays. Langmuir 26, 17143-17155, (2010).
Sell, "Cancer-associated carbohydrates identified by monoclonal antibodies," *Hum. Pathol.*, Oct. 1990, 21(10):1003-1019.
Serna, S. et al., Construction of N-Glycan Microarrays by Using Modular Synthesis and On-Chip Nanoscale Enzymatic Glycosylation. Chem. Eur. J 16, 13163-13175, (2010).
Severi et al., "Sialic acid utilization by bacterial pathogens," *Microbiology*, Sep. 2007, 153(Pt 9):2817-2822.
Seyrantepe et al., "Neu4, a novel human lysosomal lumen sialidase, confers normal phenotype to sialidosis and galactosialidosis cells," *J. Biol. Chem.*, Aug. 27, 2004, 279(35):37021-37029.
Shalaby et al., "Development of humanized bispecific antibodies reactive with cytotoxic lymphocytes and tumor cells overexpressing the HER2 protooncogene," *J. Exp. Med.*, Jan. 1, 1992, 175(1):217-225.
Sheu et al., "Surveillance for neuraminidase inhibitor resistance among human influenza A and B viruses circulating worldwide from 2004 to 2008," *Antimicrob. Agents Chemother.*, Sep. 2008, 52(9):3284-3292.
Shie, Jiun-Jie et al., "A concise and flexible synthesis of the potent anti-influenza agents tamiflu and tamiphosphor," Angew. Chem. Int. Ed Engl., 2008, 47(31):5788-5791.
Shie, Jiun-Jie et al., An Azido-BODIPY Probe for Glycosylation: Initiation of Strong Fluorescence Upon Triazole Formation, J. Am. Chem. Soc. 2014, 136, 9953-9961.
Shieh, Peyton et al., Fluorogenic Azidofluoresceins for Biological Imaging, J. Am. Chem. Soc. 2012, 134, 17428-17431.
Shields et al., "High resolution mapping of the binding site on human IgG1 for FcγRI, Fc65 RII, FcγRIII, and FcRn and design of IgG1 variants with improved binding to the FcγR," *J. Biol. Chem.*, Mar. 2, 2001, 276(9):6591-6604.
Shields et al., "Lack of fucose on human IgG1 N-linked oligosaccharide improves binding to human FcγRIII antibody-dependent cellular toxicity," *J. Biol. Chem.*, Jul. 26, 2002, 277(30):26733-26740.
Shinkawa et al., "The absence of fucose but not the presence of galactose or bisecting N-acetylglucosamine of human IgG1 complex-type oligosaccharides shows the critical role of enhancing antibody-dependent cellular cytotoxicity," *J. Biol. Chem.*, Jan. 31, 2003, 278(5):3466-3473.
Shivatare, S. S. et al. Efficient convergent synthesis of bi-, tri-, and tetra-antennary complex type N-glycans and their HIV-1 antigenicity. J. Am. Chem. Soc. 135, 15382-15391, (2013).
Shivatare, S. S. et al., Modular Synthesis of N-Glycans and Arrays for the Hetero-Ligand Binding Analysis of HIV Antibodies, Nature Chemistry, Mar. 7, 2016, vol. 8(4), p. 338-346.
Shriver, Zachary et al., Glycomics: a Pathway to a Class of New and Improved Therapeutics, Nat Rev Drug Disc, 2004, 3, 863-873.
Sidhu et al., "Phage-displayed antibody libraries of synthetic heavy chain complementarity determining regions," *J. Mol. Biol.*, Apr. 23, 2004, 338(2):299-310.
Siebenlist et al., "*E. coli* RNA polymerase interacts homologously with two different promoters," *Cell*, Jun. 1980, 20(2):269-281.

(56) References Cited

OTHER PUBLICATIONS

Sieber et al., "Proteomic profiling of metalloprotease activities with cocktails of active-site probes," *Nat. Chem. Biol.*, May 2006, 2(5):274-281.

Simmons et al., "Expression of full-length immunoglobulins in *Escherichia coli*: Rapid and efficient production of aglycosylated antibodies," *J. Immunol. Methods*, May 1, 2002, 263(1-2):133-147.

Sims et al., "A humanized CD18 antibody can block function without cell destruction," *J. Immunol.*, Aug. 15, 1993, 151(4):2296-2308.

Sivakumar, Krishnamoorthy et al., "A fluorogenic 1,3-dipolar cycloaddition reaction of 3-azidocoumarins and acetylenes." Org. Lett. 2004,24, 4603-4606.

Skehel, John et al., Receptor Binding and Membrane Fusion in Virus Entry: The Influenza Hemagglutinin, Ann. Rev Biochem, 69:531, 2000.

Skerra, "Bacterial expression of immunoglobulin fragments," *Curr. Opinion in Immunol.*, Apr. 1993, 5(2):256-262.

Slamon DJ, et al., Human breast cancer: correlation of relapse and survival with amplification of the HER-2/neu oncogene, *Science*. Jan. 9, 1987; 235(4785):177-82.

Sletten et al., "Bioorthogonal Chemistry: Fishing for Selectivity in a Sea of Functionality," *Angew. Che. Int. Ed. Engl.*, Aug. 27, 2009, 48(38):6974-6998.

Smith RA et al., "The active form of tumor necrosis factor is a trimer" *J Biol Chem*. May 25, 1987;262(15):6951-4.

Smyth MJ, et al., "CD4+CD25+ T regulatory cells suppress NK cell-mediated immunotherapy of cancer" *J Immunol*. Feb. 1, 2006;176(3):1582-7.

Sok, Devin et al., SnapShot: Broadly Neutralizing Antibodies. Cell 155, 728-728, (2013).

Solomons, G. and Fryhle, C., Chapter 5 Titled, Stereochemistry: Chiral Molecules, p. 184-228, in "Organic Chemistry," 7th Edition, Wiley, Jun. 18, 2001.

Soriano del Amo, David et al. Chemoenzymatic synthesis of the sialyl Lewis X glycan and its derivatives. Carbohydr. Res. 345, 1107-13, (2010).

Spinosa, Maria Rita et al., The Neisseria Meningitidis Capsule is Important for Intracellular Survival in Huamn Cells, Infect Immun 2001, 75, 3594-3603.

Srinivasan, Quantitative et al., Biochemical Rationale for Differences in Transmissibility of 1918 Pandemic Influenza A Viruses, Proc. Natl. Acad. Sci., 105, 2800-2805, 2008.

Stein, K.E. et al., The Immune Response to an Isomaltohexosyl-Protein Conjugate, a Thymus-Dependent Analogue of Alpha(1 Replaced by 6) Dextran., J Immunol 1982, 128, 1350-1354.

Stein, K.E., Thymus-Independent and Thymus-Dependent Responses to Polysaccharide Antigens, J Infect Dis 1992, 165 Suppl 1, S49-52.

Stephens, David, Conquering the Meningococcus, FEALS Microbial Rev 2007, 31, 3-14.

Stephens, D.S. et al., Epidemic Meningitis, Meningococcaemia, and Neisseria Meningitidis, Lancet 2007, 369, 2196-2210.

Stephenson et al., "Neuraminidase inhibitor resistance after oseltamivir treatment of acute influenza A and B in children," Clin. Infect. Dis., Feb. 15, 2009, 48(4):389-396.

Stevanovic, Stefan, Identification of Tumour-Associated T-Cell Epitopes for Vaccine Development, Nat. Rev. Cancer, 2002, 2, 514-520.

Stevens, James et al., Structure of the Uncleaved Human H1 Hemagglutinin From the Extinct 1918 Influenza Virus, Science, 303:1866, 2004.

Stevens, James et al., Structure and Receptor Specificity of the Hemagglutinin From an H5N1 Influenza Virus, Science, 312:404, 2006.

Stevens et al., Glycan Microarry Analysis of the Hemagglutinins From Modern and Pandemic Influenza Viruses Reveals Different Receptor Specificities. Journal of Molecular Biology 355.5 (2006): 1143-1155.

Stickings, Paul et al., Transcutaneous Immunization with Cross-Reacting Material CRM197 of Diphtheria Toxin Boosts Functional Antibody Levels in Mice Primed Parenterally with Adsorbed Diphtheria Toxoid Vaccine, Infection and Immunity, 2008, 76, 1766-1773.

Stockmann, H. et al., Development and Evaluation of New Cyclootynes for Cell Surface Glycan Imaging in Cancer Cells, J. Chem. Sci. 2011, 2, 932-936.

Streicher et al., "Building a successful structural motif into sialylmimetics-cyclohexenephosphonate monoesters as pseudo-sialosides with promising inhibitory properties," Bioorg. Med Chem., Feb. 15, 2006, 14(4):1047-1057.

Stubbs et al., "Synthesis and use of mechanism-based protein-profiling probes for retaining β-D-glucosaminidases facilitate identification of *Pseudomonas aeruginosa* NagZ," *J. Am. Chem. Soc.*, Jan. 9, 2008, 130(1):327-335.

Su, G. Hahner, W. Zhou "Investigation of the pore formation in anodic aluminum oxide" J Mater. Chem. 2008, 18 5787-5795.

Sun, B., Srinibasan, B., Huang, X., Pre-activation-based one-pot synthesis of an alpha-(2,3)-sialylated core-fucosylated complex type bi-antennary N-glycan dodecasaccharide. Chem. Eur. J 14 (23), 7072-81, (2008).

Supplementary European Search Report in European Application No. EP 13775664.9, dated Oct. 27, 2015, in 7 pages.

Suresh et al., "Bispecific monoclonal antibodies from hybrid hybridomas," *Methods in Enzymology*, 1986, 121:210-228.

Sutton, VR et al., Bcl-2 Prevents Apoptosis Induced by Perforin and Granzyme B, but Not That Mediated by Whole Cytotoxic Lymphocytes, J of Immunology 1997, 158(12), 5783.

Suzuki E, et al., "A nonfucosylated anti-HER2 antibody augments antibody-dependent cellular cytotoxicity in breast cancer patients" *Clin Cancer Res*. Mar. 15, 2007;13(6): 1875-82.

Svennerholm et al., "Human brain gangliosides: Developmental changes from early fetal stage to advanced age," *Biochim. Biophys. Acta*, Sep. 25, 1989, 1005 (2): 109-117.

Syrigos et al., "Antibody directed enzyme prodrug therapy (ADEPT): a review of the experimental and clinical considerations," *Anticancer Research*, Jan.-Feb. 1999, 19(1A):605-614.

Tahir et al., "Loss of IFN-γ production by invariant NK T cells in advanced cancer," *J. Immunol.*, Oct. 1, 2001, 167(7):4046-4050.

Takakura, Yoshimitsu et al., Molecular cloning, expression and properties of an alpha/beta-Galactoside alpha 2,3-sialyltransferase from *Vibrio* sp. JT-FAJ-16. J. Biochem. 142, 403-412, (2007).

Takano, Ryo et al., Sialylation and Malignant Potential in Tumour Cell Glycosylation Mutants, Glycobiology 4, 665-674 (1994).

Takeda et al., "Construction of chimaeric processed immunoglobulin genes containing mouse variable and human constant region sequences," *Nature*, Apr. 4-10, 1985, 314(6010):452-454.

Taki, Takao et al., Glycolipids of Metastatic Tissue in Liver From Colon Cancer: Appearance of Sialylated Lex and Lex Lipids, J. Biochem. 103, 998-1003, 1998.

Talmadge et al., Murine models to evaluate novel and conventional therapeutic strategies for cancer, Am. J. Pathol, 170(3): 793-804 (2007).

Tanaka, Hiroshi et al., An Efficient Convergent Synthesis of GP1c Ganglioside Epitope, J Am Chem Soc. 2008, 130, 17244.

Tanaka, Katsunori et al., Synthesis of a Sialic Acid Containing Complex-Type N-Glycan on a Solid Support, Chemistry—an Asian Journal, 2009, vol. 4 (4), p. 574-580.

Taton, T. Andrew et al., Scanometric DNA Array Detection with Nanoparticle Probes, Science 289 (2000) 1757-1760.

Taton, T. Andrew et al., Two-Color Labeling of Oligonucleotide Arrays Via Size-Selective Scattering of Nanoparticle Probes, J. Am. Chem. Soc. (2001), 123, 5164-5165.

Taylor-Papadimitriou et al., "Exploiting altered glycosylation patterns in cancer: Progress and challenges in diagnosis and therapy," *Trends Biotechnol.*, Jun. 1994, 12(6):227-233.

Telford et al., "The Aspergillus Fumigatus Sialidase is a 3'-Deoxy-D-galacto-2-nonulosonic Acid Hydrolase (KDNase)," The Journal of Biological Chemistry, 286(12), 10783-10792 (Mar. 25, 2011).

"The Human Protein Atlas", B3GALT5 URL:http://www.proteinatlas.org/ENSG00000183778-B3GALT5/cancer, Sep. 9, 2015.

Thorpe, (1985) "Antibody Carriers of Cytotoxic Agents in Cancer Therapy: A Review," in *Monoclonal Antibodies '84: Biological and Clinical Applications*, A. Pinchera et al. (ed.s), pp. 475-506.

(56) References Cited

OTHER PUBLICATIONS

Thurber, Greg et al., Antibody Tumor Penetration: Transport Opposed by Systemic and Antigen-Mediated Clearance, Adv Drug Deliv Rev, 60: 1421-1434, 2008.
Toba, et al., "Synthesis and biological evaluation of truncated α-glaactosylceramide derivatives focusing on cytokine induction profile," Bioorganic & Medicinal Chemistry 20(2012): 2850-2859.
Tomlinson et al., "The repertoire of human germline $V_H$ sequences reveals about fifty groups of $V_H$ segments with different hypervariable loops," J. Mol. Biol., Oct. 5, 1992, 227(3):776-798.
Torres-Sanchez et al., "Synthesis and Biological Evaluation of Phophono Analogues of Capsular Polysaccharide Fragments From Neisseria Meningtitidis A" Chem Eur J (2007) vol. 13, pp. 6623-6635.
Toshima, K. Glycosyl fluorides in glycosidations. Carbohydr. Res. 327, 15-26 (2000).
Traunecker et al., "Bispecific single chain molecules (Janusins) target cytotoxic lymphocytes on HIV infected cells," EMBO J., Dec. 1991, 10(12):3655-3659.
Traylor et al., "Gangliosides of human cerebral astrocytomas," J. Neurochem., Jan. 1980, 34(1):126-131.
Trinchieri, "Interleukin-12: a proinflammatory cytokine with immunoregulatory functions that bridge innate resistance and antigen-specific adaptive immunity," Annu. Rev. Immunol., 1995, 13:251-276.
Tsai et al., "Design and synthesis of activity probes for glycosidases," Org. Lett., Oct. 17, 2002, 4(21):3607-3610.
Tsai, Charng-sheng et al., Development of Trifunctional Probes for Glycoproteomic Analysis, Chem. Commun. 2010, 46, 5575-5577.
Tsai Ti, et al., "Effective sugar nucleotide regeneration for the large-scale enzymatic synthesis of Globo H and SSEA4" J Am Chem Soc. Oct. 2, 2013;135(39):14831-9, Epub Sep. 17, 2013.
Tseng, Susan Y. et al., Glycan Arrays on Aluminum Coated Glass Slides. Chem. Asian J, 2008, 3, 1395-1405.
Tsuji, et al., "Preparation of glycolipids and analogs as antigens for NKT cells for use in vaccines and immunotherapy," CAPLUS 149:492050 (2008).
Tsukamoto, Hiroshi et al., Photobacterium sp. JT-ISH-224 produces two sialyltransferases, alpha-/beta-galactoside alpha2,3-sialyltransferase and betagalactoside alpha2,6-sialyltransferase. J. Biochem. 143, 187-197, 2008.
Tumpey, Terrence et al., Characterization of the Reconstructed 1918 Spanish Influenza Pandemic Virus, Science, 310:77, 2005.
Tutt et al., "Trispecific F(ab')₃ derivatives that use cooperative signaling via the TCR/CD3 complex and CD2 to activate and redirect resting cytotoxic T cells," J. Immunol., Jul. 1, 1991, 147(1):60-69.
Tyagarajan K et al., "Exoglycosidase purity and linkage specificity: assessment using oligosaccharide substrates and high-pH anion-exchange chromatography with pulsed amperometric detection" Glycobiology. Jan. 1996;6(1):83-93.
Tzeng, Y. L. et al, Epidemiology and Pathogenesis of Neisseria Meningitidis, Microbes Infect 2000, 2, 687-700.
Uchida, Tsuyoshi et al., Diphtheria Toxin and Related Proteins, J Biol. Chem. 218; 3838-3844 (1973).
Udommaneethanakit et al., "Dynamic behavior of avain influenza A virus neuraminidase subtype H5N1 in complex with oseltamivir, zanamivir, peramivir, and their phosphonate analogues," J Chem. Inf Model, Oct. 2009, 49(10):2323-2332.
Ulevitch, RJ et al., Receptor-Dependent Mechanisms of Cell Stimulation by Bacterial Endotoxin, 1995, Annu. Rev. Immunol., 13: 437.
Ulrich, G.; Ziessel, R.; Harriman, A. "The chemistry of fluorescent bodipy dyes: Versatility unsurpassed." Angew. Chem. Int. Ed. 2008, 47, 1184-1201.
Urlaub et al., "Isolation of Chinese hamster cell mutants deficient in dihydrofolate reductase activity." Proc. Natl. Acad. Sci. U.S.A., Jul. 1980, 77(7):4216-4220.
Valentine MA, et al., "Phosphorylation of the CD20 phosphoprotein in resting B lymphocytes. Regulation by protein kinase C" J Biol Chem. Jul. 5, 1989;264(19):11282-7.
Van Beek et al., "Increased sialic acid density in surface glycoprotein of transformed and malignant cells—a general phenomenon?" Cancer Res., Nov. 1973, 33(11):2913-2922.
Van der Horst et al., "Photoaffinity labeling of a bacterial sialidase with an aryl azide derivative of sialic acid," J. Biol. Chem., Jul. 5, 1990, 265(19), 10801-10804.
Van Hest, Jan C.M. et al., Efficient Introduction of Alkene Functionality Into Proteins in Vivo (1998) FEES Lett. 428:68.
Vaki, Ajit et al., Symbols Nomenclatures for Glycan Representation, Proteomics. Dec. 2009, 9(24): 5398-5399.
Van Meir et al., "Exciting new advances in neuro-oncology: the avenue to a cure for malignant glioma," CA Cancer J. Clin., May-Jun. 2010, 60(3):166-193.
Van Slambrouck et al., "Clustering of monosialyl-Gb5 initiates downstream signalling events leading to invasion of MCF-7 breast cancer cells," Biochem. J., Feb. 1, 2007, 401(3):689-699.
Varghese et al., Three-dimensional structure of the complex of 4-guanidino-Neu5Ac2en and nfluenza virus neuraminidase. Protein Sci. Jun. 1995;4(6):1081-7.
Varki, "Glycan-based interactions involving vertebrate sialic-acid-recognizing proteins," Nature, Apr. 26, 2007, 446(7139):1023-1029.
Vasella et al., "Synthesis of a phosphonic acid analogue of N-Acetyl-2,3-didehydro-2-deoxyneuraminic acid, an inhibitor of Vibrio cholerae sialidase," Hely. Chim. Acta, Mar. 13, 1991, 74(2):451-463.
Vaswani et al., "Humanized antibodies as potential therapeutic drugs," Ann. Allergy, Asthma Immunol., Aug. 1998, 81(2):105-116, 119.
Vavricka, Christopher et al., Influenza Neuraminidase Operates Via a Nucleophilic Mechanism and Can Be Targeted by Covalent Inhibitors, Nature Communcations, 4:1491 (2013).
Verhoeyen et al., "Reshaping human antibodies: grafting an antilysozyme activity," Science, Mar. 25, 1988, 239(4847):1534-1536.
Vermeer AW et al., "The thermal stability of immunoglobulin: unfolding and aggregation of a multi-domain protein" Biophys J. Jan. 2000;78(1):394-404.
Vinogradova et al., "Molecular mechanism of lysosomal sialidase deficiency in galactosialidosis involves its rapid degradation," Biochem. J., Mar. 1, 1998, 330(Pt 2.):641-650.
Vippagunta, Sudha et al., Crystalline Solids, Advanced Drug Delivery Reviews 48, 3-26 (2001).
Virji, Mumtaz et al., Pathogenic Neisseriae: Surface Modulation, Pathogenesis and Infection Control, Nat Rev, Microbiol 2009, 7, 274-286.
Vitetta, ES et al., Redesigning Nature's Poisons to Create Anti-Tumor Reagents, Science 23(8): 1098 (1987).
Vocadlo et al., "A strategy for functional proteomic analysis of glycosidase activity from cell lysates," Angew. Chem. Int. Ed. Engl., Oct. 11, 2004, 43(40):5338-5342.
Von Itzstein et al., "Rational design of potent sialidase-based inhibitors of influenza virus replication," Nature, Jun. 3, 1993, 363(6428):418-423.
Voskoglou-Nomikos, Clinical predictive value of the in vitro cell line, human xenograft, and mouse allograft preclinical cancer models, Clin Can Res, 9: 4227-4239 (2003).
Wada et al., "A crucial role of plasma membrane-associated sialidase in the survival of human cancer cells," Oncogene, Apr. 12, 2007, 26(17):2483-2490.
Wagner, R et al., "Functional balance between haemagglutinin and neuraminidase in influenza virus infections," Rev. Med Viral., May-Jun. 2002, 12(3): 159-166.
Walls et al., "Activity-based protein profiling of protein tyrosine phosphatases," Methods Mol. Biol., 2009, 519:417-429.
Walker, L. M. et al. Broad neutralization coverage of HIV by multiple highly potent antibodies. Nature 477, 466-470, (2011).
Wang, Chao et al., Tuning the Optical Properties of BODIPY Dye Through Cu(I) Catalyzed Azide-Alkyne Cycloaddition (CuAAC) Reaction, Sci. China Chemistry 2012, 55, 125-130.
Wang, Zhen et al., Multi-Component One-Pot Synthesis of the Tumor-Associated Carbohydrate Antigen Globo-H Based on Preactivation of Thioglycosyl Donors, J Org. Chem. 2007, 72, 6409.

(56) References Cited

OTHER PUBLICATIONS

Wang et al., "Glycan microarray of Globo H and related structures for quantitative analysis of breast cancer," Proc. Natl. Acad. Sci. U.S.A., Aug. 19, 2008, 105 (33): 11661-11666.
Wang et al., "A continuous colorimetric assay for rhinovirus-14 3C protease using peptide p-nitroanilides as substrates," Anal. Biochem., Oct. 15, 1997, 252(2):238-245.
Wang et al., "Synthesis of Neisseria Meningitidis Serogroup W135 Capsular Oligosaccharides for Immunogenicity Comparison and Vaccine Development" Angew Chem Int Ed (2013) vol. 52, pp. 9157-9161.
Wang, Michael et al., "Mechanism by which mutations at his274 alter sensitivity of influenza A virus NI neuraminidase to oseltamivir carboxylate and zanamivir," Antimicrob. Agents Chemother., Dec. 2002, 46(12):3809-3816.
Wang, D., Liu, S., Trummer, B. J., Deng, C. & Wang, A. Carbohydrate microarrays for the recognition of cross-reactive molecular markers of microbes and host cells. Nat. Biotechnol . 20, 275-281, (2002).
Wang et al., Computational Studies of HSN1 Influenza Virus Resistance to Oseltamivir. Protein Sci. 2009, 18(4): 707-715; p. 713.
Wang, C. C. et al. Glycans on Influenza Hemagglutinin Affect Receptor Binding and Immune Response, Proc. Natl. Acad. Sci. 2009, 106, 18137-18142.
Wang, L. X. Carbohydrate-based vaccines against HIV/AIDs. Acs Sym. Ser. 932, 133-160 (2006).
Wang, L. X. Synthetic carbohydrate antigens for HIV vaccine design. Curr. Opin. Chem. Biol. 17, 997-1005, (2013).
Wang, W. et al. A systematic study of the N-glycosylation sites of HIV-I envelope protein on infectivity and antibody-mediated neutralization. Retrovirology, 10, 14, (2014).
Wang, Zhen et al. A general strategy for the chemoenzymatic synthesis of asymmetrically branched N-glycans. Science 341, 379-383, (2013).
Ward et al., "Binding activities of a repertoire of single immunoglobulin variable domains secreted from *Escherichia coli*," *Nature*, Oct. 12, 1989, 341(6242):544-546.
Waterhouse et al., "Combinatorial infection and in vivo recombination: a strategy for making large phage antibody repertoires," *Nuc. Acids Res.*, May 11, 1993, 21(9):2265-2266.
Watts et al., "The Synthesis of Some Mechanistic Probes for Sialic Acid Processing Enzymes and the Labeling of a Sialidase from Trypanosoma Rangeli," Canadian Journal of Chemistry, 82(11), 1581-1588 (2004).
Watts et al., "*Trypanosoma cruzi* trans-sialidase operates through a covalent sialyl-enzyme intermediate: tyrosine is the catalytic nucleophile," *J. Am. Chem. Soc.*, Jun. 25, 2003, 125(25):7532-7533.
Weibel, Robert et al., Tumor-Associated Membrane Sialoglycoprotein on Human Small Cell Lung Carcinoma Identified by The 1gG2a Monoclonal Antibody SWA20, (1988) Cancer Res. 48, 4318-4323.
Wen, Wen Hsien et al., "Synergistic effect of zanamivir-porphyrin conjugates on inhibition of neuraminidase and inactivation of influenza virus," J Med Chem., Aug. 13, 2009, 52(15):4903-4910.
White, Clinton et al., "A sialic acid-derived phosphonate analog inhibits different strains of influenza virus neuraminidase with different efficiencies," J Mol. Biol., Feb. 3, 1995, 245(5):623-634.
Wikstrand et al., "Monoclonal antibody therapy of human gliomas: Current status and future approaches," *Cancer Metastasis Rev.*, 1999, 18(4):451-464.
Wilen et al., "Strategies in optical resolutions," Tetrahedron, 1977, 33(21):2725-2736.
Williams et al., "Cloning and sequencing of human immunoglobulin V lambda gene segments." *Eur. J. Immunol.*, Jul. 1993, 23(7):1456-1461.
Wiltshire, S. et al. Proc. Natl. Acad. Sci. (2000) 97, 10113-10119.
Winter et al., "Making antibodies by phage display technology," *Annu. Rev. Immunol.*, 1994, 12:433-455.
Wiseman, GA et al., Phase I/II 90Y-Zevalin (yttrium-90 Ibritumomab Tiuxetan, IDEC-Y2B8) Radioimmunotherapy Dosimetry Results in Relapsed or Refractory Non-Hodgkin's Lymphoma, Eur Jour Nucl Med 27(7): 766-77 (2000).
Wiseman, Gregory et al., Ibritumomab Tiuxetan Radioimmunotherapy for Patients with Relapsed or Refractory Non-Hodgkin Lymphoma and Mild Thrombocytopenia: a Phase II Multicenter Trial, Blood 99(12): 4336-42 (2002).
Witte et al., "Ultrasensitive in situ visualization of active glucocerebrosidase molecules," *Nat. Chem. Biol.*, Dec. 2010, 6(12):907-913.
Witzig, Thomas et al., Randomized Controlled Trial of Yttrium-90-Labeled Ibritumomab Tiuxetan Radioimmunotherpay Versus Rituximab Immunotherapy for Patients with Relapsed or Refractory Low-Grade, Follicular, or Transformed B-Cell Non-Hodgkin's Lymphoma, J Clin Oncol 20(10):2453-63 (2002).
Witzig, Thomas et al., Treatment with Ibritumomab Tiuxetan Radioimmunotherapy in Patients with Rituximab-Refractory Follicular Non-Hodgkin's Lymphoma, J Clin Oncol 20(15):3262-69 (2002).
Wong et al., α-Galactosyl Ceramide Analogs and Their use as Therapeutic, 2010:50988, 2 Pages.
Woo et al. Cytokine profiles induced by the novel swine-origin influenza A/HINI virus: mplications for treatment strategies. J Infect Dis. 2010 Feb 1;201(3):346-53.
Woof et al., "Human antibody-Fc receptor interactions illuminated by crystal structures," *Nat. Rev. Immunol.*, Feb. 2004, 4(2):89-99.
Woyke, Tanja et al., Effect of Auristatin PHE on Microtubule Integrity and Nuclear Localization in Cryptococcus Neoformans, Antimicrob. Agents and Chemother. 45(12): 3580-3584 (2001).
Wright et al. Antibody variable region glycosylation: biochemical and clinical effects, Springer Semin Immunopathology, 15:259-273 (1993).
Wu et al., "Avidity of CD1d-ligand-receptor ternary complex contributes to T-helper 1 (Th1) polarization and anticancer efficacy," *Proc. Natl. Acad. Sci. USA*, Oct. 18, 2011, 108(42):17275-17280.
Wu, Xueling et al. Rational design of envelope identifies broadly neutralizing human monoclonal antibodies to HIV-I. Science 329, 856-861, (2010).
Wu, Liangxing et al., Fluorescent Cassettes for Monitoring Three-Component Interactions in Vitro and in Living Cells, Journal of the American Chemical Society (2009), 131(26), 9156-9157.
Wu et al., "Catalytic azide-alkyne cycloaddition: reactivity and applications," Aldrichimica Acta, 2007, 40(1):7-17.
Xie, F.; Sivakumar, K.; Zeng, Q. B.; Bruckman, M. A.; Hodges, B.; Wang, Q. "A fluorogenic 'click' reaction of azidoanthracene derivatives." Tetrahedron 2008, 64, 2906-2914.
Yamaguchi, Kazunori et al., "Evidence for mitochondrial localization of a novel human sialidase (NEU4)," *Biochem. J.*, Aug. 15, 2005, 390(Pt 1):85-93.
Yamane-Ohnuki, Naoko et al., Production of Therapeutic Antibodies with Controlled Fucosylation, mAbs 2009, 1;3:230-236.
Yamashita et al., CS-8958, a prodrug of the new neuraminidase inhibitor R-125489, shows ong-acting anti-influenza virus activity. Antimicrob Agents Chemother. Jan. 2009;53(1): 186-92.
Yamashita, Yoshito et al., Alterations in Gastric Mucin with Malignant Transformation: Novel Pathway for Mucin Synthesis, (1995) J. Natl. Cancer Inst. 87, 441-446.
Yang, JM et al., Alterations of )-Glycan Biosynthesis in Human Colon Cancer Tissues, (1994) Glycobiology 4, 873-884.
Yaniv, Nature 297: 17-18, 1982.
Yansura et al., "Nucleotide sequence selection for increased expression of heterologous genes in *Escherichia coli*," *Methods: A Companion to Methods in Enzymol.*, Aug. 1992, 4(2):151-158.
Yates AJ et al., Brain Tumors in Childhood. Childs Brain 5(1), 31-39 (1979).
Ye et al., "Stage-specific embryonic antigen 4 expression in epithelial ovarian carcinoma," *Int. J. Gynecol. Cancer*, Aug. 2010, 20(6):958-964.
Yelton et al., "Affinity maturation of the BR96 anti-carcinoma antibody by codon-based mutagenesis." *J. Immunol.*, Aug. 15, 1995, 155(4):1994-2004.
Yguerabide, Juan et al., Light-Scattering Submicroscopic Particles as Highly Fluorescent Analogs and Their Use as Tracer Labels in

(56) References Cited

OTHER PUBLICATIONS

Clinical and Biological Applications: II. Experimental Characterization, Anal. Biochem. (1998), 262, 157-176.
Ying et al., One-bead-one-inhibitor-one-substrate screening of neuraminidase activity. Chembiochem. Oct. 2005;6(10):1857-65.
Yoshida M, et al. Glycoconjugate J. 1993, 10, 324.
Yoshimoto et al., "CD4$^{pos}$, NK1.1$^{pos}$ T cells promptly produce interleukin 4 in response to in vivo challenge with anti-CD3," *J. Exp. Med.*, Apr. 1, 1994, 179(4):1285-1295.
Yu et al., "Anti-GD2 antibody with GM-CSF, interleukin-2, and isotretinoin for neuroblastoma," *N. Engl. J. Med.*, Sep. 30, 2010, 363(14):1324-1334.
Yuen et al., Human infection by avian influenza A H5N1. Hong Kong Med J. Jun. 2005;1 1(3):189-99.
Zapata et al., "Engineering linear F(ab')$_2$ fragments for efficient production in *Escherichia coli* and enhanced antiproliferative activity," Protein Eng., Oct. 1995, 8(10): 1057-1062.
Zarei et al., "Separation and identification of GM1b pathway Neu5Ac- and Neu5Gc gangliosides by on-line nanoHPLC-QToF MS and tandem MS: toward glycolipidomics screening of animal cell lines," *Glycobiology*, Jan. 2010, 20(1):118-126.
Zhang et al., "New cerebrosides from Acanthopanax gracilistylus," CAPLUS 156:225776 (2011).
Zhang et al., "Selection of tumor antigens as targets for immune attack using immunohistochemistry: I. Focus on gangliosides," *Int. J. Cancer*, Sep. 26, 1997, 73(1):42-49.
Zheng et al., Delayed antiviral plus immunomodular treatment still reduces mortality in mice infected by high inoculum of influenza A/H5N1 virus. Proc Natl Acad Sci U S A. Jun. 10, 2008;105(23):8091-6.
Zhou et al., A fluorogenic probe for the copper(I)-catalyzed azide-alkyne ligation reaction: modulation of the fluorescence emission via $^3(n,\pi)$-$^1(\pi,\pi^*)$ inversion, *J. Am. Chem. Soc.*, Jul. 28, 2004, 126(29):8862-8863.
Zhu, X et al., Mass spectrometric characterization of the glycosylation pattern of HIV-gp120 expressed in CHO cells. Biochemistry 39, 11194-11204 (2000).
Zou, et al., Chemoenzymatic synthesis and Fc gamma receptor binding of homogenous glycoforms of antibody Fc to FcIIIa receptor. J Am Chem Soc. 2011, 133(46):18975-91.
Zimmermann et al., Multi-target therapeutics: when the whole is greater than the sum of the parts. Drug Discov Today. Jan. 2007;12(1-2):34-42. Epub Nov. 28, 2006.
Bacteroides Fragilis NCTC 9343, Complete Genome., Mar. 3, 2005, XP002775523, Database Accession No. CR626927, 2 Pages.
Bacteroides Thetaiotaomicron VPI-5482, Section 8 of 21 of the Complete Genome, XP002775522, Jan. 6, 2006, Database Accession No. AE016933, 2 Pages.
Berg, Jan-Olof et al., Purification of Glycoside Hydrolases From Bacteroides Fragilis, Applied and Environmental Microbiology, vol. 40, No. 1, Jul. 1980, p. 40-47.
Dicker, Martina et al., Using Glyco-Engineering to Produce Therapeutic Proteins, Expert Opinion on Biological Therapy, vol. 15, Jan. 1, 2015, pp. 1501-1516.
Extended European Search Report, App. No. 15799789.1, dated Nov. 28, 2017, 10 Pages.
Extended European Search Report, App. No. 158001917, dated Nov. 28, 2017, 12 Pages.
Extended European Search Report, App. No. 15799981.4, dated Nov. 29, 2017, 9 Pages.
Huang, Wei et al., CHemoenzymatic Glycoengineering of Intact IgG Antibodies for Gain of Functions, Journal American Chemical Socirty, vol. 134, No. 9, Jul. 25, 2012, pp. 12308-12318.
Liao, Shih-Fen et al., Immunization of Fucose-Containing Polysaccharides From Reishi Mushroom Induces Antibodies to Tumor-Associated Globo H-Series Epitopes, Proceedings National Academy of Sciences PNAS, vol. 110, No. 34, Aug. 1, 2013, pp. 13809-13814.
Lin, Chin-Wei et al., A Common Glycan Structure on Immunoglobulin G for Enhancement of Effector Functions, vol. 112, No. 34, 7 Aug. 2015, pp. 10611-10616.
Sakurama, Haruko et al., Differences in the Substrate Specificities and Active-Site Structures of Two α-L-Fucosidases (Glycoside Hydrolase Family 29) From Bacteroides Thetaiotaomicron, Bioscience Biotechnology Biochemistry, vol. 76, No. 5, May 23, 2012, pp. 1022-1024.
Tsai, Tsung-I et al., An Effective Bacterial Ducosidase for Glycoprotein Remodeling, ACS Chemical Biology, vol. 12, No. 1, Jan. 20, 2017, pp. 63-72.
Chu, Kuo-CHINGet al., Efficient and Stereoselective Synthesis of [alpha](2->9) Oligosialic Acids: From Monomers to Dodecamers, Angewandte Chemie International Edition, vol. 50, No. 40, Sep. 2011, 9391-9395.
Frank, Natasha et al., the Therapeutic Promise of the Cancer Stem Cell Concept, Journal of Clinical Investigation, 120(1) 41-50, Jan. 2010.
Hsu, Nien-Yeen et al., Desorption Ionization of Biomolecules on Metals, Anal. Chem., 80, 5203-5210, 2008.
Katagiri, Yohko et al., Laminin Binding Protein, 34/67 Laminin Receptor, Carries Stage-Specific Embryonic Antigen-4 Epitope Defined by Monoclonal Antibody Raft.2, Biochemical and Biophysical Research Communcations, 332, 1004-1011, 2005.
Liang, Yuh-Jin et al., Switching of the Core Structures of Glycosphingolipids From Blobo- and Lacto- to Ganglio-Series Upon Human Embryonic Stem Cell Differentiation, PNAS, 107(52), Dec. 2010, 22564-22569.
Merck, MAB4304, Anti-Stage-Specific Embryonic Antigen-4 Antibody, Clone MC-813-70, 4 Pages, 2017.
Moal, E. LE et al., Enhanced Fluorescence Cell Imaging with Metal-Coated Slides, Biophysical Journal, vol. 92, 2150-2161, Mar. 2007.
Oberli, Matthias et al., A Possible Oligosaccharide-Conjugate Vaccine Candidate for Clostridium Difficile is Antigenic and Immunogenic, Chemistry & Biology, vol. 18, No. 5, May 2011, 580-588.
Pan, Yanbin et al., Synthesis and Immunological Properties of N-Modified GM3 Antigens as Therapeutic Cancer Vaccines, J. Med. Chem., 48(3), 875-883, 2005.
Shevinsky, LH et al., Monoclonal Antibody to Murine Embryos Defines a Stage-Specific Embryonic Antigen Expressed on Mouse Embryos and Human Teratocarinoma Cells., CELL vol. 30, Issue 3, Oct. 1982, pp. 697-705.
Zhang, Hai-Long et al., A Novel Combined Conjugate Vaccine: Enhanced Immunogenicity of bFGF with CRM197 as a Carrier Protein, Molecular Medicine Reports, 4, 857-863, 2011.
Cheung et al., Meeting Info: 23rd International Symposium on Glycoconjugates, GLYCO 23. Split, Croatia. Sep. 15, 2015-Sep. 20, 2015, vol. 32, No. 5, pp. 323.
International Search Report and Written Opinion in International Application No. PCT/US2017/048074, dated Dec. 26, 2017, 17 pages.
Lei, Jianqing et al., Potential antitumor applications of a monoclonal antibody specifically targeting human papilloma virus 16 E749-57 peptide, Microbiology and Immunology, 2012, vol. 56, pp. 456-462.
Tsai, Charng-Sheng et al., Cell-Permeable Probe for Identification and Imaging of Sialidases, PNAS, vol. 110, No. 7, 2013, 2466-2471.
European Application 14817316.4, Communication pursuant to Article 94(3), dated Apr. 16, 2018, 5 pages.

\* cited by examiner

Fig. 3A
Fig. 3B
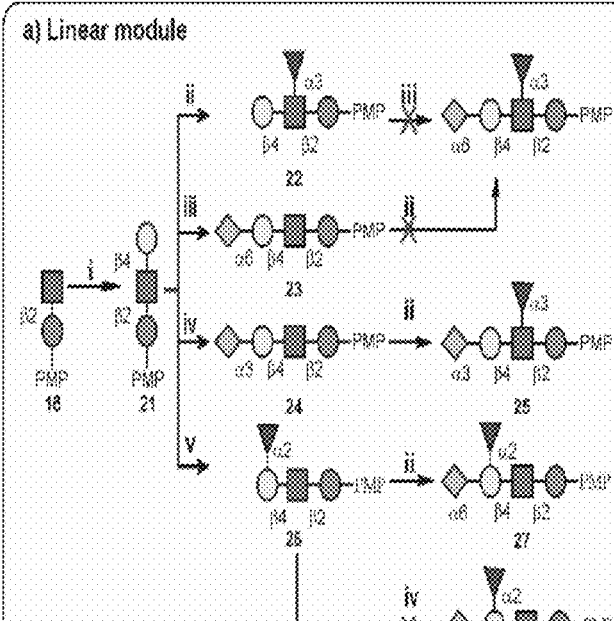
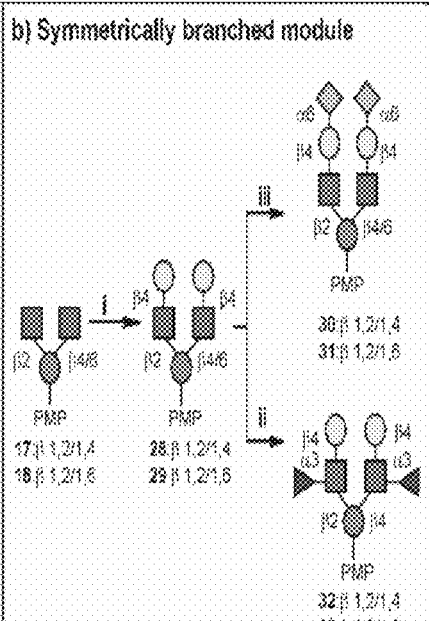
Fig. 3C
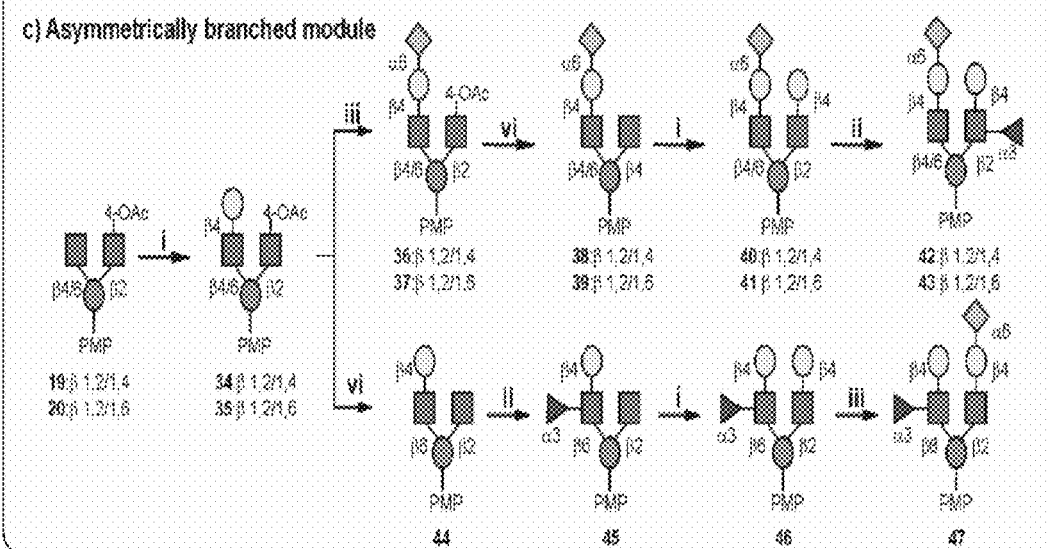

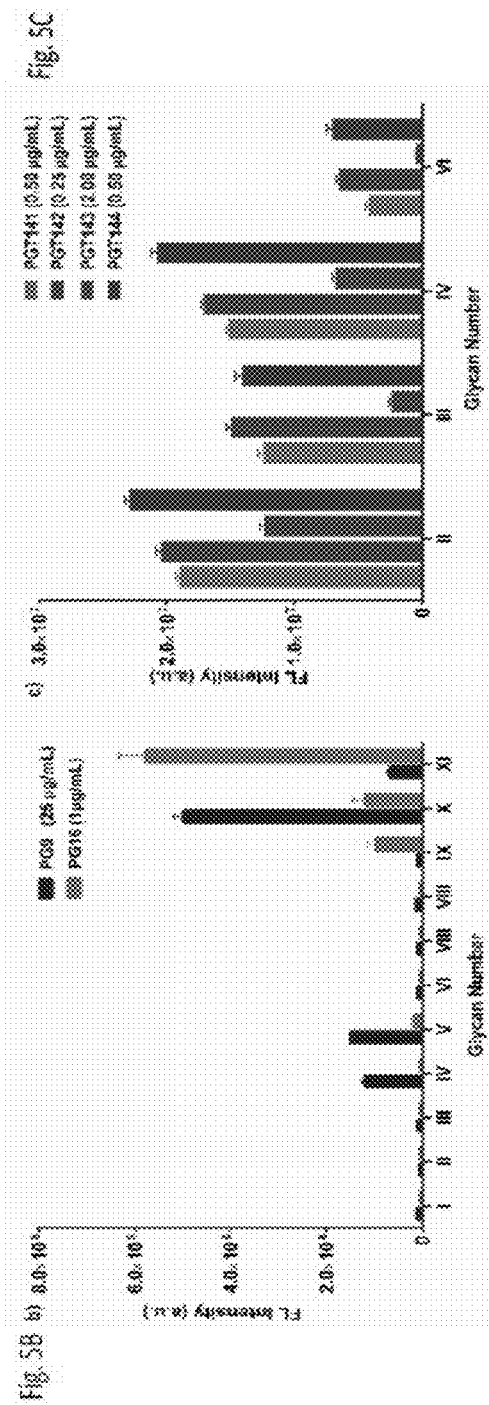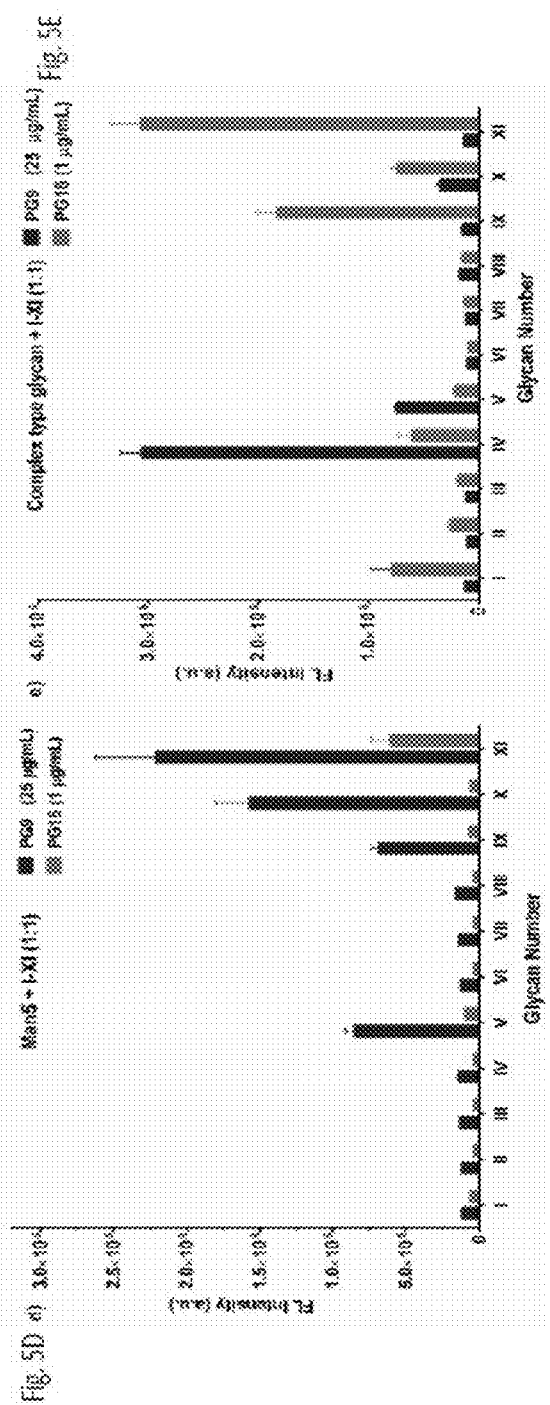

(I)

S1c

S1d

S1e

2

3

S1g

4

5

6

S4c

Fig. 37B
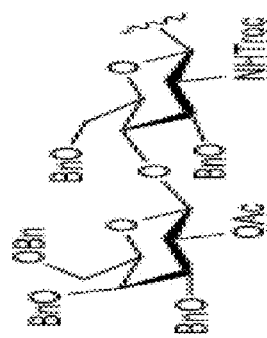
10; R² = Bn, R¹ =
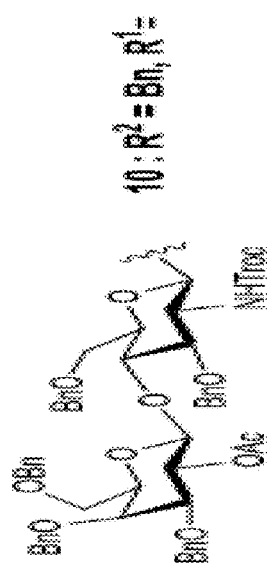
S5c; R² = Bn, R¹ =

S5a; R² = Bn, R¹ =
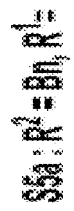

S5c

S9c

G4

S10b

G6

S11a

S12b

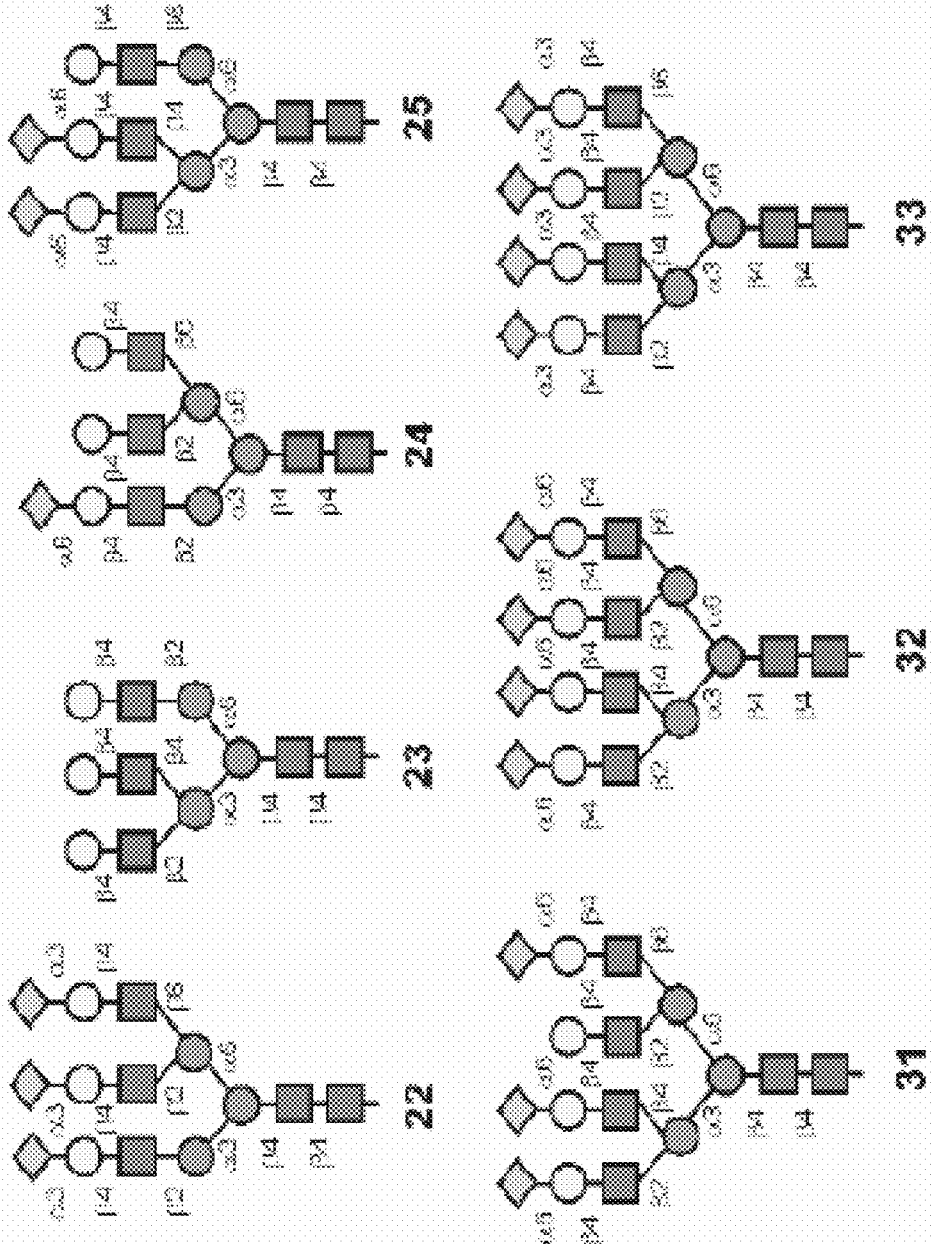

S17b

S18a

S20c

S20d

S20k

XI

S22c

S22d

S22f

26

33

43

45

46

48

49

50

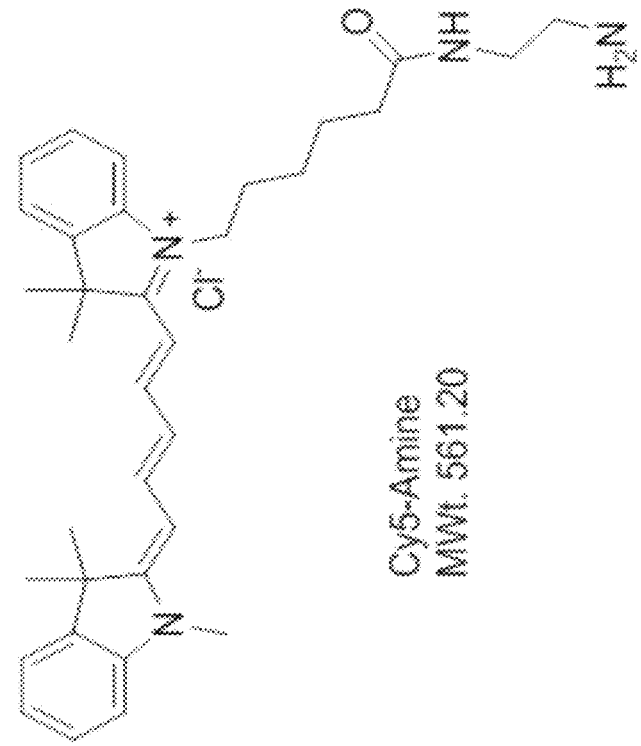
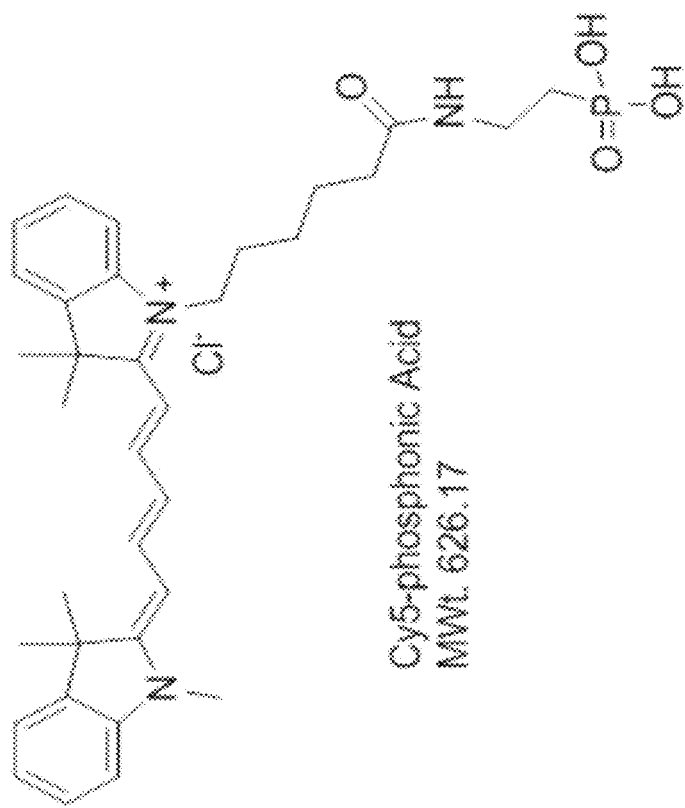
Fig. 193

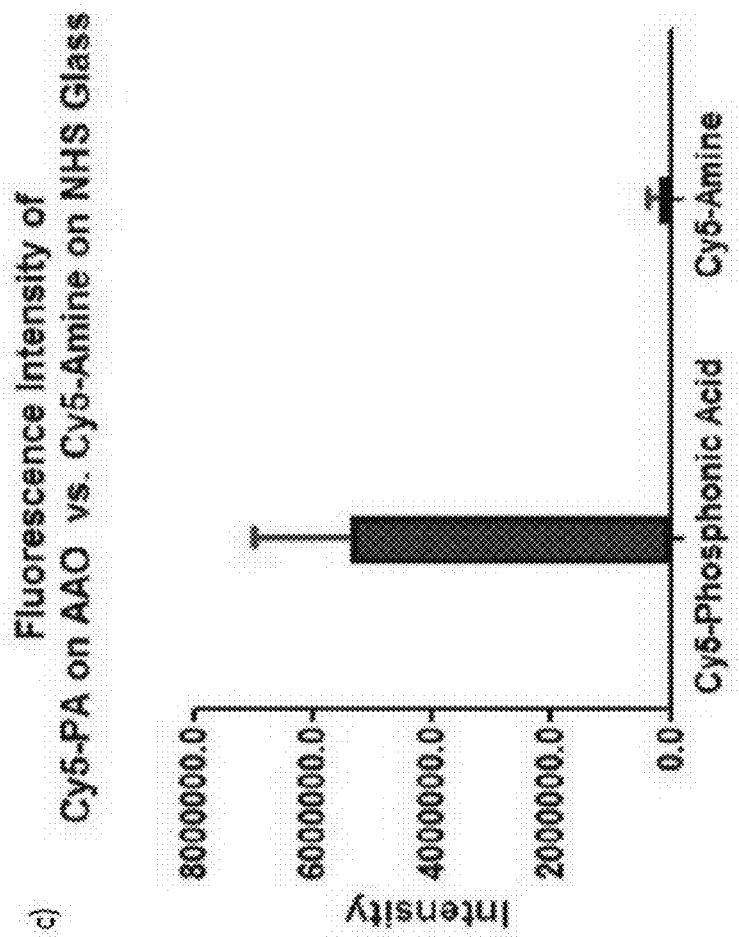
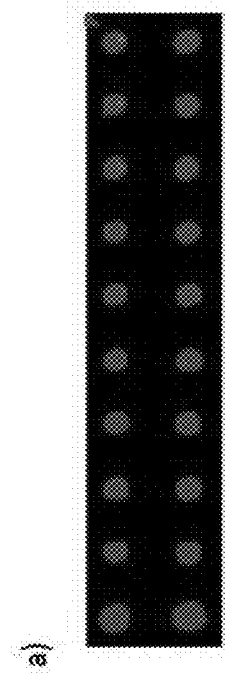
Fig. 195A
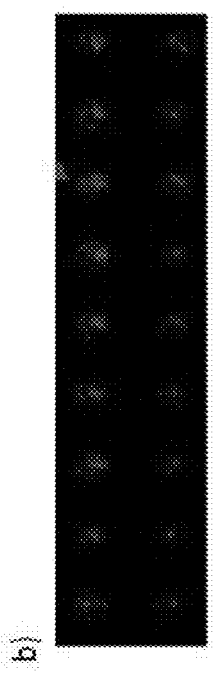
Fig. 195B

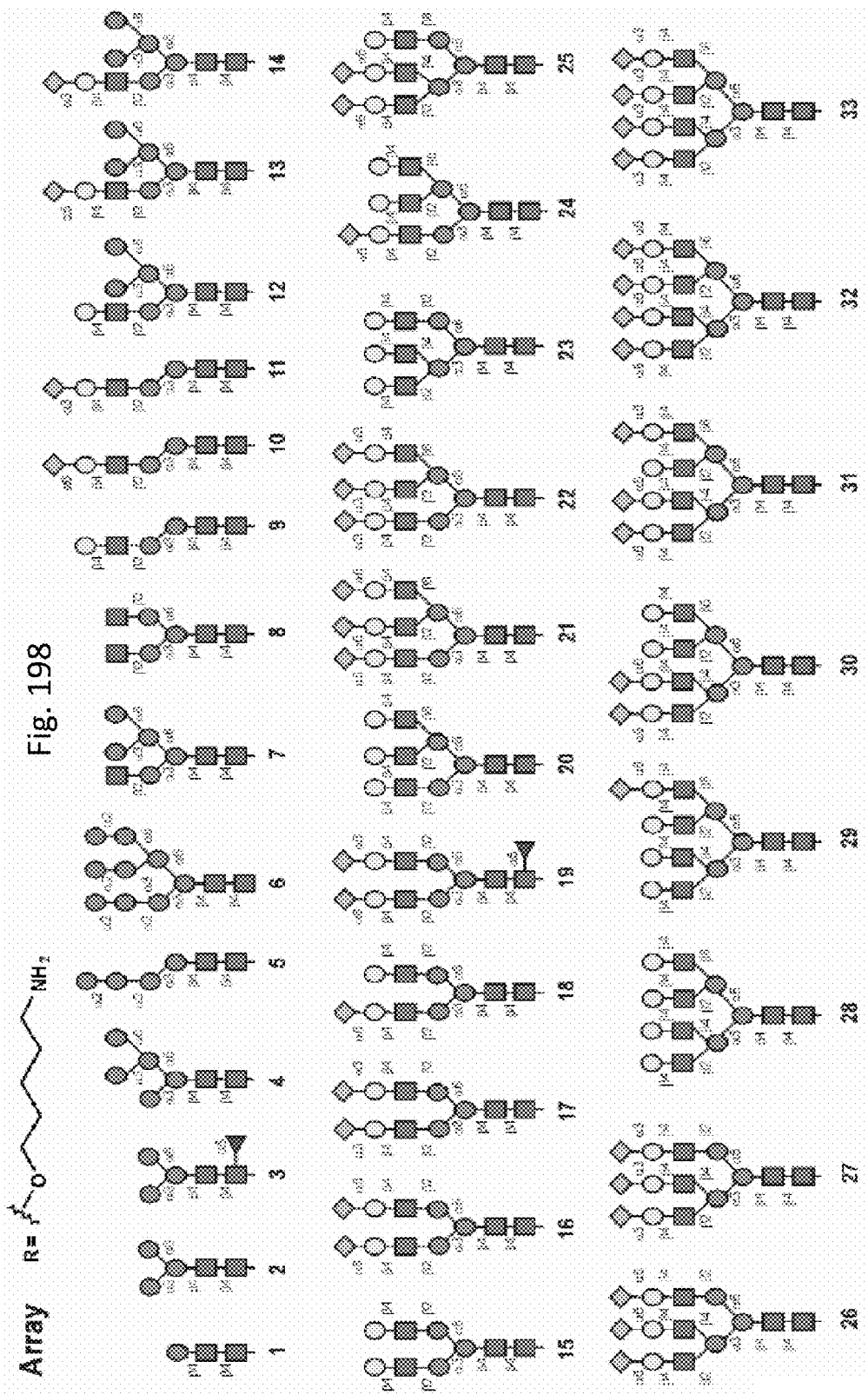

METHODS FOR MODULAR SYNTHESIS OF N-GLYCANS AND ARRAYS THEREOF

RELATED APPLICATION

This application claims the benefit of priority to U.S. provisional application No. 62/305,441 filed on Mar. 8 2016. The contents of which is incorporated by reference herein in its entirety.

FIELD

The present disclosure is related generally to chemical and chemo-enzymatic methods for synthesis of highly diverse N-glycans of high mannose, hybrid and complex types, arrays made from said glycans, and use of said arrays. Specifically, the present disclosure relates to methods of synthesis of N-glycan arrays on aluminum oxide coated substrate using a novel modular N-glycans synthetic approach, and the use of said N-glycan arrays for detection and analysis of binding reactions by glycan-binding molecules such as broadly neutralizing HIV antibodies.

BACKGROUND

N-linked glycosylation of proteins is a fundamental and important post-translational modification found both in eukaryotes and in prokaryotes. This protein modification results in the covalent attachment of an oligosaccharide onto asparagine residues of polypeptide chains. Glycans are typically the most important interface between cells and their environment. As a vital constituent of all living systems, glycans are involved in most of the essential biological processes such as protein folding, cell signaling, fertilization, embryogenesis, and the proliferation of cells and their organization into specific tissues. Abnormal cell surface glycosylation and/or glycan-profiles are usually related to diseases such as cancer and atherosclerosis. Accordingly, altered glycosylation is an indication of an early and possibly critical point in development of human pathologies. Thus, insights into the carbohydrate related biological and pathological processes, and for developing diagnostics and therapeutics for human diseases.

The biosynthesis of complex oligosaccharides generally results in tremendous complexity and diversity, mainly due to the variable and multiple connectivity of glycan building blocks (monosaccharides). These cell-identifying glycosylated molecules include glycoproteins and glycolipids and are specifically recognized by various glycan binding molecules such as lectins, antiglycan antibodies, chemical compounds and also other glycans and glycolipids, etc. However, the enormous complexity of these interactions, and the lack of well-defined glycan libraries and analytical methods have been shown to be major obstacles in the development of glycomics. Moreover, naturally occurring glycans are typically isolated in tiny amounts and exist only as admixtures of isomers. As such, the limited availability and limited purity of said naturally occurring glycans do not allow their use as a reliable source of well-characterized oligosaccharides. Thus, novel synthesis methods are useful for the preparation of diverse glycan libraries for biological and structural applications.

The development of nucleotide and protein microarrays has revolutionized genomic, gene expression and proteomic research. Similarly, the development of glycan microarrays has allowed an unprecedented high-throughput exploration of the specificities of a diverse range of glycan-binding molecules. The systematic arrangement of glycans on arrays allow for efficient probing of low affinity protein-glycan interactions through multivalent presentation. Since their establishment, various types of "arrays" have been developed, including the one available from the Consortium of Functional Glycomics (CFG) which contains more than 600 oligosaccharides on an N-hydroxysuccinimide (NHS)-activated glass slide. However, the spacer group and immobilization chemistry used in different array formats clearly result in differences in the density, distribution and orientation of glycan presentation, which dramatically affects the binding affinity and even specificity in glycan-protein interactions. Therefore, cross-comparison among different array platforms and development of new glycan arrays to improve the sensitivity of detection, for example, of hetero-ligand bindings are particularly important. Moreover, pharmaceutical companies and research institutions would greatly benefit from glycan arrays for various screening and drug discovery applications, including arrays that facilitate analysis of the structural elements of glycans that contribute to binding to glycan binding molecules including antibodies, receptors and other biomolecules.

SUMMARY

The present disclosure provides compositions and methods of preparation of diverse N-linked oligosaccharides (N-glycans) of high mannose, hybrid and complex types. The methods of the present disclosure include chemical synthesis, and/or enzymatic synthesis. In certain embodiments, one or more of said synthesized N-glycans are spotted onto a substrate in a given area (known as a "spot"), wherein one or more of said spots are pooled to generate an N-glycan array for use in, for example, binding profiling, rapid screening and identification of optimal glycans recognized by glycan-binding molecules, such as antibodies and viruses.

In one aspect, the present disclosure provides the method wherein the strategically protected building blocks termed as "D1 and D2/D3 arm modules" can be regio- and stereospecifically glycosylated at the 3-O and/or 6-O position of the orthogonally protected Manβ1-4GlcNAcβ1-4GlcNAcβ1 core. In certain embodiments, the resulting glycans can be deprotected and/or unmasked in order to yield a final oligosaccharide product, or in certain embodiments, it can be selectively extended enzymatically to yield the final complex oligosaccharide products. In certain embodiments, the final oligosaccharide products are equipped with amino alkyl linker at the reducing end to restore its structural integrity and to act as handle for immobilization on arrays, or in certain other embodiments, said products can alternatively be conjugated to carrier proteins.

In one aspect, a preferred orthogonally protected Manβ1-4GlcNAcβ1-4GlcNAcβ1 core trisaccharide contains at least two orthogonal protecting groups, and has the formula (I)

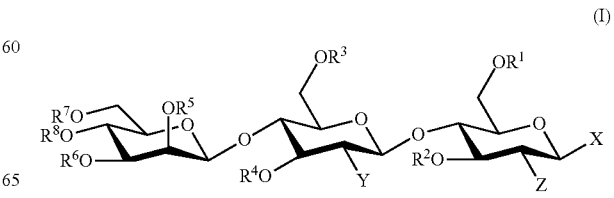

Wherein each of $R^1$, $R^2$, $R^3$, $R^4$, $R^5$, $R^6$, $R^7$, and $R^8$ is independently selected from the group consisting of an orthogonal or a permanent protecting group; wherein, each of the orthogonal protecting group at $R^6$ is preferably selected from para-methoxy benzyl ether (PMB), methoxy phenyl ether (PMP), levulinoyl (Lev), benzoyl (Bz), allyl ether (Allyl), and silyl ethers; and $R^7$ and $R^8$ are fused to form benzylidene ring which can be cleaved to form either 4-OH and/or 6-OH;

Each of $R^2$, $R^3$, $R^4$, and $R^5$ is independently a permanent protecting group that is stable under conditions used to remove the orthogonal protecting groups and is preferably benzyl (Bn) or acetyl (Ac);

$R^1$ is a permanent protecting group that is stable under conditions used to remove the orthogonal protecting groups and is preferably benzyl (Bn) or acetyl (Ac); or a protected fucoside residue connected via α1,6 linkage;

X is $-OR^9$; wherein $R^9$ is $-H$ or optionally substituted $C_3$-$C_{10}$ alkyls chain terminated with groups consisting of $-N_3$ or $NR^{10}$; and $R^{10}$ is $-H$ or benzyl (Bn) or carbobenzoyl (Cbz);

Y and Z are $-NHR^{11}$; and $R^{11}$ is preferably selected from the group consisting of 9-fluorenylmethoxycarbonyl (Fmoc), allyloxycarbonyl (Alloc), [2,2,2-Trichloroethoxycarbonyl] (Troc), acetyl (Ac), phthalimido (Phth), carbobenzyloxy (Cbz) or tert-butoxycarbonyl (Boc).

As used herein, a "permanent protecting group" can be a chemical moiety that prevents functionalization of a functional group when exposed to conditions which would normally functionalize said functional group. The permanent protecting group can be selectively removed to expose the functional group in the resulting molecule. In some aspects, the exposed functional group can be further reacted with another moiety, or can be left unfunctionalized.

In a second aspect, the preferred D1 and D2/D3 arm modules has the general formula (II)

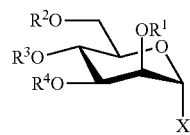

(II)

Wherein, each of $R^1$, $R^2$, $R^3$, and $R^4$ is $-H$ or a permanent protecting group that is stable under conditions used to remove the orthogonal protecting groups and is preferably benzyl (Bn) or acetyl (Ac) or benzoyl (Bz), or independently selected from

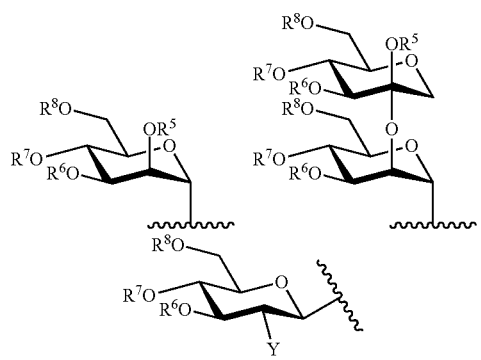

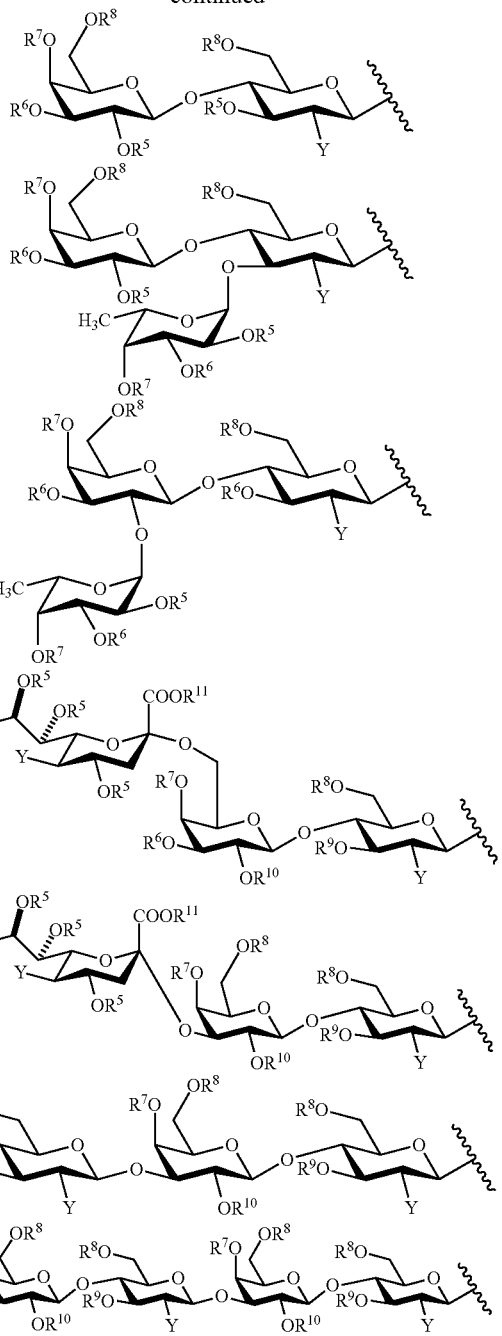

Wherein, Each of $R^5$, $R^6$, $R^7$, and $R^8$ is $-H$ or independently a permanent protecting group that is stable under conditions used to remove the orthogonal protecting groups and is preferably benzyl (Bn) or acetyl (Ac) or benzoyl (Bz);

Each of $R^9$ and $R^{10}$ is $-H$ or independently a permanent protecting group that is stable under conditions used to remove the orthogonal protecting groups and is preferably benzyl (Bn) or acetyl (Ac) or benzoyl (Bz), or a protected fucoside residue connected via α1,3 linkage to GlcNAc and/or α1,2 linkage to Galactose;

$R^{11}$ is $-H$ or Me, Et;

$R^{12}$ is $-H$ or independently a permanent protecting group that is stable under conditions used to remove the orthogonal protecting groups and is preferably benzyl (Bn) or acetyl (Ac) or benzoyl (Bz), or protected Neu5Ac residue connected via α2,6 linkage;

$R^{13}$ is —H or independently a permanent protecting group that is stable under conditions used to remove the orthogonal protecting groups and is preferably benzyl (Bn) or acetyl (Ac) or benzoyl (Bz), or independently selected from

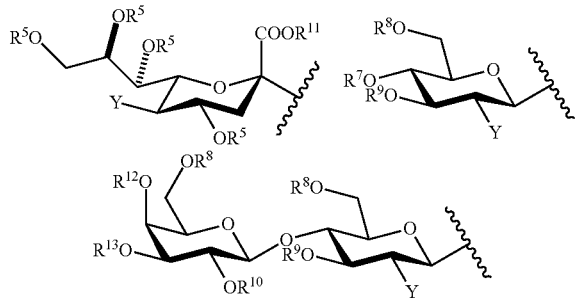

X is —$OR^{14}$ or —$SR^{15}$

Wherein, $R^{14}$ is H, alkyl, alkenyl, alkynyl, aryl or substituted aryl; a protecting group such as a silyl or substituted silyl, preferably thexyldimethylsilyl (TDS), t-butyldimethylsilyl (TBS), t-butyldiphenyl silyl (TBDPS), triisopropylsilyl (TIPS), trimethylsilyl (TMS), or triethylsilyl (TES); methyl (Me), acetyl (Ac), benzyl (Bn), 2-naphthylmethyl (Nap) or 1-naphthylmethyl (1-Nap); para-methoxy benzyl ether (PMB), methoxy phenyl ether (PMP), allyl ether (Allyl), or an anomeric leaving group such as fluoride —F, trichloroacetimidate —C(NH)—$CCl_3$, phenyltrifluoroacetimidate —C(NPh)-$CF_3$, trifluoroacetimidate —C(NH)—$CF_3$; thioalkyl, thiophenyl;

$R^{15}$ is H, alkyl, aryl, or substituted aryl, preferably methyl, ethyl, phenyl, tosyl, or tolyl.

Y is —$NHR^{16}$; and $R^{16}$ is preferably selected from the group consisting of 9-fluorenylmethoxycarbonyl (Fmoc), allyloxycarbonyl (Alloc), [2,2,2-Trichloroethoxycarbonyl] (Troc), acetyl (Ac), phthalimido (Phth), carbobenzyloxy (Cbz) or tert-butoxycarbonyl (Boc).

In accordance with said second aspect, the D1 and D2/D3 arm modules of general formula (II) are prepared chemically or preferably chemo-enzymatically.

In another embodiment of said second aspect, the exemplars of chemically synthesized D1 and D2/D3 arm modules are selected from the group consisting of

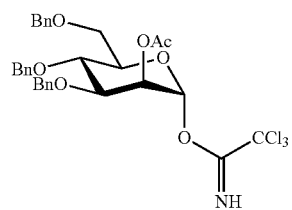

1

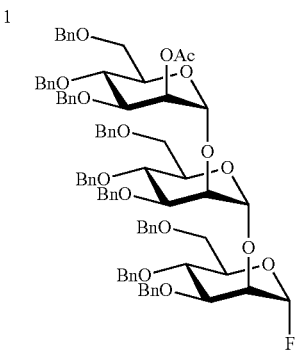

2

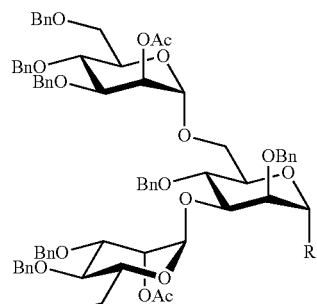

3: R = -STol
4: R = -F

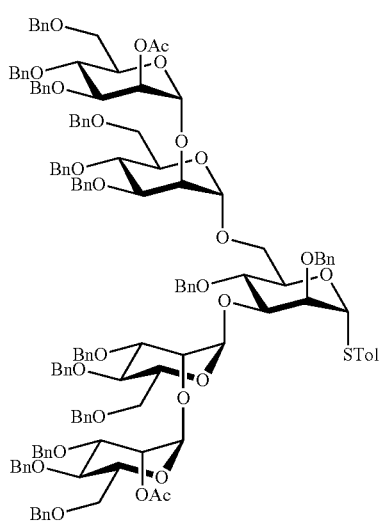

5

7
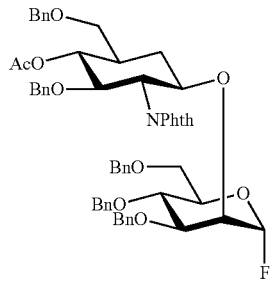
8
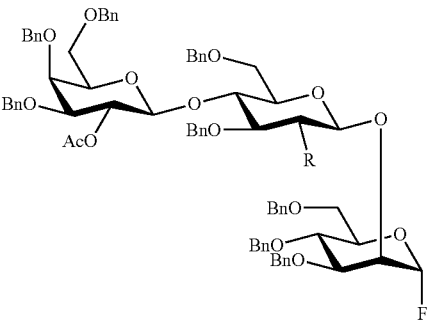
7: R = -NPhth
8: R = -NHTroc
9
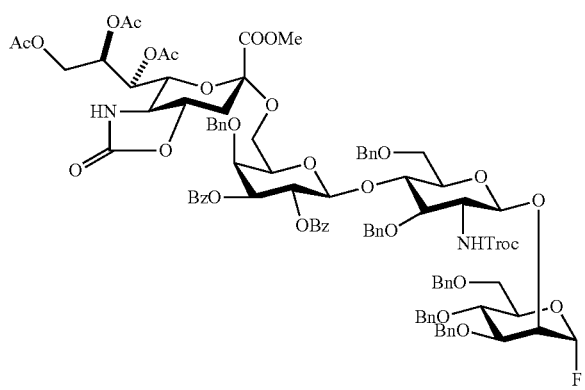
10
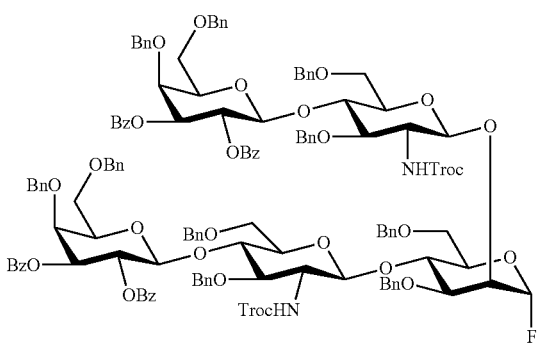
11
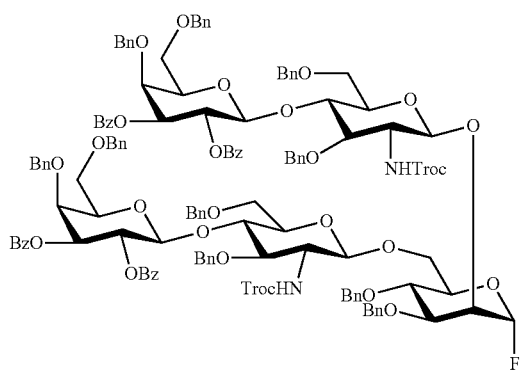
12
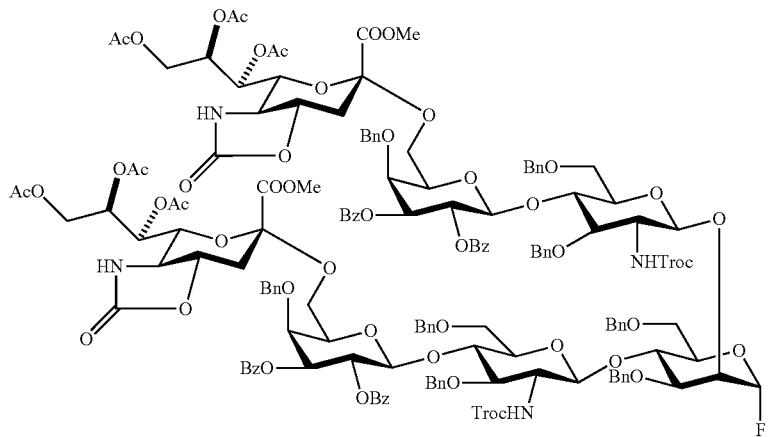

-continued

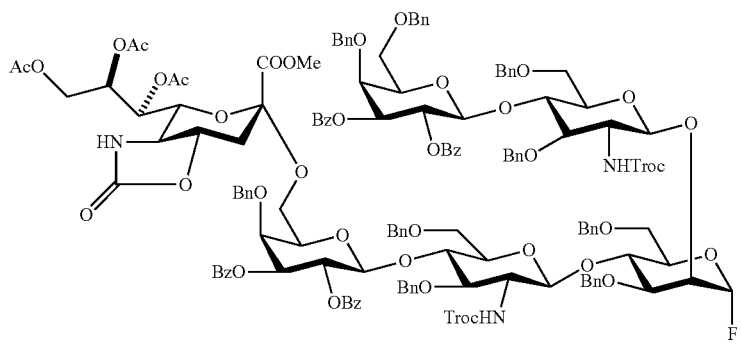

13

In another embodiment of said second aspect, the chemo-enzymatic synthesis of D1 and D2/D3 arm modules commenced with chemically prepared acceptors substrates of formula (III)

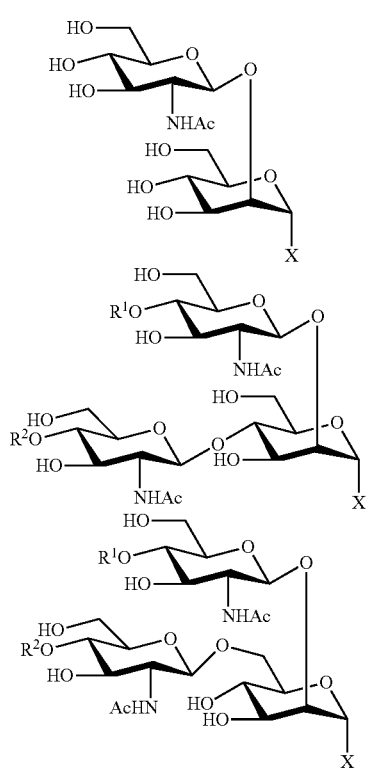

Wherein, each of $R^1$ and $R^2$ is independently selected from —H or the protecting groups acetyl (Ac) or benzoyl (Bz);

X is —$OR^3$ and $R^3$ is H, benzyl (Bn), 2-naphthylmethyl (Nap) or 1-naphthylmethyl (1-Nap); para-methoxy benzyl ether (PMB), methoxy phenyl ether (PMP), allyl ether (Allyl).

In another embodiment of said second aspect, the chemo-enzymatically prepared acceptor substrates of formula (III) are subjected to enzymatic extensions, wherein the enzymes are independently selected from the group consisting of β (1→4) Galactosyltransferase, α (1→3) Fucosyltransferase, α (1→2) Fucosyltransferase, β (1→3) N-acetyl glucosamine transferase, α (2→3) sialyltransferase, and α (2→6) sialyltransferase.

In another embodiment, the chemo-enzymatically prepared modules of formula (II) can be transformed into their acetates or benzoates form.

In another embodiment, the fully acetylated or benzoylated modules of formula (II) can undergo reducing end modification to form an anomeric leaving group such as trichloroacetimidate —C(NH)—CCl$_3$, phenyltrifluoroacetimidate —C(NPh)-CF$_3$, trifluoroacetimidate —C(NH)—CF$_3$; thioalkyl, thiophenyl, and more preferable fluoride —F.

In a third aspect, chemically or chemo-enzymatically prepared D1 and D2/D3 arm modules of formula (II) are independently selected for chemical glycosylation at 3-O and/or 6-O positions of Manβ1-4GlcNAc$_{β1}$-4GlcNAcβ1 core trisaccharide of formula (I).

The present disclosure also provides an orthogonally protected Manβ1-4GlcNAcβ1 core containing at least two orthogonal protecting groups, and has the formula (IV)

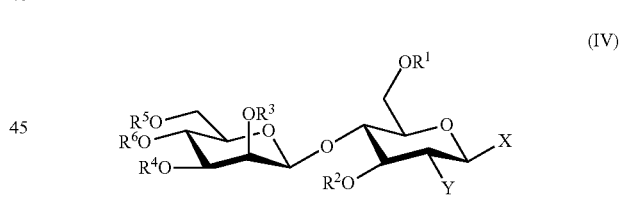

Wherein each of $R^1$, $R^2$, $R^3$, $R^4$, $R^5$, and $R^6$ is independently selected from the group consisting of an orthogonal or a permanent protecting groups; wherein, each of the orthogonal protecting groups at $R^4$ is preferably selected from para-methoxy benzyl ether (PMB), methoxy phenyl ether (PMP), levulinoyl (Lev), benzoyl (Bz), allyl ether (Allyl), and silyl ethers; and $R^5$ and $R^6$ are fused to form benzylidene ring which can be cleaved to form either 4-OH and/or 6-OH;

Each of $R^1$, $R^2$, and $R^3$ is independently a permanent protecting group that is stable under conditions used to remove the orthogonal protecting groups and is preferably benzyl (Bn) or acetyl (Ac);

X is —$OR^7$; wherein $R^7$ is —H or benzyl (Bn) or allyl (All);

Y is —$NHR^8$; and $R^8$ is preferably selected from the group consisting of 9-fluorenylmethoxycarbonyl (Fmoc), allyloxycarbonyl (Alloc), [2,2,2-Trichloroethoxycarbonyl]

(Troc), acetyl (Ac), phthalimido (Phth), carbobenzyloxy (Cbz) or tert-butoxycarbonyl (Boc).

In some embodiments, conditions effective to cause cleavage of each of the different orthogonal protecting groups preferably do not cause cleavage of other protecting groups present on the oligosaccharide building blocks.

The N-glycan core structure is optionally equipped with a spacer or linker and includes —$(CH_2)_5NH_2$ at the reducing end to facilitate efficient immobilization on arrays and conjugation to carrier proteins. The present disclosure also provides spacers such as —$(CH_2)_n$NH—CO—O—$[(CH_2)_2$—O—$(CH_2)_2]_{2-3}$—O—$PO(OH)_2$ to facilitate efficient immobilization on aluminum oxide arrays through phosphonate chemistry.

In another aspect, the present disclosure provides a method for making an orthogonally protected Manβ1-4GlcNAcβ1-4GlcNAcβ1 core.

In another aspect, the present disclosure provides chemical and chemo-enzymatic methods for making D1 and D2/D3 arm modules.

In one aspect, the present disclosure provides the strategy to prepare thousands of structurally-distinct complex N-linked oligosaccharides (N-glycans), wherein the material can be used for (1) development of glycan arrays to determine binding specificities of carbohydrate binding molecules such as lectins, galactose binding proteins (galectins), antiglycan antibodies, HIV broadly neutralizing antibodies, and preferably of influenza hemagglutinin, chemical compounds and also other glycans and glycolipids; (2) standards for glycan sequencing using mass spectrometry; (3) preparation of diverse glycoforms at Fc-region of therapeutic antibodies such as Rituxan, Herceptin, Humira for enhancement of their effector functions; and (4) oligosaccharides standards for glycobiology research laboratories.

In one aspect, the present disclosure comprises an array of carbohydrate moieties immobilized on a substrate, the array comprising: a plurality of glycans wherein one or more glycan moieties are deposited at a discrete location (e.g. a spot) on the substrate, wherein the diverse glycans comprises homo- and/or mixed N-glycans of high-mannose-, hybrid-, and complex-types wherein the array is useful for the detection of hetero-glycan binding behavior.

In one aspect, the present disclosure comprises a method for detecting hetero-glycan binding behavior comprising contacting the array with one or a plurality of hetero-glycans. In some aspects, the hetero-glycans can be part of broadly neutralizing HIV-1 antibodies.

In certain embodiments, the glycans comprising homo- and/or mixed N-glycans of high-mannose-, hybrid-, and complex-types are prepared by modular chemo-enzymatic methods. In certain embodiments, the use of an array for the detection of hetero-glycan binding behavior comprises the steps of detecting binding specificity of broadly neutralizing HIV-1 antibodies.

In certain embodiments, the glycans comprises one or more of the compounds G1-G33 as set forth in FIG. 198 and/or any one or more of the compounds I-XI as set forth in FIG. 200.

In certain embodiments, the glycans can include or exclude one or more of the compounds G1-G33 as set forth in FIG. 198 and includes or excludes any one or more of the compounds I-XI as set forth in FIG. 200.

In another aspect, a method for synthesizing the glycan moieties of any one of claims 1-6 wherein the method of synthesis is based on or derived from synthetic schemes in part or in whole as set forth in FIGS. 1-4, is provided.

In another aspect, a method for generating vaccine targets comprising screening and identification of optimal cell surface glycans recognized by neutralizing HIV-1 antibodies, wherein the method further comprises contacting the HIV antibodies with the array of any one of claims 1-6, is provided.

In one aspect, a glycan microarray on an aluminium oxide-coated glass (ACG) slide, or an indium tin-oxide-coated (ITO) glass slide, containing a diverse set of glycans, including homo- and mixed N-glycans of high-mannose-, hybrid-, and complex-type prepared by modular chemo-enzymatic methods is provided. In certain embodiments, the array is useful for the detection of hetero-glycan binding behaviors.

In one related aspect, the method of generating/fabricating said glycan microarray is provided. In certain embodiments, synthetic strategy based on diversity can be created by assembly of the so called "D1 and D2/D3 arm modules", followed by the α-specific mannosylation at the 3-O and/or 6-O position of the mannose residue of the common core trisaccharide.

In certain other embodiments, the glycosyl fluoride strategy was combined with enzymatic sialylation to build a library of symmetric bi-, tri- and tetraantennary complex-type glycans 50. In certain embodiments, modular synthetic methods for preparation of high mannose, hybrid and asymmetrically sialylated multi-antennary glycans are provided (e.g. FIG. 1*b*).

In one aspect, a method for rapid screening and identification of optimal glycans recognized by neutralizing antibodies is provided. In certain embodiments, the screening directly facilitates development of HIV-1 vaccines targeting cell surface glycans.

In one aspect, this disclosure relates to screening libraries of glycan binding partners to identify N-glycan binding partners that bind to an array comprising one or more N-glycans as disclosed herein. In some aspects, the molecules in said libraries may comprise, for example, antibodies, nanobodies, antibody fragments, aptamers, lectins, peptides, biomolecules, or combinatorial library molecules. In one embodiment, said screening comprises a detection step, wherein the detection step comprises the detection of N-glycan binding by a HIV antibody. In one embodiment, the detection of said HIV antibody comprises the use of a N-glycan array, comprising one or more N-glycans as disclosed herein.

In one aspect, this disclosure relates to a method of detecting N-glycan binding wherein a complex is formed by contacting the array with one or a plurality of N-glycans, and contacting the complex with a label. In some aspects, the label can then be detected. In some aspects, the label can be a labeled antibody. In some aspects, the labeled antibody can further comprise a label comprising an enzyme, fluorophore, a chemiluminescent moiety, or a nanoparticle.

In one aspect, this disclosure relates to a method of detecting HIV antibodies, the method comprising: providing an array of N-linked glycans as described herein, contacting the array with HIV antibodies; forming a complex between the HIV antibodies and the glycans on the array; contacting the HIV antibody-glycan array complex with a label; and detecting the label. In some aspects, the label can be a labeled antibody further comprising an enzyme, fluorophore, chemiluminescent moiety, or a nanoparticle.

In some embodiments, the array comprises a substrate and a multitude of defined glycan probe locations on the solid support, each glycan probe location defining a region of the solid support that has multiple copies of one or more type of similar glycan molecules attached thereto. In some embodiments, each glycan probe location defines a region of the solid support that has multiple copies of more than one types of similar glycan molecules attached thereto.

The interaction between A and X can, in some embodiments, be a covalent bond, Van der Waals interaction, hydrogen bond, ionic bond, or hydrophobic interaction.

The details of one or more embodiments of the present disclosure are set forth in the description below. Other features or advantages of the present disclosure will be apparent from the following drawings and detailed description of several embodiments, and also from the appending claims.

DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A) The synthesis of high mannose-, hybrid-, and complex-type N-glycans through the regio- and stereoselective glycosidation of orthogonally protected core trisaccharide at the 3-O and 6-O positions with a modular set of diverse glycosyl donors. FIG. 1B) The representative N-glycans that can be generated by this strategy FIG. 1C) Retrosynthetic disconnections of high-mannose-, hybrid- and complex-type glycans showing the required building blocks for assembly.

FIGS. 3A, 3B and 3C shows exemplary chemo-enzymatic synthesis of modules. A representative chemo-enzymatic approach to the synthesis of FIG. 3A, linear; FIG. 3B, symmetric and FIG. 3C, asymmetrically branched modules essential for N-glycan assembly. Reagents and conditions: i), UDP-galactose, β-1,4-GalT; ii), GDP-fucose, α-1,3-FucT; iii), CMP-Neu5Ac, α-2,6-SiaT; iv), CMP-Neu5Ac, α-2,3-SiaT; v), GDP-fucose, α-1,2-FucT; vi), NaOH.

FIGS. 5A, 5B, 5C, 5D, and 5E shows exemplary glycan specificities of HIV-1 bNAbs on ACG array. FIG. 5A.), Synthetic N-glycans are chemically modified with a phosphonic acid tail for covalent attachment to the aluminium oxide-coated glass (ACG) slide through phosphonate chemistry. FIG. 5B), FIG. 5C), Binding of PG9, PG16 and PGTs 141-144 to structures I-XI printed on an ACG slide FIG. 5D), FIG. 5E), Binding of PG9 and PG16 to each of the glycan mixtures was evaluated to determine the effect of adjacent glycans on binding affinity. Arrays were printed by mixing 100 μM of $Man_5GlcNAc_2$ or the complex-type glycan with every structure from I-XI in a 1:1 ratio. The molar concentrations in μM for antibodies are given in the legend. The mean signal intensities and standard error calculated for five independent replicates on the array are shown.

FIG. 11A shows an exemplary structure embodiments of the present disclosure. FIG. 11B shows an exemplary structure embodiments of the present disclosure. FIG. 11C shows an exemplary structure embodiments of the present disclosure.

(FIG. 15A=High Mannose type; FIG. 15B=hybrid type, FIG. 15C=complex type).

FIG. 32A shows exemplary structure embodiments in a representative synthetic scheme embodiments of the present disclosure. FIG. 32B shows exemplary structure embodiments in a representative synthetic scheme embodiments of the present disclosure.

FIG. 32C shows exemplary structure embodiments in a representative synthetic scheme embodiments of the present disclosure.

FIGS. 37A, 37B and 37C: FIG. 37A shows exemplary structure embodiments and synthetic scheme embodiments of the present disclosure. FIG. 37B shows exemplary structure embodiments and synthetic scheme embodiments of the present disclosure. FIG. 37C shows exemplary structure embodiments and synthetic scheme embodiments of the present disclosure.

FIG. 42A shows exemplary structure embodiments in a representative synthetic scheme embodiment of the present disclosure. FIG. 42B shows exemplary structure embodiments in a representative synthetic scheme embodiment of the present disclosure.

FIG. 47A shows exemplary structure embodiments in a representative synthetic scheme embodiment of the present disclosure. FIG. 47B shows exemplary structure embodiments in a representative synthetic scheme embodiment of the present disclosure. FIG. 47C shows exemplary structure embodiments in a representative synthetic scheme embodiment of the present disclosure.

FIG. 59A: Exemplary structure embodiments in representative synthetic scheme embodiments of the present disclosure. FIG. 59B: Exemplary structure embodiments in representative synthetic scheme embodiments of the present disclosure.

FIG. 60A: Exemplary structure embodiments in representative synthetic scheme embodiments of the present disclosure. FIG. 60B: Exemplary structure embodiments in representative synthetic scheme embodiments of the present disclosure.

FIG. 75A: Exemplary structure embodiments in representative synthetic scheme embodiments of the present disclosure. FIG. 75B: Exemplary structure embodiments in representative synthetic scheme embodiments of the present disclosure.

FIG. 82A: Exemplary structure embodiments in representative synthetic scheme embodiments of the present disclosure. FIG. 82B: Exemplary structure embodiments in representative synthetic scheme embodiments of the present disclosure. FIG. 82C: Exemplary structure embodiments in representative synthetic scheme embodiments of the present disclosure. FIG. 82D: Exemplary structure embodiments in representative synthetic scheme embodiments of the present disclosure.

FIG. 89A: Exemplary structure embodiments in representative synthetic scheme embodiments of the present disclosure. FIG. 89B: Exemplary structure embodiments in representative synthetic scheme embodiments of the present disclosure.

FIGS. 93A, 93B, and 93C: FIG. 93A: Exemplary Structures of complex type glycans. FIG. 93B: Exemplary Structures of complex type glycans. FIG. 93C: Exemplary Structures of complex type glycans.

FIG. 102A: Exemplary structure embodiments in representative synthetic scheme embodiments of the present disclosure. FIG. 102B: Exemplary structure embodiments in representative synthetic scheme embodiments of the present disclosure.

Figure 118A:
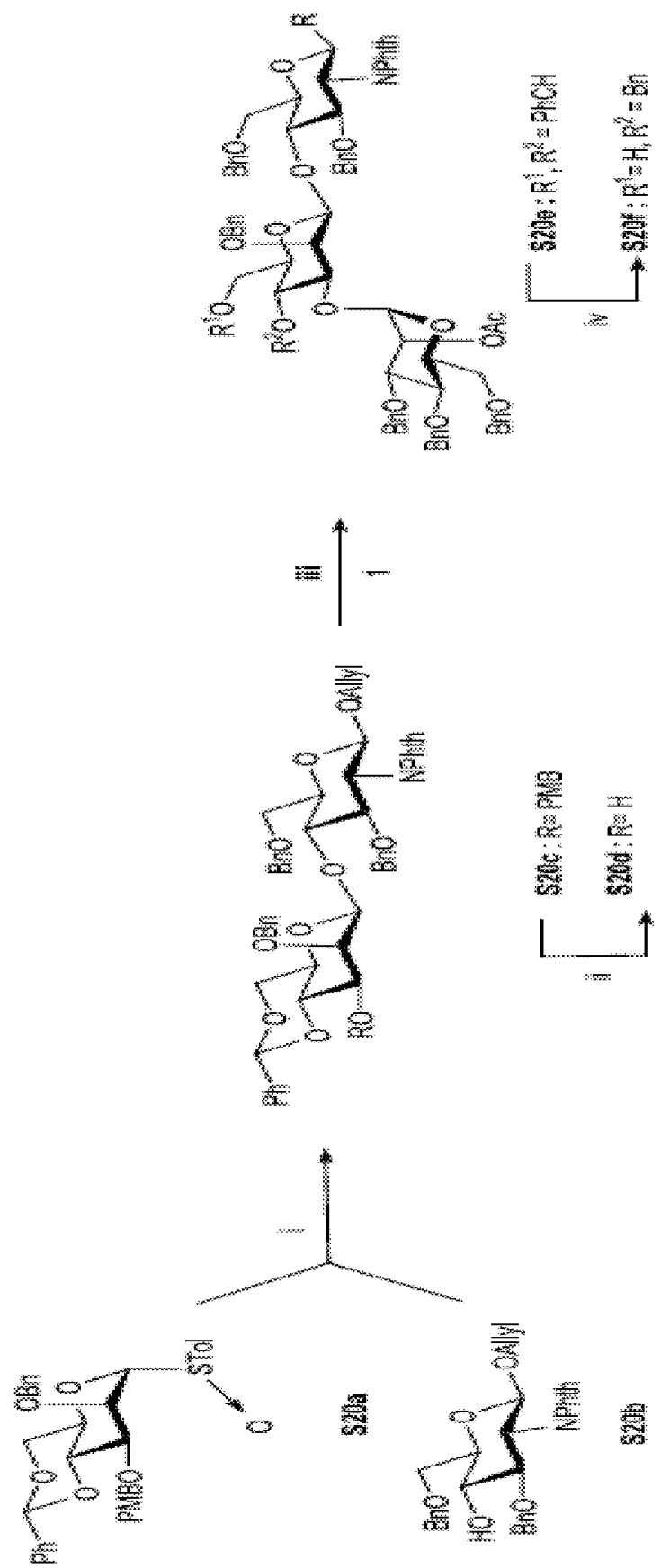
Figure 118B:
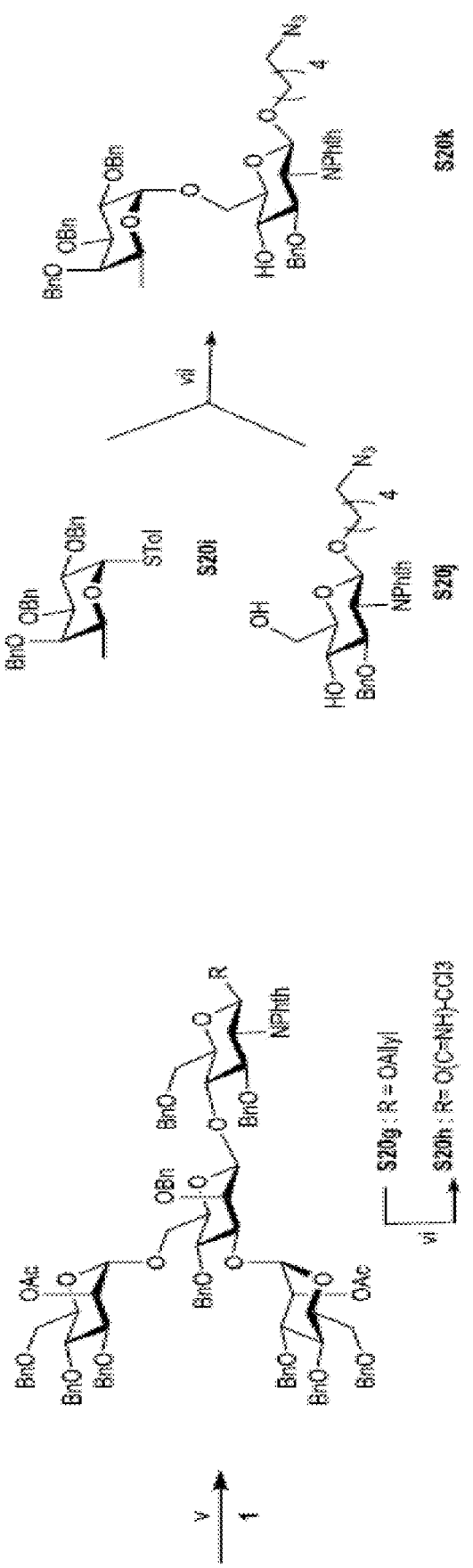
Figure 118C:
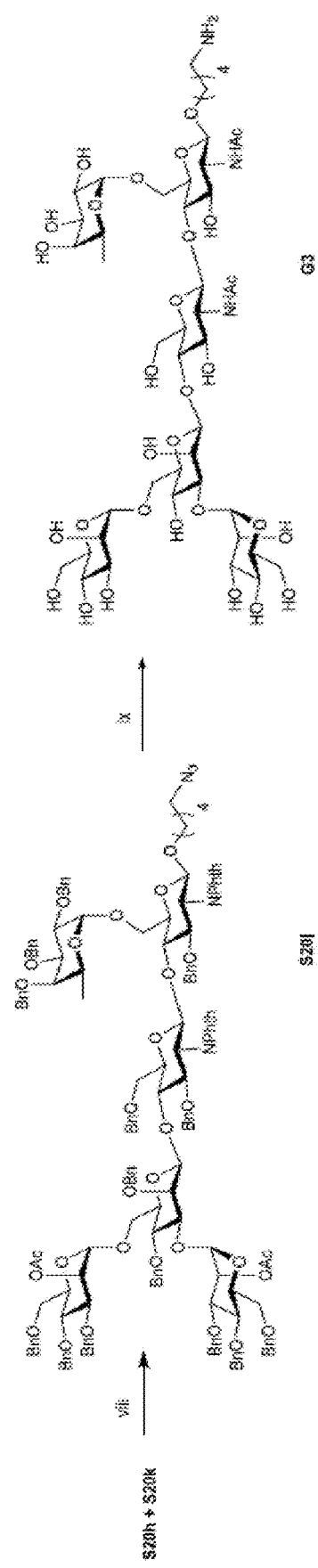

FIGS. 118A, 118B, and 118C: FIG. 118A Exemplary structure embodiments in representative synthetic scheme embodiments of the present disclosure. FIG. 118B: Exemplary structure embodiments in representative synthetic scheme embodiments of the present disclosure. FIG. 118C: Exemplary structure embodiments in representative synthetic scheme embodiments of the present disclosure.

Figure 119:
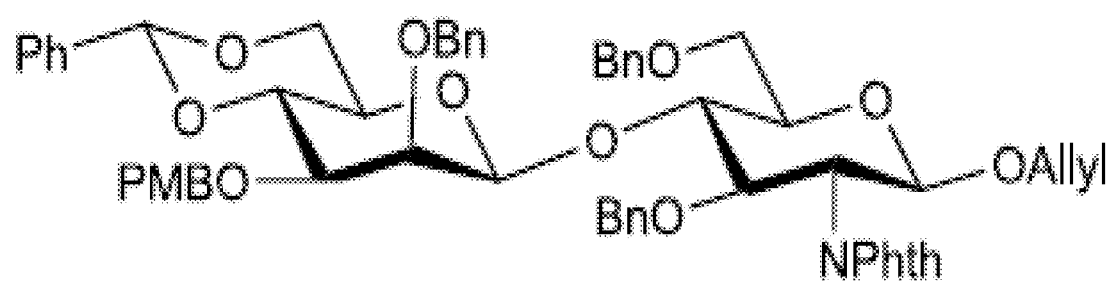

FIG. 119 Exemplary structure embodiments and synthetic scheme embodiments of the present disclosure.

Figure 120:
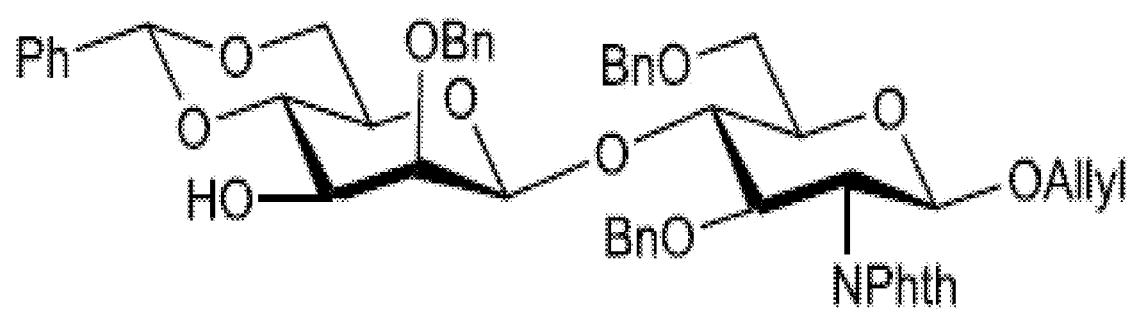

FIG. 120 Exemplary structure embodiments and synthetic scheme embodiments of the present disclosure.

Figure 121:
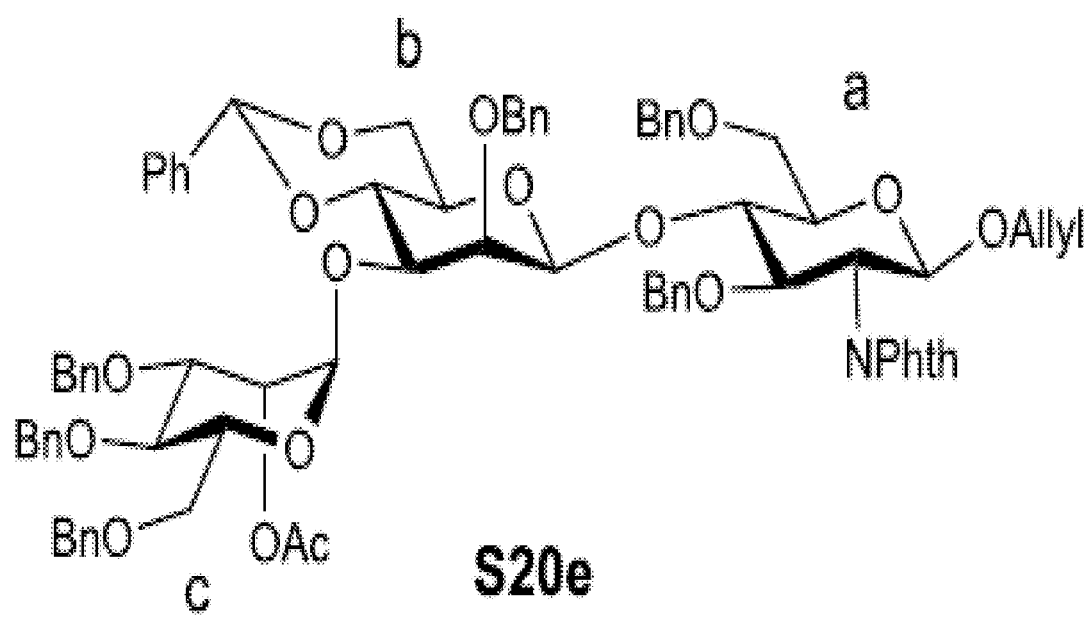

FIG. 121 Exemplary structure embodiments and synthetic scheme embodiments of the present disclosure.

Figure 122:
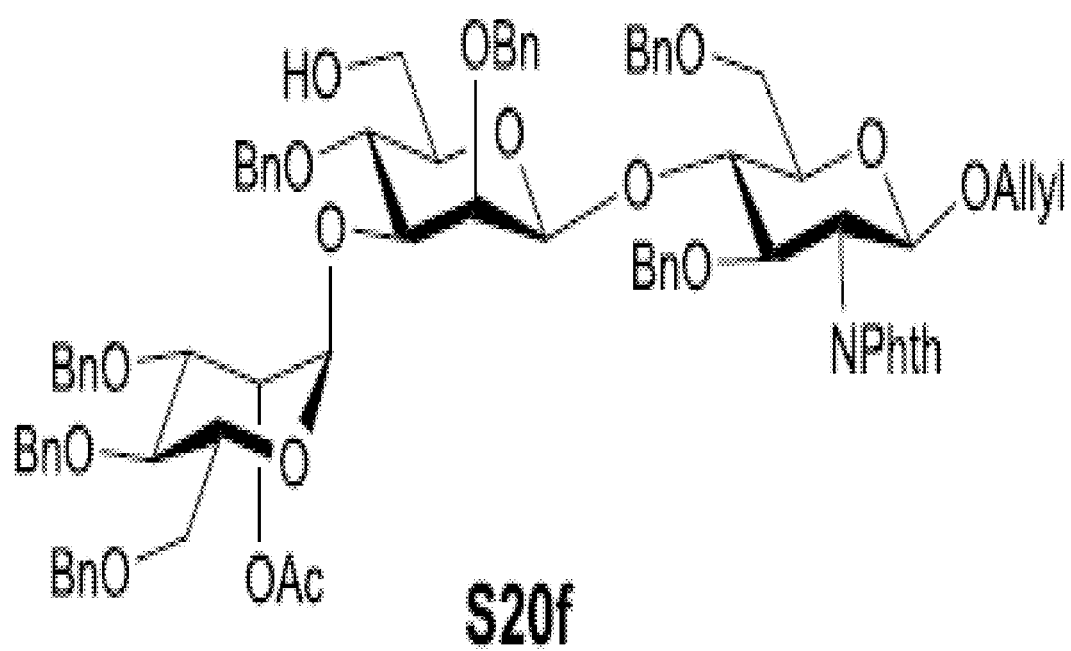

FIG. 122 Exemplary structure embodiments and synthetic scheme embodiments of the present disclosure.

Figure 123:
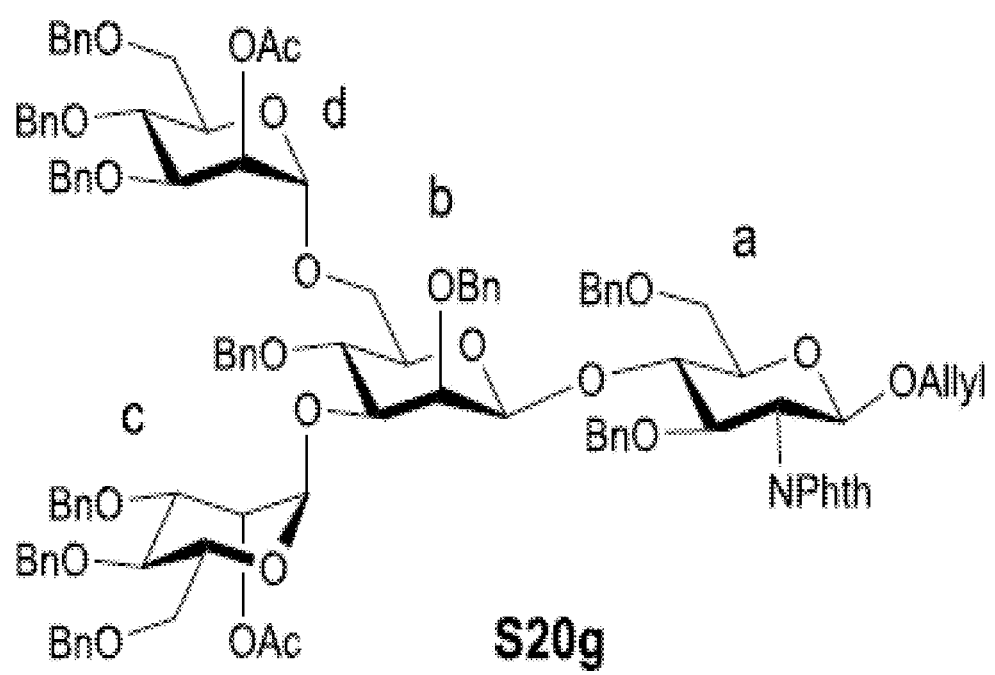

FIG. 123 Exemplary structure embodiments and synthetic scheme embodiments of the present disclosure.

Figure 124:
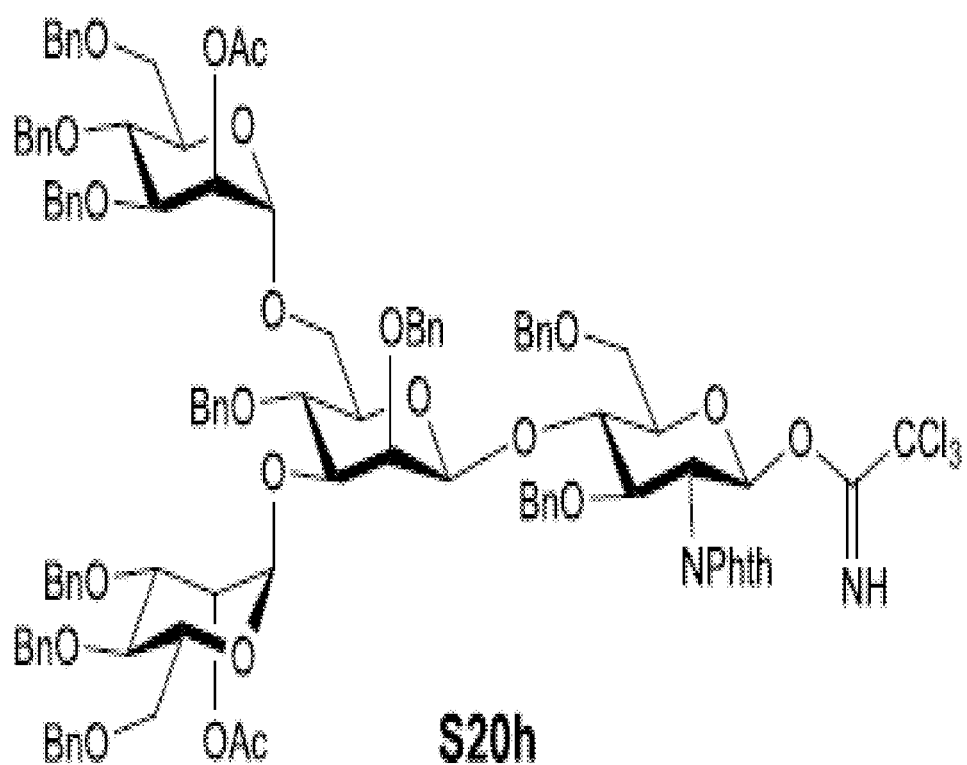

FIG. 124 Exemplary structure embodiments and synthetic scheme embodiments of the present disclosure.

Figure 125:
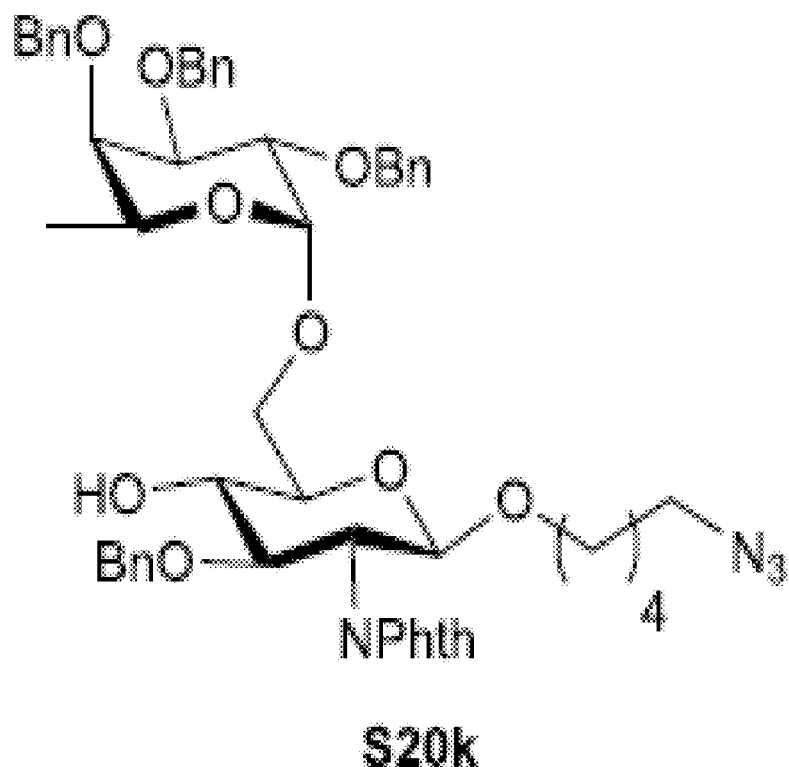

FIG. 125 Exemplary structure embodiments and synthetic scheme embodiments of the present disclosure.

Figure 126:
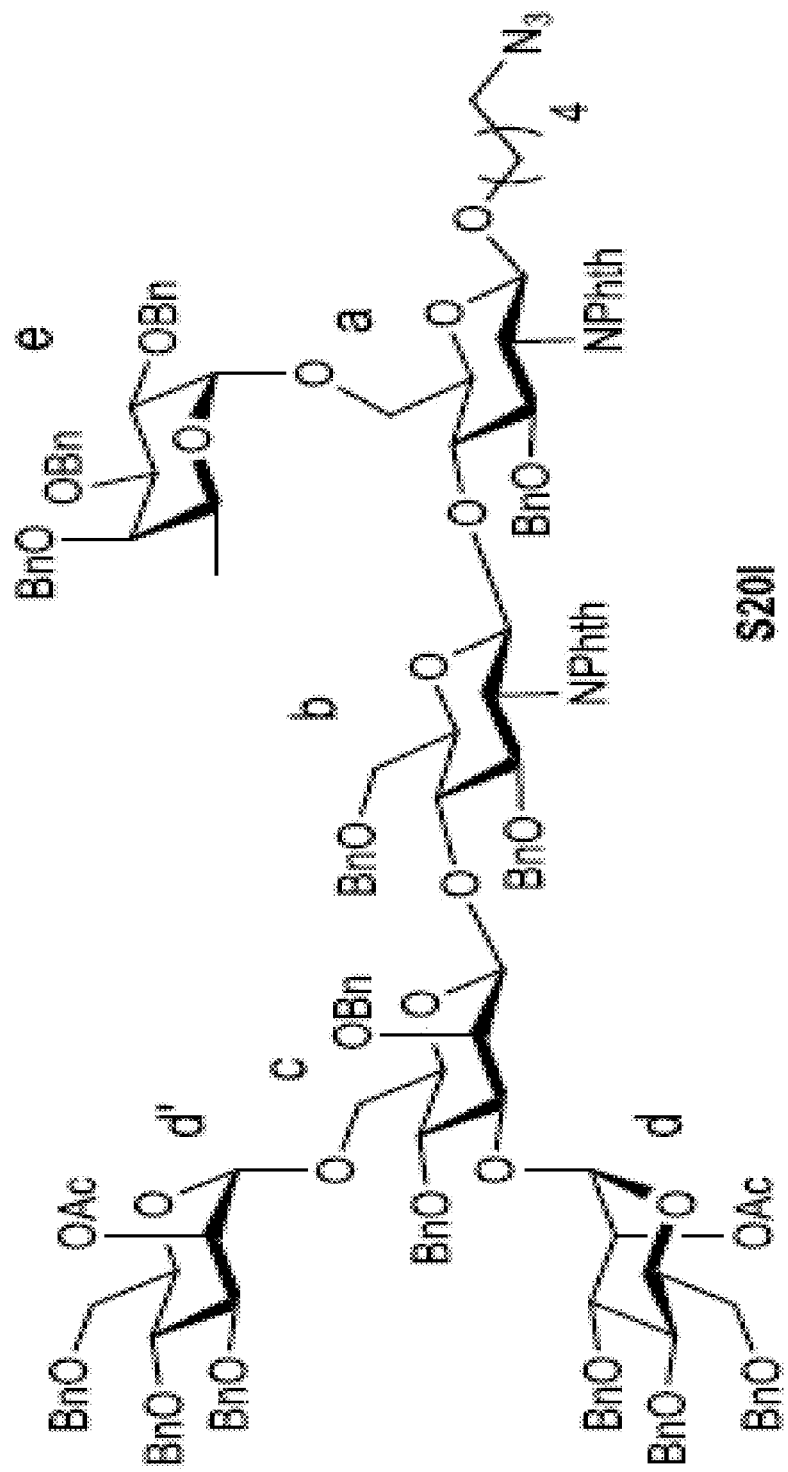

FIG. 126 Exemplary structure embodiments and synthetic scheme embodiments of the present disclosure.

Figure 127:
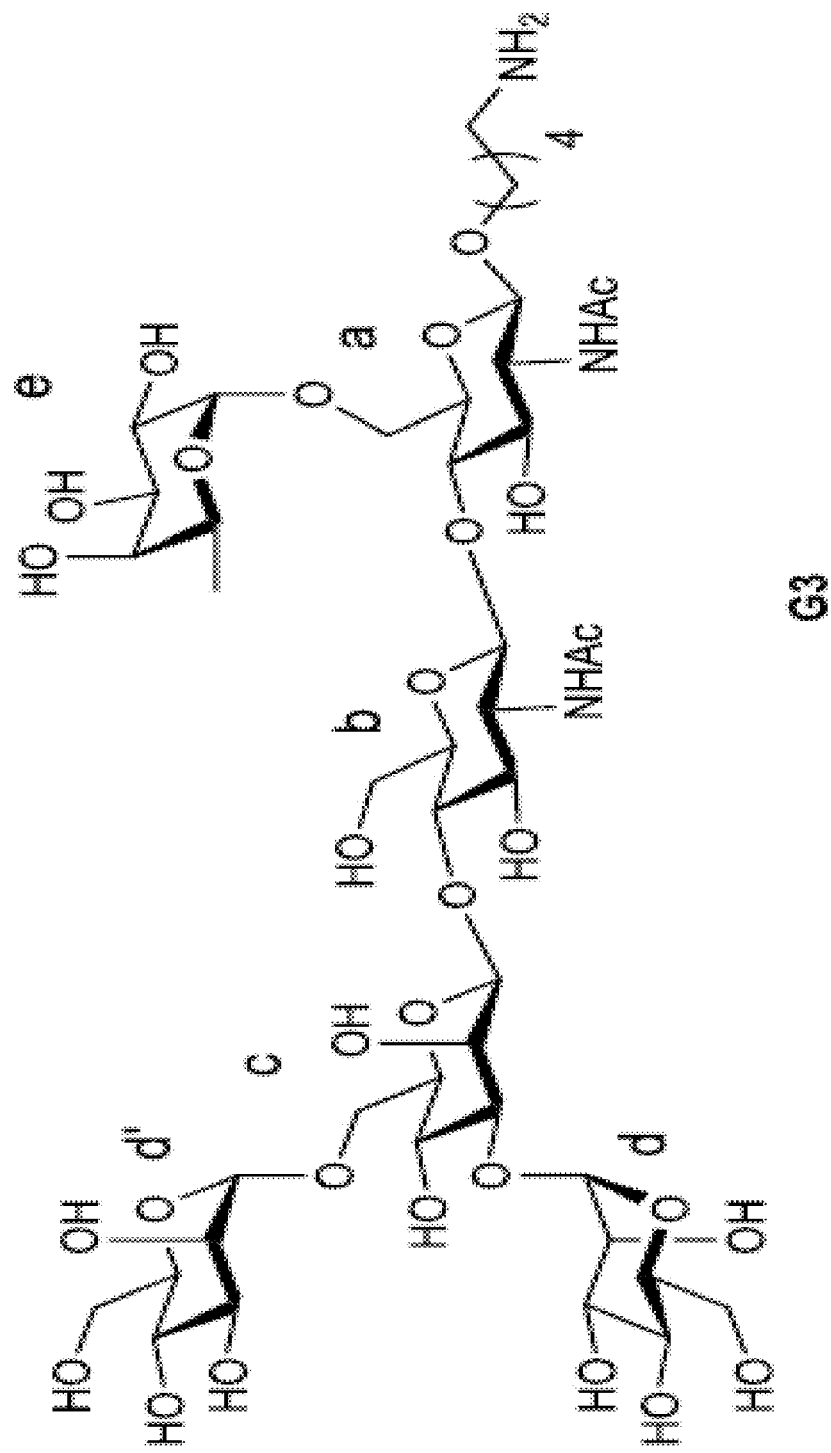

FIG. 127 Exemplary structure embodiments and synthetic scheme embodiments of the present disclosure.

Figure 128:
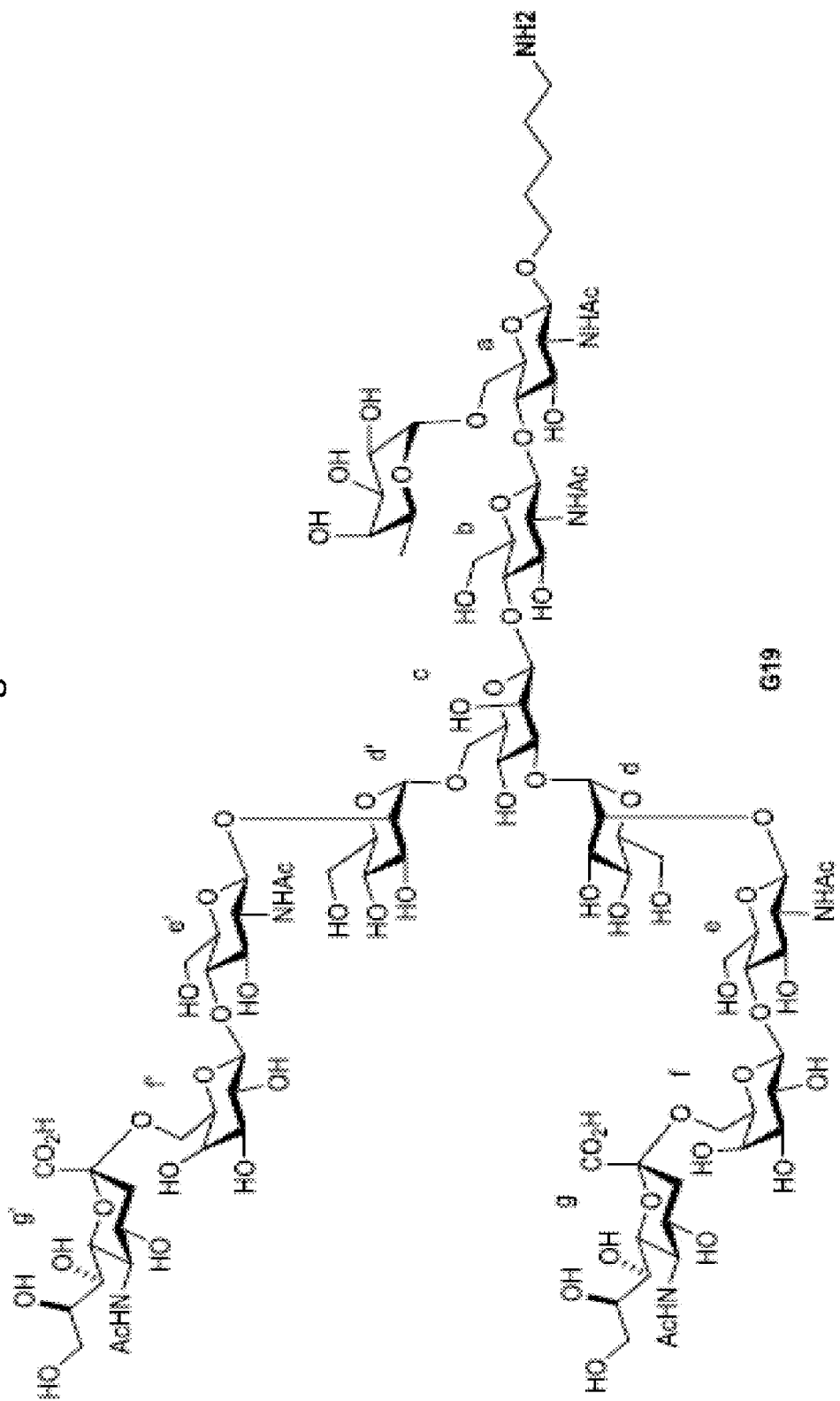

FIG. 128 Exemplary structure embodiments and synthetic scheme embodiments of the present disclosure.

Figure 129:
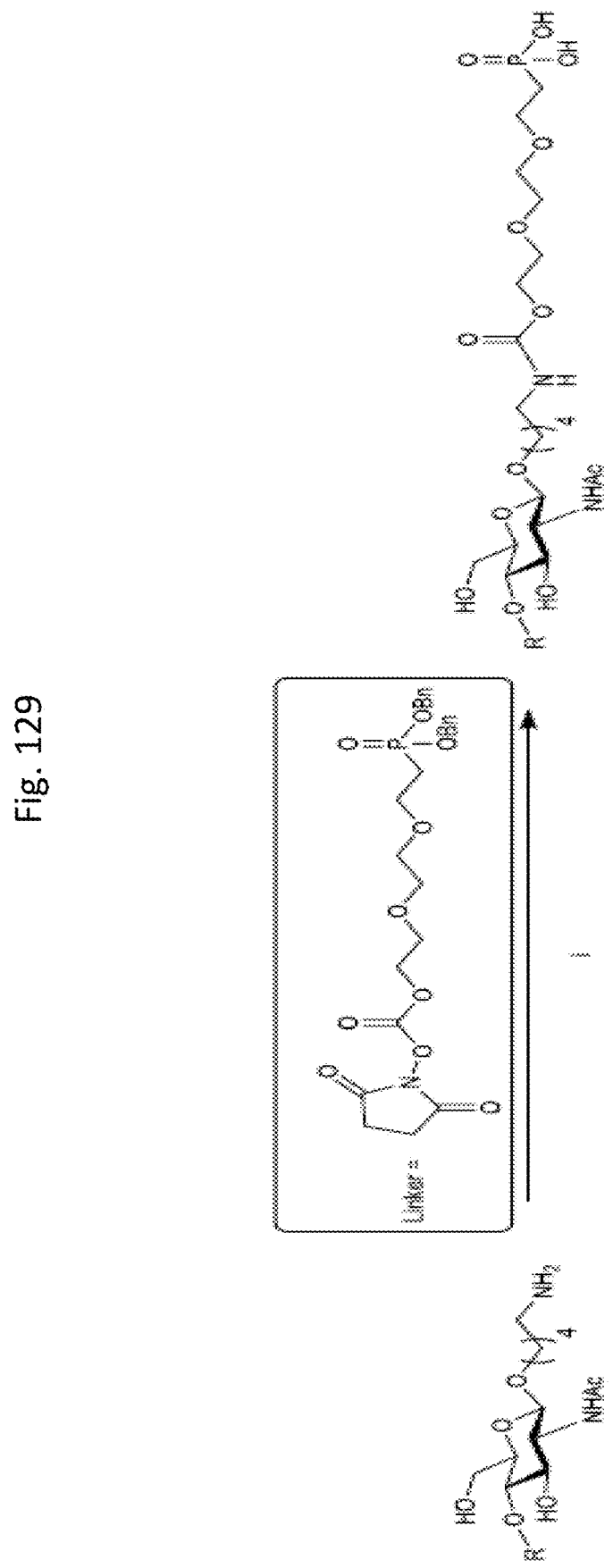

FIG. 129 Exemplary structure embodiments and synthetic scheme embodiments of the present disclosure.

Figure 130:
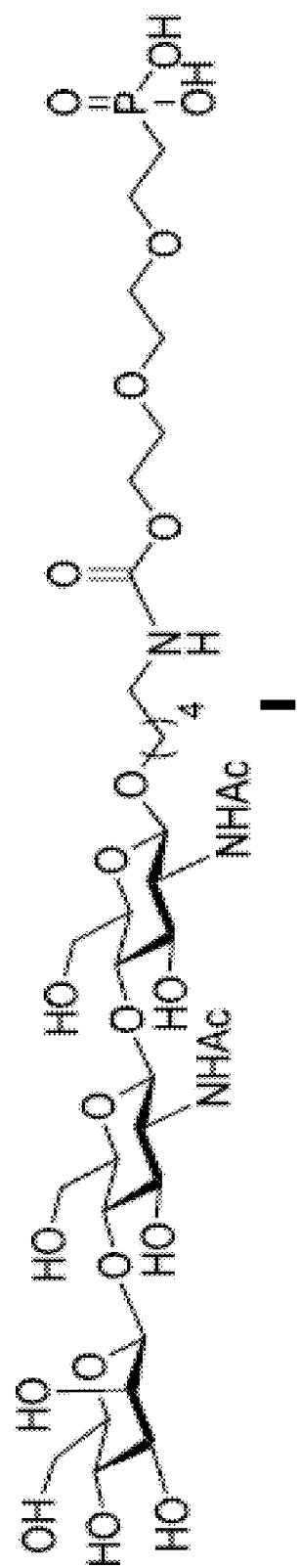

FIG. 130 Exemplary structure embodiments and synthetic scheme embodiments of the present disclosure.

Figure 131:
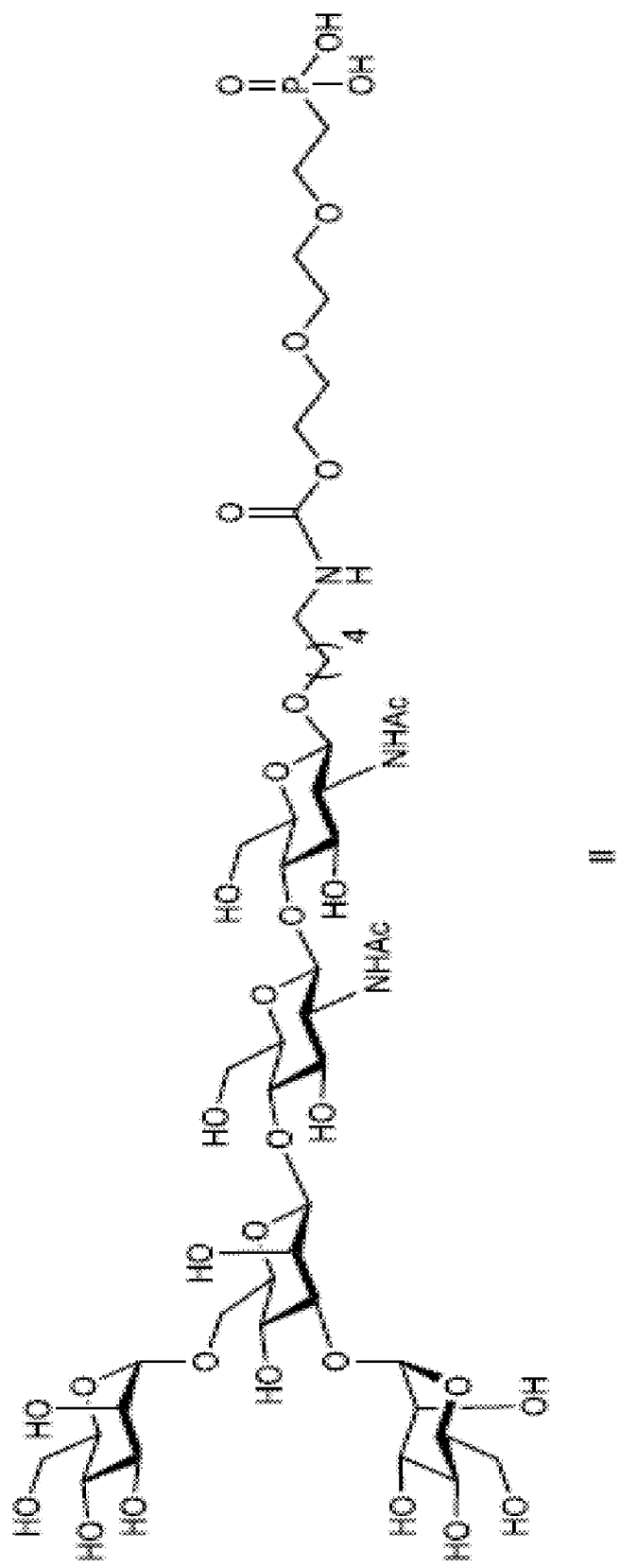

FIG. 131 Exemplary structure embodiments and synthetic scheme embodiments of the present disclosure.

Figure 132:
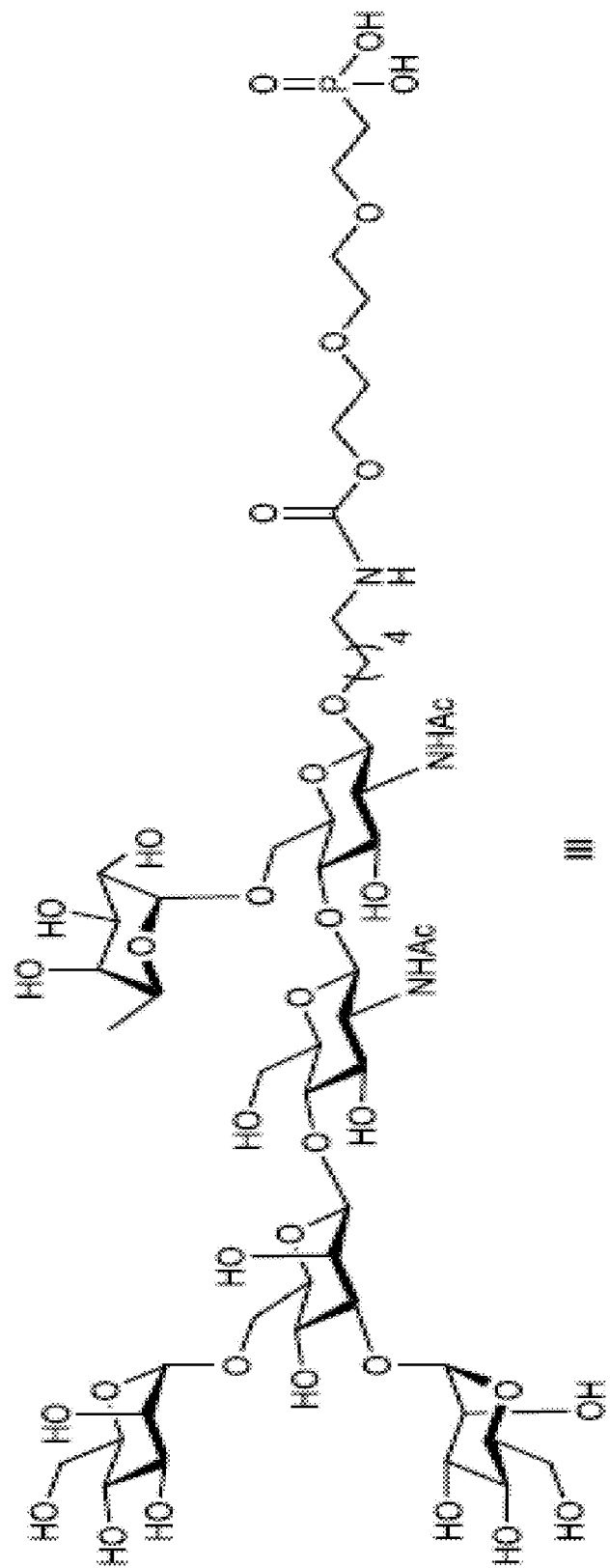

FIG. 132 Exemplary structure embodiments and synthetic scheme embodiments of the present disclosure.

Figure 133:
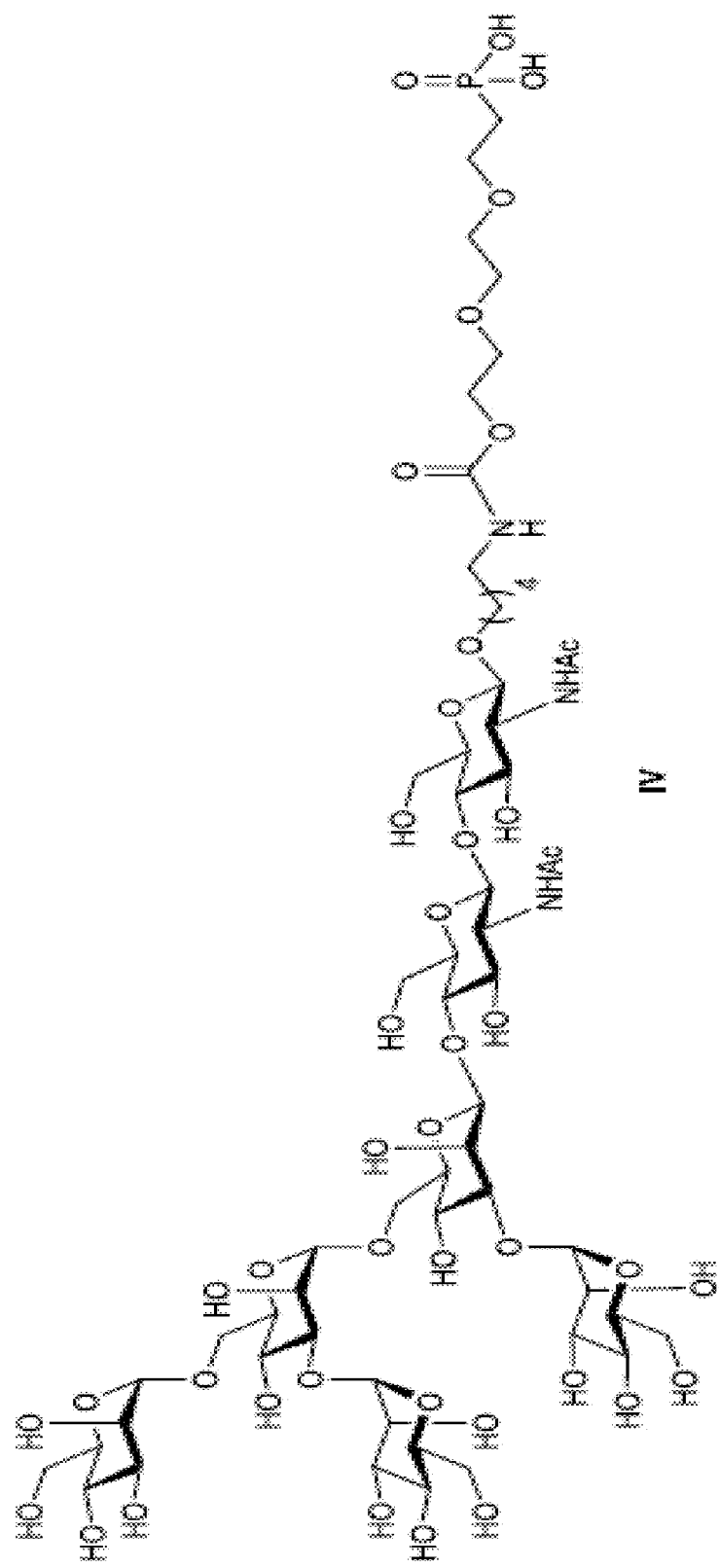

FIG. 133 Exemplary structure embodiments and synthetic scheme embodiments of the present disclosure.

Figure 134:
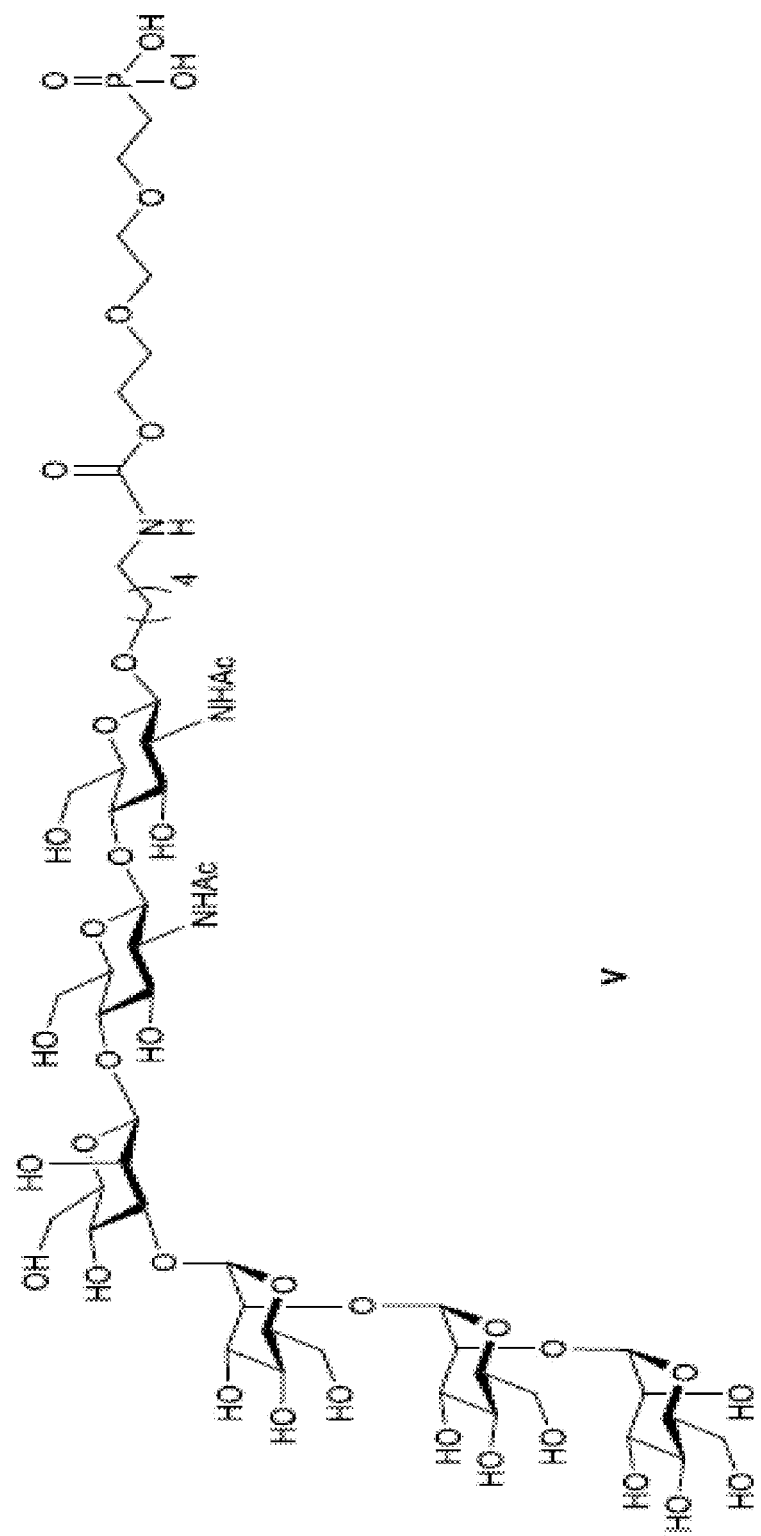

FIG. 134 Exemplary structure embodiments and synthetic scheme embodiments of the present disclosure.

Figure 135:
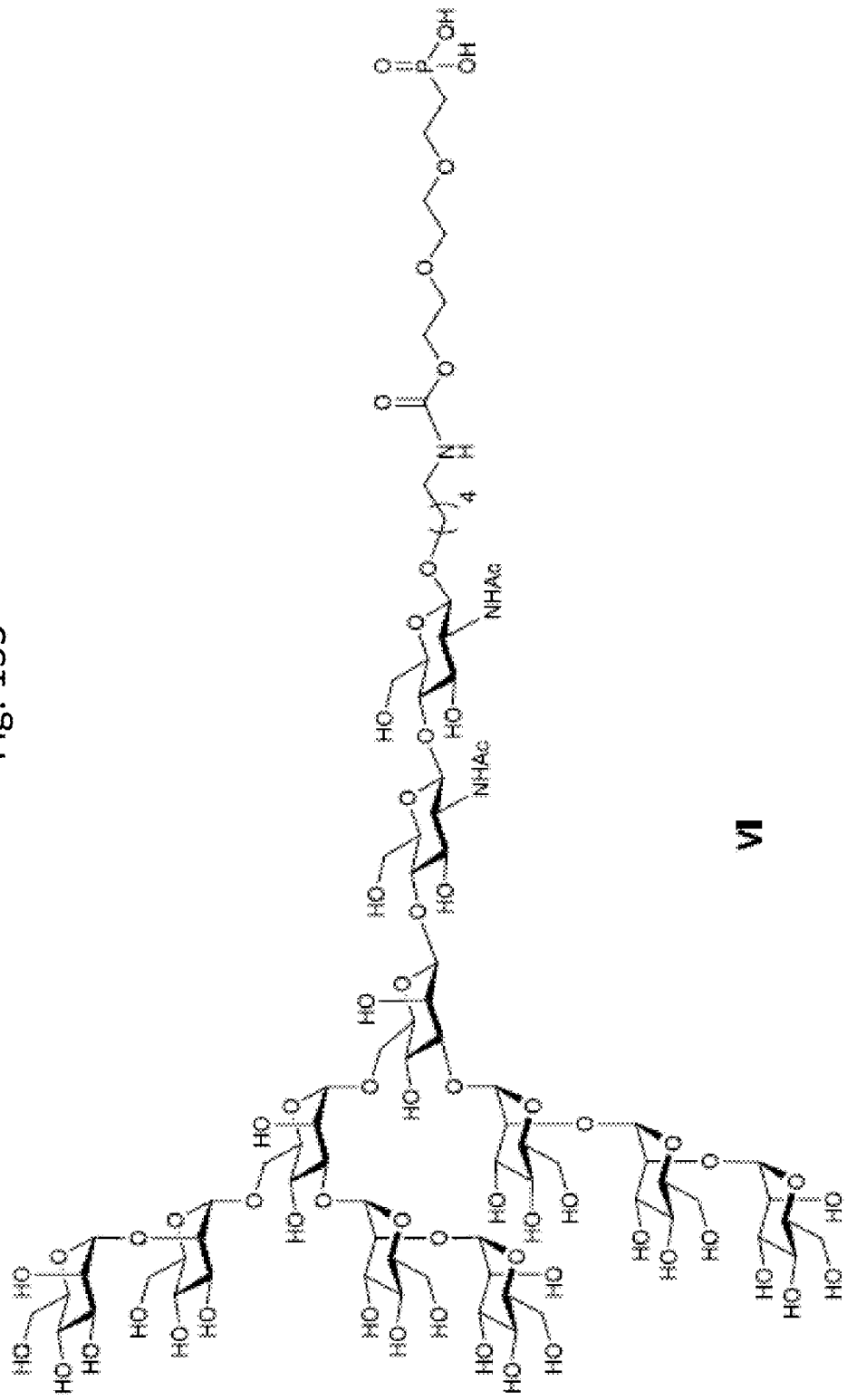

FIG. 135 Exemplary structure embodiments and synthetic scheme embodiments of the present disclosure.

Figure 136:
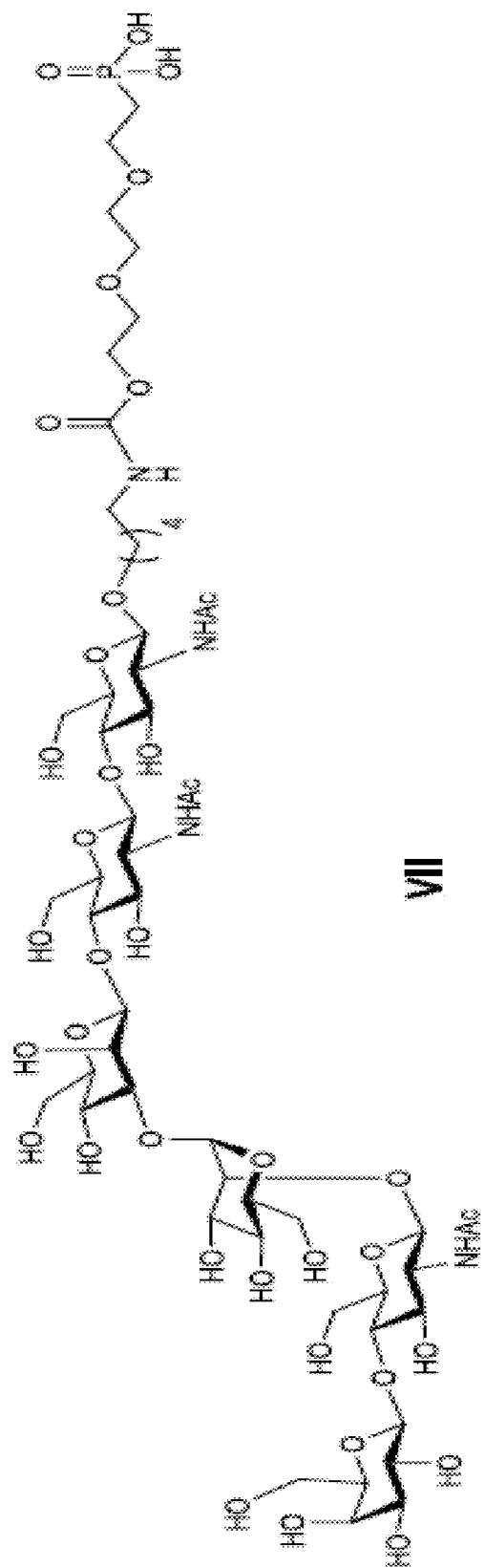

FIG. 136 Exemplary structure embodiments and synthetic scheme embodiments of the present disclosure.

Figure 137:
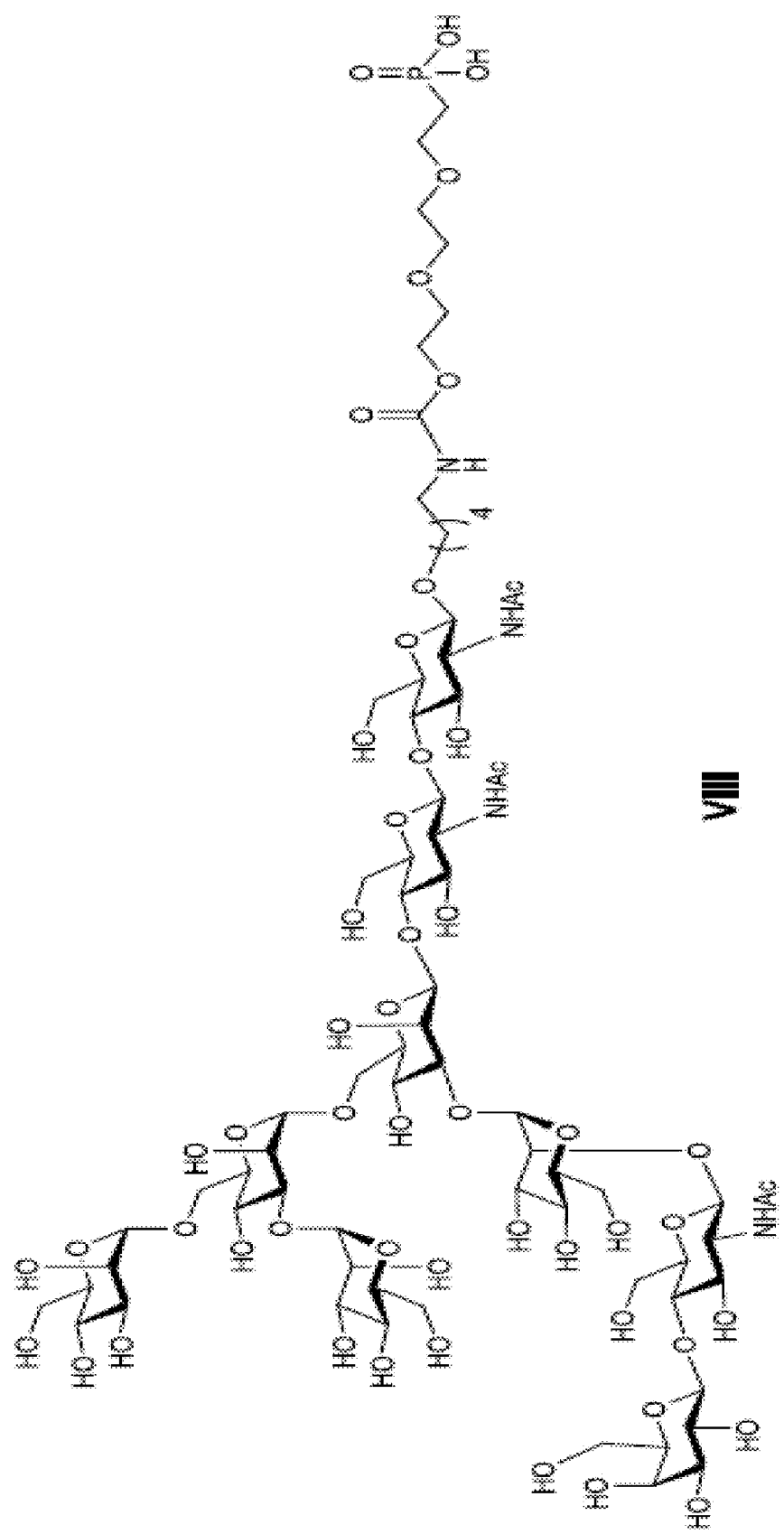

FIG. 137 Exemplary structure embodiments and synthetic scheme embodiments of the present disclosure.

Figure 138:
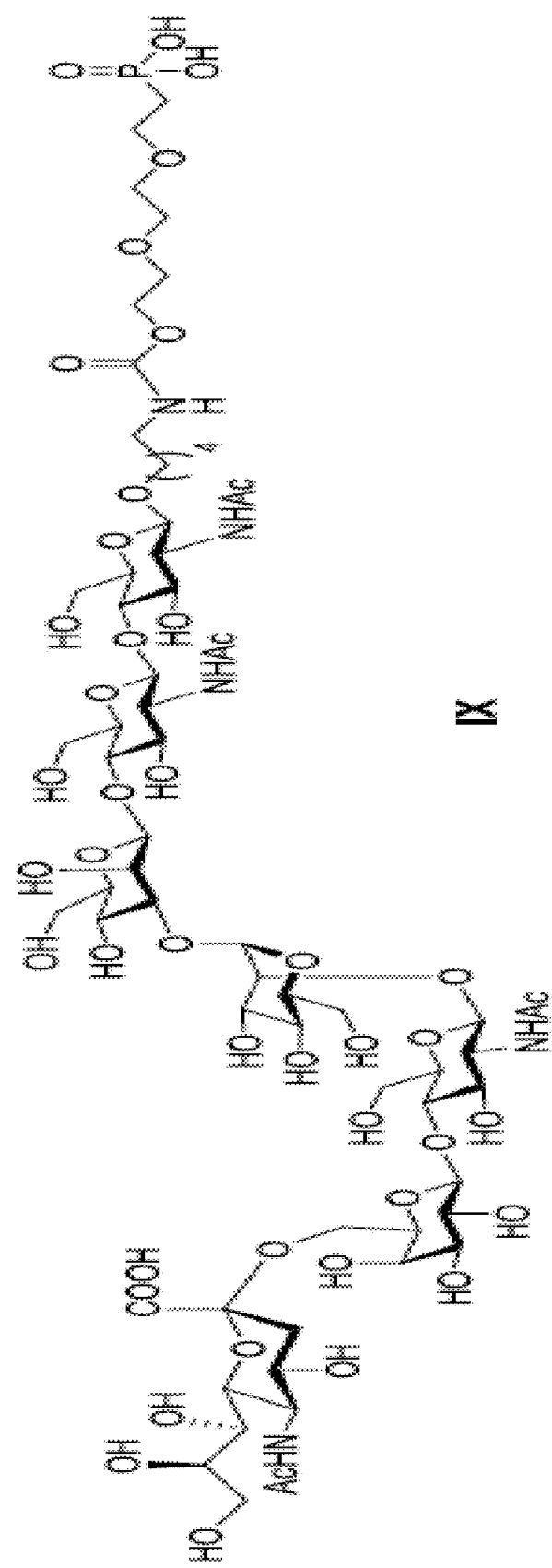

FIG. 138 Exemplary structure embodiments and synthetic scheme embodiments of the present disclosure.

Figure 139:
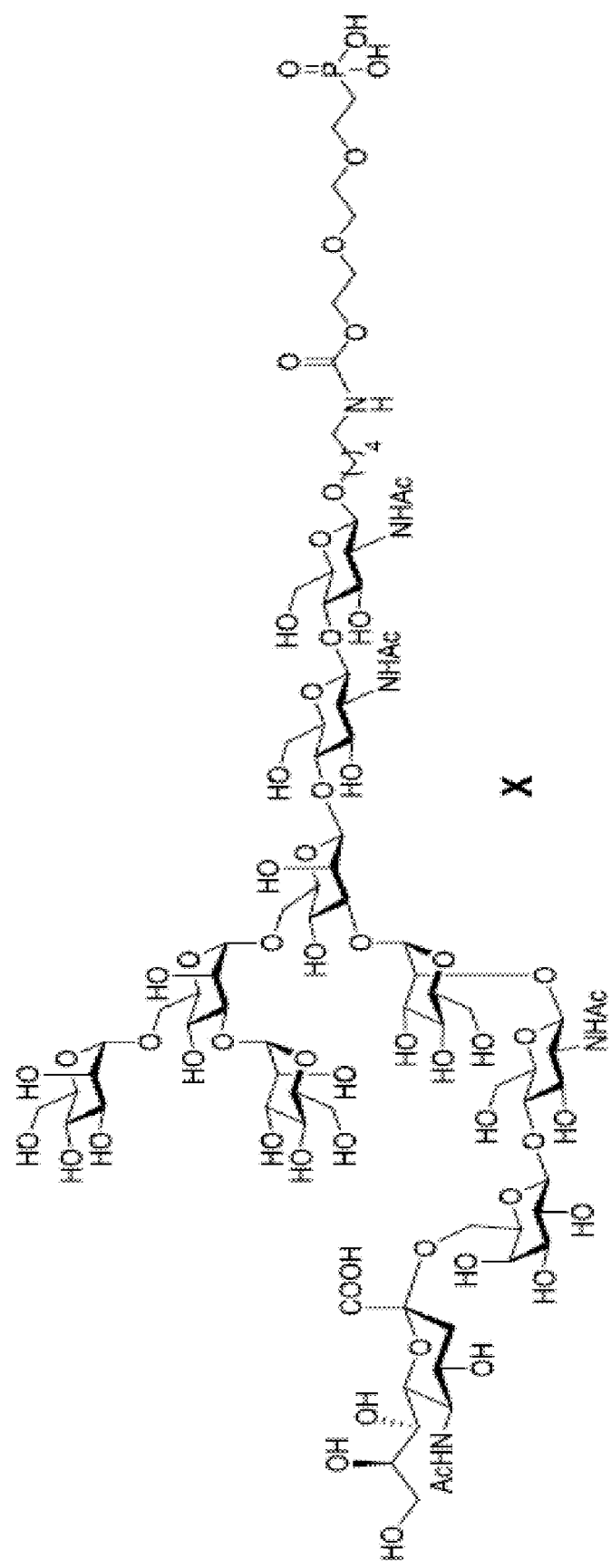

FIG. 139 Exemplary structure embodiments and synthetic scheme embodiments of the present disclosure.

Figure 140:
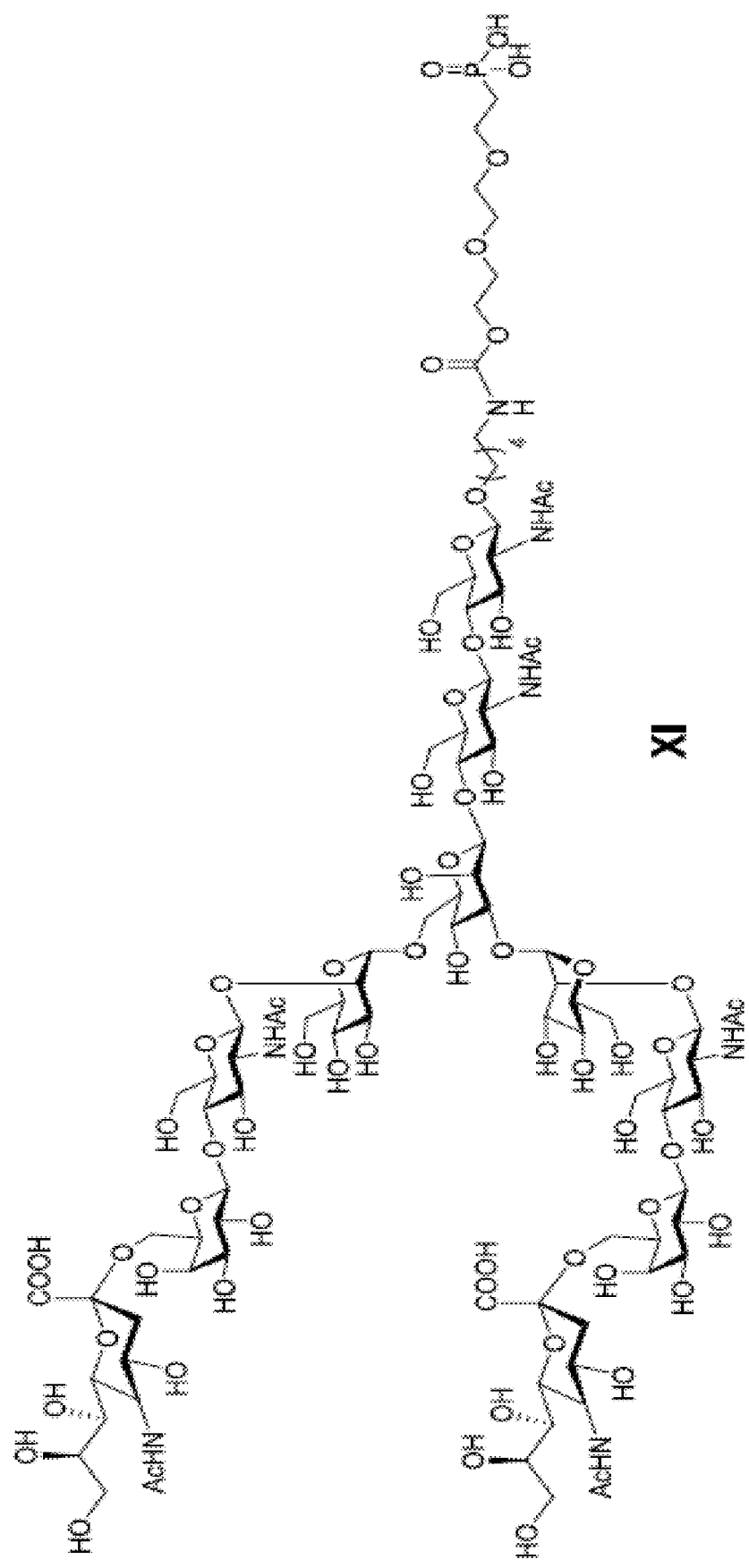

FIG. 140 Exemplary structure embodiments and synthetic scheme embodiments of the present disclosure.

Figure 141:
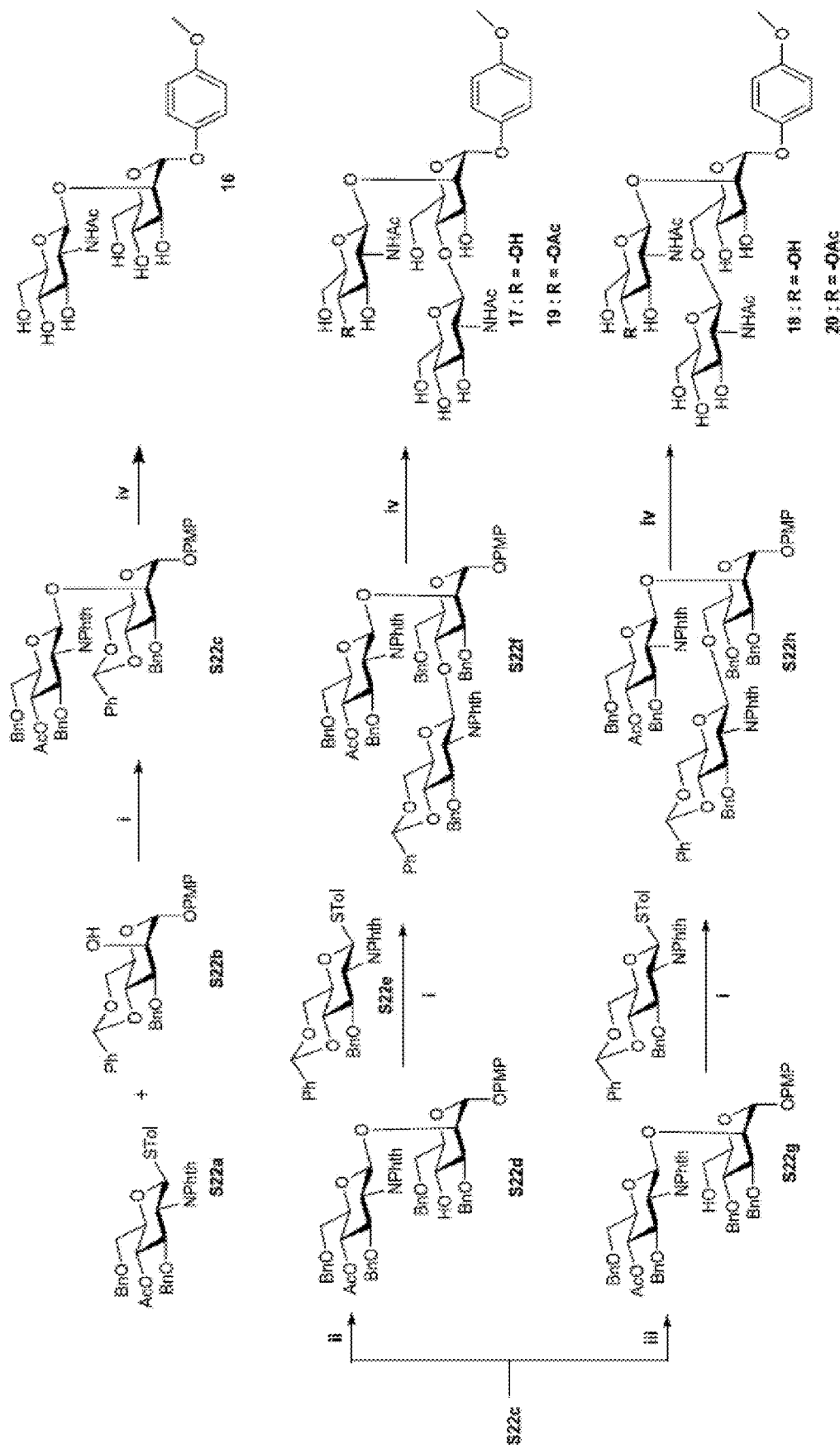

FIG. 141 Exemplary structure embodiments and synthetic scheme embodiments of the present disclosure.

Figure 142:
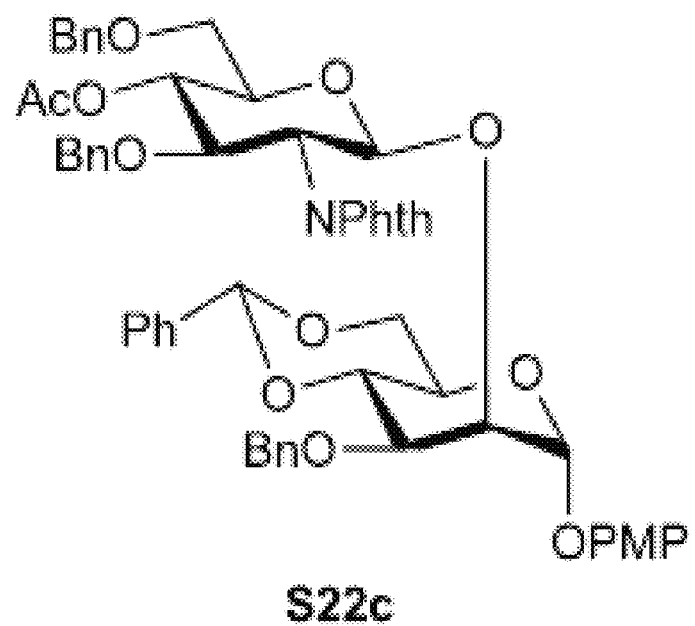

FIG. 142 Exemplary structure embodiments and synthetic scheme embodiments of the present disclosure.

Figure 143:
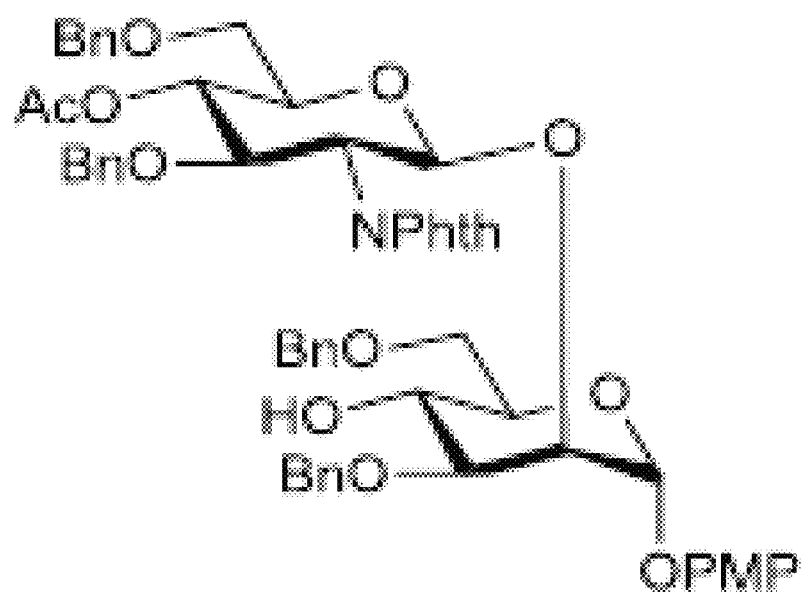

FIG. 143 Exemplary structure embodiments and synthetic scheme embodiments of the present disclosure.

Figure 144:
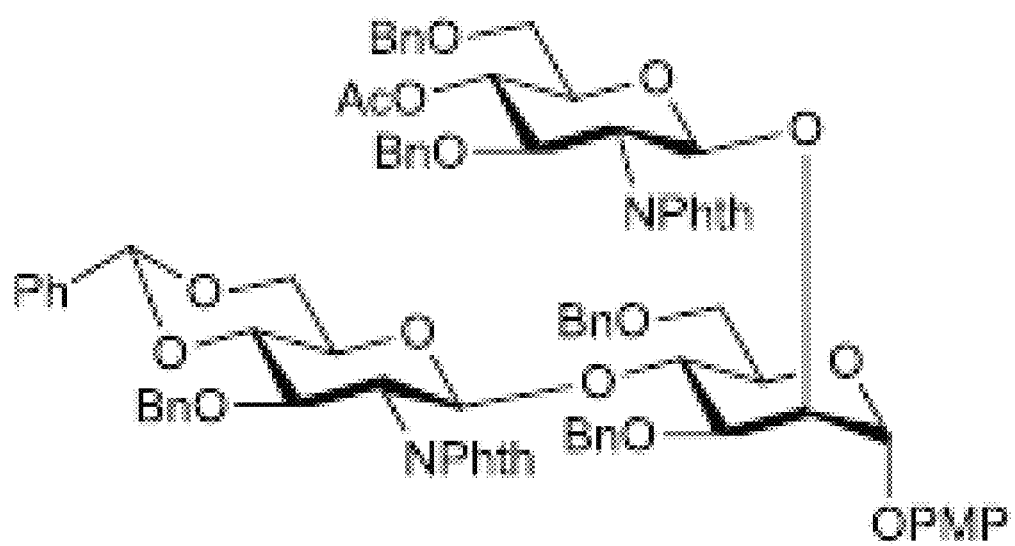

FIG. 144 Exemplary structure embodiments and synthetic scheme embodiments of the present disclosure.

Figure 145:
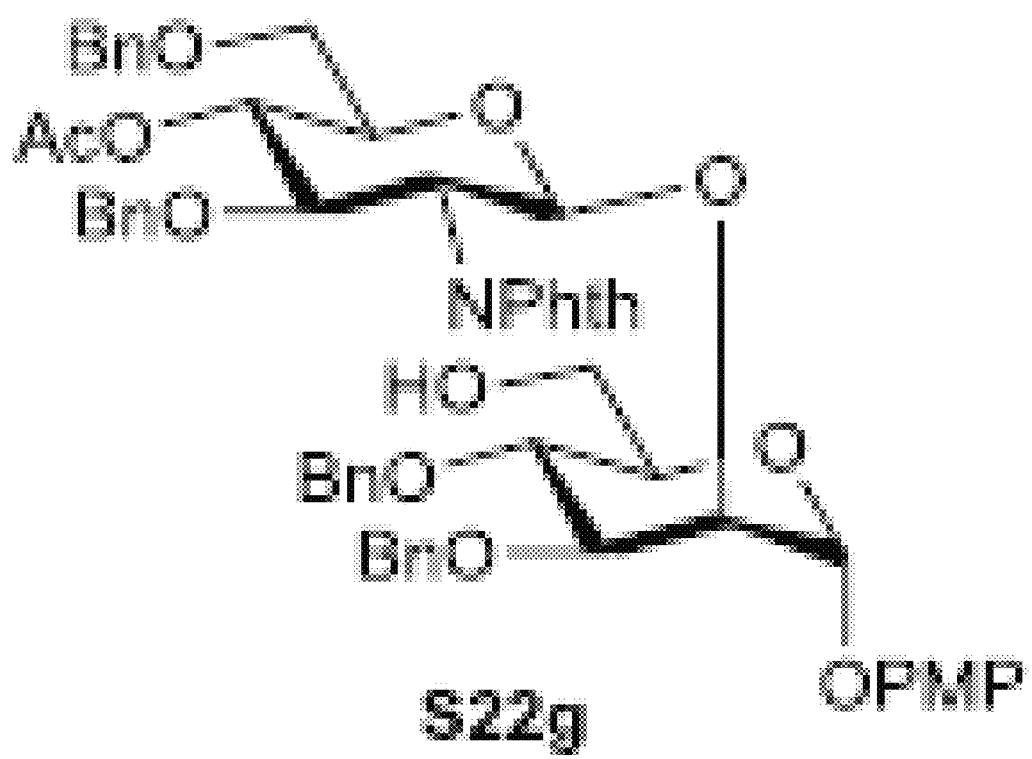

FIG. 145 Exemplary structure embodiments and synthetic scheme embodiments of the present disclosure.

Figure 146:
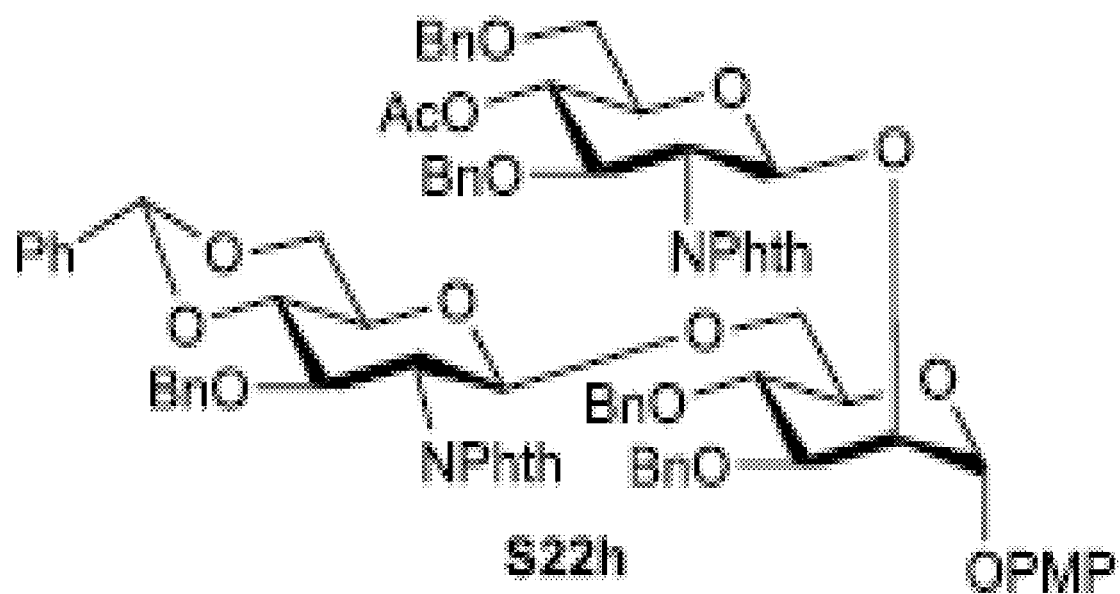

FIG. 146 Exemplary structure embodiments and synthetic scheme embodiments of the present disclosure.

Figure 147:
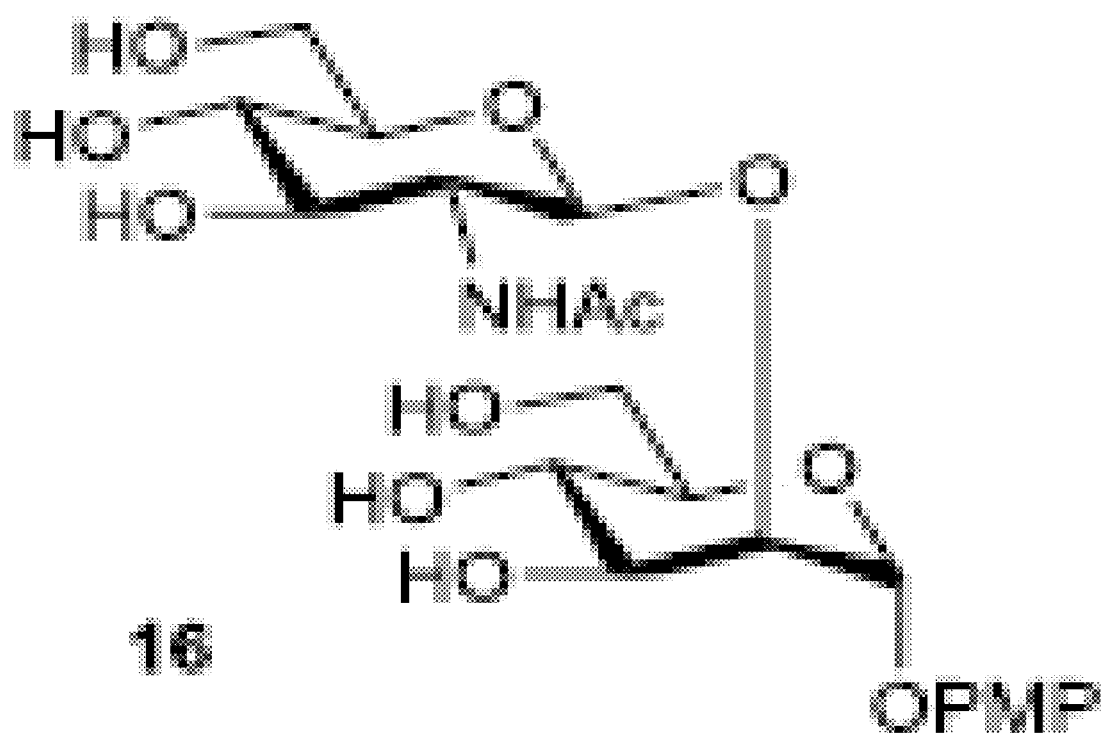

FIG. 147 Exemplary structure embodiments and synthetic scheme embodiments of the present disclosure.

Figure 148:
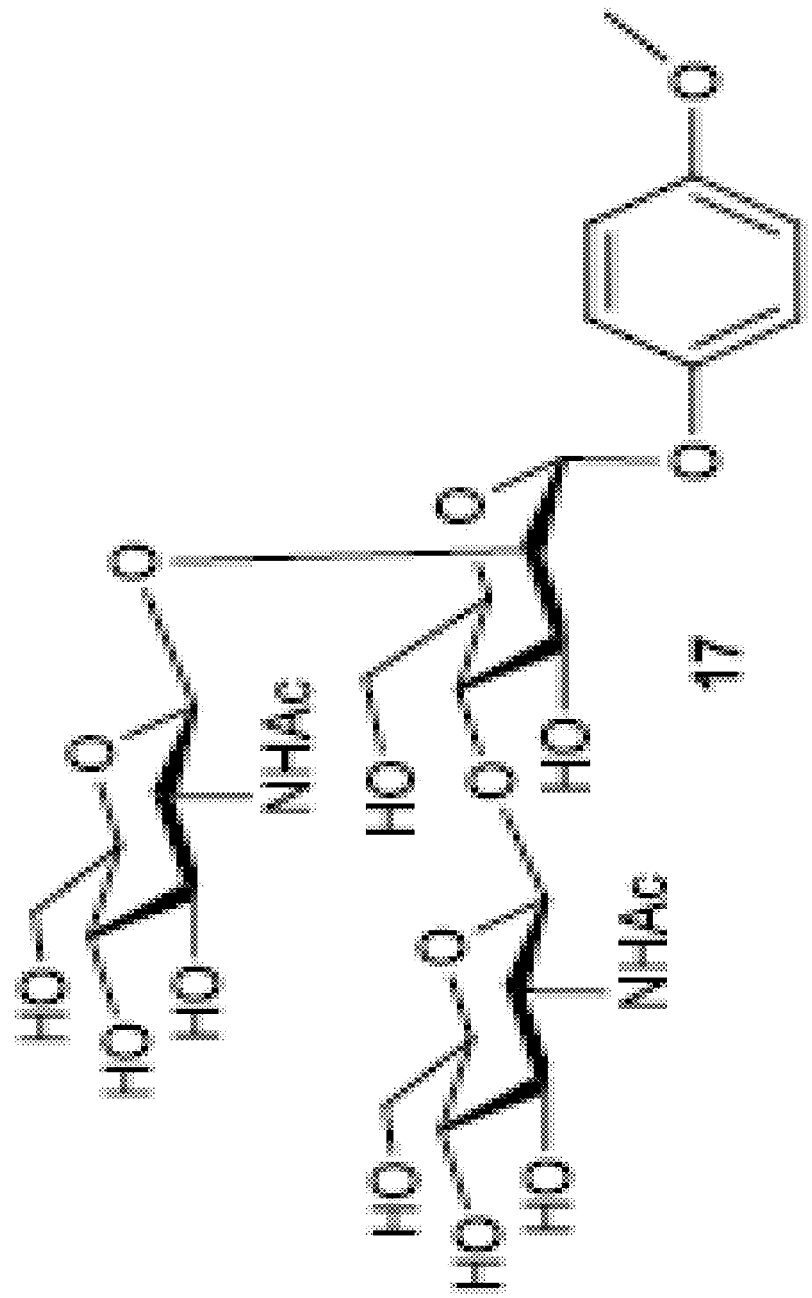

FIG. 148 Exemplary structure embodiments and synthetic scheme embodiments of the present disclosure.

Figure 149:
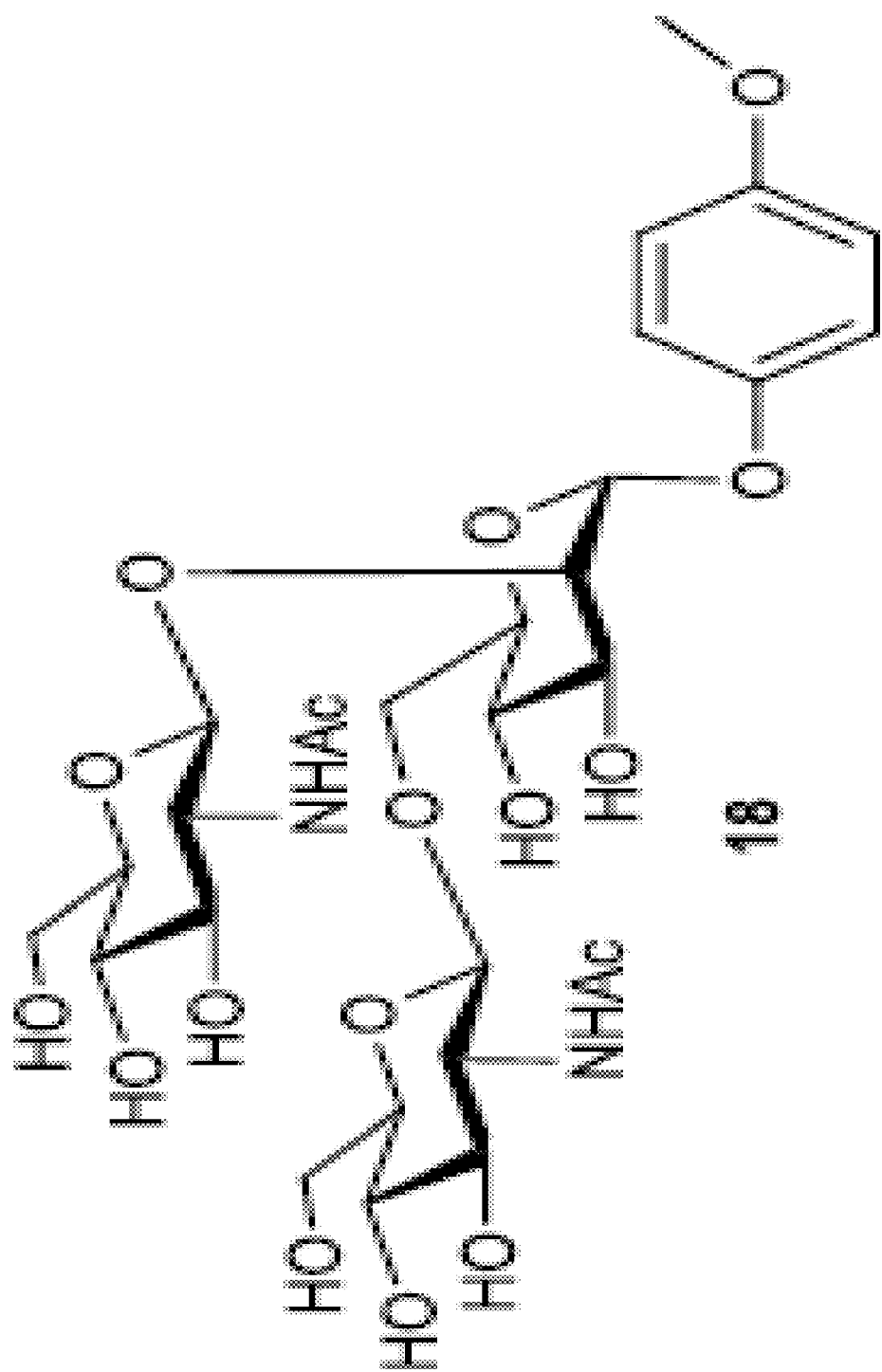

FIG. 149 Exemplary structure embodiments and synthetic scheme embodiments of the present disclosure.

Figure 150:
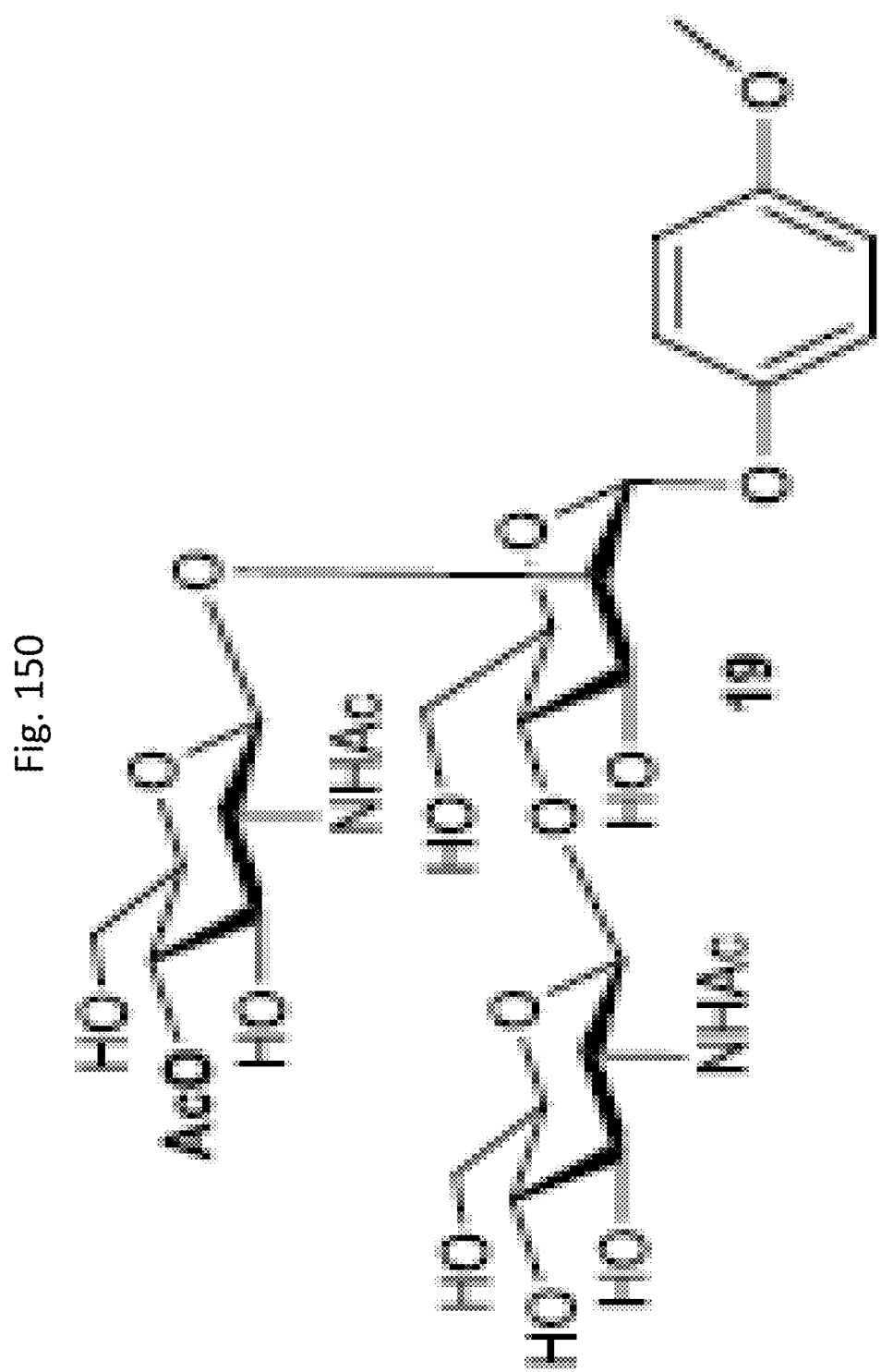

FIG. 150 Exemplary structure embodiments and synthetic scheme embodiments of the present disclosure.

Figure 151:
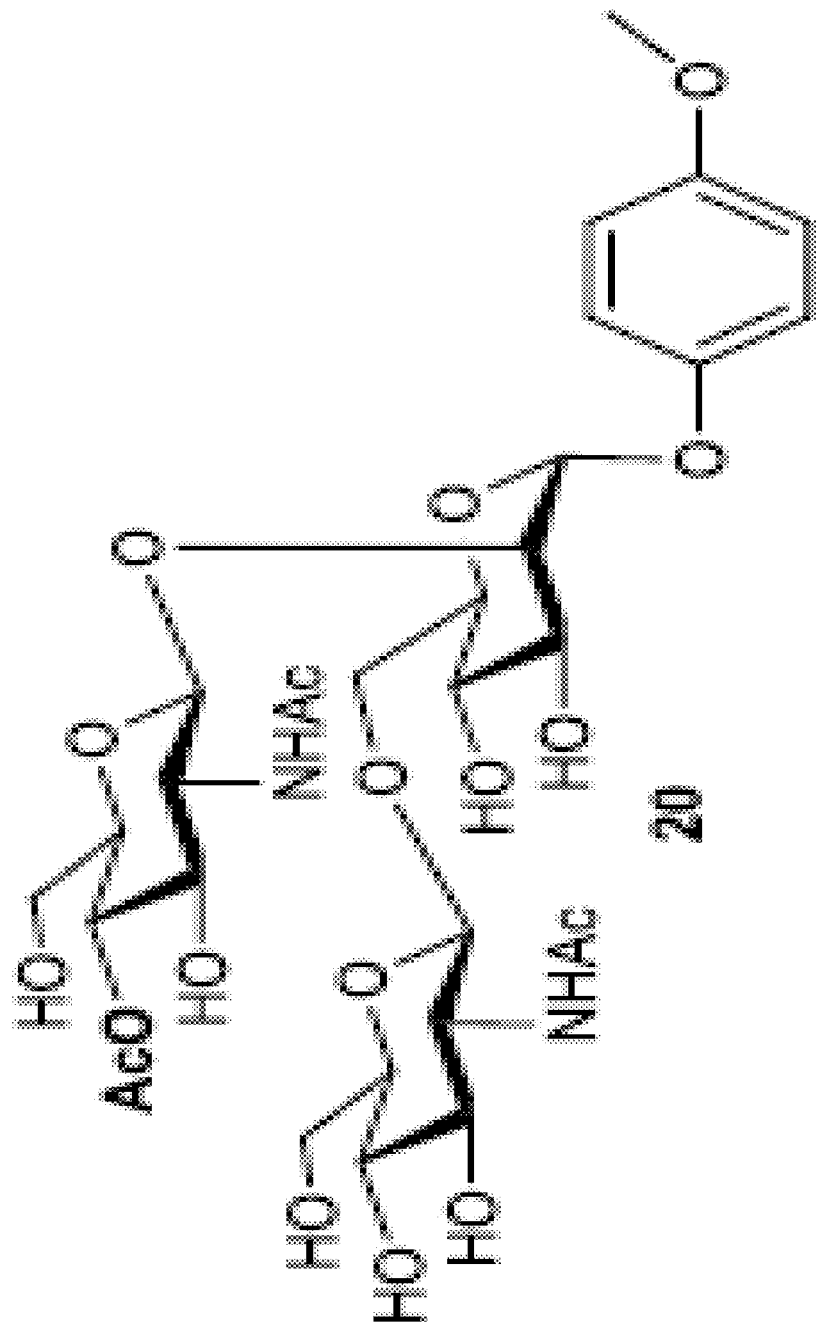

FIG. 151 Exemplary structure embodiments and synthetic scheme embodiments of the present disclosure.

Figure 152:
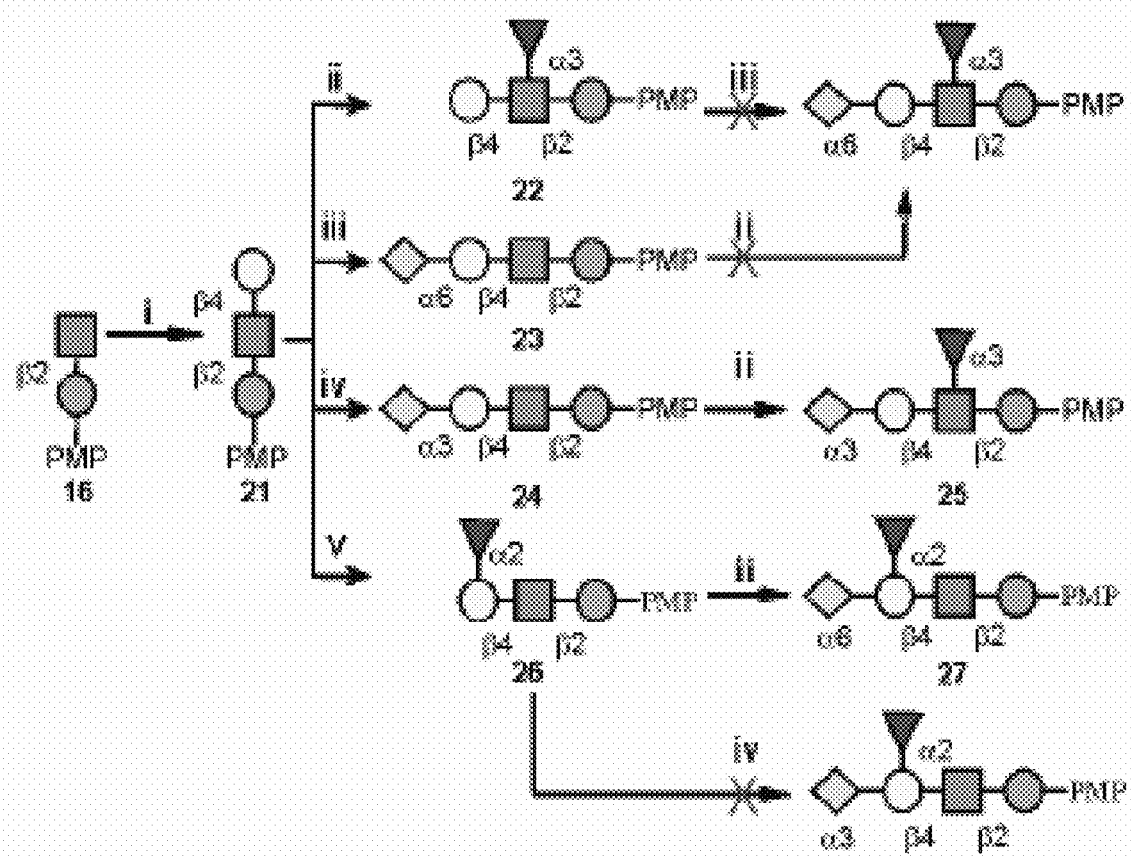

FIG. 152 Scheme S23|Exemplary Preparation scheme of linear modules.

Figure 153:
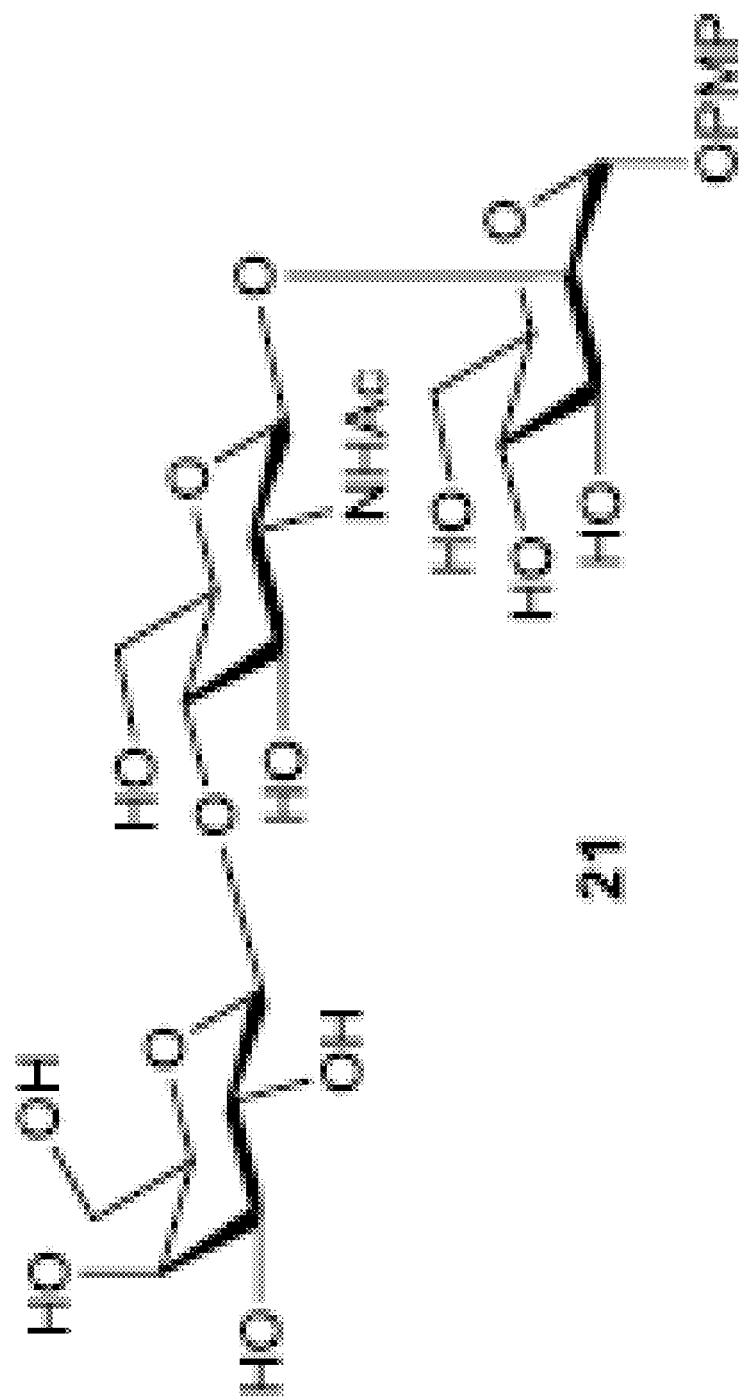

FIG. 153 Exemplary structure embodiments and synthetic scheme embodiments of the present disclosure.

Figure 154:
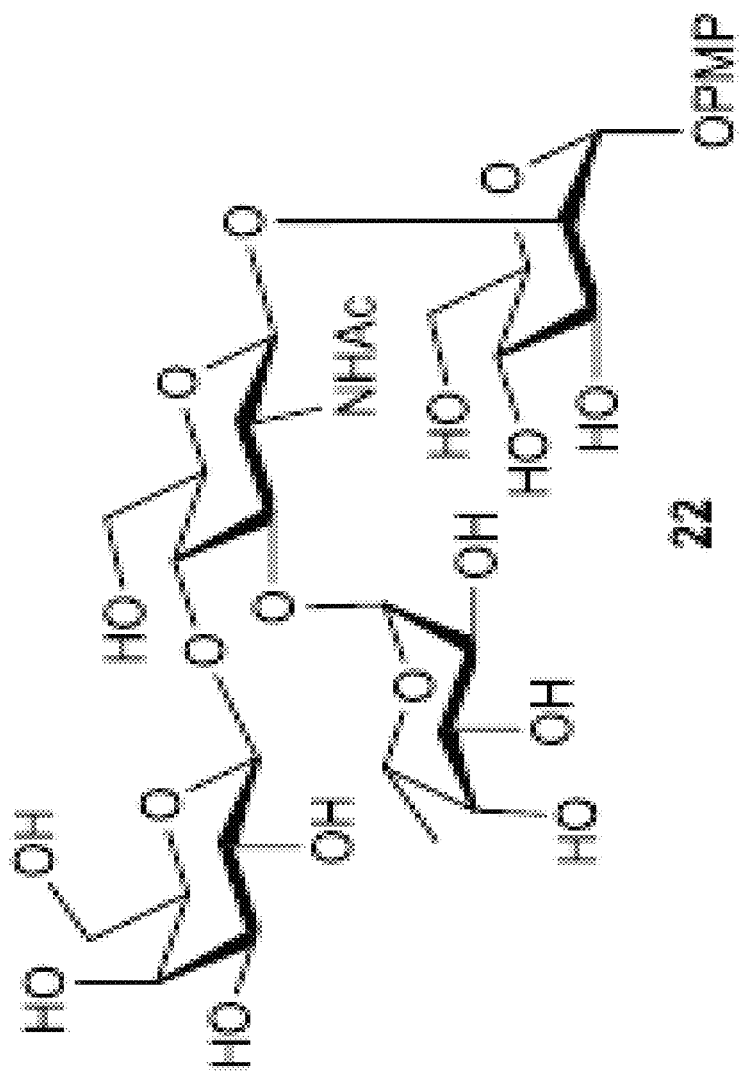

FIG. 154 Exemplary structure embodiments and synthetic scheme embodiments of the present disclosure.

Figure 155:
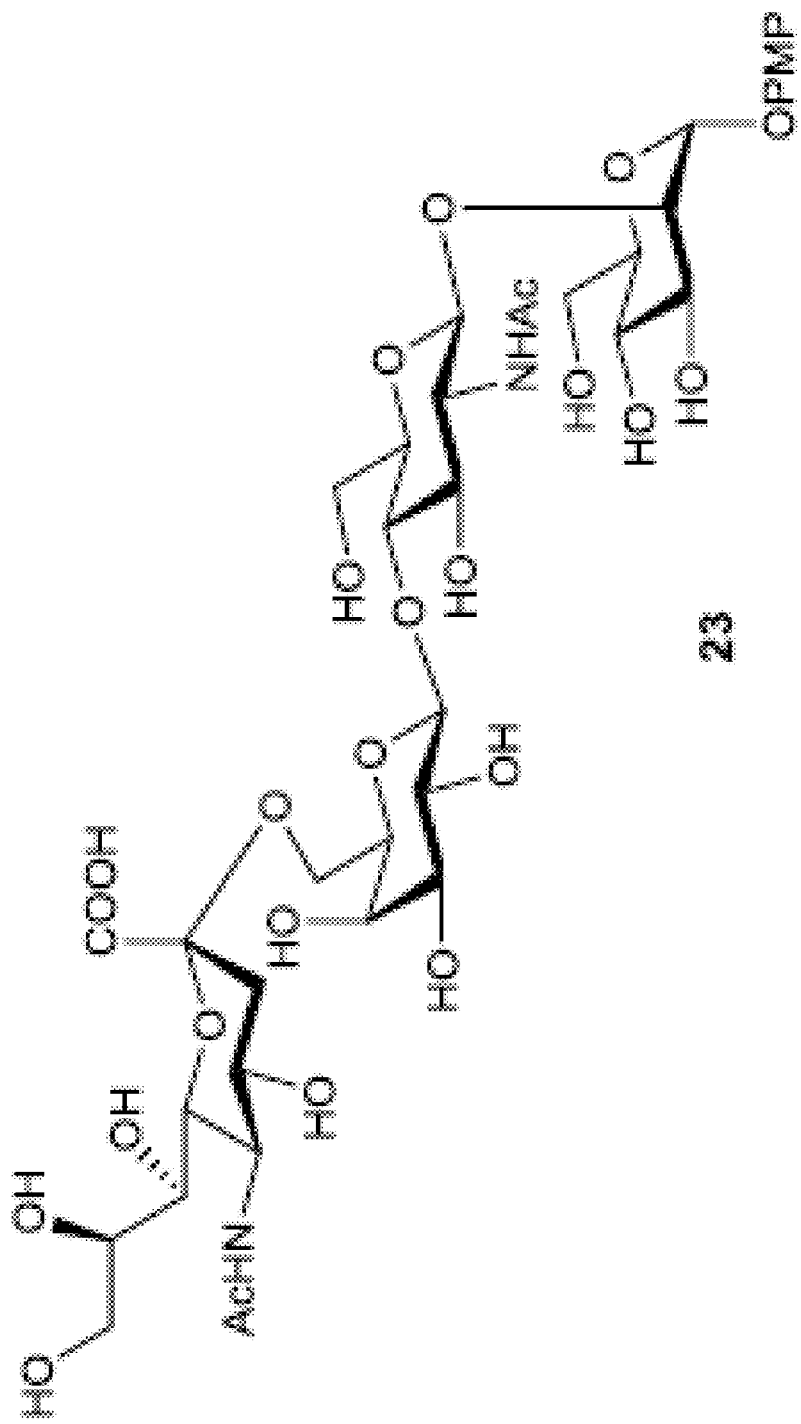

FIG. 155 Exemplary structure embodiments and synthetic scheme embodiments of the present disclosure.

Figure 156:
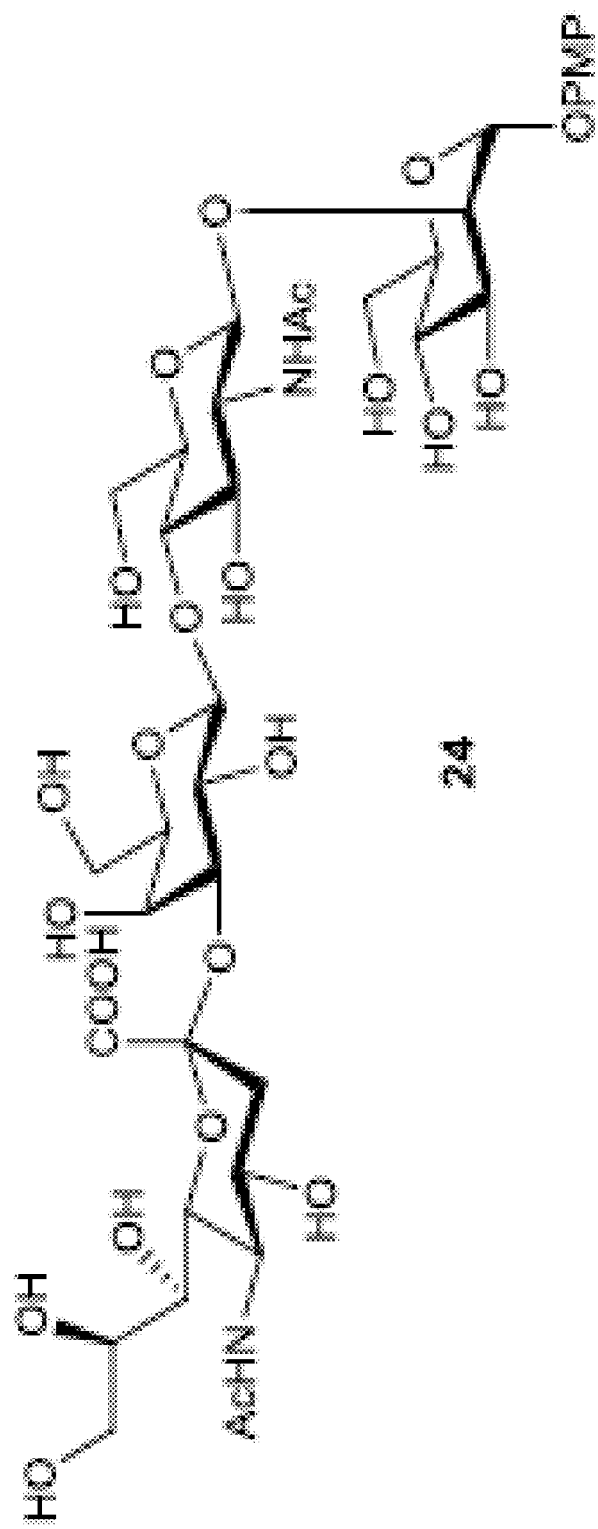

FIG. 156 Exemplary structure embodiments and synthetic scheme embodiments of the present disclosure.

Figure 157:
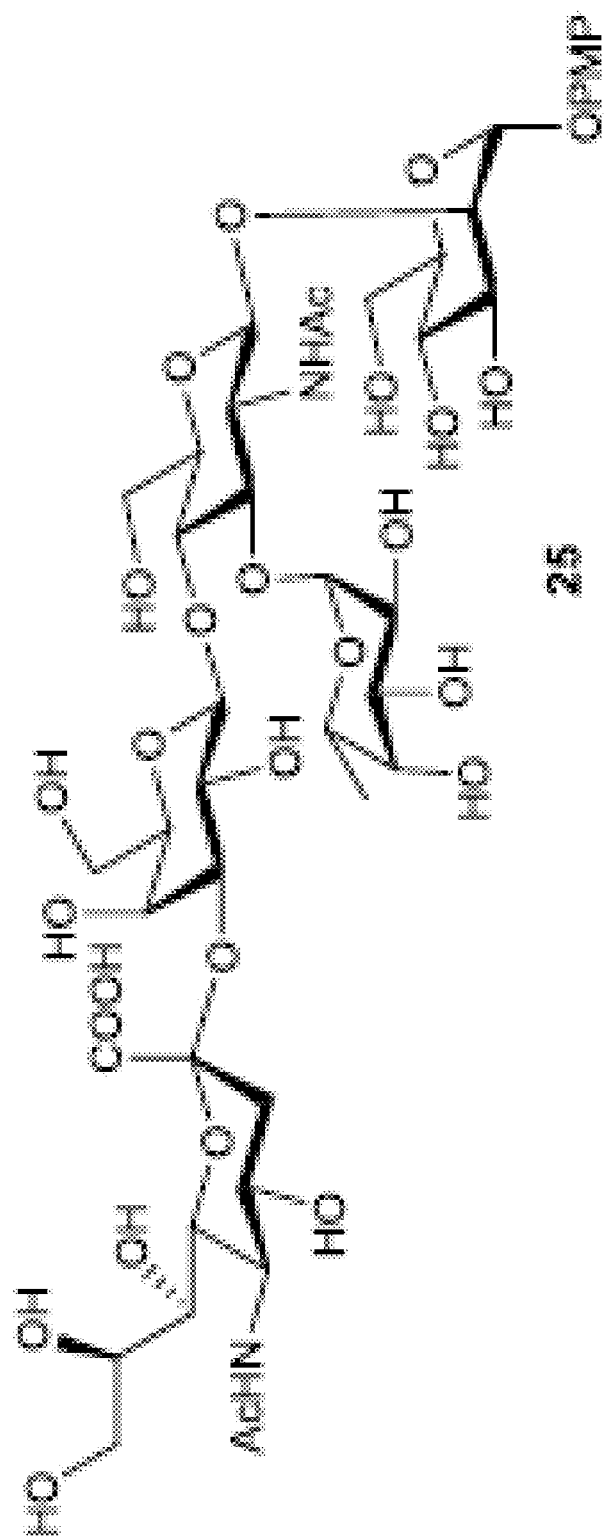

FIG. 157 Exemplary structure embodiments and synthetic scheme embodiments of the present disclosure.

Figure 158:
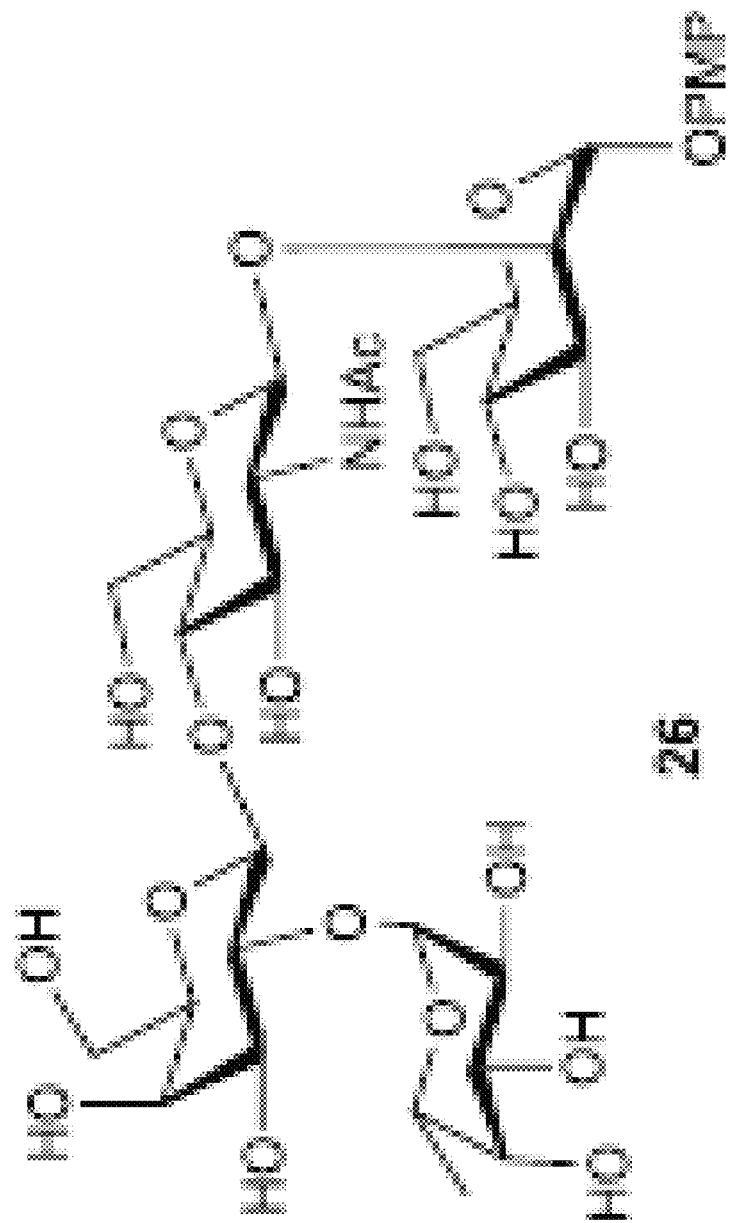

FIG. 158 Exemplary structure embodiments and synthetic scheme embodiments of the present disclosure.

Figure 159:
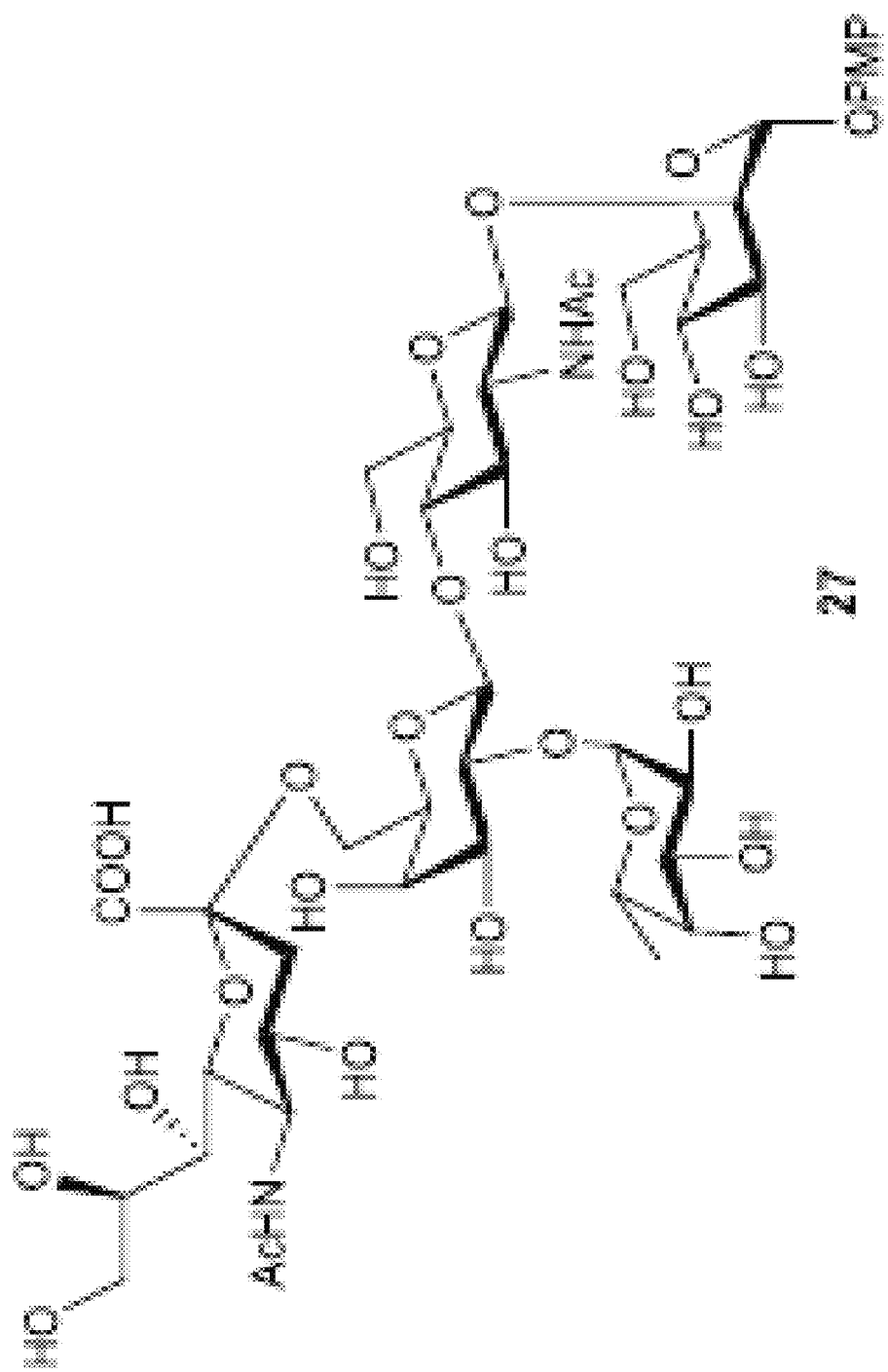

FIG. 159 Exemplary structure embodiments and synthetic scheme embodiments of the present disclosure.

Figure 160:
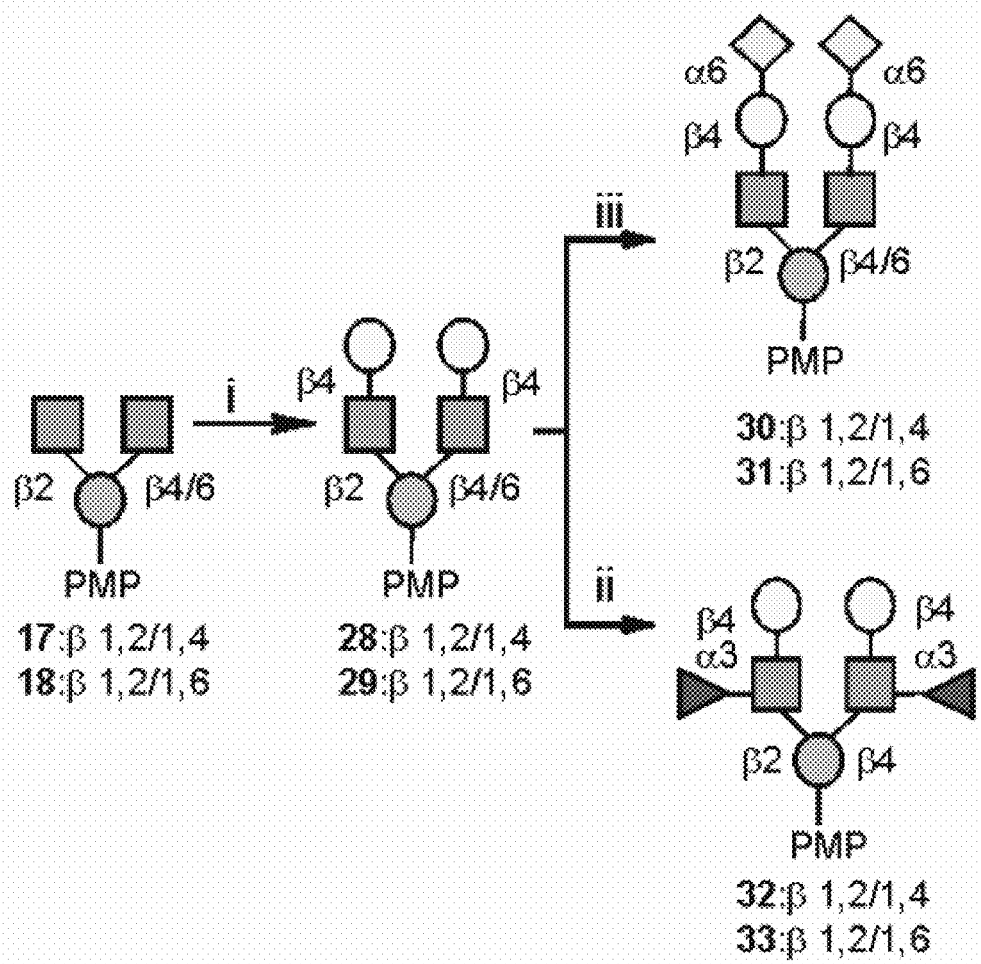

FIG. 160 Scheme S24|Exemplary Preparation scheme of symmetrically branched modules.

Figure 161:
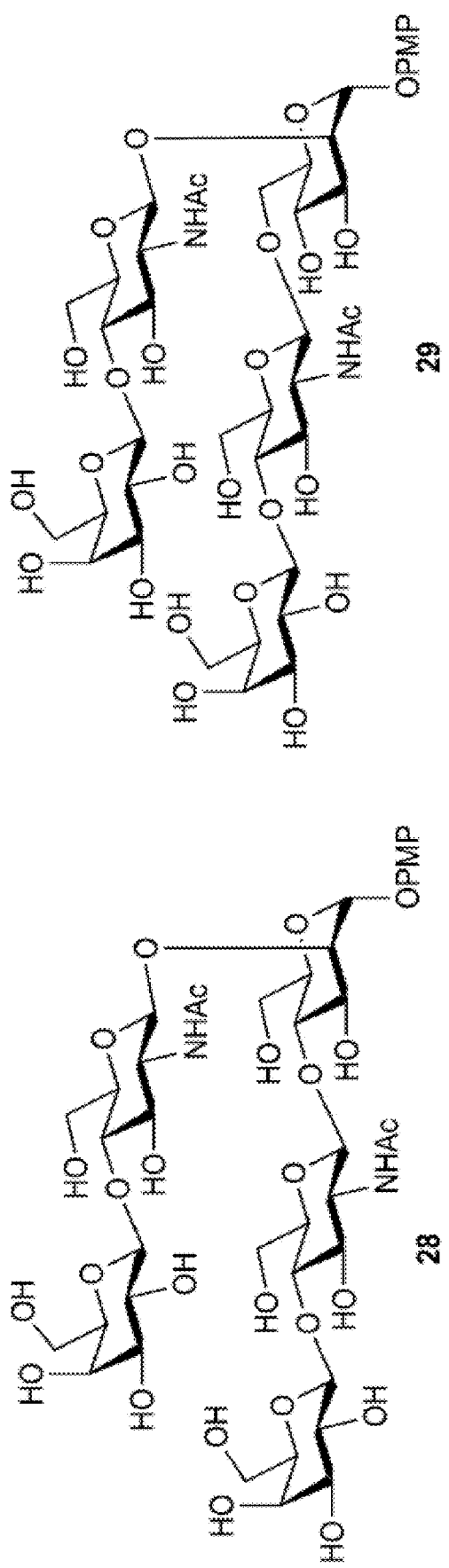

FIG. 161 Exemplary structure embodiments and synthetic scheme embodiments of the present disclosure.

Figure 162:
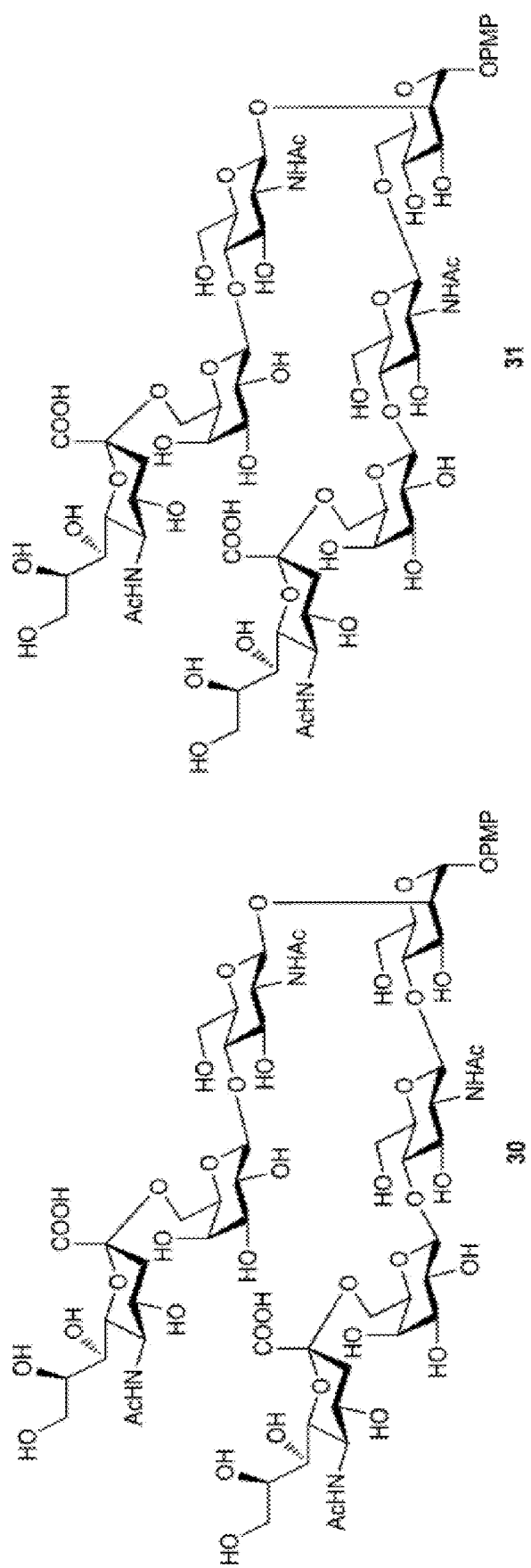

FIG. 162 Exemplary structure embodiments and synthetic scheme embodiments of the present disclosure.

Figure 163:
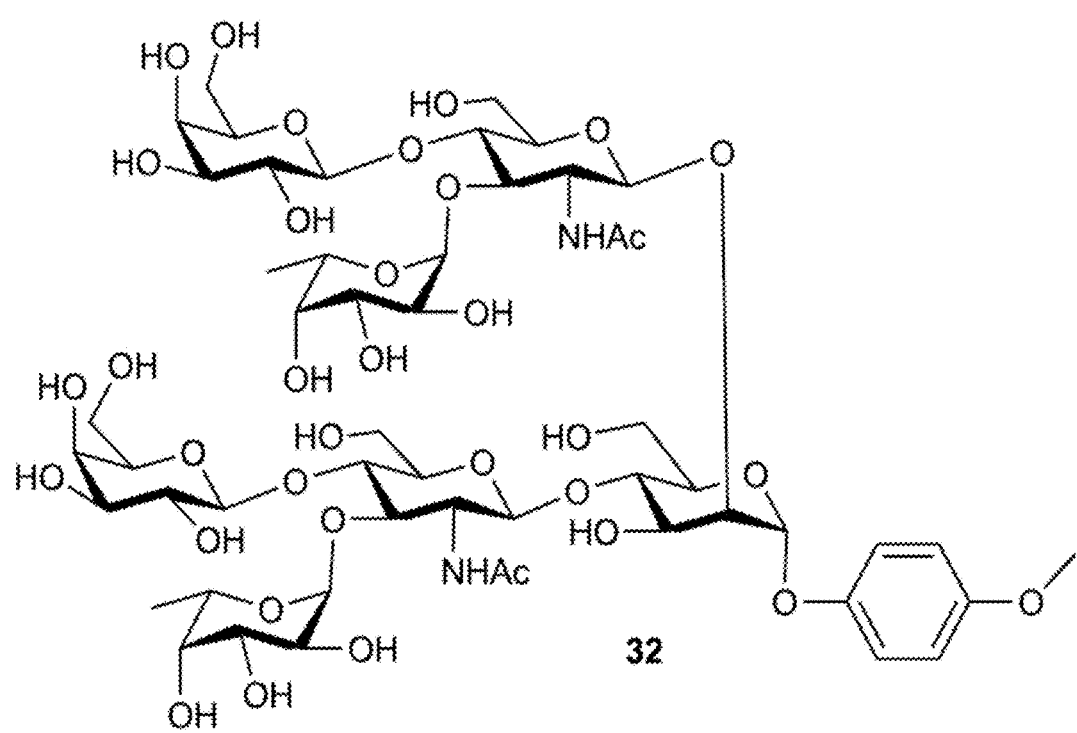

FIG. 163 Exemplary structure embodiments and synthetic scheme embodiments of the present disclosure.

Figure 164:
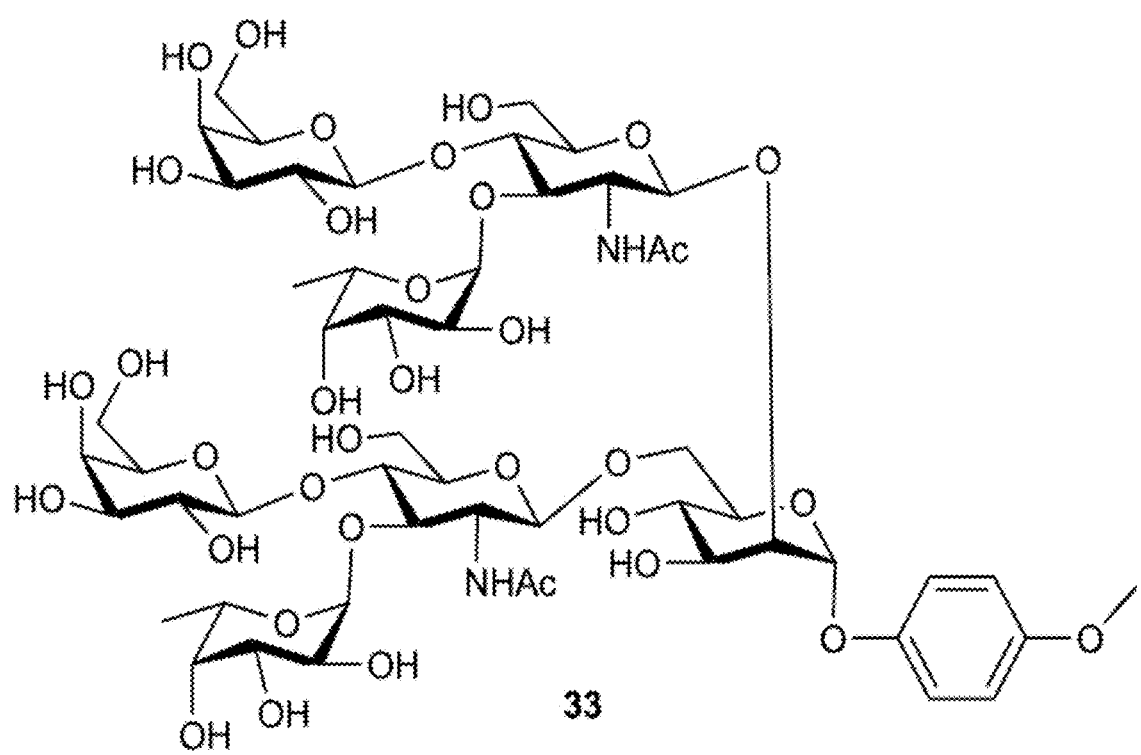

FIG. 164 Exemplary structure embodiments and synthetic scheme embodiments of the present disclosure.

Figure 165:
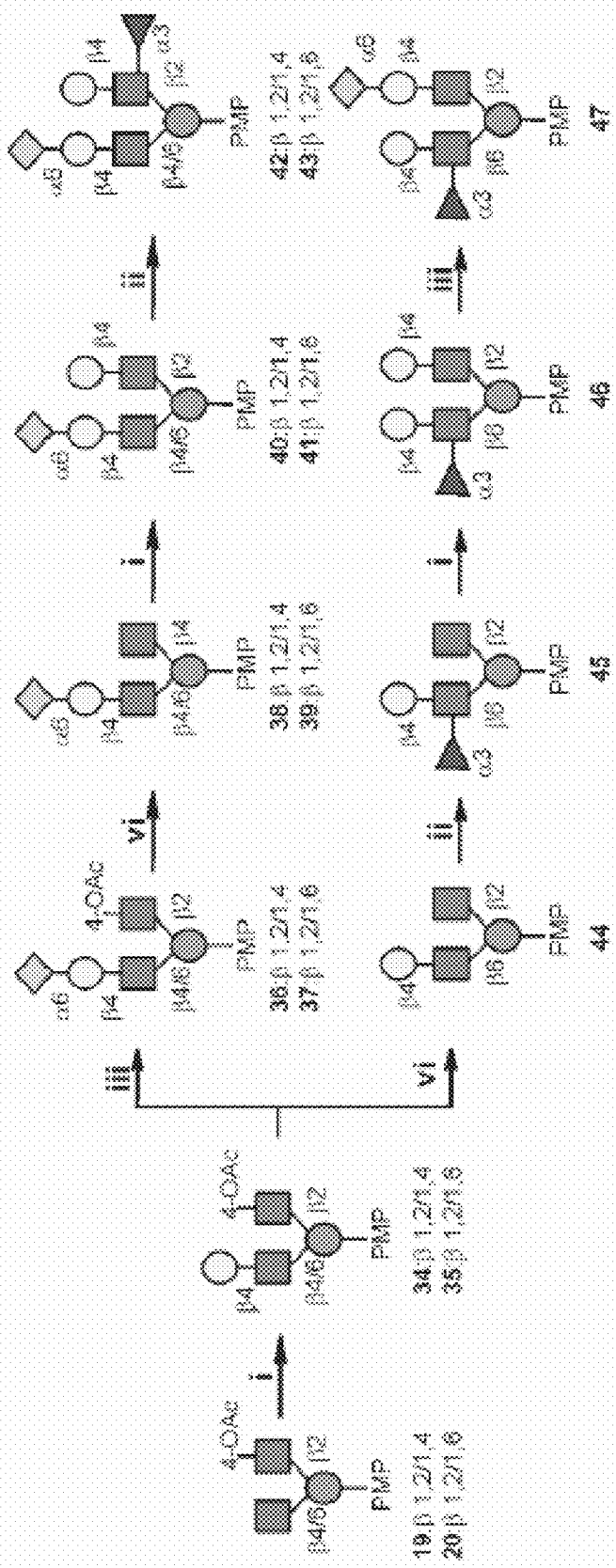

FIG. 165 Scheme S25|Exemplary Preparation scheme of assymetric module.

Figure 166:
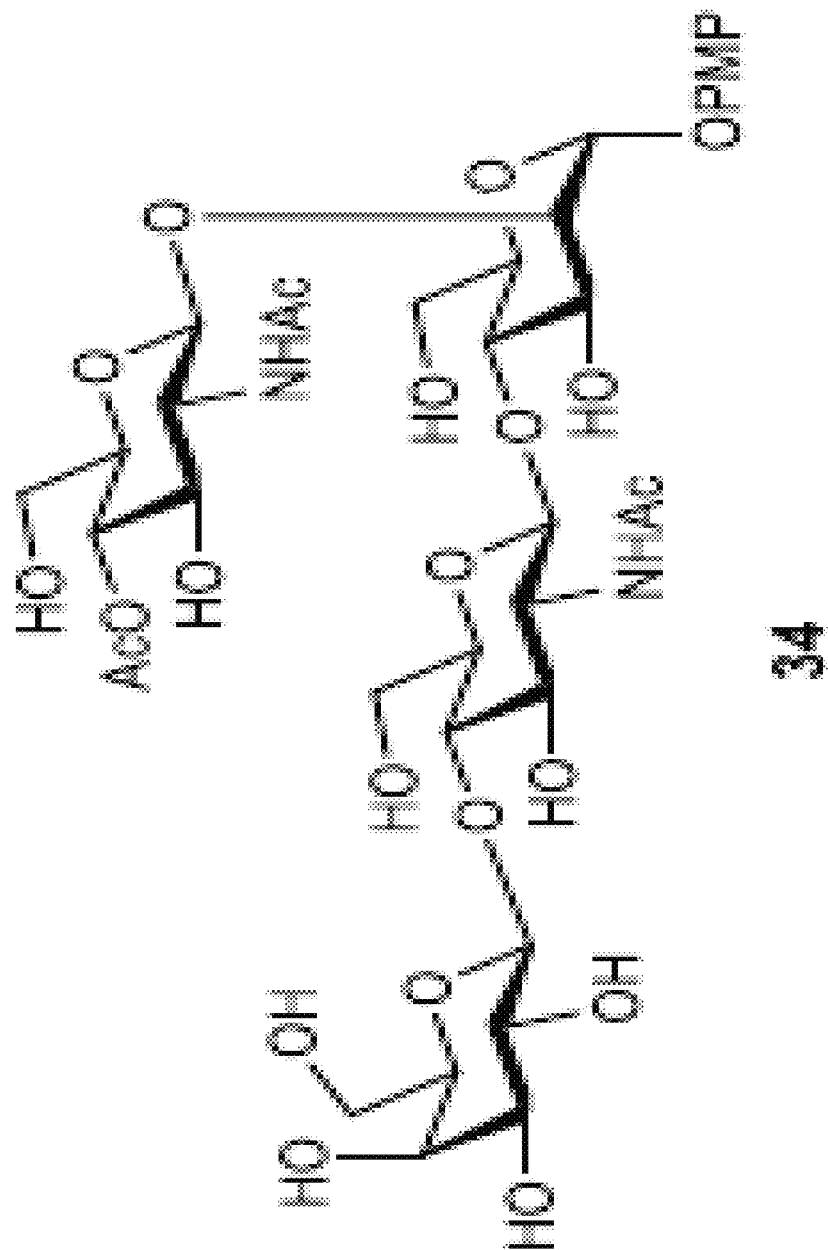

FIG. 166 Exemplary structure embodiments and synthetic scheme embodiments of the present disclosure.

Figure 167:
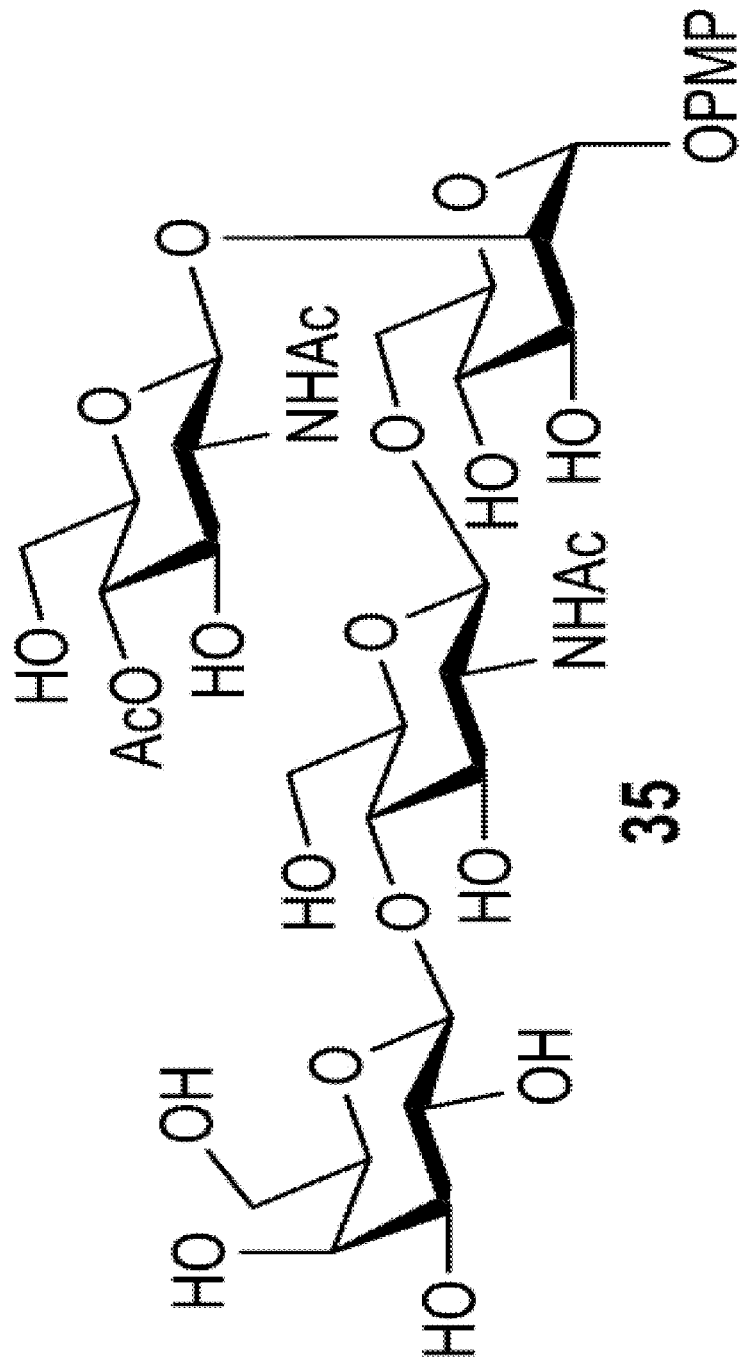

FIG. 167 Exemplary structure embodiments and synthetic scheme embodiments of the present disclosure.

Figure 168:
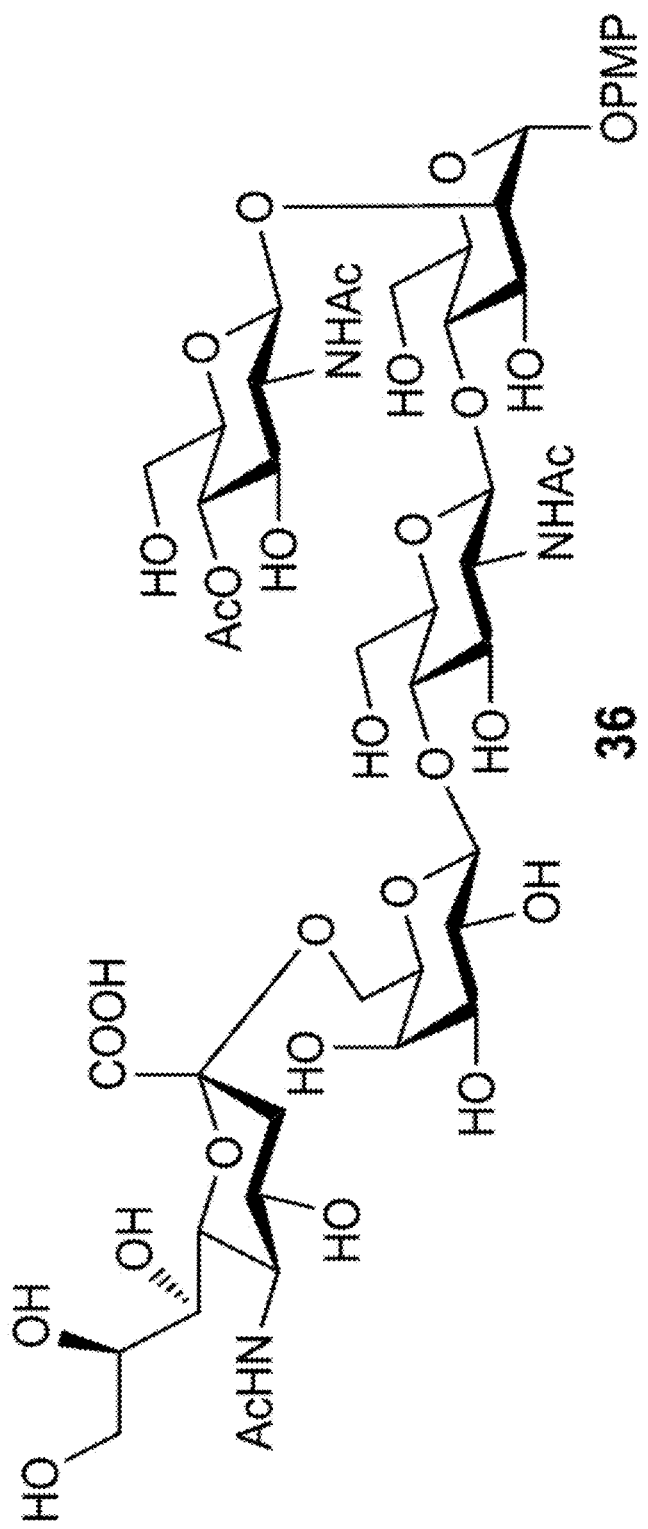

FIG. 168 Exemplary structure embodiments and synthetic scheme embodiments of the present disclosure.

Figure 169:
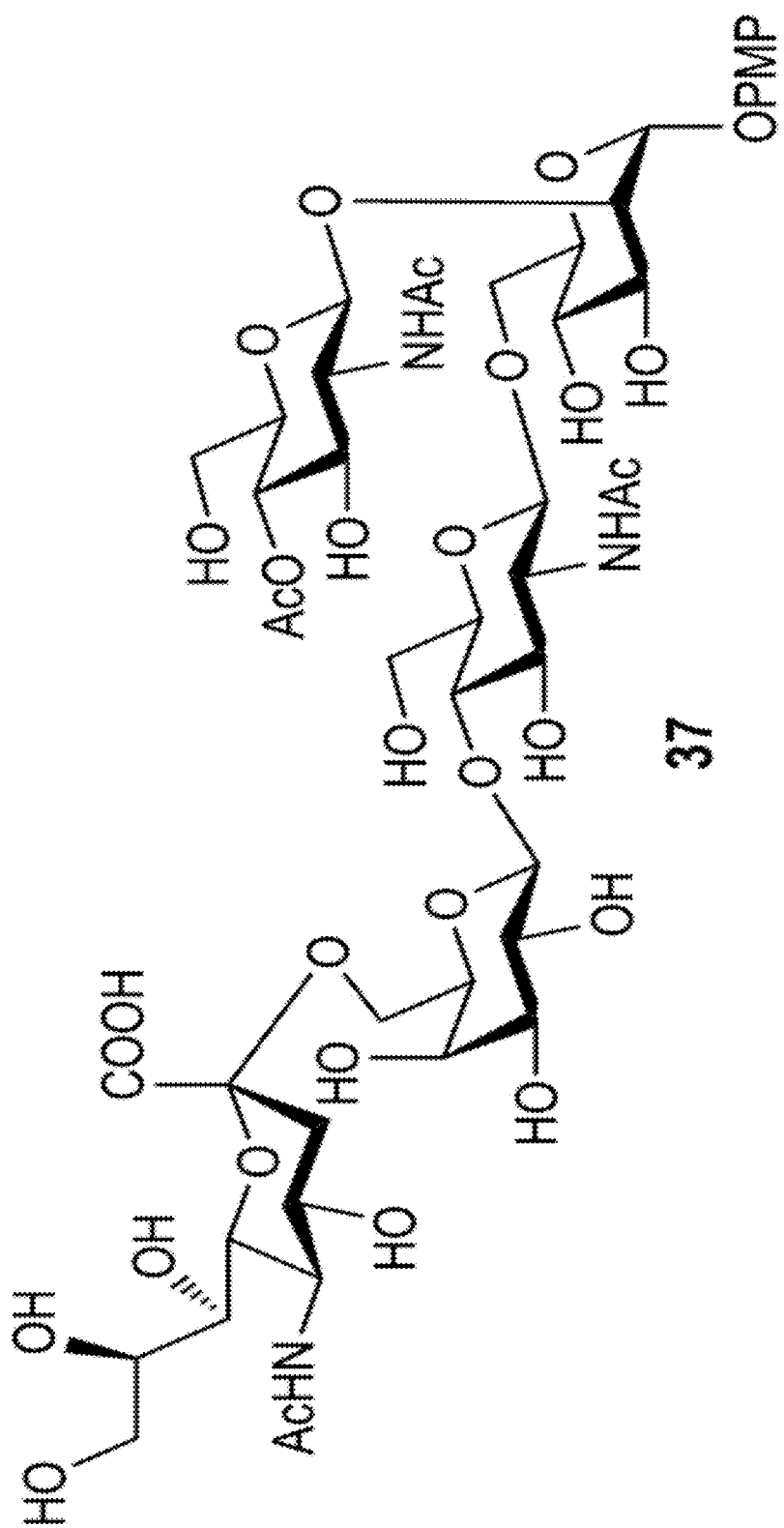

FIG. 169 Exemplary structure embodiments and synthetic scheme embodiments of the present disclosure.

Figure 170:
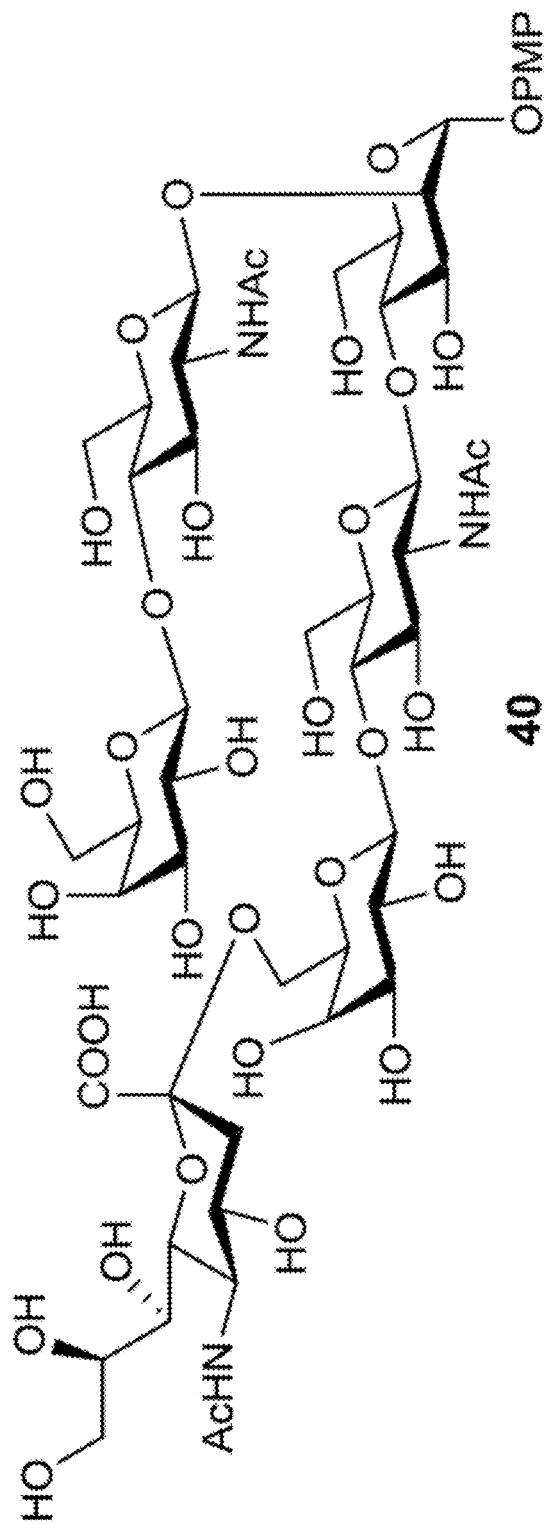

FIG. 170 Exemplary structure embodiments and synthetic scheme embodiments of the present disclosure.

Figure 171:
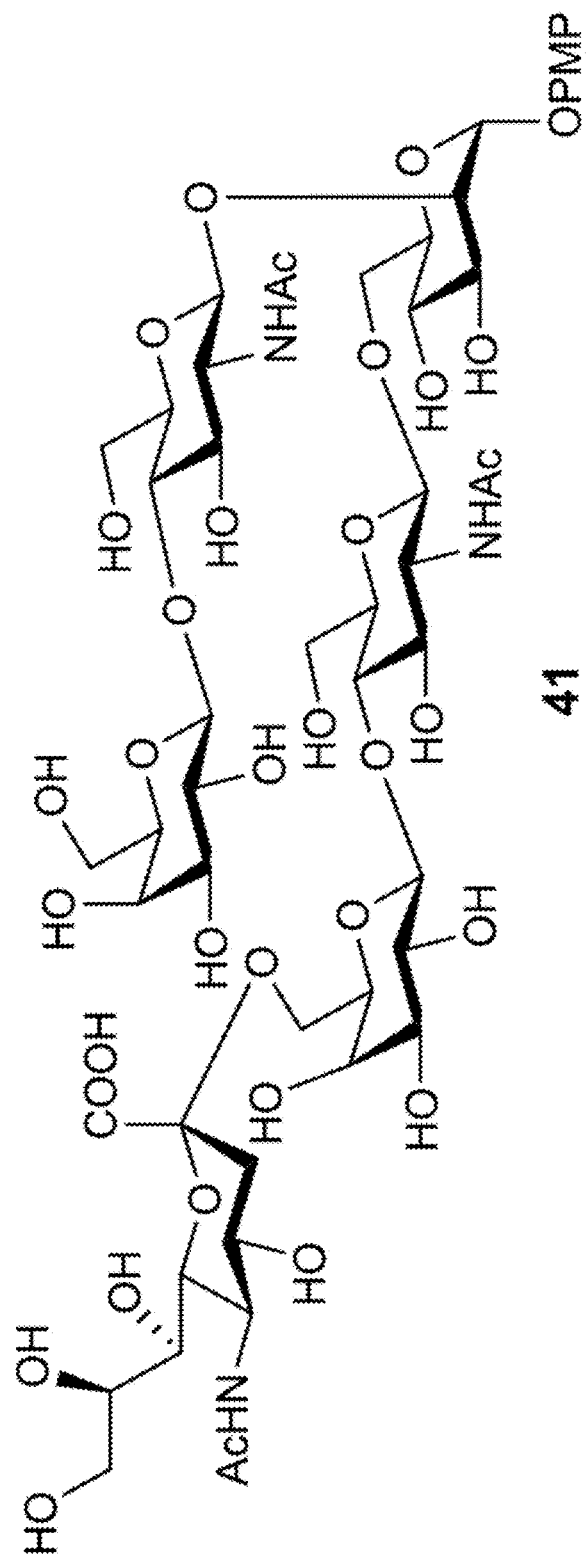

FIG. 171 Exemplary structure embodiments and synthetic scheme embodiments of the present disclosure.

Figure 172:
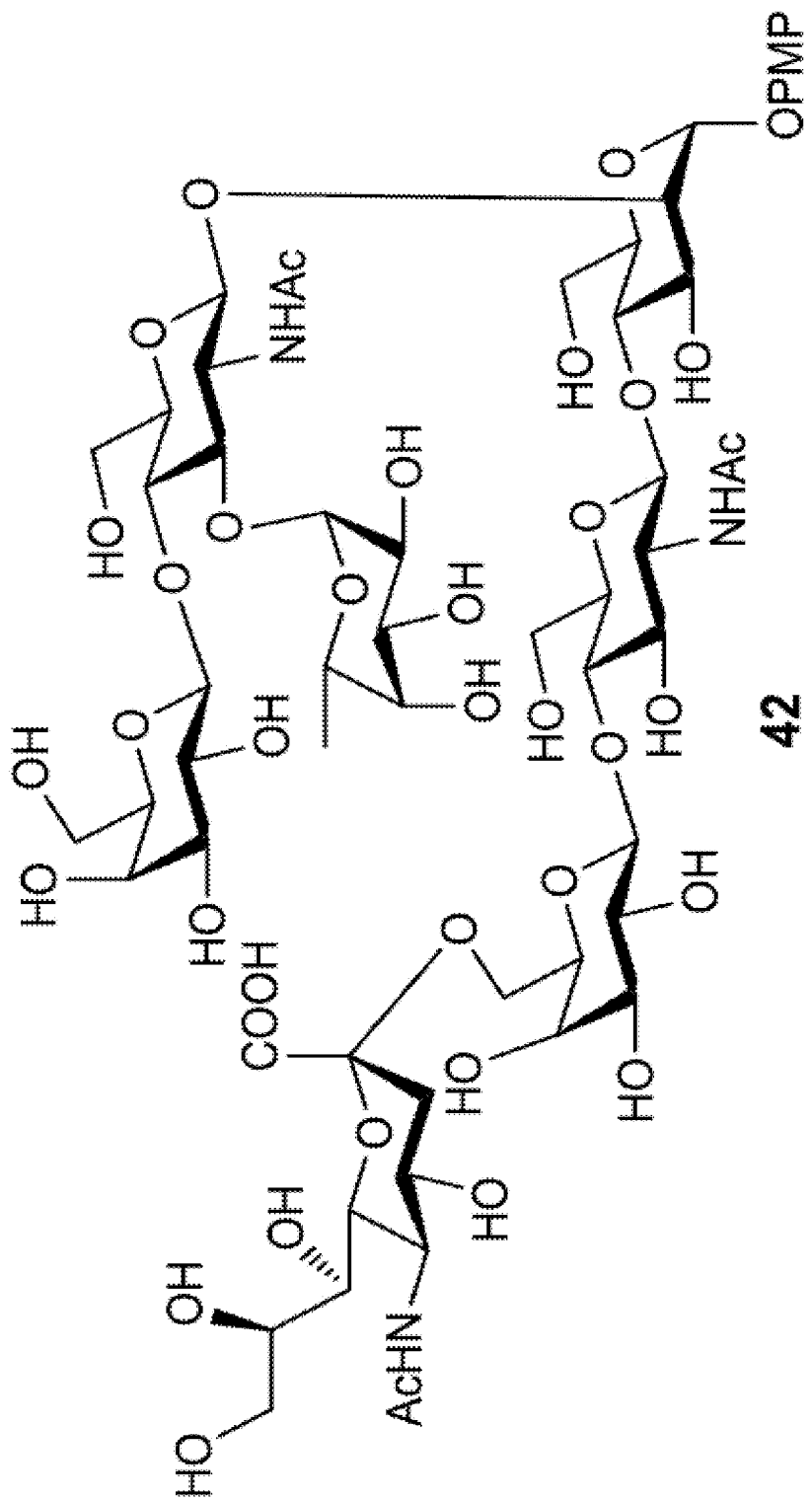

FIG. 172 Exemplary structure embodiments and synthetic scheme embodiments of the present disclosure.

Figure 173:
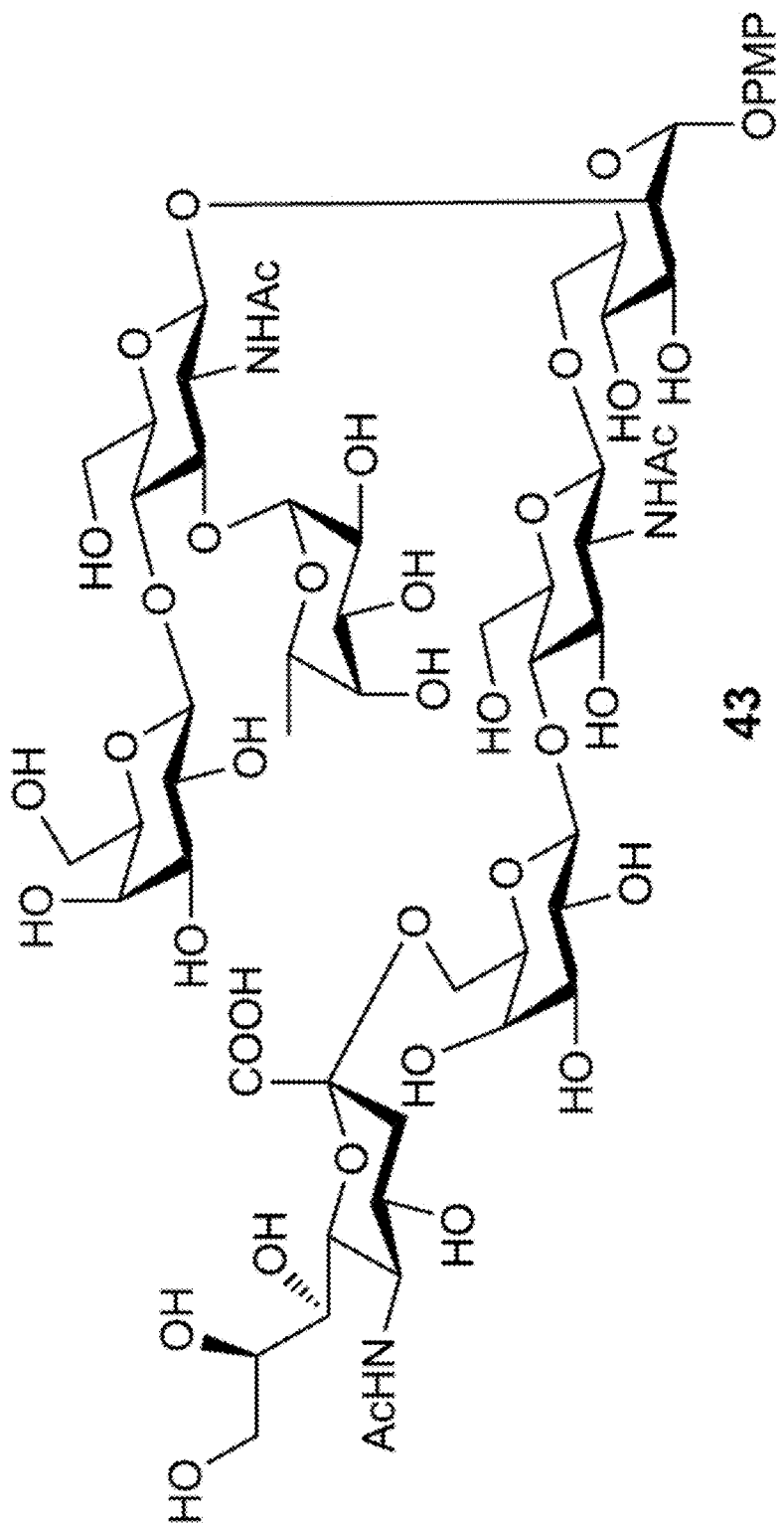

FIG. 173 Exemplary structure embodiments and synthetic scheme embodiments of the present disclosure.

Figure 174:
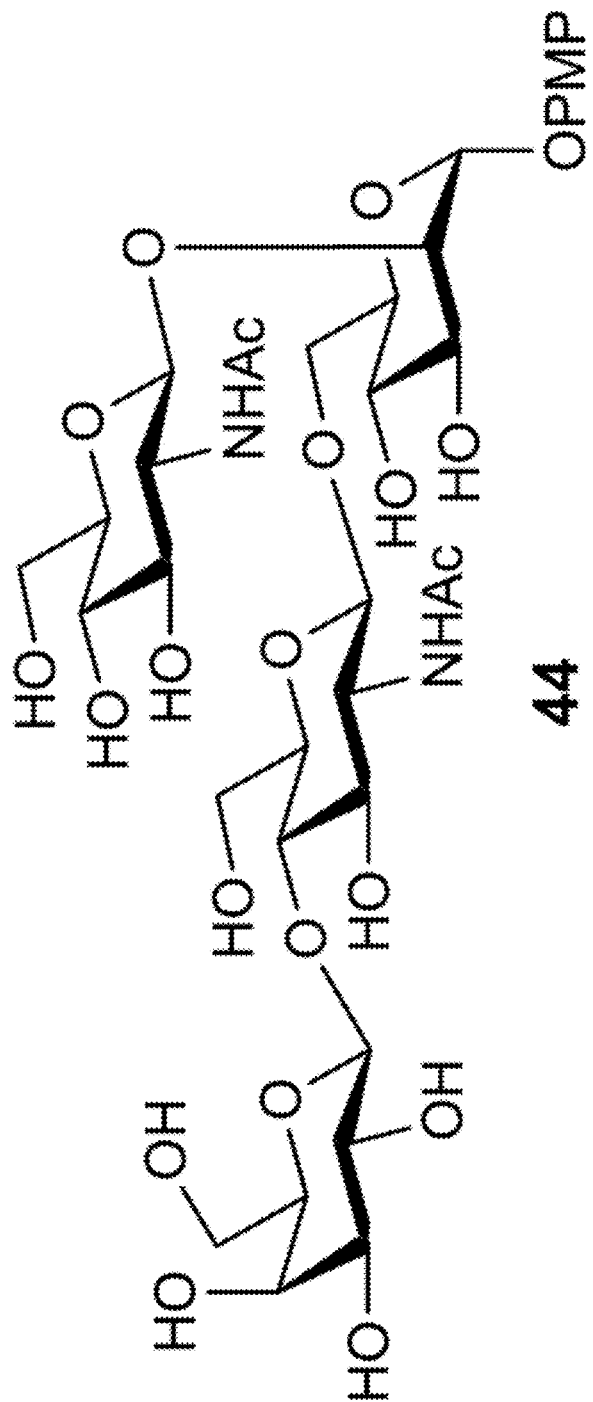

FIG. 174 Exemplary structure embodiments and synthetic scheme embodiments of the present disclosure.

Figure 175:
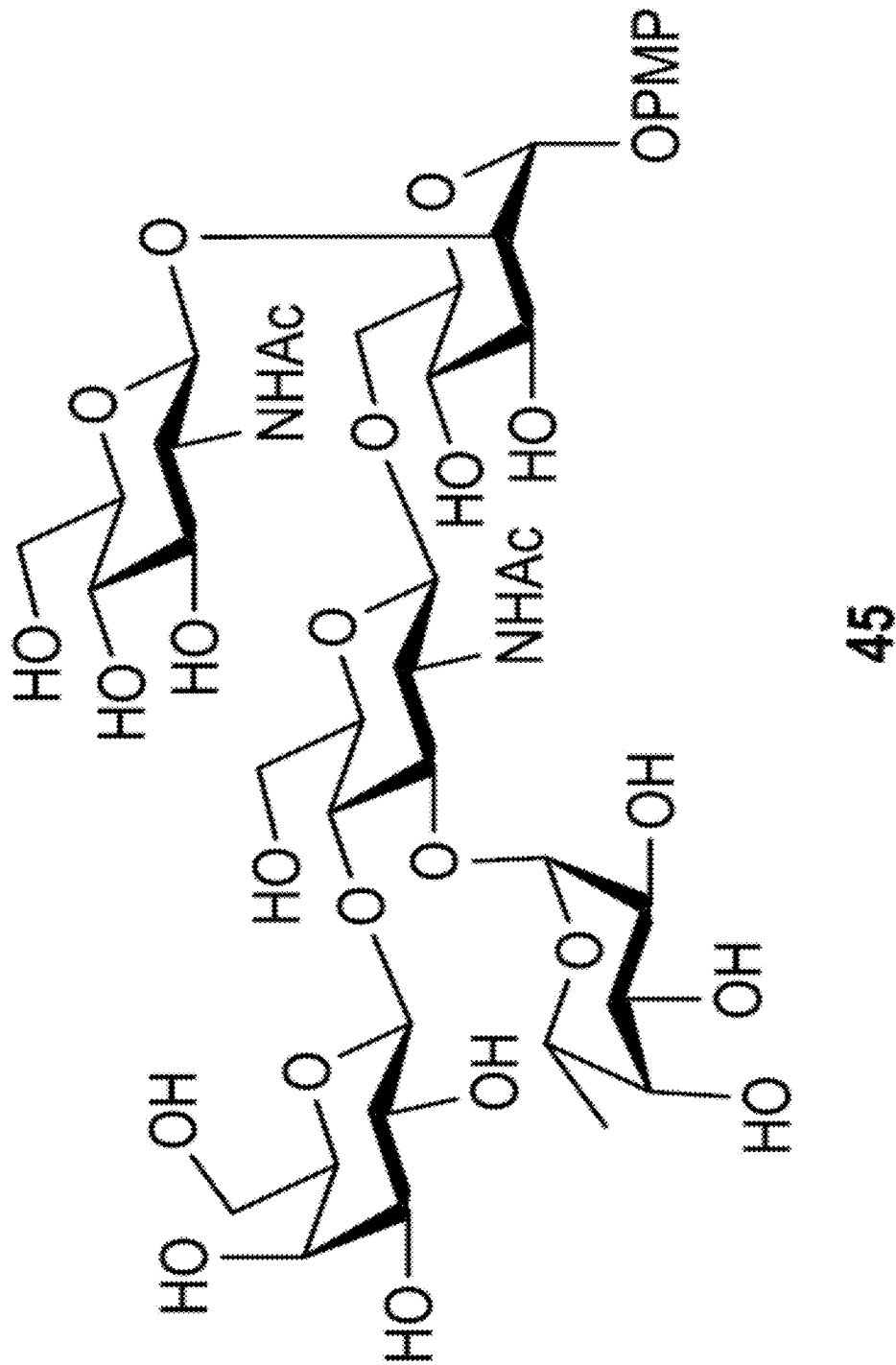

FIG. 175 Exemplary structure embodiments and synthetic scheme embodiments of the present disclosure.

Figure 176:
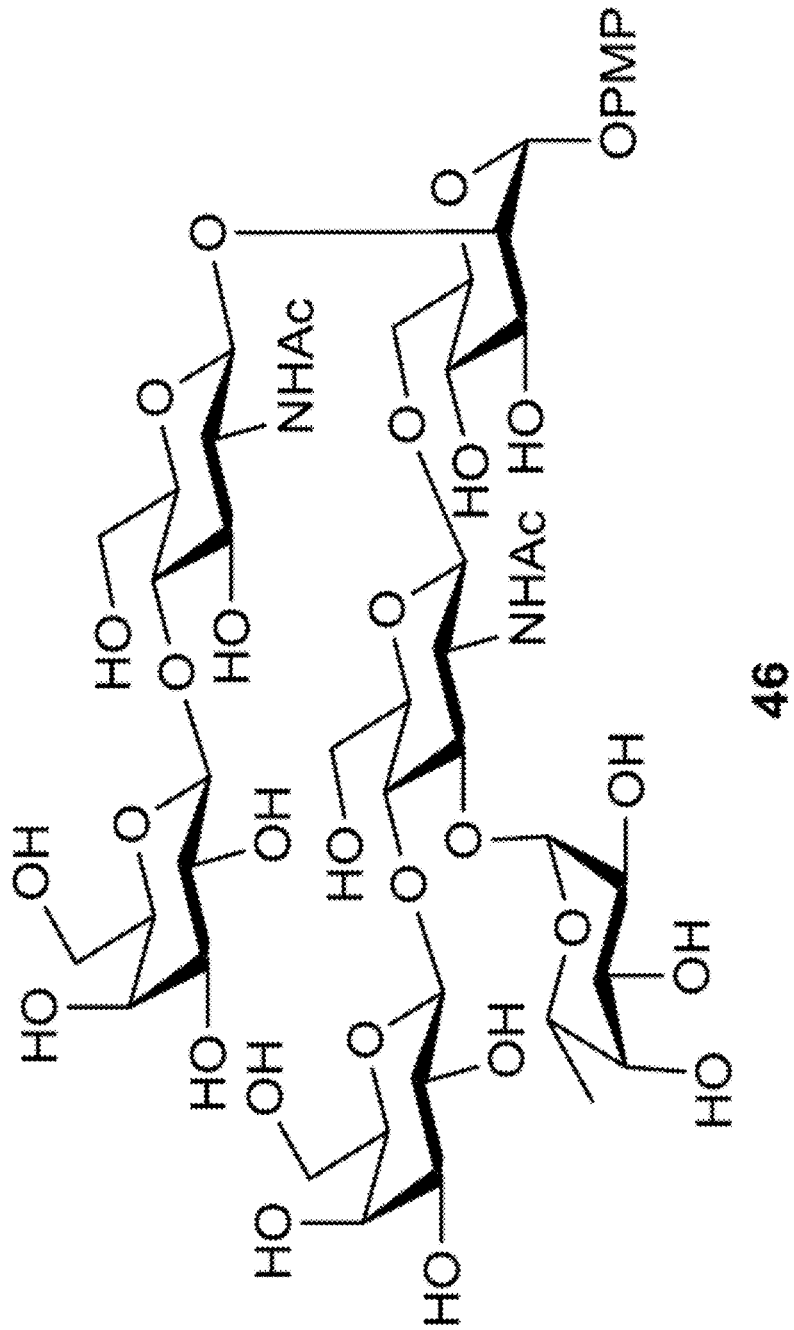

FIG. 176 Exemplary structure embodiments and synthetic scheme embodiments of the present disclosure.

Figure 177:
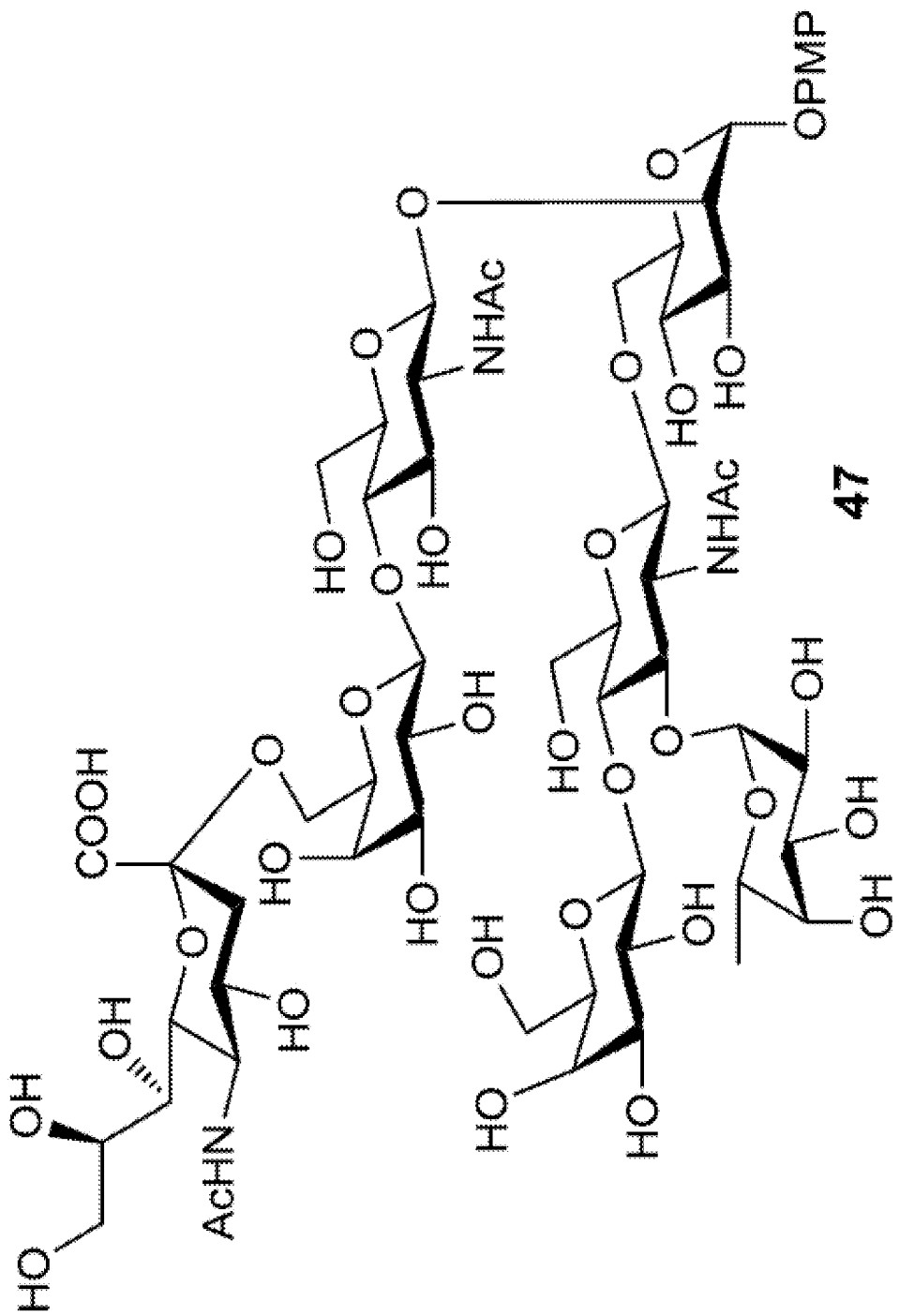

FIG. 177 Exemplary structure embodiments and synthetic scheme embodiments of the present disclosure.

Figure 178:
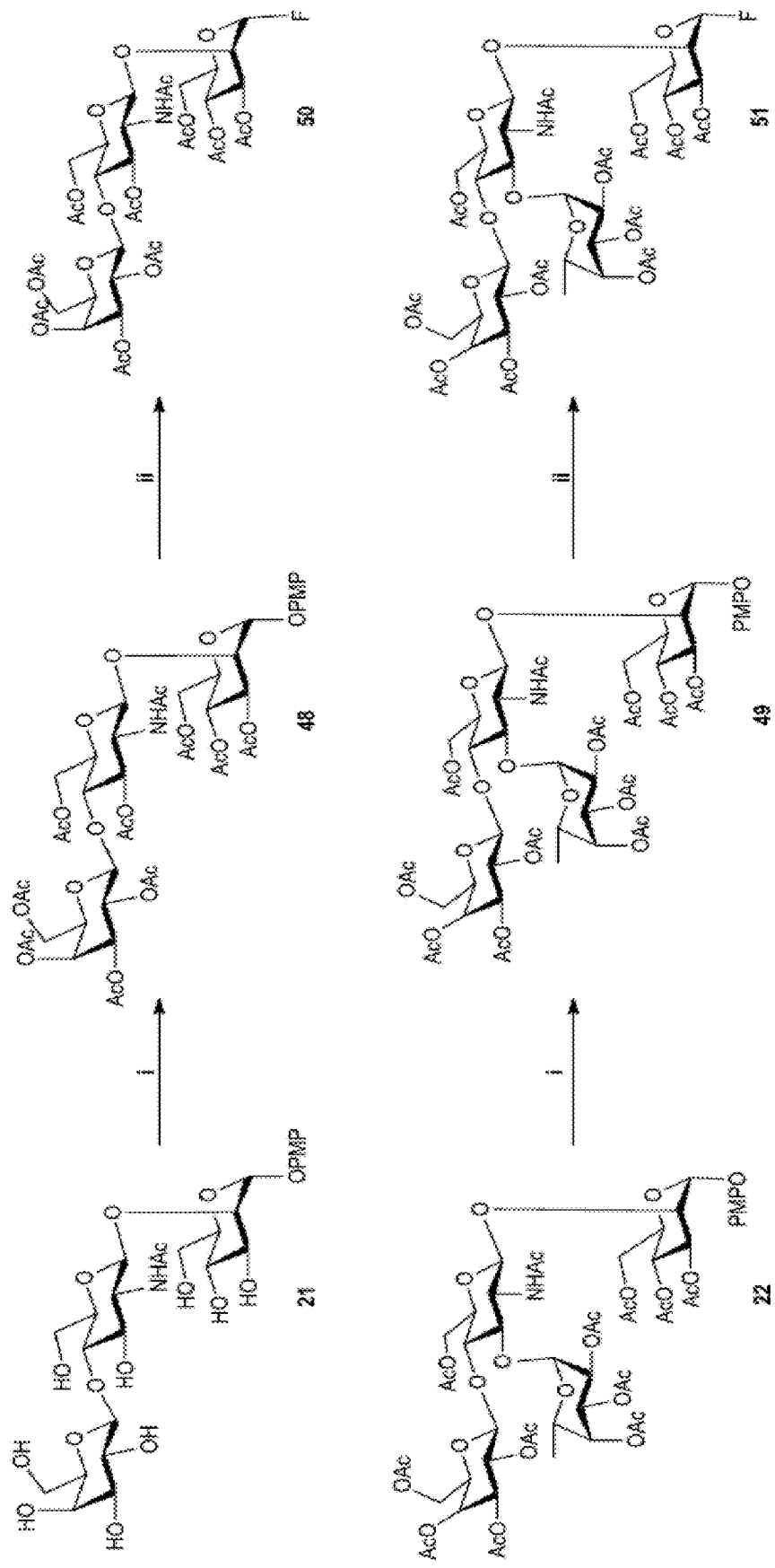

FIG. 178 Exemplary structure embodiments and synthetic scheme embodiments of the present disclosure.

Figure 179:
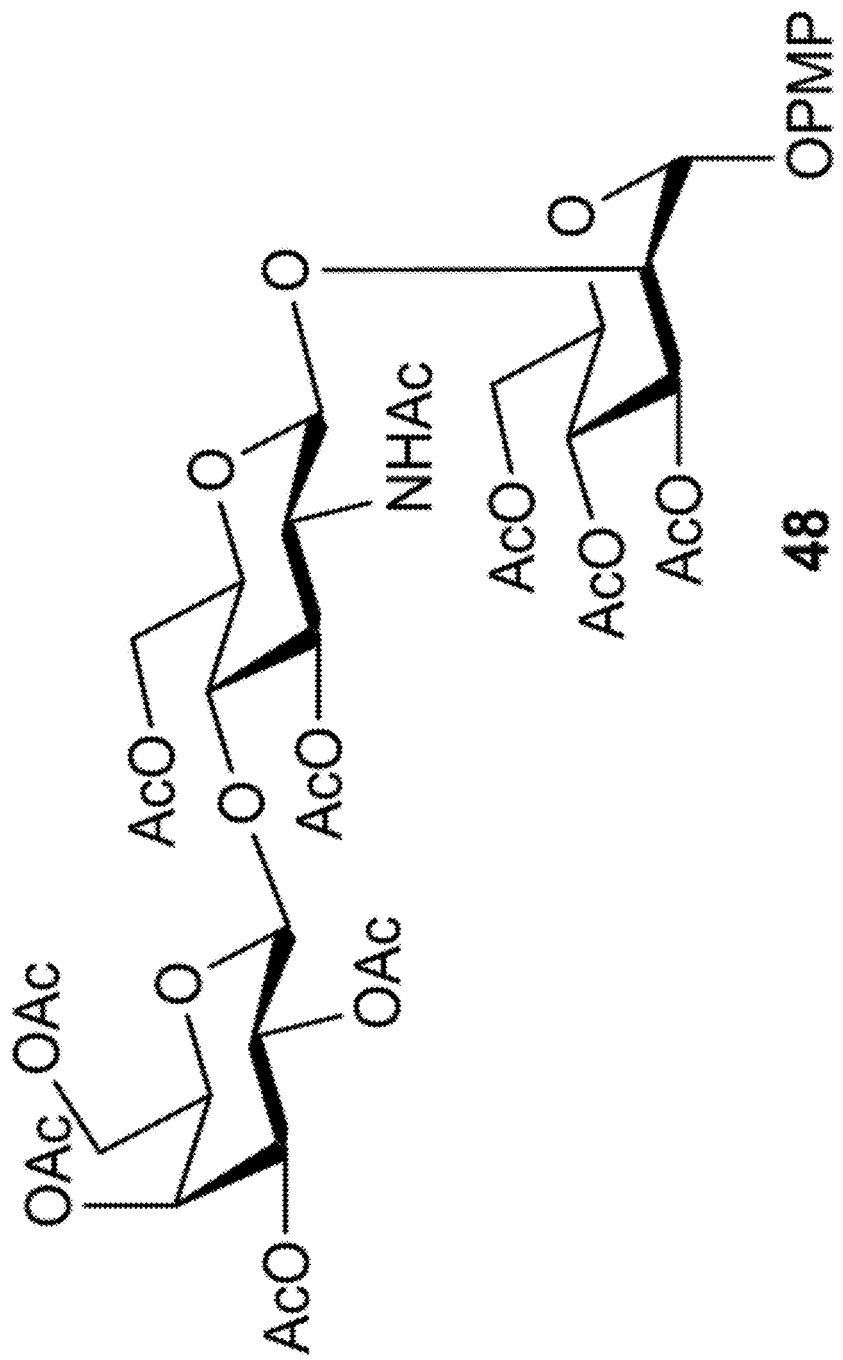

FIG. 179 Exemplary structure embodiments and synthetic scheme embodiments of the present disclosure.

Figure 180:
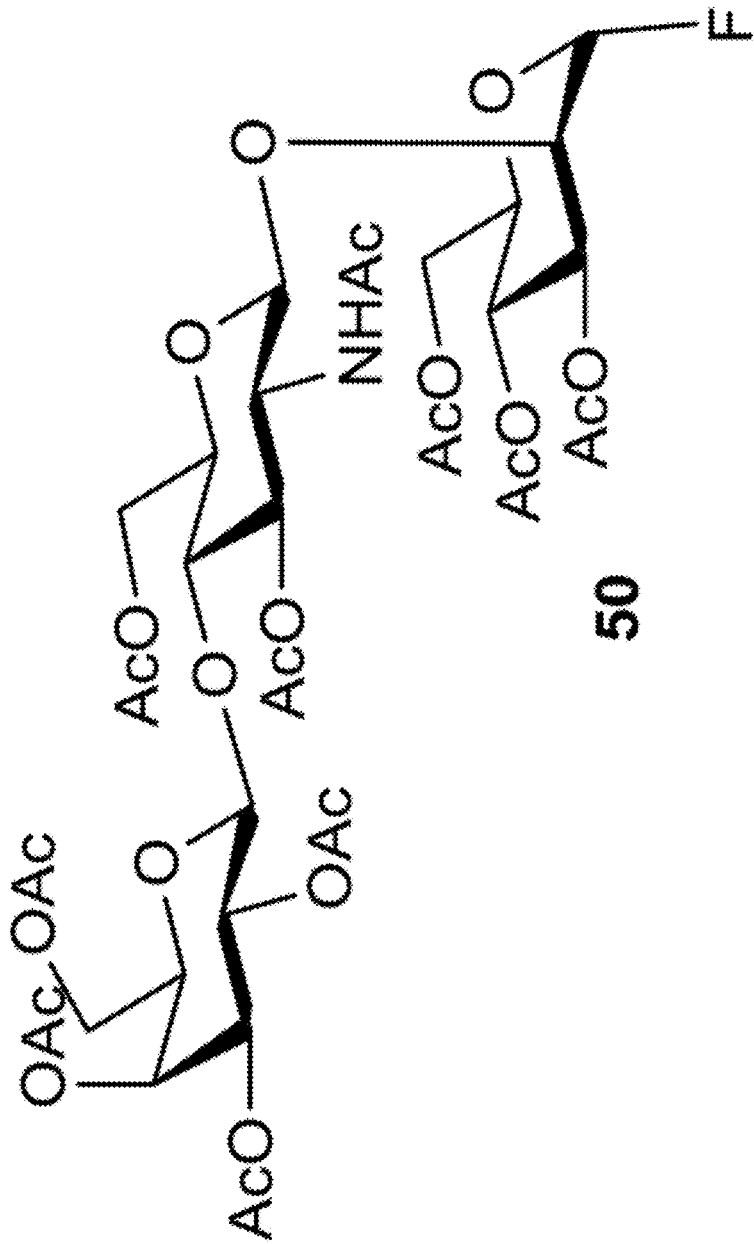

FIG. 180 Exemplary structure embodiments and synthetic scheme embodiments of the present disclosure.

Figure 181:
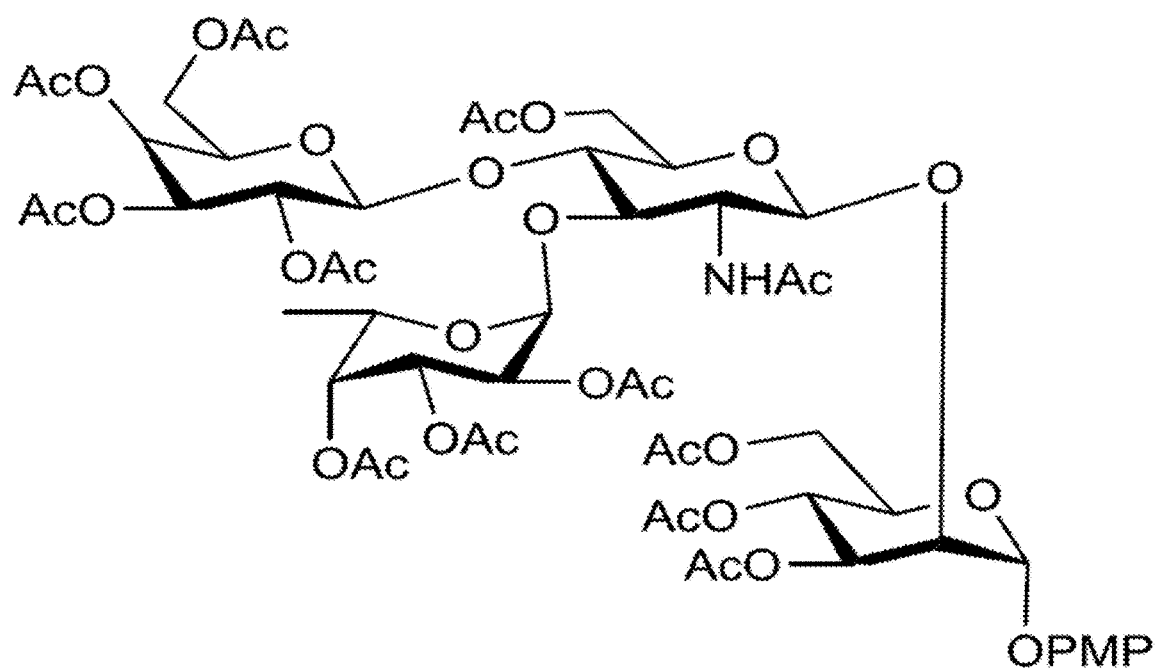

FIG. 181 Exemplary structure embodiments and synthetic scheme embodiments of the present disclosure.

Figure 182:
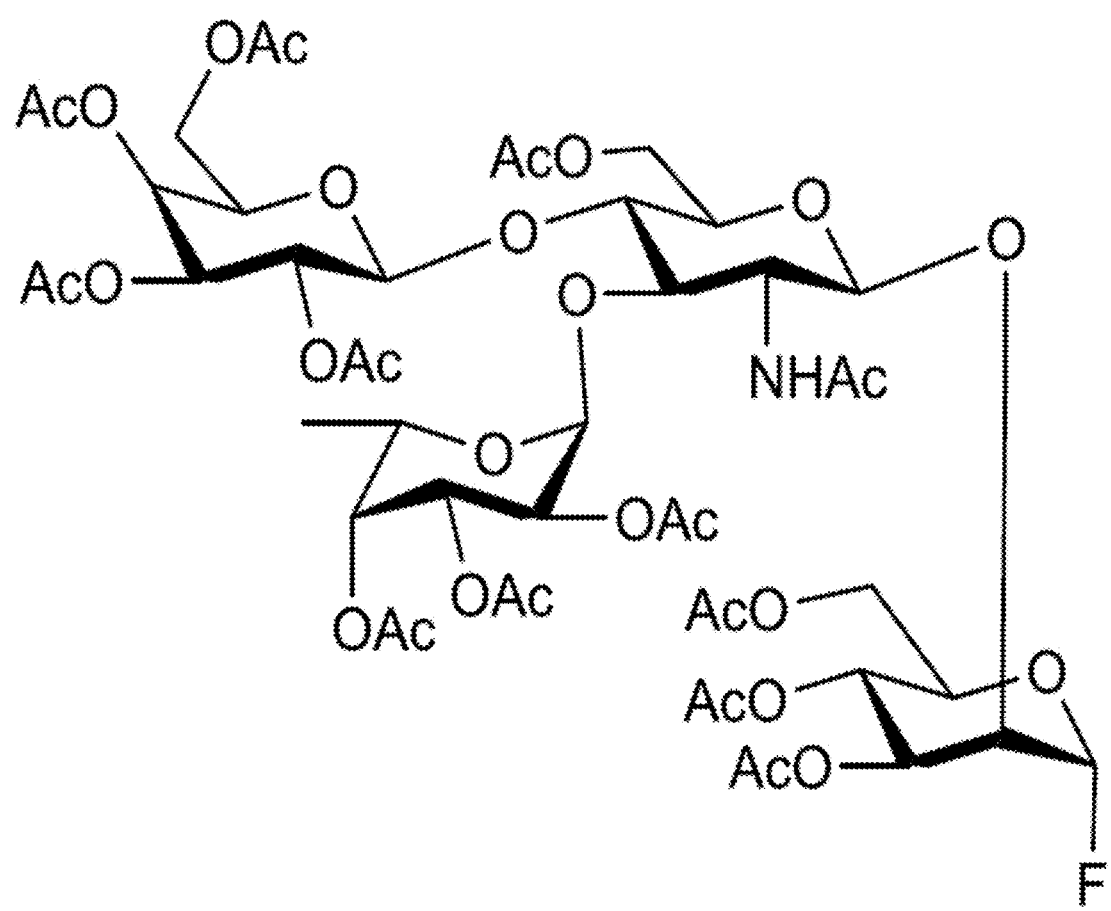

FIG. 182 Exemplary structure embodiments and synthetic scheme embodiments of the present disclosure.

Figure 183A:
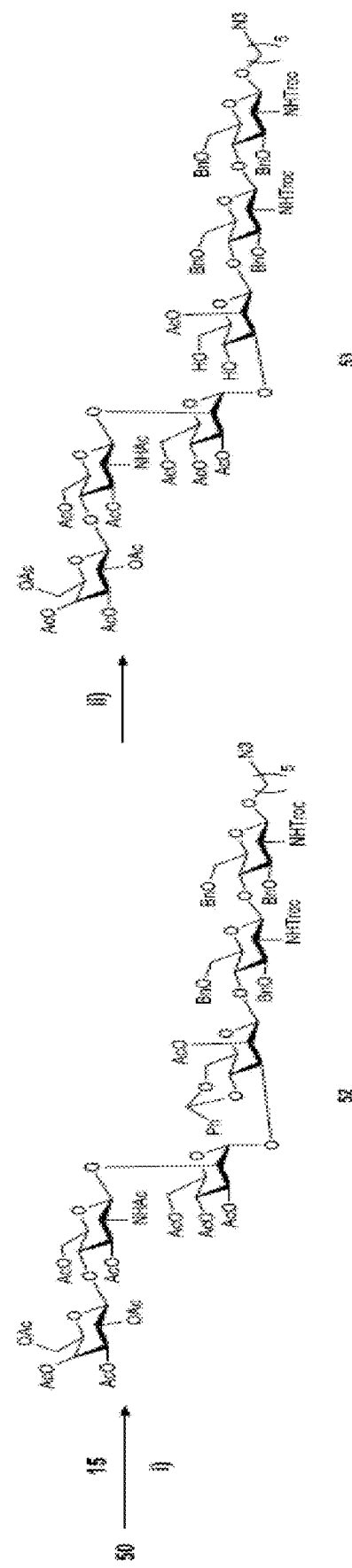
Figure 183B:
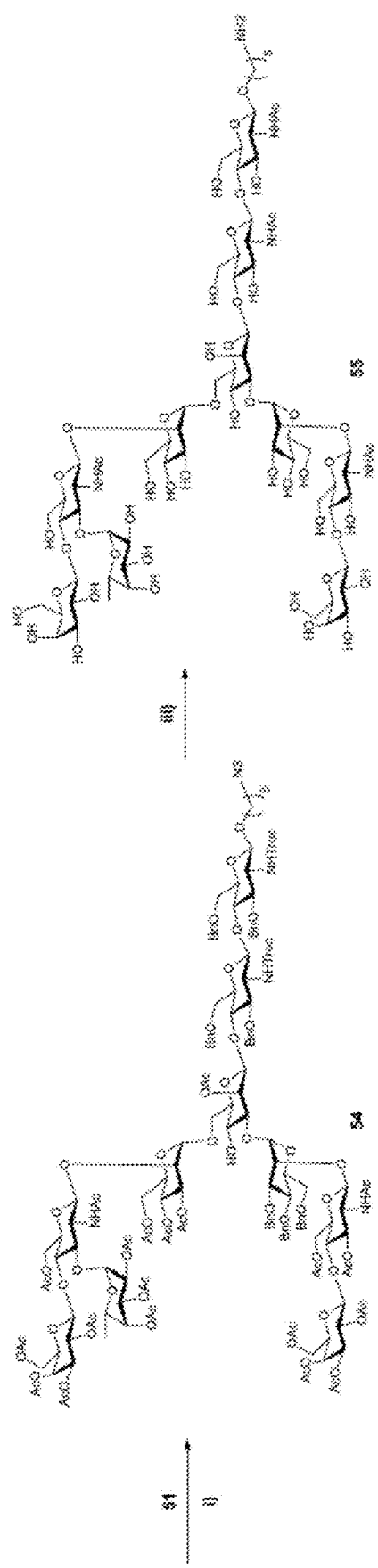

FIGS. 183A and 183B: FIG. 183A: Exemplary structure embodiments in representative synthetic scheme embodiments of the present disclosure. FIG. 183B: Exemplary structure embodiments in representative synthetic scheme embodiments of the present disclosure.

Figure 184:
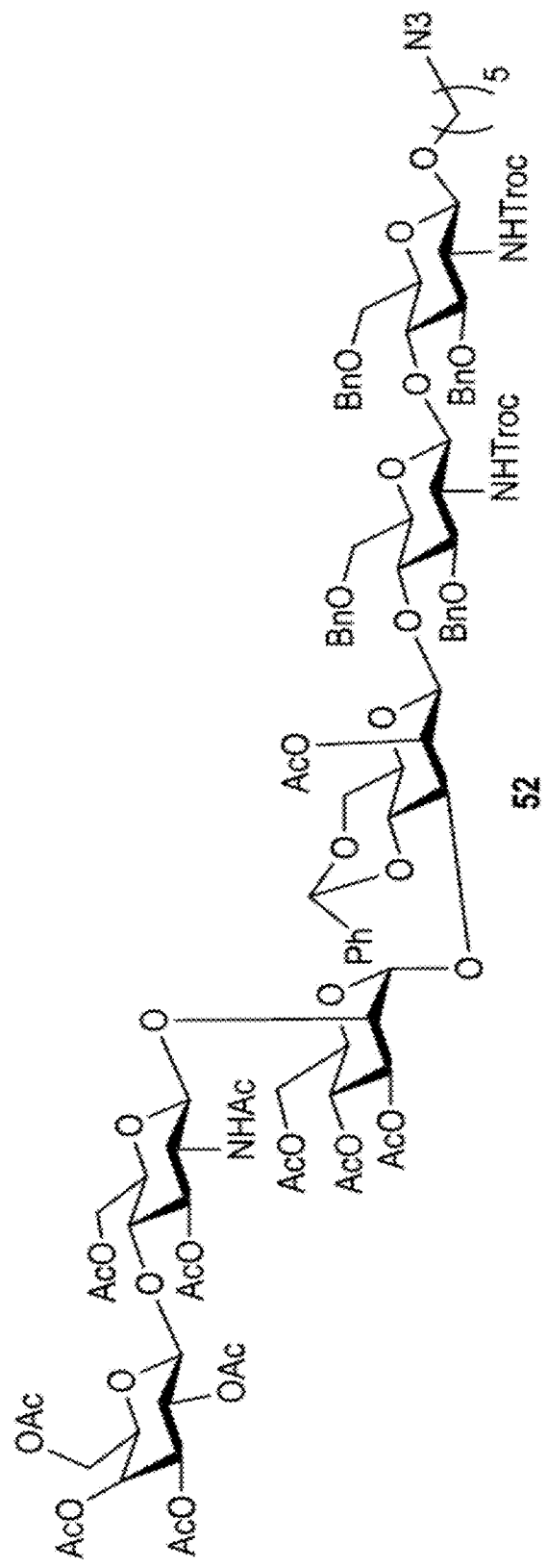

FIG. 184 Exemplary structure embodiments and synthetic scheme embodiments of the present disclosure.

Figure 185:
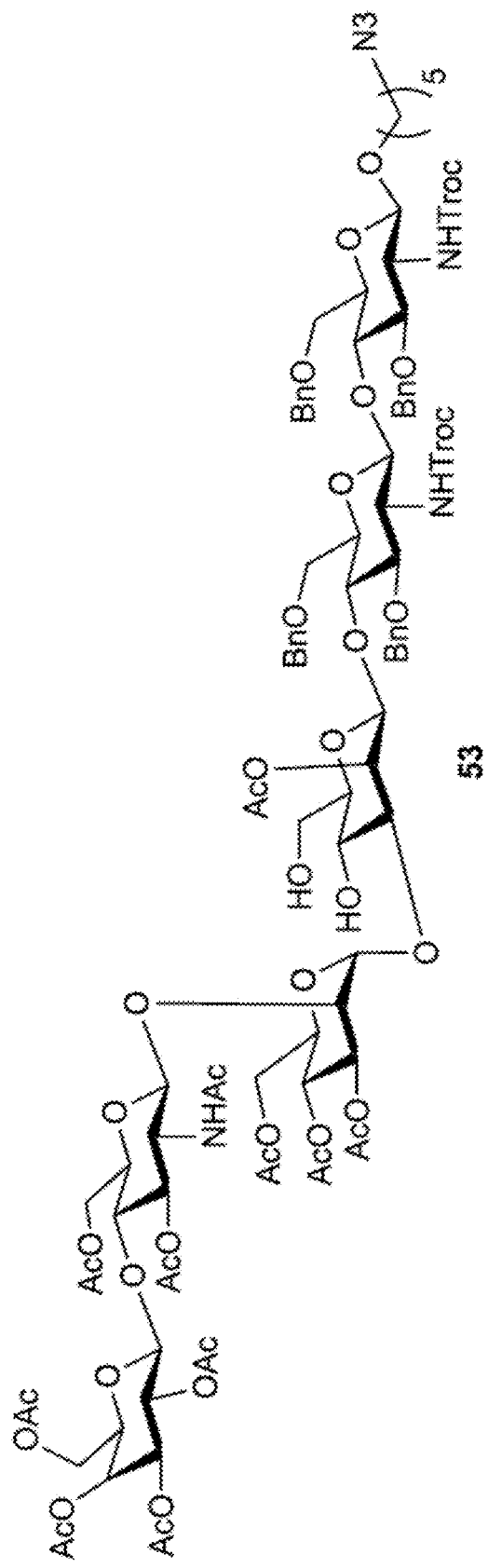

FIG. 185 Exemplary structure embodiments and synthetic scheme embodiments of the present disclosure.

Figure 186:
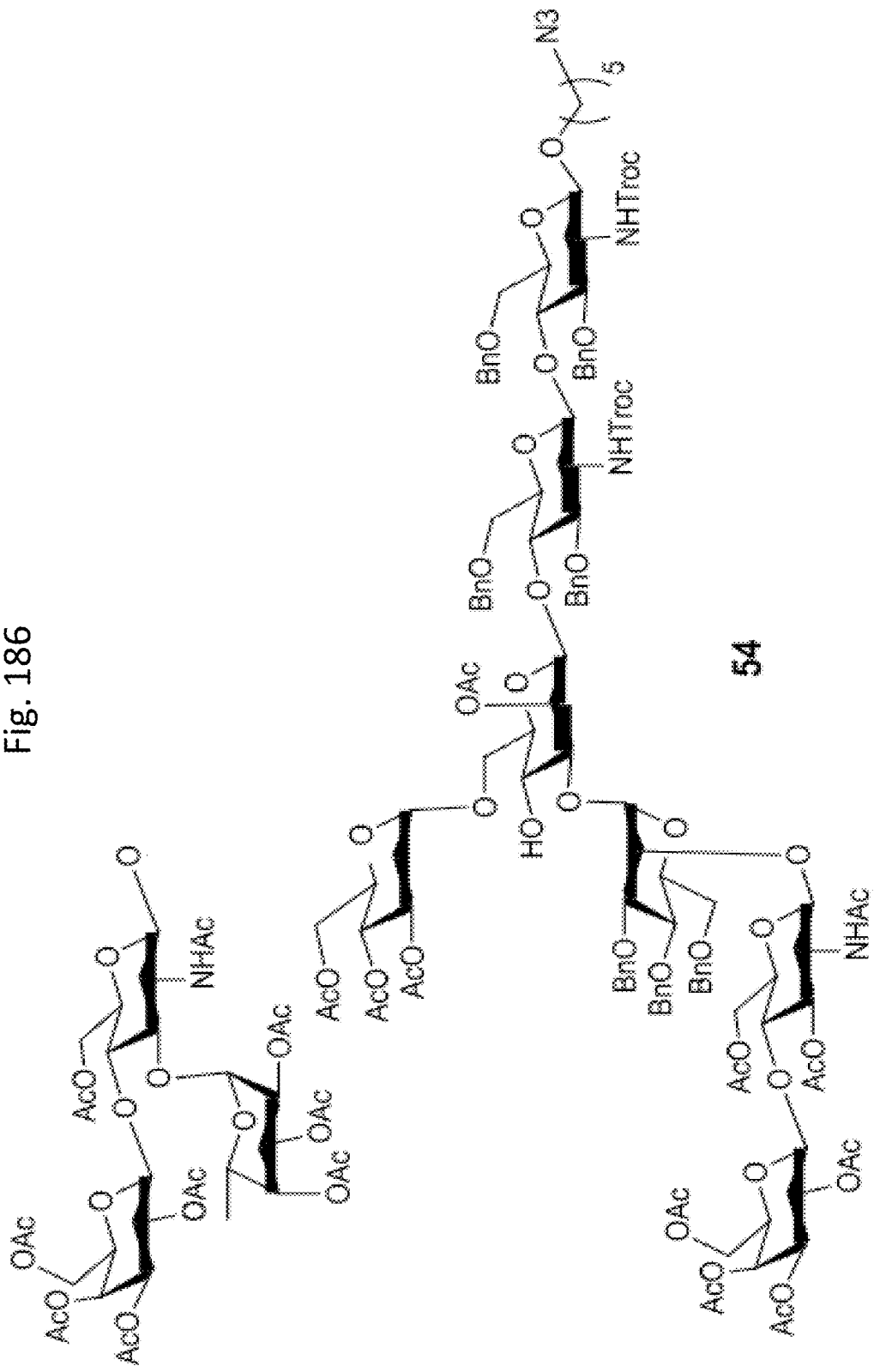

FIG. 186 Exemplary structure embodiments and synthetic scheme embodiments of the present disclosure.

Figure 187:
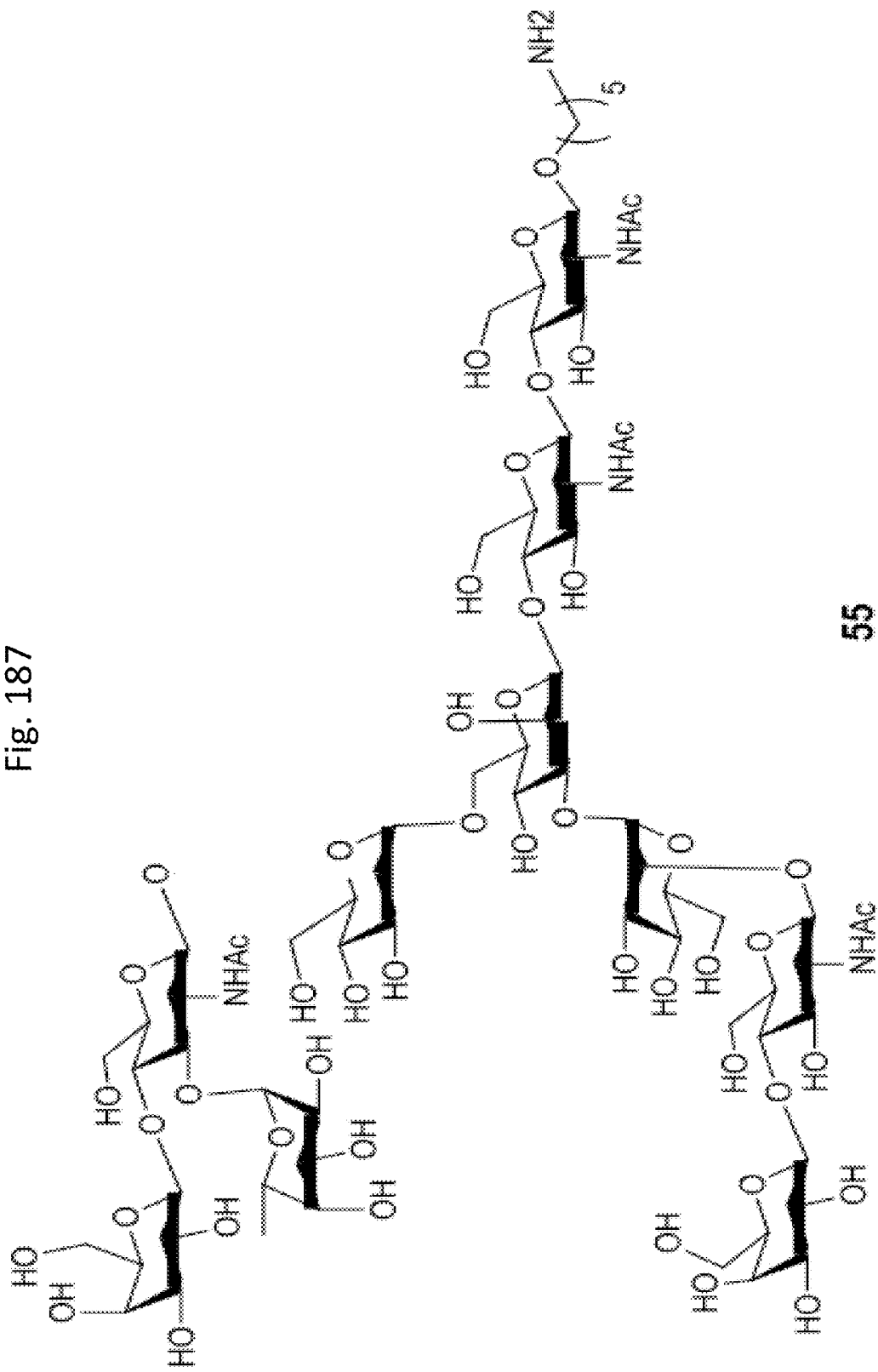

FIG. 187 Exemplary structure embodiments and synthetic scheme embodiments of the present disclosure.

Figure 188:
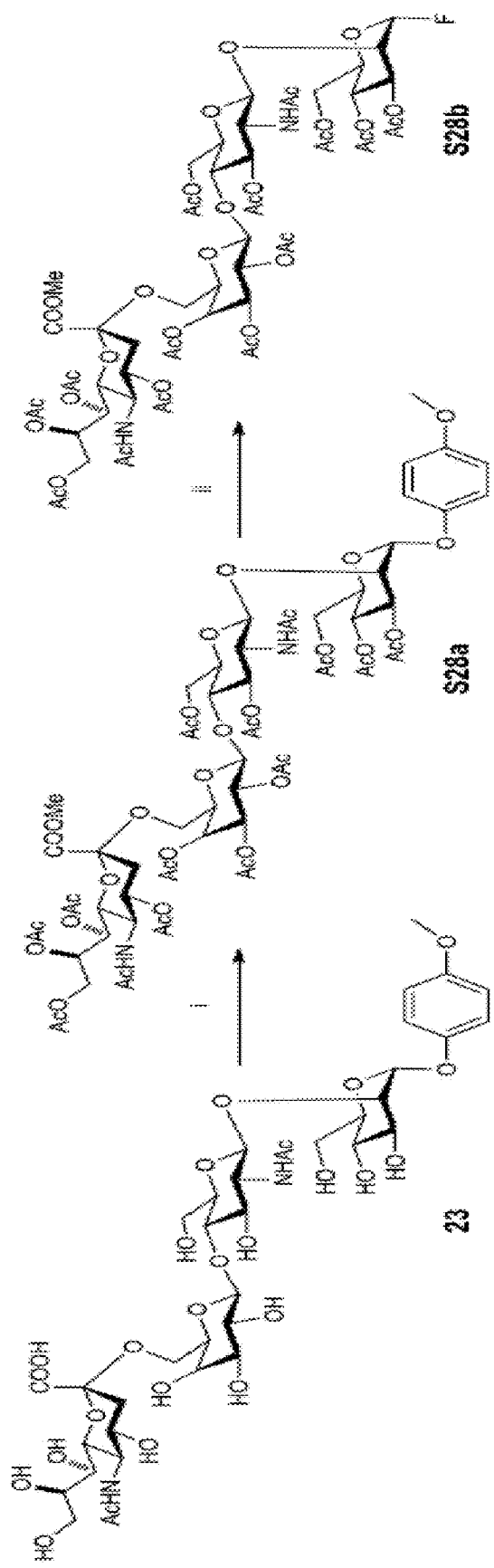

FIG. 188 Exemplary structure embodiments and synthetic scheme embodiments of the present disclosure.

Figure 189:
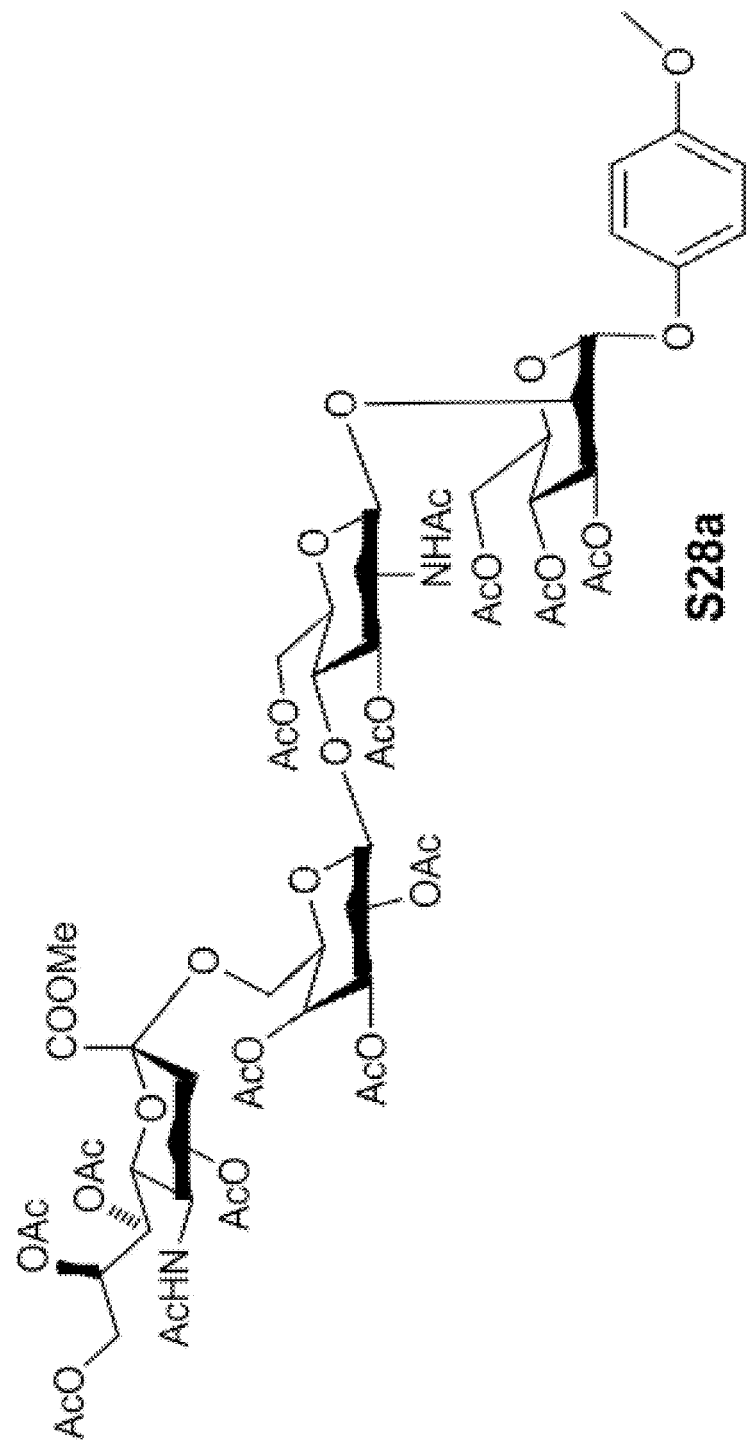

FIG. 189 Exemplary structure embodiments and synthetic scheme embodiments of the present disclosure.

Figure 190:
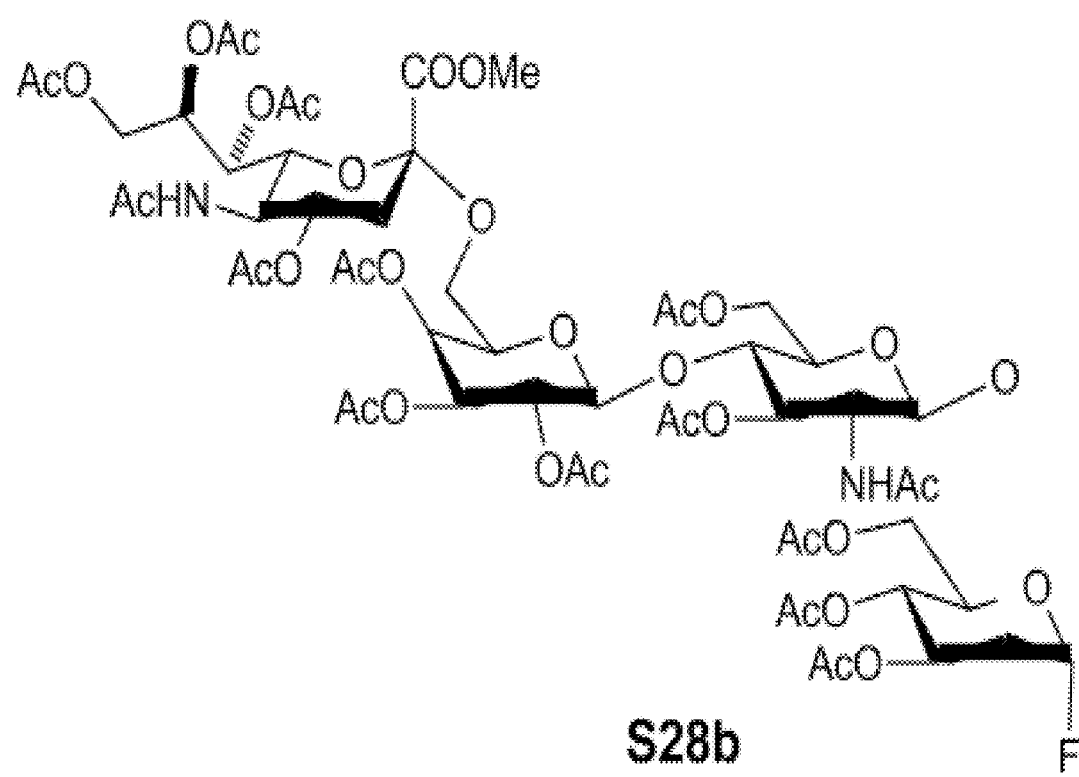

FIG. 190 Exemplary structure embodiments and synthetic scheme embodiments of the present disclosure.

Figure 191:
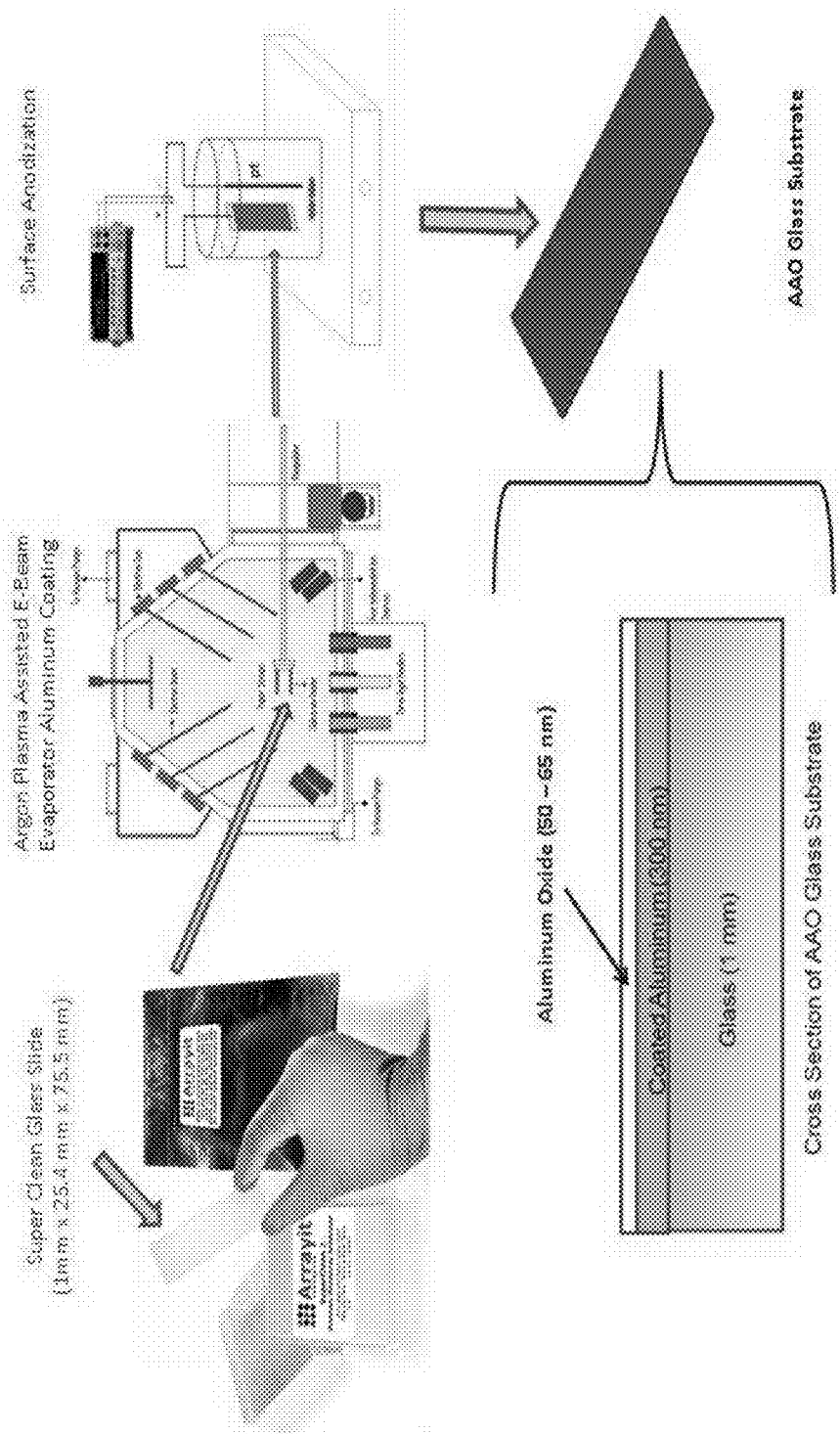

FIG. 191 Schematic drawing of the fabrication of anodized aluminum oxide (AAO) glass substrate.

Figure 192B:
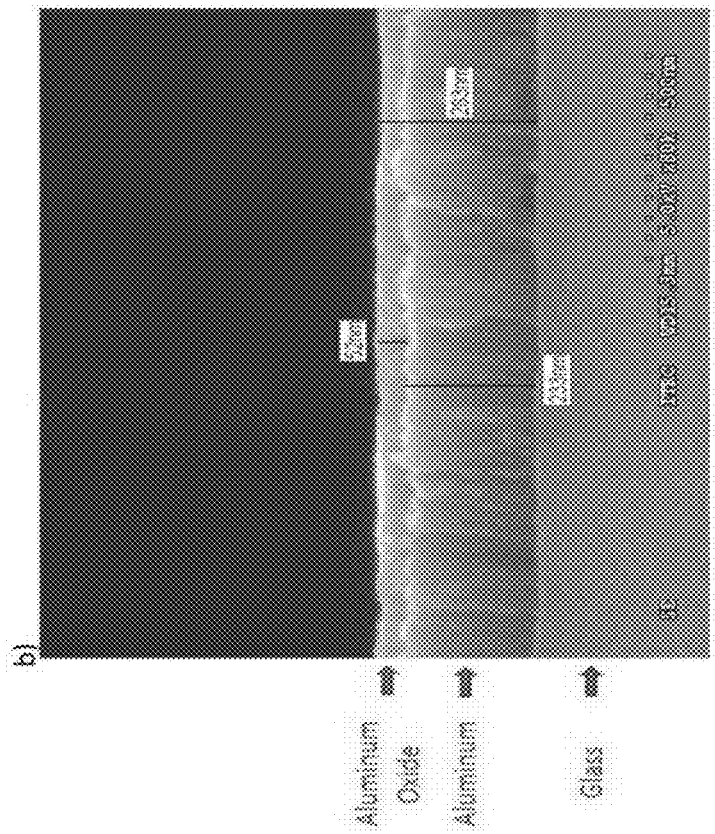
Figure 192A:
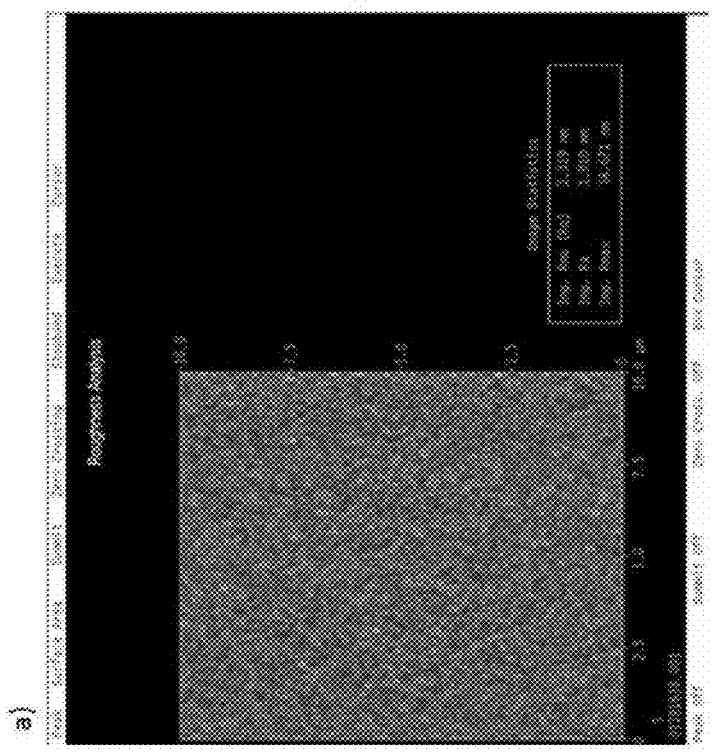

FIGS. 192A and 192B: FIG. 192A) AFM picture—Roughness Analysis of the surface. Img. Rms (Rq) 2.319 nm and FIG. 192B) Cross Section SEM picture of the AAO Glass Substrate.

FIG. 193 Structures of Cy5-phosphonic acid linker and Cy5-amine linker.

Figure 194:
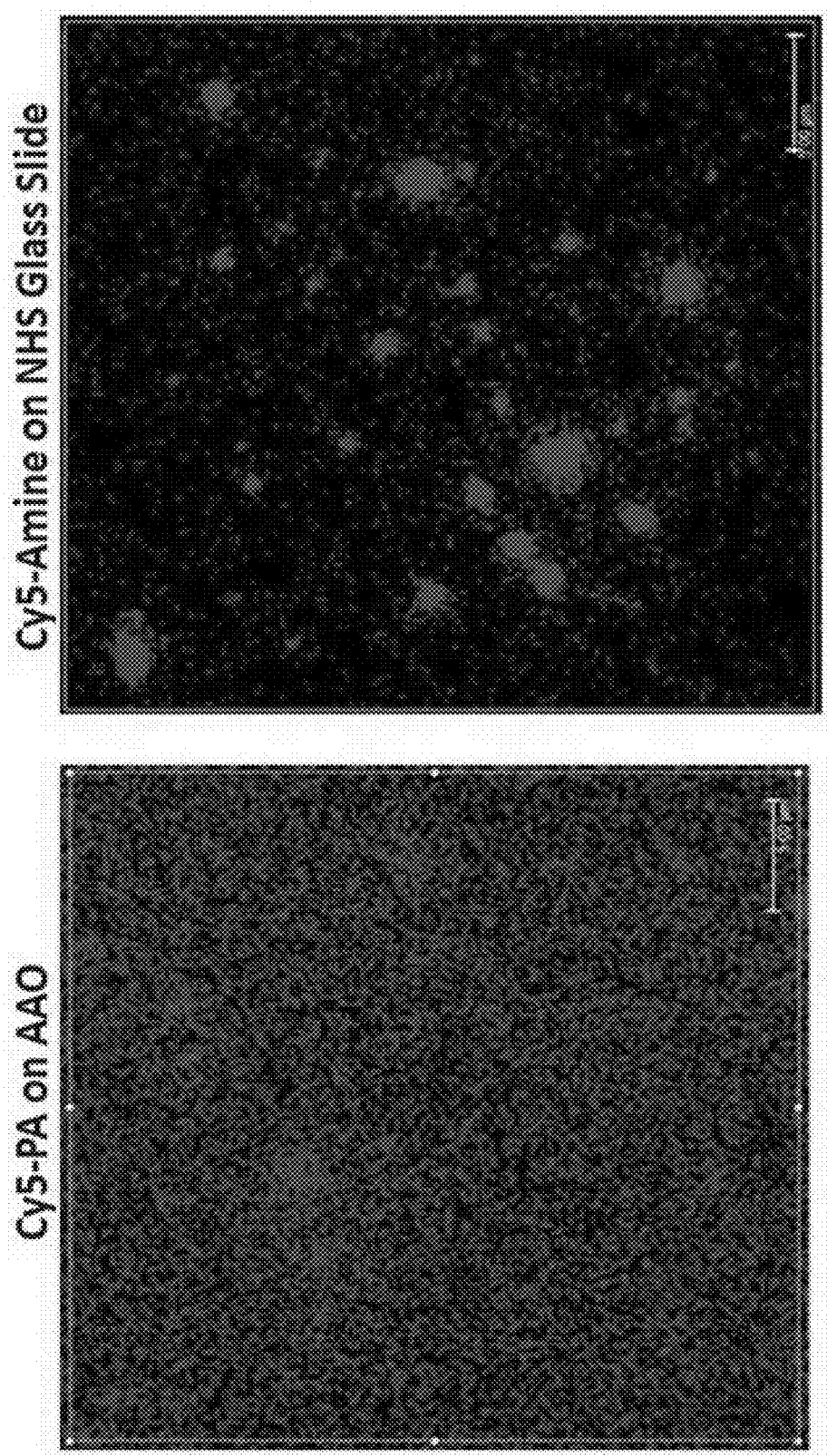

FIG. 194 Representative Confocal Microscopes pictures Cy5-phosphonic Acid, and Cy5-Amine on AAO glass substrate and NHS glass slide. Selective 900 µm2 area within the spots FIGS. 195A, 195B, and 195C. GenePix Scanning (at PMT 450) of 1 mM of (FIG. 195A) Cy5-phosphonic Acid on AAO glass substrate (FIG. 195B) Cy5-Amine on NHS glass slide, and (FIG. 195C) their averaged 20 spots.

Figure 196:
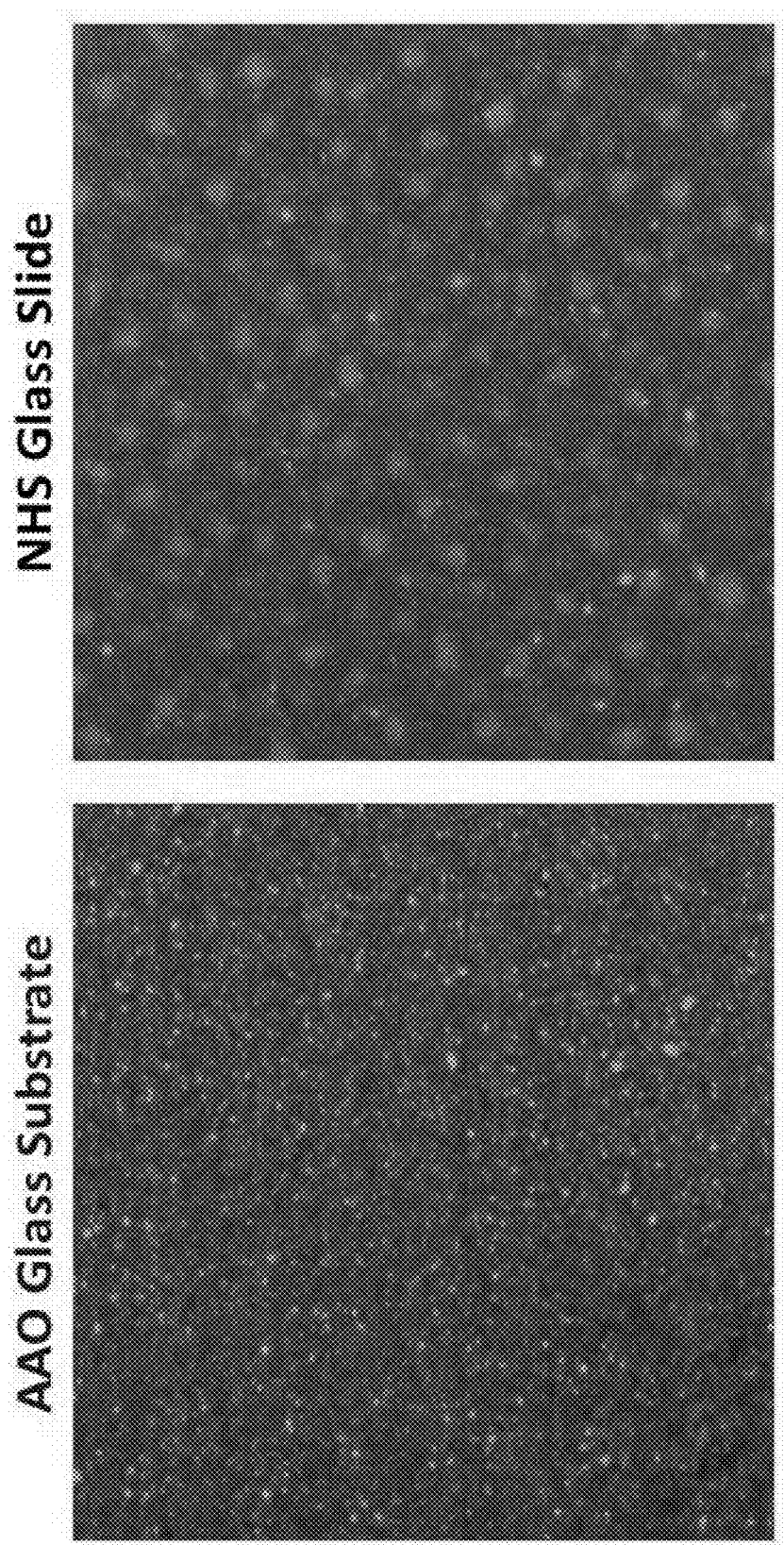

FIG. 196 Confocal Microscope of ConA488/Mannose binding on AAO glass Substrate vs. NHS-Glass Slide.

Figure 197A:
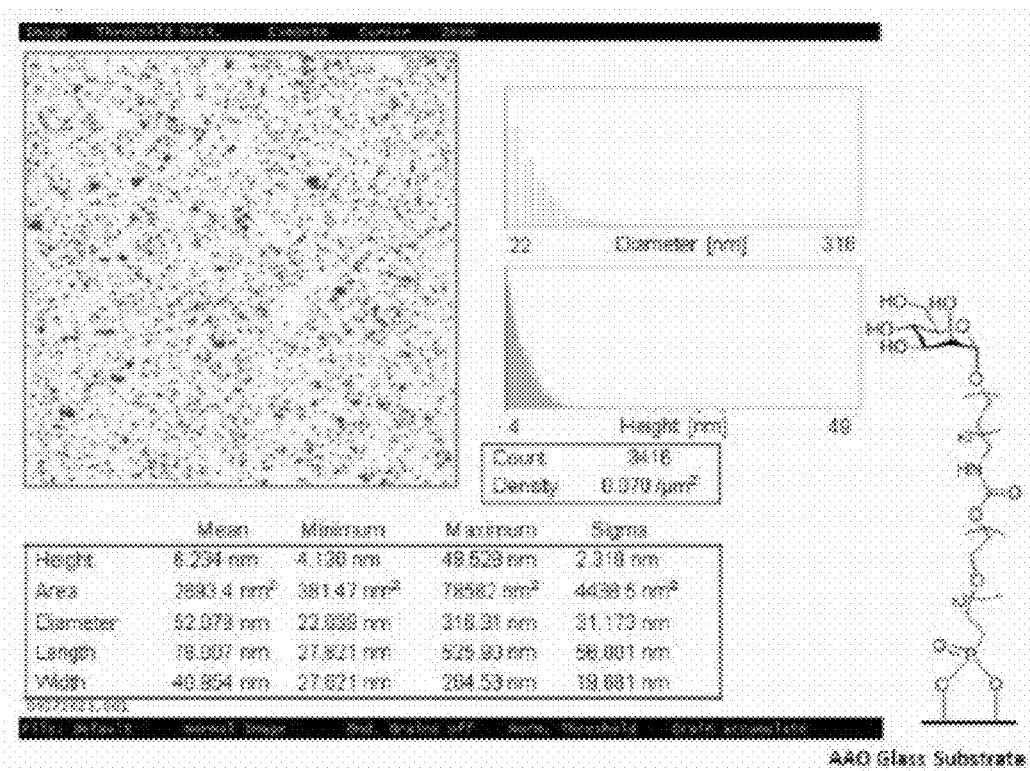
Figure 197B:
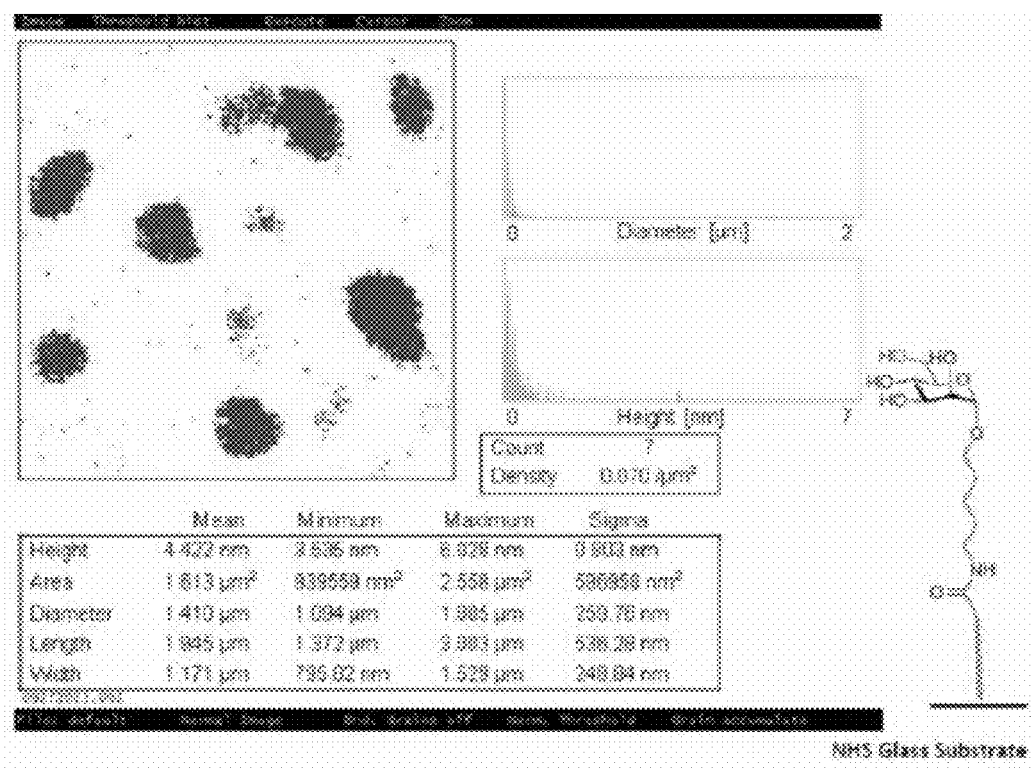

FIGS. 197A and 197B Atomic force microscopy image showing sugar distribution on FIG. 197A) aluminum-oxide coated glass slide, and FIG. 197B) NHS coated glass slide FIG. 198 Schematic representation of N-glycans printed on NHS coated glass slide.

Figure 199:
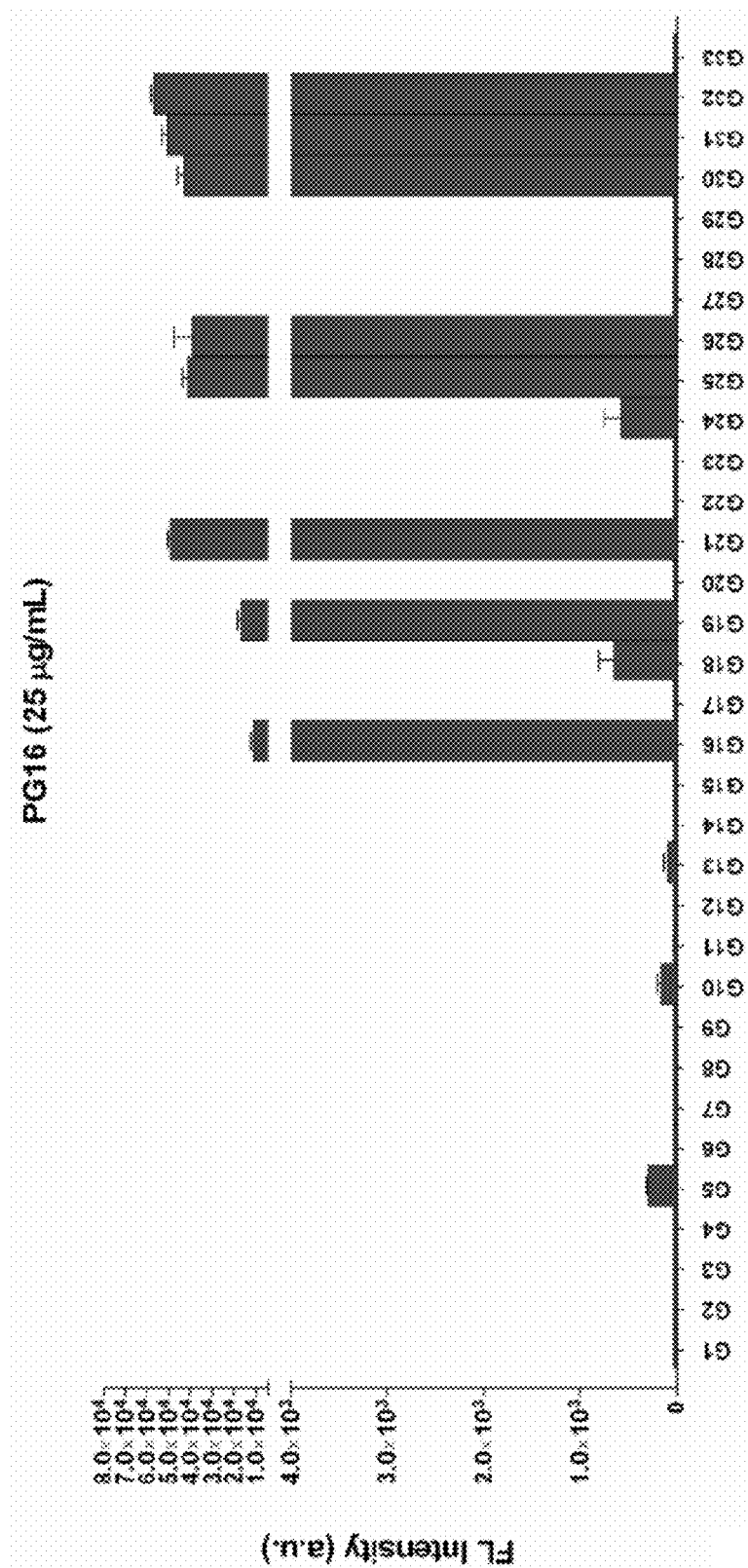

FIG. 199 Binding behavior of PG16 using NHS-coated glass slide. Bindings of PG16 to panel of N-glycans represented in bar chart.

Figure 200:
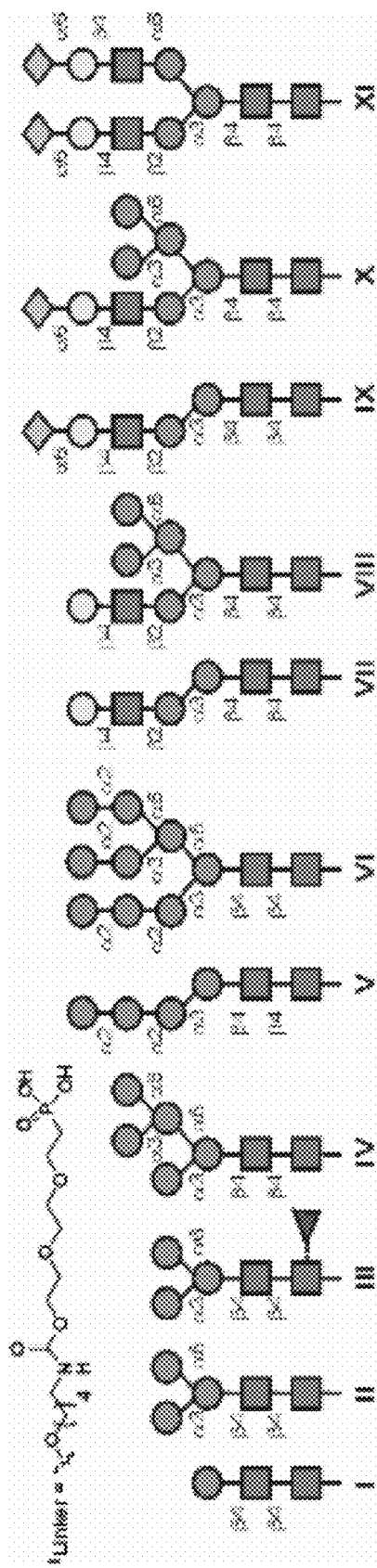

FIG. 200 Cartoon represents glycans printed on ACG array. The structure of linker is shown on the upper left corner.

Figure 201A:
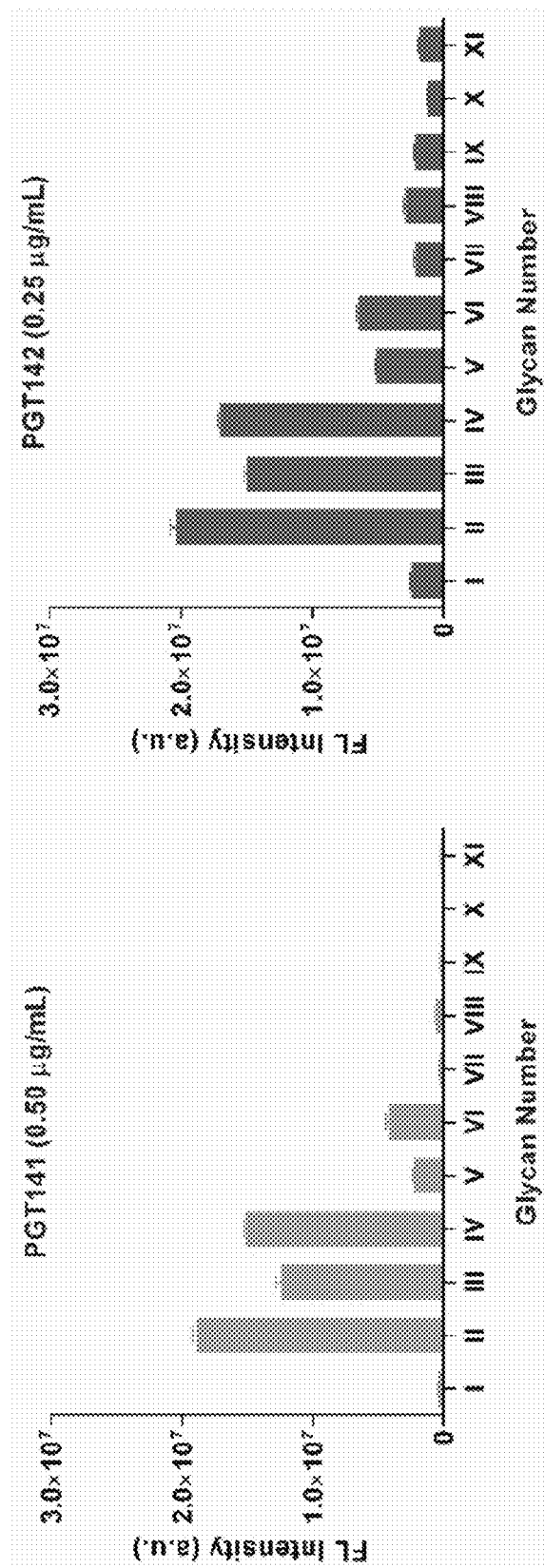
Figure 201B:
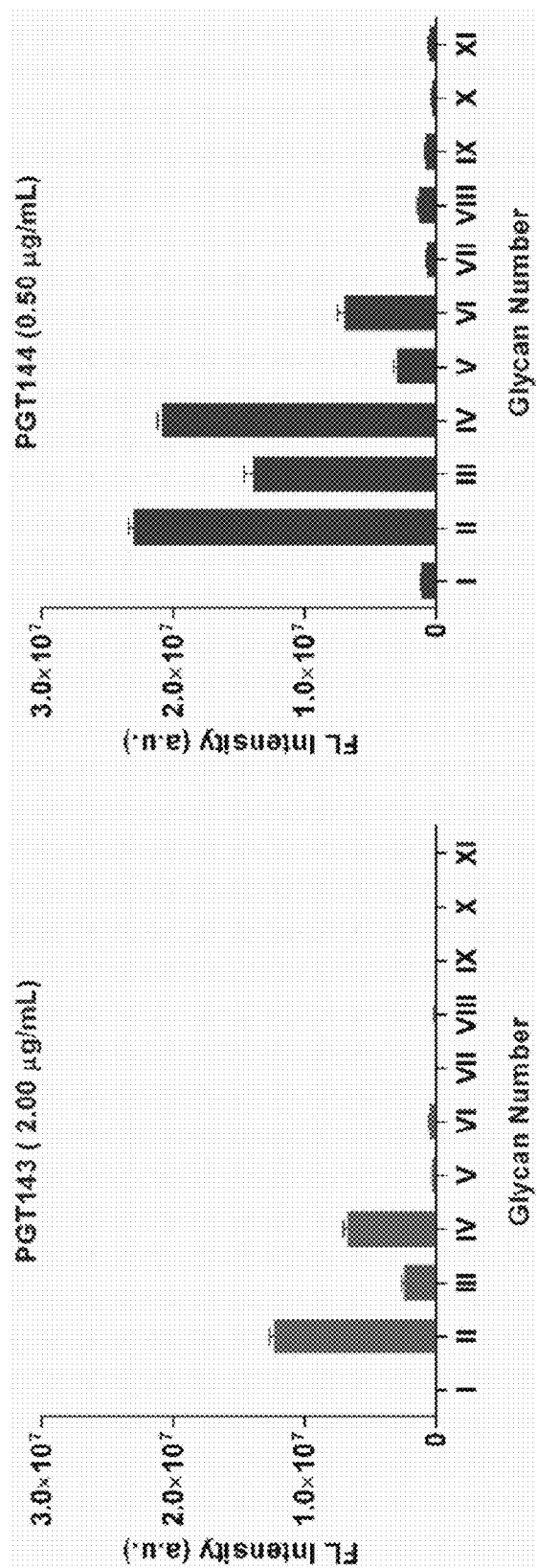

FIGS. 201A and 201B Bindings of PGTs 141-144 towards panel of N-glycans on ACG array is shown in bar chart.

Figure 202A:
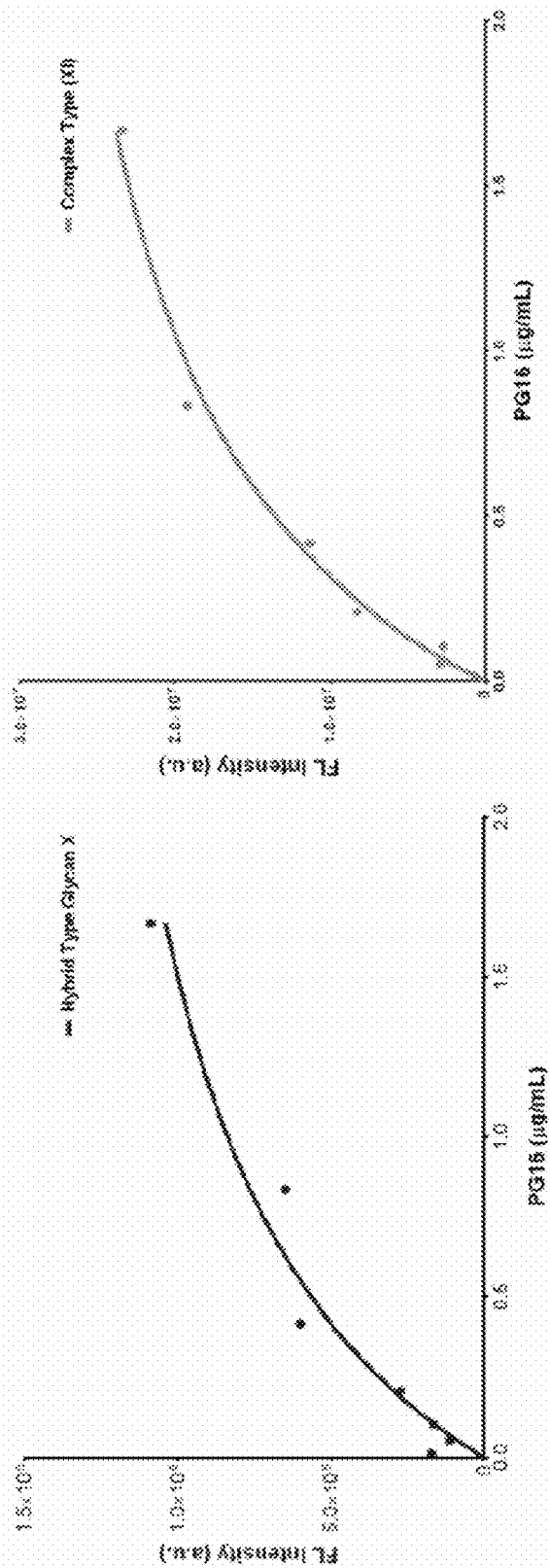
Figure 202B:
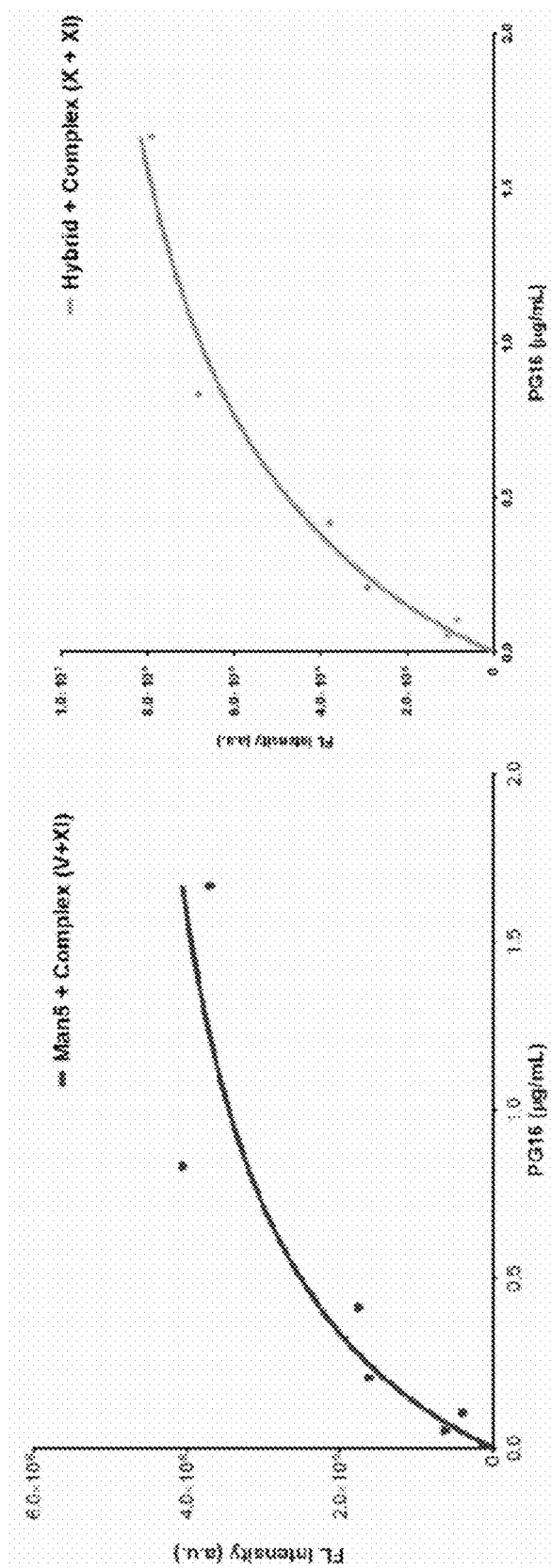

FIGS. 202A and 202B Antibody PG16 binding curves observed for glycans X, XI and mixtures V+XI and X+XII at 100 µM concentration. The curves were obtained by using DyLight649-conjugated donkey anti-Human IgG secondary antibody.

Figure 203:
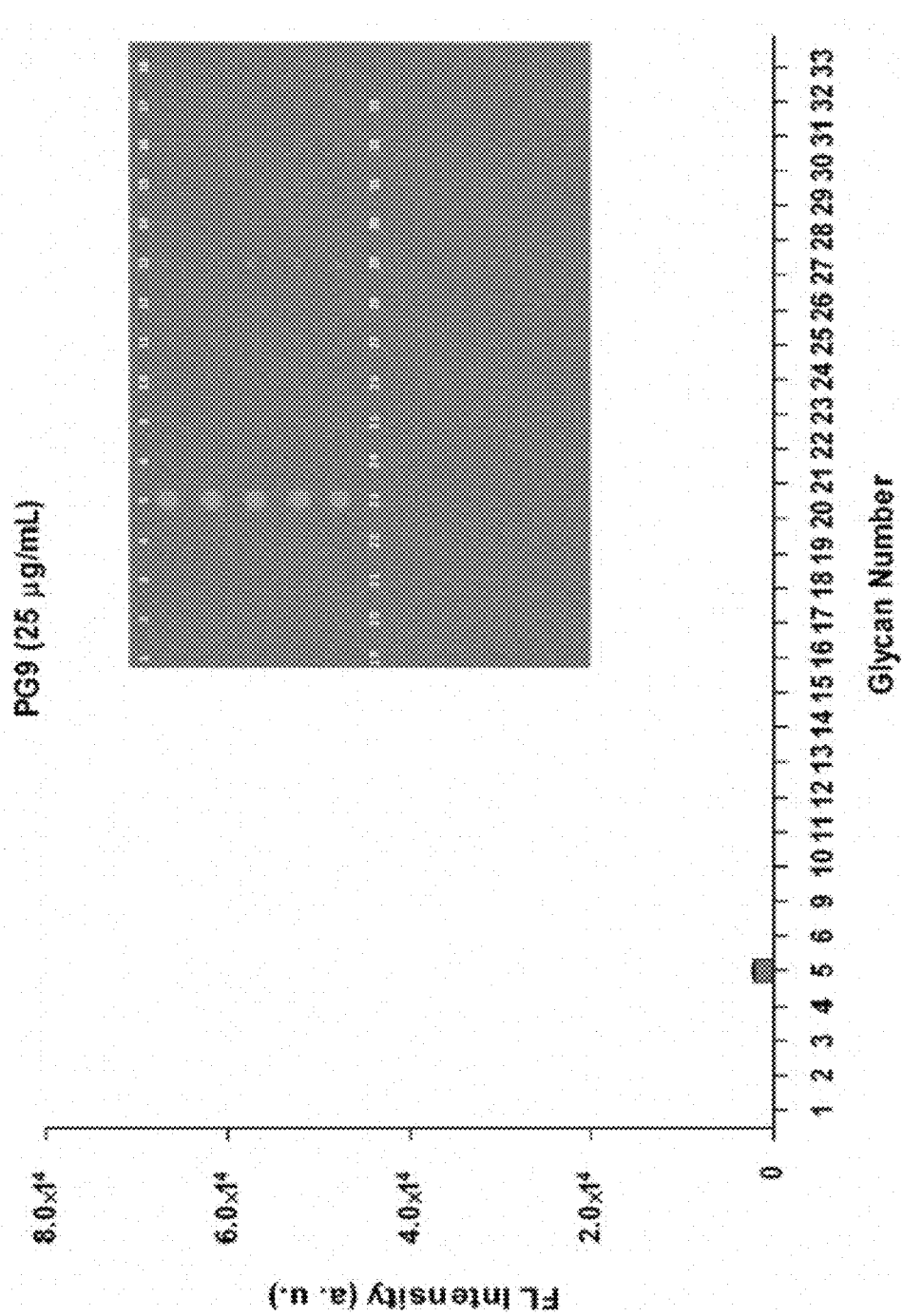

FIG. 203 show binding behavior of PG9 using NHS-coated glass slide.

Figure 204A:
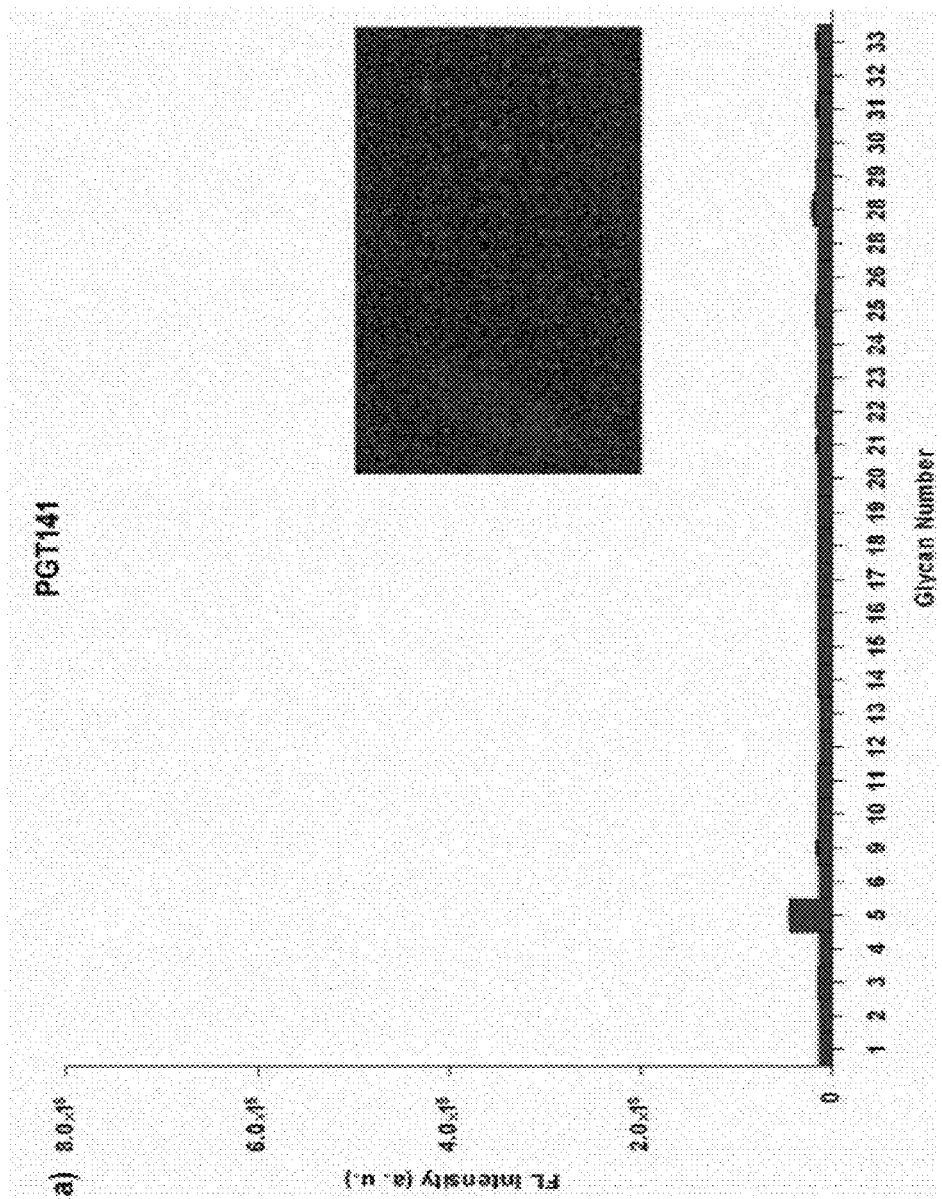
Figure 204B:
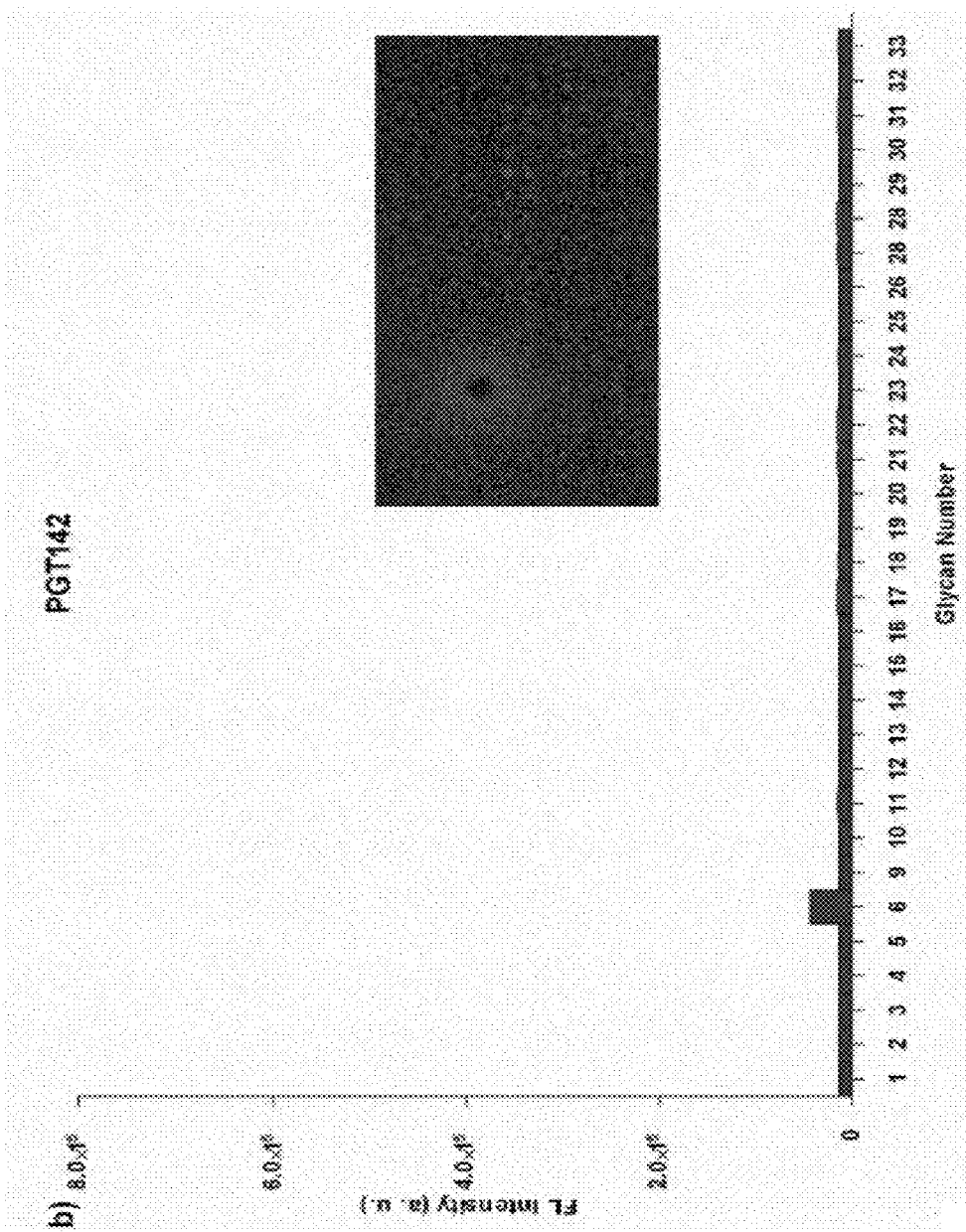
Figure 204C:
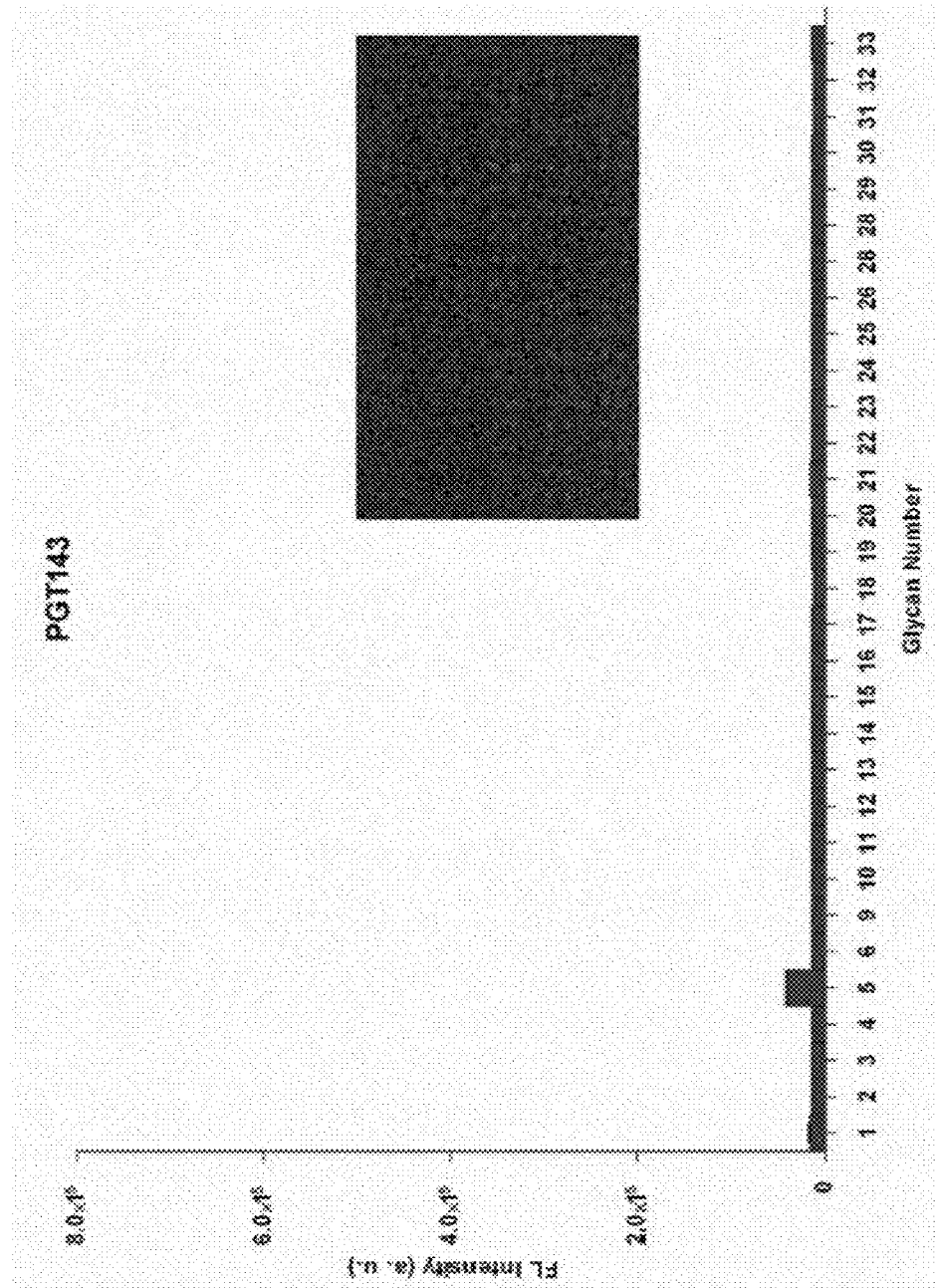

FIGS. 204A, 204B and 204C show binding behavior of PGTs 141-143 using NHS-coated glass slide.

Figure 205A:
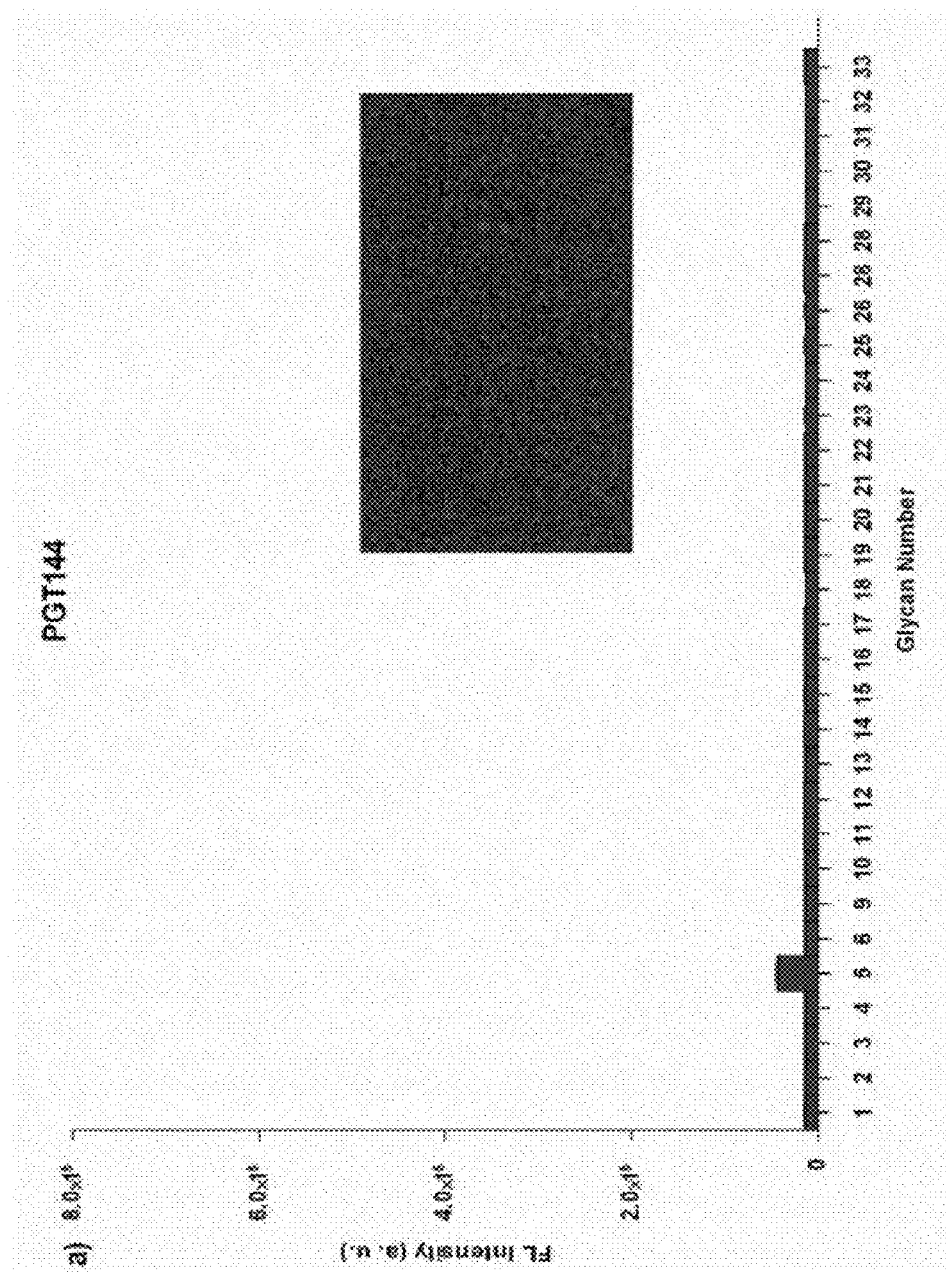
Figure 205B:
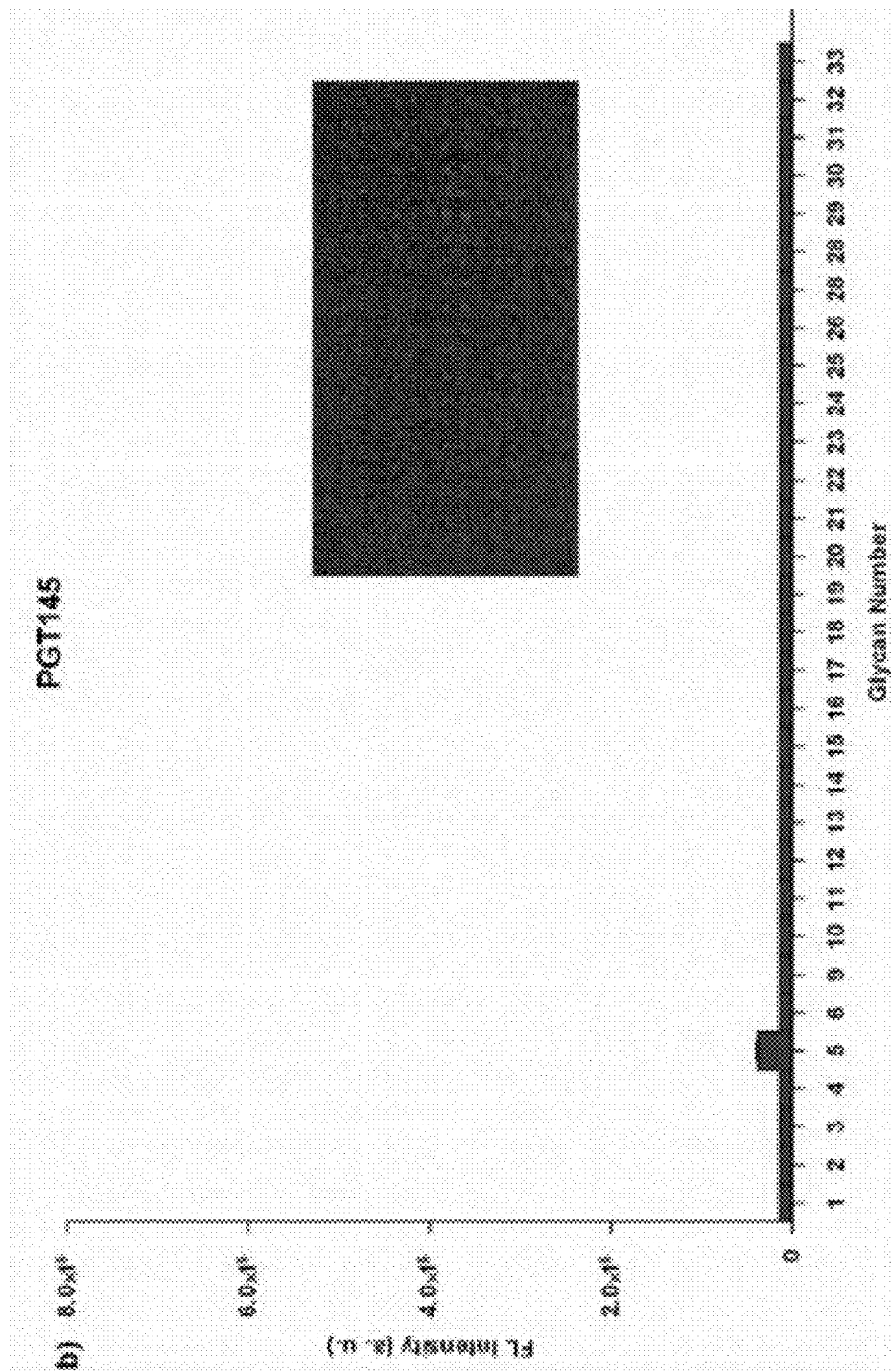

FIGS. 205A and 205B show binding behavior of PGTs14-145 using NHS-coated glass slide.

Figure 206:
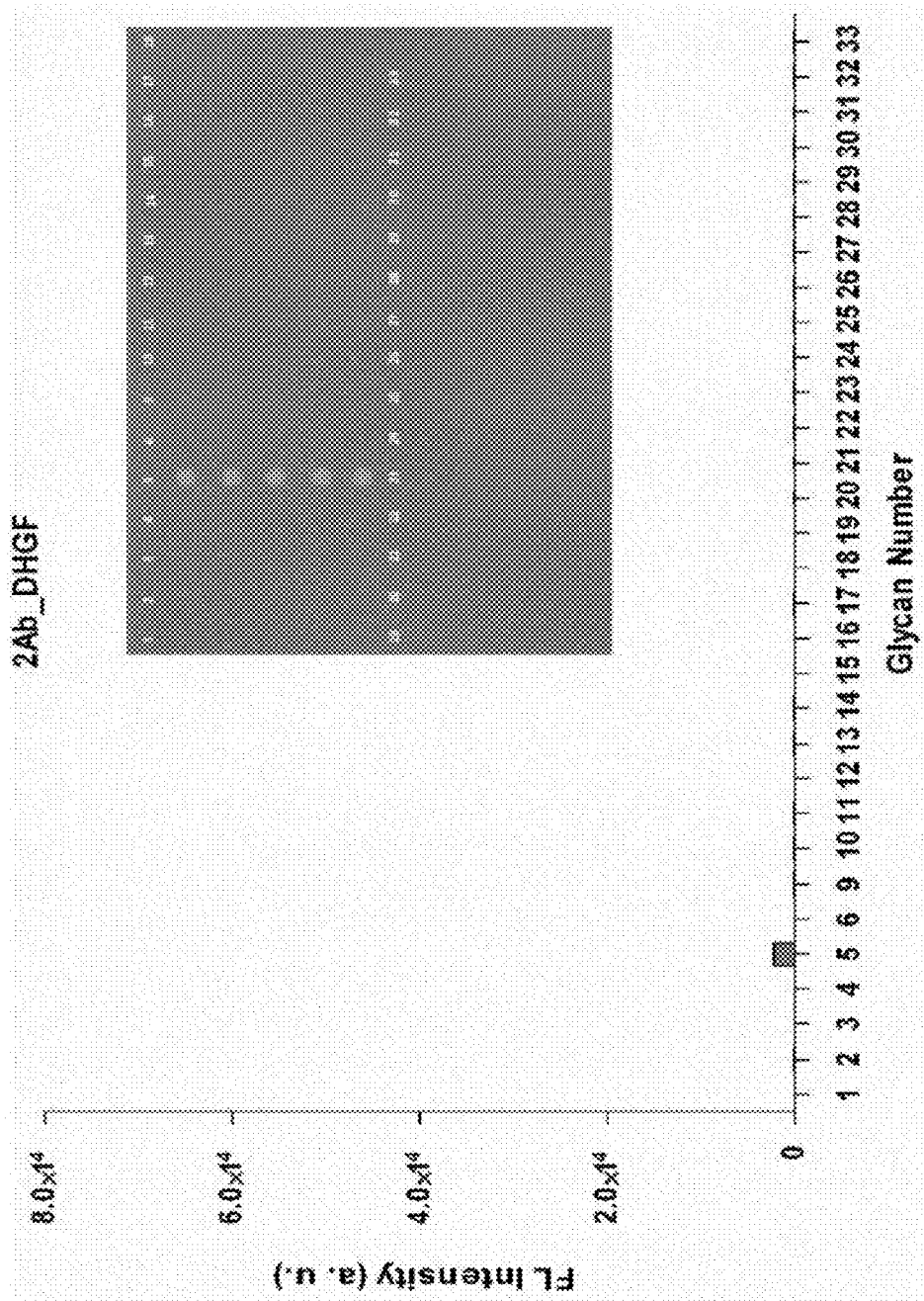

FIG. 206 shows a strong fluorescent signal against glycan 5, $Man_4GlcAc_2$.

DETAILED DESCRIPTION OF THE INVENTION

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press, 1989); DNA Cloning, Volumes I and II (D. N. Glover ed., 1985); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Antibodies: A Laboratory Manual, by Harlow and Lanes (Cold Spring Harbor Laboratory Press, 1988); and Handbook Of Experimental Immunology, Volumes I-IV (D. M. Weir and C. C. Blackwell, eds., 1986).

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., Inside Cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers. Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The present disclosure additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (e.g., —$CH_3$). In certain embodiments, the alkyl group is substituted $C_{1-10}$ alkyl.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), ydroxy[2.2.1]heptanyl ($C_7$), ydroxy[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused to one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In certain embodiments, the heteroatom is independently selected from nitrogen, sulfur, and oxygen. In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiorenyl. Exemplary 4-membered heterocyclyl groups containing one heteroatom include, without limitation, azetidinyl, oxetanyl, and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl, and thiepanyl. Exemplary 8-membered heterocyclyl groups containing one heteroatom include, without limitation, azocanyl, oxecanyl, and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Arylalkyl" is a subset of alkyl and aryl, as defined herein, and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen, and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl, as defined herein, and refers to an optionally substituted alkyl group substituted by an optionally substituted heteroaryl group.

Alkyl, alkenyl, alkynyl, carbocyclyl, heterocyclyl, aryl, and heteroaryl groups, as defined herein, which are divalent bridging groups are further referred to using the suffix -ene, e.g., alkylene, alkenylene, alkynylene, carbocyclylene, heterocyclylene, arylene, and heteroarylene.

As used herein, the term "optionally substituted" refers to a substituted or unsubstituted moiety.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this present disclosure, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$(=O)R$^{aa}$, —NR$^{bb}$CO$_2$R$^{aa}$, —NR$^{bb}$(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —Osi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)NR$)_2$, —OP(=O)NR$^{bb}$)$_2$, —NR$^{bb}$P(=O))OR$^{cc}$)$_2$, —NR$^{bb}$P(=O)NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —Osi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ to aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O) C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —Osi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two R$^{gg}$ substituents can be joined to form =O or =S; wherein X$^-$ is a counterion.

"Halo" or "halogen" refers to fluorine (fluoro, —F), chlorine (chloro, —Cl), bromine (bromo, —Br), or iodine (iodo, —I).

"Acyl" as used herein refers to a moiety selected from the group consisting of —C(=O)R$^{aa}$, —CHO, —CO$_2$R$^{aa}$, —C(=O)N(R$^{bb}$)$_2$, —C(=NR$^{bb}$)R$^{aa}$, C(=NR$^{bb}$)OR$^{aa}$, —C(=NR$^{bb}$)N(R$^{bb}$)$_2$, —C(=O)NR$^{bb}$SO$_2$R$^{aa}$, —C(=S)N(R$^{bb}$)$_2$, —C(=O)SR$^{aa}$, and —C(=S)SR$^{aa}$, wherein R$^{aa}$ and R$^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-Adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-hydroxyl, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Oxygen protecting groups are well known in the art and include those described in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris (levulinoyloxyphenyl)methyl, 4,4',4''-tris (benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a thiol protecting group). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. The term "protecting groups, and in particular sulfur protecting groups, are well known in the art and include those described in *Protecting Groups in Organic Synthesis*, T. W. Greene and P. G. M. Wuts, 3$^{rd}$ edition, John Wiley & Sons, 1999, incorporated herein by reference in its entirety.

As used herein, the term "leaving group" is given its ordinary meaning in the art of synthetic organic chemistry and refers to an atom or a group capable of being displaced by a nucleophile. Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

Definitions:

As used herein, the term "glycan" refers to a polysaccharide, oligosaccharide or monosaccharide. Glycans can be monomers or polymers of sugar residues and can be linear or branched. A glycan may include natural sugar residues (e.g., glucose, N-acetylglucosamine, N-acetyl neuraminic acid, galactose, mannose, fucose, hexose, arabinose, ribose, xylose, etc.) and/or modified sugars (e.g., 2'-fluororibose, 2'-deoxyribose, phosphomannose, 6' sulfo N-acetylglucosamine, etc). Glycan is also used herein to refer to the carbohydrate portion of a glycoconjugate, such as a glycoprotein, glycolipid, glycopeptide, glycoproteome, peptidoglycan, lipopolysaccharide or a proteoglycan. Glycans usually consist solely of O-glycosidic linkages between monosaccharides. For example, cellulose is a glycan (or more specifically a glucan) composed of β-1,4-linked D-glucose, and chitin is a glycan composed of β-1,4-linked N-acetyl-D-glucosamine. Glycans can be homo or heteropolymers of monosaccharide residues, and can be linear or branched. Glycans can be found attached to proteins as in glycoproteins and proteoglycans. They are generally found on the exterior surface of cells. O- and N-linked glycans are very common in eukaryotes but may also be found, although less commonly, in prokaryotes.

As used herein, the terms "fucose", "core fucose" and "core fucose residue" are used interchangeably and refer to a fucose in α1,6-position linked to the N-acetylglucosamine.

As used herein, the terms "N-glycan", "N-linked glycan", "N-linked glycosylation", "Fc glycan" and "Fc glycosylation" are used interchangeably and refer to an N-linked oligosaccharide attached by an N-acetylglucosamine (GlcNAc) linked to the amide nitrogen of an asparagine residue in a Fc-containing polypeptide. The term "Fc-containing polypeptide" refers to a polypeptide, such as an antibody, which comprises an Fc region.

As used herein, the term "glycosylation pattern" and "glycosylation profile" are used interchangeably and refer to the characteristic "fingerprint" of the N-glycan species that have been released from a glycoprotein or antibody, either enzymatically or chemically, and then analyzed for their carbohydrate structure, for example, using LC-HPLC, or MALDI-TOF MS, and the like. See, for example, the review in Current Analytical Chemistry, Vol. 1, No. 1 (2005), pp. 28-57; herein incorporated by reference in its entirety.

As used herein, "broadly neutralizing HIV-1 antibodies" are neutralizing antibodies which neutralize multiple HIV-1 viral strains and can include or exclude any one or more of the following antibody examplars:

| Viral Epitope | Antibody binding characteristics | Antibody clonal family |
|---|---|---|
| MPER of gp41 | Contiguous sequence | 2F5 |
| | Contiguous sequence | 4E10 |
| | Contiguous sequence | M66.6 |
| | Contiguous sequence | CAP206-CH12 |
| | Contiguous sequence | 10E8 1 |
| V1V2-glycan | Peptidoglycan | PG9, PG16 |
| | Peptidoglycan | CH01-04 |
| | Peptidoglycan | PGT 141-145 |
| Outer domain glycan | Glycan only | 2G12 |
| V3-glycan | Peptidoglycan | PGT121-123 |
| | Peptidoglycan | PGT125-131 |
| | Peptidoglycan | PGT135-137 |
| CD4 binding site | CDRH3 loop | b12 |
| | | HJ16 |
| | CDRH3 loop | CH103-106 |
| | Mimics CD4 via CDRH2 | VRC01-03 |
| | Mimics CD4 via CDRH2 | VRC-PG04, 04b |
| | Mimics CD4 via CDRH2 | VRC-CH30-34 |
| | | 3BNC117, 3BNC60 |
| | Mimics CD4 via CDRH2 | NIH45-46 |
| | | 12A12, 12A21 |
| | | 8ANC131, 134 |
| | | 1NC9, 1B2530 |

A "defined glycan probe location" as used herein is a predefined region of a solid support to which a density of glycan molecules, all having similar glycan structures, is attached. The terms "glycan region," or "selected region", or simply "region" are used interchangeably herein for the term defined glycan probe location. The defined glycan probe location may have any convenient shape, for example, circular, rectangular, elliptical, wedge-shaped, and the like. In some embodiments, a defined glycan probe location and, therefore, the area upon which each distinct glycan type or a distinct group of structurally related glycans is attached is smaller than about 1 $cm^2$, or less than 1 $mm^2$, or less than 0.5 $mm^2$. In some embodiments the glycan probe locations have an area less than about 10,000 $\mu m^2$ or less than 100 $\mu m^2$. The glycan molecules attached within each defined glycan probe location are substantially identical. Additionally, multiple copies of each glycan type are present within each defined glycan probe location. The number of copies of each glycan types within each defined glycan probe location can be in the thousands to the millions.

As used herein, the arrays of the present disclosure have defined glycan probe locations, each with "one type of glycan molecule." The "one type of glycan molecule" employed can be a group of substantially structurally identical glycan molecules or a group of structurally similar glycan molecules. There is no need for every glycan molecule within a defined glycan probe location to have an identical structure. In some embodiments, the glycans within a single defined glycan probe location are structural isomers, have variable numbers of sugar units or are branched in somewhat different ways. However, in general, the glycans within a defined glycan probe location have substantially the same type of sugar units and/or approximately the same proportion of each type of sugar unit. The types of substituents on the sugar units of the glycans within a defined glycan probe location are also substantially the same.

Detection of binding can be direct, for example, by detection of a label directly attached to the test molecule.

Alternatively, detection can be indirect, for example, by detecting a labeled secondary antibody or other labeled molecule that can bind to the test molecule. The bound label can be observed using any available detection method. For example, an array CCD analyzer can be employed to detect chemiluminescence labeled molecules that are bound to array.

As used herein, the term "antigen" is defined as any substance capable of eliciting an immune response.

As used herein, the term "immunogenicity" refers to the ability of an immunogen, antigen, or vaccine to stimulate an immune response.

As used herein, the term "epitope" is defined as the parts of an antigen molecule which contact the antigen binding site of an antibody or a T cell receptor.

As used herein, the term "vaccine" refers to a preparation that contains an antigen, consisting of whole disease-causing organisms (killed or weakened) or components of such organisms, such as proteins, peptides, or polysaccharides, that is used to confer immunity against the disease that the organisms cause. Vaccine preparations can be natural, synthetic or derived by recombinant DNA technology.

As used herein, the term "antigen specific" refers to a property of a cell population such that supply of a particular antigen, or a fragment of the antigen, results in specific cell proliferation.

As used herein, the term "specifically binding," refers to the interaction between binding pairs (e.g., an antibody and an antigen). In various instances, specifically binding can be embodied by an affinity constant of about $10^{-6}$ moles/liter, about $10^{-7}$ moles/liter, or about $10^{-8}$ moles/liter, or less.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In one embodiment, the antibody will be purified (1) to greater than 95% by weight of antibody as determined by, for example, the Lowry method, and in some embodiments more than 99% by weight, (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

The term "support" or "substrate" as used interchangeably herein refers to a material or group of materials, comprising one or a plurality of components, with which one or more molecules are directly or indirectly bound, attached, synthesized upon, linked, or otherwise associated. A support may be constructed from materials that are biological, non-biological, inorganic, organic or a combination of these. A support may be in any appropriate size or configuration based upon its use within a particular embodiment.

The term "target" as used herein refers to a species of interest within an assay. Targets may be naturally occurring or synthetic, or a combination. Targets may be unaltered (e.g., utilized directly within the organism or a sample thereof), or altered in a manner appropriate for the assay (e.g., purified, amplified, filtered). Targets may be bound through a suitable means to a binding member within certain assays. Non-limiting examples of targets include, but are not restricted to, antibodies or fragments thereof, cell membrane receptors, monoclonal antibodies and antisera reactive with specific antigenic determinants (such as on viruses, cells or other materials), drugs, oligonucleotides, nucleic acids, peptides, cofactors, sugars, lectins polysaccharides, cells, cellular membranes, and organelles. Target may be any suitable size depending on the assay.

The phrase "substantially similar," "substantially the same", "equivalent", or "substantially equivalent", as used herein, denotes a sufficiently high degree of similarity between two numeric values (for example, one associated with a molecule and the other associated with a reference/comparator molecule) such that one of skill in the art would consider the difference between the two values to be of little or no biological and/or statistical significance within the context of the biological characteristic measured by said values (e.g., Kd values, anti-viral effects, etc.). The difference between said two values is, for example, less than about 50%, less than about 40%, less than about 30%, less than about 20%, and/or less than about 10% as a function of the value for the reference/comparator molecule.

The phrase "substantially reduced," or "substantially different", as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present present disclosure. Specific illustrative embodiments are described in the following.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semisolid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azidoribose, carbocyclic sugar analogs, a-anomeric sugars, epimeric sugars such as arabinose, xyloses or lyxoses, pyranose sugars, furanose sugars, sedoheptuloses, acyclic analogs and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR2 ("amidate"), P(O)R, P(O)OR', CO or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single-stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

"Antibodies" (Abs) and "immunoglobulins" (IGs) are glycoproteins having the same structural characteristics. While antibodies exhibit binding specificity to a specific antigen, immunoglobulins include both antibodies and other antibody-like molecules which generally lack antigen specificity. Polypeptides of the latter kind are, for example, produced at low levels by the lymph system and at increased levels by myelomas.

The terms "antibody" and "immunoglobulin" are used interchangeably in the broadest sense and include monoclonal antibodies (e.g., full length or intact monoclonal antibodies), polyclonal antibodies, monovalent, multivalent antibodies, multispecific antibodies (e.g., bispecific antibodies so long as they exhibit the desired biological activity) and may also include certain antibody fragments (as described in greater detail herein). An antibody can be chimeric, human, humanized and/or affinity matured.

The "variable region" or "variable domain" of an antibody refers to the amino-terminal domains of heavy or light chain of the antibody. These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. Cellular and Mol. Immunology, 4th ed. (2000). An antibody may be part of a larger fusion molecule, formed by covalent or non-covalent association of the antibody with one or more other proteins or peptides.

The terms "full length antibody," "intact antibody" and "whole antibody" are used herein interchangeably, to refer to an antibody in its substantially intact form, not antibody fragments as defined below. The terms particularly refer to an antibody with heavy chains that contain the Fc region.

"Antibody fragments" comprise only a portion of an intact antibody, wherein the portion retains at least one, and as many as most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half-life modulation, ADCC function and complement binding. In one embodiment, an antibody fragment is a monovalent antibody that has an in vivo half-life substantially similar to an intact antibody. For example, such an antibody fragment may comprise an antigen binding arm linked to an Fc sequence capable of conferring in vivo stability to the fragment.

The term "monoclonal antibody" as used herein refers to an antibody obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies. Such monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones or recombinant DNA clones. It should be understood that the selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this present disclosure. In contrast to polyclonal antibody preparations which typically include different antibodies directed against different determinants (epitopes), each monoclonal antibody of a monoclonal antibody preparation is directed against a single determinant on an antigen. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by a variety of techniques, including, for example, the hybridoma method (e.g., Kohler et al., Nature, 256: 495 (1975); Harlow et al., Antibodies: A Laboratory Manual, (Cold Spring Harbor Laboratory Press, 2nd ed. 1988); Hammerling et al., in: Monoclonal Antibodies and T-Cell hybridomas 563-681 (Elsevier, N.Y., 1981)), recombinant DNA methods (see, e.g., U.S. Pat. No. 4,816,567), phage display technologies (See, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO98/24893; WO96/34096; WO96/33735; WO91/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; 5,661,016; Marks et al., Bio. Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996) and Lonberg and Huszar, Intern. Rev. Immunol. 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region of the recipient are replaced by residues from a hypervariable region of a non-human species (donor antibody) such as mouse, rat, rabbit or nonhuman primate having the desired specificity, affinity, and/or capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994).

As used herein, "normal levels" can be, for example, a reference value or range based on measurements of the levels of TACA bound antibodies in samples from normal patients or a population of normal patients. "Normal levels" can also be, for example, a reference value or range based on measurements of the TACAs in samples from normal patients or a population of normal patients.

As used herein a "subject" is a mammal. Such mammals include domesticated animals, farm animals, animals used in experiments, zoo animals and the like. In some embodiments, the subject is a human.

A "disorder" is any condition that would benefit from treatment with an antibody of the present disclosure. This includes chronic and acute disorders or diseases including those pathological conditions which predispose the mammal to the disorder in question. Non-limiting examples of disorders to be treated herein include HIV.

The following definitions are more general terms used throughout the present application.

As used herein and in the appended claims, the singular forms "a," "and," and "the" include plural referents unless the context clearly dictates otherwise. Thus, for example, "a transport enhancer" encompasses a plurality of transport enhancers as well as a single transport enhancer. Reference to "a chelating agent" includes reference to two or more chelating agents as well as a single chelating agent, and so forth. In this specification and in the claims that follow, reference will be made to a number of terms, which shall be defined to have the following meanings:

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. The terms "preventing" and "prevention" refer to the administration of an agent or composition to a clinically asymptomatic individual who is susceptible to a particular adverse condition, disorder, or disease, and thus relates to the prevention of the occurrence of symptoms and/or their underlying cause. Unless otherwise indicated herein, either explicitly or by implication, if the term "treatment" (or "treating") is used without reference to possible prevention, it is intended that prevention be encompassed as well.

"Optional" or "optionally present"—as in an "optional substituent" or an "optionally present additive" means that the subsequently described component (e.g., substituent or additive) may or may not be present, so that the description includes instances where the component is present and instances where it is not.

By "pharmaceutically acceptable" is meant a material that is not biologically or otherwise undesirable, e.g., the material may be incorporated into a formulation of the present disclosure without causing any undesirable biological effects or interacting in a deleterious manner with any of the other components of the dosage form formulation. However, when the term "pharmaceutically acceptable" is used to refer to a pharmaceutical excipient, it is implied that the excipient has met the required standards of toxicological and manufacturing testing and/or that it is included on the Inactive Ingredient Guide prepared by the U.S. Food and Drug Administration. As explained in further detail infra, "pharmacologically active" (or simply "active") as in a "pharmacologically active" derivative or analog refers to derivative or analog having the same type of pharmacological activity as the parent agent.

As used herein, the term "antigen" is defined as any substance capable of eliciting an immune response.

As used herein, the term "immunogen" refers to an antigen or a substance capable of inducing production of an antigen, such as a DNA vaccine.

The present disclosure provides libraries and arrays of glycans that can be used for identifying which types of proteins, receptors, antibodies, lipids, nucleic acids, carbohydrates and other molecules and substances can bind to a given glycan structure.

The arrays and methods of the present disclosure also provide highly accurate results. The libraries and arrays of the present disclosure provide large numbers and varieties of glycans. As a non-limiting example, the libraries and arrays of the present disclosure have at least one, at least two, at least three, at least ten, or at least 100 glycans. In some embodiments, the libraries and arrays of the present disclosure have about 1 to about 100,000, or about 1 to about 10,000, or about 1 to about 1,000, or about 1 to about 100, or about 2 to about 100, or about 2 to about 10, or about 1 to about 10 different glycans per array. Such large numbers of glycans permit the simultaneous assay of a multitude of glycan types. As described herein, the present arrays have been used for successfully screening a variety of glycan binding proteins. The composition of glycans on the arrays of the present disclosure can be varied as appropriate. Many different glycoconjugates can be incorporated into the arrays of the present disclosure including, for example, naturally occurring or synthetic glycans, glycoproteins, glycopeptides, glycolipids, bacterial and plant cell wall glycans and the like.

Exemplary arrays configured suitably in accordance with various embodiments of the present disclosure include, for example, U.S. Pat. No. 8,383,554 B2, "Quantitative Microarray of Intact Glycolipid CD1d Interaction and Correlation with Cell-Based Cytokine Production," U.S. Pat. No. 8,906,832 B2 "QUANTITATIVE ANALYSIS OF CARBOHYDRATE-PROTEIN INTERACTIONS USING GLYCAN MICROARRAYS: DETERMINATION OF SURFACE AND SOLUTION DISSOCIATION CONSTANTS," U.S. Pat. No. 8,680,020 B2 "Glycan arrays on PTFE-like aluminum coated glass slides and related methods," U.S. Pat. No. 8,507,660 B2 "Alpha-Selective Sialyl Phosphate Donors For Preparation Of Sialosides And Sialoside Arrays For Influenza Virus Detection," U.S. Publication No. US20150160217 (also published as WO2011130332 A1) "Glycan Arrays For High Throughput Screening Of Viruses," all of which are herein incorporated by reference in their entirety.

The substrate may be, in some embodiments, a surface, solid surface, non-transparent solid, a solid transparent to selected wavelengths of visible or non-visible light, a particle, an array, a microbubble, or a bead. In some embodiments, the bead can be on a surface, embedded in a surface, or connected to a surface. In some embodiments the substrate may be coated.

The substrate of the present disclosure can be a surface. The surface can be flat, featured, round, curved, rough, porous, solid, gelatinous, polymeric, oligomeric, or a bead. The substrate can be composed of glass, polymer, or plastic. The bead can be round, cylindrical, egg-shaped, oval, approximately round, disc-shaped, square-shaped, hexagonal-shaped, or any polyhedral-shaped entity. In some embodiments, the substrate can be chemically modified so as to present a reactive group at the surface capable of binding to another molecule. In some embodiments, the reactive group can be a carboxylic acid. In some embodiments, the bead can be a silica bead. In some embodiments, the bead can be a silica-functionalized coated silica bead. In some embodiments, the silica-functionalization can be a functionalization achieved by contacting the silica bead with a functionalized silane molecule. In some embodiments, the functionalized silane molecule can be a functionalized trichlorosilane, functionalized dichlorisilane, or functionalized monochlorosilane molecule. In some embodiments, the silica-functionalization can be a functionalization achieved by contacting the silica bead with a functionalized tri-alkoxy functionalized silane. In some embodiments, the silica-functionalization can be a functionalization achieved by contacting the silica bead with a functionalized di-alkoxy functionalized silane. In some embodiments, the silica-functionalization can be a functionalization achieved by contacting the silica bead with a functionalized mono-alkoxy functionalized silane. The functionalization can be an amino, aldehyde, halide, epoxy, NHS (N-hydroxy succinimide), maleimide, alkynyl, ethynyl, carbonyl (including carboxyl) or hydroxyl functional group. In some embodiments, the functionalization can be contacted with the silane via an $C_1$-$C_6$ alkyl group, alkoxy group, or aryl group.

In certain aspects, immobilization procedures for attaching different glycans to the arrays of the present disclosure are readily controlled to easily permit array construction. In some embodiments, each glycan can be adhered to a specific bead type, so as to form a glycan-specific association with that bead type. In some embodiments, the bead can further comprise a distinct marker which distinguishes that particular bead type from other bead types. In some embodiments, a plurality of different glycans, each adhered to a distinct bead type can be mixed in a multiplex reaction. The bead types and multiplex reaction detection methods can be those described in U.S. Pat. No. 6,696,304 and PCT Patent App. No. PCT/US2004/038416, both of which are herein incorporated by reference.

In some embodiments, the substrate can be coated with a material which can present a reactive group at the surface capable of binding to another molecule. In some embodiments, the material coating the substrate is a nitrocellulose membrane or a polymer. Such coatings present a 3D surface with high surface area, enabling a lower limit of detection compared to flat surfaces. In some embodiments an avidin, streptavidin, or neutravidin protein can be presented to the coated surface, such as a nitrocellulose membrane coating, for the attachment of biotinylated molecules. In some embodiments, a chemical linker can be presented to the surface, either directly to the surface or to a coating previously presented to the surface.

In one embodiment, the present disclosure provides linkers that may be used in a variety of applications. For example, the linkers of the present disclosure may be used to attach molecules to substrates, such as surfaces, solid surfaces, particles, arrays or beads.

In one embodiment, the present disclosure relates to a bead for use in disease diagnosis and drug discovery, the bead comprising: (a) a unique identifier on or within each bead; and (b) a glycan attached to the surface of the bead through a linker moiety. The glycan can be any of the diverse glycans described herein. In some aspects, the bead can be coated with a homogeneous population of glycan type.

In some embodiments, the present disclosure relates to methods of making glycan-linker-beads, comprising (a) providing a bead comprising a unique identifier on or within each bead; (b) contacting a glycan-linker with the bead; and (c) forming a conjugate between the glycan-linker and the bead. In some embodiments, the unique identifier on or within each bead can be a holographic image impregnated within the silica or glass bead, a specific amino acid sequence or oligonucleotide sequence attached to each bead, or a specific fluorophore attached to each bead. In some embodiments, the specific amino acid sequence or oligonucleotide sequence attached to each bead can be further linked to a linker moiety which is further conjugated to the specific glycan attached to each bead.

In some embodiments, the present disclosure relates to glycan-linker beads made by a process comprising: (a) providing a bead comprising a unique identifier on or within each bead; (b) contacting a glycan-linker with the bead; and (c) forming a conjugate between the glycan-linker and the bead.

Immobilization procedures for attaching different glycans to the arrays of the present disclosure are readily controlled to easily permit array construction. In some embodiments, each glycan can be adhered to a specific bead type, so as to form a glycan-specific association with that bead type. In some embodiments, the bead can further comprise a distinct marker which distinguishes that particular bead type from other bead types. In some embodiments, the distinct marker can be an amino acid sequence, oligonucleotide sequence, fluorophore, or dye contacted to or within each bead type. In some embodiments, the fluorophore or dye can be those known within the art. In some embodiments, the amino acid sequence or oligonucleotide sequence can be detected by an antibody or another oligonucleotide sequence complementary to the oligonucleotide sequence contacted to the bead. In some embodiments, the oligonucleotide sequence complimentary to the oligonucleotide sequence contacted to the bead surface can be labeled with one or a plurality of fluorophores. The fluorophores can be any of those known in the art (e.g., FAM, Cy3, Cy5, Cy 7, Cy3.5, Cy5.5, BHQ quenchers, TAMRA, ROX, Texas Red, Alexa fluors, those described in the Molecular Probes/Invitrogen/ThermoFisher catalog as of the filing date of the present application, etc.). In some embodiments, a plurality of different glycans, each adhered to a distinct bead type can be mixed in a multiplex reaction.

Arrays comprising unique libraries of different glycans adhered to defined regions on the solid support of an array surface can be adhered by any available procedure. In general, arrays are made by obtaining a library of glycan-linked glycopeptide molecules described herein, obtaining a substrate that has a surface modified to react with the specific linking moieties present on the glycan-linked glycopeptide molecules of the library and attaching the glycan molecules to the solid support by forming a van der Waals interaction between the linking moieties of the glycan-linked glycopeptide molecules and the modified surface of the substrate.

The modification reagent can be attached to the substrate via carbon-carbon bonds using, as a non-limiting example, siloxane bonds (using, for example, glass or silicon oxide, or activated silicon dioxide wherein the activated silicon dioxide is the result of the reaction of a silane molecule (e.g., those available from the Geleste, Inc. catalog as of the filing date of the present application, herein incorporated by reference), as the solid substrate). In some embodiments, siloxane bonds with the surface of the substrate are formed in via reactions of derivatization reagents bearing mono-, di-, or tri-chlorosilyl, or mono-, di-, or tri-alkoxysilyl groups. The non-leaving (chloro- or alkoxy-) groups on the silane can be hydrocarbons. In some embodiments, the non-leaving groups can be linear or branched alkyl chains so as to form van der Waals interactions with the peptide chains of the glycan-linked glycopeptide.

The modification reagent can be applied to the substrate via other deposition methods known to those skilled in the art for applying coatings. Such methods include chemical vapor deposition, solution-phase deposition, Langmuir-Blodgett film formation, chemical plasma treatment to expose a reactive surface molecule, spin-coating, spray-drying, or electrospinning. In some embodiments, the modification reagent can be a polymer. The polymer can be selected from polystyrene, polypropylene, polyethylene, polyethylimine, polycaprolactine, modified polycaprolactone, polymethyl methacrylate, polyacrylamide, poly-N,N-alkyl acrylamide, polyalkyl methacrylate, polyalkyl acrylate, a polysaccharide, or copolymers thereof. The polysaccharide can be cellulose, nitrocellulose, chitosan, amylose, cellulose acetate, xanthan gum, dextran, welan gum, guar gum, gellan gum, diutan gum or pullulan. The polysaccharide can further be functionalized by the reaction of an oxidizing group. In some embodiments, the oxidizing group can be sodium periodate. In some embodiments, the glycan can be reacted to the polysaccharide in the presence of a reducing agent. In some embodiments, the reducing agent can be a functionalized borohydride moiety. In some embodiments, the functionalized borohydride moiety can be a hydro-borohydride (e.g., sodium or potassium borohyride)), cyanoborohydride, or alkylborohydide moiety).

In some embodiments, each type of glycan can be contacted or printed onto a solid support at a defined glycan probe location. A microarray gene printer can be used for applying the various glycan-linked glycopeptide to defined glycan probe locations. For example, about 0.1 microliter to about 10 nanoliter (nL), or about 0.5 nL of glycan solution can be applied per defined glycan probe location or bead. Various concentrations of the glycan-linked glycopeptide solutions can be contacted or printed onto the solid support. For example, a glycan-linked glycopeptide solution of about 0.1 to about 1000 micromolar (μM) glycan-linked glycopeptide or about 1.0 to about 500 μM glycan-linked glycopeptide or about 10 to about 100 μM glycan-linked glycopeptide can be employed. In general, it may be advisable to apply each concentration to a replicate of several (for example, three to six) defined glycan probe locations. Such replicates provide internal controls that confirm whether or not a binding reaction between a glycan-linked glycopeptide and a test molecule is a real binding interaction.

Arrays of detector molecules are useful for detecting the presence of multiple analytes in a sample in parallel. The elements of an array of detector molecules comprises a substrate, the presentation of a coating of a bio-active molecule on the substrate, the presentation of one or a plurality of analytes to the coated substrate, the formation of a complex between the analyte and the bio-active molecule on the substrate, and a mechanism of detection. As used herein the term "bio-active molecule" means its ordinary meaning in the art and any molecule which exists or mimics a molecule known in biology or chemistry and which is capable of binding to another molecule via electrostatic, van der Waals interactions, hydrophobic interactions, covalent bonds, and/or hydrogen bonds.

The substrate of the current present disclosure can be a surface. The surface can be flat, featured, round, curved, rough, porous, solid, gelatinous, polymeric, oligomeric, or a bead. The substrate can be composed of glass, polymer, or plastic. The bead can be round, cylindrical, egg-shaped, oval, approximately round, disc-shaped, square-shaped, hexagonal-shaped, or any polyhedral-shaped entity. In some embodiments, the substrate can be chemically modified so as to present a reactive group at the surface capable of binding to another molecule. In some embodiments, the reactive group can be a carboxylic acid.

In some embodiments, the substrate can be coated with a material which can present a reactive group at the surface capable of binding to another molecule. In some embodiments, the material coating the substrate is a nitrocellulose membrane or a polymer. Such coatings present a 3D surface with high surface area, enabling a lower limit of detection compared to flat surfaces. In some embodiments, a chemical linker can be presented to the surface, either directly to the surface or to a coating previously presented to the surface.

In some embodiments, the substrate can be a functionalized bead as commercialized by Illumina, Inc. with the BeadXpress, or Luminex systems, as of the filing date of the present disclosure.

Figure 14:
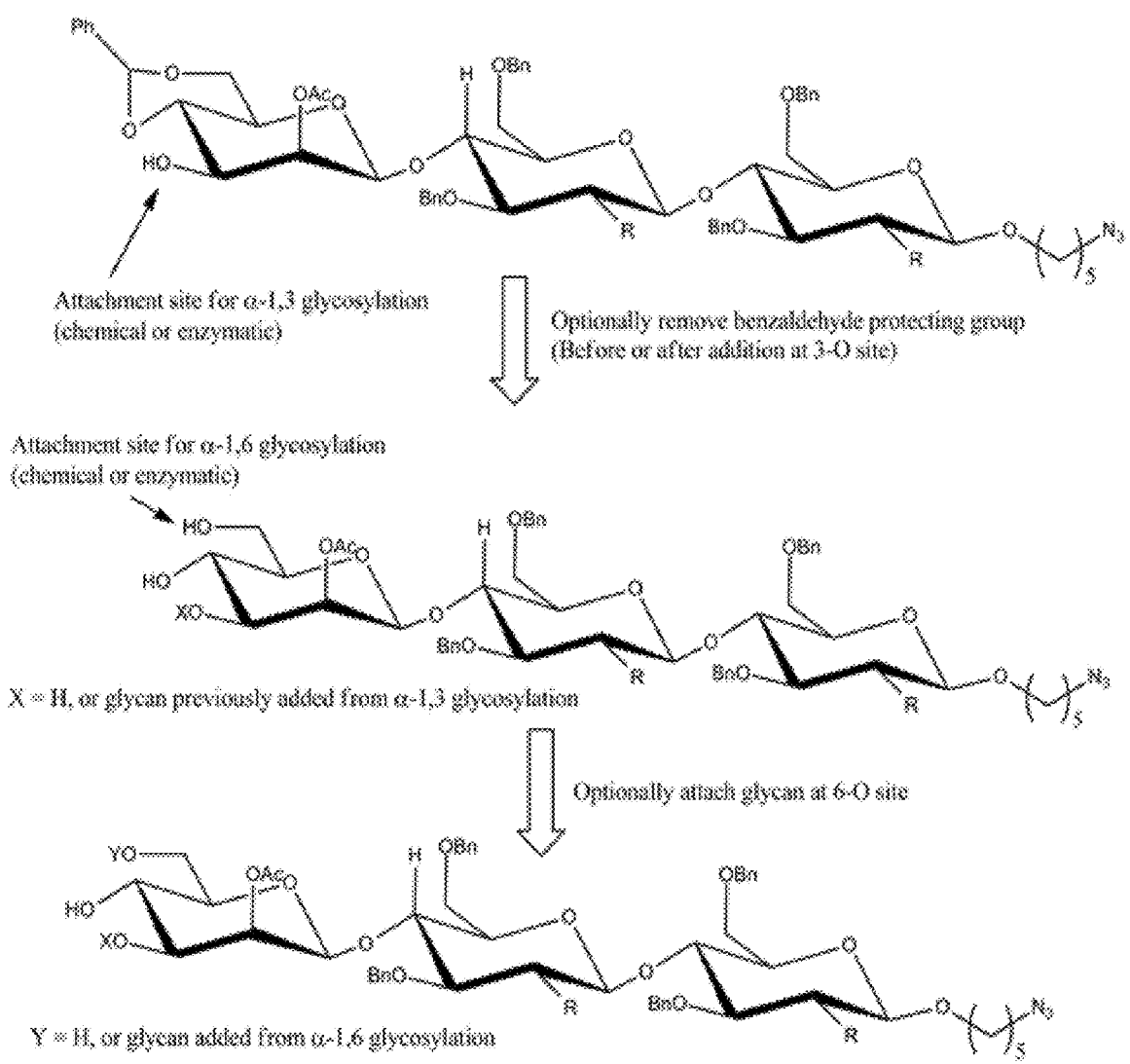
FIG. 14 Exemplary Modular synthesis of high mannose, hybrid- and complex-type N-glycans.

General Aspects of the Present Disclosure
Modular Synthesis of High Mannose, Hybrid- and Complex-type N-glycans The exemplary method embodiment as disclosed herein is designed on the basis that diversity can be created by assembly of the so called "D1 and D2/D3 arm modules", followed by the a-specific mannosylation at the 3-O and/or 6-O position of the mannose residue of the common core trisaccharide as shown in FIG. 14.

Figure 1A:
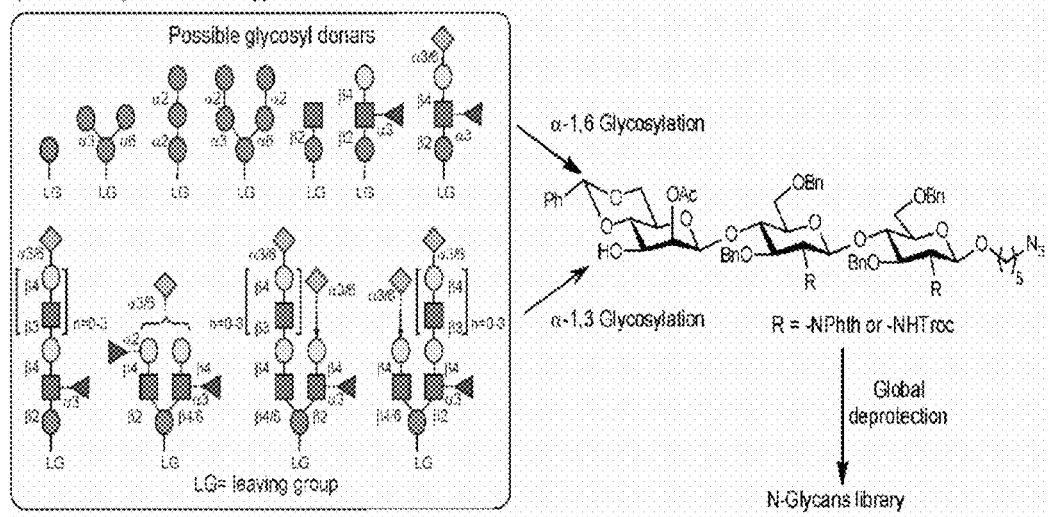
FIGS. 1A, 1B and 1C shows an exemplary general strategy for the modular synthesis of N-glycans. Due to the large number of possible glycosidic linkages and the generation of a diversity of structures, especially from the GlcNAc residues to the non-reducing end, a modular approach is used to minimize the reaction steps and create enough diversity to reflect the nature of N-glycosylation.
Figure 1B:
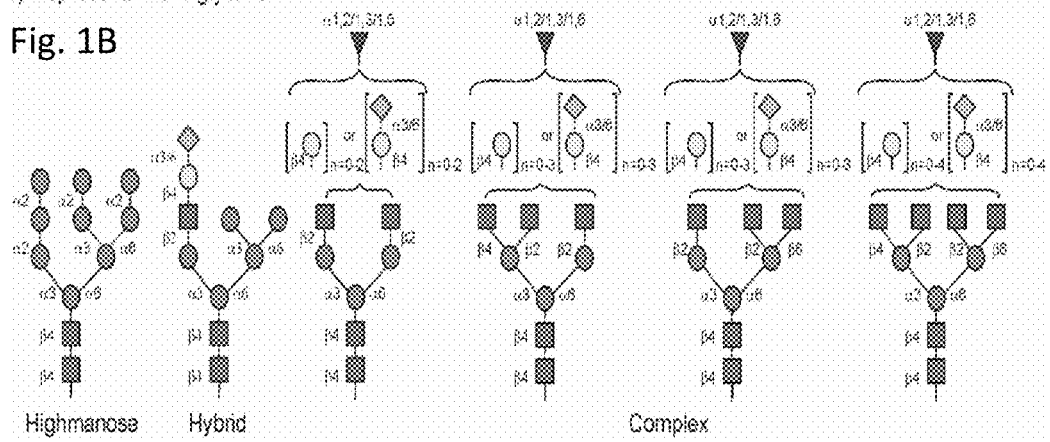
Figure 1C:
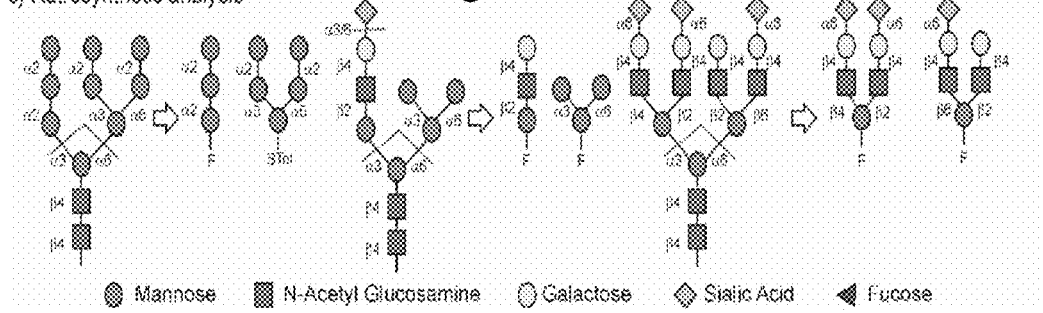
Figure 2:
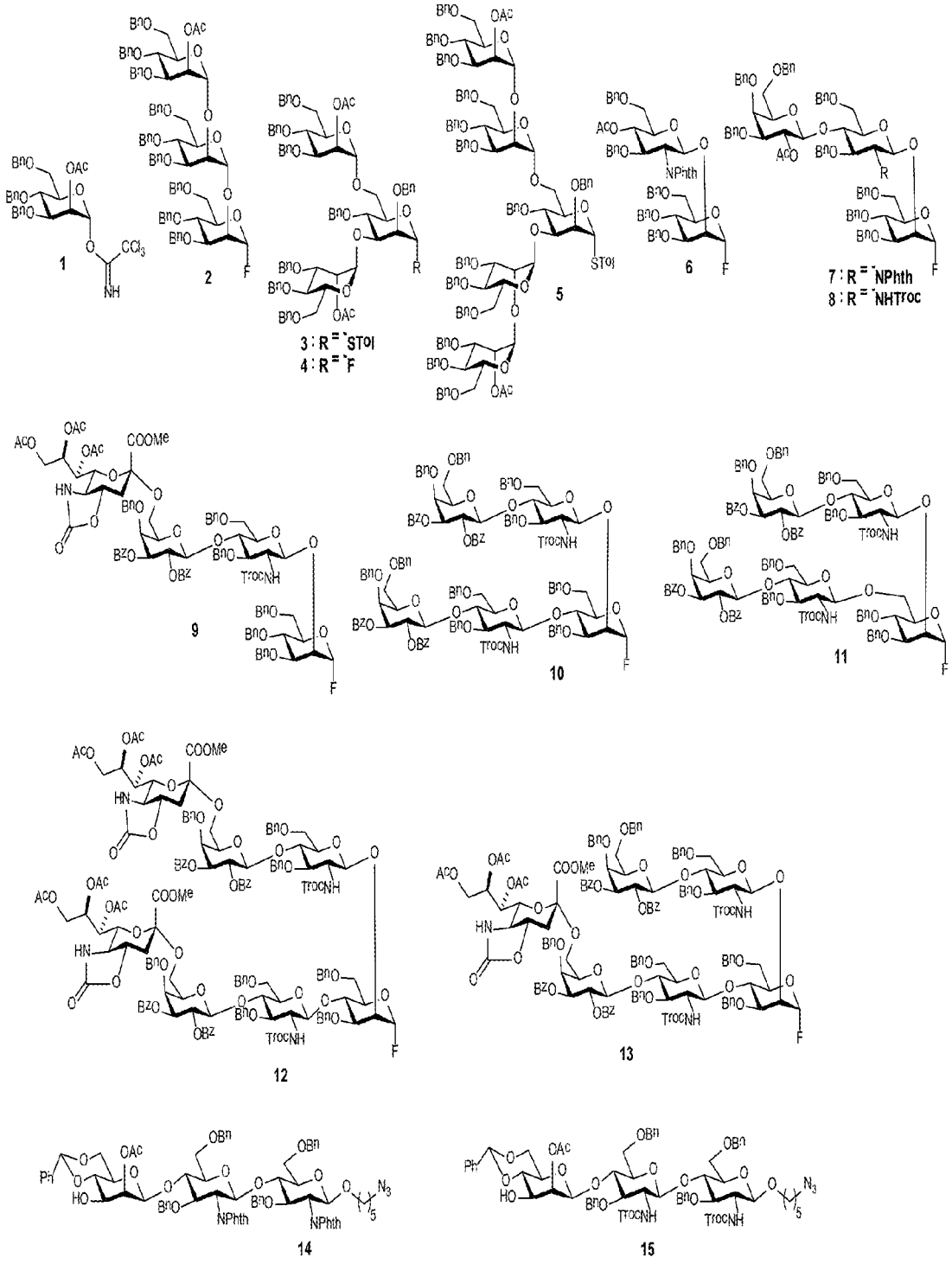
FIG. 2 shows exemplary structures of D1 and D2/D3 arm building blocks. A modular set of building blocks that are prepared by total chemical synthesis and used for oligosaccharide assembly.
Figure 74:
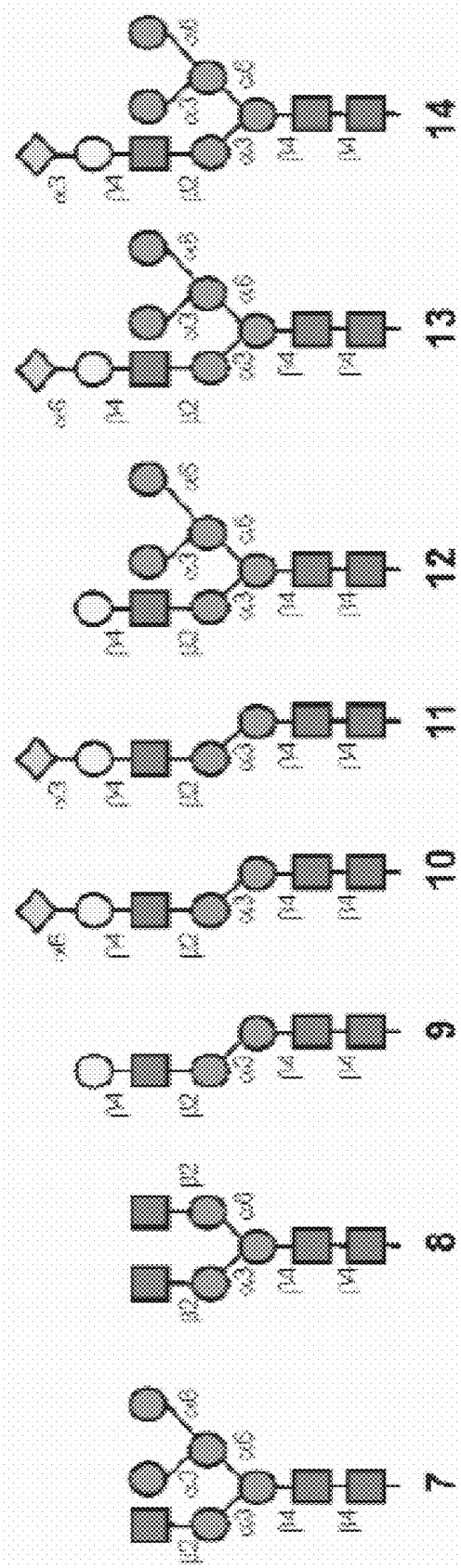
FIG. 74 Exemplary Structures of hybrid type glycans and their fragments.

Based on the retrosynthetic disconnection of N-glycan structures (FIG. 1c), the inventors surprisingly discovered that a modular set of building blocks 1-13 and the core trisaccharides 14-15 with crucial β-mannoside linkage (FIG. 2) can be used as starting materials for the preparation of various N-glycans (G1-33, Supplementary FIG. 198). To demonstrate the effectiveness and utility of this strategy, the oligomannose-type (mono- to pentasaccharides, 1-5), the complex-type (di- to heptasaccharides, 6-13) and the core trisaccharide (14-15) building blocks were first chemically synthesized on multigram scales, with temporary anomeric protecting groups installed prior to transformation into fluorides. For the high-mannose series (Man3/Man4/Man5/Man9 GlcNAc2) glycans, donors 1 and 2, and for the hybrid series glycans, donors 6 and 7 were stereoselectively linked to the 3-O position of 14. Then, the benzylidene ring was removed to get 4, 6-diol and finally a regioselective glycosylation was achieved at the 6-O position with donors 1-7. In the course of glycosylation reactions, various promoters were employed depending on the choice of glycosyl donors. The phthalimide protections at all glucosamine residues were modified to acetamides, and deacetylation and finally debenzylation were performed to obtain free glycans (FIG. 58: Glycans 1, 2, 4-9, 12). Utilizing the high specificity, the complex type D1 arm of the hybrid glycan was enzymatically sialylated to get α-2,3/6-Neu5Ac isoforms (FIG. 74—Glycans 10-11, 13-14).

Figure 93A:
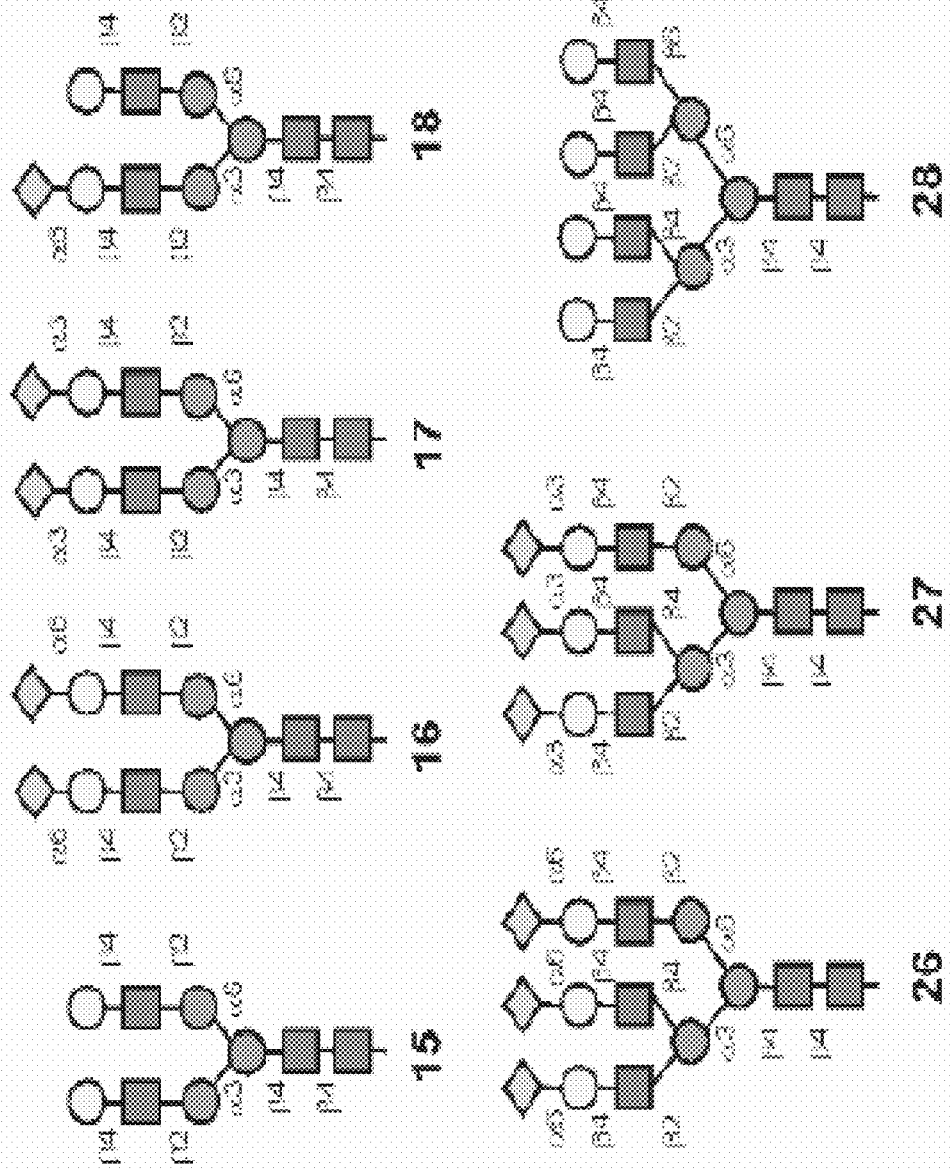
Figure 93B:
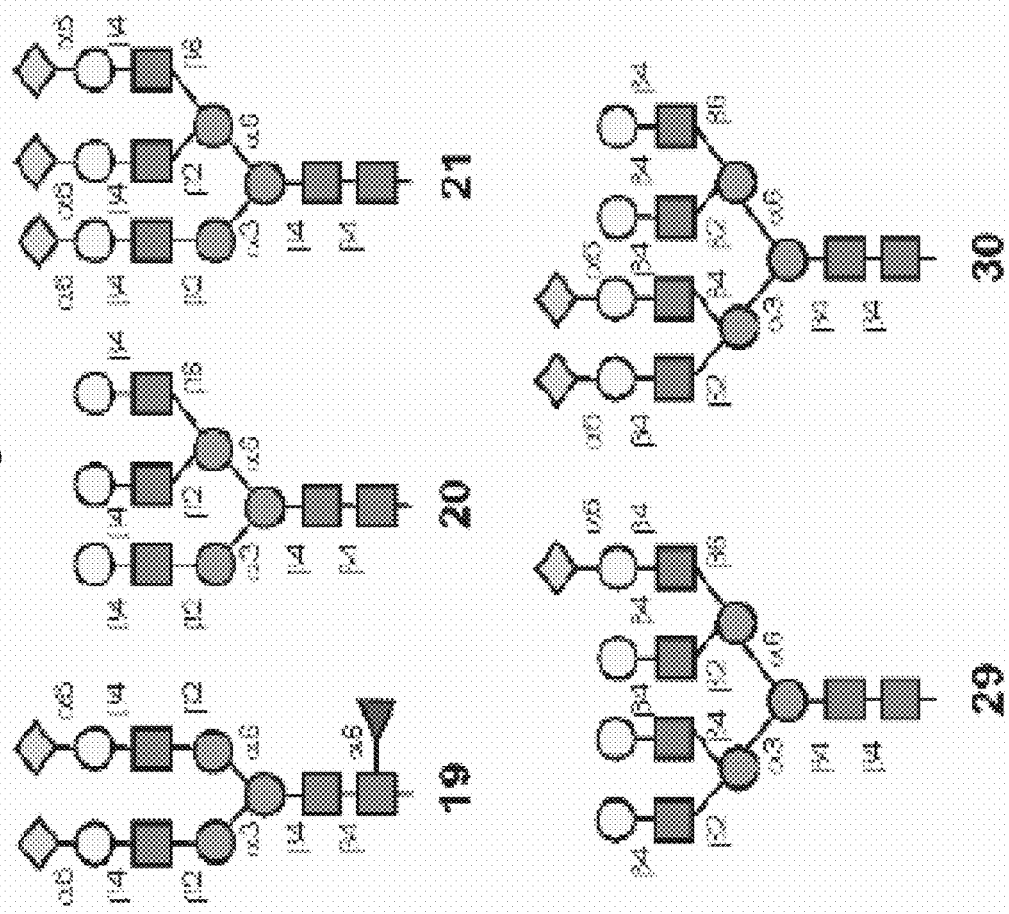

Having established a rapid way to synthesize the complex type glycans (Glycans 15-17, 20-23, 26-28 and 32-33, Supplementary FIGS. 93A, 93B and 93C), the inventors set out to generate more diverse asymmetric glycans and focused on the α-2, 6-sialylated antigens recognized by PG9 and PG16 using building blocks 9-13 prepared on gram quantities (Supplementary Schemes S4-S8 shown in FIGS. 32A, 32B, 32C, 37A, 37B, 37C, 42A, 42B, 47A, 47B, 47C and 55). Fluoride donors 8-13 were then used for the glycosidation of core 15 under the promotion of AgOTf/ $Cp_2HfCl_2$. Surprisingly, all these complex conjugations were found to be very clean (Supplementary Scheme S14-S19 as shown in FIGS. 94, 99, 102A, 102B, 107, 112 and 115), and the stereoselectivity was excellent. The glycosylation of 8 resulted in a mixture of isomers. At last, a global deprotection afforded naturally occurring positional isomers of bi-, tri and tetraantennary asymmetric N-glycans (Supplementary as shown in FIGS. 93A, 93B and 93C, Glycans 18, 24, 25, 29-31). To study the role of core fucose, examples 3 and 19 were also prepared.

With this convergent synthesis strategy in place, a chemo-enzymatic approach to the synthesis of D1 and D2/D3 N-glycan arm donors was implemented to allow a rapid assembly of diverse N-glycans. Various glycosyl transferases were used, including β-1,4-galactosyltransferases, α-2,3/2,6 sialyltransferases, and α-1,3/1,2 fucosyltransferases, for the preparation of linear and branched modules by enzymatic extension of chemically synthesized acceptors 16-20 (FIG. 3). The GlcNAc moiety of acceptor 16 was transformed into LacNAc by using β-1,4-galactosyltransferase and uridine 5'-diphosphogalactose (UDP-Gal) to form 21, which was further extended by α-2,6/2,3 sialyltransferase in the presence of cytidine-5'-monophospho-N-avetylneuraminic acid (CMP-Neu5Ac) to provide targets 23 and 24 respectively. Next, treatment of 21, 23-24 with the α-1,3-fucosyltransferase from *Helicobacter pylori* (Hpα1, 3FT) resulted in the modification of LacNAc and α-2,3-sialyl LacNAc but not 2,6-sialyl LacNAc to afford 22 and 25. In addition, the α-1,3-fucosylated LacNAc was found to restrict the access of enzymatic α-2,3/6-sialylation to the terminal galactose. Acceptor 21 was modified with the α-1,2-fucosyltransferase from HEK293 cells in the presence of guanosine 5'-diphospho-β-L-fucose (GDP-fucose) to provide 26 (FIG. 3a). It was observed that the α-1,2 fucosylated module 26 was accepted by the α-2,6 sialyltransferase to give 27, but the α-2,3 sialyltransferase failed to accept this substrate (FIG. 3a and Supplementary Scheme S23 as shown in FIG. 152). Next, the symmetric modules 28-33 were prepared from acceptors 17-18 (FIG. 3b).

In the case of asymmetric modules, selective incorporation of sialic acid or fucose to one of the antennae is necessary. Therefore, acceptors 19-20 were designed in such a way that the GlcNAc at the mannose 2-O position was differentiated from the GlcNAc at the 4 or 6-O position by masking the 4-hydroxy group through acetylation to prevent enzymatic galactosylation while retaining its water solubility. This strategy allowed a selective extension of one arm while keeping the other intact. As depicted in FIG. 3c, a Gal residue was added by β-1,4-GalT to the GlcNAc residue at the β-1,4/1,6 mannose branch, whereas the GlcNAc residue at the β-1,2 branch remained intact. By taking advantage of their specificity, α-1,3-FucT and α-2,6-SiaT were used for the preparation of the asymmetric modules 36-43, and 45-47 (FIG. 3c and Supplementary Scheme S25 as shown in FIG. 165) which were purified and fully characterized (Supplementary III).

Figure 4:
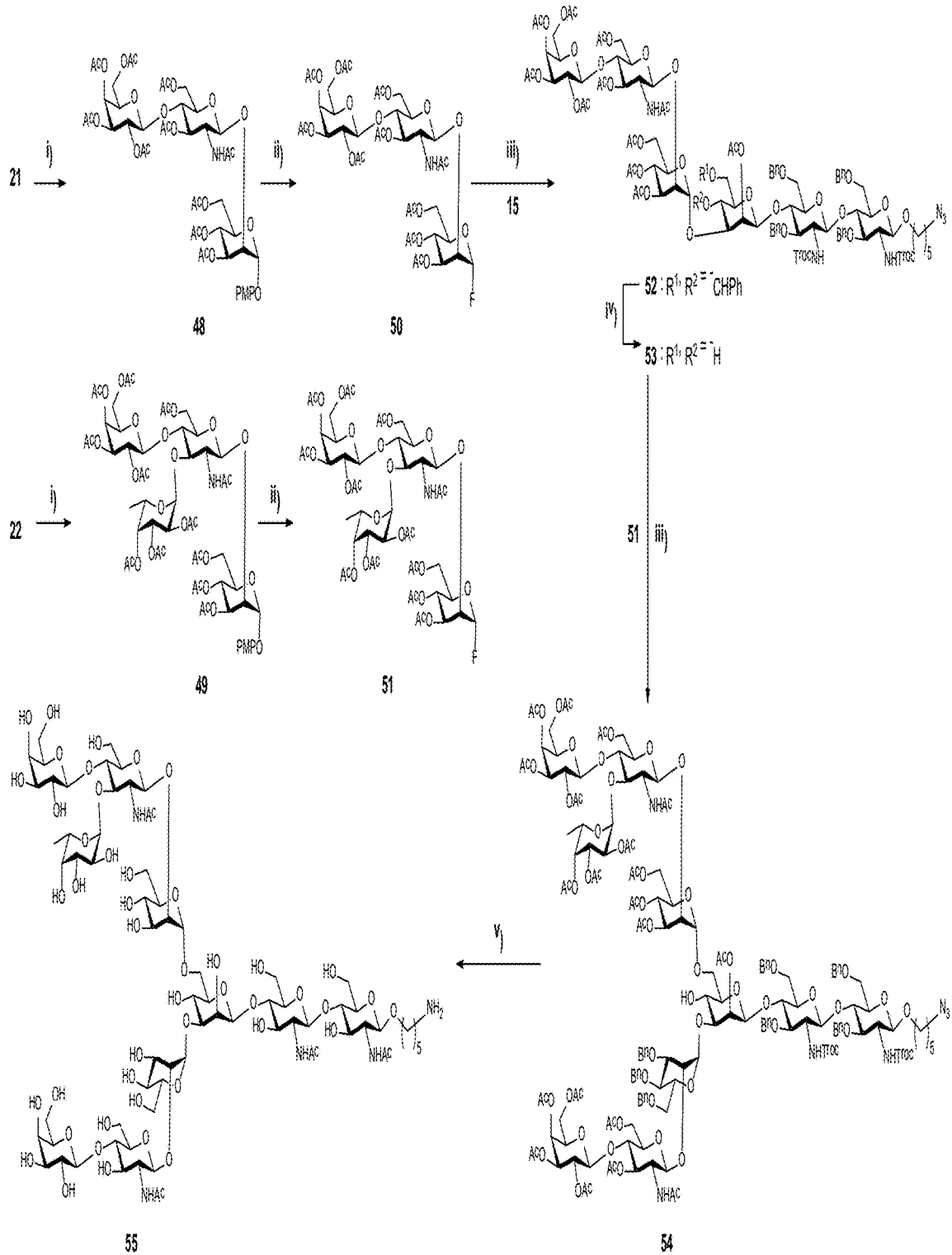
FIG. 4 is a representative proof-of-concept demonstration of chemo-enzymatic strategy to N-glycan synthesis. Reagents and conditions. i), acetic anhydride, pyridine; ii), (1) CAN, toluene:ACN:$H_2O$:toluene; (2) DAST, $CH_2Cl_2$, −30° C.; iii), AgOTf, $Cp_2HfCl_2$, toluene, 4 Å MS, 0° C. to rt; iv), p-TSA, acetonitrile, rt; v), (1) LiOH, 1,4-dioxane: $H_2O$; 90° C., overnight; (2) $Ac_2O$, pyridine, overnight; (3) NaOMe, MeOH, overnight; (4) $Pd(OH)_2$, MeOH:$H_2O$: HCOOH (5:3:2), $H_2$. CAN: Cerium ammonium nitrate; DAST: Diethylaminosulfur trifluoride; AgOTf: Silver trifluoromethanesulfonate; $Cp_2HfCl_2$: Bis(cyclopentadienyl) hafnium dichloride, MS: molecular sieves.

To illustrate the use of modules prepared by the chemo-enzymatic method for further glycosylation, modules 21 and 22 were selected for the proof-of-concept experiment (FIG. 4). Peracetylation of modules 21 and 22, followed by transformation into the glycosyl fluoride provided donors 50 and 51 respectively. Glycosylation with fluoride 50, in the presence of AgOTf/Cp2HfCl2, indeed provided the expected hexasaccharide 52 in 70% yield. Next, the benzylidene was cleaved in the presence of p-toluene sulfonic acid catalyst, and the donor 51 was stereospecifically installed at the 6-position to give decasaccharide 54 which was deprotected to afford glycan 55 (Supplementary Scheme S26 in FIG. 178 and S27 in FIGS. 183A & 183B).

Taken together, the inventors have demonstrated an efficient way to prepare the complex type N-glycans of interest through a proper selection of a defined set of modules that are generated chemically as well as chemo-enzymatically. The versatility of oligosaccharyl fluoride donors, allowed a clean conjugation of highly branched modules to the core with excellent stereo- and regio-selectivity. The oligosaccharides with a preinstalled alkyl amine linker at the reducing end can be used directly for reaction with NHS (N-hydroxy succinimide, although epoxy functionalized slides would also work) slides through amide bond formation, or further modified or other array formats, or conjugated to proteins for structural and functional studies.

Glycan Microarray on NHS-activated and Aluminum Oxide-coated Glass Slides

It was reported that PG9, PG16 and PGTs 128, 141-145 were able to neutralize 70-80% of circulating HIV-1 isolates with potent activity[20], suggesting that the targeted epitopes are highly conserved among the HIV-1 variants, and could guide the design of immunogens. To gain insights into the glycan specificities of these antibodies, the inventors used our newly developed array to profile the ligands of HIV-1 bNAbs. The synthetic N-glycan ligands were printed on NHS-activated glass slides through amide bond formation with 100 μM each of glycans 1-33 (FIG. 198). Each sample was printed with five replicates and slide images were obtained from a fluorescence scan after incubation with DyLight649-conjugated donkey anti-Human IgG antibody. Our results revealed that PG16 binds to the α-2,6-sialylated complex-type oligosaccharides, consistent with our previous results[50], and the binding affinity is proportional to the number of terminal sialic acid residues (FIG. 199). In addition, the inventors found that the PG16 binding was not affected by the presence of the core fucose (glycan 19 vs 16). Interestingly, the binding of PG16 to asymmetric glycans 29-33 suggest the importance of sialic acid on the D1 arm. Finally, the inventors could not observe binding to the high-mannose-type glycan Man5GlcNAc2 (FIG. 199). Furthermore, PG9 and PGTs 141-145 were not detected to bind any of the glycans on the NHS array, probably due to their extremely weak binding. (FIGS. 203, 204A, 204B, 204C, 205A, 205B and 206). In our binding studies, the inventors observed a strong fluorescent signal against glycan 5, Man4GlcAc2, which was later confirmed to be from the non-specific binding of secondary antibody (FIG. 206).

Figure 5A:
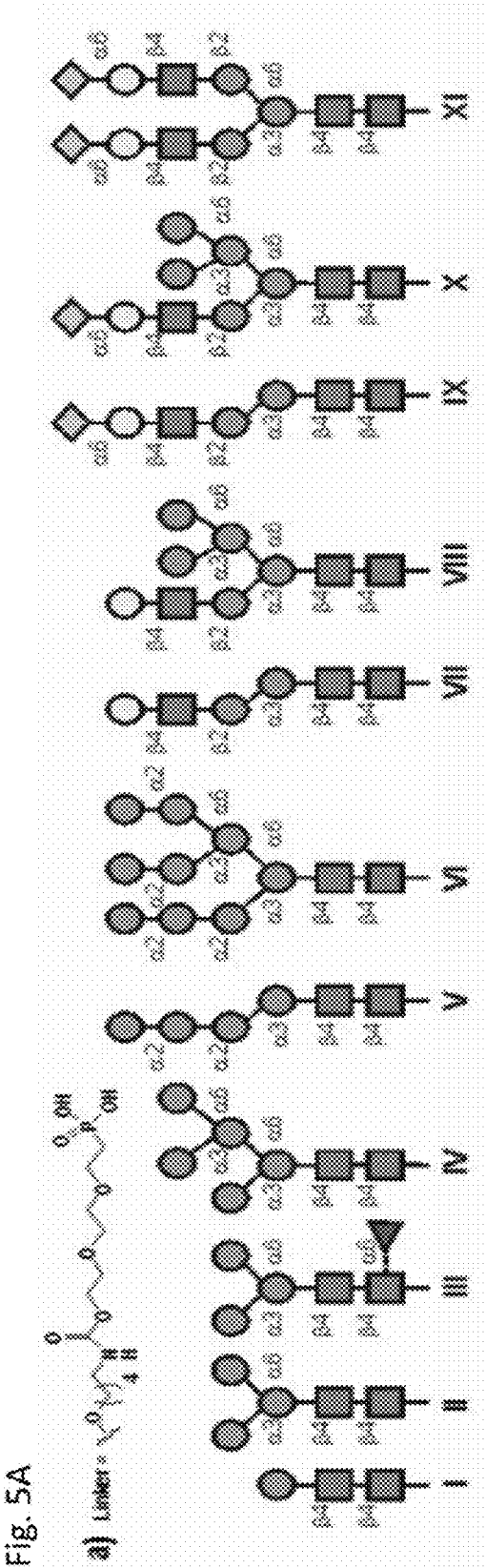

To further understand why glycan binding to these bNAbs was not readily observed on the NHS-coated glass slides, the inventors conducted a specificity test with the ACG array. A comparison of homogeneity between the ACG and NHS-coated glass slides showed that the ACG slide provided a more homogeneous glycan distribution on its surface (FIGS. 91, 192A, 192B, 193, 195A, 195B, 195C, 194 and 196), and based on atomic force microscopy (AFM), the structural orientation of the glycans on the ACG slide was in a more extended conformation (FIGS. 197A and 197B). Therefore, the inventors can simply adjust the concentration of glycan to control the density and distance of glycans on the ACG surface. To prepare a representative ACG array, glycans I-XI (FIG. 5a) were linked to a phosphonic acid tail for spontaneous covalent immobilization on the ACG slide (Supplementary Scheme S21, as shown in FIG. 129). After incubation with a secondary antibody, the inventors determined the dissociation constant ($K_D$.surf.)[59] of the glycans interacting with the antibody of interest. Using the ACG slide, the signal intensity was enhanced, as shown by the use of PG16 at 1 µg/mL on the ACG slide in comparison to 25 µg/mL used on the NHS-coated glass slide (FIG. 5b and Supplementary FIG. 199). The binding affinity of PG16 to the bi-antennary complex-type N-glycan (XI) ($K_D$=0.320 µM) was higher than that to the hybrid-type glycan (X) ($K_D$=0.935 µM) (Supplementary FIGS. 202A and 202b and Table S2), supporting the proposed existence of these glycans at Asn173 as suggested by the structural study of PG16 in complex with gp120[30].

To evaluate whether the ACG array format could enhance the detection sensitivity, the inventors performed a ligand specificity profiling at various concentrations of PG9. Interestingly, on the ACG array, PG9 showed an apparent specificity for the hybrid-type glycan (X) (FIG. 5b) and detectable binding to $Man_5GlcNAc_2$ (IV) and the α2,6-sialylated bi-antennary complex-type oligosaccharide (XI). Previously, it was shown that PG9 required $Man_5GlcNAc_2$ at primary (Asn160) and secondary (Asn156 or Asn173) binding sites together with a short peptide strand in gp120 recognition[26], whereas the composition of glycan at Asn156 or Asn173 was defined as a complex-type glycan in later studies[30,31]. In the present study, the strong PG9 interaction with the hybrid-type structure compared to both $Man_5GlcNAc_2$ and complex-type glycans indicated the presence of a hybrid-type glycan or an oligomannose and a complex-type glycan in close proximity as ligand(s). Nonetheless, to our knowledge, these results represent the first evidence of PG9 binding to carbohydrates without protein or peptide domains.

To understand the exact glycan epitopes recognized by antibodies PGTs 141-145[20], a panel of glycans I-XI on the ACG slide was prepared for analysis. The result revealed that PGTs 141-144 could recognize the oligomannose glycans $Man_{3/5/9}GlcNAc_2$, and the observed trend in binding affinity was PGT142>PGT144>PGT141>PGT143 (FIG. 5c and Supplementary FIGS. 201A and 201B); however, PGT145, the most potent of the group, failed to show detectable binding. The significant decrease in the affinity for PGTs 141-144 towards $Man_9GlcNAc_2$ was probably due to the shielding of the inner core ($Man_{3/5}GlcNAc_2$) by terminal mannose residues. Taken together, these results demonstrate the efficiency of the ACG array format in detecting low affinity interactions of recently isolated HIV-1 bNAbs.

Heteroglycan Binding of PG9 and PG16

Due to the absence of a co-crystal structure of PG9 in complex with a hybrid-type glycan, it is difficult to determine the molecular details of the interaction. The structural features suggest that PG9 could accommodate the high-mannose-type D2/D3 arm and the complex-type D1 arm present in a hybrid-type glycan, or has binding sites that can accommodate $Man_5GlcNAc_2$ at Asn160 and complex-type glycans at Asn156 or 173[30,31]; however, both complex- and hybrid-type glycans contain the α-2,6-NeuAc-Gal-GlcNAc arm.

To evaluate the glycan combination at Asn160 and Asn156/Asn173 of gp120 that best fits into the PG9 binding pocket, the inventors printed two different mixed-glycan arrays. In one array, $Man_5GlcNAc_2$ (IV) was mixed with every glycan from I-XI in a 1:1 mole ratio (FIG. 5d), while in the other, the bi-antennary complex-type structure (XI) was mixed with every glycan from I-XI (FIG. 5e). The binding profile of PG9 to various mixtures suggests that a mixture containing $Man_5GlcNAc_2$ and a bi-antennary glycan [(IV+XI) or (XI+IV)] interacted more strongly with PG9 compared to IV or XI alone. Furthermore, the inventors also observed a comparable binding to $Man_5$ combined with X and XI, suggesting that $Man_5GlcNAc_2$ at Asn160 was the primary binding site, while structures IX, X, and XI used the complex-type D1 arm for interaction with the secondary binding site. Based on the homogeneous array results of PG9 (FIG. 5b), $Man_5GlcNAc_2$ IV or complex-type glycan XI alone did not seem to provide sufficient binding affinity; on the other hand, the hybrid-type glycan X showed a significant enhancement in binding. In the mixed glycans study (FIG. 5c), however, a combination of IV and XI was found to achieve the strongest binding to PG9, followed by a combination of $Man_5$ and hybrid type. In a similar manner, the inventors studied the binding specificity of PG16 (FIG. 5e), and it was found that the combination of $Man_5GlcNAc_2$ and complex-type N-glycan (IV+XI) ($K_D$=0.827 µM) or the combination of hybrid and complex glycans (X+XI) ($K_D$=0.988 µM) was weaker than the complex type glycan alone ($K_D$=0.320 µM) (Supplementary FIGS. 202A and 202B and Table S2). These results indicate the importance of sialylated antennae in the PG16 binding site, including possibly the tri- and tetra-antennary complex-type N-glycans reported previously[50].

Figure 6A:
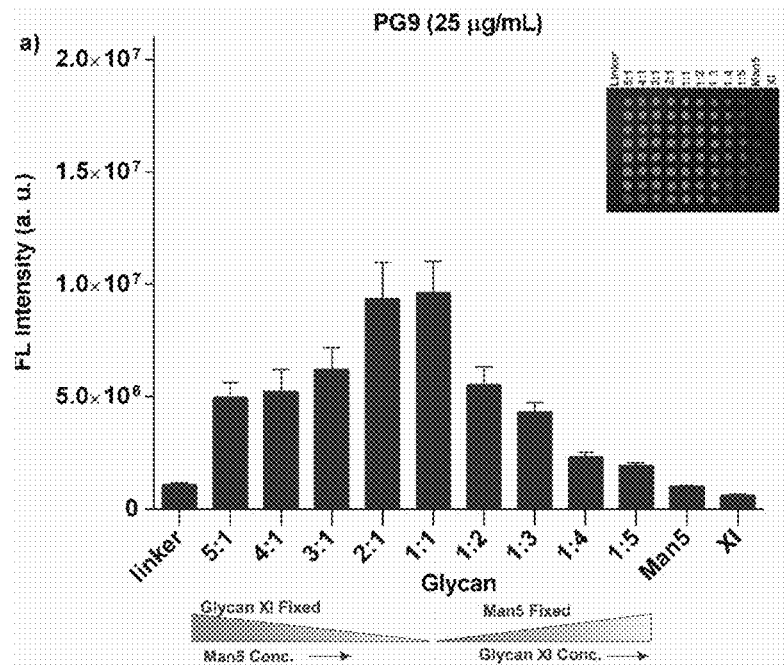
FIGS. 6A and 6B shows exemplary glycan specificities of PG9 (panel A—FIG. 6A) and PG16 (panel B—FIG. 6B) to mixture of Man5 and XI at various ratios. Arrays were printed by 100 μM of linker, $Man_5GlcNAc_2$ (IV), complex type glycan (XI) and each of the mixtures of (IV+XI) or (XI+IV) in a 1:1/2/3/4/5 ratio. The molar concentrations in μM for antibodies are given in the legend. The mean signal intensities and standard error calculated for eight independent replicates on the array are shown.
Figure 6B:
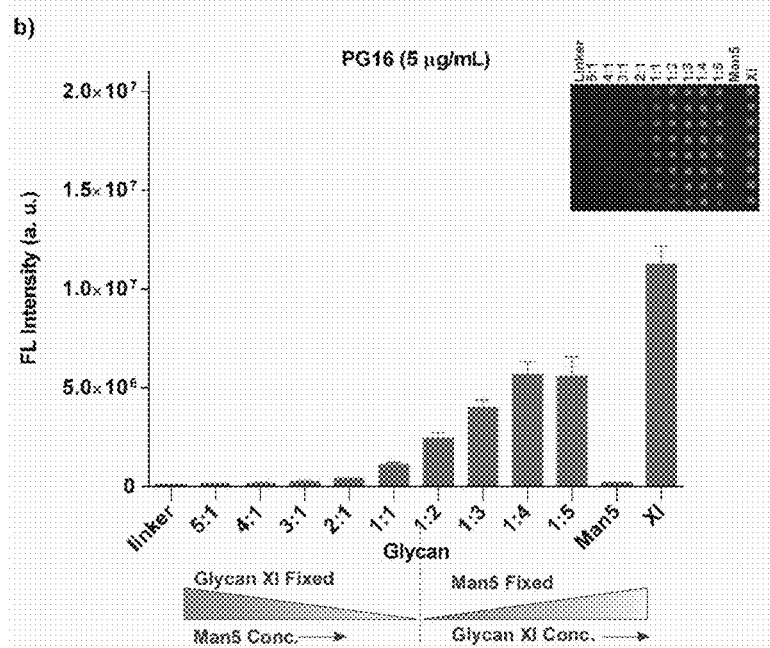
Figure 7:
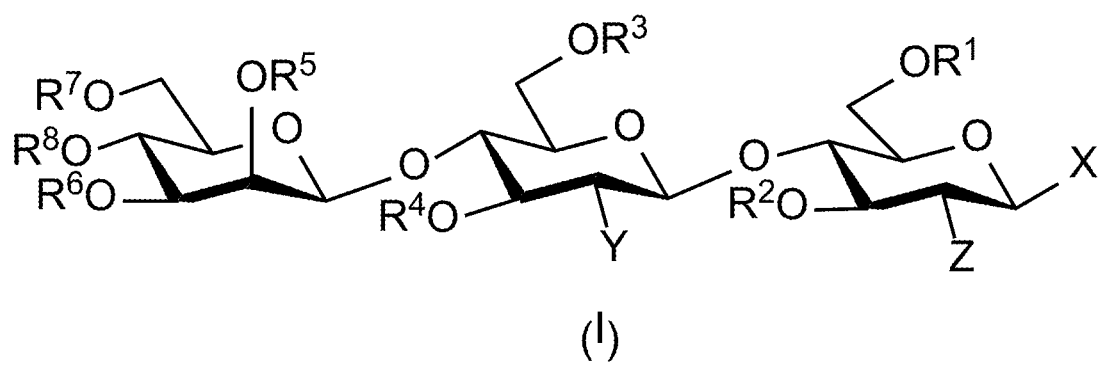
FIG. 7 shows an exemplary structure embodiments of the present disclosure.
Figure 8:
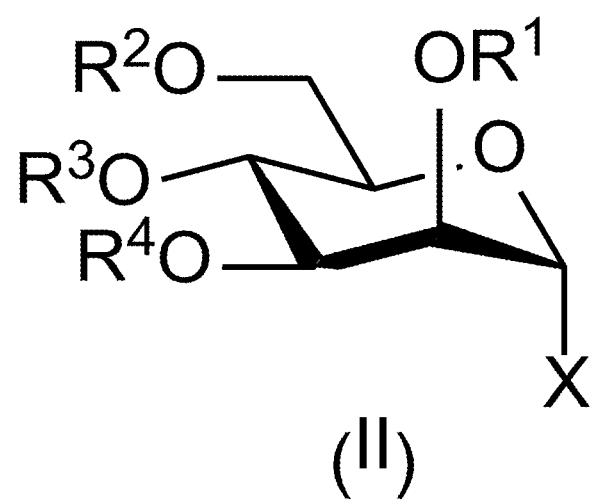
FIG. 8 shows an exemplary structure embodiments of the present disclosure.
Figure 9:
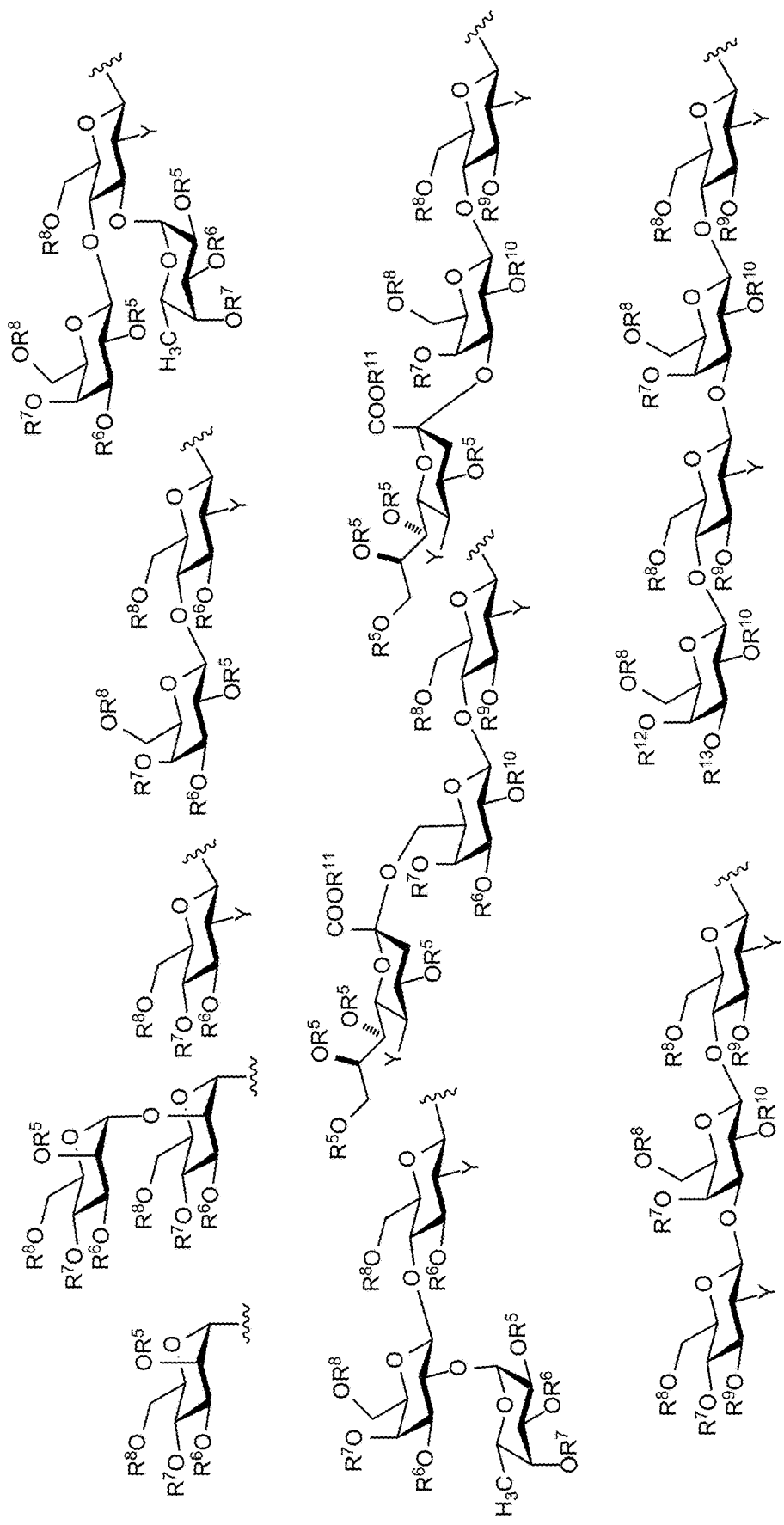
FIG. 9 shows an exemplary structure embodiments of the present disclosure.
Figure 10:
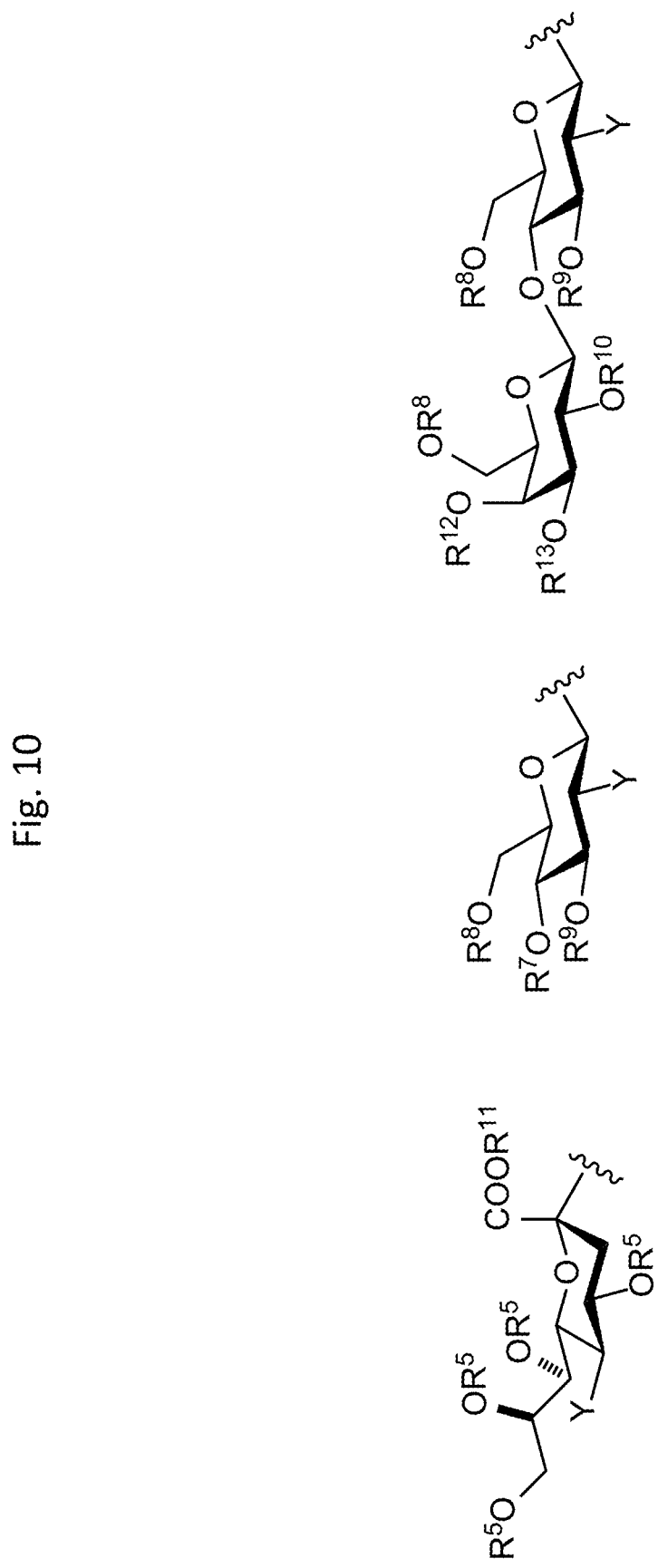
FIG. 10 shows an exemplary structure embodiments of the present disclosure.
Figure 11A:
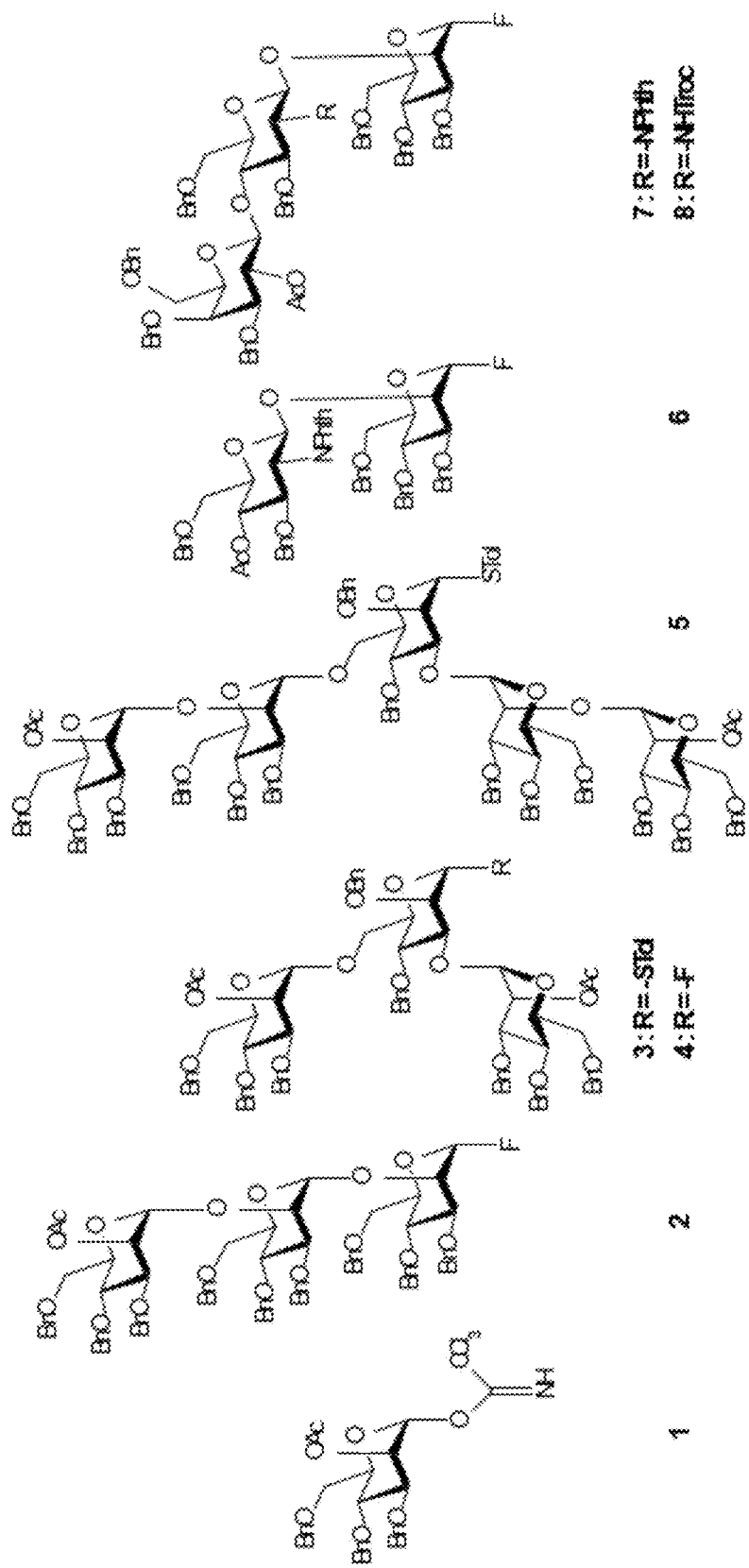
FIGS. 11A, 11B, and 11C.
Figure 11B:
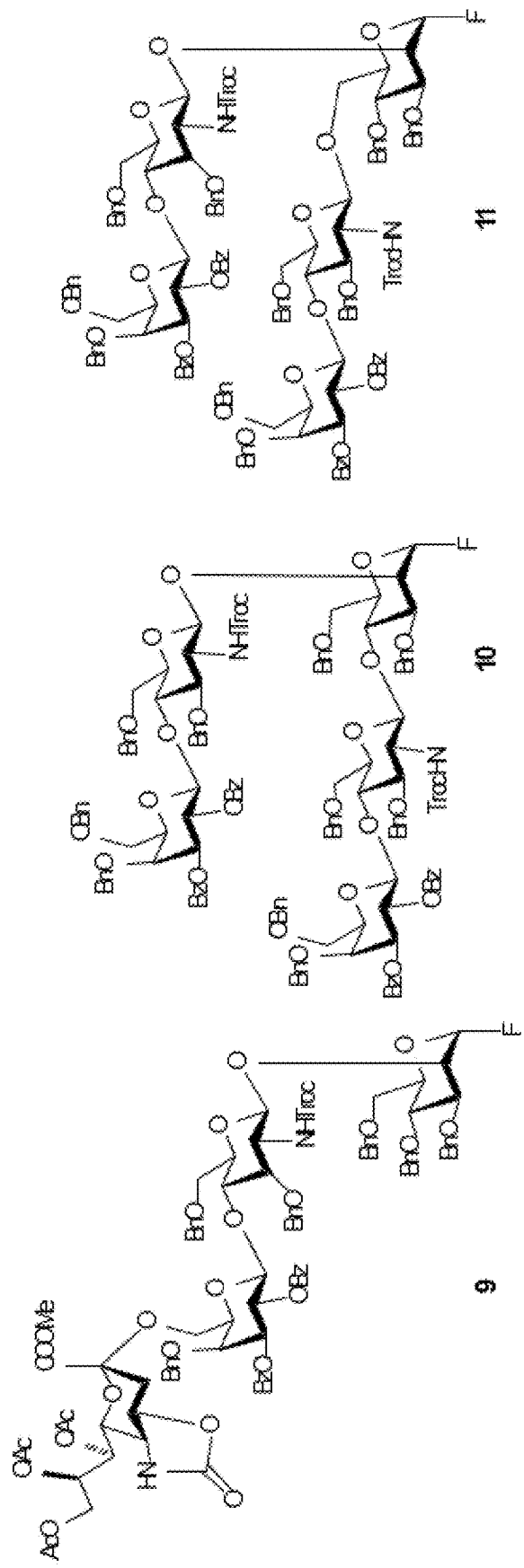
Figure 11C:
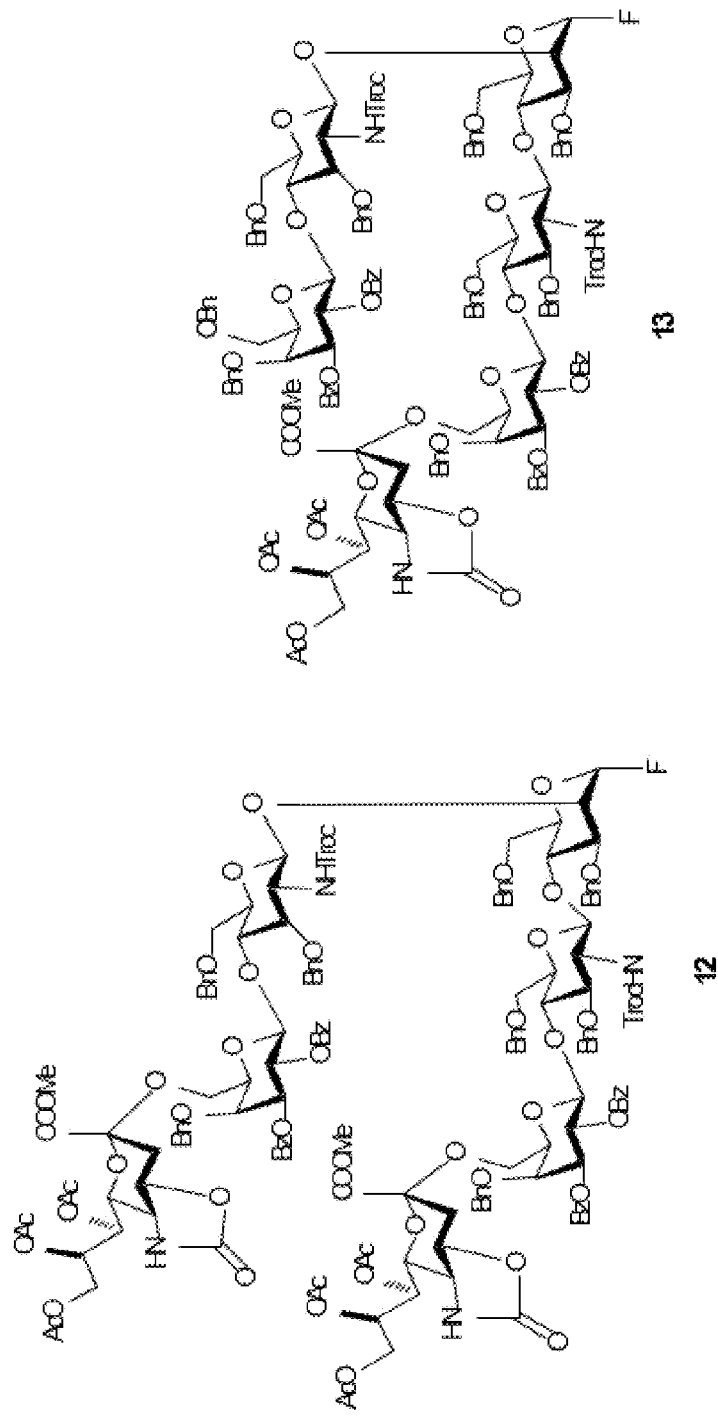
Figure 12:
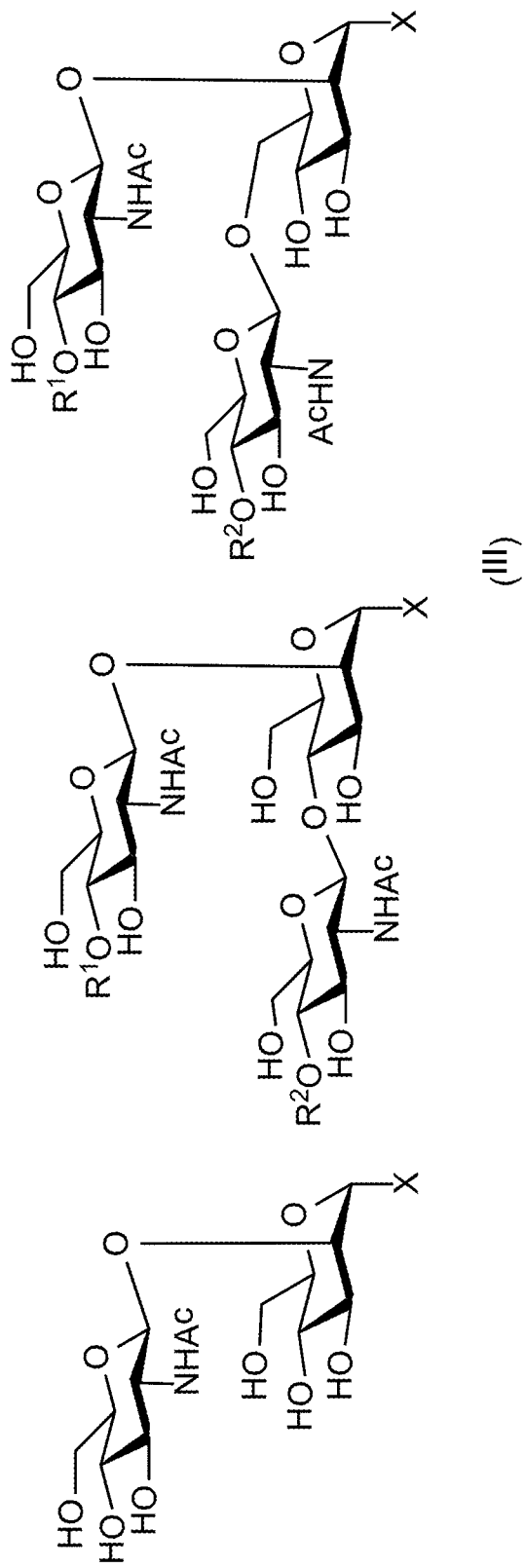
FIG. 12 shows an exemplary structure embodiments of the present disclosure.
Figure 13:
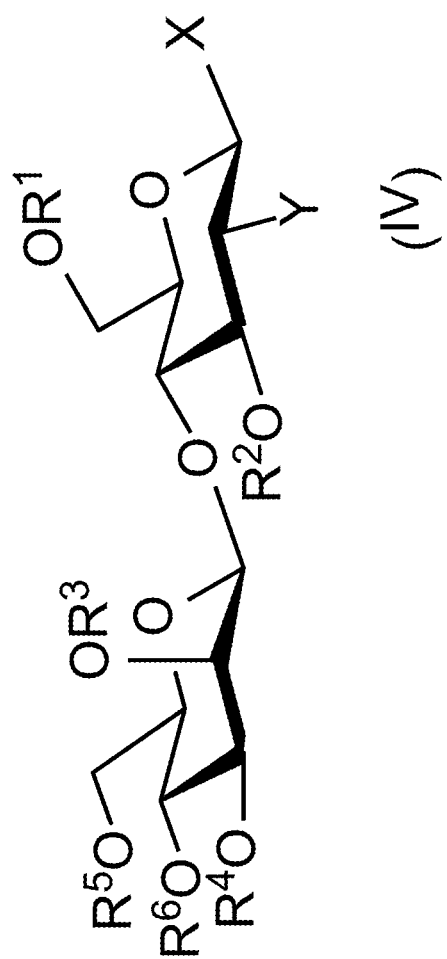
FIG. 13 shows an exemplary structure embodiments of the present disclosure.

To further understand the exact ratio of IV and XI in the mixture, the inventors performed a serial dilution experiment. IV was mixed with XI in various ratios (1:1/2/3/4/5) and vice versa. A 100 µM solution of each of these mixtures was printed on the ACG surface together with linker and glycans alone as control. Interestingly, at fixed IV, the PG9 binding was gradually decreased by increasing the XI ratio in the mixture. By changing the IV ratio at fixed XI, PG9 achieved the strongest binding at the ratio of 1:1 and 2:1 of IV to XI (FIG. 6a). These results suggest that the glycan ratio of 1:1 is the best ligands for PG9. However, PG16 responded in a different manner to each of these mixtures where the interactions were greatly enhanced by the presence of complex type glycan in the mixtures (FIG. 6b). However, the inventors were unable to detect PG16 binding to $Man_5GlcNAc_2$. The inventors conclude that PG9 recognizes a mixture of $Man_5$ and complex type glycan, whereas, the complex type glycan alone is enough to elicit PG16 response.

Conclusion

In conclusion, the inventors have successfully developed a modular synthetic strategy for the rapid production of a diverse array of high-mannose-, hybrid- and complex-type N-linked oligosaccharides in highly pure and sufficient amounts, making possible the study of various N-glycans and the development of new glycan array platforms to determine the glycan specificities of newly discovered HIV-1 bNAbs. The ACG array together with the binding measurements obtained in a high-throughput manner provide an effective means for detecting the extremely weak binding of HIV-1 bNAbs to glycans and enable the discovery and understanding of essential epitopes and heteroligands recognized by antibodies. These findings may aid speedy design of effective carbohydrate-based vaccines against HIV-1.

METHODS AND SUMMARY

All reactions were performed under an inert atmosphere using dry solvents in anhydrous conditions, unless otherwise noted. Full experimental details, glycan microarray analysis, and characterization data ($^1$H and $^{13}$C nuclear magnetic resonance, high-resolution mass spectrometry, and $R_f$ value) for all new compounds are included in the Supplementary Information I-III.

All patents, publications, scientific articles, web sites, and other documents and materials referenced or mentioned herein are indicative of the levels of skill of those skilled in the art to which the present disclosure pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The specific methods and compositions described herein are representative of preferred embodiments and are exemplary and not intended as limitations on the scope of the present disclosure. Other objects, aspects, and embodiments will occur to those skilled in the art upon consideration of this specification, and are encompassed within the spirit of the present disclosure as defined by the scope of the claims. It will be readily apparent to one skilled in the art that varying substitutions and modifications may be made to the present disclosure disclosed herein without departing from the scope and spirit of the present disclosure. The present disclosure illustratively described herein suitably may be practiced in the absence of any element or elements, or limitation or limitations, which is not specifically disclosed herein as essential. Thus, for example, in each instance herein, in embodiments or examples of the present disclosure, any of the terms "comprising", "consisting essentially of", and "consisting of" may be replaced with either of the other two terms in the specification. Also, the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the present disclosure as claimed. Thus, it will be understood that although the present disclosure has been specifically disclosed by preferred embodiments and optional features, modification and variation of the concepts herein disclosed may be resorted to by those skilled in the art, and that such modifications and variations are considered to be within the scope of this present disclosure as defined by the appended claims.

The present disclosure has been described broadly and generically herein. Each of the narrower species and subgeneric groupings falling within the generic disclosure also form part of the present disclosure. This includes the generic description of the present disclosure with a proviso or negative limitation removing any subject matter from the genus, regardless of whether or not the excised material is specifically recited herein.

Other embodiments are within the following claims. In addition, where features or aspects of the present disclosure are described in terms of Markush groups, those skilled in the art will recognize that the present disclosure is also thereby described in terms of any individual member or subgroup of members of the Markush group. Other embodiments are within the following claims. In addition, where features or aspects of the present disclosure are described in terms of Markush groups, those skilled in the art will recognize that the present disclosure is also thereby described in terms of any individual member or subgroup of members of the Markush group.

EXAMPLES

The instant disclosure and examples herein documents the discovery of surprising efficacy and efficiency in synthesizing and generating N-glycans in arrays to achieve surprising efficacy in disease state (e.g. HIV-1) determination, prediction, and/or diagnosis.

The following table of content sets forth exemplars of embodiments of various attributes of the present disclosure:
Chemical Synthesis
Materials and Methods All reagents were purchased from Sigma Aldrich, Across and used without further purification. Dry solvents were purchased from a commercial source without further distillation. Pulverized Molecular Sieves MS-4 Å (Aldrich) for glycosylation was activated by heating at 350° C. for 3 h. Reactions were monitored by analytical thin-layer chromatography (TLC) in EM silica gel 60 F254 plates and visualized under UV (254 nm) and/or by staining with acidic ceric ammonium molybdate or p-anisadehyde. Flash chromatography was performed on silica gel (Merck) of 40-63 µm particle size. $^1$H NMR spectra were recorded on a Bruker AVANCE 600 (600 MHz) spectrometer at 25° C. All $^1$H Chemical shifts (in ppm) were assigned according to $CDCl_3$ ($\delta$=7.24 ppm) and $D_2O$ ($\delta$=4.80 ppm). $^{13}$C NMR spectra were obtained with Bruker AVANCE 600 spectrometer and were calibrated with $CDCl_3$ ($\delta$=77.00 ppm). Coupling constants (J) are reported in hertz (Hz). Splitting patterns are described by using the following abbreviations: s, singlet; brs, broad singlet; d, doublet; t, triplet; q, quartet; dd, doublet of doublet; m, multiplet. $^1$H NMR spectra are reported in the following order: chemical shift, multiplicity, coupling constant(s) and number(s) of protons. All NMR signals were assigned on the basis of $^1$H NMR, COSY, HSQC, HMQC, TOCSY, and $^{13}$C experiments. High resolution ESI mass spectra were recorded on a Bruker Daltonics spectrometer. NHS coated glass slides were purchased from SCHOTF (Nexterion H). Broadly neutralizing HIV antibodies PG9, PG16 and PGT141-145 were kindly gifted by Prof. Peter Kwong, NIH (PG9/PG16 also purchased from Polymun, Vienna Austria). PGT128 was kindly gifted by Prof. Dennis Burton, TSRI. Secondary antibody DyLight649-conjugated donkey anti-Human IgG was purchased from Jackson Immuno Research. Cytidine 5'-triphosphate (CTP), N-Acetylneuraminic acid (Neu5Ac), UDP galactose, L-fucose and Phospho (enol) pyruvic acid (PEP) were purchase from Sigma-Aldrich.

Figure 15A:
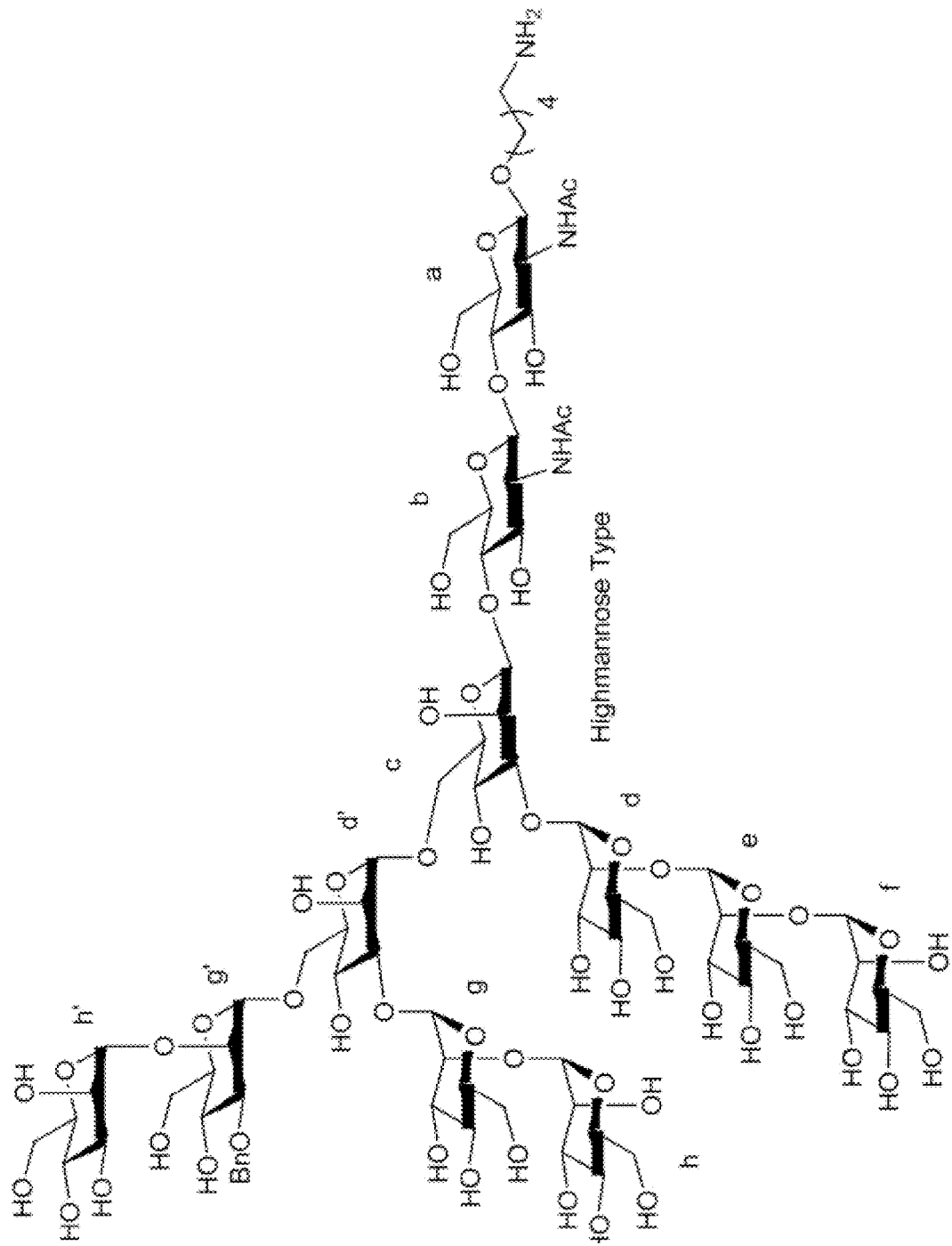
FIG. 15A to 15C Exemplary sugar residues of representative highmannose, hybrid and complex type oligosaccharides.
Figure 15B:
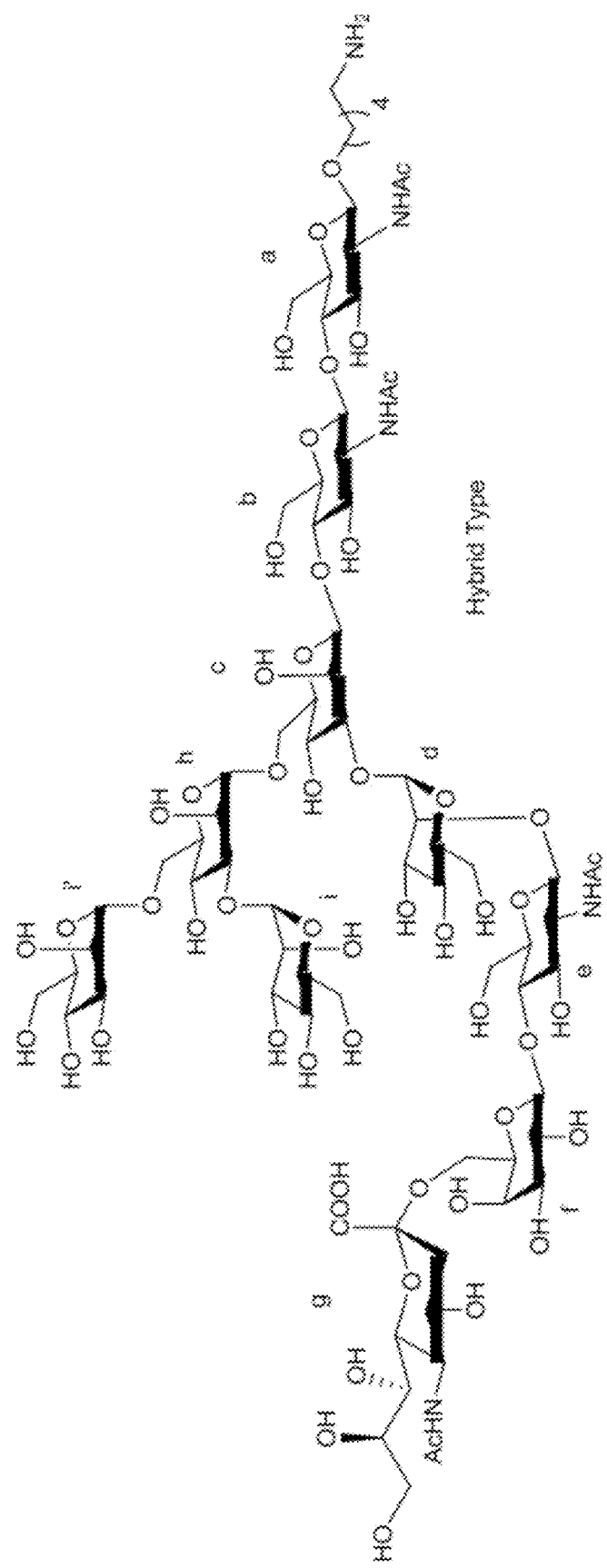
Figure 15C:
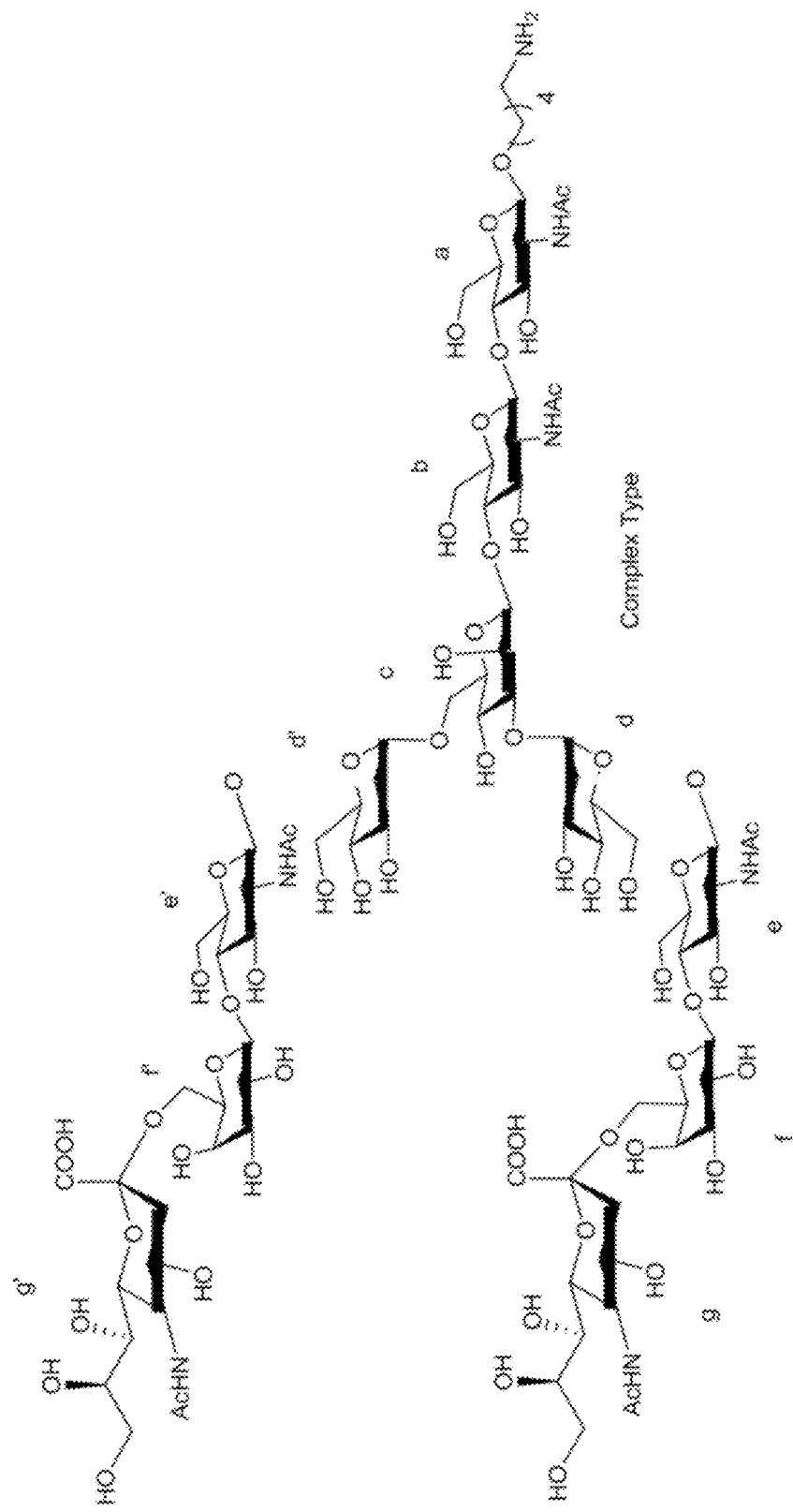

NMR Nomenclature. The individual sugar residues of highmannose, hybrid and complex type oligosaccharides have been labeled as shown below (FIGS. 15A, 15B and 15C).

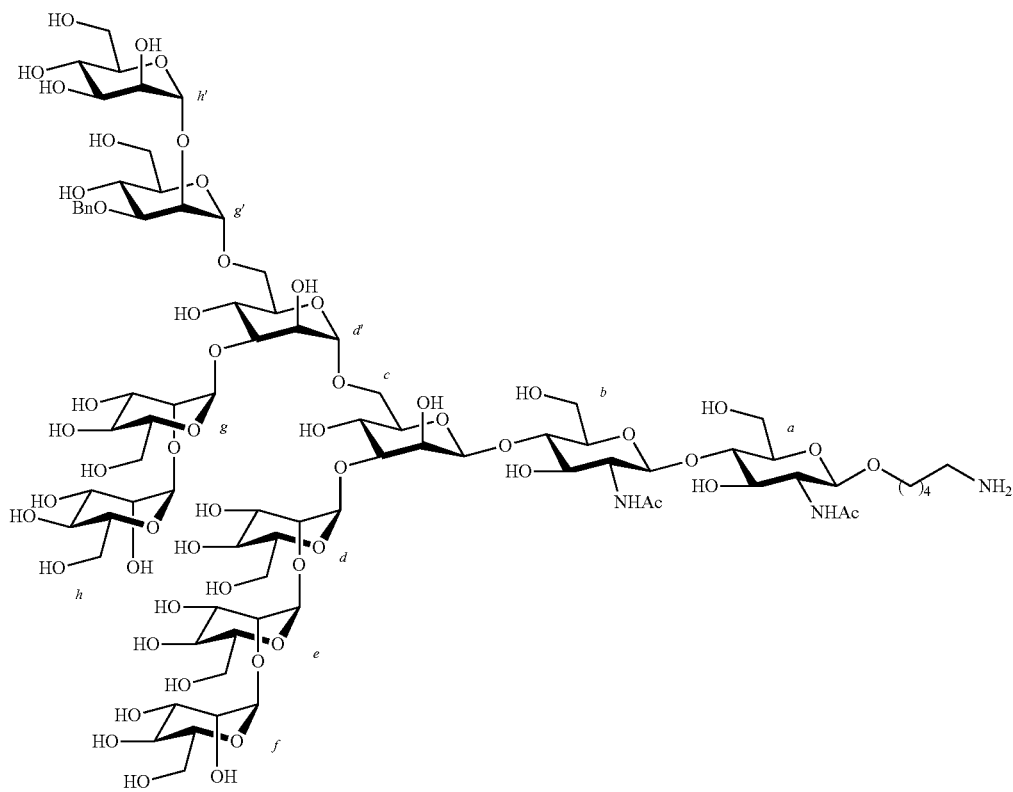
Highmannose Type
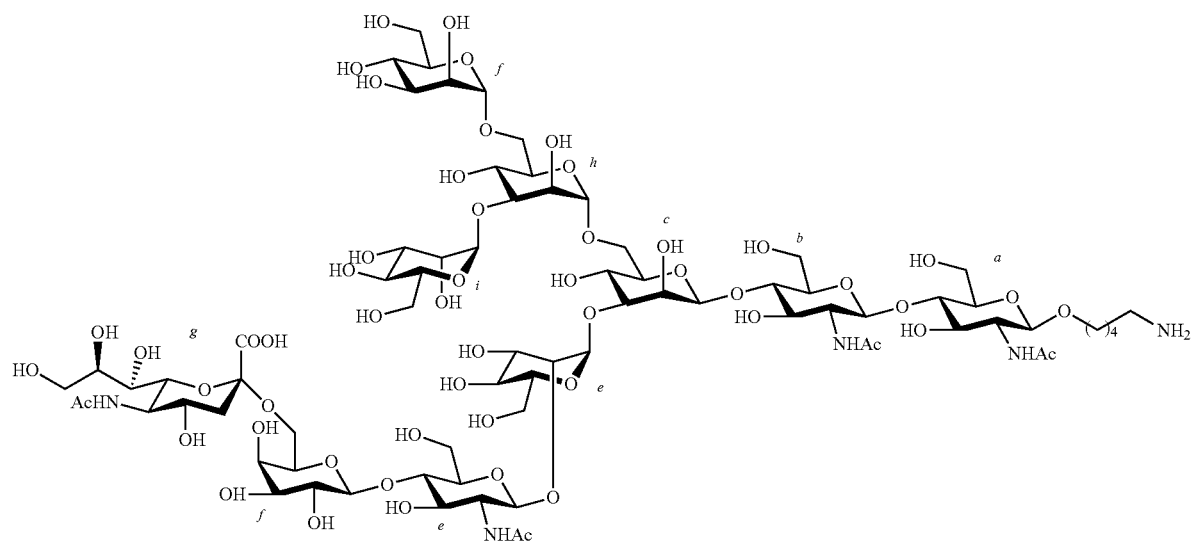
Hybrid Type

-continued

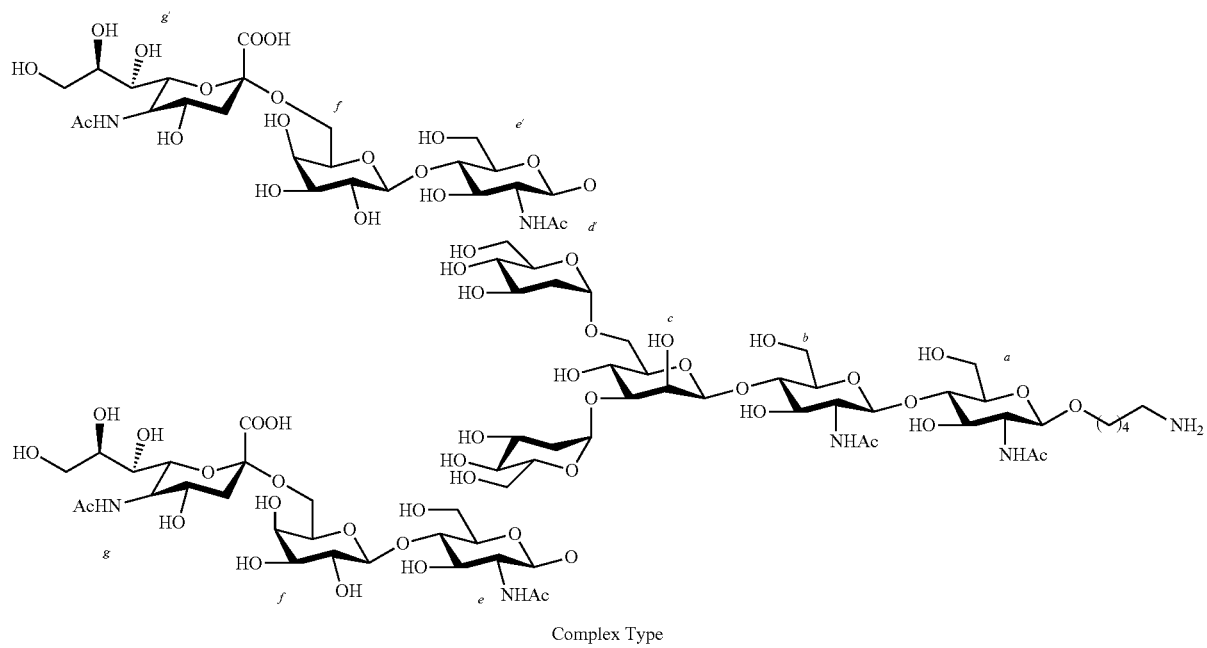

Complex Type

General Procedures S

Enzyme Expression, Purification and Reactions:
The functional domain of α-2,3 sialyltransferase (JTFAJ-16)[1] and α-2,6 sialyltransferase (JT-ISH-224)[2] were obtained according to our previous report[3]. Enzymes β-1,4 Galactosyl Transferases from bovine milk was purchased from Sigma. Enzyme α-1, 2 Fucosyl Transferases (Human Fut2 derived from HEK-293 cells) was purchased from R&D SYSTEMS. The enzymes used in this work including *Bacteroides fragilis* L-fucokinase/GDP-fucose pyrophosphorylase (FKP), pyruvate kinase (PK), pyrophosphatase (PPA), cytidine monophosphate kinase (CMK), CMP-sialic acid synthetases (CSS) and α1-3-fucosyltransferase from *Helicobacter pylori* (Hp1-3FTA26695) are examples of suitable recombinant enzymes that are expressed and purified in our laboratory. Enzymatic reactions with cofactor regeneration were carried out according to the procedure reported previously from our group[4].

Global Deprotection:

Method 1 (for glycans with -Nphthallamide protection at all glucosamine residues): A mixture of protected glycans (50 mmol) and 10 mL of ethylene diamine:nBuOH (1:4) was stirred at 90° C. for overnight. Volatiles were then evaporated and the crude product was reacted with 10 mL Ac$_2$O/pyridine (1:2) for overnight. The solvents were removed using high vacuum and product was purified by flash column chromatography (acetone:toluene, 2/8, v/v). Product was de-acetylated using sodium methoxide in MeOH (10 mL) for overnight. The reaction mixture was neutralized by using IR-120, filtered and concentrated in vacuo. The residue was purified by flash column chromatography (acetone:toluene, 3/7, v/v). Product was dissolved in 10 mL MeOH:H$_2$O: HCOOH (6:3:1), Pd(OH)$_2$ (50% by weight) was added and the reaction mixture was hydrogenated for overnight. The reaction mixture was filtered through Celite and concentrated in vacuo. The residue was purified by Bio-Gel P-2 (BIO-RAD) column chromatography using water as eluent, and the product was lyophilized to get desired oligosaccharides as a white color powder.

Method 2 (for glycans with —NHTroc protection at all glucosamine residues): A mixture of protected glycans (50 mmol) and lithium hydroxide (250 mmol) in 10 mL of 1,4 dioxane:H2O (4:1) was stirred at 90° C. for overnight. Volatiles were then evaporated and the crude product was reacted with 10 mL Ac$_2$O:pyridine (1:2) for overnight. The solvents were removed using high vacuum and product was purified by C18 gel column chromatography (MeOH:H2O as an eluent). The product was de-acetylated using sodium methoxide in MeOH (10 mL) for overnight. The reaction mixture was neutralized by using IR-120, filtered and concentrated in vacuo. The residue was purified by C18 gel column chromatography (MeOH:H2O as an eluent). The product was dissolved in 10 mL MeOH:H$_2$O:HCOOH (6:3:1), Pd(OH)$_2$ (50% by weight) was added and the mixture was hydrogenated for overnight. The reaction mixture was filtered through Celite and concentrated in vacuo. The residue was purified by Bio-Gel P-2 (BIO-RAD) column chromatography using water as eluent. The product was lyophilized to get desired oligosaccharides as a white color powder.

Enzymatic sialylation with cofactor regeneration: Glycans (5 μmol), Neu5Ac (10 μmol), ATP (0.05 μmol), CTP (1 μmol), phosphoenolpyruvate (10 μmol, monopotassium salt), cytidine monophosphate kinase (CMK, 80 units), CMP-sialic acid synthetases (CSS, 120 units), pyruvate kinase (PK, 40 units), pyrophosphatase (PPA, 40 units) and α2,6/2,3 sialyltransferase (150 units) were dissolved in 50 μmol Tris buffer (25 mM, pH 7.5). The reaction was incubated at 37° C. with gentle agitation. Complete consumption of starting material was confirmed by mass spectrometric analysis. The reaction mixture was centrifuged and the supernatant subjected to gel filtration over P2-Biogel (eluent water). Fractions containing the product were combined and lyophilized to give the respective products as amorphous white solids.

Enzymatic β-1,4-galactosylation:

Glycans (1 eq.) and UDP galactose (2 eq. per galactose) were dissolved in Tris buffer (25 mM, pH 7.5) containing MnCl$_2$ (10 mM). Enzyme β-1,4-GalT-1 (150 units) was added to achieve a final concentration of glycan ranging from 2-5 mM. The resulting reaction mixture was incubated at 37° C. for 24 h. In di-galactosylation case, when TLC showed mono-galactosylated intermediate, additional UDP-galactose (2eq), β-1,4-GalT (100 units) were added and incubated at 37° C. until complete consumption of intermediate. The reaction mixture was centrifuged and the supernatant was subjected to gel filtration over P2-Biogel (eluent water). Fractions containing the product were combined and lyophilized to give the respective products as amorphous white solids.

Enzymatic α-1,2/3-fucosylation: To a solution of glycans (5 μmol), L-fucose (5 μmol), ATP (0.5 μmol), of GTP (0.5 μmol), PEP (10 μmol), and 10 mM MnCl$_2$ in a 25 mM Tris buffer (pH 7.4) was added L-fucokinase/GDP-fucose pyrophosphorylase (FKP, 200 units), PK (200 units), PPA (200 units), and α-1,2/1,3-fucosyltransferase (200 units), and the mixture was incubated at 37° C. for overnight. The reaction mixture was centrifuged and the supernatant was subjected to gel filtration over P2-Biogel (eluent water). Fractions containing the product were combined and lyophilized to give the respective products as amorphous white solids.

Synthesis of Building Blocks 1-13 S

Figure 16:
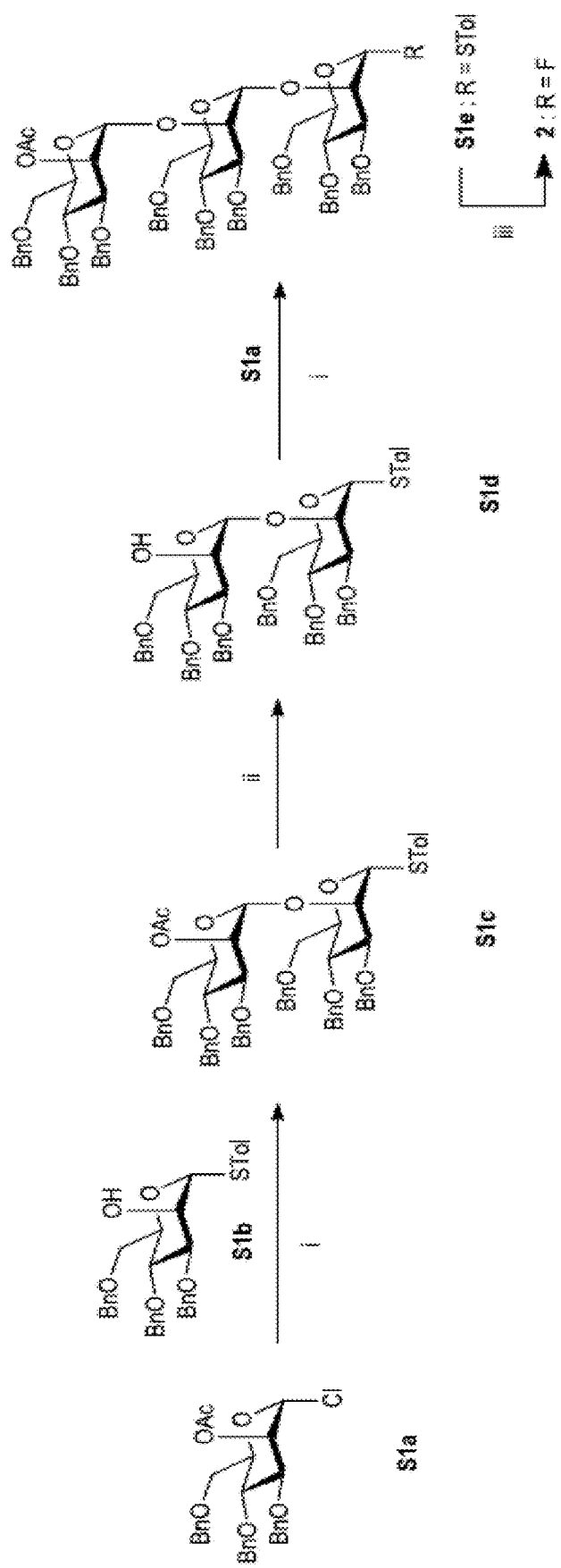
FIG. 16 shows exemplary structure embodiments and synthetic scheme embodiments of the present disclosure.
Figure 17:
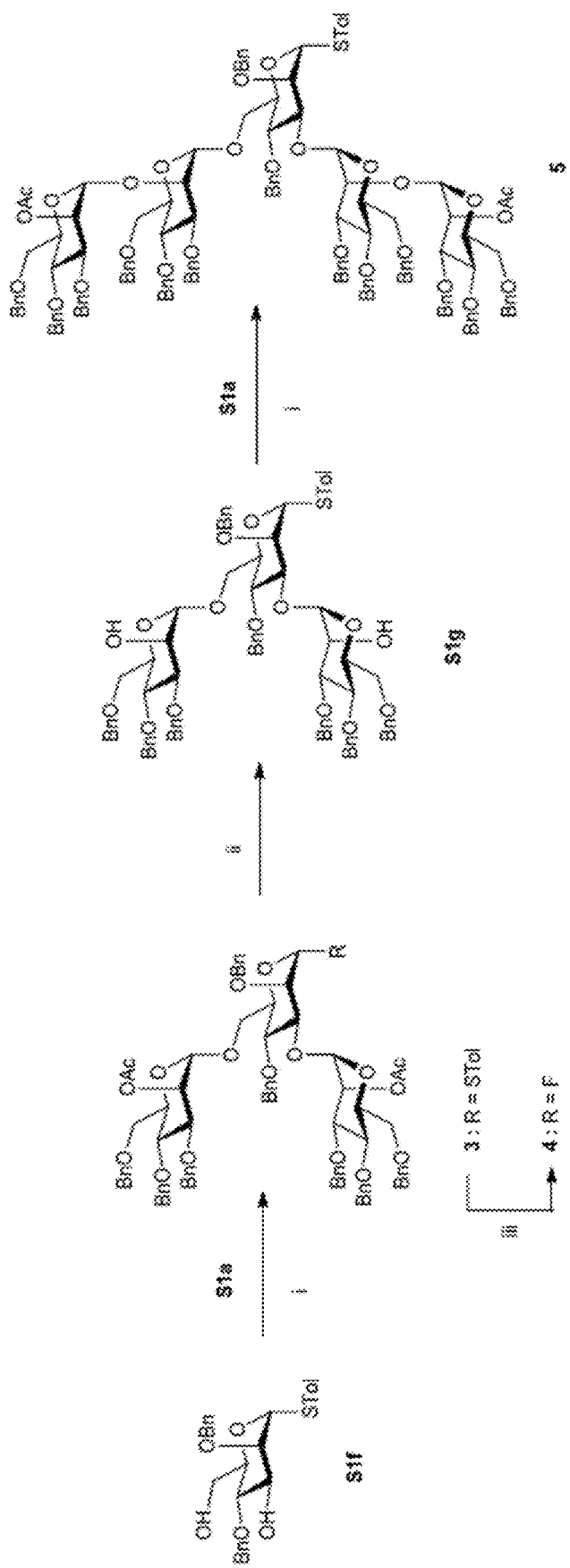
FIG. 17 shows exemplary structure embodiments and synthetic scheme embodiments of the present disclosure.
Figure 18:
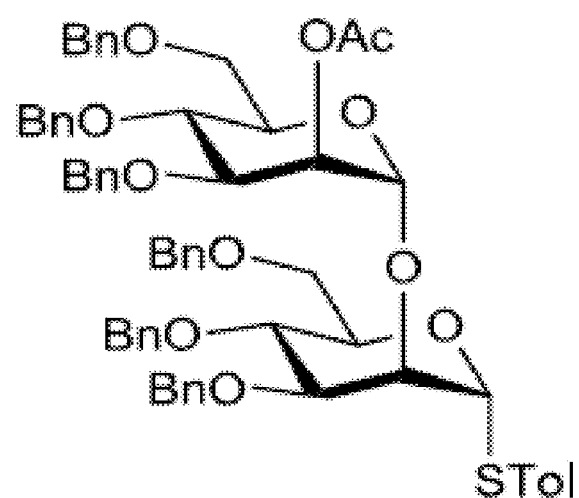
FIG. 18 shows exemplary structure embodiments and synthetic scheme embodiments of the present disclosure.
Figure 19:
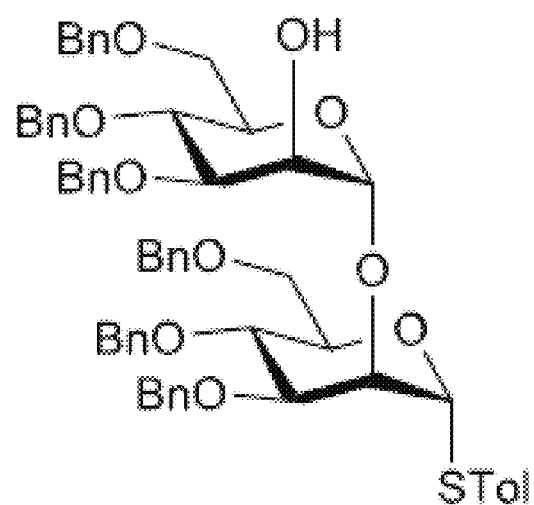
FIG. 19 shows exemplary structure embodiments and synthetic scheme embodiments of the present disclosure.
Figure 20:
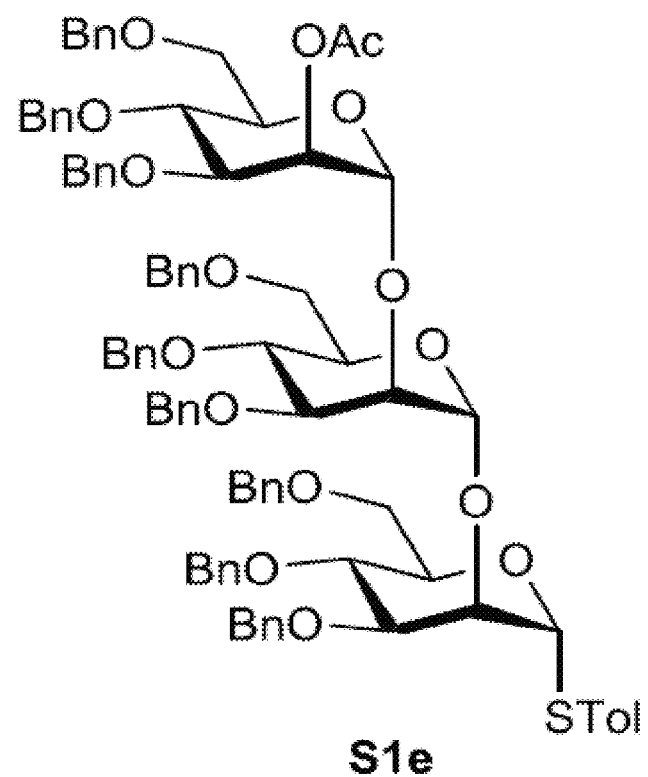
FIG. 20 shows exemplary structure embodiments and synthetic scheme embodiments of the present disclosure.
Figure 21:
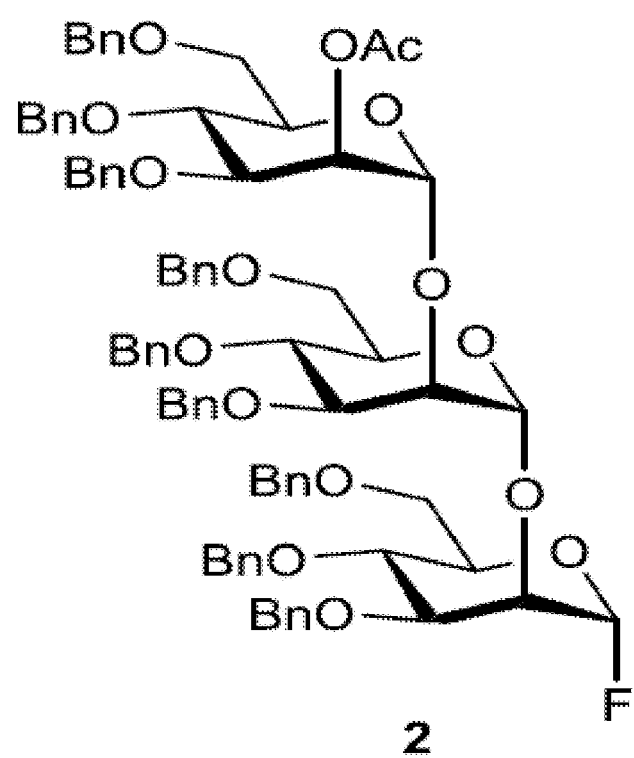
FIG. 21 shows exemplary structure embodiments and synthetic scheme embodiments of the present disclosure.
Figure 22:
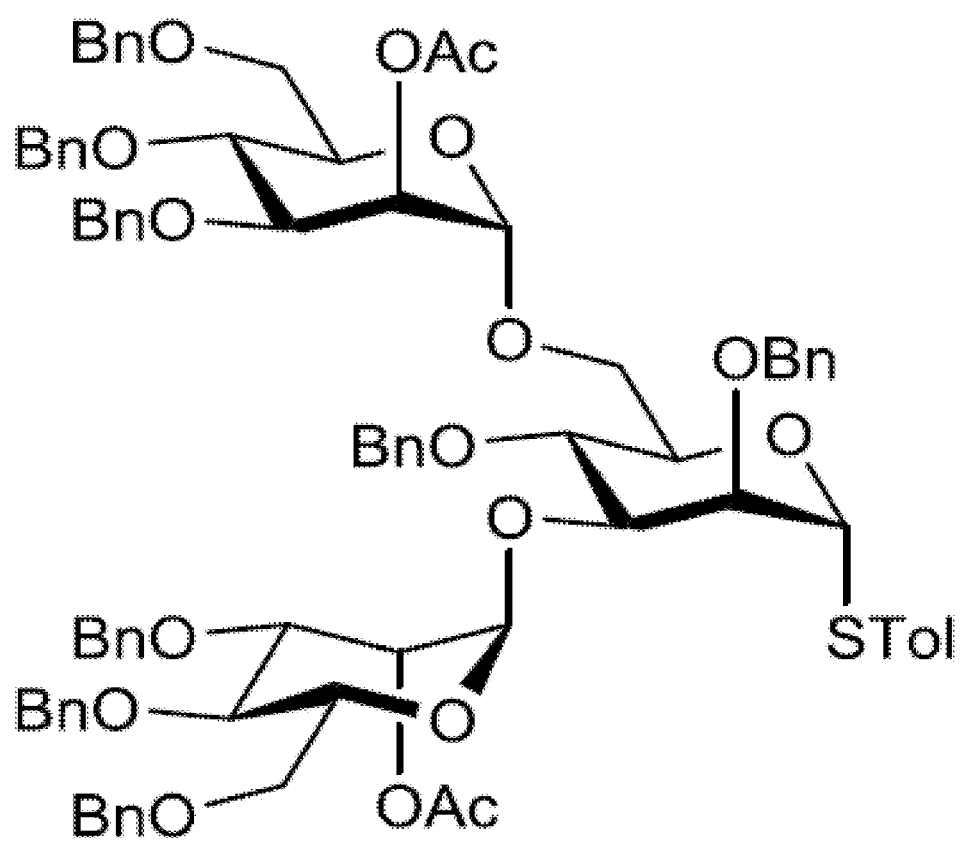
FIG. 22 shows exemplary structure embodiments and synthetic scheme embodiments of the present disclosure.
Figure 23:
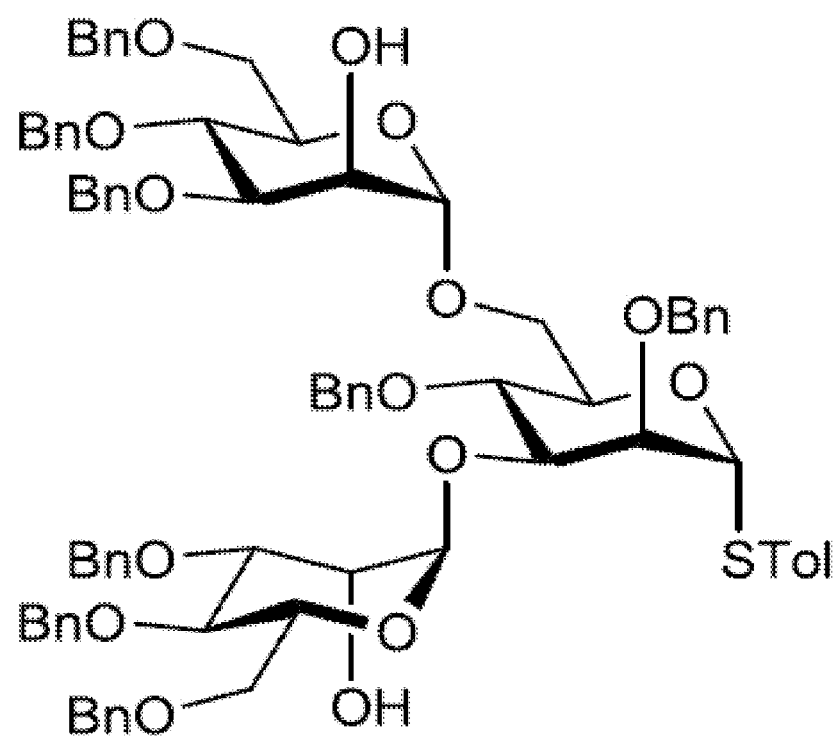
FIG. 23 shows exemplary structure embodiments and synthetic scheme embodiments of the present disclosure.
Figure 24:
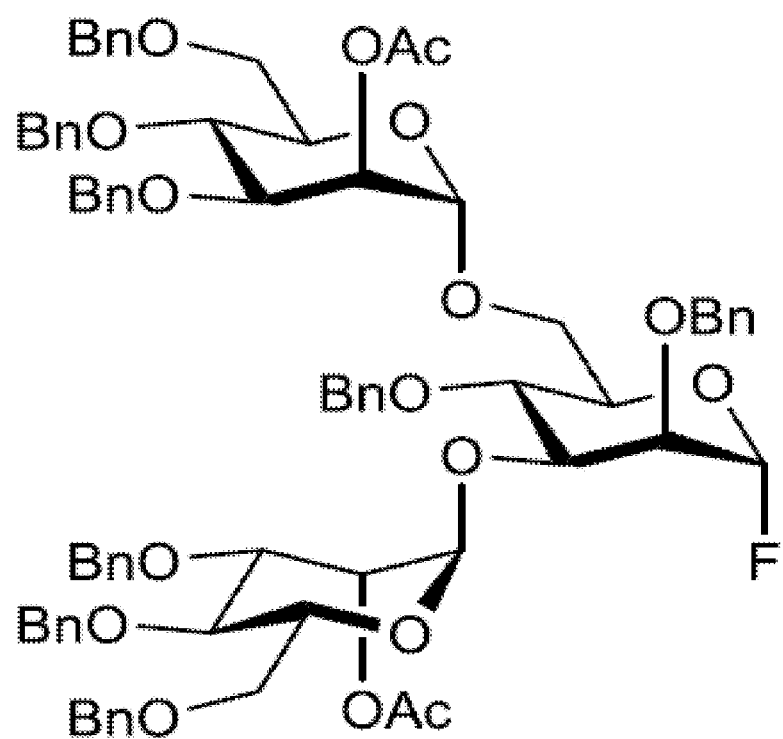
FIG. 24 shows exemplary structure embodiments and synthetic scheme embodiments of the present disclosure.
Figure 25:
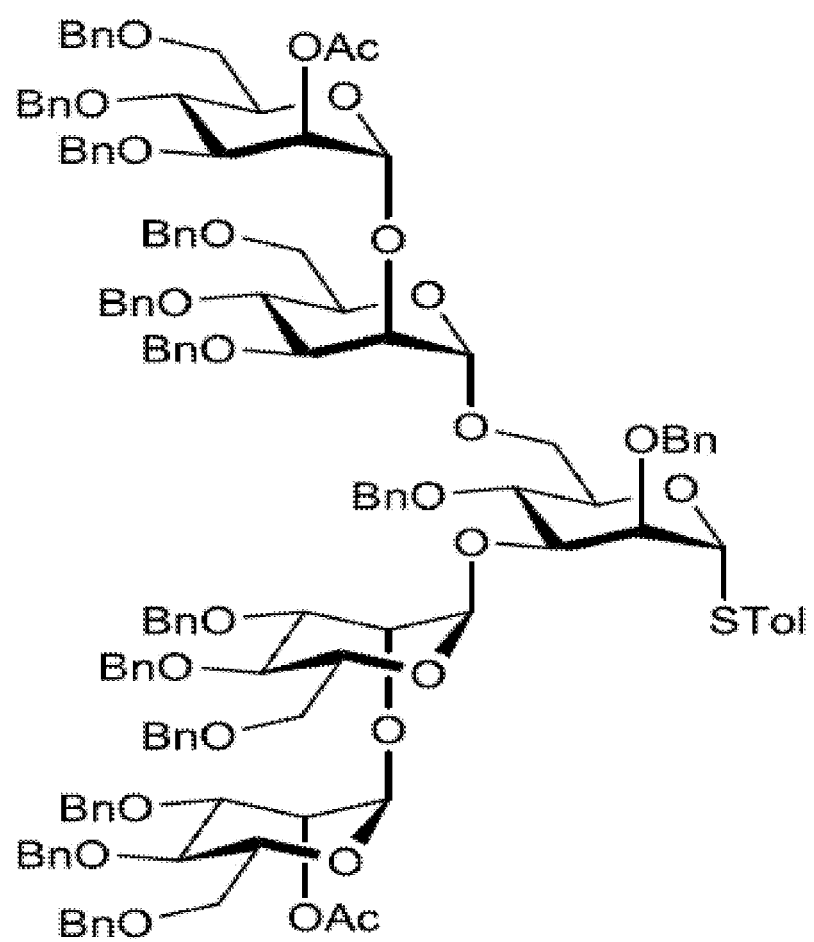
FIG. 25 shows exemplary structure embodiments and synthetic scheme embodiments of the present disclosure.

Synthesis of mono-, tri- and pentasaccharide building blocks 1-5. The mannosyl trichloroacetimidate building block 1 was obtained by reported procedure[5]. The preparation of D1 arm trisaccharide 2 of Man$_9$GlcNAc$_2$ began by glycosylation of mannosyl chloride S1a[6] and thioglycoside acceptor S1b[7] under the treatment of 2,6-di-tert-butylpyridine (DTBP) and silver triflate (AgOTf) to obtain disaccharide S1c (Scheme S1 as shown in FIGS. 16 and 17). Zemplén deacetylation of S1c at 2-O position followed by glycosylation with S1a by employing DTBP and AgOTf gave desired trisaccharide S1e in 93% yield. The leaving group modification of S1e from thioglycoside to glycosyl fluoride 2 was performed under the action of N-bromosuccinimide (NBS) and diethylaminosulfur trifluoride (DAST). The fluoride transformation provided us better results in terms of α-selectivity and excellent yield during glycosylation with chitobiose trisaccharide. Under the activation of AgOTf, the condensation of donor S1a[6] and acceptor S1f[7] was performed to afford trimannose 3, which was subsequently deacetylated and further di-glycosylated with S1a to afford D2/D3 arm pentasaccharide 5 in 71% yield. Compound 3 was next subjected to leaving group modification to trimannosyl fluoride 4 by using NBS and DAST in 68% yield. Careful observation of our strategy revealed that a single mannosyl chloride donor S1a and a unique DTBP/AgOTf mediated glycosylation condition was utilized to get D1, D2/D3 arm tri- and pentasaccharide intermediates in excellent yield (FIGS. 16 and 17).

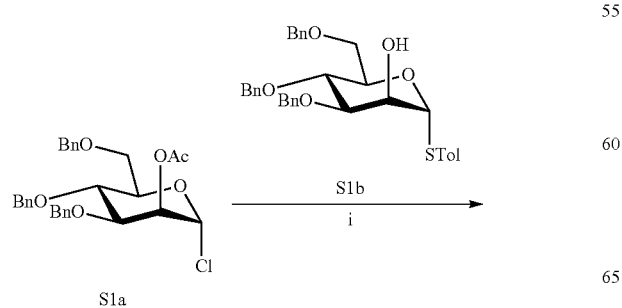

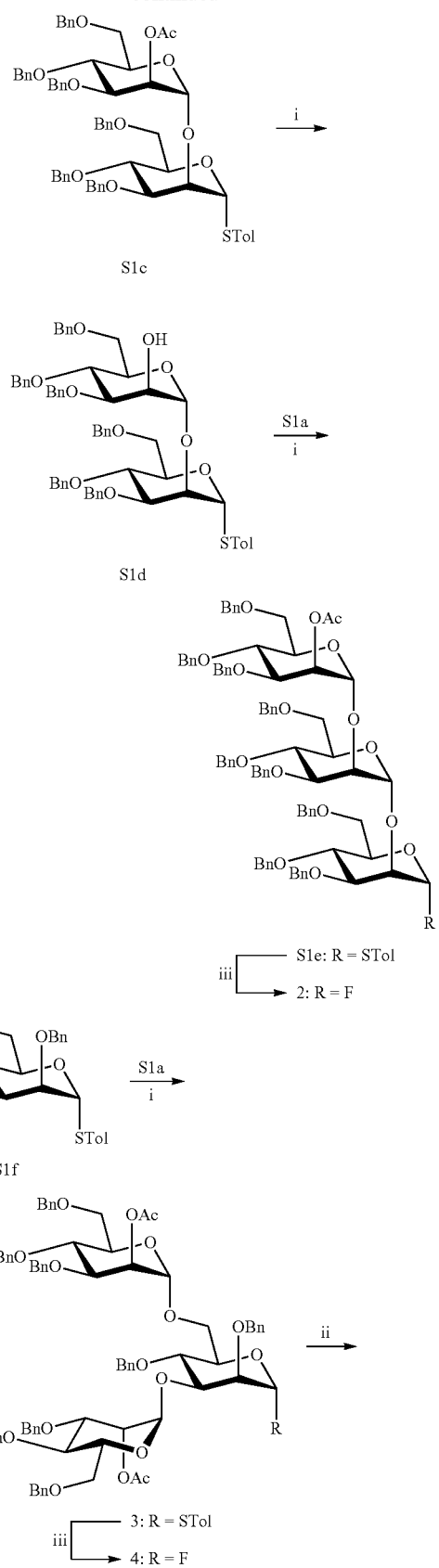

-continued

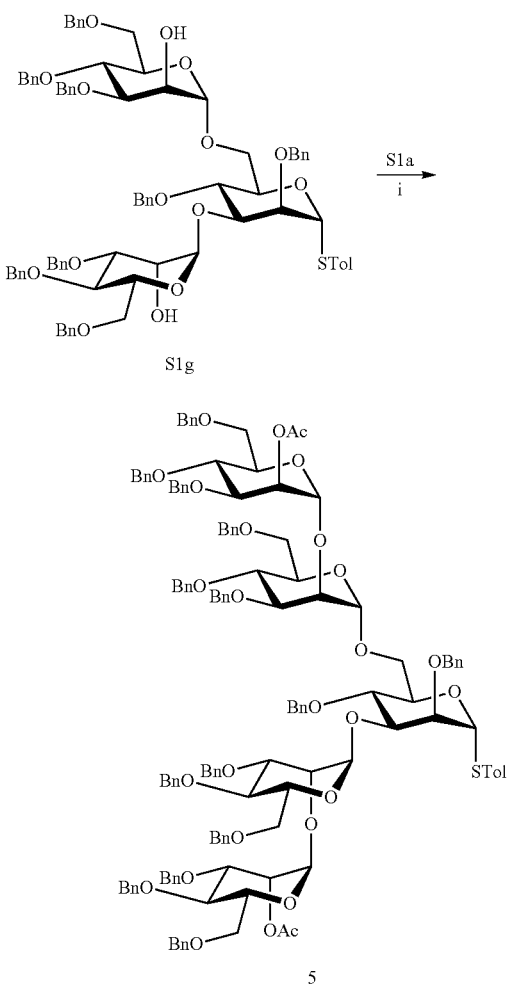

S1g

S1c

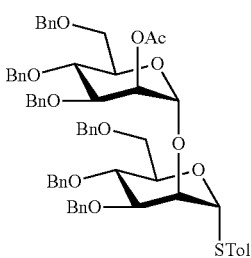

p-Tolyl-2-O-acetyl-3,4,6-tri-O-benzyl-α-D-mannopyranosyl-(1→2)-3,4,6-tri-O-benzyl-1-thio-α-D-mannopyranoside (S1c): To a solution of acceptor S1b (1.70 g, 3.05 mmol) and donor S1a (2.34 g, 4.58 mmol) in 20 mL CH$_2$Cl$_2$ was added activated 4 Å molecular sieves and stirred for 1 h at RT. In a separate flask, AgOTf (1.19 g, 4.58 mmol) and DTBP (1.03 mL, 4.58 mmol) in 10 mL of CH$_2$Cl$_2$ were stirred with 4 Å MS for 1 h. The flask containing the AgOTf/DTBP was cooled to −30° C. and solution containing mixture of donor and acceptor was added over 5 min. The solution was stirred with gradual warming up to room temperature over 24 h. TLC (ethyl acetate:hexane, 2/8) indicated formation of product with consumption of starting material, the reaction was quenched with Et$_3$N, filtered through Celite, the filtrate was washed with aqueous NaHCO$_3$ (2×50 mL) and a brine (50 mL) solution. The organic layer was dried over Na$_2$SO$_4$, and concentrated in vacuo. The residue was purified by silica gel column chromatography (0%→15% EA in hexane) to afford S1c (2.90 g, 93%) as colorless foam TLC (ethyl acetate:hexane=2/8 v/v): R$_f$=0.35;

$^1$H NMR (600 MHz, CDCl$_3$): δ 7.38-7.16 (m, 30H, Ar—H), 7.11-7.09 (m, 2H, Ar—H), 7.00 (d, J=8.4 Hz, 2H, Ar—H), 5.44 (s, 1H, H-1$^a$), 5.51 (d, J=2.4 Hz, 1H), 5.06 (s, 1H, H-1$^b$), 4.88 (d, J=11.8 Hz, 1H), 4.81 (d, J=11.2 Hz, 1H), 4.73-4.37 (m, 10H), 4.29 (t, J=8.9 Hz, 1H), 4.22 (s, 1H), 3.96-3.88 (m, 4H), 3.83-3.71 (m, 2H), 3.69-3.63 (m, 2H), 3.55 (d, J=12.1 Hz, 1H), 2.26 (s, 3H, —C(O)CH$_3$), 2.13 (s, 3H, —CH$_3$ of STol); $^{13}$C NMR (150 MHz, CDCl$_3$): δ 170.49, 138.75, 138.67, 138.62, 138.42, 138.32, 138.24, 137.87, 132.55, 130.51, 128.77, 128.64, 128.61, 128.56, 128.52, 128.39, 128.29, 128.20, 128.15, 128.03, 127.99, 127.94, 127.78, 127.63, 99.99, 87.78, 80.19, 78.35, 76.88, 75.48, 75.32, 75.03, 74.56, 73.46, 73.08, 72.47, 72.21, 72.18, 68.48, 69.02, 68.85, 21.42, 21.36; ESI-MS: m/z calcd for C$_{63}$H$_{66}$O$_{11}$S; 1030.4218; found 1053.4228 (M+Na)$^+$.

Scheme S1 as shown in FIGS. 16 and 17 depicts the preparation of compound 1-5.i, DTBP, AgOTf, 4 Å MS, CH$_2$Cl$_2$, −30° C. to RT, overnight; S1c: 93%, S1e: 91%, 3: 66%, 5: 74%; ii, NaOMe, MeOH: CH$_2$Cl$_2$=1/1; S1d: 89%, S1g: 90%; iii, N-bromo succinimide (NBS), DAST, CH$_2$Cl$_2$, −30° C. to −10° C.; 2: 58%, 4:61%. DTBP: 2,6-di-tert-butylpyridine; DAST: Diethylaminosulfur trifluoride; AgOTf: Silver trifluromethanesulfonate.

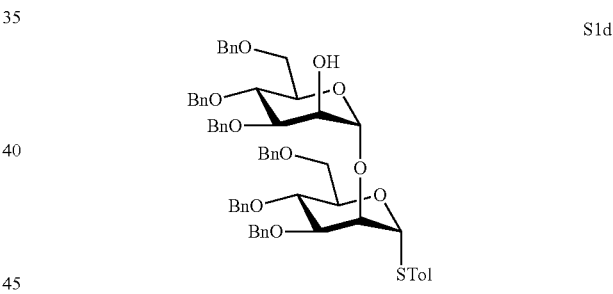

S1d p-Tolyl-3,4,6-tri-O-benzyl-α-D-mannopyrannnosyl-(1→2)-3,4,6-tri-O-benzyl-1-thio-α-D-manno pyranoside (S1d): To a solution of compound S1c (1.01 g, 0.970 mmol) in 20 mL of methanol:CH$_2$Cl$_2$ (1/1) was added sodium methoxide (0.024 g, 0.42 mmol), stirre at RT until TLC (ethyl acetate:hexane, 3/7) indicated formation of a product with consumption of the starting material. The reaction mixture was neutralized with IR-120, filtered and concentrated in vacuo and the residue was purified by silica gel column chromatography (0%→30% EA in hexane) to afford S1d (0.859 g, 89%) as a colorless oil. TLC (ethyl acetate:hexane=3/7 v/v): R$_f$=0.29; $^1$H NMR (600 MHz, CDCl$_3$): δ 7.33-7.10 (m, 32H, Ar—H), 6.96 (d, J=7.8 Hz, 1H, Ar—H), 5.56 (s, 1H, H-1), 5.11 (s, 1H, H-1), 4.85 (d, J=10.8 Hz, 1H), 4.75 (d, J=10.8 Hz, 1H), 4.69-4.62 (m, 3H), 4.52-4.38 (m, 6H), 4.37 (d, J=12.1 Hz, 1H), 4.25 (d, J=12 Hz, 2H), 4.09 (s, 1H), 3.90-3.77 (m, 4H), 3.70 (d, J=10.8 Hz, 1H), 3.62 (dd, J=4.8, 8.2 Hz, 1H), 3.54 (d, J=10.2 Hz, 1H), 2.23 (s, 3H, CH$_3$, STol); $^{13}$C NMR (150 MHz, CDCl$_3$): δ 138.61, 138.42, 138.33, 138.24, 137.97, 137.51, 132.18, 130.38, 129.73, 128.55, 128.47, 128.38, 128.29, 128.24, 127.93, 127.91, 127.89, 127.86, 127.85, 127.78, 127.68, 127.57, 127.48, 127.45, 127.33, 101.23, 87.62, 80.06, 79.99, 76.52, 75.18, 75.01, 74.95, 94.35, 73.21, 73.18, 72.87, 72.38, 72.18, 71.69, 69.28, 68.70, 68.56, 19.45; ESI-MS: m/z calcd for $C_{61}H_{64}O_{10}S$; 988.4112; found 1011.4125 (M+Na)+.

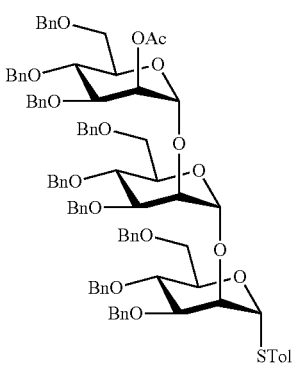

S1e p-Tolyl-2-O-acetyl-3,4,6-tri-O-benzyl-α-D-mannopyranosyl-(1→2)-3,4,6-tri-O-benzyl-α-D-mannopyranosyl-(1→2)-3,4,6-tri-O-benzyl-1-thio-α-D-mannopyranoside (S1e): To a solution of acceptor S1d (2.6 g, 2.62 mmol) and donor S1a (2.01 g, 3.94 mmol) in 10 mL $CH_2Cl_2$ was added activated 4 Å molecular sieves and stirred for 1 h at RT. In a separate flask, AgOTf (1.02 g, 3.94 mmol) and DTBP (893 μL, 3.94 mmol) in 30 mL of $CH_2Cl_2$ were stirred with activated 4 Å molecular sieves for 1 h. The mixture of AgOTf/DTBP was cooled to −30° C. and a solution of donor and acceptor was added over 5 min. The solution was stirred with gradual warming up to RT over 24 h until TLC (ethyl acetate: hexane, 2/8) indicated formation of product with consumption of starting material. The reaction was quenched with $Et_3N$, filtered through Celite. The filtrate was washed with aqueous $NaHCO_3$ (2×50 mL) and a brine (50 mL) solution. The organic layer was dried over $Na_2SO_4$, filtered and concentrated in vacuo. The residue was purified by silica gel column chromatography (0%→20% EA in hexane) to afford S1e (3.50 g, 91%) as colorless foam. TLC (ethyl acetate:hexane=2/8 v/v): $R_f$=0.41; $^1H$ NMR (600 MHz, $CDCl_3$): δ 7.34-7.11 (m, 45H, Ar—H), 7.05-7.03 (m, 2H, Ar—H), 6.93 (d, J=7.2 Hz, 1H, Ar—H), 5.65 (s, 1H, H-1), 5.50 (d, J=3.0 Hz, 1H, H-1), 5.10 (d, J=3.2 Hz, 1H, H-1), 4.82 (dd, J=3.1, 10.2 Hz, 2H), 4.75 (d, J=12.1 Hz, 1H), 4.68 (s, 2H), 4.60-4.54 (m, 8H), 4.35-4.19 (m, 9H), 3.90-3.84 (m, 5H), 3.78-3.72 (m, 2H), 3.66-3.63 (m, 3H), 3.55-3.52 (m, 1H), 3.46 (d, J=4.2 Hz, 1H), 3.41 (dd, J=3.4, 9.2 Hz, 1H), 3.31 (d, J=9.8 Hz, 1H), 2.20 (s, 3H, —C(O)CH₃), 2.05 (s, 3H, CH₃, STol); $^{13}C$ NMR (150 MHz, $CDCl_3$): δ 170.84, 139.12, 138.85, 138.79, 138.65, 138.60, 138.52, 138.37, 138.25, 137.94, 137.60, 132.30, 130.75, 129.97, 129.90, 128.98, 128.63, 128.52, 128.33, 128.20, 128.03, 127.88, 127.64, 100.79, 96.52, 88.06, 80.83, 80.45, 76.45, 76.42, 76.04, 75.65, 75.21, 75.14, 74.69, 73.63, 73.05, 73.01, 72.95, 71.99, 71.87, 71.43, 69.66, 69.51, 69.35, 68.40, 68.34, 21.40, 21.36, 21.31; ESI-MS: m/z calcd for $C_{90}H_{94}O_{16}S$; 1462.6155; found 1485.6190 (M+Na)+.

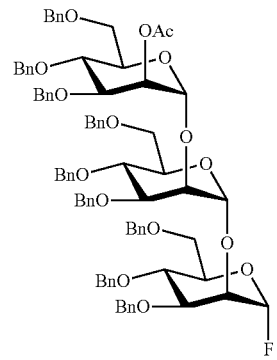

2

2-O-acetyl-3,4,6-tri-O-benzyl-α-D-mannopyranosyl-(1→2)-3,4,6-tri-O-benzyl-α-D-mannopyranosyl-(1→2)-3,4,6-tri-O-benzyl-1-α-D-mannopyranosyl fluoride (2): To a solution of trisaccharide S1e (0.600 g, 0.410 mmol) in CH2Cl2 (10 mL) at −30° C. was added NBS (0.218 mg, 1.23 mmol), stirred for 10 minutes. DAST (324 μL, 2.46 mmol) was added slowly and the resulting reaction mixture was stirred at −10° C. for 6 h. TLC (ethyl acetate: hexane, 3/7) indicated formation of product with consumption of starting material, the reaction was quenched with aq.NaHCO3, and the filtrate was washed with aqueous NaHCO3 (2×50 mL) and a brine (50 mL) solution. The organic layer was dried over Na2SO4, filtered and concentrated in vacuo. The residue was purified by silica gel column chromatography (0%→25% EA in hexane) to afford fluoride 2 (0.320 g, 58%) as white foam and 0.200 g alcohol (anomeric-OH) as side product. TLC (ethyl acetate:hexane=3/7, v/v): Rf=0.31; 1H NMR (600 MHz, CHCl3): δ 7.32-7.12 (m, 45H, Ar—H), 5.67 (d, J=50.4 Hz, 1H, Ar—H), 5.49 (s, 1H, H-1), 5.16 (s, 1H, H-1), 4.99 (s, 1H, H-1), 4.82-4.77 (m, 3H), 4.65-4.38 (m, 15H), 4.30 (d, J=12.1 Hz, 1H), 4.03 (s, 1H), 3.97-3.94 (m, 3H), 3.90-3.64 (m, 11H), 3.54 (d, J=10.2 Hz, 1H), 2.11 (s, 3H, —C(O)CH3); 13C NMR (150 MHz, CDCl3): δ 170.44, 138.77, 138.64, 138.60, 138.54, 138.46, 138.41, 138.28, 128.76, 128.64, 128.61, 128.54, 128.44, 128.31, 128.19, 128.13, 128.09, 128.04, 128.01, 127.95, 127.90, 127.87, 127.84, 127.79, 127.73, 107.65, 106.19, 101.04, 99.72, 78.56, 78.31, 75.45, 75.41, 75.31, 74.86, 74.59, 74.31, 74.10, 73.86, 73.68, 73.65, 73.57, 72.69, 72.49, 72.38, 72.17, 69.51, 69.31, 69.01, 68.95, 21.44; ESI-MS: m/z calcd for C, 83; H, 87; FO, 016; 1358.5870; found 1381.5891 (M+Na)+.

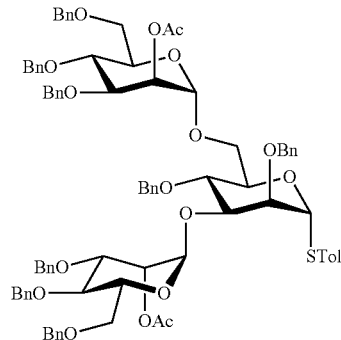

3 p-Tolyl-2-O-acetyl-3,4,6-tri-O-benzyl-α-D-mannopyranosyl-(1→3)-2-O-acetyl-3,4,6-tri-O-benzyl-α-D-mannopyranosyl-(1→6)-2,4-di-O-benzyl-1-thio-α-D-mannopyranoside (3): To a solution of acceptor S1f (0.545 g, 1.23 mmol) and donor S1a (1.57 g, 3.07 mmol) in CH2Cl2 (10 mL) was added 4 Å activated MS and stirred for 1 h at room temperature. In a separate flask, AgOTf (0.787 g, 3.07 mmol) and DTBP (690 μL, 3.07 mmol) in 10 mL of CH2Cl2 were stirred with MS4 Å. After stirring for 1 h, the flask containing the AgOTf/DTBP was cooled to −30° C. and a solution containing a mixture of donor and acceptor was added over 5 min. The solution was stirred with gradual warming up to room temperature over 24 h. TLC (ethyl acetate:hexane, 2/8) indicated formation of product with consumption of starting material. The reaction was quenched with Et3N, filtered through Celite, the filtrate was washed with aqueous NaHCO3 (2×50 mL) and a brine (50 mL) solution. The organic layer was dried over Na2SO4, filtered and concentrated in vacuo. The residue was purified by silica gel column chromatography (0%→20% EA in hexane) to afford 3 (1.10 g, 66%) as colorless foam. TLC (ethyl acetate:hexane=2/8, v/v): Rf=0.36; 1H NMR (600 MHz, CDCl3): δ 7.35-7.10 (m, 32H, Ar—H), 7.05 (d, J=8.0 Hz, 2H, Ar—H), 5.51 (s, 1H), 5.47 (s, 1H, H-1), 5.45 (dd, J=2.0, 2.8 Hz, 1H), 5.21 (s, 1H, H-1), 4.91 (d, J=1.5 Hz, 1H, H-1), 4.86 (t, J=10.2 Hz, 2H), 4.75 (d, J=11.2 Hz, 1H), 4.67-4.58 (m, 5H), 4.54-4.36 (m, 8H), 4.23 (dd, J=3.9, 9.6 Hz, 1H), 4.12-4.06 (m, 2H), 4.01 (dd, J=3.2, 9.2 Hz, 1H), 3.97-3.86 (m, 5H), 3.82 (t, J=9.2 Hz, 1H) 3.79-3.75 (m, 1H), 3.72 (dd, J=3.9, 10.7 Hz, 1H), 3.70-3.56 (m, 4H), 2.17 (s, 3H, —C(O)CH3), 2.13 (s, 3H, —C(O)CH3), 2.09 (s, 3H, CH3, STol); 13C NMR (150 MHz, CDCl3): δ 170.27, 170.10, 138.57, 138.53, 138.18, 138.16, 137.81, 137.77, 137.42, 131.46, 130.85, 129.83, 128.44, 128.42, 128.36, 128.27, 128.21, 128.06, 127.81, 127.72, 127.68, 127.63, 127.53, 127.48, 99.83, 98.17, 85.23, 78.98, 78.08, 77.76, 75.15, 74.98, 74.89, 74.32, 74.15, 73.52, 73.30, 72.23, 72.05, 71.85, 71.48, 71.43, 71.36, 69.05, 68.72, 68.60, 68.41, 66.60, 60.39, 21.15, 21.00, 20.94; ESI-MS: m/z calcd for C, 85; H, 90; O, 17S; 1414.5791; found 1437.5821 (M+Na)+.

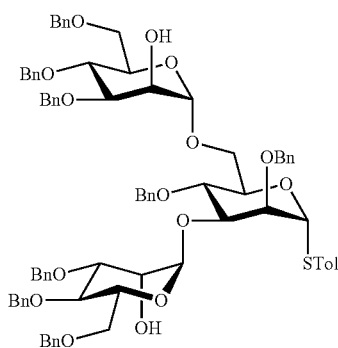

S1g p-Tolyl-3,4,6-tri-O-benzyl-α-D-mannopyranosyl-(1→3)-3,4,6-tri-O-benzyl-α-D-mannopyranosyl-(1→6)]-2,4-di-O-benzyl-1-thio-α-D-mannopyranoside (S1g): To a solution of trisaccharide 3 (1.30 g, 0.918 mmol) in 10 mL methanol: CH2Cl2 (1/1) was added sodium methoxide (0.024 g, 0.459 mmol), stirred at RT until TLC (ethyl acetate:hexane, 3/7) indicated formation of a product with consumption of the starting material. The reaction mixture was neutralized with IR-120, filtered and concentrated in vacuo and the residue was purified by silica gel column chromatography (0%→25% EA in hexane) to afford S1g (1.10 g, 90%) as a colorless oil. TLC (ethyl acetate:hexane=3/7, v/v): Rf=0.26; 1H NMR (600 MHz, CDCl3): δ 7.36-7.12 (m, 42H, Ar—H), 7.06 (d, J=8.0 Hz, 2H, Ar—H), 5.46 (s, 1H, H-1), 5.24 (s, 1H, H-1), 5.01 (d, J=1.1 Hz, 1H, H-1), 4.82 (t, J=11.1 Hz, 2H), 4.69 (d, J=11.6 Hz, 1H), 4.65-4.44 (m, 13H), 4.23 (dd, J=4.1, 9.6 Hz, 1H), 4.16 (s, 1H), 4.07 (dd, J=2.8, 9.4 Hz, 1H), 4.03 (d, J=10.1 Hz, 1H), 3.96-3.88 (m, 4H), 3.87-3.81 (m, 3H), 3.80-3.75 (m, 1H), 3.73-3.64 (m, 4H), 3.62 (dd, J=1.6, 10.8 Hz, 1H), 2.38 (s, 1H), 2.34 (s, 1H, —C(O)CH3), 2.19 (s, 3H, CH3, STol); 13C NMR (150 MHz, CDCl3): δ 138.12, 138.11, 137.69, 131.75, 130.12, 128.82, 128.76, 128.73, 128.67, 128.63, 128.57, 128.54, 128.53, 128.41, 128.35, 128.29, 128.19, 128.12, 128.08, 128.03, 127.95, 128.92, 127.82, 124.43, 99.90, 85.55, 80.32, 80.00, 78.49, 79.46, 75.46, 75.41, 75.27, 75.19, 75.13, 74.66, 74.50, 74.39, 73.85, 73.81, 73.62, 72.32, 72.24, 71.85, 71.71, 71.40, 71.33, 69.48, 69.00, 68.96, 68.90, 68.32, 66.51, 21.15; ESI-MS: m/z calcd for C, 81; H, 86; O, 15S; 1330.5580; found 1353.5614 (M+Na)+.

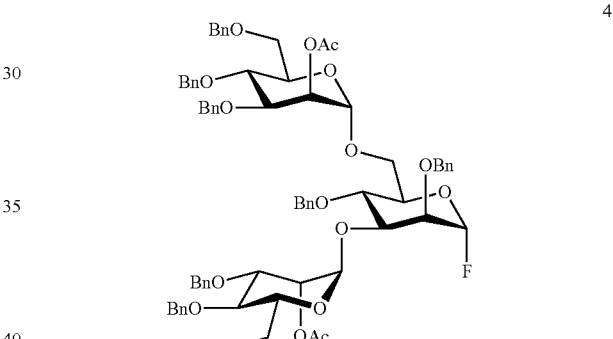

4

2-O-acetyl-3,4,6-tri-O-benzyl-α-D-mannopyranosyl-(1→3)-2-O-acetyl-3,4,6-tri-O-benzyl-α-D-mannopyranosyl-(1→6)-2,4-di-O-benzyl-α-D-mannopyranosyl fluoride (4): To a solution of compound 3 (0.270 g, 0.197 mmol) in CH2Cl2 (10 mL) at −30° C. was added NBS (0.052 g, 0.296 mmol), stirred for 10 min. DAST (52 μL, 0.395 mmol) was then added slowly and the resulting reaction mixture was stirred for 4 h at −10° C. TLC (ethyl acetate: hexane, 3/7) indicated formation of product with consumption of starting material. The reaction mixture was quenched with aq.NaHCO3, and the filtrate was washed with aqueous NaHCO3 (2×50 mL) and a brine (50 mL) solution. The organic layer was dried over Na2SO4 and concentrated in vacuo. The residue was purified by silica gel column chromatography (0%→8% EA in toluene) to afford 4 (0.150 g, 61%) as white foam. TLC (ethyl acetate:toluene=1/9, v/v): Rf=0.19; 1H NMR (600 MHz, CHCl3): δ 7.29-7.10 (m, 40H, Ar—H), 5.50 (s, 1H, H-1), 5.47 (d, J=50 Hz, 1H, H-1), 5.46 (s, 1H, H-1), 5.18 (s, 1H), 4.92 (s, 1H), 4.86 (d, J=11.2 Hz, 1H), 4.83 (d, J=10.8 Hz, 1H), 4.72 (d, J=10.0 Hz, 1H), 4.72-4.56 (m, 6H), 4.48-4.40 (m, 7H), 4.10 (d, J=8.9 Hz, 1H), 4.00-3.92 (m, 4H), 4.90-3.77 (m, 5H), 3.71-3.64 (m, 5H), 3.57 (d, J=7.2 Hz, 1H), 2.13 (s, 3H, —C(O)CH3), 2.06

(s, 3H, —C(O)CH3); 13C NMR (150 MHz, CHCl3): δ 170.56, 170.36, 138.80, 138.74, 138.50, 138.39, 138.11, 138.04, 137.89, 137.88, 129.70, 128.81, 128.70, 128.68, 128.65, 128.58, 128.56, 128.54, 128.43, 128.27, 128.18, 128.12, 128.07, 128.04, 128.00, 127.97, 127.89, 127.82, 126.55, 106.66, 105.18, 100.02, 98.84, 98.81, 78.31, 77.70, 76.31, 76.03, 75.42, 75.37, 75.23, 74.62, 74.41, 74.27, 73.90, 73.80, 73.65, 73.16, 72.66, 72.14, 71.92, 71.58, 69.42, 68.96, 68.70, 68.61, 66.53, 42.20, 32.21, 29.98, 29.65, 22.98, 21.63, 21.44, 21.27, 14.71, 14.41; ESI-MS: m/z calcd for C, 78; H, 83; O, 17 F; 1310.5507; found 1333.5536 (M+Na)+.

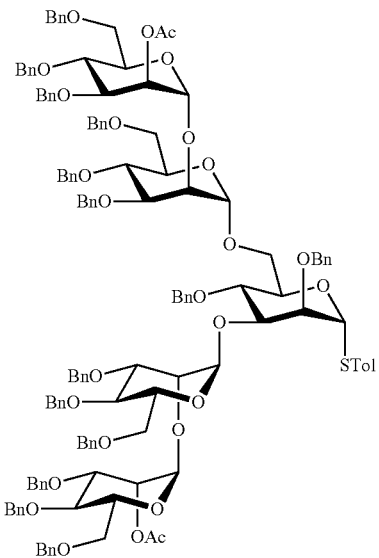

p-Tolyl-2-O-acetyl-3,4,6-tri-O-benzyl-α-D-mannopyranosyl-(1→2)-3,4,6-tri-O-benzyl-α-D-mannopyranosyl-(1→3)-[2-O-acetyl-3,4,6-tri-O-benzyl-α-D-mannopyranosyl-(1→2)-3,4,6-tri-O-benzyl-α-D-mannopyranosyl-(1→6)]-2,4-di-O-benzyl-1-thio-α-D-mannopyranoside (5): To a solution of acceptor S1g (1.01 g, 0.739 mmol) and donor S1a (0.947 g, 1.84 mmol) in 20 mL CH2Cl2 was added 4 Å activated MS and stirred for 1 h at room temperature. In a separate flask, AgOTf (0.472 g, 1.85 mmol) and DTBP (415 μL, 1.85 mmol) in 10 mL of CH2Cl2 were stirred with MS 4 Å. After stirring for 1 h, the flask containing the AgOTf/DTBP was cooled to −30° C. and a solution containing a mixture of donor and acceptor in CH2Cl2 was added over 5 min. The solution was stirred with gradual warming up to room temperature over 24 h. TLC (ethyl acetate:hexane, 3/7) indicated formation of product with consumption of starting material. The reaction was then quenched with Et3N, filtered through Celite, and the filtrate was washed with aqueous NaHCO3 (2×50 mL) and a brine (50 mL) solution. The organic layer was dried over Na2SO4, filtered and concentrated in vacuo. The residue was purified by silica gel column chromatography (0%→25% EA in hexane) to afford 5 (1.25 g, 74%) as white solid. TLC (ethyl acetate:hexane=3/7, v/v): Rf=0.33; 1H NMR (600 MHz, CDCl3): δ 7.27-7.04 (m, 72H, Ar—H), 7.02 (d, J=8.0 Hz, 2H, Ar—H), 5.52 (d, J=1.5 Hz, 2H, 2×H-1), 5.46 (s, 1H, H-1), 5.18 (s, 1H, H-1), 5.04 (d, J=8.2 Hz, 1H), 4.85 (t, J=11.0 Hz, 2H), 4.78 (t, J=11.1 Hz, 2H), 4.72-4.44 (m, 18H), 4.41-4.30 (m, 8H), 4.27 (d, J=12.3 Hz, 2H), 4.20 (s, 2H), 4.05-3.92 (m, 6H), 3.91-3.73 (m, 8H), 3.68-3.56 (m, 6H), 3.48 (d, J=10.1 Hz, 1H), 3.40 (d, J=10.3 Hz, 1H), 3.34 (d, J=10.5 Hz, 1H), 2.10 (s, 6H, —C(O)CH3), 2.01 (s, 3H, CH3, STol); 13C NMR (150 MHz, CDCl3): δ 170.22, 152.99, 152.78, 152.57, 138.43, 138.38, 138.24, 138.05, 138.02, 137.86, 137.81, 131.15, 129.80, 128.44, 128.30, 128.20, 128.05, 127.95, 127.85, 127.72, 127.70, 127.62, 127.55, 127.53, 127.47, 127.41, 127.38, 127.35, 127.23, 126.94, 101.16, 99.37, 98.86, 84.97, 79.24, 78.07, 78.02, 75.22, 74.99, 74.87, 74.77, 74.55, 74.47, 74.29, 74.17, 73.94, 73.82, 73.38, 73.24, 73.18, 73.01, 72.58, 71.93, 71.85, 71.77, 71.60, 71.55, 71.47, 70.99, 69.41, 68.64, 68.57, 68.46, 68.01, 29.69, 21.22, 20.91; ESI-MS: m/z calcd for C, 139; H, 146; O, 27; S; 2279.9698; found 2302.9747 (M+Na)+.

Synthesis of disaccharides building block 6.

Condensation of acceptor S2a8 with donor S2b9 mediated by NIS and TfOH supplied the disaccharide S2c with exclusively β-linkage (J1',2'=8.5 Hz) in 64% yield. Compound S2c was next modified to fluoride 6 via anomeric deallylation followed by conversion of free —OH to —F in presence of DAST (Scheme S2 as shown in FIG. 26).

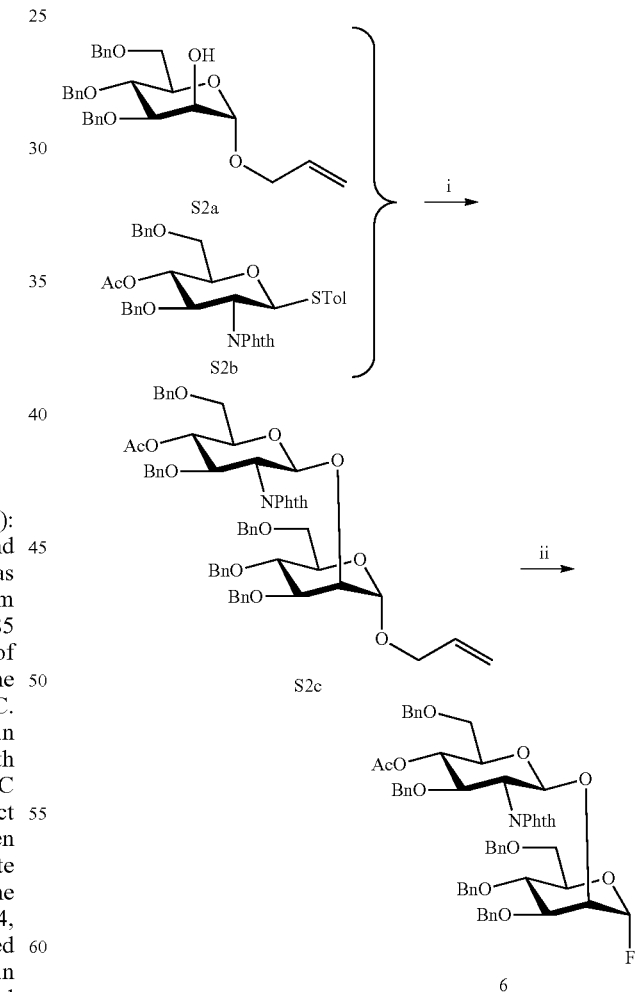

Figure 26:
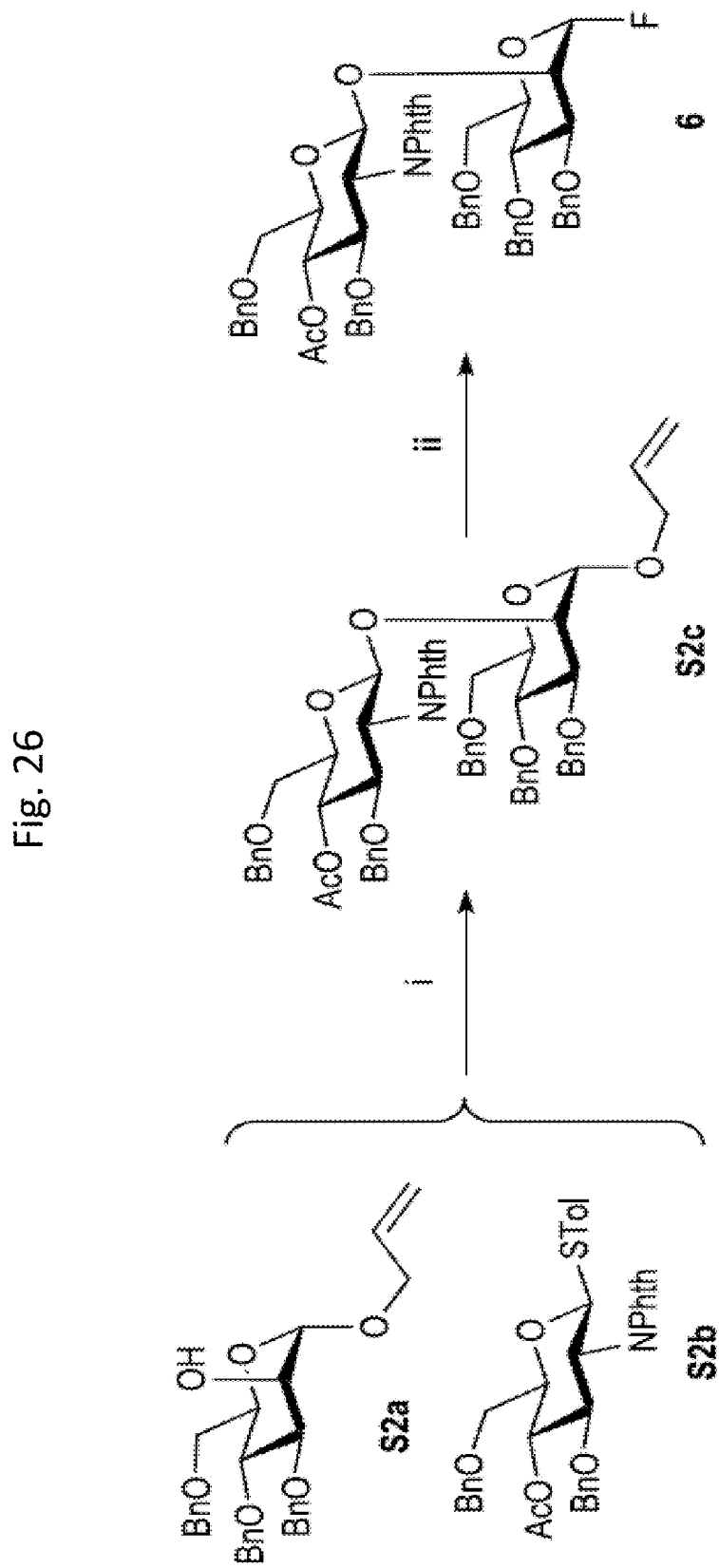
FIG. 26 shows exemplary structure embodiments and synthetic scheme embodiments of the present disclosure.
Figure 27:
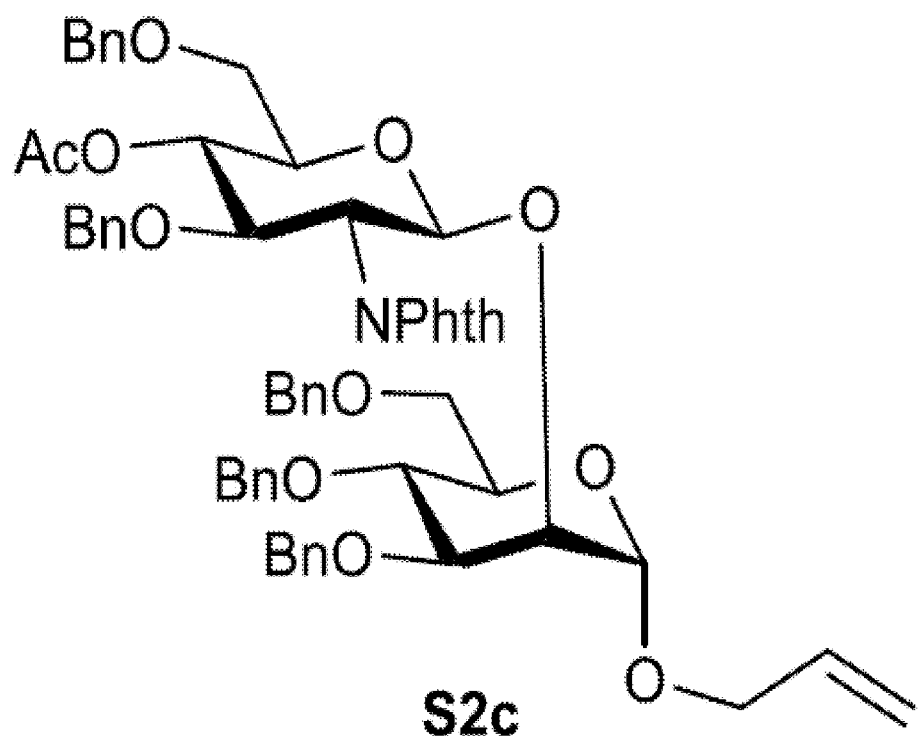
FIG. 27 shows exemplary structure embodiments and synthetic scheme embodiments of the present disclosure.
Figure 28:
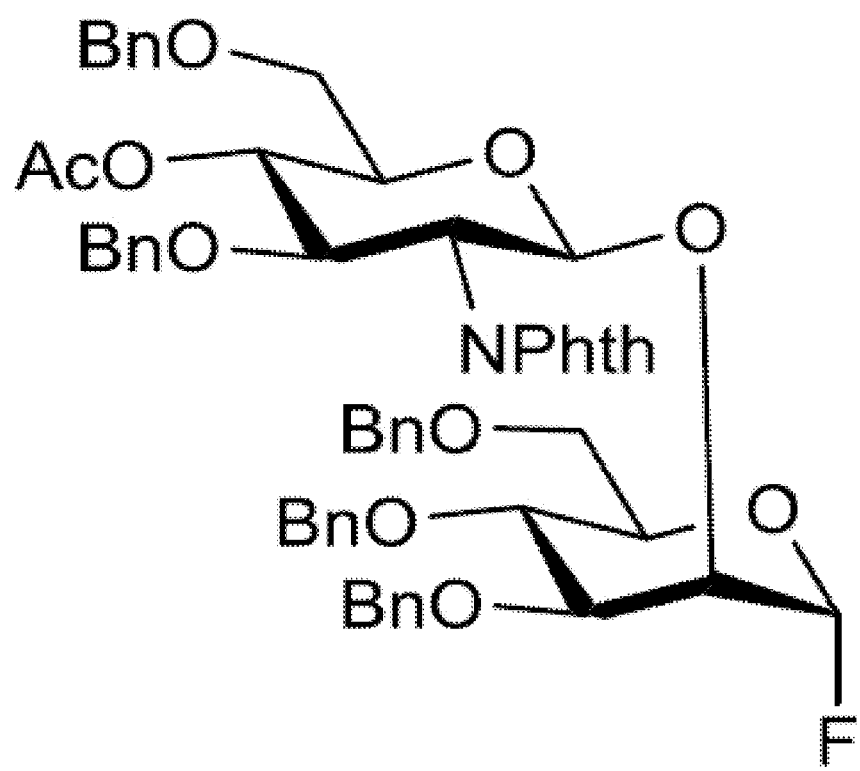
FIG. 28 shows exemplary structure embodiments and synthetic scheme embodiments of the present disclosure.

Scheme S2 as shown in FIG. 26 depicts the preparation of compound 6. i, NIS, TfOH, CH2Cl2, 4 Å MS, −40° C., 2h, 64%; ii, (1) PdCl2, MeOH: CH2Cl2=1/1, (2) DAST, CH2Cl2, −30° C. to −10° C., 3-5 h, 61%.

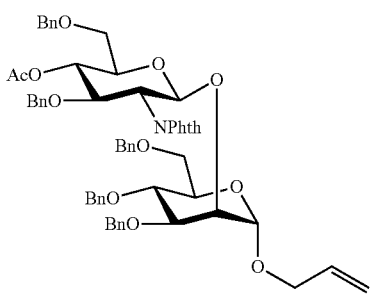

Allyl-O-4-O-acetyl-3,6-O-di-benzyl-2-deoxy-2-phthalimido-β-D-glucopyranosyl-(1→2)-O-3,4,6-tri-O-benzyl-α-D-mannopyranoside (S2c): A mixture of thioglycoside donor S2b (2.33 g, 3.65 mmol), acceptor S2a (1.50 g, 3.05 mmol) and activated 4 Å molecular sieves (3 g) in 30 mL dry CH2Cl2 was stirred for 1h at room temperature. NIS (1.35 g, 6.01 mmol) and TfOH (66.2 µL, 0.75 mmol) were added slowly at −40° C. and stirred for 2 h until TLC (ethyl acetate:toluene, 1/9) indicated formation of product with consumption of starting material. The reaction mixture was quenched with Et3N, filtered through Celite, and the filtrate was washed with aq. NaHCO3 (2×50 mL), aq.Na2S2O3 (2×50 mL) and finally with brine (50 mL) solution. The organic layer was dried over Na2SO4 and concentrated in vacuo. The residue was purified by flash column chromatography (0%→10% EA in toluene) to afford S2c (2.10 g, 64%) as white solid. TLC (ethyl acetate:toluene=1/9, v/v): Rf=0.29; 1H NMR (600 MHz, CDCl3): δ 7.52-7.50 (m, 4H, Ar—H), 7.33-7.10 (m, 16H, Ar—H), 7.10-7.09 (m, 4H, Ar—H), 7.00-6.90 (m, 2H, Ar—H), 6.89-6.81 (m, 3H, Ar—H), 5.73-5.71 (m, 1H, —OCH2-CH=CH2), 5.26 (d, J=8.4 Hz, 1H,H-1), 5.14-5.06 (m, 3H), 4.71 (t, J=7.8 Hz, 2H), 4.58 (d, J=12.1 Hz, 1H), 4.50-4.39 (m, 6H), 4.34 (d, J=4.8 Hz, 1H), 4.32 (d, J=6.6 Hz, 1H), 4.10 (t, J=8.6 Hz, 1H), 4.07-4.00 (q, 2H), 3.78 (dd, J=3.2, 6.1 Hz, 1H), 3.81-3.78 (m, 2H), 3.71-3.70 (dd, J=3.2, 6.3 Hz, 1H), 3.65-3.60 (m, 1H), 3.58 (dd, J=3.1, 6.5 Hz, 1H), 3.56 (t, J=8.9 Hz, 1H), 3.48 (t, J=10.2 Hz, 1H), 3.39 (d, J=8.4 Hz, 1H), 2.97-2.96 (m, 1H), 1.93 (s, 3H, —C(O)CH3); 13C NMR (150 MHz, CDCl3): δ 169.9, 138.69, 138.6, 138.5, 137.9, 137.9, 134, 133.8, 133.7, 131.9, 130.3, 128.5, 128.4, 128.4, 128.3, 128.2, 128.0, 127.9, 127.7, 127.7, 127.6, 127.5, 127.5, 123.3, 117.5, 97.1, 96.4, 77.9, 76.9, 75.1, 74.8, 73.9, 73.8, 73.8, 73.05, 72.8, 71.9, 71.0, 70.4, 70.1, 68.1, 55.5, 28.7, 21.5, 21.1; ESI-MS: m/z calcd for C, 60; H, 61; NO, 13; 1003.4035 found 1026.4043 (M+Na)+.

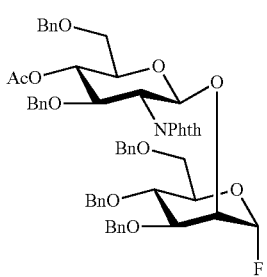

4-O-acetyl-3,6-O-di-benzyl-2-deoxy-2-phthalimido-β-D-glucopyranosyl-(1→2)-O-3,4,6-tri-O-benzyl-α-D-mann-opyranosyl fluoride (6): To a solution of S2c (0.750 g, 0.747 mmol) in 10 mL CH2Cl2:MeOH (1/1) was added PdCl2 (0.02 g) and stirred at rt for overnight until TLC (ethyl acetate:toluene, 2/8) indicated formation of a product with consumption of the starting material. The reaction mixture was then concentrated in vacuo, and the residue was purified by flash column chromatography to afford alcohol (0.6 g, 80%) as colorless foam. To a solution of alcohol (0.270 g, 0.197 mmol) in CH2Cl2 (10 mL) at −30° C. was DAST (52 µL, 0.395 mmol) and the resulting reaction mixture was stirred at −10° C. for 8 h until TLC indicated formation of product with consumption of starting material. The reaction was quenched with aq.NaHCO3, and the filtrate was washed with aqueous NaHCO3 (2×50 mL) and a brine (50 mL) solution. The organic layer was dried over Na2SO4 and concentrated in vacuo. The residue was purified by silica gel column chromatography (0%→25% EA in hexane) to afford 6 (0.150 g, 61%) as white foam. TLC (ethyl acetate:hexane=3/7, v/v): Rf=0.45; 1H NMR (600 MHz, CDCl3): δ 7.57-7.55 (m, 4H, Ar—H), 7.35-7.21 (m, 11H, Ar—H), 7.07 (d, J=6.4 Hz, 4H, Ar—H), 6.99 (d, J=7.2 Hz, 2H, Ar—H), 6.88-6.82 (m, 3H, Ar—H), 5.30 (d, J=50.4 Hz, 1H, H-1Man), 5.30 (d, J=12.2 Hz, 1H, H-1GlcNAc), 4.88 (d, J=11.2 Hz, 1H), 4.80-4.71 (m, 3H), 4.64 (d, J=11.3 Hz, 1H), 4.49-4.46 (m, 2H), 4.43 (d, J=11.8 Hz, 2H), 4.34-4.28 (m, 3H), 4.23 (dd, J=6.1, 11.3 Hz, 1H), 4.16 (s, 1H), 4.06 (d, J=12.1 Hz, 1H), 4.02 (d, J=12.3 Hz, 1H), 3.76-3.57 (m, 5H), 3.32 (d, J=10.8 Hz, 1H), 3.02 (dd, J=4.2, 11.3 Hz, 1H), 1.97 (s, 3H, —C(O)CH3); 13C NMR (150 MHz, CDCl3): δ 170.99, 138.40, 138.28, 138.16, 137.94, 137.70, 133.94, 131.82, 128.90, 128.63, 128.57, 128.47, 128.40, 128.31, 128.27, 128.04, 127.89, 127.89, 127.76, 123.54, 106.33, 104.85, 97.45, 79.55, 78.48, 75.43, 75.23, 74.09, 73.84, 73.70, 73.16, 72.78, 72.54, 71.36, 69.18, 63.40, 55.80, 31.21, 29.98, 21.11; ESI-MS: m/z calcd for C, 57; H, 56; FNO, 12; 965.3679. found 988.3690 (M+Na)+.

Synthesis of trisaccharide building blocks 7 and 8.

Figure 29:
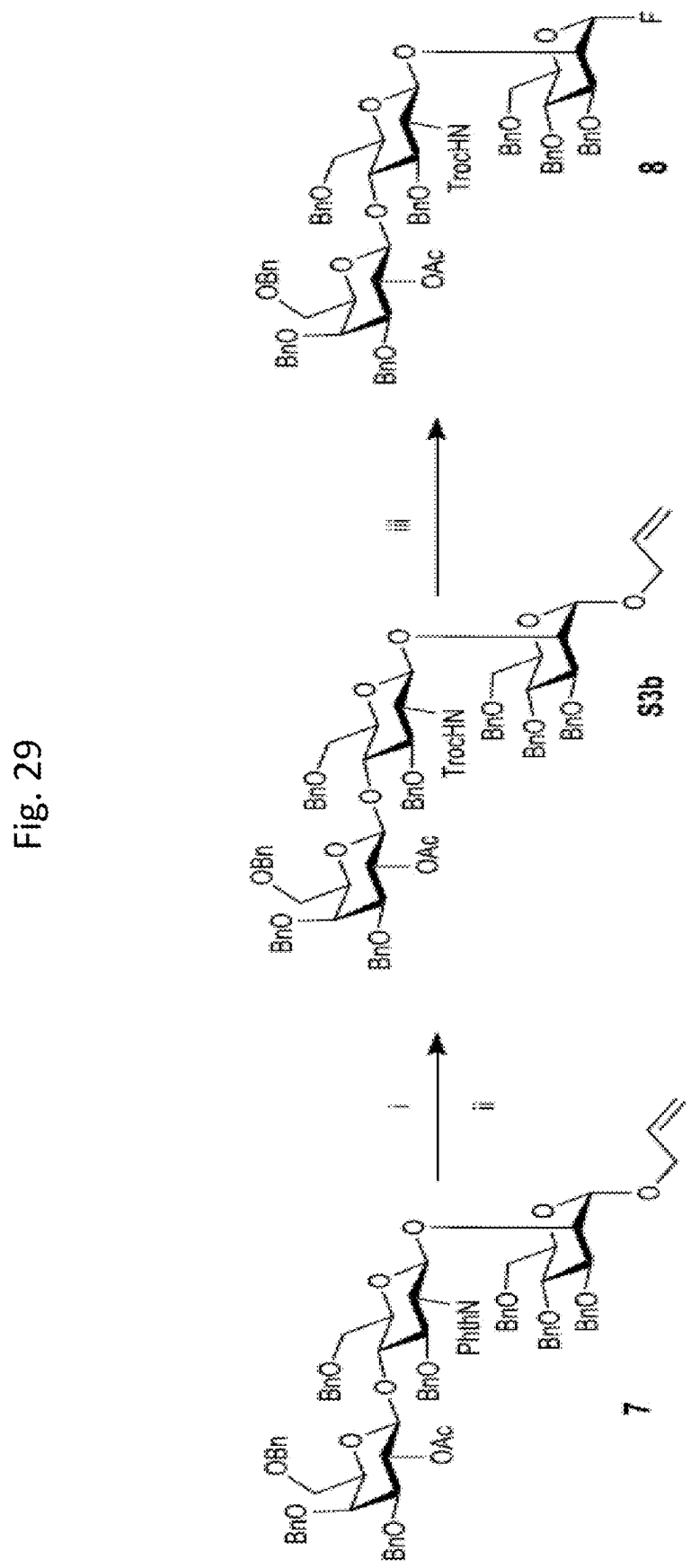
FIG. 29 shows exemplary structure embodiments and synthetic scheme embodiments of the present disclosure.
Figure 30:
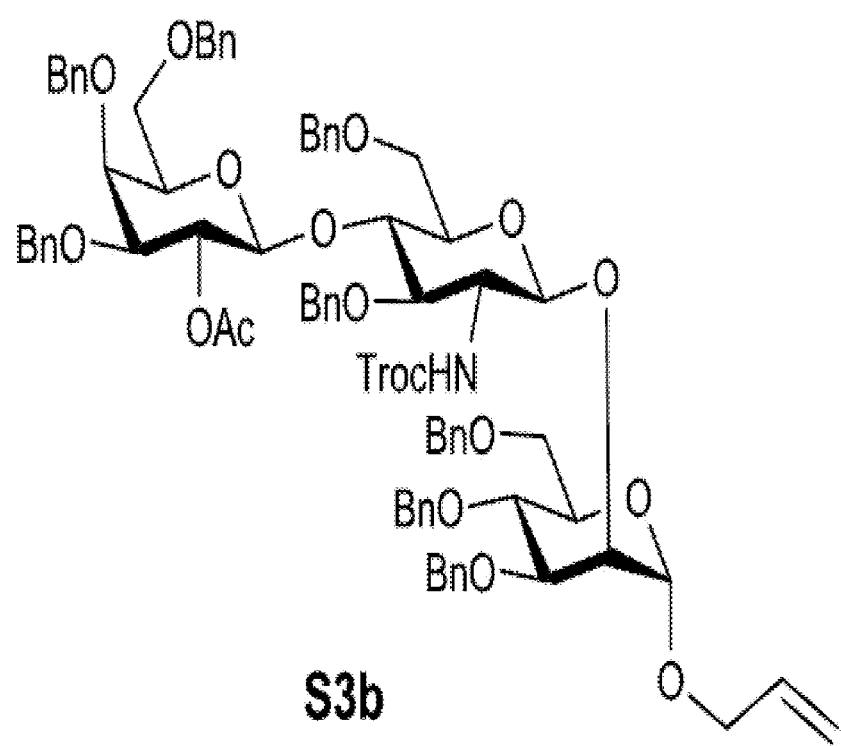
FIG. 30 shows exemplary structure embodiments and synthetic scheme embodiments of the present disclosure.
Figure 31:
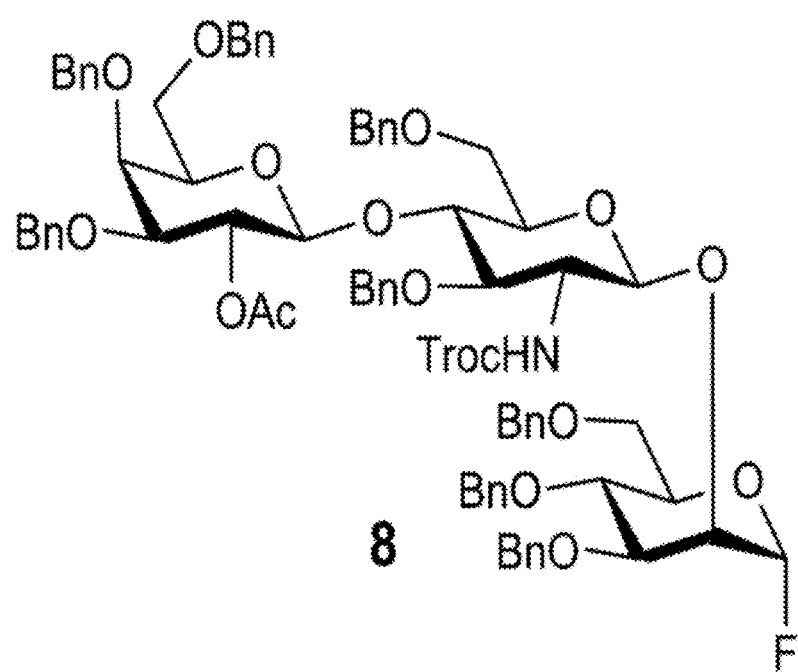
FIG. 31 shows exemplary structure embodiments and synthetic scheme embodiments of the present disclosure.

Building block 7 (FIG. 2) was obtained according to previous report3. The N-pthallamide protection at Glucosamine residues was modified to NH-Troc to prepare building block 8 (Scheme S3 as shown in FIG. 29).

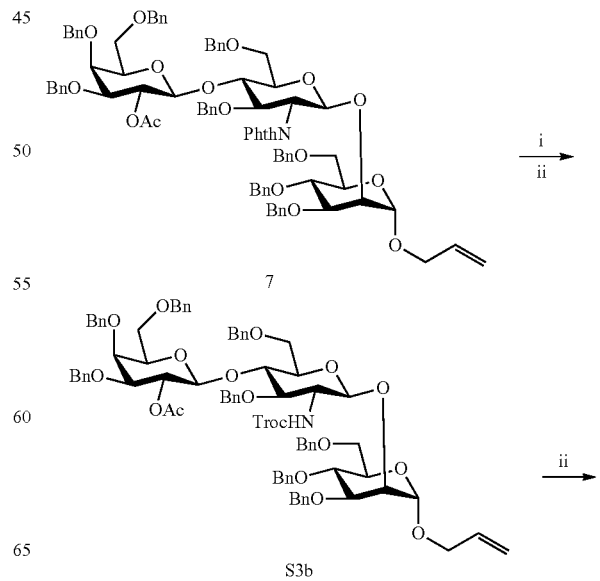

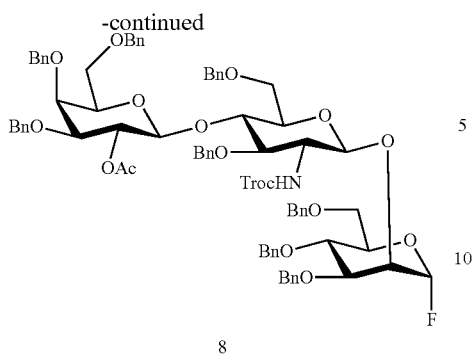

8

Scheme S3 as shown in FIG. 29 depicts the preparation of compound 8. i, (1) EDA, n-BuOH, 90° C., (2) Troc-Cl, NaHCO3, CH2Cl2, ii, Ac2O, pyridine, RT, overnight, 72% over 3 steps; iii, (1) PdCl2, MeOH: CH2Cl2, (2) DAST, CH2Cl2, −30° C., 66% over 2 steps.

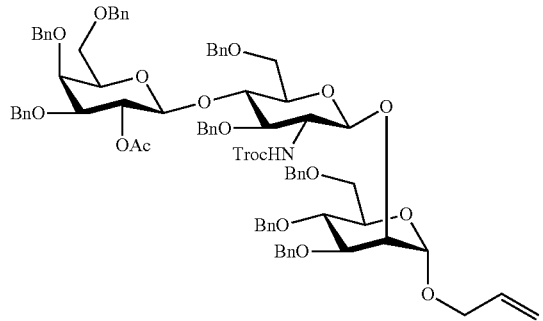

S3b

Allyl-O-2-O-acetyl-3,4,6-O-tri-benzyl-β-D-galactopyranosyl-(1→4)-O-3,6-O-di-benzyl-2-deoxy-2-(2,2,2-trichloroethoxy)carbonylamino-β-D-glucopyranosyl-(1→2)-O-3,4,6-tri-O-benzyl-α-D-mannopyranoside (S3b): A mixture of compound S3a (1 g, 0.693 mmole) and 10 mL of ethylene diamine:n-BuOH (1:4) was stirred at 90° C. overnight. Volatiles were evaporated, and the crude product was dried using high vacuum. It was then dissolved in CH2Cl2 (20 mL), NaHCO3 (0.376 g, 6.93 mmol) and 2,2,2-trichloro ethyl chloroformate (0.665 mL, 6.93 mmol) were added at 0° C., allowed it to warm to rt and stirred for overnight. TLC (ethyl acetate:toluene, 2/8) indicated formation of product with consumption of starting material. The reaction mixture was diluted with CH2Cl2 (100 mL), washed with water (2×50 mL) and brine (50 mL) solution. The organic layer was dried over Na2SO4 and concentrated in vacuo. The residue was purified by silica gel column chromatography (0%→15% EA in toluene). The product was then acetylated using 10 mL of pyridine/acetic anhydride (6:4) until TLC indicated (ethyl acetate:toluene, 2/8) complete consumption of starting material. The reaction mixture was then concentrated in vacuo and purified by silica gel column chromatography to afford S3b (0.760 g, 72%) as a white foam. TLC (ethyl acetate:toluene=2/8, v/v): Rf=0.64; 1H NMR (600 MHz, CDCl3): δ 7.34-7.13 (m, 40H, -Ph), 5.86-5.77 (m, 1H, allyl —CH), 5.30-5.28 (t, J=8.2 Hz, 1H, H2 gal), 5.25 (bd, 1H, —NHTroc), 5.16 (d, J=17.6 Hz, 1H, Troc), 5.10 (d, J=10.2 Hz, 1H), 4.90 (t, 3H), 4.82-4.76 (m, 3H), 4.74 (s, 1H), 4.65-4.61 (dd, J=8.4 & 2.8 Hz, 3H), 4.55-4.41 (m, 8H), 4.30 (d, J=12.3 Hz, 2H), 4.20 (d, J=12.2 Hz, 2H), 4.10-4.01 (m, 3H), 3.90-3.84 (m, 5H), 3.76-3.61 (m, 5H), 3.55-3.40 (m, 3H), 3.35-3.30 (m, 3H), 3.13 (d, J=7.2 Hz, 1H), 1.92 (s, 3H, —C(O)CH3); 13C NMR (150 MHz, CDCl3): δ 170.23, 154.11, 139.17, 138.98, 138.75, 138.25, 138.20, 134.04, 127.41, 100.7, 97.5, 96.80, 80.55, 78.53, 75.36, 72.87, 73.55, 72.78, 72.49, 72.10, 71.96, 69.98, 68.90, 68.65, 57.64, 41.51, 21.30. ESI-MS: m/z calcd for C, 82; H, 88; C, 13; N, 1; O, 18; 1458.4960 found 1504.4956 (M+Na)+.

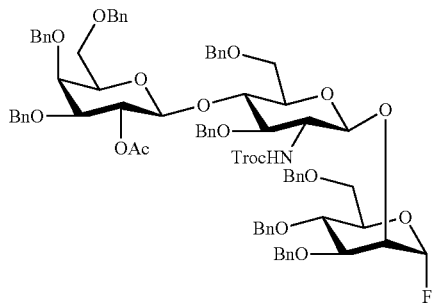

8

2-O-acetyl-3,4,6-O-tri-benzyl-β-D-galactopyranosyl-(1→4)-O-3,6-O-di-benzyl-2-deoxy-2-(2,2,2-trichloroethoxy)carbonylamino-β-D-glucopyranosyl-(1→2)-O-3,4,6-tri-O-benzyl-α-D-mannopyranosyl fluoride (8): PdCl2 (0.030 g) was added to a solution of S3b (1.3 g, 0.942 mmol) in 10 mL of CH2Cl2:MeOH (1:1). The reaction mixture was stirred at room temperature for 2 h until TLC (ethyl acetate: toluene, 2/8) indicated formation of product with consumption of the starting material. The reaction mixture was then filtered through Celite and concentrated in vacuo. The residue was purified by flash column chromatography to afford 1-OH compound (0.980 g) as white color foam. The residue (0.850 g, 0.608 mmol) was dissolved in CH2Cl2 (10 mL) at −30° C., then DAST (160 μL, 1.21 mmol) was added slowly. The resulting reaction mixture was stirred for 1 h. When TLC (ethyl acetate:toluene, 2/8) indicated formation of product with consumption of starting material, the reaction was quenched with aq. NaHCO3. The filtrate was washed with aqueous NaHCO3 (2×50 mL) and brine (50 mL) solution. The organic layer was dried over Na2SO4 and concentrated in vacuo. The residue was purified by silica gel column chromatography (0%→15% EA in toluene) to afford 8 (0.700 g, 66% over 2 steps) as white foam. TLC (ethyl acetate:toluene=2/8, v/v): Rf=0.64; 1H NMR (600 MHz, CDCl3): δ 7.35-7.10 (m, 40H), 4.57 (d, J=51.4 Hz, 1H), 5.33 (t, J=10.2 Hz, 1H), 5.22 (d, J=8.2 Hz, 1H), 4.99-4.91 (m, 3H), 4.82 (d, J=7.8 Hz, 1H), 4.75 (t, J=10.3 Hz, 1H), 4.64-4.44 (m, 12H), 4.38 (dd, J=3.4 & 10.2 Hz, 2H), 4.26 (s, 2H), 4.06-4.33 (m, 5H), 3.76-3.64 (m, 4H), 3.54-3.46 (m, 2H), 3.40-3.34 (m, 3H), 3.12 (d, J=8.4 Hz, 1H), 1.65 (S, 3H); 13C NMR (150 MHz, CDCl3): δ 169.5, 154.0, 139.0, 138.8, 138.7, 138.5, 138.4, 138.3, 138.1, 129.4, 128.7, 128.6, 128.4, 128.2, 128.0, 127.9, 127.7, 127.5, 127.4, 127.2, 127.1, 125.5, 107.6, 105.4, 100.7, 98.7, 95.8, 80.5, 77.4, 74.3, 73.6, 73.3, 73.1, 72.3, 72.1, 72.0, 71.9, 68.9, 68.7, 68.3, 57.4, 41.4, 21.7, 21.2; ESI-MS: m/z calcd for C, 79; H, 83; C, 13; FN, 1; O, 17; 1443.4602 found 1466.4608 (M+Na)+.

Synthesis of complex type D1 Arm Tetrasaccharide 9.

Preparation of sialylated D1 arm was achieved through coupling of two main building units S4c and S4d. Use of sialyl phosphate donor S4a for the α-2,6 glycosylation of Gal S4b resulted in complete a-selectivity 10. The N-Phth protection at glucosamine of S2c was modified NHTroc, while doing so, the 4-OAc group was removed to afford the desired S4d. At last the coupling of S4c and S4d afforded the desired tetrasaccharide, which further underwent anomeric modification to get donor 9.

Figure 32A:
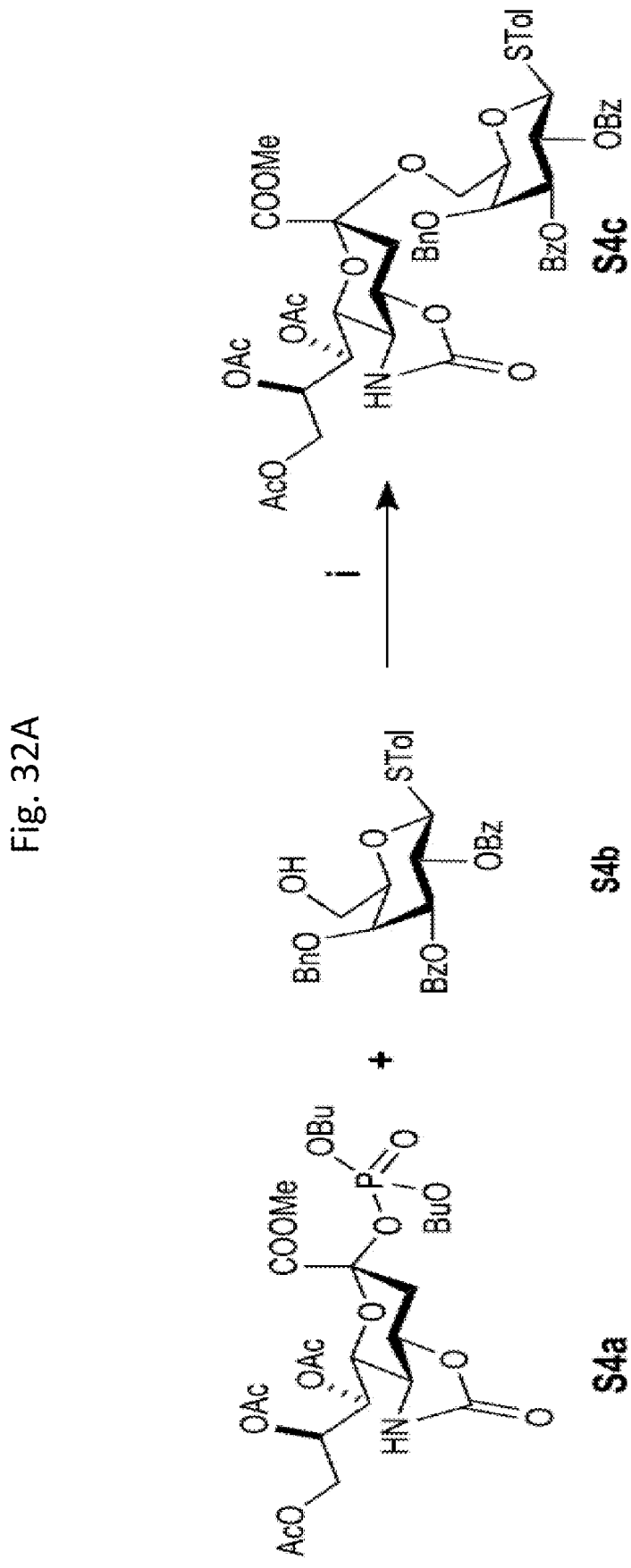
FIGS. 32A, 32B, and 32C.
Figure 32B:
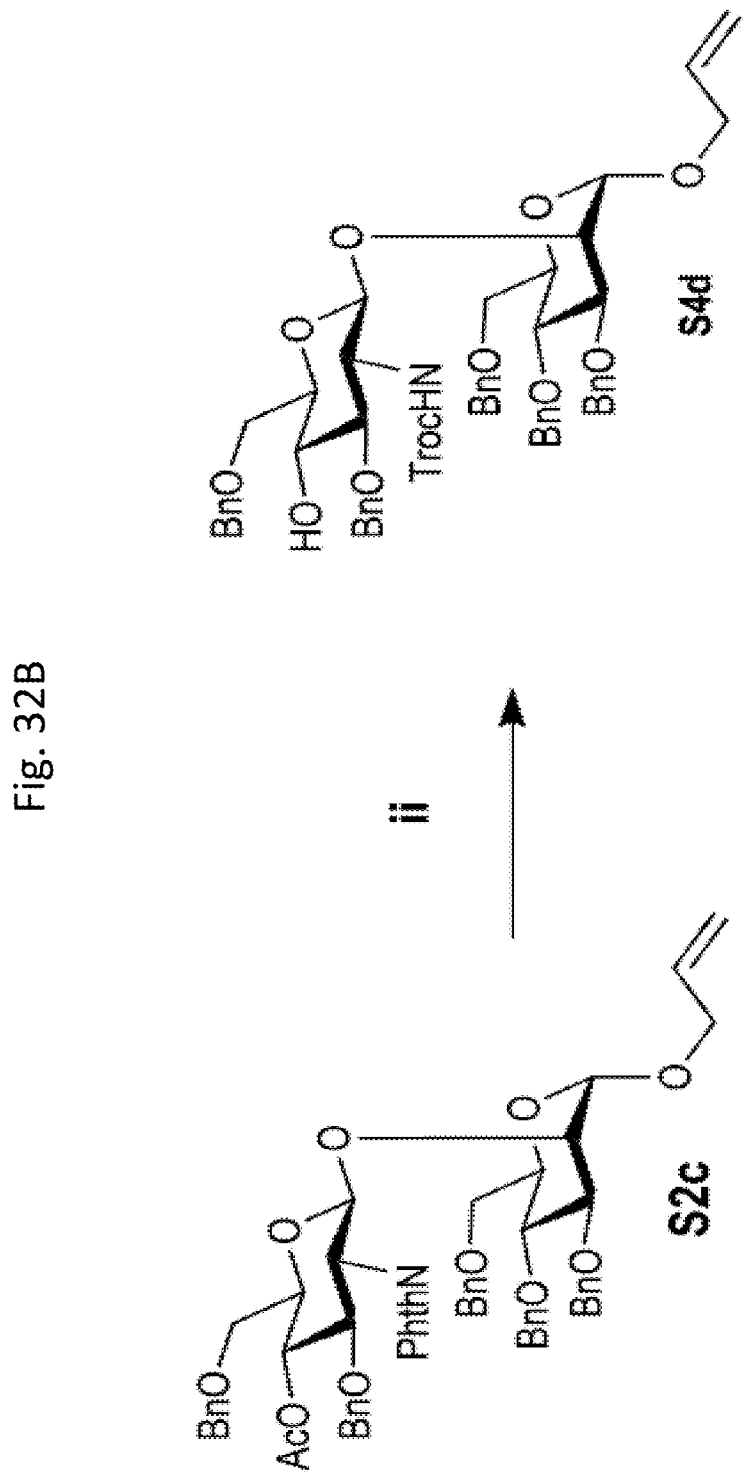
Figure 32C:
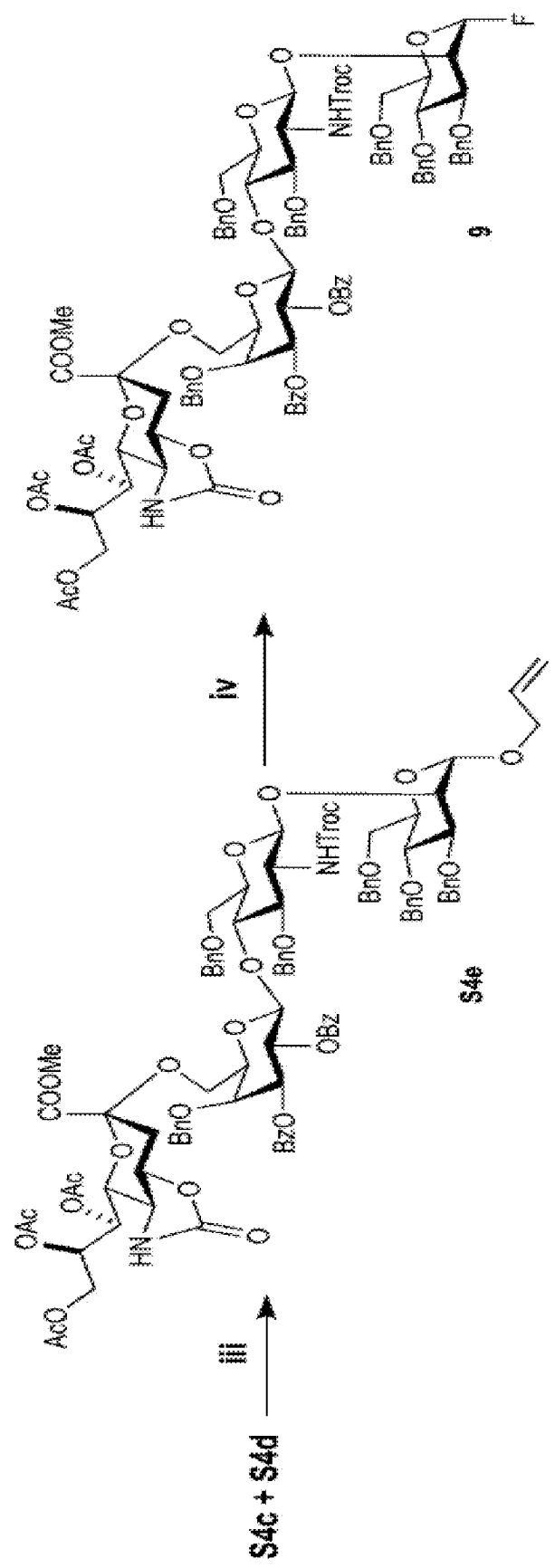
Figure 33:
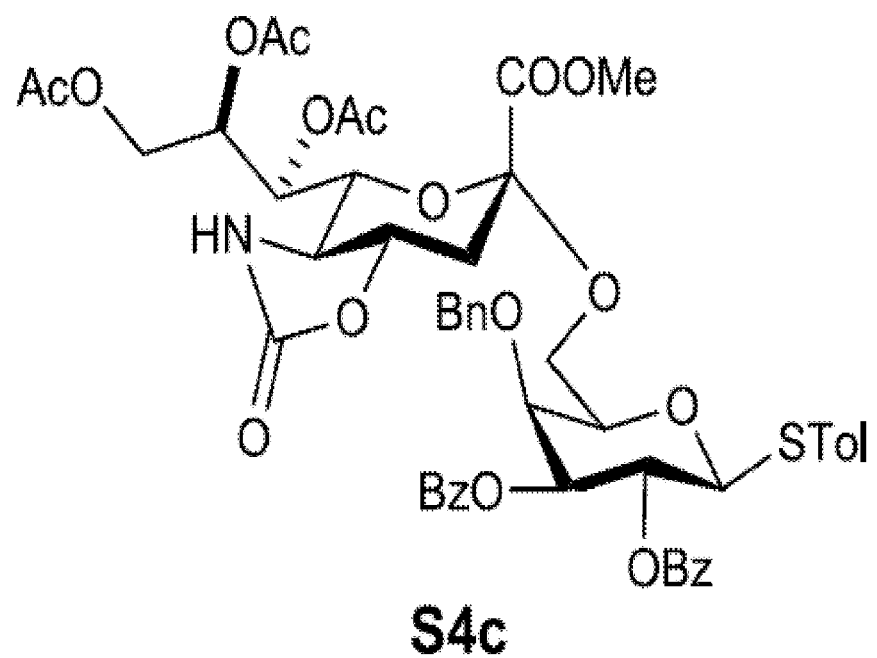
FIG. 33 shows exemplary structure embodiments and synthetic scheme embodiments of the present disclosure.
Figure 34:
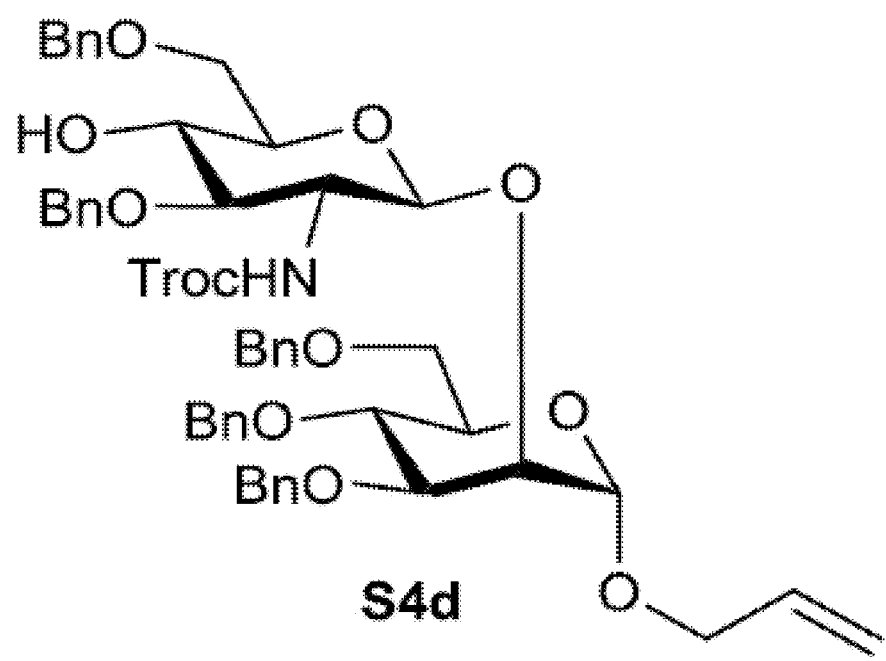
FIG. 34 shows exemplary structure embodiments and synthetic scheme embodiments of the present disclosure.
Figure 35:
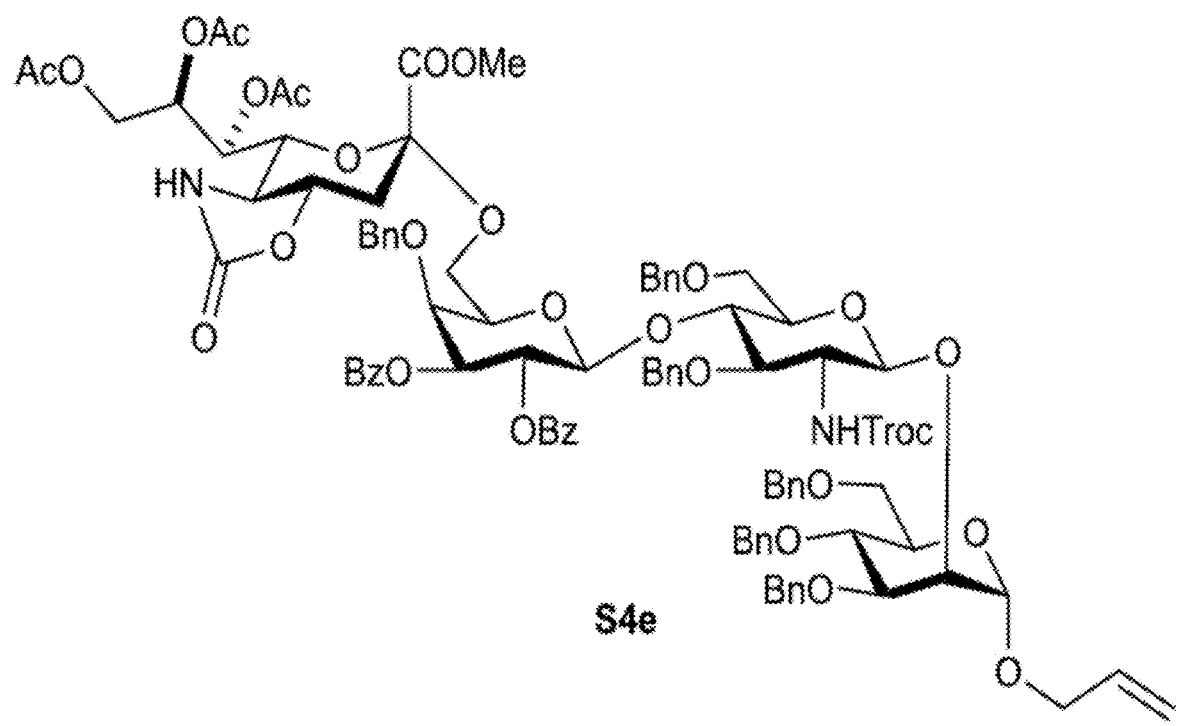
FIG. 35 shows exemplary structure embodiments and synthetic scheme embodiments of the present disclosure.
Figure 36:
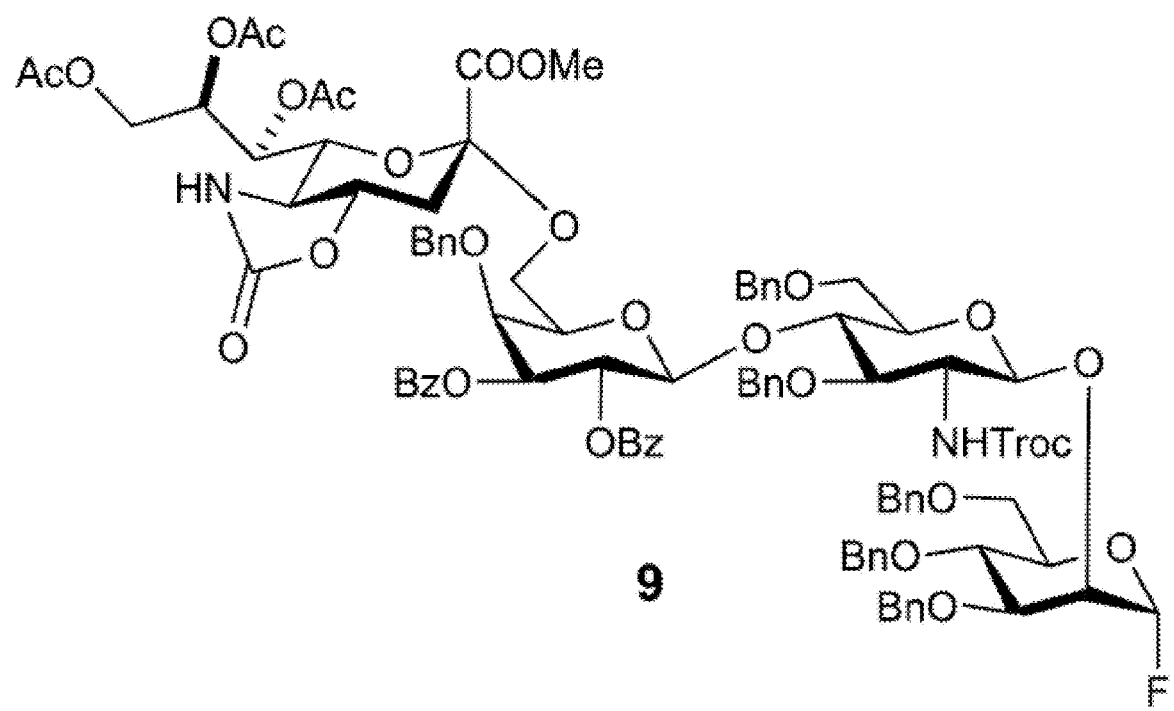
FIG. 36 shows exemplary structure embodiments and synthetic scheme embodiments of the present disclosure.

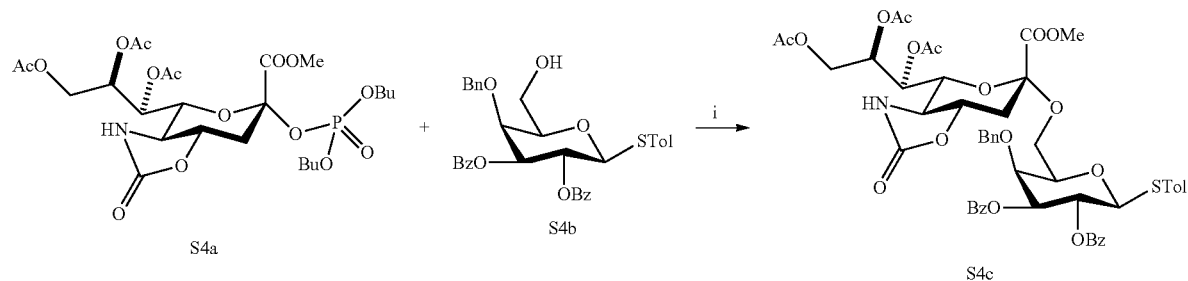
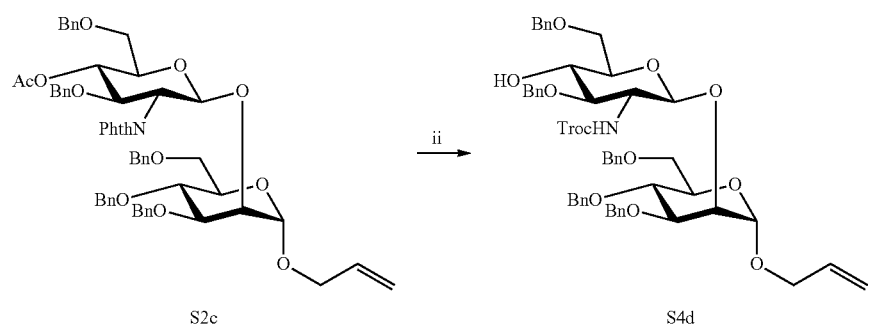
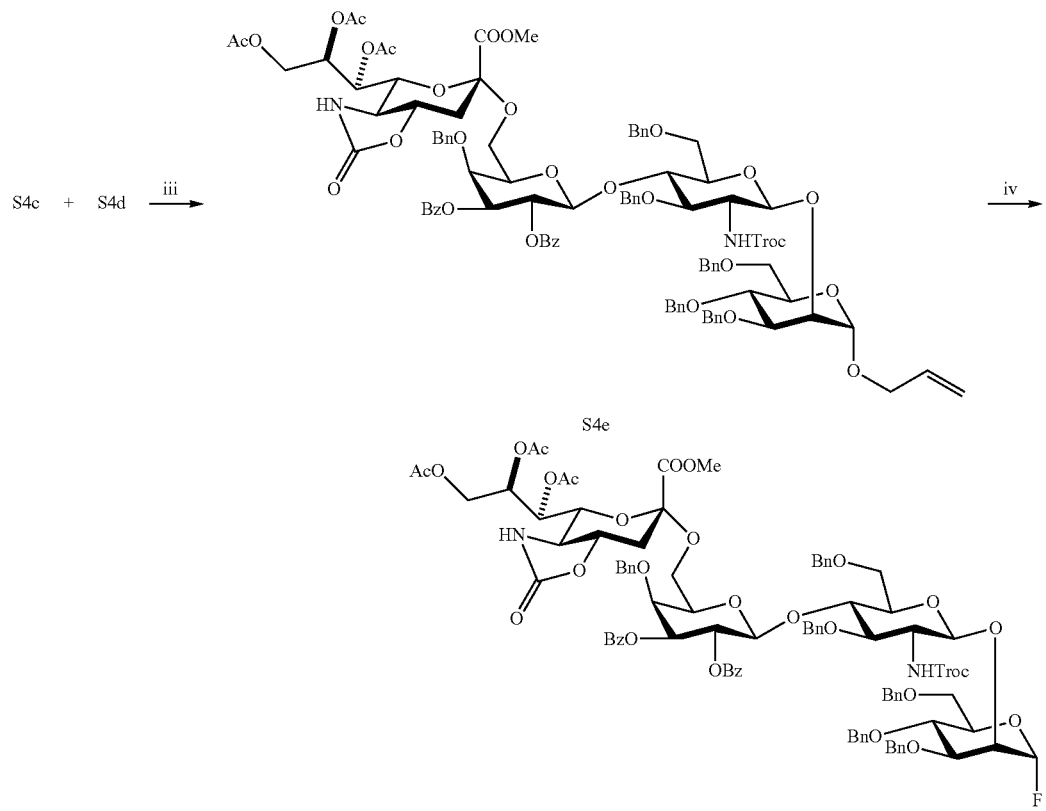
Scheme S4 as shown in FIGS. 32A, 32B and 32C depicts the preparation of compound 9. i, TMSOTf, CH2Cl2, −50° C., 64%; ii, (1) EDA, n-BuOH, 90° C., (2) Troc-Cl, NaHCO3, CH2Cl2, 78% over 2 steps; iii, NIS, TfOH, CH2Cl2, −50° C., 65%; iv, (1) PdCl2, MeOH:CH2Cl2, (2) DAST, CH2Cl2, −30° C., 55% over 2 steps.

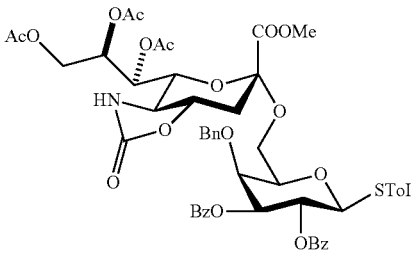

S4c

Methyl-5-acetamido-7,8,9-tri-O-acetyl-3,5-dideoxy-D-glycero-α-D-galacto-non-2-ulopyranosylonate-(2→6)-p-tolyl-4-O-benzyl-2,3-di-O-benzoyl-1-thio-β-D-galactopyranoside (S4c): A mixture of donor S4a (0.113 g, 0.178 mmol), acceptor S4b (0.220 g, 0.119 mmol) and activated 4 Å molecular sieves in dry CH2Cl2 (10 mL) was stirred at rt for 1 h. The reaction was cooled to −50° C., trimethylsilyl triflate (12 µL, 0.06 mmol) was added slowly and the resulting reaction mixture was stirred for 2 h. The reaction was quenched by adding Et3N, diluted with CH2Cl2, filtered through Celite, extracted with saturated NaHCO3, dried over sodium sulfate and concentrated in vacuo. The residue was purified by flash column chromatography (0%→25% EA in hexane) to afford S4c (0.190 g, 64%) as colorless foam. TLC: (ethyl acetate:hexane=3/7, v/v): Rf=0.46; 1H NMR (600 MHz, CDCl3): δ 7.93 (d, J=7.8 Hz, 2H), 7.89 (d, J=8.4 Hz, 2H), 7.50-7.45 (m, 2H), 7.42-7.30 (m, 6H), 7.24-7.13 (m, 5H), 7.04 (d, J=8.2 Hz, 2H), 5.80 (t, J=10.3 Hz, 1H), 5.47 (d, J=8.9 Hz, 1H), 5.37 (s, 3H), 5.32 (dd, J=4.2 & 7.8 Hz, 1H), 5.12 (dd, J=4.1 & 7.2 Hz, 1H), 4.90 (d, J=12.2 Hz, 1H), 4.65 (d, J=12.1 Hz, 1H), 4.20 (dd, J=3.2 & 7.8 Hz, 1H), 4.18 (d, J=6.8 Hz, 1H), 3.94-3.91 (m, 3H), 3.74-3.72 (m, 3H), 3.71 (s, 3H), 3.65 (dd, J=3.2 & 7.8 Hz, 1H), 3.06 (t, J=10.2 Hz, 2H), 2.87 (dd, J=3.6 & 8.6 Hz, 1H), 2.33 (s, 3H), 2.17 (s, 3H), 2.15 (t, J=7.8 Hz, 1H), 2.13 (s, 3H); 13C NMR (150 MHz, CDCl3): δ 171.9, 170.8, 169.8, 168.2, 166.8, 165.2, 159.2, 138.1, 133.7, 133.3, 130.0, 129.8, 129.4, 129.3, 129.2, 128.7, 128.6, 128.5, 128.4, 127.8, 127.7, 125.5, 100, 5, 86.8, 76.8, 76.1, 74.7, 73.8, 68.9, 68.5, 68.3, 67.2, 63.7, 62.0, 58.1, 53.3, 37.7, 25.88, 21.7, 21.5, 21.3, 21.0, 20.9; ESI-MS: m/z calcd for C, 51; H, 53; NO, 18; S; 999.2876 found 1022.2882 (M+Na)+.

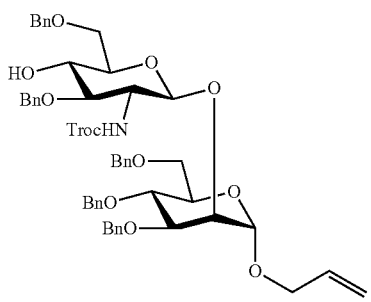

S4d

Allyl-O-3,6-O-di-benzyl-2-deoxy-2-(2,2,2-trichloroethoxy)carbonylamino-β-D-glucopyranosyl-(1→2)-O-3,4,6-tri-O-benzyl-α-D-mannopyranoside (S4d): A mixture of compound S2c (2 g, 1.99 mmole) and 20 mL of ethylene diamine:n-BuOH (1:4) was stirred at 90° C. overnight. Volatiles were evaporated, and the crude product was dried using high vacuum. It was then dissolved in CH2Cl2 (20 mL), NaHCO3 (1.05 g, 19.9 mmol) and 2,2,2-trichloro ethyl chloroformate (1.9 mL, 19.9 mmol) were added at 0° C., allowed it to warm to rt and stirred for overnight until TLC (ethyl acetate:toluene, 1.5/8.5) indicated formation of product with consumption of starting material. The reaction mixture was diluted with CH2Cl2 (100 mL), washed with water (2×50 mL) and brine (50 mL) solution. The organic layer was dried over Na2SO4 and concentrated in vacuo. The residue was purified by silica gel column chromatography (0%→10% EA in toluene) to afford S4d (1.5 g, 78%) as a white foam. TLC (ethyl acetate:toluene=1.5/8.5, v/v): Rf=0.44; 1H NMR (600 MHz, CDCl3): δ 7.30-7.15 (m, 25H), 5.87-7.78 (m, 1H), 5.33 (d, J=5.2 Hz, 1H), 5.21 (d, J=3.2 Hz, 1H), 5.14 (d, J=7.2 Hz, 1H), 4.94 (d, J=5.8 Hz, 1H), 4.80 (d, J=8.5 Hz, 1H), 4.73-4.44 (m, 10H), 4.12-4.06 (m, 3H), 3.97-3.86 (m, 3H), 3.78-3.49 (m, 7H); 13C NMR (150 MHz, CDCl3): δ 153.97, 138.45, 138.37, 138.28, 137.98, 137.45, 133.63, 128.94, 128.43, 128.40, 128.26, 128.16, 127.97, 127.91, 127.78, 127.65, 127.53, 127.41, 125.20, 117.23, 97.93, 96.88, 95.50, 79.33, 79.08, 75.08, 74.47, 74.37, 73.53, 73.19, 73.00, 71.98, 71.65, 70.83, 69.16, 67.91, 57.41, 44.53; ESI-MS: m/z calcd for C, 53; H, 58; C, 13; NO, 12; 1005.3025 found 1006.3089 (M+H)+.

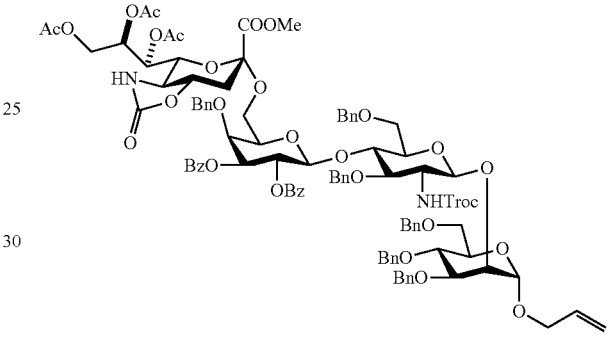

S4e

Allyl-[Methyl-5-acetamido-7,8,9-tri-O-acetyl-3,5-dideoxy-D-glycero-α-D-galacto-non-2-ulopyranosylonate]-(2→6)-4-O-benzoyl-2,3-di-O-benzoyl-1-β-D-galactopyranosyl-(1→4)-O-3,6-O-di-benzyl-2-deoxy-2-(2,2,2-trichloroethoxy)carbonylamino-β-D-glucopyranosyl-(1→2)-O-3,4,6-tri-O-benzyl-α-D-mannopyranoside (S4e): Activated 4 Å molecular sieves (1 g) were added to a solution of acceptor S4d (0.208 g, 0.169 mmol) and donor S4c (0.310 g, 0.199 mmol) in anhydrous CH2Cl2 (10 mL). The mixture was stirred for 1 h at room temperature. The reaction mixture was cooled to −50° C., NIS (0.076 g, 0.338 mmol) and TfOH (3.7 µL, 0.042 mmol) were added slowly. The resulting reaction mixture was stirred for 2 h. When TLC (ethyl acetate:toluene, 1.5/8.5) indicated formation of product with consumption of starting material, the reaction was quenched by adding Et3N and filtered through Celite. The filtrate was washed with aqueous NaHCO3 (2×50 mL), aqueous Na2S2O3 (2×50 mL), and brine (50 mL) solution. The organic layer was dried over Na2SO4 and concentrated in vacuo. The residue was purified by flash column chromatography (0%→10% EA in toluene) to afford S4e (390 g, 65%) as clear foam. TLC (ethyl acetate:toluene=1.5/8.5, v/v): Rf=0.51; 1H NMR (600 MHz, CDCl3): δ 7.91-7.85 (m, 4H, Ph), 7.50-7.46 (n, 1H, Ph), 7.35-7.19 (m, 35H), 5.82-5.76 (m, 2H), 5.39-5.36 (m, 3H), 5.24 (d, J=6.4 Hz, 1H), 5.22 (d, J=7.2 Hz, 1H), 5.19 (d, J=3.4 Hz, 1H), 5.15 (d, J=3.4 Hz, 1H), 5.11-5.08 (dd, J=6.3 & 3.1 Hz, 2H), 4.96 (d, J=12.1 Hz, 2H), 4.83 (d, J=12.1 Hz, 2H), 4.73-4.57 (m, 10H), 4.47-4.42 (m, 6H), 4.25-4.15 (m, 8H), 4.08-3.93 (m, 10H), 3.91 (s, 3H,), 3.39 (d, J=7.8 Hz, 1H), 3.21 (bd, 1H), 2.93 (t, J=7.8 Hz, 1H), 2.78 (dd, J=3.6 & 7.8 Hz, 1H), 2.11 (s, 3H), 2.01 (s, 3H), 1.66 (s, 3H); 13C NMR (150 MHz, CDCl3): δ 171.83, 170.84, 169.91, 168.03, 166.15, 165.43, 159.57, 154.17, 139.14, 138.85, 138.36, 134.08, 133.78, 132.66, 13.54, 129.67, 128.78, 128.43, 128.23, 127.78, 127.67, 127.56, 127.43, 127.23, 127.10, 117.53, 100.67, 100.32, 98.94, 97.18, 75.90, 78.31, 75.32, 74.95, 7.81, 74.43, 73.99, 73.58, 73.45, 73.33, 73.29, 73.23, 73.12, 69.90, 69.56, 68.66, 67.56, 58.70, 53.43, 21.28, 21.07, 20.98; ESI-MS: m/z calcd for C, 97; H, 103; C, 13; N, 2; O, 13; 1982.5562 found 1905.5558 (M+Na)+.

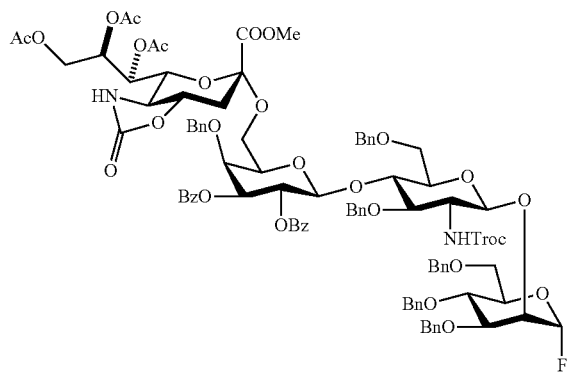

Methyl-5-acetamido-7,8,9-tri-O-acetyl-3,5-dideoxy-D-glycero-α-D-galacto-non-2-ulopyranosylonate-(2→6)-4-O-benzyl-2,3-di-O-benzoyl-1-β-D-galactopyranosyl-(1→4)-O-3,6-O-di-benzyl-2-deoxy-2-(2,2,2-trichloroethoxy) carbonylamino-β-D-glucopyranosyl-(1→2)-O-3,4,6-tri-O-benzyl-α-D-mannopyranosyl fluoride (9): PdCl2 (0.050 g) was added to a solution of S4e (2.7 g, 1.42 mmol) in 20 mL of CH2Cl2:MeOH (1:1). The reaction mixture was stirred at room temperature for 5 h until TLC (ethyl acetate:toluene, 2/8) indicated formation of product with consumption of the starting material. The reaction mixture was then filtered through Celite and concentrated in vacuo. The residue was purified by flash column chromatography (0%→15% EA in toluene) to afford 1-OH compound (2.0 g) as white color foam. The residue (2 g, 1.07 mmol) was dissolved in CH2Cl2 (10 mL) at −30° C., then DAST (284 μL, 2.14 mmol) was added slowly. The resulting reaction mixture was stirred for 1 h. When TLC (ethyl acetate:toluene, 2/8) indicated formation of product with consumption of starting material, the reaction was quenched with aq. NaHCO3. The filtrate was washed with aqueous NaHCO3 (2×50 mL) and brine (50 mL) solution. The organic layer was dried over Na2SO4 and concentrated in vacuo. The residue was purified by silica gel column chromatography (0%→15% EA in toluene) to afford 9 (1.45 g, 55% over 2 steps) as white foam. TLC (ethyl acetate:toluene=2/8, v/v): Rf=0.64; 1H NMR (600 MHz, CDCl3): δ 7.96 (m, 4H), 7.55 (m, 2H), 7.40-7.17 (m, 34H), 5.86 (t, J=10.2 Hz, 1H), 5.50 (d, J=52 Hz, 1H), 5.44-5.40 (m, 2H), 5.29 (dd, J=1.6 & 7.8 Hz, 1H), 5.15 (dd, J=1.7 & 7.2 Hz, 1H), 5.05-4.99 (m, 2H), 4.84-4.44 (m, 10H), 4.33-4.20 (m, 3H), 4.27-4.20 (m, 4H), 4.03-3.90 (m, 3H), 3.72-3.65 (s, 3H), 3.70-3.06 (m, 12H), 3.46-3.30 (m, 1H), 3.00 (t, J=10.2 Hz, 1H), 2.86 (dd, J=3.2 & 12.3 Hz, 1H), 2.19 (s, 3H), 2.16 (s, 3H), 2.12 (t, J=8.4 Hz, 1H), 2.0 (s, 3H); 13C NMR (150 MHz, CDCl3): δ 170.8, 170.0, 168.0, 166.1, 165.2, 159.5, 154.1, 138.9, 138.4, 138.2, 138.1, 133.7, 133.6, 133.4, 130.0, 129.9, 129.6, 129.3, 128.8, 128.6, 128.5, 128.4, 128.3, 128.1, 127.9, 127.5, 127.2, 125.5, 107.7, 100.7, 100.1, 99.2, 95.8, 78.1, 77.1, 76.6, 75.3, 74.9, 74.6, 74.4, 74.1, 73.9, 73.7, 73.5, 73.3, 73.0, 72.6, 72.5, 69.2, 69.0, 67.3, 63.2, 61.8, 58.1, 57.3, 53.4, 37.3, 21.7, 21.3, 21.0, 20.9; ESI-MS: m/z calcd for C, 94; H, 98; C, 13; FN, 2; O, 29; 1844.5204 found 1867.5192 (M+Na)+.

Synthesis of uilding blocks 10 and 11.

Pentasaccharides S5a and S5b were obtained according to our previous report3, in which the functional group was further modified from N-pthallamide to N-Troc. Finally, the anomeric p-methoxy phenyl group was removed and resulting —OH was changed to fluoride in presence of DAST.

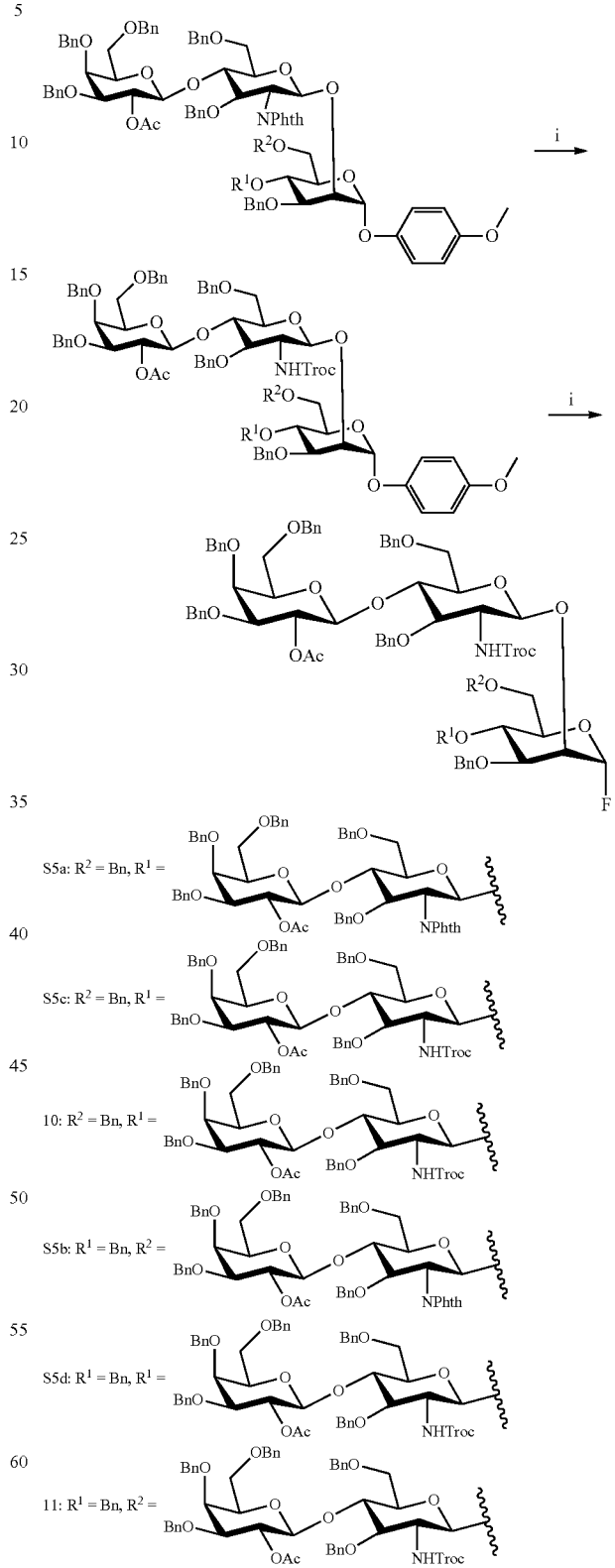

Figure 37A:
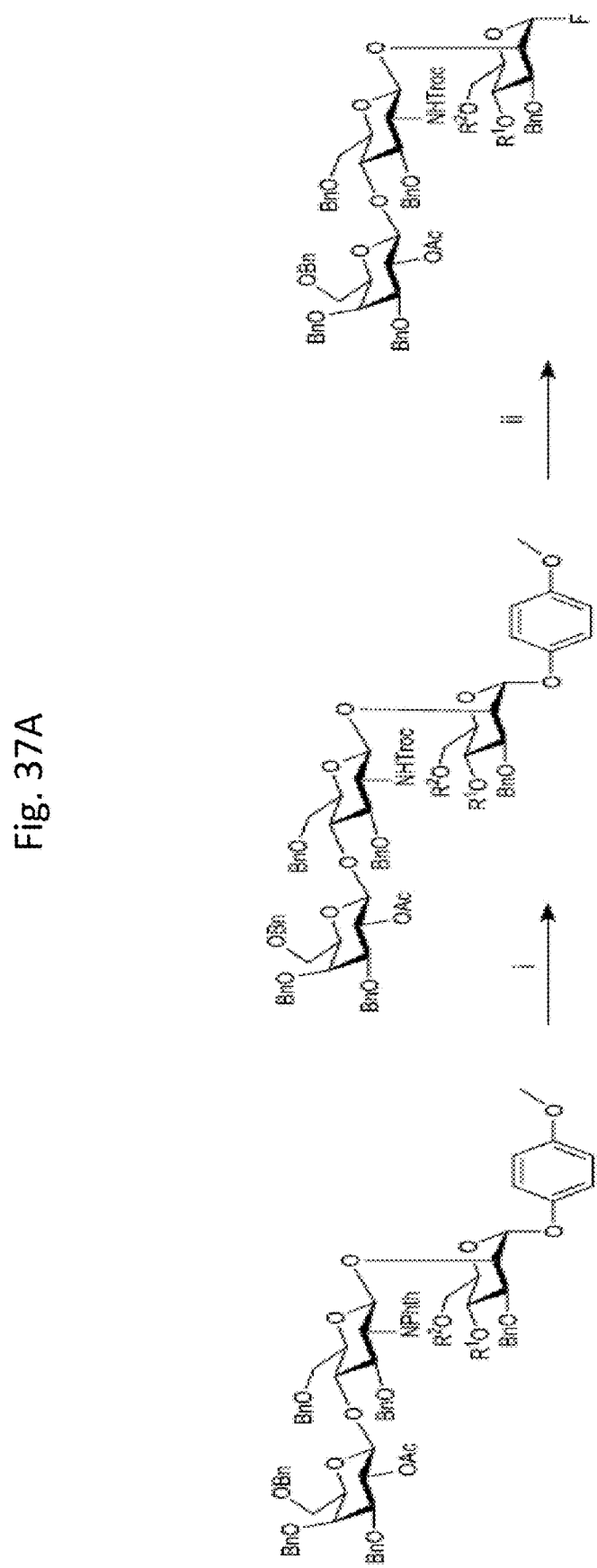
Figure 37C:
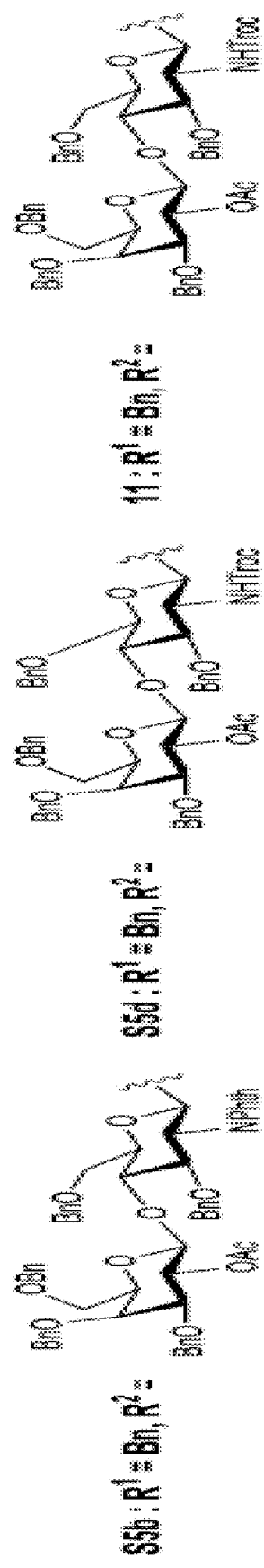
Figure 38:
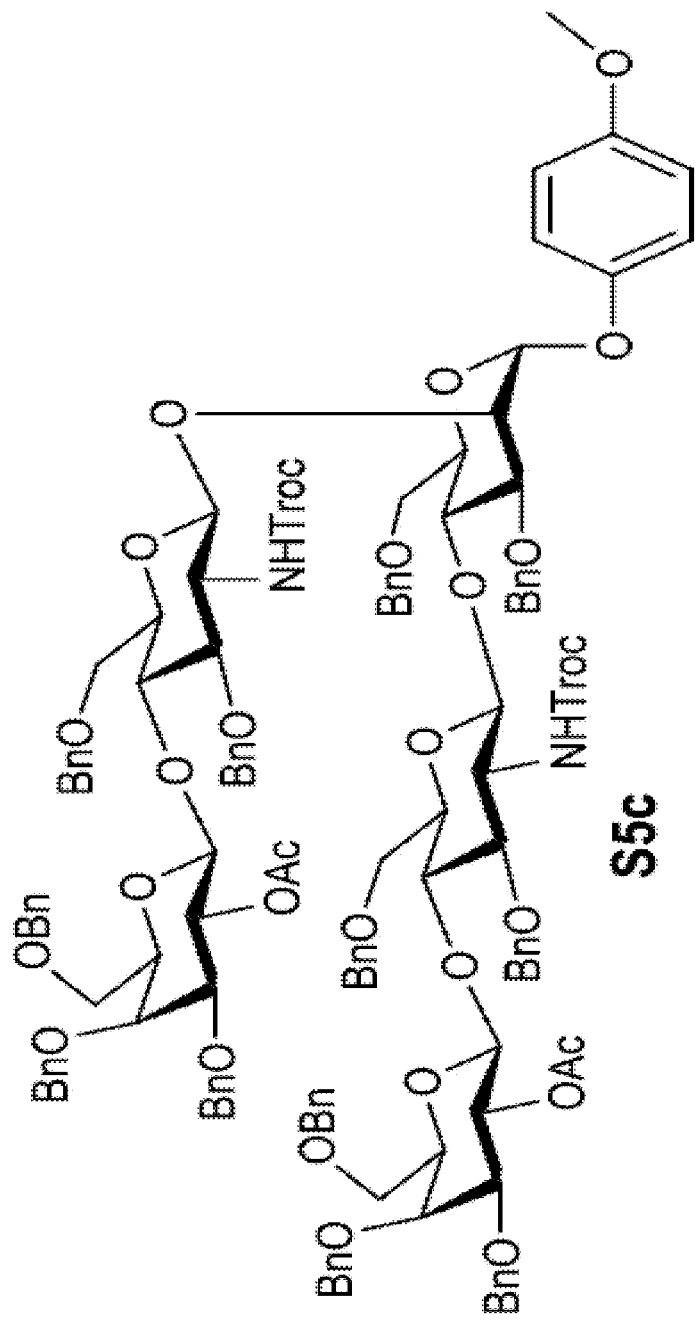
FIG. 38 shows exemplary structure embodiments and synthetic scheme embodiments of the present disclosure.
Figure 39:
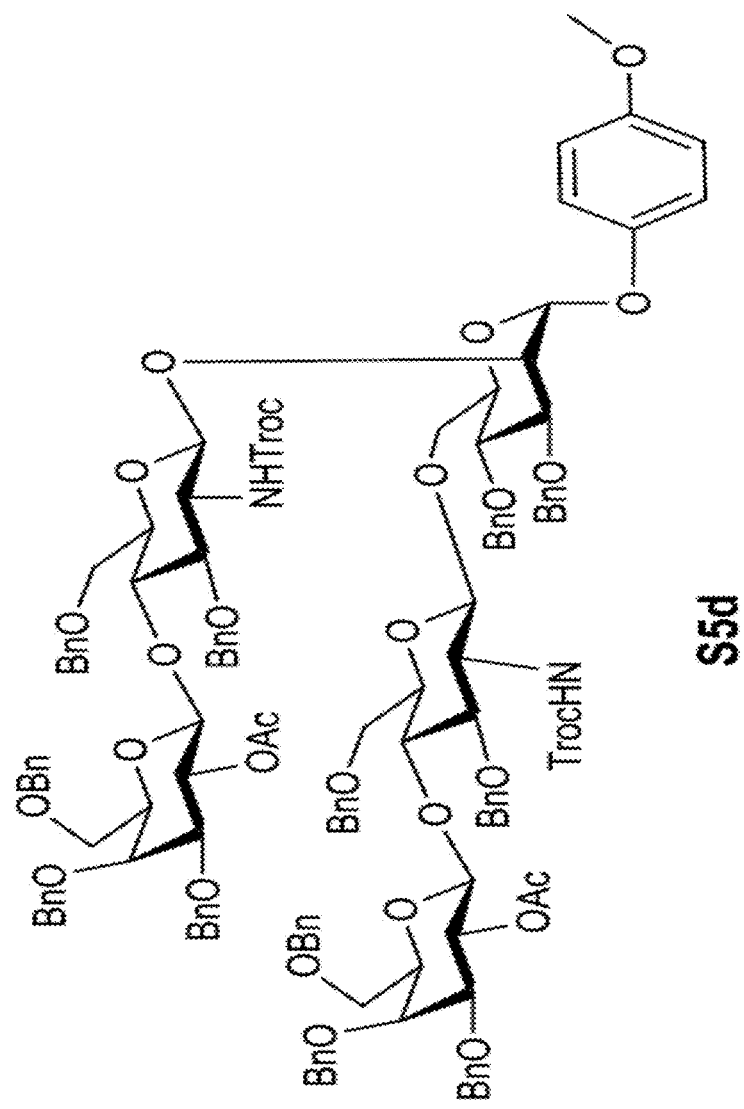
FIG. 39 shows exemplary structure embodiments and synthetic scheme embodiments of the present disclosure.
Figure 40:
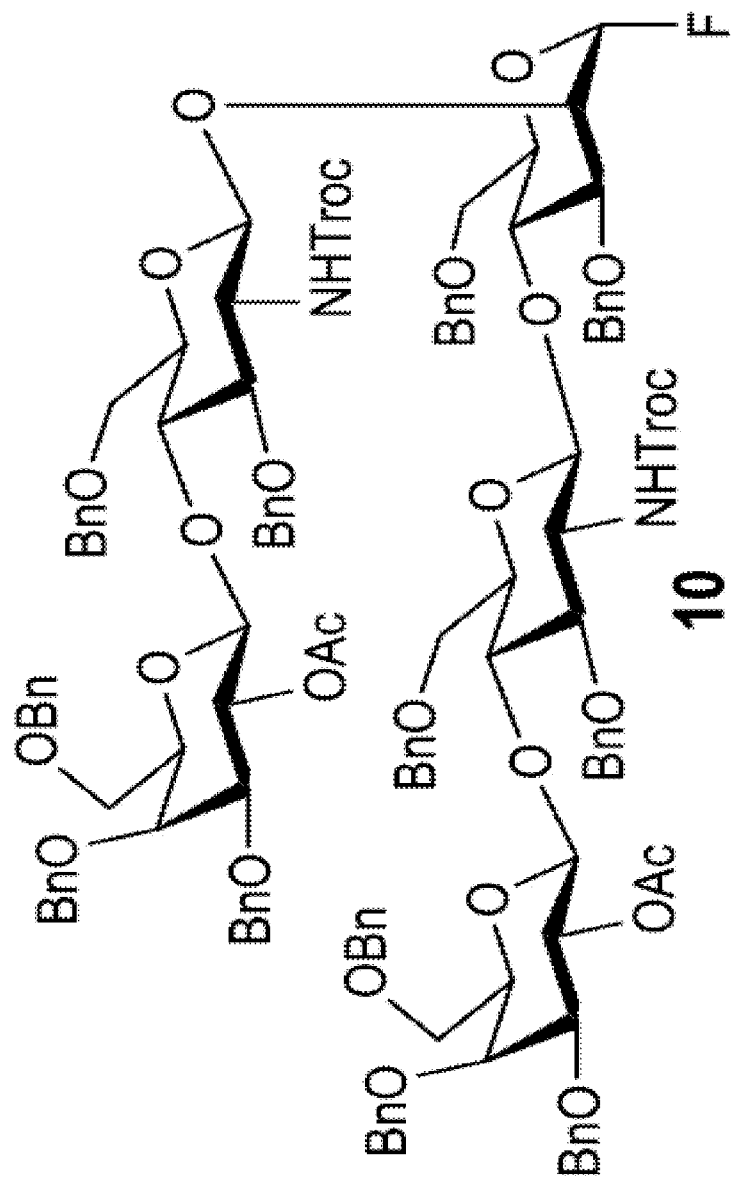
FIG. 40 shows exemplary structure embodiments and synthetic scheme embodiments of the present disclosure.
Figure 41:
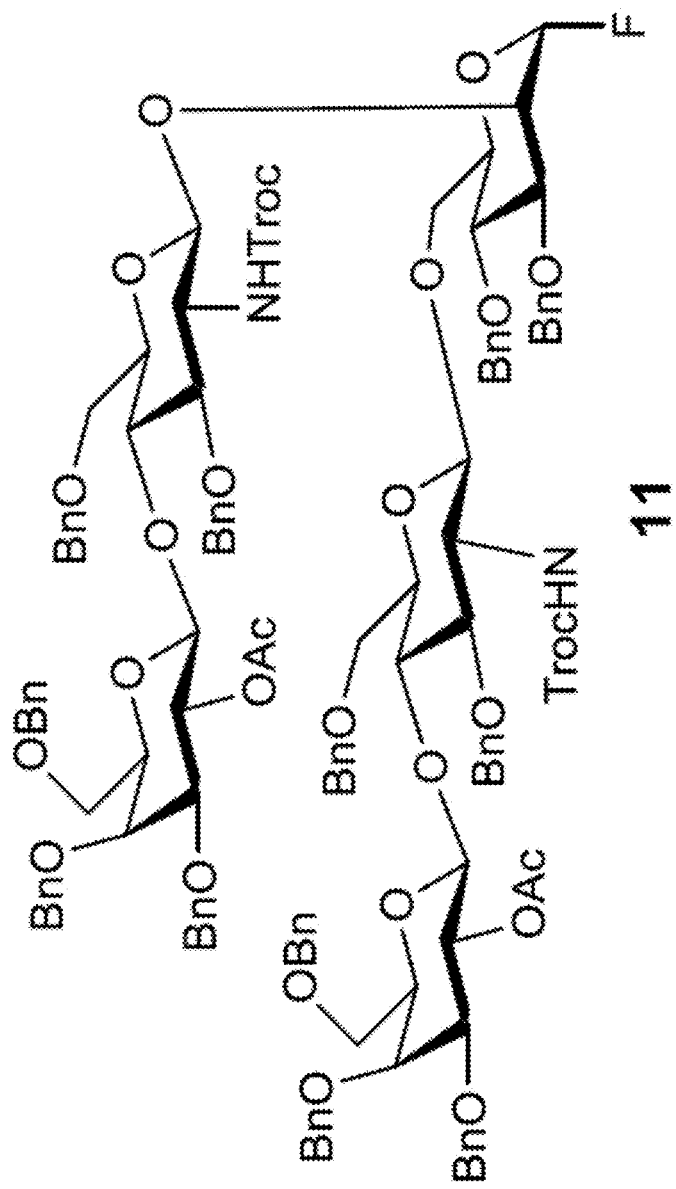
FIG. 41 shows exemplary structure embodiments and synthetic scheme embodiments of the present disclosure.

Scheme S5 as shown in FIGS. 37A, 37B and 37C depicts the preparation of compound 10 and 11. i, (1) EDA, n-BuOH, 90° C.; (2) Troc-Cl, NaHCO3, CH2Cl2; (3) Ac2O, pyridine; ii, (1) CAN, ACN:Toluene:H2O; (2) DAST, CH2Cl2, −30° C.

General procedure for step i: A mixture of compound S5a and S5b (0.500 g, 0.212 mmole) and 10 mL of ethylene diamine:n-BuOH (1:4) was stirred at 90° C. overnight. Volatiles were evaporated, and the crude product was dried using high vacuum. It was then dissolved in CH2Cl2 (20 mL), NaHCO3 (0.114 g, 2.12 mmol) and 2,2,2-trichloro ethyl chloroformate (0.2 mL, 2.12 mmol) were added at 0° C., allowed it to warm to RT and stirred for overnight. TLC (ethyl acetate:toluene, 2/8) indicated formation of product with consumption of starting material. The reaction mixture was diluted with CH2Cl2 (100 mL), washed with water (2×50 mL) and brine (50 mL) solution. The organic layer was dried over Na2SO4 and concentrated in vacuo. The residue was purified by silica gel column chromatography (0%→15% EA in toluene). The product was then acetylated using 10 mL of pyridine/acetic anhydride (6:4) until TLC indicated (ethyl acetate:toluene, 2/8) complete consumption of starting material. The reaction mixture was then concentrated in vacuo and purified by silica gel column chromatography (0%→15% EA in toluene) to afford S5c (0.332 g 65%) and S5d (0.340 g, 68%) as a colorless foam.

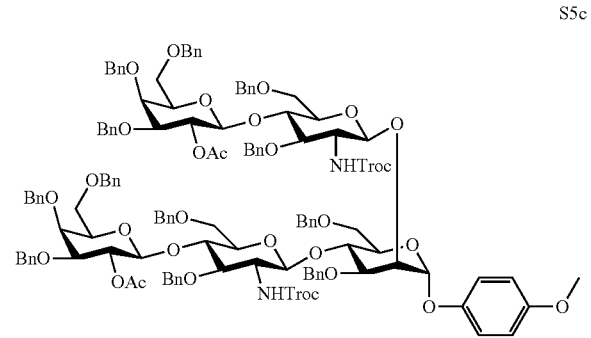

S5c p-methoxyphenyl-O-2-O-acetyl-3,4,6-O-tri-benzyl-β-D-galactopyranosyl-(1→4)-O-3,6-O-di-benzyl-2-deoxy-2-(2,2,2-trichloroethoxy)carbonylamino-β-D-glucopyranosyl-(1→2)-[2-O-acetyl-3,4,6-O-tri-benzyl-β-D-galactopyranosyl-(1→4)-O-3,6-O-di-benzyl-2-deoxy-2-(2,2,2-trichloroethoxy)carbonylamino-β-D-glucopyranosyl-(1→4)]-3,6-O-di-benzyl-α-D-mannopyranoside (S5c): Compounds S5c was prepared according to the above mentioned general procedure. TLC (ethyl acetate:toluene=2/8, v/v): Rf=0.64; 1H NMR (600 MHz, CDCl3): δ 7.40-7.08 (m, 50H, Ar—H), 6.92-6.72 (m, 10H, Ar—H), 6.63-6.53 (m, 2H, PMP-H), 5.31-5.24 (m, 2H'), 5.22 (d, J=7.8 Hz, 1H), 5.15 (d, J=8.4 Hz, 1H,), 4.94 (d, J=3 Hz,), 4.88 (d, J=3.6 Hz, 1H), 4.86 (d, J=3.6 Hz, 1H), 4.80-4.71 (m, 7H), 4.64-4.56 (m, 3H), 4.49-4.44 (m, 10H,), 4.39-4.10 (m, 14H), 4.15-4.05 (m, 2H), 4.03 (t, J=8.4 Hz, 1H), 3.98-3.86 (m, 3H), 3.79-3.72 (m, 1H), 3.69 (s, 3H), 3.58-3.56 (m, 1H), 3.49-3.25 (m, 13H), 3.08 (d, J=8.4 Hz, 1H), 3.05 (d, J=8.9 Hz, 1H), 2.90 (bs, 1H), 1.93 (s, 3H), 1.92 (s, 3H); 13C NMR (150 MHz, CDCl3): δ 169.5, 169.4, 168.3, 167.8, 154.8, 150.3, 139.2, 139.1, 139.0, 138.9, 138.8, 138.5, 138.3, 138.2, 138.0, 134.0, 133.6, 132.1, 131.9, 131.7, 129.2, 128.6, 128.5, 128.3, 128.2, 128.1, 128.0, 127.9, 127.9, 127.8, 127.7, 127.6, 127.5, 127.4, 127.4, 127.3, 127.1, 127.0, 126.8, 123.5, 123.4, 123.3, 118.1, 114.4, 108.9, 100.9, 100.7, 98.5, 97.6, 97.1, 80.5, 50.5, 79.7, 77.9, 77.8, 77.7, 77.4, 77.2, 75.4, 74.9, 74.6, 74.5, 73.7, 73.6, 73.6, 73.4, 73.3, 73.0, 72.8, 72.7, 72.2, 71.9, 71.8, 71.7, 71.2, 69.2, 68.5, 68.3, 68.2, 67.6, 67.3, 56.4, 55.9, 55.7, 21.3, 21.2, 21.2; ESI-MS: m/z calcd for C, 131; H, 138; C, 16; N, 2; O31; 2449.7492; found 2449.7272 (M+H)+.

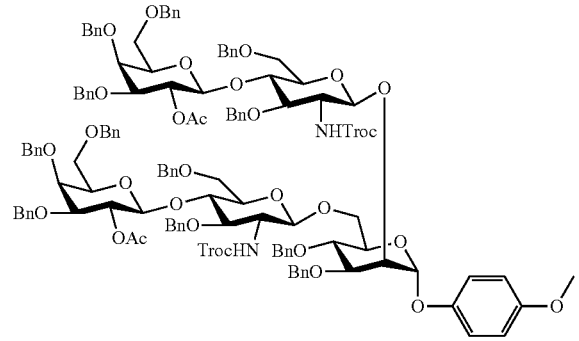

S5d p-methoxyphenyl-O-2-O-acetyl-3,4,6-O-tri-benzyl-β-D-galactopyranosyl-(1→4)-O-3,6-O-di-benzyl-2-deoxy-2-(2,2,2-trichloroethoxy)carbonylamino-β-D-glucopyranosyl-(1→2)-[2-O-acetyl-3,4,6-O-tri-benzyl-β-D-galactopyranosyl-(1→4)-O-3,6-O-di-benzyl-2-deoxy-2-(2,2,2-trichloroethoxy)carbonylamino-β-D-glucopyranosyl-(1→6)]-3,6-O-di-benzyl-α-D-mannopyranoside (S5d): Compounds S5d was prepared according to the above mentioned general procedure. TLC (ethyl acetate:toluene=2/8, v/v): Rf=0.61; 1H NMR (600 MHz, CDCl3): δ 7.42-7.05 (m, 60H), 7.02 (d, J=9.2 Hz, 2H), 6.85 (d, J=9.0 Hz, 2H), 5.59 (s, 1H), 5.42 (bs, 1H), 5.39-5.29 (m, 2H), 5.15 (d, J=3.8 Hz, 1H), 5.00-4.84 (m, 7H), 4.80-4.25 (m, 20H), 4.10 (dd, J=3.8 & 7.8 Hz, 2H), 4.00-3.83 (m, 6H), 3.76 (s, 3H), 3.62-3.20 (m, 23H), 1.99 (s, 3H), 1.96 (s, 3H); 13C NMR (150 MHz, CDCl3): δ 169.9, 169.5, 168.5, 155.0, 154.6, 150.1, 138.9, 138.4, 138.2, 138.1, 134.3, 132.0, 129.2, 128.6, 128.4, 128.3, 128.2, 128.1, 128.0, 127.9, 127.8, 127.6, 127.5, 127.3, 125.5, 123.6, 117.8, 117.2, 114.9, 106.1, 101.5, 100.9, 100.7, 98.3, 96.4, 95.7, 80.3, 80.1, 79.4, 78.3, 77.9, 78.3, 75.6, 74.8, 74.5, 74.4, 74.3, 73.6, 73.4, 73.2, 73.0, 72.6, 72.3, 71.8, 68.9, 68.1, 67.9, 67.5, 57.9, 56.7, 55.8, 41.3, 40.4, 37.7, 29.9, 21.6, 21.2, 21.1; ESI-MS: m/z calcd for C, 131; H, 138; C, 16; N, 2; O31; 2448.7492 found 2449.7414 (M+H)+.

General procedure for Step ii: Cerium ammonium nitrate (0.616 g, 0.725 mmol) was added to a solution of compound S5c or S5d (0.350 g, 0.145 mmol) in 10 mL of acetonitrile:toluene:H2O (4:2:1). The resulting reaction mixture was stirred at 0° C. for 2 h. The reaction was diluted with EtOAc (100 mL) and washed with H2O (30×2 mL) and brine (30 mL). The organic layer was dried over Na2SO4 and concentrated in vacuo. The product was purified by flash column chromatography (0%→15% EA in toluene) to afford 1-OH compound (0.180 m) as clear foam. The residue (0.180 g, 0.078 mmol) was dissolved in CH2Cl2 (10 mL) at −30° C. Then, DAST (30 μL, 0.234 mmol) was added slowly, and the resulting reaction mixture was stirred for 1 h. When TLC (ethyl acetate:toluene, 1/9) indicated formation of product with consumption of starting material, the reaction was quenched with aq. NaHCO3. The filtrate was washed with aqueous NaHCO3 (2×50 mL) and brine (50 mL) solution. The organic layer was dried over Na2SO4 and concentrated in vacuo. The residue was purified by silica gel column chromatography (0%→8% EA in toluene) to afford 10 (0.120 g, 34% over 2 steps) and 11 (0.150 g, 42% over 2 steps).

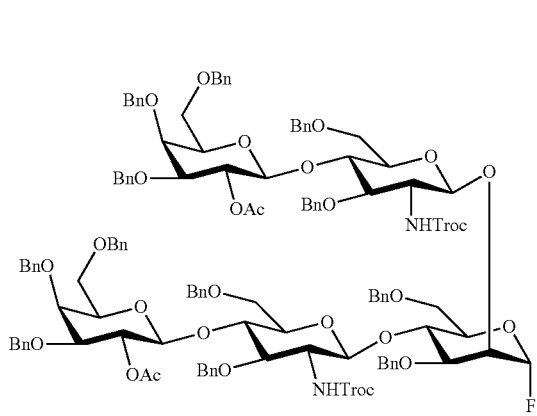

2-O-acetyl-3,4,6-O-tri-benzyl-β-D-galactopyranosyl-(1→4)-O-3,6-O-di-benzyl-2-deoxy-2-(2,2,2-trichloroethoxy)carbonylamino-β-D-glucopyranosyl-(1→2)-[2-O-acetyl-3,4,6-O-tri-benzyl-β-D-galacto-pyranosyl-(1→4)-O-3,6-O-di-benzyl-2-deoxy-2-(2,2,2-trichloroethoxy) carbonylamino-β-D-glucopyranosyl-(1→4)]-3,6-O-di-benzyl-α-D-mannopyranosyl fluoride (10): TLC (ethyl acetate: toluene=1/9, v/v): Rf=0.34; 1H NMR (600 MHz, CDCl3): δ 7.34-7.13 (m, 60H), 5.41 (s, 1H), 5.50 (d, J=51.1 Hz, 1H), 5.30-5.25 (m, 2H), 5.12 (d, J=8.4 Hz, 1H), 4.92-4.85 (m, 5H), 4.69-4.38 (m, 20H), 4.32-4.14 (m, 8H), 3.91-3.77 (m, 7H), 3.70 (dd, J=3.8 and 7.8 Hz, 1H), 3.60-3.56 (m, 3H), 3.49-3.24 (m, 14H), 2.03 (s, 3H), 1.98 (s, 3H); 13C NMR (150 MHz, CHCl3): δ 169.68, 169.58, 154.31, 154.09, 139.06, 138.97, 138.93, 138.32, 138.29, 138.27, 138.20, 138.17, 129.32, 128.99, 128.69, 128.63, 128.50, 128.49, 128.45, 128.27, 128.24, 128.16, 128.15, 128.07, 128.05, 128.00, 127.97, 127.94, 127.91, 127.82, 127.72, 127.60, 127.57, 127.44, 125.58, 100.64, 100.45, 95.86, 80.54, 80.51, 76.81, 76.70, 76.03, 75.34, 75.08, 86, 74.77, 74.66, 74.57, 74.47, 73.74, 73.70, 73.67, 73.64, 73.58, 73.46, 73.42, 73.27, 72.90, 72.19, 72.17, 71.99, 71.95, 68.49, 68.27, 68.14, 68.01, 57.53, 21.40, 21.27; ESI-MS: m/z calcd for C, 124; H, 131; C, 16; FN, 2; O, 29; 2340.6953 found 2363.7200 (M+Na)+.

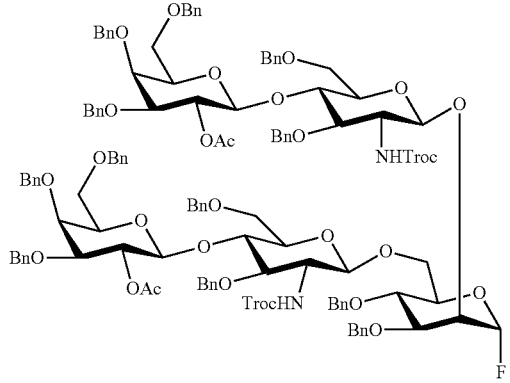

2-O-acetyl-3,4,6-O-tri-benzyl-β-D-galactopyranosyl-(1→4)-O-3,6-O-di-benzyl-2-deoxy-2-(2,2,2-trichloroethoxy)carbonylamino-β-D-glucopyranosyl-(1→2)-[2-O-acetyl-3,4,6-O-tri-benzyl-β-D-galacto-pyranosyl-(1→4)-O-3,6-O-di-benzyl-2-deoxy-2-(2,2,2-trichloroethoxy) carbonylamino-β-D-glucopyranosyl-(1→4)]-3,6-O-di-benzyl-α-D-mannopyranosyl fluoride (11): TLC (ethyl acetate:toluene=1/9, v/v): Rf=0.38; 1H NMR (600 MHz, CDCl3): δ 7.33-7.09 (m, 60H), 5.60 (d, J=52.1 Hz, 1H), 5.32-5.28 (m, 2H), 5.10 (d, J=2.1 Hz, 1H), 4.93-4.80 (m, 5H), 4.78 (d, J=8.4 Hz, 1H), 4.74 (d, J=8.2 Hz, 1H), 4.65-4.40 (m, 28H), 3.95 (dd, J=8.4 Hz, 1H), 3.79-3.69 (m, 10H), 3.50-3.40 (m, 4H), 3.39-3.20 (m, 8H), 1.91 (s, 6H); 13C NMR (150 MHz, CHCl3): δ 169.69, 169.56, 154.72, 154.66, 139.55, 139.02, 139.00, 138.43, 138.34, 138.27, 138.20, 138.19, 128.93, 128.80, 128.76, 128.72, 128.65, 128.45, 128.41, 128.30, 128.28, 128.21, 127.67, 127.34, 127.10, 106.45, 105.33, 101.82, 101.21, 100.00, 97.86, 97.46, 95.60, 75.46, 75.27, 74.86, 74.58, 74.26, 74.10, 73.50, 73.47, 73.10, 72.90, 72.88, 72.37, 72.30, 71.40, 71.37, 71.09, 70.57, 70.35, 70.45, 69.78, 69.46, 29.99, 25.78, 22.87, 21.36, 21.29, 15.57, 14.49, 144.42; ESI-MS: m/z calcd for C, 124; H, 131; C, 16; FN, 2; O, 29; 2340.6953 found 2362.7225 (M+Na)+.

Synthesis of building blocks 12.

Preparation of disialylated antennae was commensed with β-1,2 and β-1,4 glycosylation of mannosyl acceptor S6a with donor S2b. Compound S6b was then modified to S6c and subsequently glycosylated with S4c to get desired heptasaccharide S6d. At last, the reducing end was modified to get donor 12.

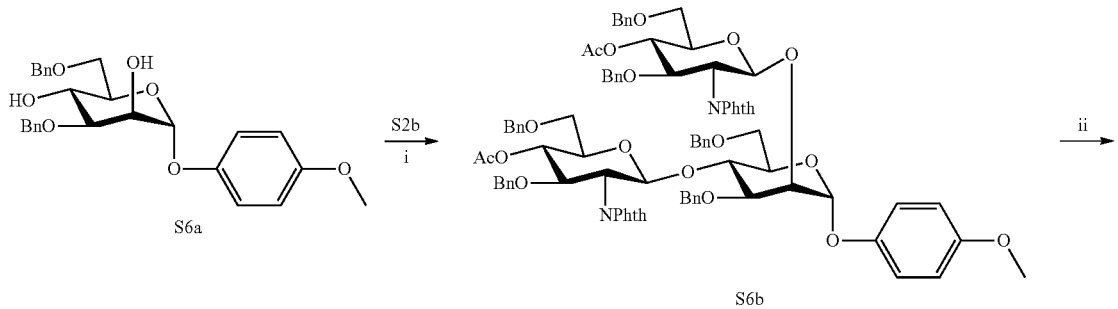

Figure 42A:
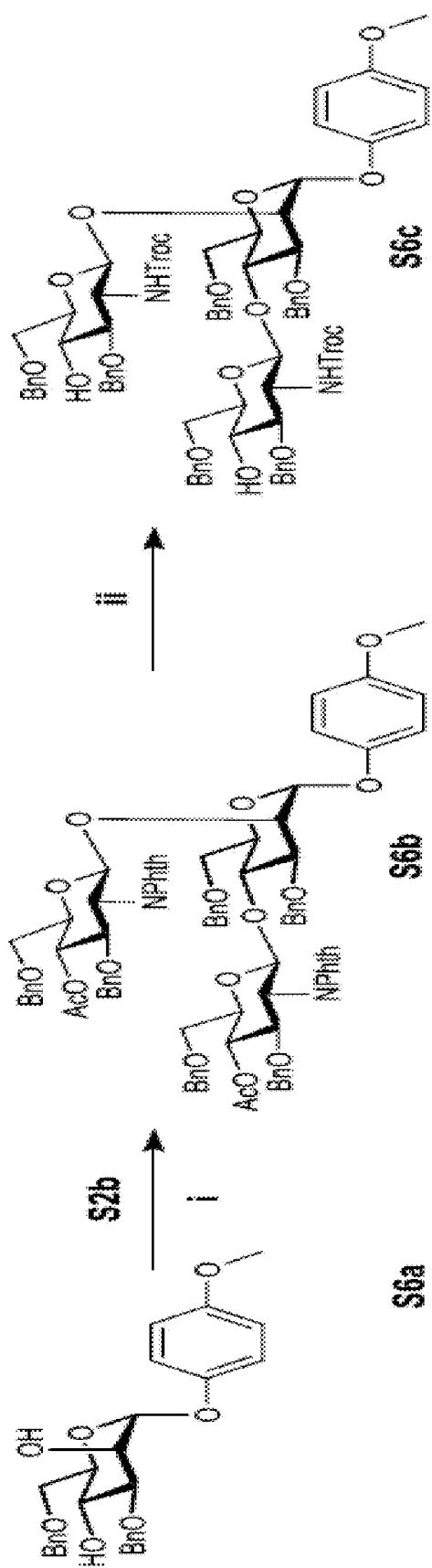
FIGS. 42A and 42B.
Figure 42B:
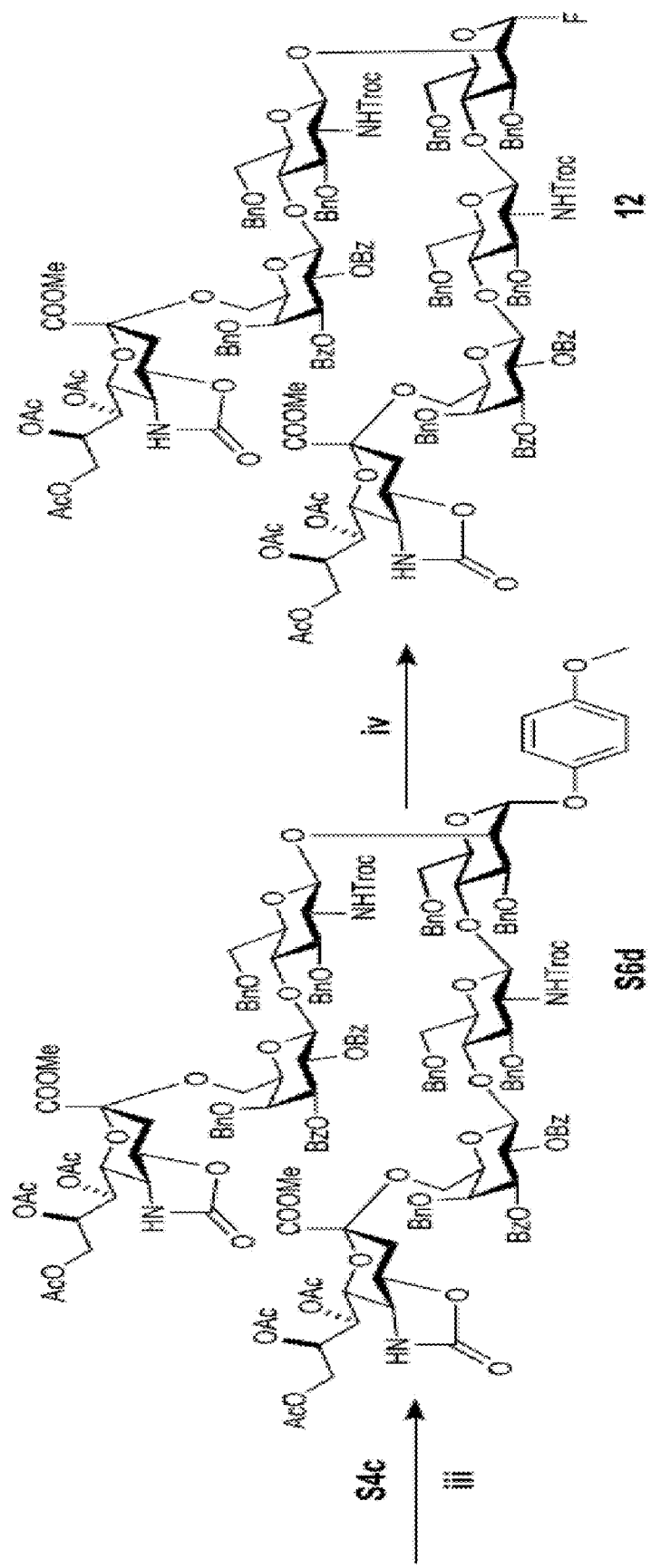
Figure 43:
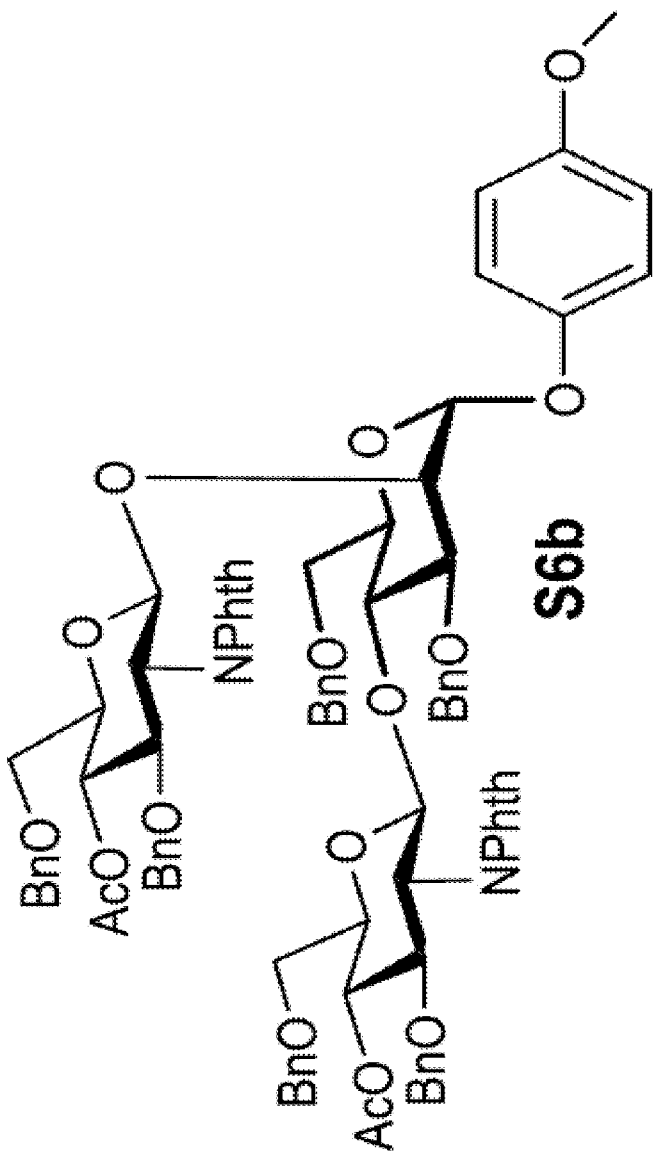
FIG. 43 shows exemplary structure embodiments and synthetic scheme embodiments of the present disclosure.
Figure 44:
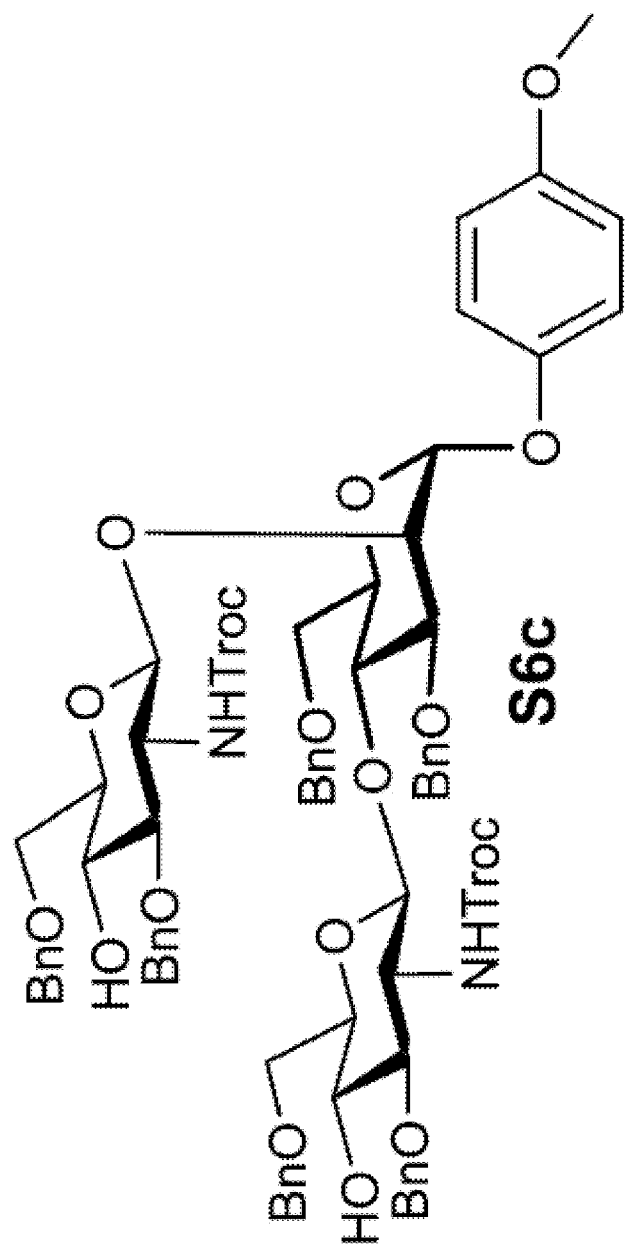
FIG. 44 shows exemplary structure embodiments and synthetic scheme embodiments of the present disclosure.
Figure 45:
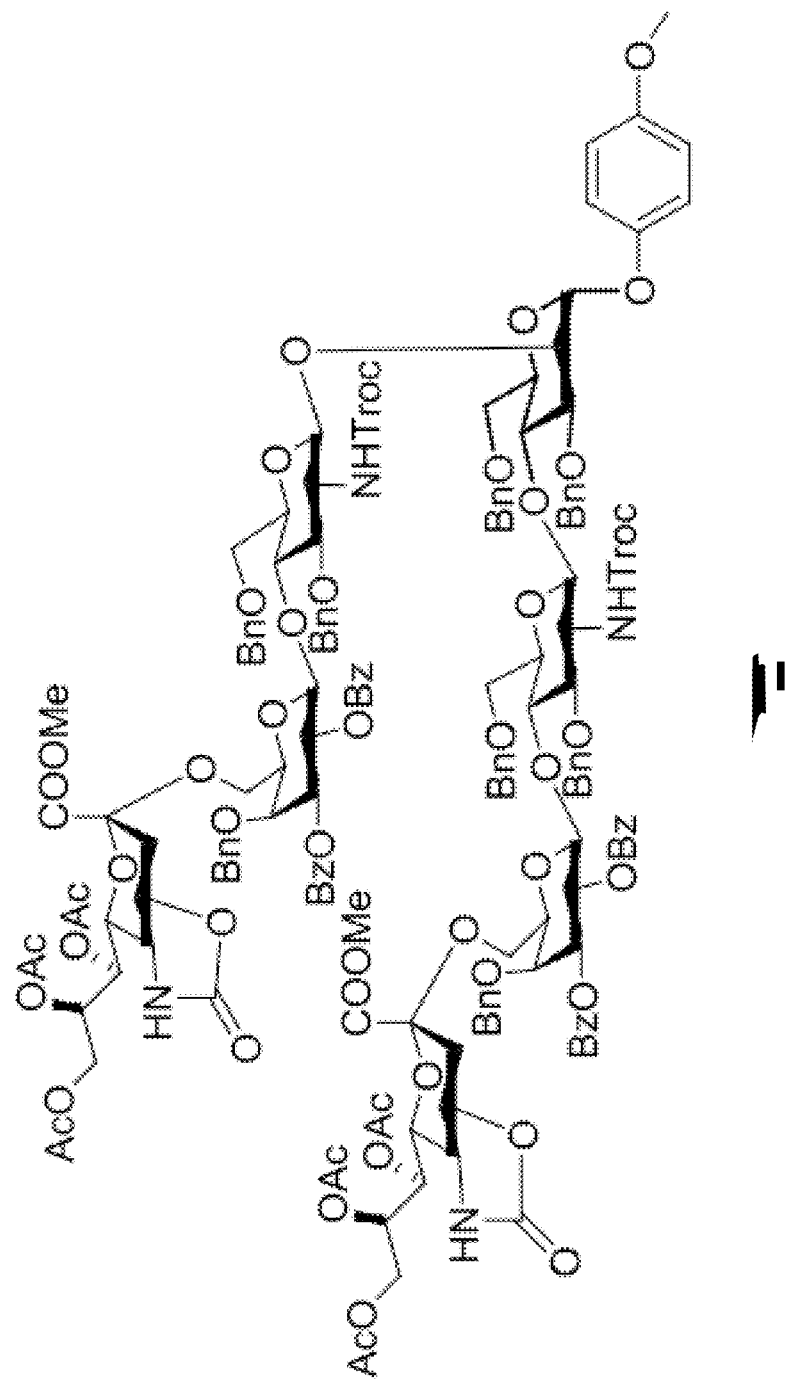
FIG. 45 shows exemplary structure embodiments and synthetic scheme embodiments of the present disclosure.
Figure 46:
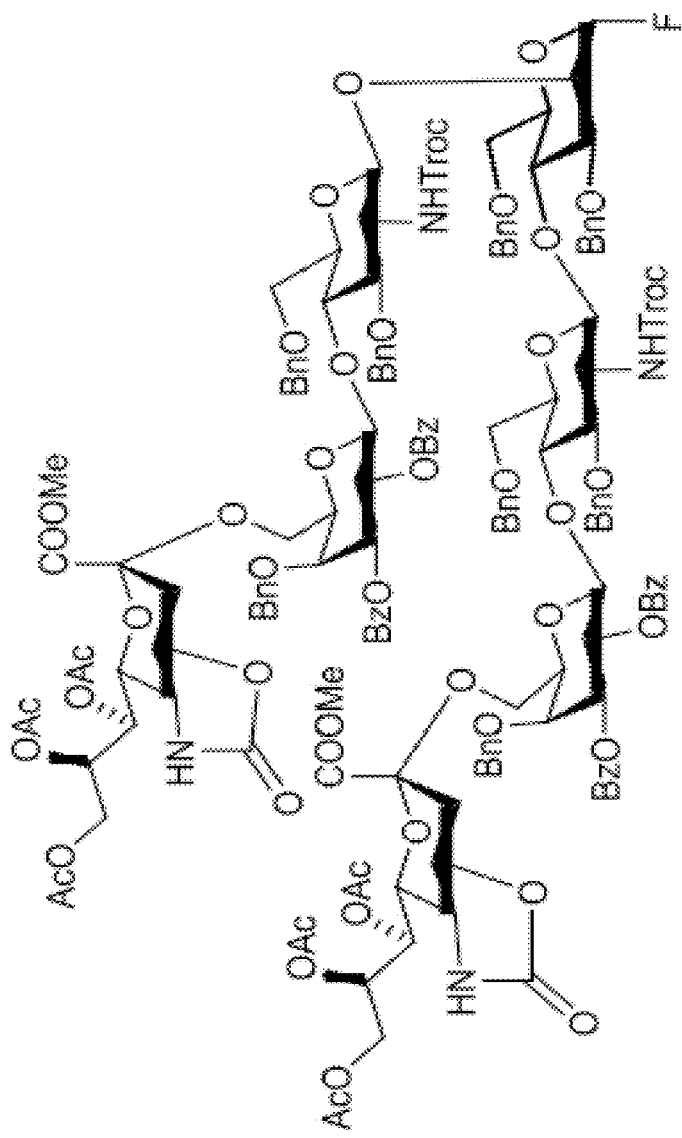
FIG. 46 shows exemplary structure embodiments and synthetic scheme embodiments of the present disclosure.

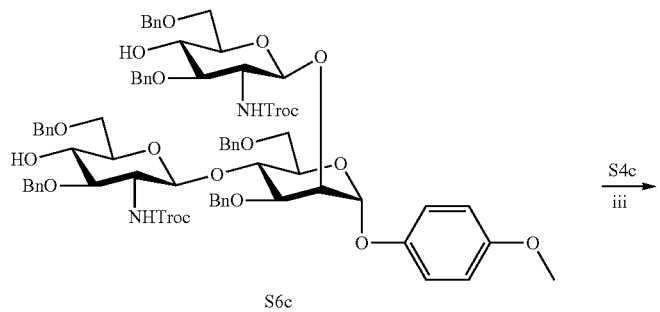
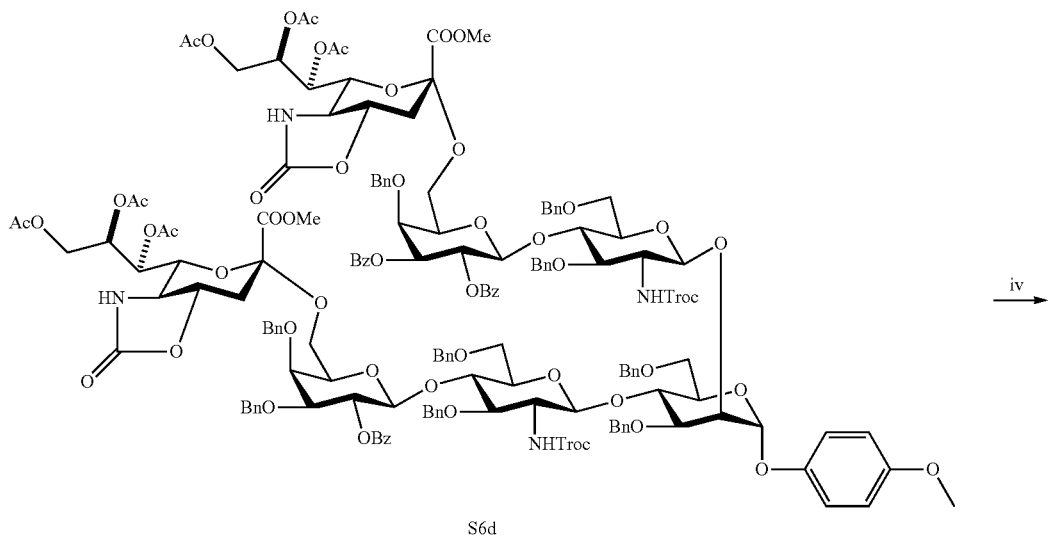
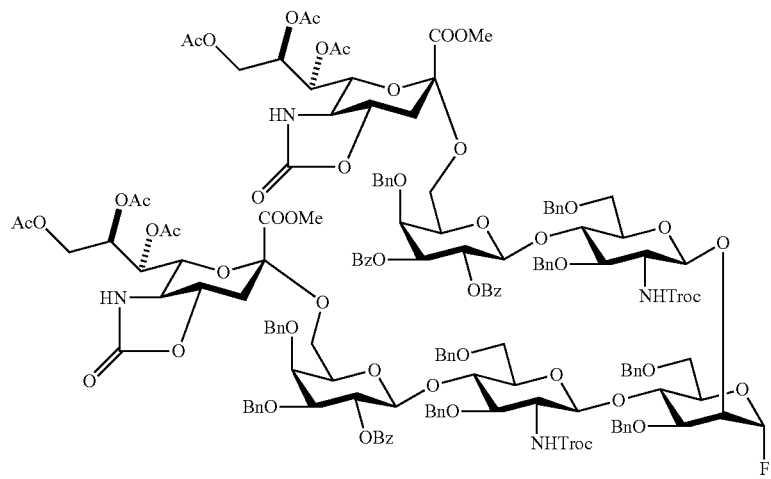
Scheme S6 as shown in FIGS. 42A and 42B depicts the pPreparation of compound 12. i, NIS, TfOH, CH$_2$Cl$_2$, −50° C., 76%; ii, (1) EDA, n-BuOH, 90° C., (2) Troc-Cl, NaHCO3, CH$_2$Cl$_2$, 72% over 2 steps; iii, MS, TfOH, CH$_2$Cl$_2$, −50° C., 86%; iv, (1) CAN, ACN:Toluene:H$_2$O, (2) DAST, CH$_2$Cl$_2$, −30° C., 40% over 2 steps.

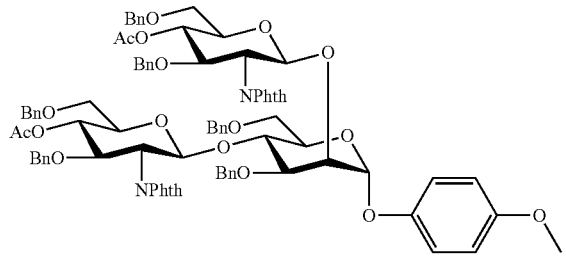

S6b

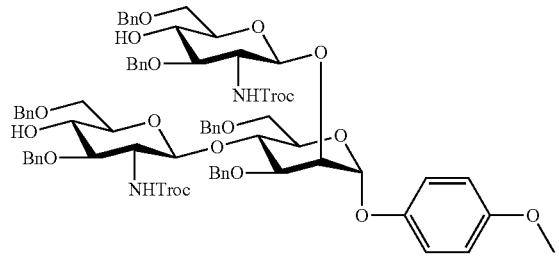

S6c p-methoxyphenyl-O-4-O-acetyl-3,6-O-di-benzyl-2-deoxy-2-phthalimido-β-D-glucopyranosyl-(1→2)-[4-O-acetyl-3,6-O-di-benzyl-2-deoxy-2-phthalimido-β-D-glucopyranosyl-(1→4)]-3,6-O-di-benzyl-α-D-mannopyranoside (S6b): Activated 4 Å molecular sieves (1 g) were added to a solution of acceptor S6a (0.560 g, 1.19 mmol) and donor S2b (1.74 g, 2.74 mmol) in anhydrous CH$_2$Cl$_2$ (10 mL). The reaction mixture was stirred for 1 h at room temperature then cooled to −50° C. NIS (1.07 g, 4.75 mmol) and TfOH (52 μL, 0.595 mmol) were added slowly, and the resulting reaction mixture was stirred for 2 h. When TLC (ethyl acetate:toluene, 1.5/8.5) indicated formation of product with consumption of starting material, the reaction was quenched by adding Et3N then filtered through Celite. The filtrate was washed with aqueous NaHCO$_3$ (2×50 mL), aqueous Na$_2$S$_2$O$_3$ (2×50 mL), and brine (50 mL) solution. The organic layer was dried over Na2SO4 and concentrated in vacuo. The residue was purified by flash column chromatography (0%→10% EA in toluene) to afford S6b (1.27 g, 76%) as clear foam. TLC (ethyl acetate:toluene=1.5/8.5, v/v): R$_f$=0.57; $^1$H NMR (600 MHz, CDCl$_3$): δ 7.66-7.16 (m, 18H), 6.97 (m, 12H), 6.66-6.49 (m, 4H), 5.25 (t, J=10 Hz, 2H), 5.08-5.00 (dd, J=9.6 & 3.4 Hz, 2H), 4.90 (d, J=4.6 Hz, 1H), 4.69 (d, J=12 Hz, 1H), 4.57 (t, 3H), 4.42-4.21 (m, 10H), 4.12 (dd, J=3.2 & 8.4 Hz, 2H), 3.90 (dd, J=3.2 & 7.8 Hz, 1H), 3.84-3.60 (m, 7H), 3.66 (s, 3H), 3.54-3.31 (m, 7H), 3.01 (d, J=7.8 Hz, 1H), 1.84 (s, 3H), 1.80 (s, 3H); $^{13}$C NMR (150 MHz, CDCl$_3$): δ 169.61, 169.12, 154.49, 150.07, 138.69, 138.21, 137.99, 137.77, 137.60, 133.52, 131.29, 128.28, 128.19, 127.99, 127.94, 127.91, 127.83, 127.68, 127.59, 127.47, 127.25, 127.08, 127.94, 123.17, 117.55, 114.08, 98.10, 97.37, 96.54, 78.89, 74.56, 73.56, 73.27, 72.98, 72.42, 72.32, 71.91, 71.43, 71.02, 69.91, 69.25, 68.90, 55.73, 55.45, 55.26, 20.80; ESI-MS: m/z calcd for C$_{77}$H$_2$C$_{16}$N$_2$O$_{21}$; 1585.3589 found 1586.5687 (M+H)$^+$.

p-methoxyphenyl-O-3,6-O-di-benzyl-2-deoxy-2-(2,2,2-trichloroethoxy)carbonylamino-p-D-glucopyranosyl-(1→2)-[3,6-O-di-benzyl-2-deoxy-2-(2,2,2-trichloroethoxy)carbonylamino-β-D-glucopyranosyl-(1→4)]-3,6-O-di-benzyl-α-D-mannopyranoside (S6c): A mixture of compound S6b (1.9 g, 1.27 mmol) and 20 mL of ethylene diamine:n-BuOH (1:4) was stirred at 90° C. overnight. Volatiles were evaporated, and the crude product was dried using high vacuum. It was then dissolved in CH2Cl2 (20 mL), NaHCO3 (0.687 g, 12.7 mmol) and 2,2,2-trichloro ethyl chloroformate (1.75 mL, 12.7 mmol) were added at 0° C., allowed it to warm to rt and stirred for overnight until TLC (acetone:toluene, 1/9) indicated formation of product with consumption of starting material. The reaction mixture was diluted with CH2Cl2 (100 mL), washed with water (2×50 mL) and brine (50 mL) solution. The organic layer was dried over Na2SO4 and concentrated in vacuo. The residue was purified by silica gel column chromatography (0%→8% EA in toluene) to afford S6c as a colorless solid (1.35 g, 72%). TLC (acetone:toluene=1/9, v/v): Rf=0.54; 1H NMR (600 MHz, CDCl3): δ 7.35-7.14 (m, 30H), 6.90 (d, J=8.4 Hz, 2H), 6.79 (d, J=8.6 Hz, 2H), 5.32 (d, J=3.2 Hz, 1H), 5.27 (d, J=7.2 Hz, 1H), 4.93 (d, J=8.4 Hz, 1H), 4.73-4.58 (m, 10H), 4.48-4.43 (m, 7H), 4.19 (d, J=7.2 Hz, 1H), 4.05-3.96 (m, 3H), 3.68 (s, 3H), 3.62-3.56 (m, 8H), 3.26 (q, 1H), 3.26-3.15 (m, 3H), 2.93 (m, 3H), 2.96 (s, 1H), 2.12 (s, 1H); 13C NMR (150 MHz, CDCl3): δ 155.26, 154.37, 154.27, 150.53, 138.93, 138.63, 138.48, 137.83, 137.74, 131.18, 128.96, 128.76, 128.67, 128.36, 128.21, 128.15, 127.89, 127.78, 118.00, 114, 85, 101.31, 98.79, 97.79, 95.81, 81.39, 79.59, 75.90, 74.70, 74.47, 74.01, 73.93, 73.53, 73.02, 72.83, 71.63, 71.37, 70.97, 68.99, 57.73, 57.40, 55.94; ESI-MS: m/z calcd for C, 73; H, 78; C, 16; N, 2; O, 19; 1499.3338 found 1499.3419.

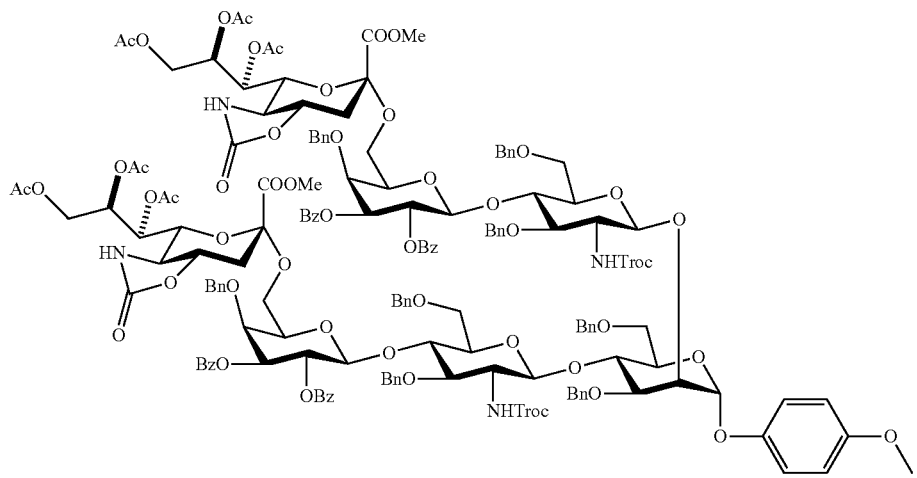

p-methoxyphenyl-O-[Methyl-5-acetamido-7,8,9-tri-O-acetyl-3,5-dideoxy-D-glycero-α-D-galacto-non-2-ulopyranosylonate]-(2→6)-4-O-benzyl-2,3-di-O-benzoyl-1-β-D-galactopyranosyl-(1→4)-O-3,6-O-di-benzyl-2-deoxy-2-(2,2,2-tri-chloroethoxy)carbonylamino-β-D-glucopyranosyl-(1→2)-[Methyl-5-acetamido-7,8,9-tri-O-acetyl-3,5-dideoxy-D-glycero-α-D-galacto-non-2-ulopyranosylonate]-(2→6)-4-O-benzyl-2,3-di-O-benzoyl-1-β-D-galactopyranosyl-(1→4)-O-3,6-O-di-benzyl-2-deoxy-2-(2,2-trichloroethoxy)carbonylamino-β-D-glucopyranosyl-(1→4)-O-3,4,6-tri-O-benzyl-α-D-mannopyranoside (S6d): Activated 4 Å molecular sieves (1 g) were added to a solution of acceptor S6c (0.500 g, 0.341 mmol) and donor S4c (0.772 g, 0.751 mmol) in anhydrous CH2Cl2 (10 mL). The mixture was stirred for 1 h at rt and then cooled to −50° C. NIS (0.383 g, 1.70 mmol) and TfOH (15 µL, 0.170 mmol) were added slowly. The resulting reaction mixture was stirred for 2 h. When TLC (acetone:toluene, 2/8) indicated formation of product with consumption of starting material, the reaction was quenched by adding Et3N and filtered through Celite. The filtrate was washed with aqueous NaHCO3 (2×50 mL), aqueous Na2S2O3 (2×50 mL), and brine (50 mL) solution. The organic layer was dried over Na2SO4 and concentrated in vacuo. The residue was purified by flash column chromatography (0%→15% EA in toluene) to afford S6d (0.950 g, 86%) as clear foam. TLC (acetone:toluene=2/8, v/v): Rf=0.48; 1H NMR (600 MHz, CDCl3): δ 7.90-7.87 (m, 7H), 7.81-7.79 (m, 3H), 7.50-7.07 (m, 50H), 6.98 (d, 2H), 6.40 (d, 2H), 5.78-5.73 (m, 2H), 5.36-5.26 (m, 4H), 5.20 (d, J=8.6 Hz, 1H), 5.19-5.15 (dd, J=3.2 & 8.4 Hz, 2H), 5.05 (dd, J=4.3 & 8.4 Hz, 2H), 4.94-4.78 (m, 4H), 4.68-4.15 (m, 30H), 3.96-3.86 (m, 6H), 3.71 (S, 6H), 3.70-3.59 (m, 15H), 3.57 (s, 3H), 3.34-3.26 (m, 5H), 2.98-2.76 (m, 4H), 2.15 (s, 3H), 2.09 (s, 3H), 2.00 (S, 3H), 1.98 (s, 3H), 1.89 (S, 3H), 1.89 (S, 3H); 13C NMR (150 MHz, CDCl3): δ 171.56, 170.89, 169.56, 167.20, 165.28, 165.00, 159.11, 154.79, 138.78, 138.56, 138.21, 137.29, 137.00, 133.67, 133.24, 130.79, 129.70, 129.60, 129.26, 128.78, 128.56, 128.42, 128.32, 128.11, 127.69, 127.56, 127.44, 127.32, 127.14, 117.78, 100.89, 100.56, 99.87, 99.68, 95.41, 79.13, 75.56, 74.18, 73.48, 73.26, 73.12, 71.00, 72.90, 72.78, 71.76, 68.78, 68.40, 68.42, 61.78, 57.78, 57.33, 55.89, 53.80, 38.90, 38.7, 30.98, 30.76, 28.87, 23.89, 22.65, 20.87, 20.65, 20.54, 14.08, 10.86; ESI-MS: m/z calcd for C, 161; H, 168; C, 16; N, 4; O, 55; 3251.8695 found 3251.8657 (M+Na)+.

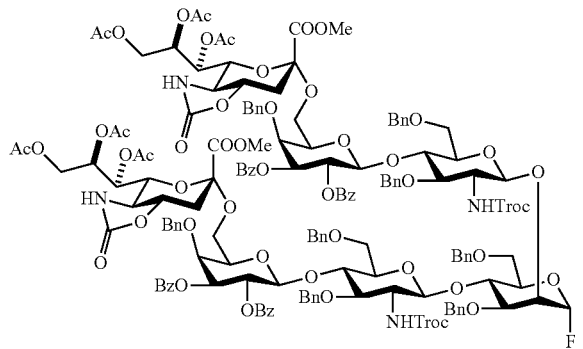

[Methyl-5-acetamido-7,8,9-tri-O-acetyl-3,5-dideoxy-D-glycero-α-D-galacto-non-2-ulopyranosylonate]-(2→6)-4-O-benzyl-2,3-di-O-benzoyl-1-β-D-galacto pyranosyl-(1→4)-O-3,6-O-di-benzyl-2-deoxy-2-(2,2,2-trichloroethoxy)carbonylamino-β-D-glucopyranosyl-(1→2)-[Methyl-5-acetamido-7,8,9-tri-1-acetyl-3,5-dideoxy-D-glycero-α-D-galacto-non-2-ulopyranosylonate]-(2→6)-4-O-benzyl-2,3-di-O-benzoyl-1-β-D-galactopyranosyl-(1→4)-O-3,6-O-di-benzyl-2-deoxy-2-(2,2-trichloroethoxy)carbonylamino-β-D-glucopyranosyl-(1→4)-O-3,4,6-tri-O-benzyl-α-D-mannopyranosyl fluoride (12): Cerium ammonium nitrate (0.470 g, 0.554 mmol) was added to a solution of compound S6d (0.300 g, 0.092 mmol) in 10 mL of acetonitrile:toluene:H2O (4:2:1). The resulting reaction mixture was stirred at rt for 3 h. The reaction was diluted with EtOAc (100 mL) and washed with H2O (30×2 mL) and brine (30 mL). The organic layer was dried over Na2SO4 and concentrated in vacuo. The product was purified by flash column chromatography (0%→20% EA in toluene) to afford 1-OH compound (0.180 g) as a foam. The residue (0.180 g, 0.057 mmol) was dissolved in CH2Cl2 (10 mL) at −30° C. Then, DAST (22 µL, 0.171 mmol) was added slowly, and the resulting reaction mixture was stirred for 1 h. When TLC (acetone:toluene, 2/8) indicated formation of product with consumption of starting material, the reaction was quenched with aq. NaHCO3. The filtrate was washed with aqueous NaHCO3 (2×50 mL) and brine (50 mL) solution. The organic layer was dried over Na2SO4 and concentrated in vacuo. The residue was purified by silica gel column chromatography (0%→15% EA in toluene) to afford 13 (0.120 g, 41% over 2 steps) as white solid. TLC (acetone:toluene=2/8, v/v): Rf=0.24; 1H NMR (600 MHz, CDCl3): δ 7.92-7.83 (m, 10H), 7.54-7.47 (m, 5H), 7.40-6.93 (m, 45H), 5.83 (m, 2H), 5.40-5.35 (m, 6H), 5.2 (dd, J=3.2 & 7.8 Hz, 2H), 5.11 (dd, J=4.3 & 8.4 Hz, 2H), 4.98-4.89 (m, 4H), 4.76-4.56 (m, 15H), 4.28-4.10 (m, 11H), 4.00-3.89 (m, 6H), 3.79-3.72 (m, 6H), 3.65 (s, 3H), 3.67 (s, 3H), 3.62-3.43 (m, 6H), 3.36-3.21 (m, 5H), 3.02-2.98 (m, 4H), 2.16 (s, 3H), 2.14 (s, 3H), 2.11 (s, 3H), 2.06 (s, 3H), 2.01 (s, 3H), 1.98 (s, 3H), 1.89-1.76 (m, 2H); 13C NMR (150 MHz, CDCl3): δ 171.80, 170.85, 170.06, 168.03, 166.12, 165.41, 159.56, 154.16, 138.75, 138.34, 133.73, 130.11, 129.94, 129.57, 129.19, 128.79, 128.72, 128.50, 128.38, 128.03, 127.75, 127.56, 100.69, 100.00, 96.67, 95, 78, 95.35, 95.12, 74.91, 74.65, 74.29, 73.00, 70.91, 69.01, 67.35, 61.87, 58.15, 57.60, 53.42, 37.17, 21.28, 20.97; ESI-MS: m/z calcd for C, 154; H, 161; C, 16; FN, 4; O, 53; 3147.6554 found 3169.8022 (M+Na)+.

Synthesis of building blocks 13.

Figure 47A:
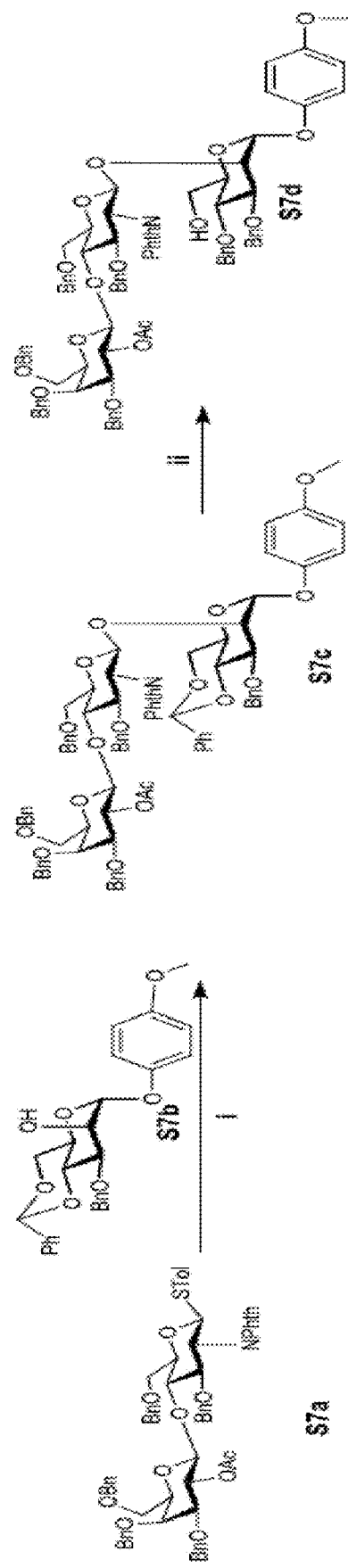
FIGS. 47A, 47B and 47C.
Figure 47B:
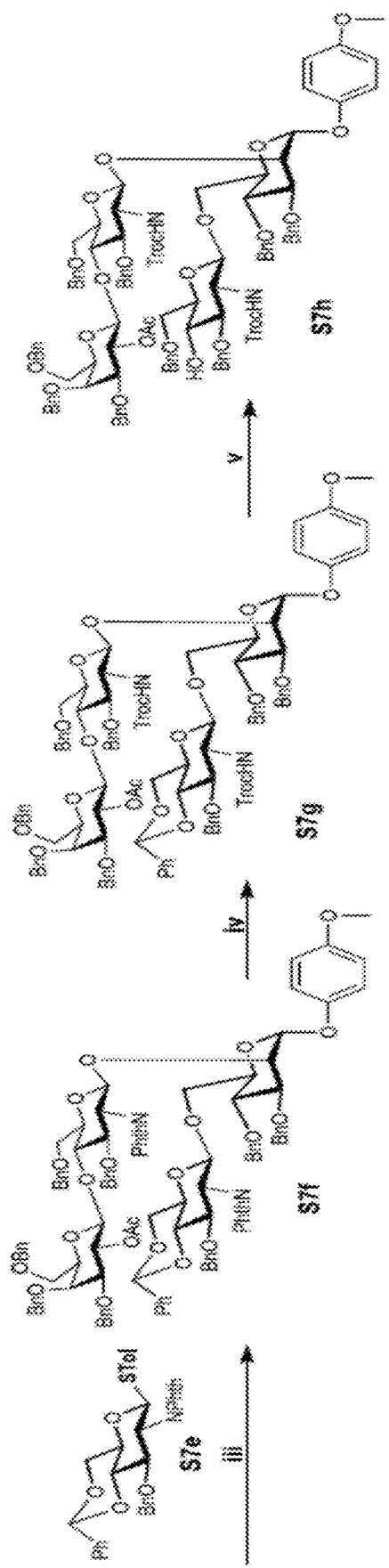
Figure 47C:
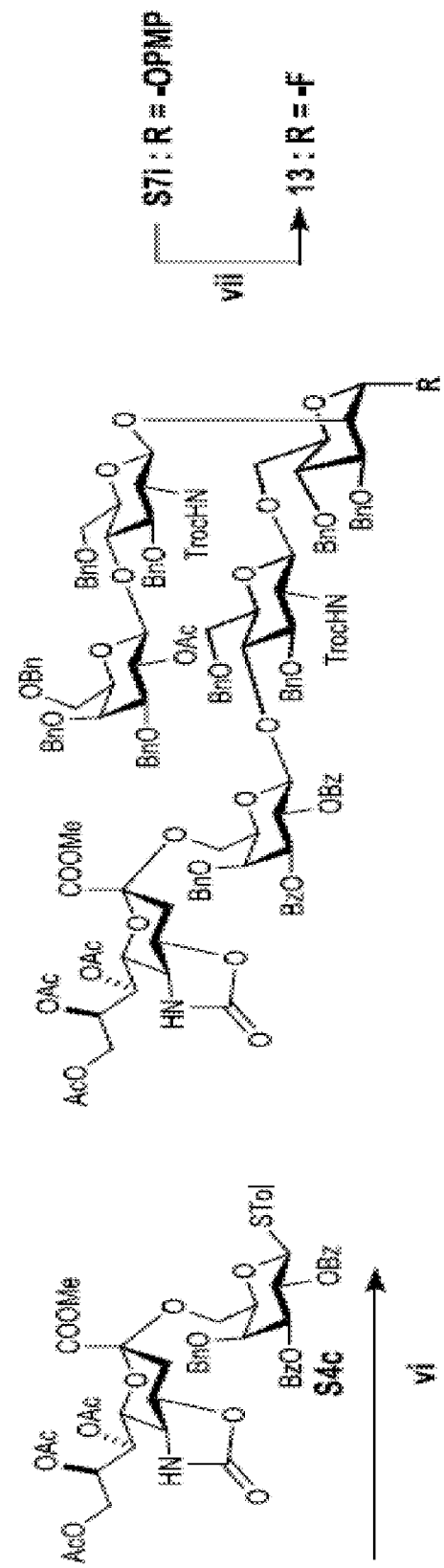
Figure 48:
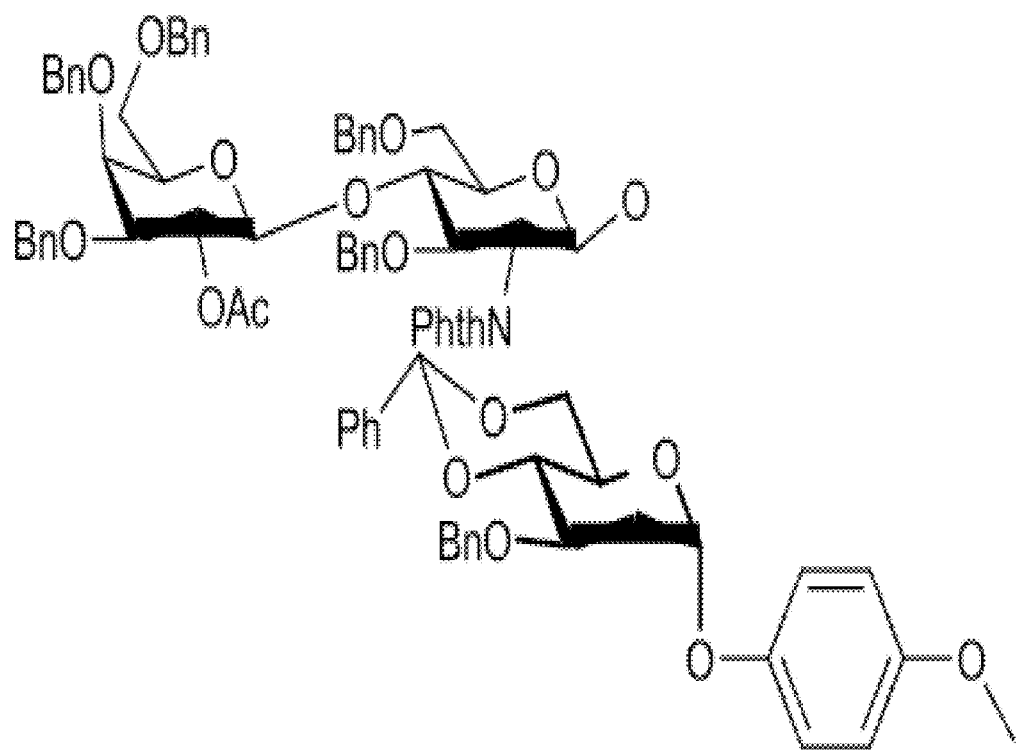
FIG. 48 shows exemplary structure embodiments and synthetic scheme embodiments of the present disclosure.
Figure 49:
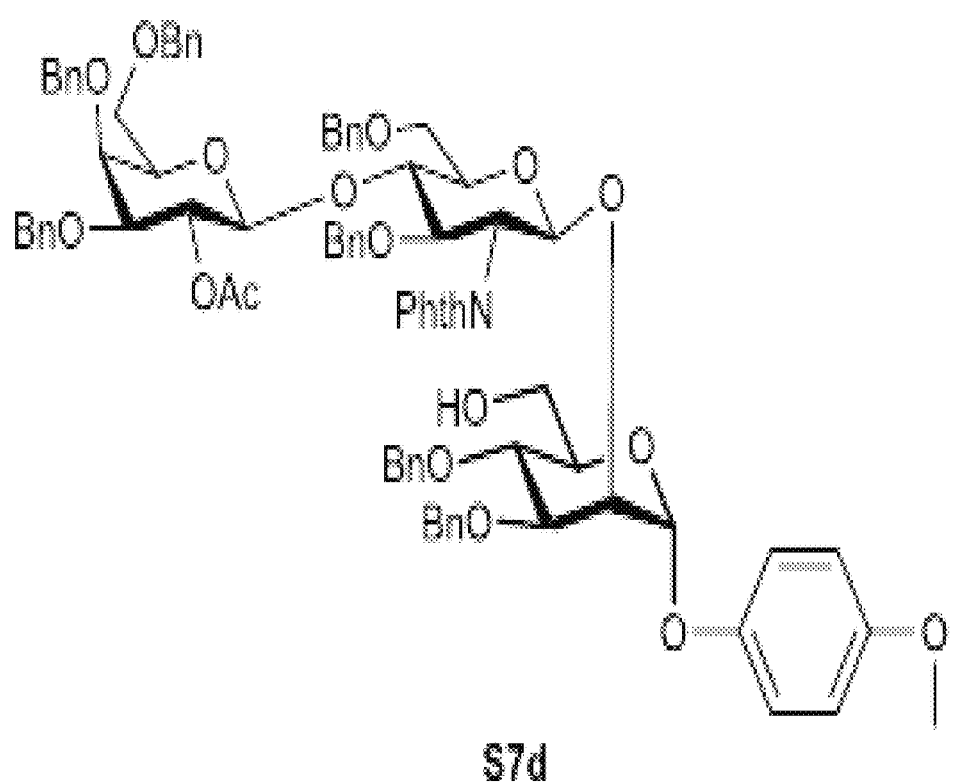
FIG. 49 shows exemplary structure embodiments and synthetic scheme embodiments of the present disclosure.
Figure 50:
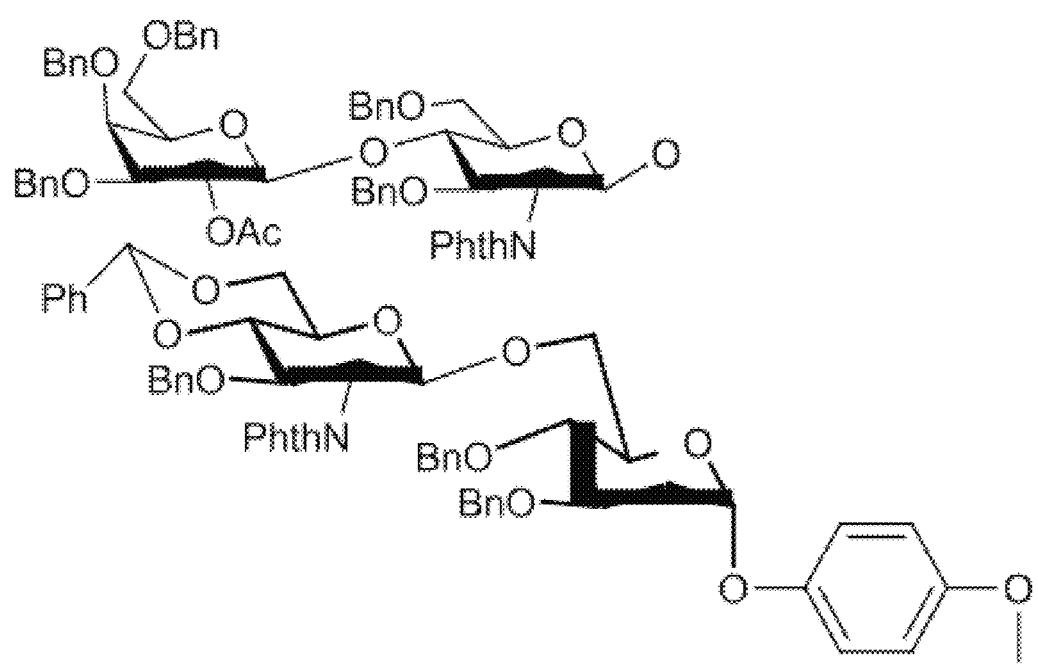
FIG. 50 shows exemplary structure embodiments and synthetic scheme embodiments of the present disclosure.
Figure 51:
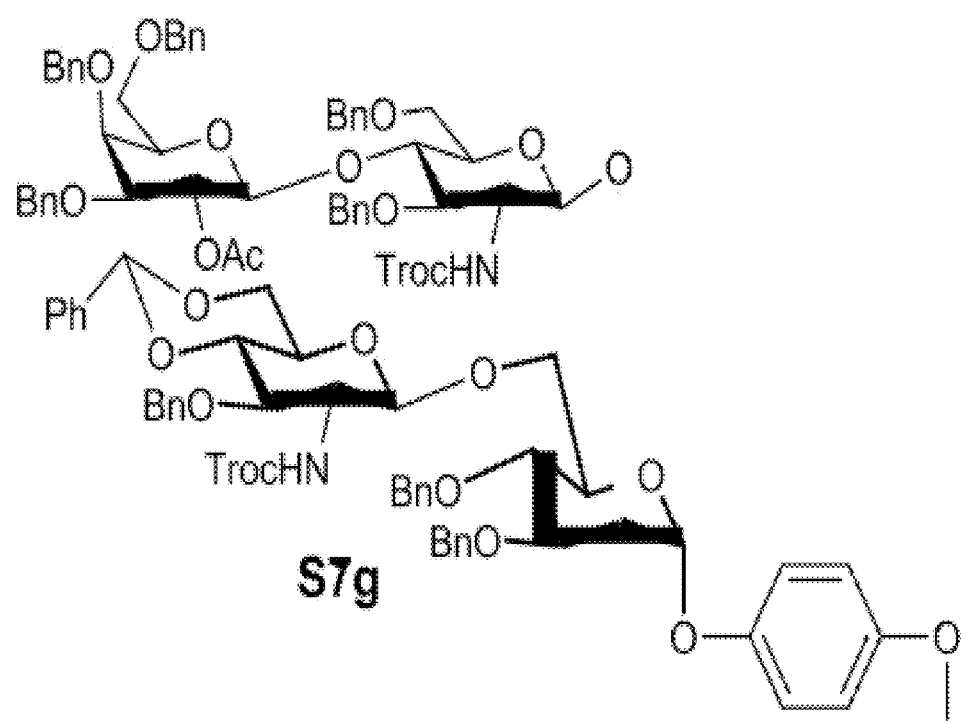
FIG. 51 shows exemplary structure embodiments and synthetic scheme embodiments of the present disclosure.
Figure 52:
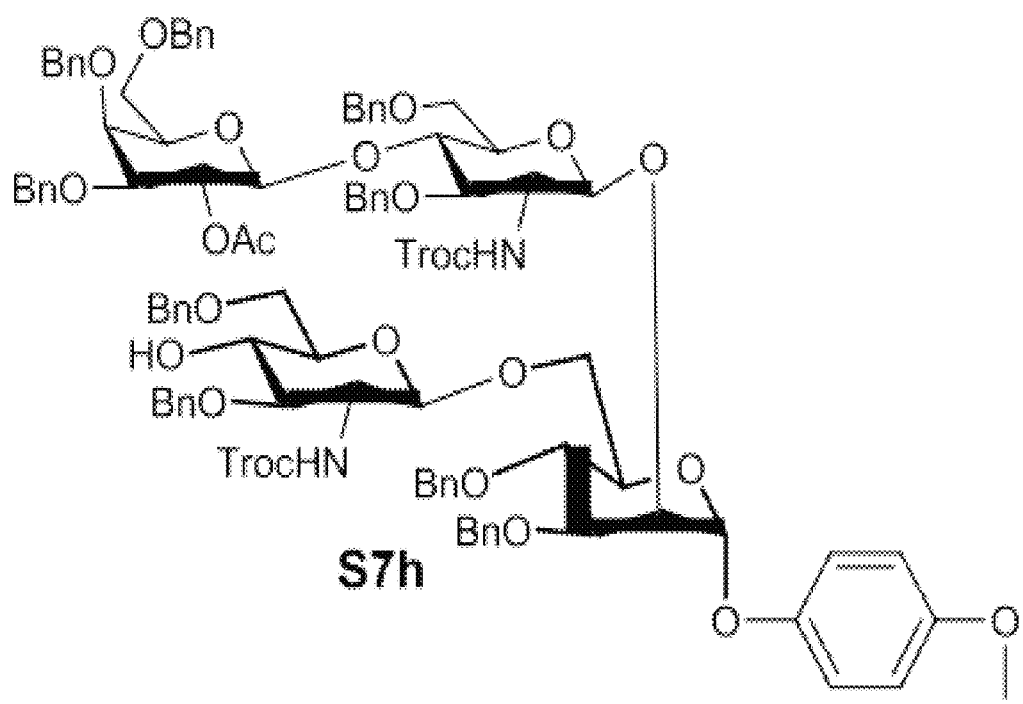
FIG. 52 shows exemplary structure embodiments and synthetic scheme embodiments of the present disclosure.
Figure 53:
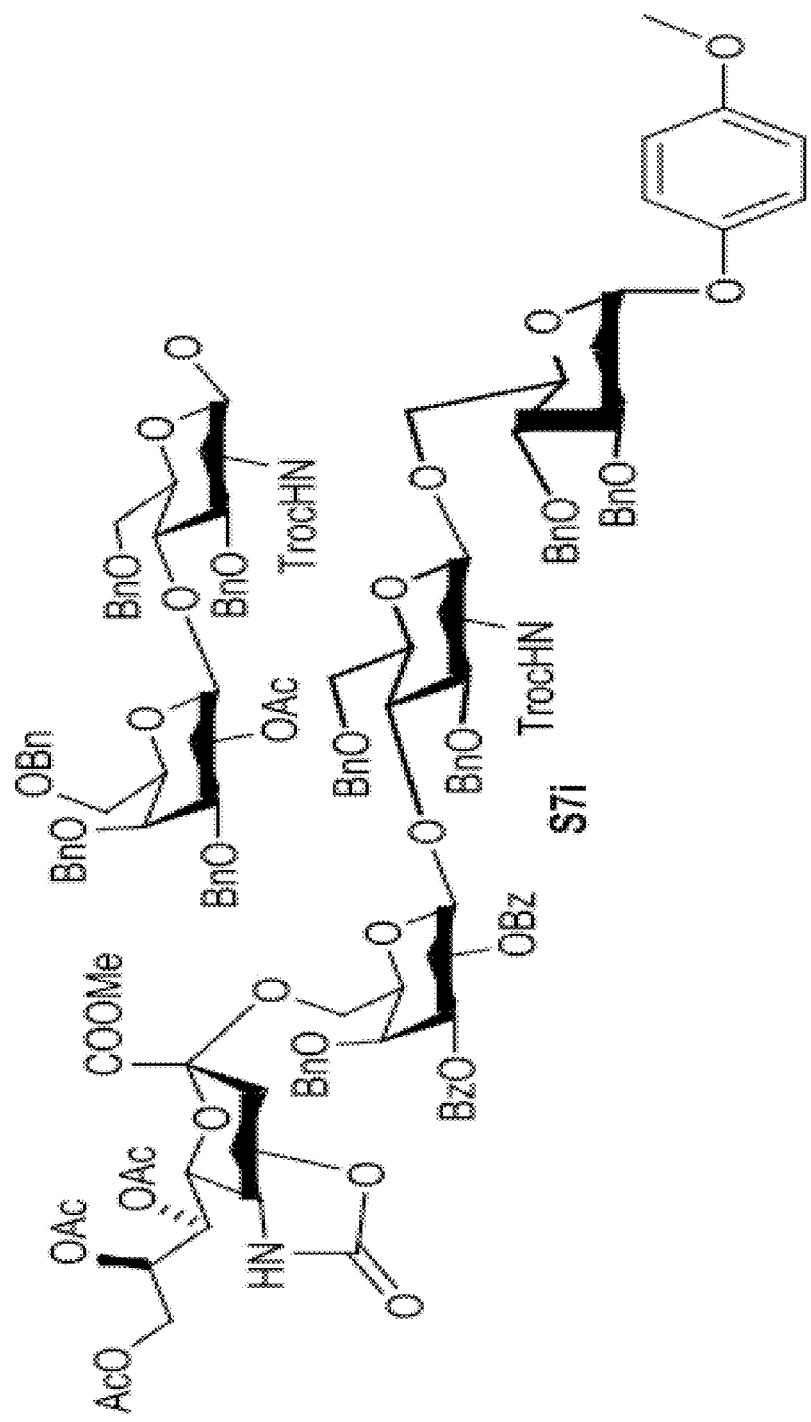
FIG. 53 shows exemplary structure embodiments and synthetic scheme embodiments of the present disclosure.
Figure 54:
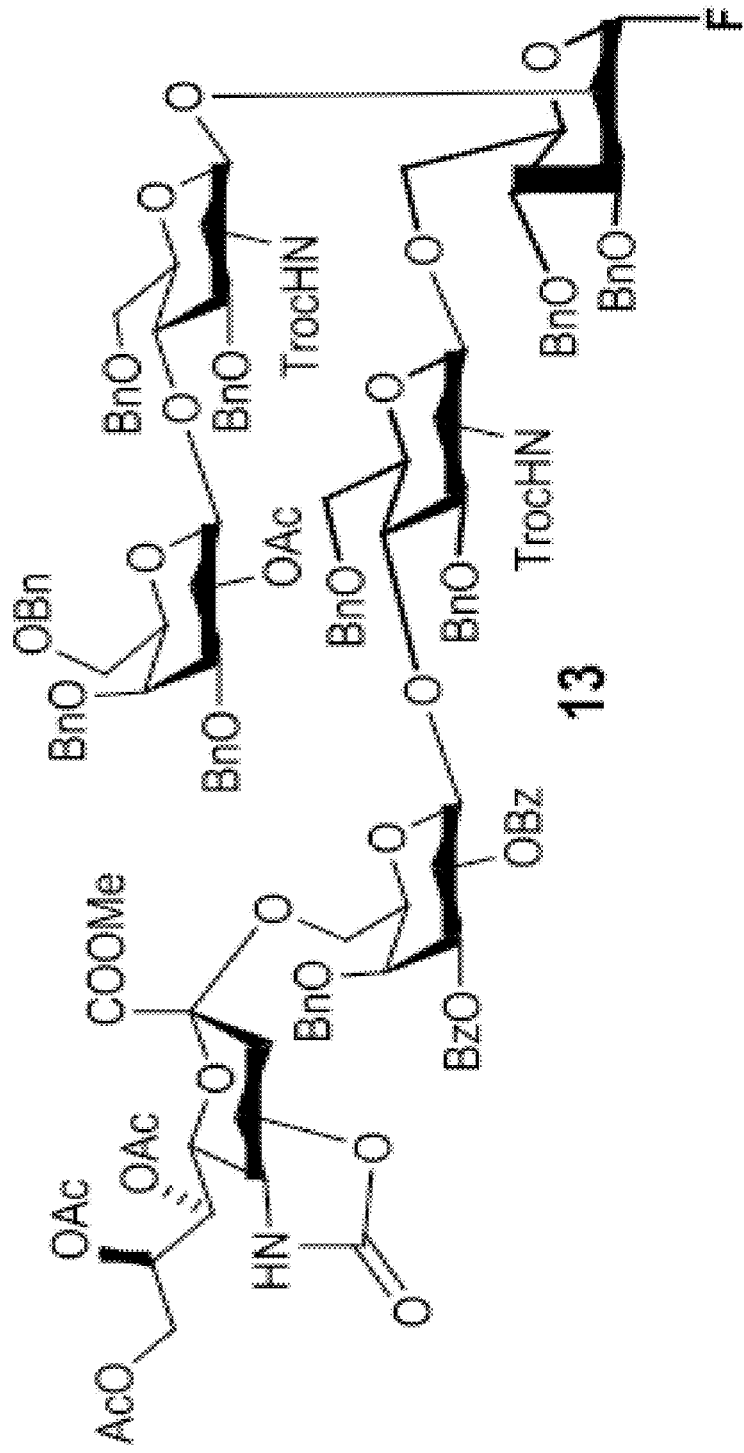
FIG. 54 shows exemplary structure embodiments and synthetic scheme embodiments of the present disclosure.

Total chemical synthesis of partially sialylated antennae 13 is shown in scheme S7 as shown in FIGS. 47A, 47B and 47C.

Scheme S7 as shown in FIGS. 47A, 47B and 47C depicts the preparation of compound 13. i, NIS, TfOH, CH2Cl2, −50° C., 86%; ii, BH3.THF, Bu2BOTf, CH2Cl2, 65%; iii, NIS, TfOH, CH2Cl2, −50° C., 76%; iv, (1) EDA, n-BuOH, 90° C., (2) Troc-Cl, NaHCO3, CH2Cl2; (3) Ac2O, pyridine, 65% over 3 steps; v, Triethyl silane, TFA, CH2Cl2, 58%; vi, NIS, TfOH, CH2Cl2, −50° C., 73%; vii, (1) CAN, ACN:Toluene:H2O, (2) DAST, CH2Cl2, −30° C., 30% over 2 steps.

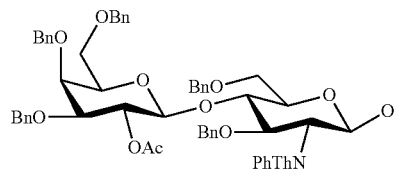

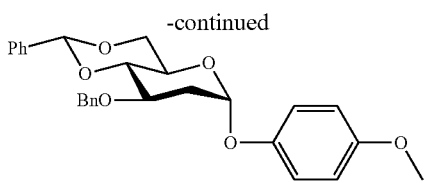

p-methoxyphenyl-O-2-O-acetyl-3,4,6-O-tri-benzyl-β-D-galactopyranosyl-(1→4)-O-3,6-O-di-benzyl-2-deoxy-2-phthalimido-β-D-glucopyranosyl-(1→2)-O-3,4-O-benzyl-α-D-mannopyranoside (S7c): Activated 4 Å molecular sieves (1 g) were added to a solution of acceptor S7a (0.500 g, 1.07 mmol) and donor S7b (1.21 g, 1.28 mmol) in anhydrous CH2Cl2 (10 mL). The reaction mixture was stirred for 1 h at room temperature then cooled to −50° C. NIS (0.481 g, 2.14 mmol) and TMSOTf (48 μL, 0.267 mmol) were added slowly, and the resulting reaction mixture was stirred for 3 h. When TLC (ethyl acetate:toluene, 1/9) indicated formation of product with consumption of starting material, the reaction was quenched by adding Et3N then filtered through Celite. The filtrate was washed with aqueous NaHCO3 (2×50 mL), aqueous Na2S2O3 (2×50 mL), and brine (50 mL) solution. The organic layer was dried over Na2SO4 and concentrated in vacuo. The residue was purified by flash column chromatography (0%→10% EA in toluene) to afford S7c (1.30 g, 86%) as a pale yellow solid. TLC (ethyl acetate:toluene=1/9, v/v): Rf=0.59; 1H NMR (600 MHz, CDCl3): δ 7.75-7.65 (m, 4H), 7.37-7.15 (m, 30H), 6.98 (d, J=8.1 Hz, 2H), 6.82 (d, J=8.4 Hz, 3H), 6.70 (d, J=8.4 Hz, 2H), 6.60 (d, J=9.2 Hz, 2H), 5.39 (s, 1H), 5.34 (t, J=10.2 Hz, 1H), 5.22 (dd, J=7.2 & 2.8 Hz, 1H), 5.06 (d, J=3.2 Hz, 1H), 4.89 (d, J=11.4 Hz, 1H), 4.82 (d, J=12.1 Hz, 1H), 4.75 (d, J=11.8 Hz, 1H), 4.66-4.62 (m, 3H), 4.54-4.38 (m, 6H), 4.32 (d, J=11.2 Hz, 1H), 4.29 (dd, J=3.1 & 7.2 Hz, 2H), 4.27 (d, J=10.8 Hz, 1H), 4.19 (t, J=8.3 Hz, 1H), 4.00-3.89 (m, 4H), 3.72 (s, 3H), 3.58-3.33 (m, 8H), 3.0 (t, J=8.7 Hz, 1H), 2.07 (s, 3H); 13C NMR (150 MHz, CDCl3): δ 169.3, 154.9, 149.6, 138.8, 138.7, 138.6, 138.5, 138.1, 138.0, 137.9, 137.5, 133.6, 131.9, 128.7, 128.4, 128.4, 128.3, 128.2, 128.1, 128.1, 128.1, 128.0, 127.8, 127.8, 127.7, 127.7, 127.7, 127.6, 127.6, 127.5, 127.4, 127.3, 127.2, 126.8, 126.0, 123.0, 117.03, 114.5, 101.4, 100.9, 97.0, 96.2, 96.2, 80.3, 78.1, 78.0, 75.6, 74.9, 74.5, 74.4, 73.7, 73.4, 73.3, 72.6, 72.6, 72.0, 71.7, 71.3, 68.4, 68.1, 68.1, 64.2, 55.6, 55.6, 55.6, 21.0; ESI-MS: m/z calcd for C, 84; H, 83; NO, 19; 1409.5559 found 1432.5499 (M+Na)+.

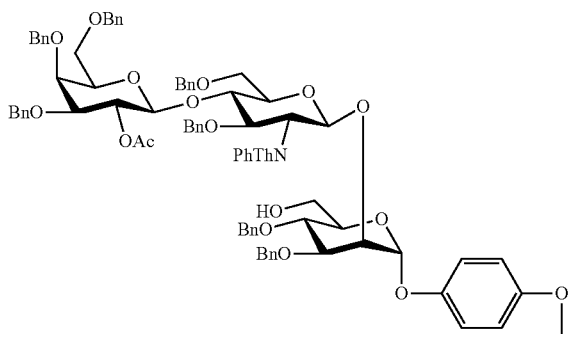

p-methoxyphenyl-O-2-O-acetyl-3,4,6-O-tri-benzyl-β-D-galactopyranosyl-(1→4)-O-3,6-O-di-benzyl-2-deoxy-2-phthalimido-β-D-glucopyranosyl-(1→2)-O-3,4-O-dibenzyl-α-D-mannopyranoside (S7d): To a mixture of compound S7c (1.30 g, 1.02 mmol) and activated molecular sieves (1 g) in anhydrous CH2Cl2 (15 mL) was added borane.THF complex (0.978 mL of a 1M solution in THF, 10.2 mmol) and Bu2BOTf (0.439 mL of a 1M solution in CH2Cl2, 10.2 mmol) were added at 0° C. The reaction mixture was allowed to stirred at room temperature for 4 h. TLC (acetone:toluene, 1/9) indicated formation of a product with consumption of the starting material. Triethyl amine was added to the reaction mixture followed by slow addition of methanol at 0° C. When no more hydrogen was produced, the reaction mixture was filtered through Celite, the filtrate was washed with aqueous NaHCO3 (2×50 mL), and brine (50 mL) solution. The organic layer was dried over Na2SO4 and concentrated in vacuo. The residue was purified by flash column chromatography (0%→7% EA in toluene) to afford S7d (0.850 g, 65%) as clear foam. TLC (acetone:toluene=1/9, v/v): Rf=0.31; 1H NMR (600 MHz, CDCl3): δ 7.84-7.66 (m, 4H), 7.42-7.02 (m, 30H), 7.03 (d, J=8.4 Hz, 2H), 6.87 (t, J=7.8 Hz, 3H), 6.67 (d, J=12.1 Hz, 2H), 6.48 (d, J=12.1 Hz, 2H), 5.39 (t, J=10.2 Hz, 1H), 5.17 (d, J=8.4 Hz, 1H), 4.93 (d, J=12 Hz, 2H), 4.88 (d, J=7.2 Hz, 1H), 4.85 (d, J=12.1 Hz, 2H), 4.67 (dd, J=4.3 & 8.4 Hz, 2H), 4.59-4.30 (m, 11H), 4.18 (t, J=7.4 Hz, 1H), 4.01-3.96 (m, 3H), 3.84-3.78 (m, 3H), 3.76 (s, 3H), 3.68 (dd, J=3.2 & 7.8 Hz, 1H), 3.54-3.34 (m, 6H), 3.25-3.20 (m, 1H), 2.01 (s, 3H); 13C NMR (150 MHz, CDCl3): δ 169.3, 167.9, 154.7, 149.6, 138.9, 138.3, 138.4, 138.2, 138.0, 138.0, 137.9, 134.1, 133.6, 131.9, 131.5, 129.0, 128.4, 128.4, 128.4, 128.3, 128.2, 128.2, 128.1, 128.1, 127.9, 127.8, 127.8, 127.7, 127.7, 127.7, 127.6, 127.6, 127.5, 127.3, 127.3, 126.8, 123.2, 123.0, 116.8, 114.4, 100.9, 97.6, 95.7, 80.3, 78.0, 76.9, 75.2, 75.1, 74.4, 74.4, 73.9, 73.6, 73.4, 73.3, 72.5, 72.3, 72.0, 71.6, 70.7, 68.6, 68.1, 62.2, 55.9, 55.6, 21.0; ESI-MS: m/z calcd for C, 84; H, 85; NO, 19; 1411.5716 found 1412.5726 (M+H)+.

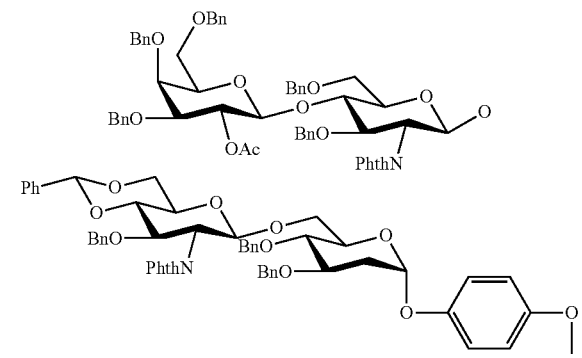

p-methoxyphenyl-O-[2-O-acetyl-3,4,6-O-tri-benzyl-β-D-galactopyranosyl-(1→4)-O-3,6-O-di-benzyl-2-deoxy-2-phthalimido-β-D-glucopyranosyl]-(1→2)-O-[3-O-benzyl-4,6-O-benzylidine-2-deoxy-2-phthalimido-β-D-glucopyranosyl]-(1→6)-3,4-O-dibenzyl-α-D-mannopyranoside (S7f): Activated 4 Å molecular sieves (1 g) were added to a solution of acceptor S7d (0.600 g, 0.470 mmol) and donor S7e (0.557 g, 0.940 mmol) in anhydrous CH2Cl2 (10 mL). The reaction mixture was stirred for 1 h at room temperature then cooled to −50° C. NIS (0.211 g, 0.940 mmol) and TfOH (10.4 μL, 0.117 mmol) were added slowly, and the resulting reaction mixture was stirred for 2 h. When TLC (ethyl acetate:toluene, 2/8) indicated formation of product with consumption of starting material, the reaction was quenched by adding Et3N then filtered through Celite. The filtrate was washed with aqueous NaHCO3 (2×50 mL), aqueous Na2S2O3 (2×50 mL), and brine (50 mL) solution. The organic layer was dried over Na2SO4 and concentrated in vacuo. The residue was purified by flash column chromatography (0%→15% EA in toluene) to afford S7f (0.610g, 76%) as clear foam. TLC (ethyl acetate:toluene=2/8, v/v): Rf=0.49; 1H NMR (600 MHz, CDCl3): δ 7.66 (m, 8H), 7.38-7.15 (m, 29H), 7.10 (d, J=8.4 Hz, 2H), 6.95-6.91 (m, 5H), 6.88-6.78 (m, 5H), 6.63 (d, J=8.4 Hz, 2H), 6.50 (d, J=8.8 Hz, 2H), 5.41 (s, 1H), 5.32 (t, J=10.2 Hz, 1H), 5.11 (d, J=8.4 Hz, 1H), 4.89 (d, J=4.3 Hz, 1H), 4.87 (s, 1H), 4.80 (t, J=8.8 Hz, 2H), 4.73 (s, 1H), 4.70 (s, 1H), 4.60 (t, J=10.8 Hz, 3H), 4.57-4.40 (m, 5H), 4.35-4.16 (m, 8H), 4.08 (t, J=10.2 Hz, 1H), 4.00-3.89 (m, 4H), 3.85 (dd, J=3.6 & 7.8 Hz, 1H), 3.78 (s, 3H), 3.70-3.61 (m, 3H), 3.52-3.41 (m, 4H), 3.40-3.28 (m, 4H), 3.20 (t, J=10.2 Hz, 2H), 2.98 (m, 1H), 1.98 (s, 3H); 13C NMR (150 MHz, CDCl3): δ 168.5, 164.8, 158.0, 153.0, 152.8, 151.6, 151.5, 150.6, 150.5, 149.2, 139.6, 138.9, 138.4, 138.1, 138.0, 137.4, 129.3, 129.2, 128.9, 128.9, 128.8, 128.9, 128.7, 128.5, 128.4, 128.2, 128.1, 128.0, 128.0, 127.9, 127.9, 127.7, 127.5, 127.4, 126.2, 125.5, 117.3, 114.9, 114.2, 102.2, 101.4, 100.9, 98.8, 96.5, 95.8, 95.7, 95.5, 95.3, 95.3, 95.0, 82.3, 80.6, 78.3, 76.2, 76.0, 75.8, 75.5, 75.4, 75.2, 74.9, 74.8, 74.7, 74.7, 74.2, 74.1, 73.8, 73.7, 73.5, 72.9, 72.3, 71.9, 68.9, 68.8, 68.2, 68.0, 66.4, 58.0, 57.1, 55.9, 44.3, 42.9, 40.8, 40.4, 40.3, 40.0, 21.7, 21.2; ESI-MS: m/z calcd for C, 111; H, 108; N, 2; O, 24; 1882.7247 found 1882.7343.

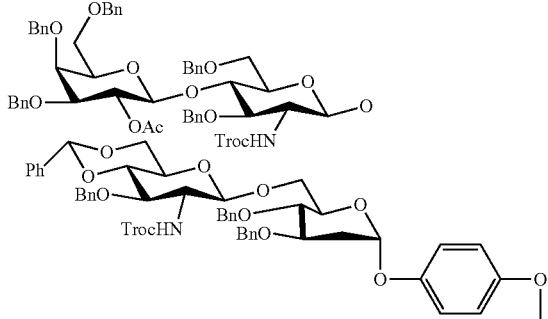

S7g p-methoxyphenyl-O-[2-O-acetyl-3,4,6-O-tri-benzyl-β-D-galactopyranosyl-(1→4)-O-3,6-O-di-benzyl-2-deoxy-2-(2,2,2-trichloroethoxy)carbonylamino-β-D-glucopyranosyl]-(1→2)-O-[3-O-benzyl-4,6-O-benzylidine-2-(2,2,2-trichloroethoxy)carbonylamino-β-D-glucopyranosyl]-(1→6)-3,4-dibenzyl-α-D-mannopyranoside (S7g): A mixture of compound S7f (0.950 g, 0.545 mmol) and 10 mL of ethylene diamine:n-BuOH (2:8) was stirred at 90° C. overnight. Volatiles were evaporated, and the crude product was dried using high vacuum. It was then dissolved in CH2Cl2 (20 mL), NaHCO3 (0.363 g, 5.45 mmol) and 2,2,2-trichloro ethyl chloroformate (0.86 mL, 5.45 mmol) were added at 0° C., allowed it to warm to rt and stirred for overnight. TLC (ethyl acetate:toluene, 2/8) indicated formation of product with consumption of starting material. The reaction mixture was diluted with CH2Cl2 (100 mL), washed with water (2×50 mL) and brine (50 mL) solution. The organic layer was dried over Na2SO4 and concentrated in vacuo. The residue was purified by silica gel column chromatography (0%→10% EA in toluene). The product was then acetylated using 10 mL of pyridine/acetic anhydride (6:4) until TLC indicated (ethyl acetate:toluene, 2/8) complete consumption of starting material. The reaction mixture was then concentrated in vacuo and purified by silica gel column chromatography (0%→10% EA in toluene) to afford S7g as a white foam (0.650 g, 65%). TLC (ethyl acetate:toluene=2/8, v/v): Rf=0.64; H NMR (600 MHz, CDCl3): δ 7.48 (d, J=7.8 Hz, 2H), 7.39 (d, J=8.2 Hz, 2H), 7.35-7.12 (m, 41H), 6.91 (d, J=10.2 Hz, 2H), 6.87 (d, J=10.3 Hz, 2H), 5.55 (s, 1H), 5.50 (s, 1H), 5.32 (t, J=10.2 Hz, 1H), 4.94-4.89 (m, 8H), 4.83-4.67 (m, 10H), 4.64-4.66 (m, 5H), 4.54-4.50 (m, 3H), 4.36-4.22 (m, 6H), 4.06-3.87 (m, 6H), 3.83-3.46 (m, 10H), 3.38-3.34 (m, 3H), 3.20-3.10 (m, 2H), 2.33 (s, 3H); 13C NMR (150 MHz, CDCl3): δ 169.5, 162.8, 155.0, 155.0, 154.8, 154.6, 154.51, 150.6, 150.5, 150.2, 139.6, 138.9, 138.4, 138.3, 138.3, 138.2, 138.1, 137.5, 129.3, 129.2, 128.7, 128.6, 128.6, 128.5, 128.5, 128.4, 128.3, 128.2, 128.1, 128.0, 128.0, 127.9, 127.9, 127.7, 127.5, 127.4, 126.2, 125.5, 117.3, 114.9, 114.2, 102.2, 101.4, 100.8, 98.3, 96.5, 95.8, 95.7, 95.5, 95.3, 95.3, 95.0, 82.3, 80.6, 78.3, 76.2, 76.0, 75.8, 75.5, 75.4, 75.2, 74.9, 74.8, 74.7, 74.7, 74.2, 74.1, 73.8, 73.7, 73.5, 72.9, 72.3, 71.9, 68.9, 68.8, 68.2, 68.0, 66.4, 58.0, 57.1, 55.9, 44.3, 42.9, 40.8, 40.4, 40.3, 40.0, 21.7, 21.2; ESI-MS: m/z calcd for C, 102; H, 106; C, 16; N, 2; O, 25; 1962.6590 found 1973.5278 (M+H)+.

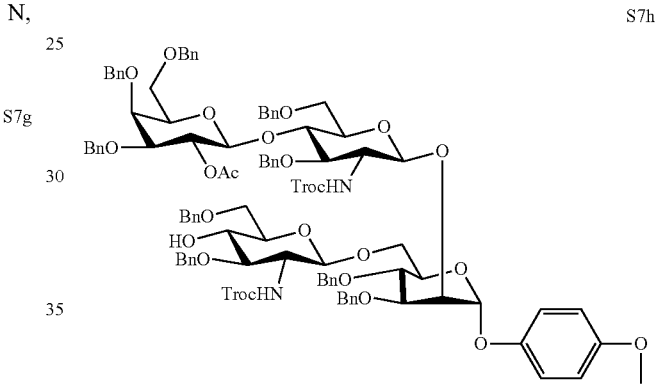

S7h p-methoxyphenyl-O-[2-O-acetyl-3,4,6-O-tri-benzyl-β-D-galactopyranosyl-(1→4)-O-3,6-O-di-benzyl-2-deoxy-2-(2,2,2-trichloroethoxy)carbonylamino-β-D-glucopyranosyl]-(1→2)-O-[3,6-O-dibenzyl-2-deoxy-2-(2,2,2-trichloroethoxy)carbonylamino-β-D-glucopyranosyl]-(1→6)-3,4-dibenzyl-α-D-mannopyranoside (S7h): To a solution of S7g (0.600 g, 0.328 mmol) in anhydrous CH2Cl2 (70 mL) was added triethyl silane (2.10 mL, 13.2 mmol) followed by trifluroacetic acid (0.953 mL, 13.2 mmol) at 0° C. The resulting reaction mixture was stirred for 2 h. After 2 h, TLC (ethyl acetate:toluene, 1.5/8.5 v/v) indicated product formation with consumption of starting material. The reaction mixture was washed with sat. NaHCO3 (2×50 mL). The aqueous layer was further extracted with CH2Cl2 (3×30 mL), and the combined organic layer were washed with brine solution (100 mL), dried over MgSO4, filtered and concentrated in vacuo. The residue was purified by flash column chromatography (0%→10% EA in toluene) to afford S7h (0.350 g, 58%) as clear oil. TLC (ethyl acetate:toluene=1.5/8.5, v/v): Rf=0.35; 1H NMR (600 MHz, CDCl3): δ 7.33-7.04 (m, 45H), 6.92 (d, J=8.2 Hz, 2H), 6.80 (d, J=8.3 Hz, 2H), 5.55 (s, 1H), 5.31 (t, J=10.1 Hz, 1H), 5.06 (d, J=3.2 Hz, 1H), 4.93-4.80 (m, 4H), 4.47-4.35 (m, 13H), 4.35-4.18 (m, 8H), 4.05 (dd, J=3.2 & 7.8 Hz, 2H), 3.82 (d, J=8.4 Hz, 2H), 3.80-3.62 (m, 14H), 3.49-3.20 (m, 6H), 3.10 (bs, 2H), 2.08 (s, 3H); 13C NMR (150 MHz, CDCl3): δ 169.5, 168.0, 155.3, 155.0, 154.7, 150.2, 138.9, 138.4, 138.3, 138.2, 137.8, 132.7, 131.1, 129.0, 128.7, 128.7, 128.6, 128.6, 128.6, 128.5, 128.4, 128.3, 128.2, 128.1, 128.1, 128.0, 127.9, 127.8, 127.7, 127.5, 127.4, 117.3, 114.9, 101.5, 100.8, 95.7, 80.6, 78.5, 75.8, 75.3, 74.9, 74.8, 74.6, 74.1, 74.0, 73.8, 73.7, 73.64, 73.5, 72.8, 72.3, 71.9, 71.1, 68.9, 68.8, 68.4, 68.2, 67.6, 58.0, 56.5, 55.9, 41.5, 39.0, 37.3, 33.7, 32.0, 31.4, 30.6, 29.9, 29.20, 26.6, 24.0, 23.2, 22.9, 21.2, 20.1, 14.6, 14.4, 14.3, 14.3, 11.2; ESI-MS: m/z calcd for C, 102; H, 108; C, 16; N, 2; O, 25; 1974.6750 found 1975.5438 (M+H)+.

127.5, 127.4, 127.1, 127.08, 116.9, 114.5, 101.3, 100.6, 100.4, 100.0, 95.3, 80.2, 79.9, 77.4, 75.5, 75.3, 74.5, 74.3, 74.1, 73.7, 73.4, 73.2, 73.1, 72.5, 72.1, 71.5, 71.2, 70.8, 68.6, 68.5, 68.3, 67.8, 67.5, 67.3, 63.1, 61.5, 57.8, 56.6, 55.5, 53.1, 38.6, 37.0, 36.8, 33.3, 32.0, 31.0, 30.9, 28.8, 26.2, 25.5, 23.6, 22.8, 22.5, 20.8, 20.6, 19.7, 14.3, 13.9, 10.8; ESI-MS: m/z calcd for C, 146; H, 153; C, 16; N, 3; O, 43; 2850.5080 found 2850.8248.

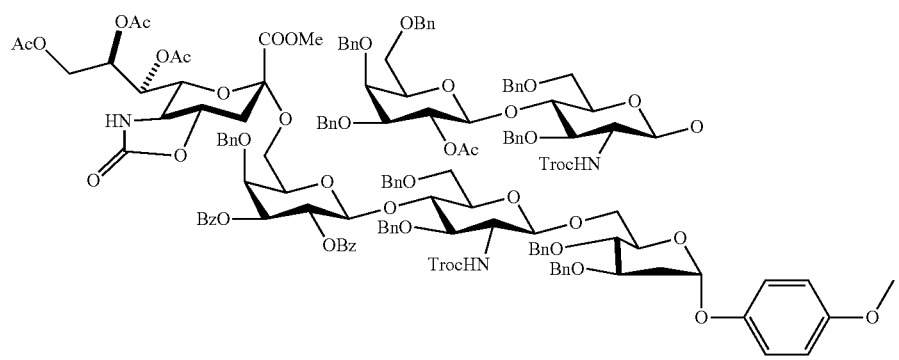

S7i p-methoxyphenyl-O-[2-O-acetyl-3,4,6-O-benzyl-β-D-galactopyranosyl-(1→4)-O-3,6-O-di-benzyl-2-deoxy-2-(2,2,2-trichloroethoxy)carbonylamino-β-D-glucopyranosyl-(1→2)-[Methyl-5-acetamido-7,8,9-tri-O-acetyl-3,5-dideoxy-D-glycero-α-D-galacto-non-2-ulopyranosylonate]-(2→6)-4-O-benzyl-2,3-di-O-benzoyl-1-β-D-galactopyranosyl-(1→4)-O-3,6-O-di-benzyl-2-deoxy-2-(2,2,2-trichloroethoxy)carbonylamino-β-D-glucopyranosyl-(1→6)-O-3,4,-di-O-benzyl-α-D-mannopyranoside (S7i): A mixture of donor S4c (0.187 g, 0.182 mmol), acceptor S7h (0.300 g, 0.151 mmol) and activated 4 Å molecular sieves (0.700 g) in dry CH2Cl2 (10 mL) was stirred at room temperature for 1 h. The reaction mixture was cooled to −50° C., NIS (0.067 g, 0.302 mmol) and TfOH (4 µL, 0.037 mmol) were added slowly and resulting reaction mixture was stirred for 2 h. The reaction was quenched by adding Et3N, diluted with CH2Cl2, filtered through Celite, extracted with saturated Na2S2O3 followed by NaHCO3, dried over sodium sulfate and concentrated in vacuo. The residue was purified by flash column chromatography (0%→10% EA in toluene) to afford S7i (0.317 g, 73%) as colorless foam. TLC: (ethyl acetate:toluene=1.5/8.5, v/v): Rf=0.61; 1H NMR (600 MHz, CDCl3): δ 7.90 (m, 4H), 5.52-7.45 (m, 2H), 7.37-7.08 (m, 59H), 6.90 (d, J=8.3 Hz, 2H), 6.80 (d, J=8.3 Hz, 2H), 5.72 (t, J=10.2 Hz, 1H), 5.53 (s, 1H), 5.35-5.32 (m, 3H), 5.20 (dd, J=3.2 & 8.3 Hz, 1H), 5.08 (dd, J=2.8 & 8.4 Hz, 2H), 4.99-4.79 (m, 7H), 4.70-4.18 (m, 26H), 4.06 (dd, J=3.2 & 7.8 Hz, 1H), 3.94 (m, 2H), 3.90-3.84 (m, 10H), 3.74 (s, 3H), 2.60 (s, 3H), 2.59-2.57 (m, 3H), 3.45-3.32 (m, 6H), 3.20 (t, J=9.8 Hz, 1H), 2.90 (t, J=10.2 Hz, 2H), 2.83 (dd, J=3.2 & 7.8 Hz, 1H), 2.08 (s, 3H), 2.06 (s, 3H), 2.02 (t, J=10.1 Hz, 1H), 1.99 (s, 3H), 1.91 (s, 3H); 13C NMR (150 MHz, CDCl3): δ 171.4, 170.5, 169.7, 169.1, 167.4, 165.7, 165.1, 159.1, 154.6, 159.8, 138.5, 138.2, 138.1, 137.9, 137.4, 133.3, 133.1, 132.3, 130.2, 129.8, 129.6, 129.4, 128.7, 128.5, 128.4, 128.1, 127.9,

13

[2-O-acetyl-3,4,6-O-benzyl-β-D-galactopyranosyl-(1→4)-O-3,6-O-di-benzyl-2-deoxy-2-(2,2,2-chloroethoxy) carbonylamino-β-D-gluopyranosyl-(1→2)-[Methyl-5-acetamido-7,8,9-tri-O-acetyl-3,5-dideoxy-D-glycero-α-D-galacto-non-2-ulopyranosylonate]-(2→6)-4-O-benzyl-2,3-di-O-benzoyl-1-β-D-galactopyranosyl-(1→4)-O-3,6-O-di-benzyl-2-deoxy-2-(2,2,2-trichloroethoxy) carbonylamino-β-D-glucopyranosyl-(1→6)-O-3,4,-di-O-benzyl-α-D-mannopyranosyl fluoride (13): To a solution of compound S7i (0.430 g, 0.150 mmol) in 10 mL of acetonitrile:toluene:H2O (4:2:1) was added cerium ammonium nitrate (0.641 g, 0.754 mmol) and the resulting reaction mixture was stirred at 0° C. for 2 h. The reaction was diluted with EtOAc (100 mL) and washed with H2O (30×2 mL) and brine (30 mL). The organic layer was dried over Na2SO4 and concentrated in vacuo. The product was purified by flash column chromatography (0%→20% EA in toluene) to afford 1-OH compound (0.240 g, 57%) as clear foam. The residue (0.200 g, 0.072 mmol) was dissolved in CH2Cl2 (10 mL) at −30° C. Then, DAST (29 µL, 0.216 mmol) was added slowly, and the resulting reaction mixture was stirred for 2 h. When TLC (ethyl acetate:toluene, 2/8) indicated formation of product with consumption of starting material, the reaction was quenched with aq. NaHCO3. The filtrate was washed with aqueous NaHCO3 (2×50 mL) and brine (50 mL) solution. The organic layer was dried over Na2SO4 and concentrated in vacuo. The residue was purified by silica gel column chromatography (0%→10% EA in toluene) to afford 13 (0.104 g, 50%) as white foam. TLC (ethyl acetate:toluene=2/8, v/v): Rf=0.44; 1H NMR (600 MHz, CDCl3): δ 7.95-7.90 (m, 4H), 7.58-7.49 (m, 2H), 7.39-7.18 (m, 59H), 5.82 (t, J=10.2 Hz, 1H), 5.65 (d, J=51 Hz, 1H), 5.34 (t, J=10.2 Hz, 2H), 5.21 (dd, J=3.6 & 7.8 Hz, 1H), 5.13-4.19 (m, 30H), 4.10-4.09 (m, 5H), 4.02-3.74 (m, 12H), 3.65 (s, 3H), 3.64-3.27 (m, 14H), 3.02 (t, J=10.2 Hz, 2H), 2.87 (dd, J=3.2 & 7.8 Hz, 1H), 2.12 (s, 3H), 2.10 (s, 3H), 2.09 (t, J=10.2 Hz, 1H), 2.00 (s, 3H), 1.97 (s, 3H); 13C NMR (150 MHz, CDCl3): δ 171.4, 170.2, 169.7, 169.1, 167.4, 165.6, 165.1, 159.1, 154.4, 139.0, 138.8, 138.2, 138.1, 138.0, 137.7, 133.3, 129.8, 129.7, 129.2, 128.7, 128.4, 128.1, 127.9, 127.7, 127.6, 127.5, 127.4, 127.3, 127, 1, 127.0, 125.2, 101.4, 100.7, 100.4, 9.9, 97.3, 95.180.2, 79.6, 78.6, 75.5, 74.5, 74.3, 73.8, 73.5, 73.3, 73.1, 72.8, 71.3, 71.3, 70.7, 70.1, 68.6, 67.8, 66.9, 63.1, 61.5, 57.8, 53.1, 37.1, 25.5, 21.3, 20.9, 20.5; ESI-MS: m/z calcd for C, 139; H, 146; C, 16; FN, 3; O, 41; 2746.3454 found 2746.7604.

Preparation of core trisaccharides 14-15

The reducing end trisaccharide (Man-β-1,4-GlcNAc-β-1,4-GlcNAc-β-linker) 14 with N-pthallamide protections was obtained according to our previous report3. Compound 14 was next modified to 15 as shown in scheme S8 as shown in FIG. 55.

Figure 55:
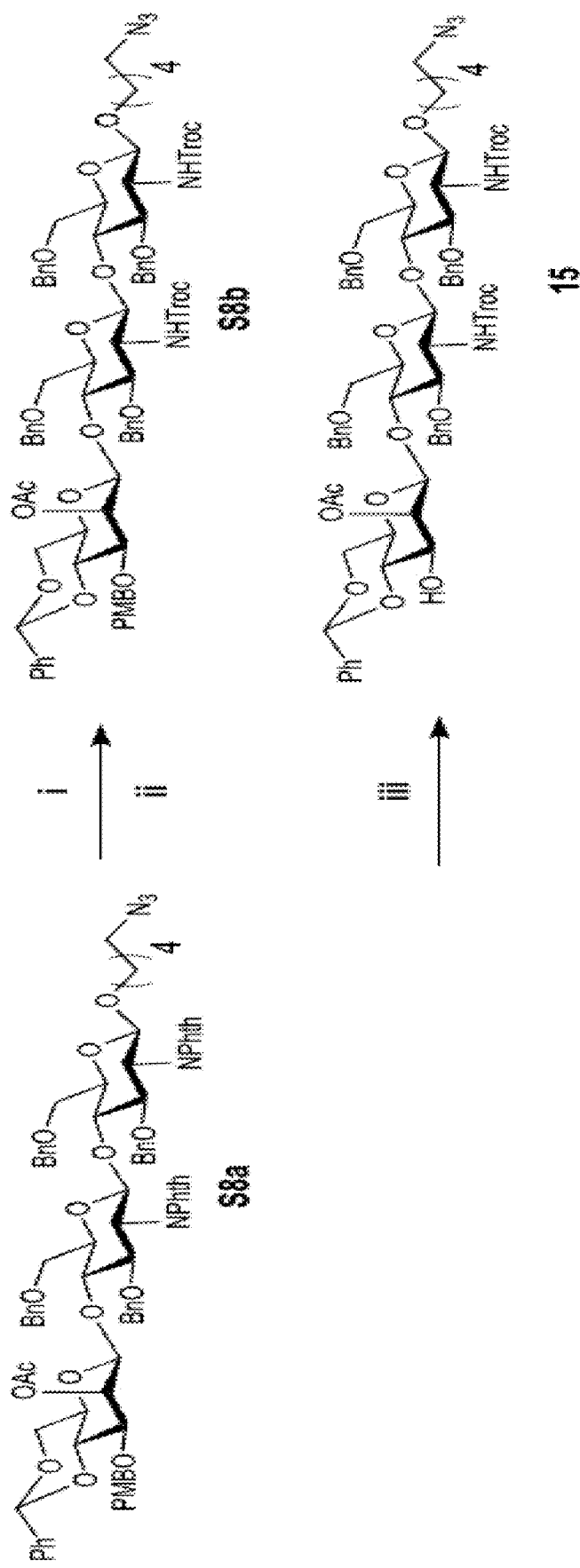
FIG. 55 shows exemplary structure embodiments and synthetic scheme embodiments of the present disclosure.
Figure 56:
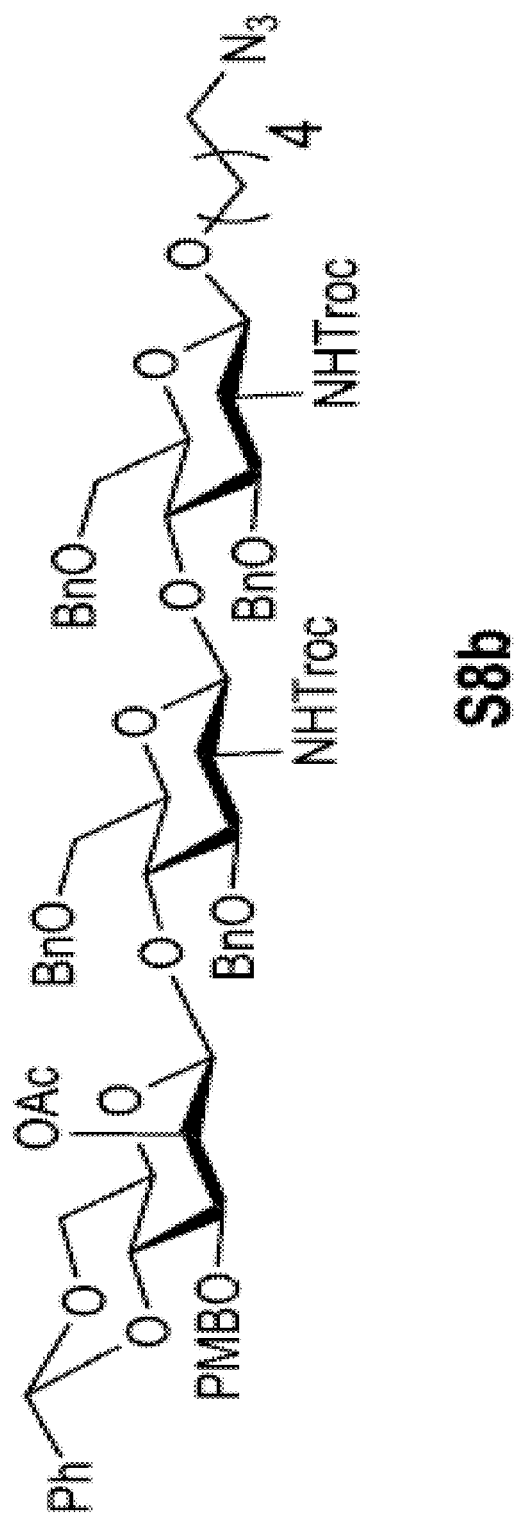
FIG. 56 shows exemplary structure embodiments and synthetic scheme embodiments of the present disclosure.
Figure 57:
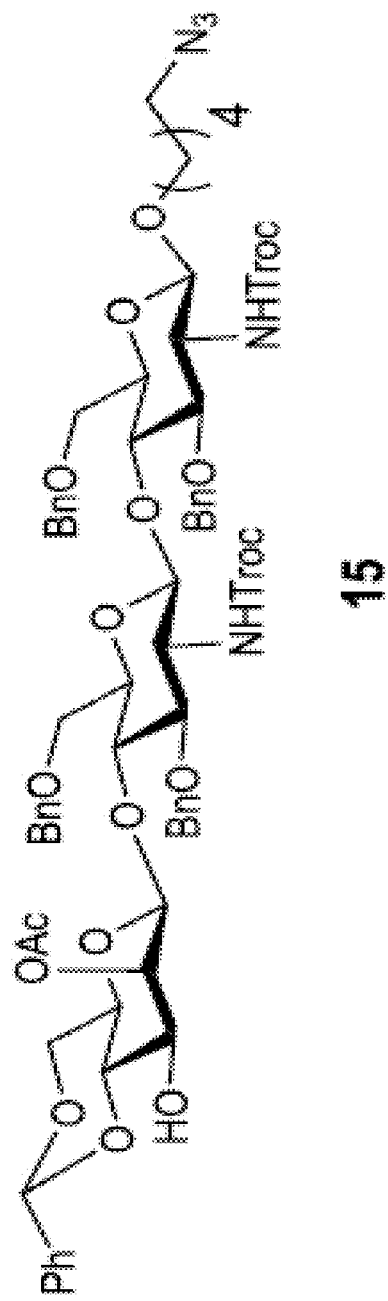
FIG. 57 shows exemplary structure embodiments and synthetic scheme embodiments of the present disclosure.

Scheme S8 as shown in FIG. 55 depicts the preparation of compound 15. i, (1) EDA, n-BuOH, 90° C., (2) Troc-Cl, NaHCO3, CH2Cl2, 72% over 2 steps; ii, Ac2O, pyridine, 79%; iii, DDQ, CH2Cl2H2O, 58%.

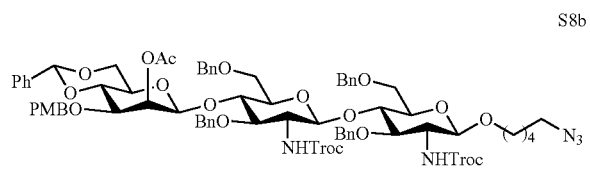

S8b

5-Azidopentyl-O-2-O-acetyl-3-O-p-methoxy-benzyl-4,6-O-benzylidine-β-D-mannopyranosyl-(1→4)-O-(3,6-di-O-benzyl-2-deoxy-2-(2,2,2-trichloroethoxy)carbonylamino-β-D-glucopyranosyl)-(1→4)-O-3,6-di-O-benzyl-2-deoxy-2-(2,2,2-trichloroethoxy)carbonylamino-β-D-glucopyranoside (S8b): A mixture of compound S8a (0.950 g, 0.545 mmol) and 10 mL of ethylene diamine:n-BuOH (2:8) was stirred at 90° C. overnight. Volatiles were evaporated, and the crude mixture was dried using high vacuum. It was then dissolved in CH2Cl2 (20 mL), NaHCO3 (0.363 g, 5.45 mmol) and 2,2,2-trichloro ethyl chloroformate (0.86 mL, 5.45 mmol) were added at 0° C., allowed it to warm to rt and stirred for overnight. TLC (ethyl acetate:toluene, 2/8) indicated formation of product with consumption of starting material. Reaction was diluted with CH2Cl2 (100 mL), washed with water (2×50 mL) and brine (50 mL) solution. The organic layer was dried over Na2SO4 and concentrated in vacuo. The residue was purified by silica gel column chromatography (0%→10% EA in toluene). The product was then acetylated using 10 mL of pyridine/acetic anhydride (6:4) until TLC indicated (ethyl acetate:toluene, 2/8) complete consumption of starting material. The reaction mixture was then concentrated in vacuo and purified by silica gel column chromatography (0%→10% EA in toluene) to afford S8b as a white foam (0.650 g, 65%). TLC (ethyl acetate:toluene=2/8, v/v): Rf=0.64; 1H NMR (600 MHz, CDCl3): δ 7.62-7.20 (m, 34H), 5.89 (s, 1H), 4.56 (d, J=3.2 Hz, 1H), 4.23 (d, J=8.9 Hz, 2H), 4.20-4.10 (m, 12H), 4.00-3.86 (m, 5H), 3.69-3.30 (m, 14H), 3.29 (s, 3H), 3.22-3.20 (m, 4H), 3.20-3.00 (m, 1H), 2.66 (s, 3H, —C(O)CH3, 1.56-1.38 (m, 4H, —CCH2C—, linker), 1.21-1.23 (m, 2H, —CCH2C—, linker); 13C NMR (150 MHz, CDCl3): δ 177.7, 169.6, 167.0, 138.5, 138.4, 138.3, 138.2, 137.2, 137.8, 137.5, 134.2, 133.2, 133.6, 131.7, 131.1, 131.45, 129.8, 129.06, 128.9, 128.2, 128.4, 128.2, 128.4, 128.7, 127.8, 127.87, 127.83, 127.4, 127.4, 127.0, 127.2, 127.29, 127.6, 127.20, 126.88, 126.24, 125.1, 123.6, 123.3, 101.5, 102.7, 99.7, 98.0, 97.1, 78.13, 78.55, 78.05, 75.82, 74.57, 75.38, 75.27, 74.25, 74.30, 72.78, 72.26, 70.89, 66.85, 68.43, 68.25, 67.75, 66.87, 55.57, 53.71, 52.10, 28.97, 28.87, 23.80, 22.77, 20.12; ESI-MS: m/z calcd for C, 74; H, 83; C, 16; N, 5; O, 20: 1575.1930; found 1576.235 (M+H)+.

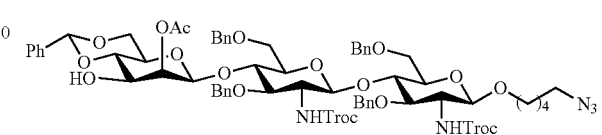

15

5-Azidopentyl-O-2-O-acetyl-4,6-O-benzylidine-β-D-mannopyranosyl-(1→4)-O-(3,6-di-O-benzyl-2-deoxy-2-(2,2,2-trichloroethoxy)carbonylamino-β-D-glucopyranosyl)-(1→4)-O-3,6-di-O-benzyl-2-deoxy-2-(2,2,2-trichloroethoxy)carbonylamino-β-D-glucopyranoside (15): To a solution of S8a (1.0 g, 0.673 mmol) in 10 mL (CH2Cl2:H2O, 10/1) was added DDQ (0.183 g, 0.808 mmol) at 0° C. and the resulting reaction mixture was stirred until TLC (ethyl acetate:toluene, 2/8) indicated formation of a product with consumption of the starting material. The reaction mixture was then filtered and the organic layer washed with H2O (2×30 mL). The aqueous layer was further extracted with CH2Cl2 (2×50 mL). The combined organic layers were washed with brine solution (40 mL), dried over Na2SO4, and concentrated in vacuo. The residue was purified by flash column chromatography (0%→15% EA in toluene) to afford 15 (0.652 g, 70%) as colorless foam. TLC (ethyl acetate:toluene=2/8 v/v): Rf=0.24; 1H NMR (600 MHz, CDCl3): δ 7.44-7.16 (m, 30H), 5.44 (s, 1H), 5.15 (d, J=3.2 Hz, 1H), 4.88 (t, J=8.9 Hz, 2H), 4.54-4.40 (m, 12H), 4.08-3.58 (m, 3H), 3.56-3.40 (m, 14H), 3.25-3.20 (m, 4H), 3.02-3.00 (m, 1H), 2.16 (s, 3H, —C(O)CH3, 1.51-1.47 (m, 4H, —CCH2C—, linker), 1.30-0.99 (m, 2H, —CCH2C—, linker); 13C NMR (150 MHz, CDCl3): δ 171.5, 168.6, 167.0, 138.7, 138.4, 138.38, 138.2, 137.2, 137.8, 137.5, 134.2, 133.2, 133.6, 131.7, 131.1, 131.45, 129.8, 129.06, 128.9, 128.2, 128.4, 128.2, 128.4, 128.7, 127.8, 127.87, 127.83, 127.4, 127.4, 127.0, 127.2, 127.29, 127.6, 127.20, 126.88, 126.24, 125.1, 123.6, 123.3, 101.5, 102.7, 99.7, 98.0, 97.1, 78.13, 78.55, 78.05, 75.82, 74.57, 74.37, 74.27, 73.25, 73.30, 72.78, 71.26, 69.89, 68.85, 69.43, 68.25, 67.73, 66.67, 56.57, 55.71, 51.10, 28.67, 28.27, 23.00, 21.47, 21.02; ESI-MS: m/z calcd for C, 66; H, 75; C, 16; N, 5; O, 19: 1455.0420; found 1476.3082 (M+Na)+.

Figure 58:
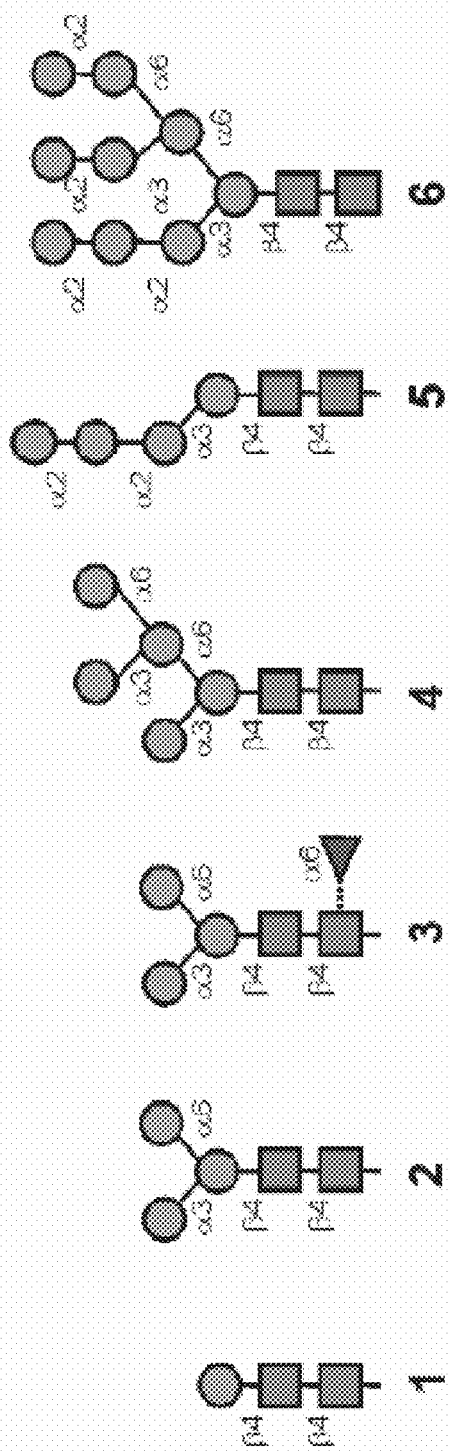
FIG. 58 Exemplary Structures of high mannose type glycans and their fragments.

Synthesis of high-mannose type oligosaccharides (G1-G6) as shown in FIG. 58 depicts the structures of high mannose type glycans and their fragments.

Figure 59A:
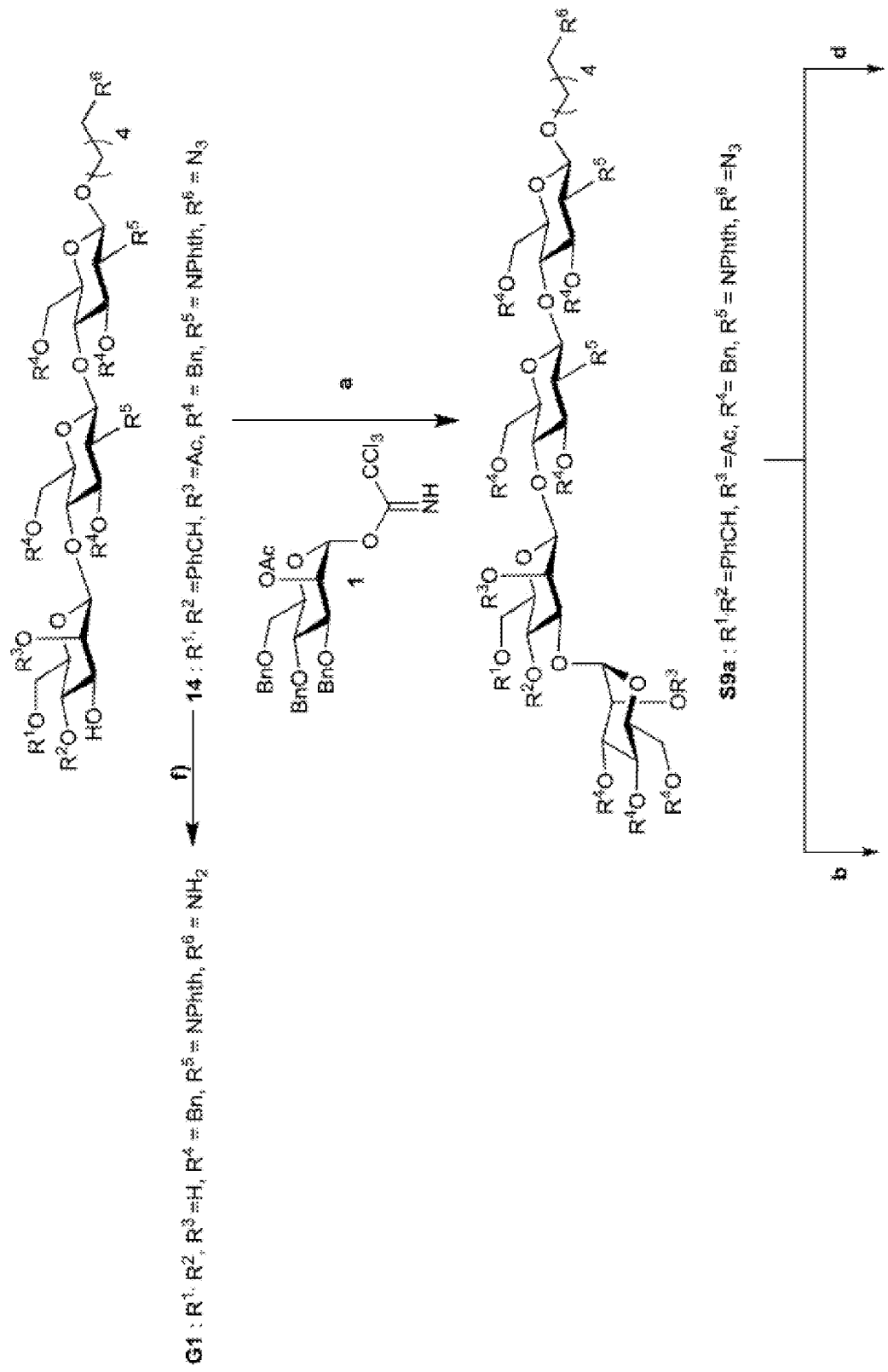
FIGS. 59A and 59B.
Figure 59B:
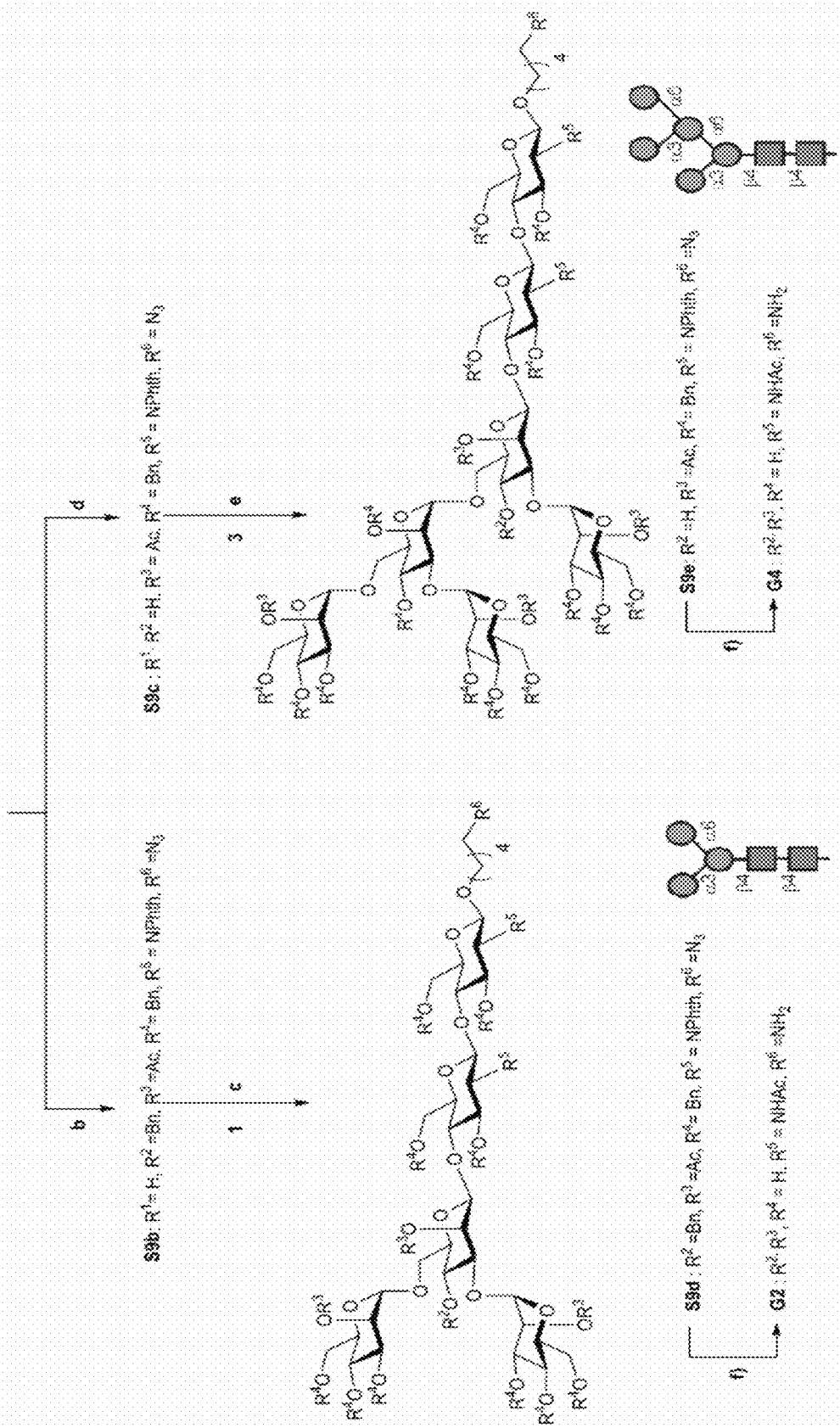

With the donors 1-5 in hand, we investigated their glycosylation with core trisaccharide acceptor 14 and the coupling products (Scheme S9 as shown in FIGS. 59A and 59B). The glycosylation of 14 with known imidate donor 1 to give tetrasaccharide S9a in 70% yield[11]. After selective benzylidene ring opening of S9a, the resulting 6″-OH S9b was glycosylated with 1 to afford the desired fully protected Man₃GlcNAc₂ pentasaccharide S9d, an early intermediate in N-Glycan biosynthesis and thus a conserved motif in all N-glycans, in 60% yield. In another pathway, reductive opening of the benzylidene group S9a resulted in diol S9c, which was further condensed with trimannosyl fluoride 4 by using Cp₂HfCl₂ and AgOTf to obtain heptasaccharide S9e, an intermediate in GlcNAc mediated branching in the Golgi apparatus, in 52% yield[11].

Scheme S9 as shown in FIGS. 59A and 59B depicts the preparation of Man₃ and Man₅GlcNAc₂. a, BF₃·OEt₂, CH₂Cl₂, 4 Å MS, −40° C., 2 h, 70%; b, Triethyl silane, PhBCl₂, CH₂Cl₂, 4 Å MS, −78° C., 1 h, 82%; c, 1, BF₃·OEt₂, CH₂Cl₂, 4 Å MS, −60° C. to −20° C., 2 h, 60%; d, pTsOH, CH₃CN, 2 h, 66%; e, 4, AgOTf, Cp₂HfCl₂, Toluene, 4 Å MS, −40° C., 2 h, 52%; f, (1) NH₂CH₂CH₂NH₂, nBuOH, 90° C., overnight; (2) Ac₂O, pyridine, overnight; (3) NaOMe, MeOH, overnight; (4) Pd(OH)₂, MeOH:H₂O:HCOOH (5:3:2), H₂; G1: 65%; G2: 52%; G4: 29%; Cp₂HfCl₂: Bis (cyclopentadienyl) hafnium Dichloride. To synthesize Man₉GlcNAc₂, a major glycoform found on HIV-1 gp120 surface and an important component of epitope recognized by broadly neutralizing antibodies, compound 14 was subjected to 3″-O glycosylation with fluoride 2 under the promotion of Cp₂HfCl₂/AgOTf to get hexasaccharide S10a in 65% yield. The p-toluene sulfonic acid mediated reductive ring opening of S10a provided diol S10b, which was further glycosylated with 5 to afford undecasaccharide S10c (Scheme S10 as shown in FIGS. 60A and 60B).

Figure 60A:
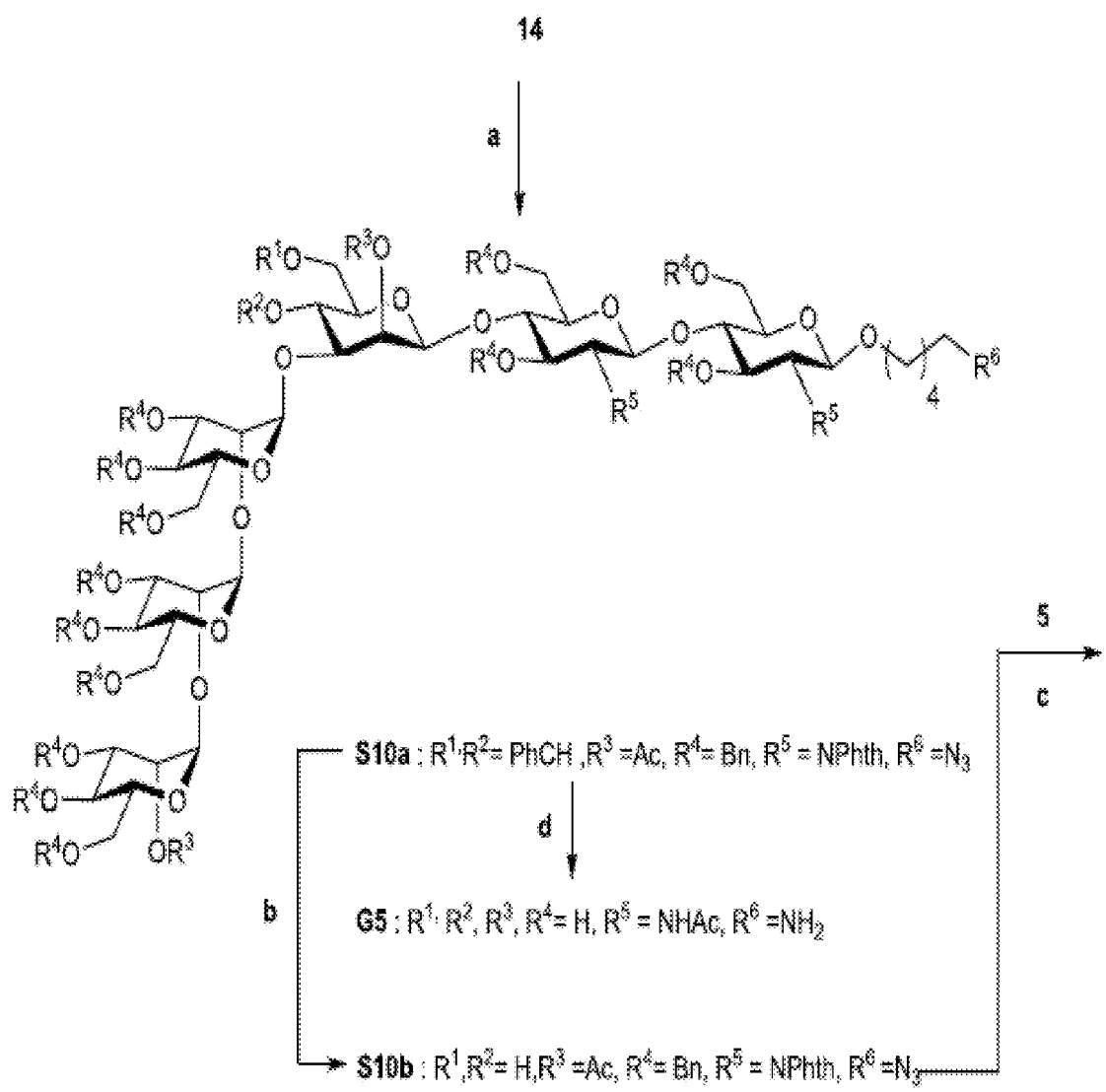
FIGS. 60A and 60B.
Figure 60B:
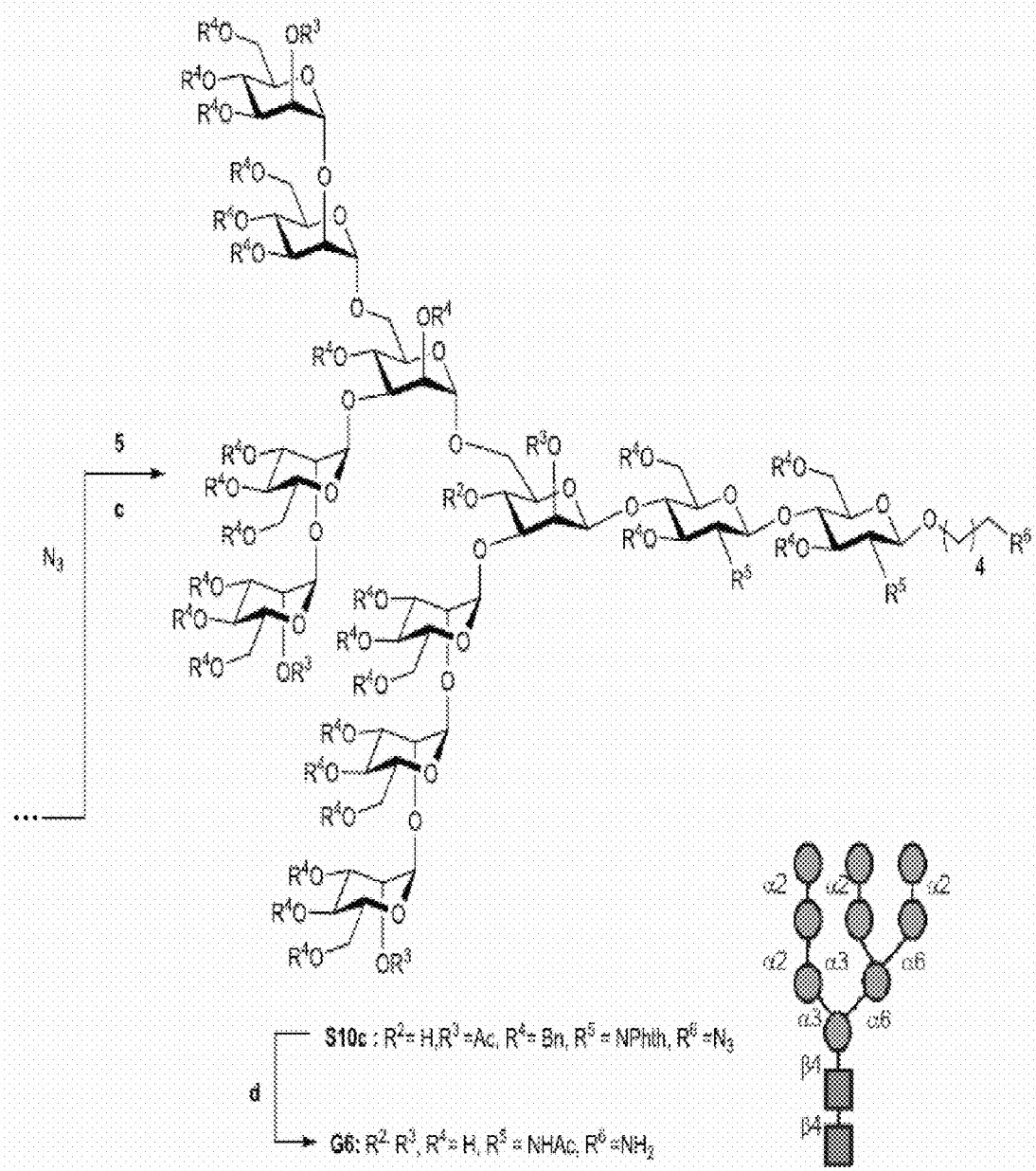
Figure 61:
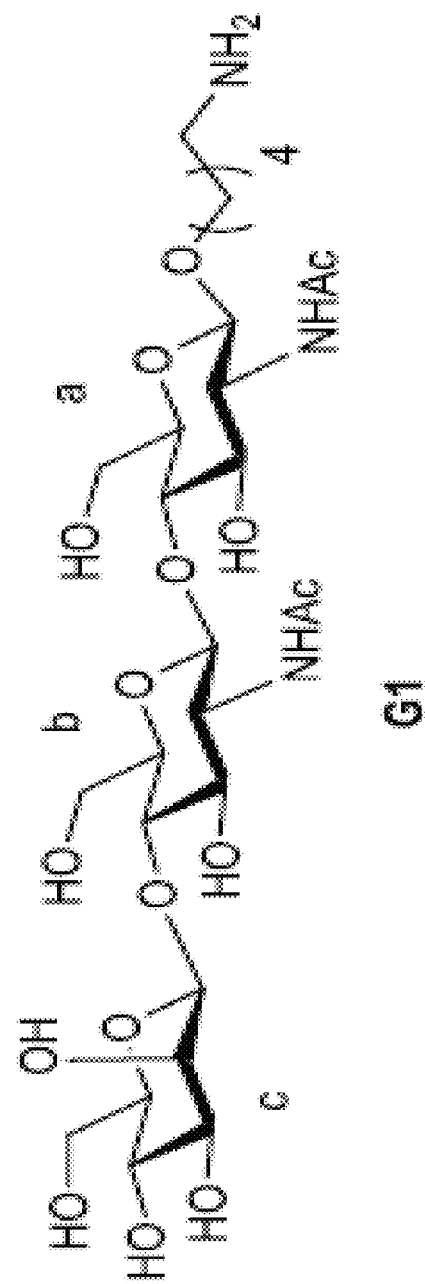
FIG. 61 Exemplary structure embodiments and synthetic scheme embodiments of the present disclosure.
Figure 62:
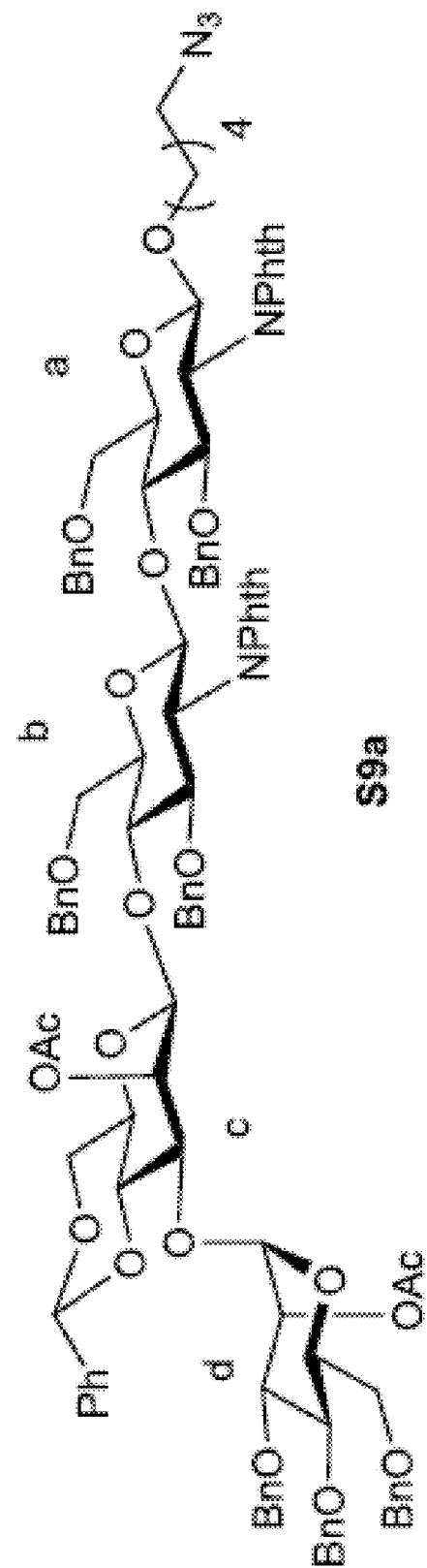
FIG. 62 Exemplary structure embodiments and synthetic scheme embodiments of the present disclosure.
Figure 63:
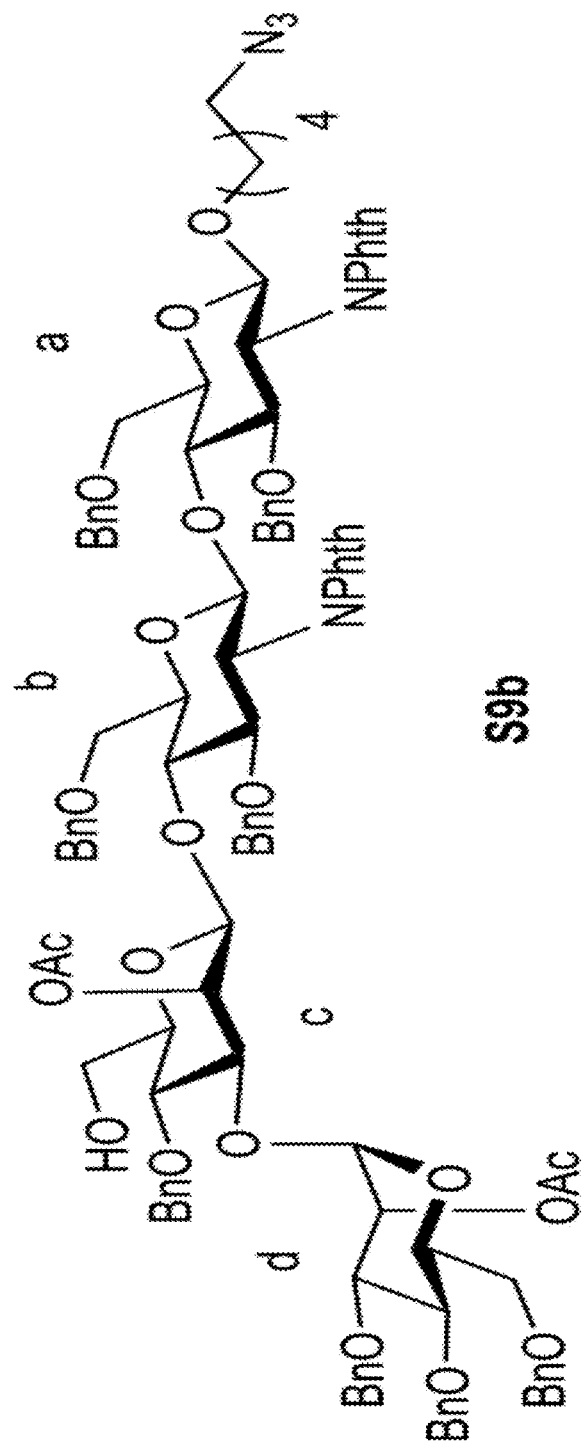
FIG. 63 Exemplary structure embodiments and synthetic scheme embodiments of the present disclosure.
Figure 64:
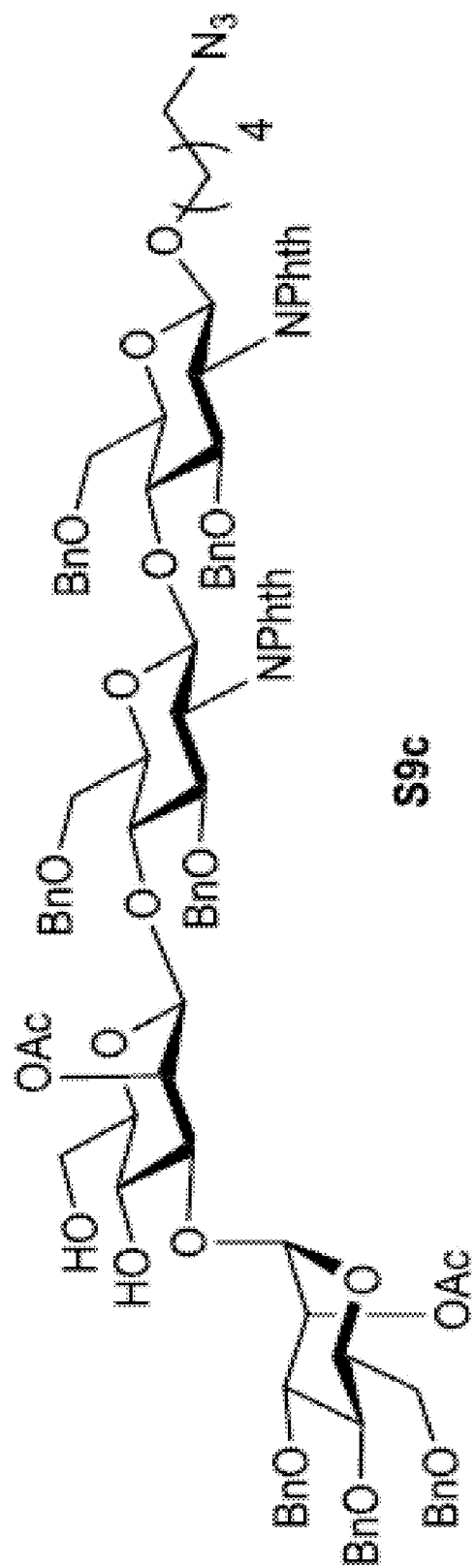
FIG. 64 Exemplary structure embodiments and synthetic scheme embodiments of the present disclosure.
Figure 65:
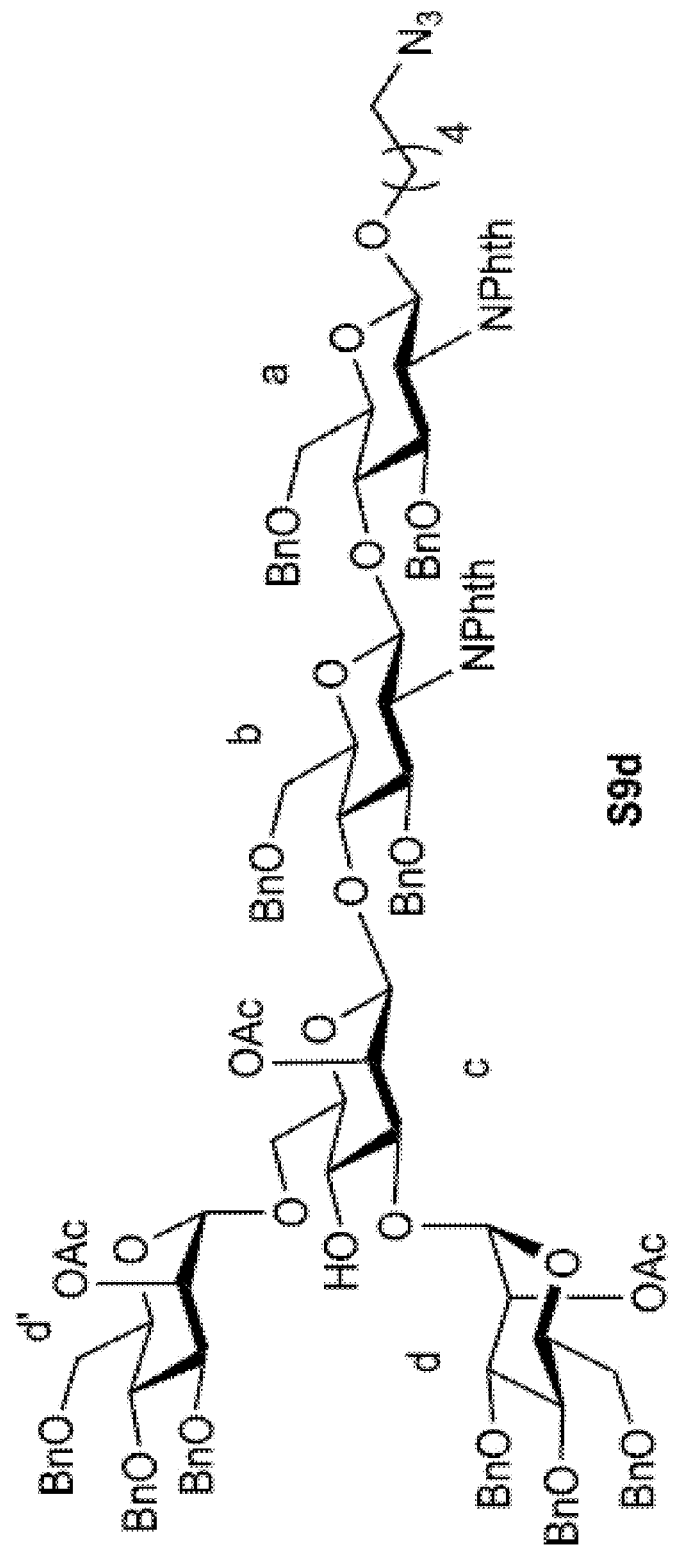
FIG. 65 Exemplary structure embodiments and synthetic scheme embodiments of the present disclosure.
Figure 66:
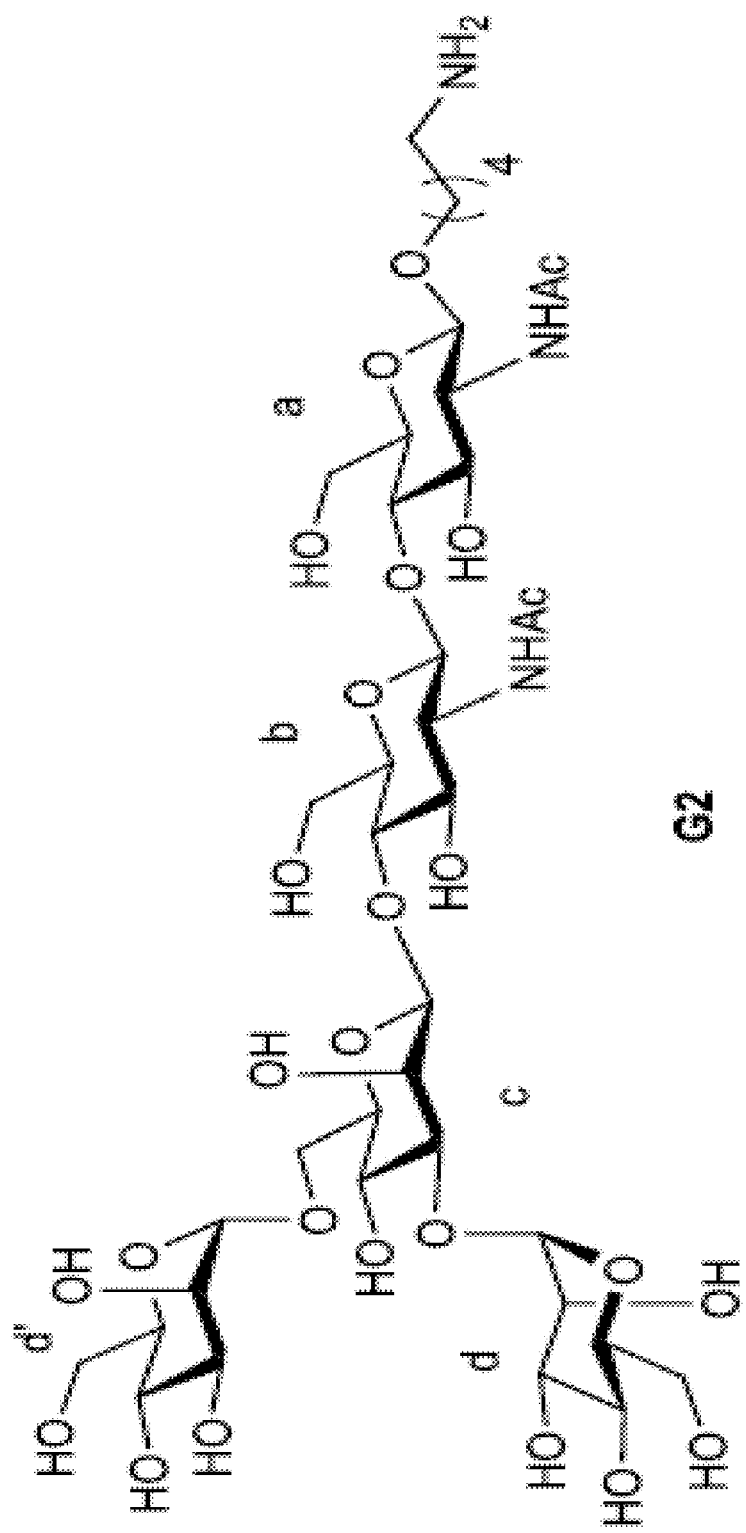
FIG. 66 Exemplary structure embodiments and synthetic scheme embodiments of the present disclosure.
Figure 67:
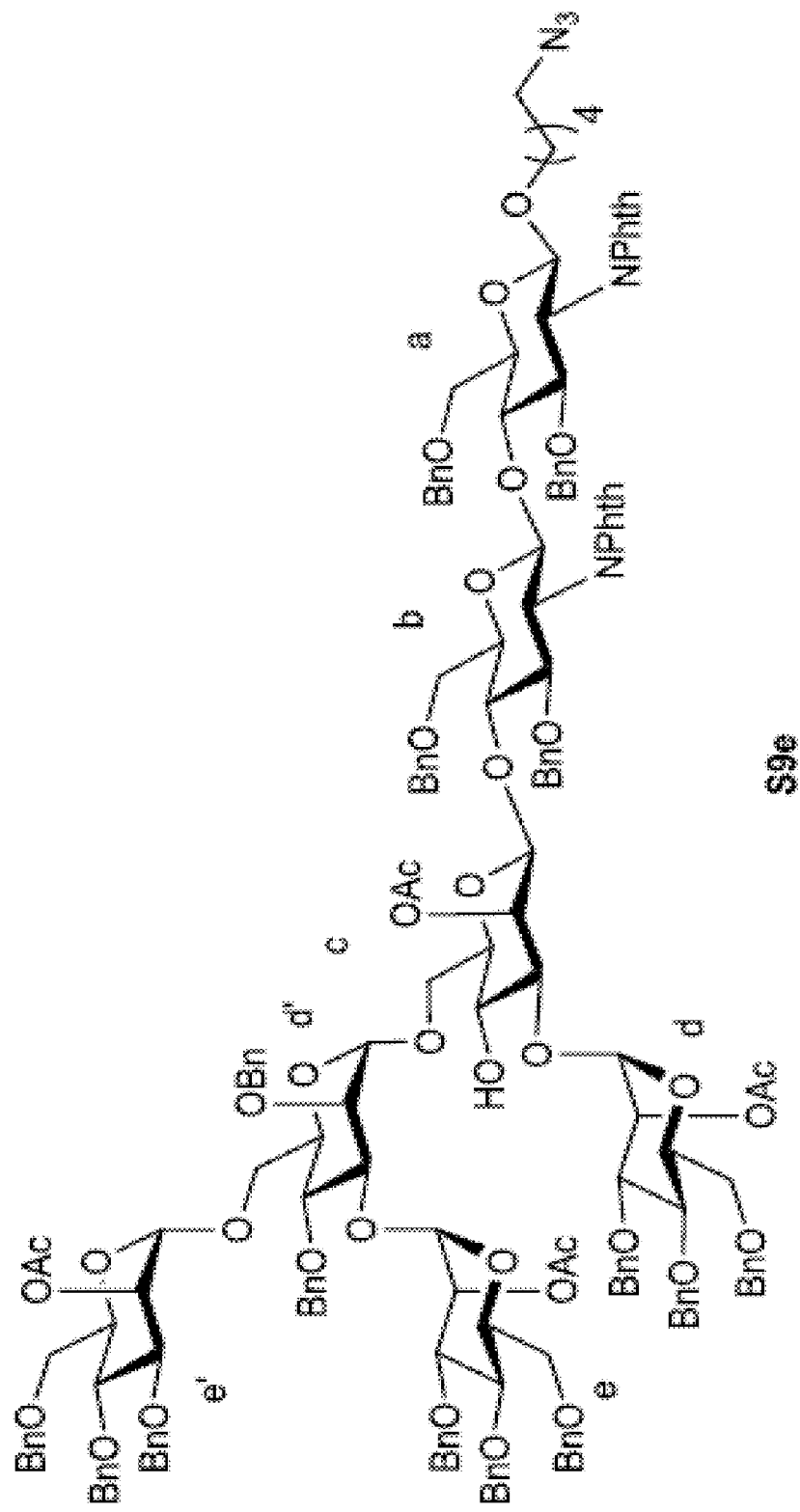
FIG. 67 Exemplary structure embodiments and synthetic scheme embodiments of the present disclosure.
Figure 68:
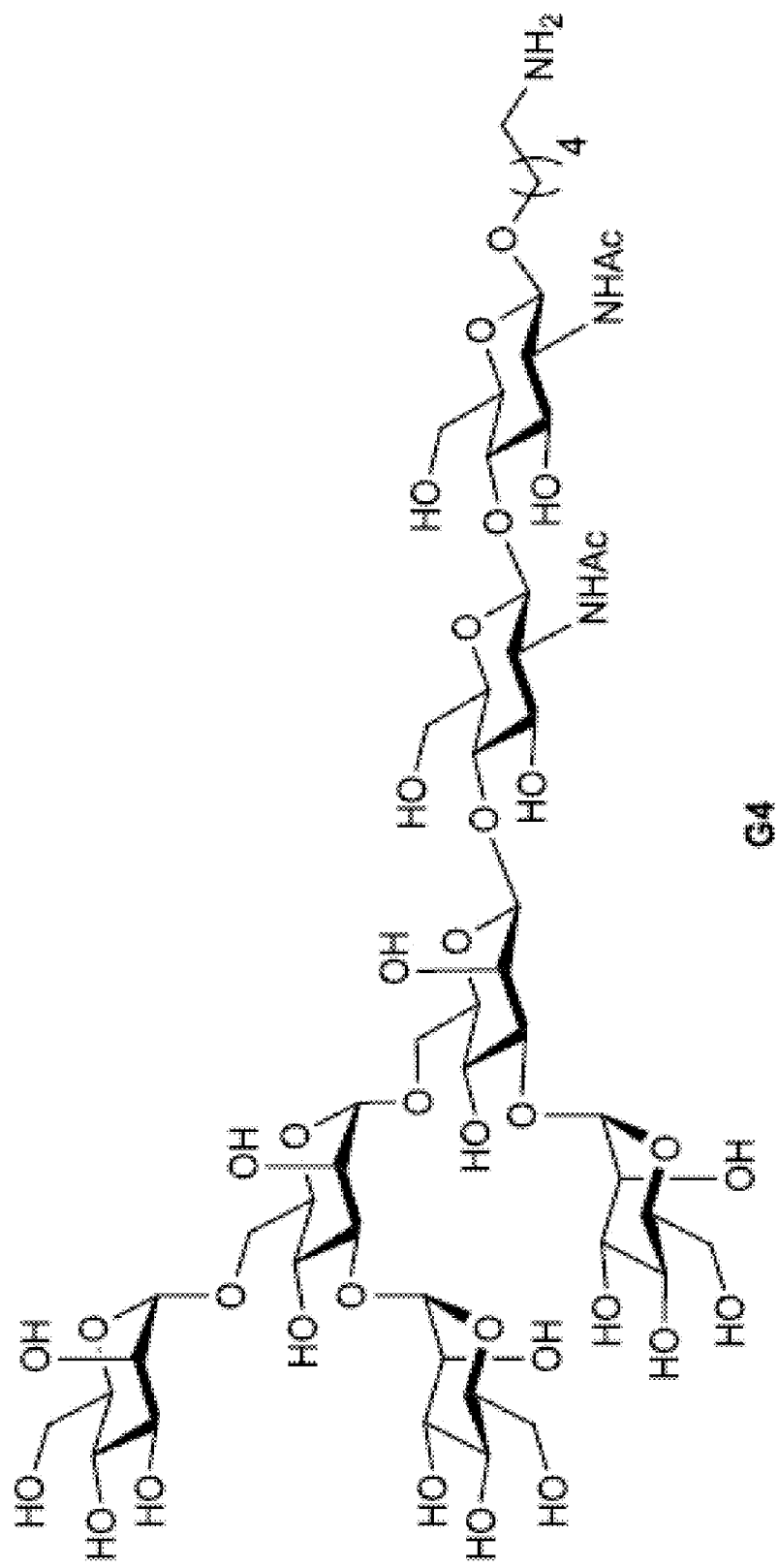
FIG. 68 Exemplary structure embodiments and synthetic scheme embodiments of the present disclosure.
Figure 69:
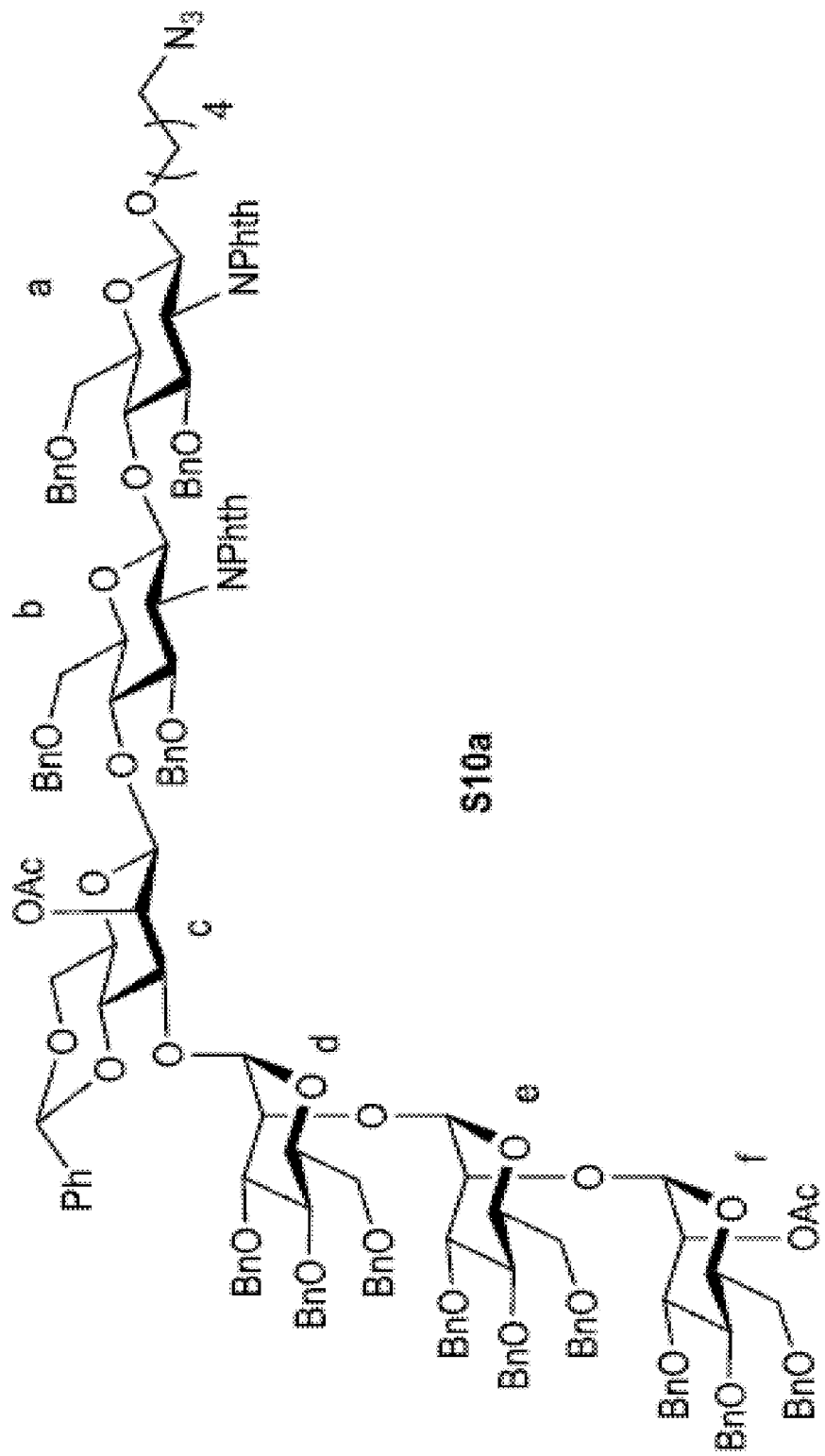
FIG. 69 Exemplary structure embodiments and synthetic scheme embodiments of the present disclosure.
Figure 70:
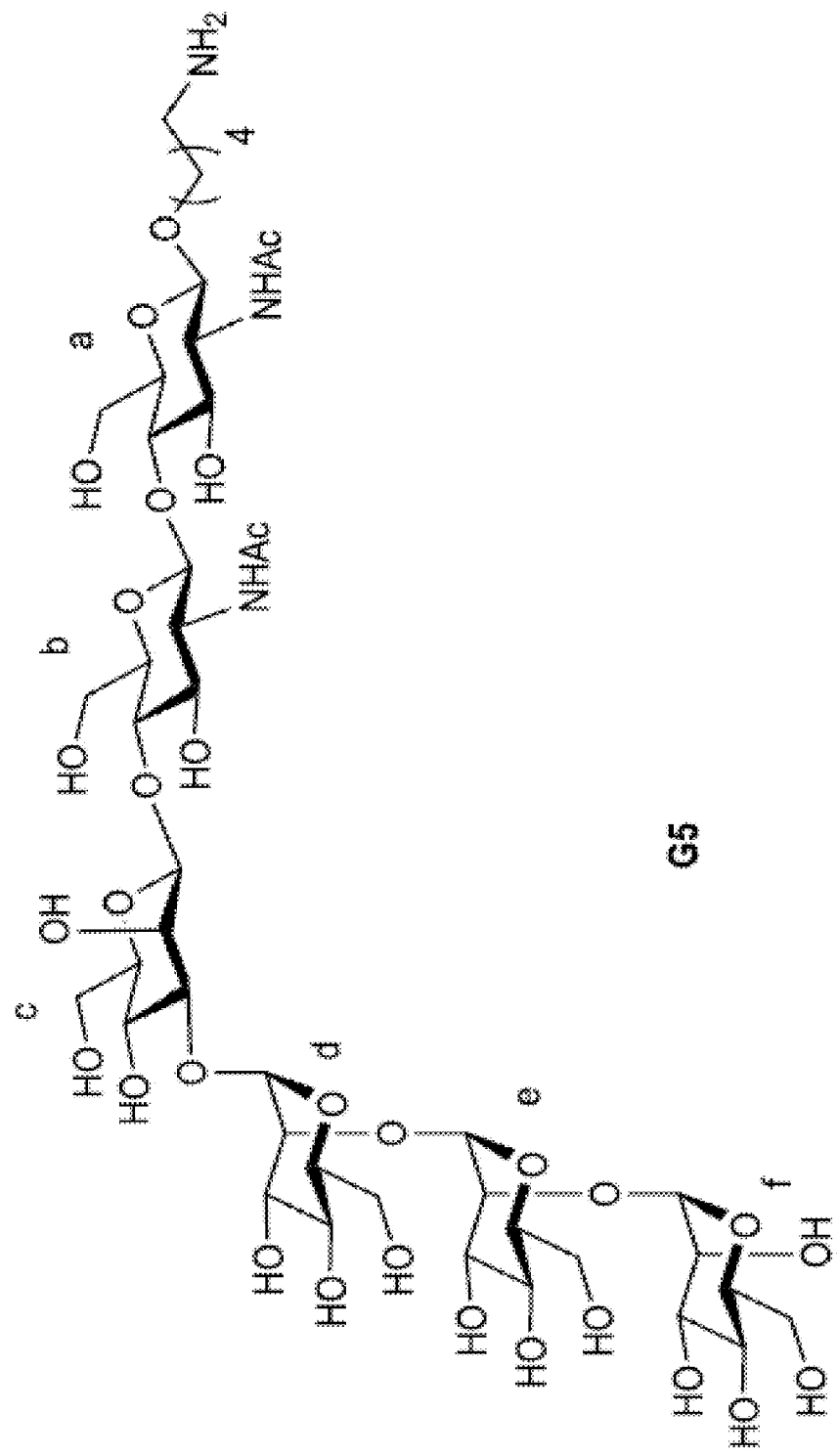
FIG. 70 Exemplary structure embodiments and synthetic scheme embodiments of the present disclosure.
Figure 71:
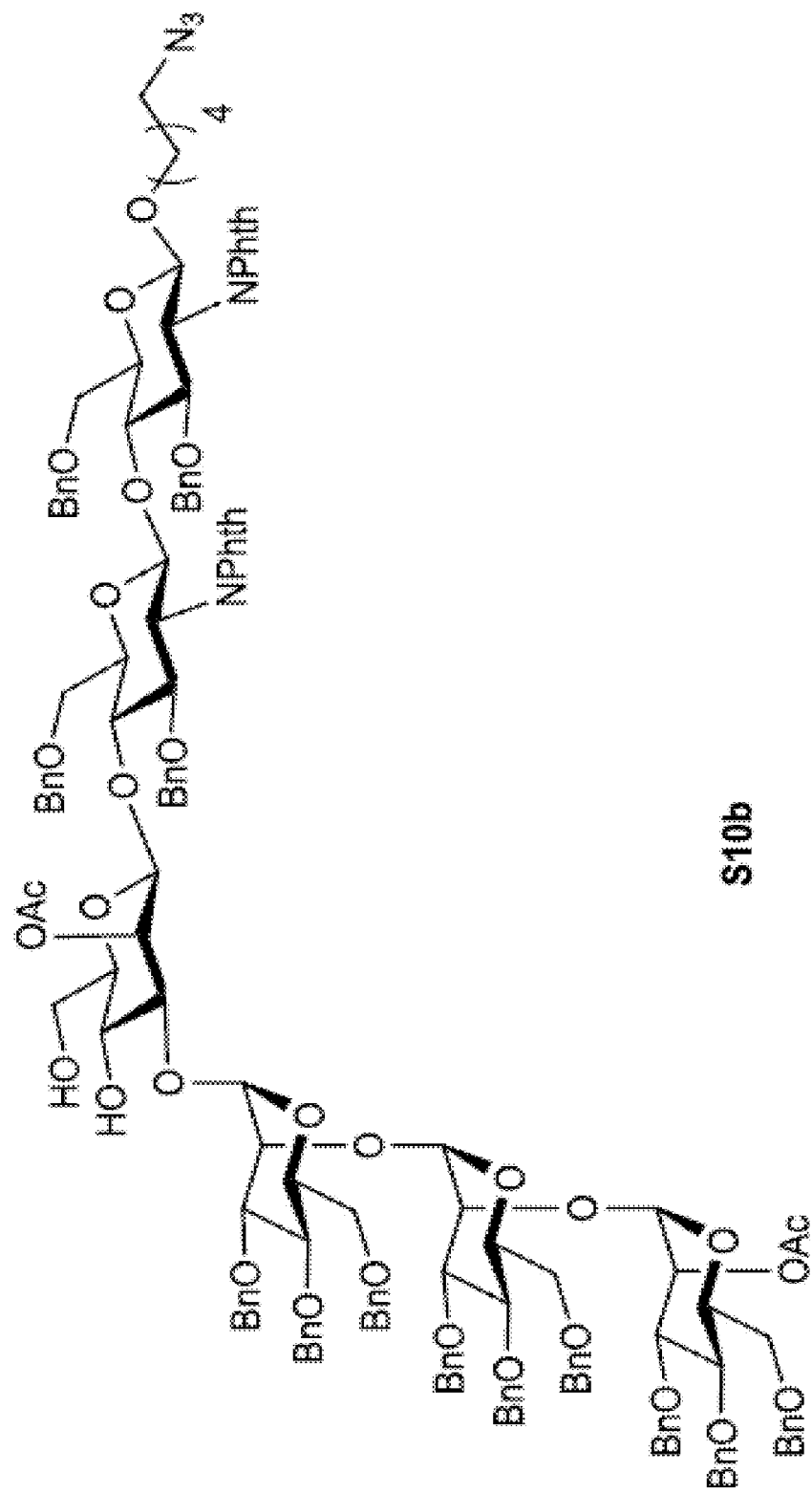
FIG. 71 Exemplary structure embodiments and synthetic scheme embodiments of the present disclosure.
Figure 72:
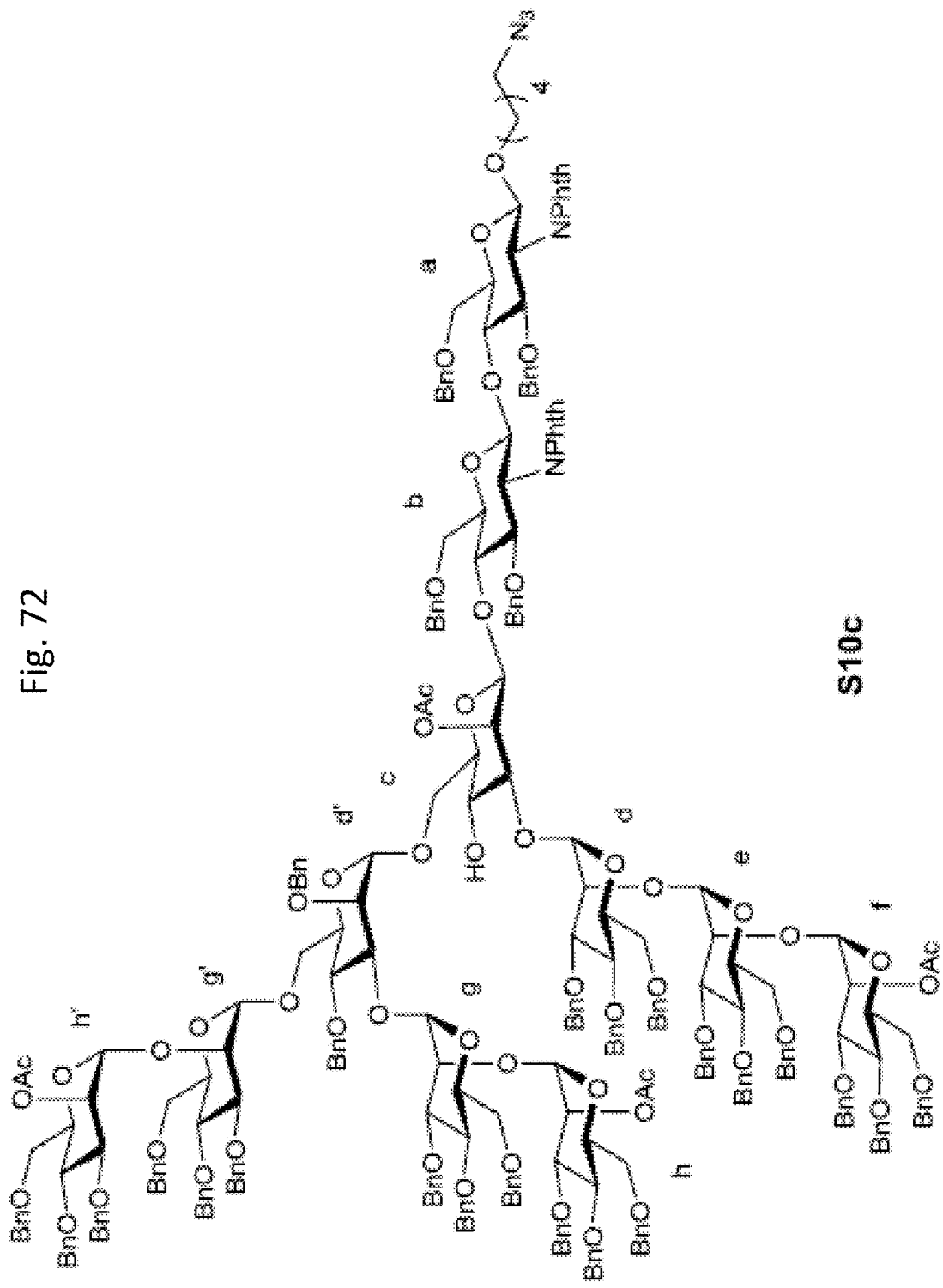
FIG. 72 Exemplary structure embodiments and synthetic scheme embodiments of the present disclosure.
Figure 73:
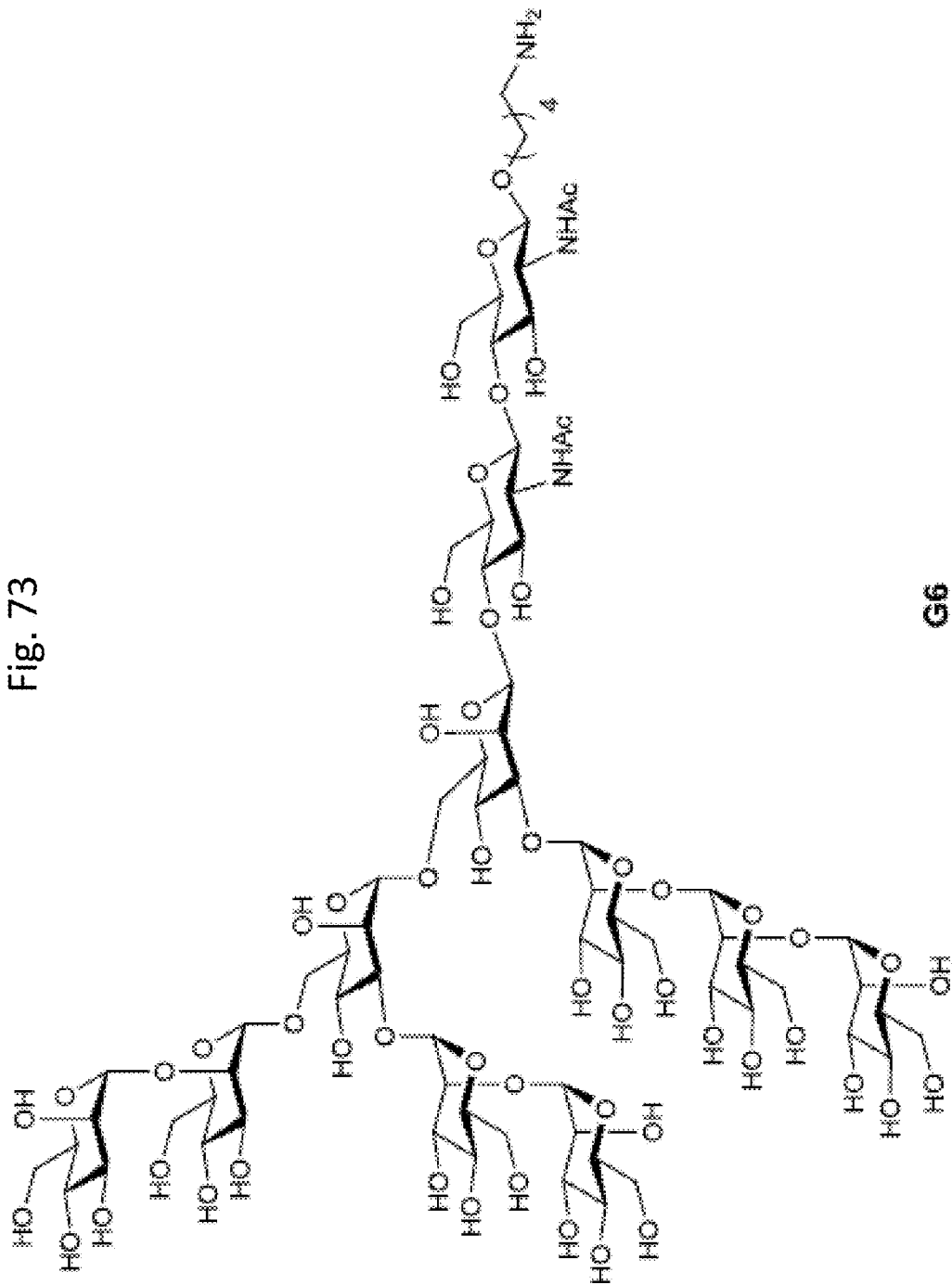
FIG. 73 Exemplary structure embodiments and synthetic scheme embodiments of the present disclosure.

Scheme S10 as shown in FIGS. 60A and 60B depicts the preparation of Man₄ (G5) and Man₉GlcNAc₂ (G6). a, 2, AgOTf, Cp₂HfCl₂, Toluene, 4 Å MS, −40° C., 2 h, 58%; b, p-TsOH, CH₃CN, 2 h, 60%; c, 5, (BrC₆H₄)₃NSbCl₆, CH₃CN, 4 Å MS, −10° C. to RT, 4 h, 52%; d, (1) NH₂CH₂CH₂NH₂, nBuOH, 90° C., overnight; (2) Ac₂O, pyridine, overnight; (3) NaOMe, MeOH, overnight; (4) Pd(OH)₂, MeOH:H₂O:HCOOH (5:3:2), H₂; G5:42%; SG6: 26%; (BrC₆H₄)₃NSbCl₆: Tris (4-bromophenyl) ammoniumyl hexachloroantimonate.

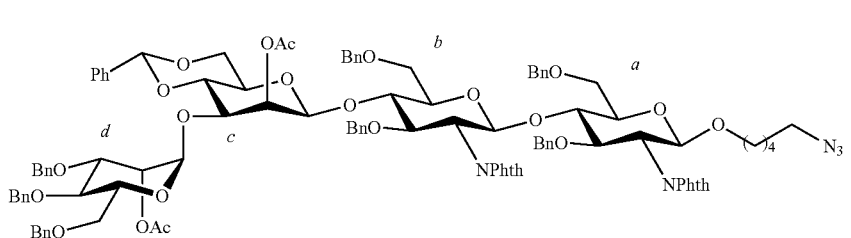

S9a 0.110 mmol) was deprotected by following general procedure 2 (Method 1) to yield desired trisaccharide G1 (0.045 g, 65%) as a white solid. 1H NMR (600 MHz, D2O): δ 4.72 (S, 1H, overlapped with D2O, H-1c), 4.60 (d, J=7.8 Hz, 1H, H-1a), 4.49 (d, J=7.8 Hz, 1H, H-1b), 4.06 (d, J=3 Hz, 1H), 3.94-3.89 (m, 4H), 3.86-3.58 (m, 14H), 3.50-3.49 (m, 1H), 3.42-3.42 (m, 1H), 2.97 (t, J=10.8 Hz, 2H, —CH2NH2, linker), 2.07 (s, 3H, —C(O)CH3), 2.03 (s, 3H, —C(O)CH3), 1.68-1.65 (m, 2H, —CCH2C—, linker), 1.60-1.58 (m, 2H, —CCH2C—, linker), 1.40-1.39 (m, 2H, —CCH2C—, linker); 13C NMR (150 MHz, D2O): δ 177.32, 177.17, 173.76, 104.12 (C-1a, 1 J C,H=163.1), 103.80 (C-1b, 1 J C,H=162.2), 102.80 (C-1c, 1 J C,H=160.2), 82.07, 81.35, 79.15, 77.31, 77.25, 75.49, 75.13, 74.68, 73.23, 72.84, 69.34, 63.65, 62.83, 62.77, 57.75, 57.72, 42.05, 30.78, 29.10, 24.86, 24.84, 24.83; ESI-MS: m/z calcd for C, 27; H, 49; N, 3; O, 16: 671.3005; found 694.3115 (M+Na)+.

5-Azidopentyl-O-(2-O-acetyl-3,4,6-tri-O-benzyl-α-D-mannopyranosyl-(1→3)-2-O-acetyl-4,6-O-benzylidine-β-D-mannopyranosyl-(1→4)-O-(3,6-di-O-benzyl-2-deoxy-2-phthalimido-β-D-glucopyranosyl)-(1→4)-O-3,6-di-O-benzyl-2-deoxy-2-phthalimido-β-D-glucopyranoside (S91): A mixture of trichloroacetimidate 1 (0.278 g, 0.437 mmol), chitobiose acceptor 14 (0.300 g, 0.219 mmol) and activated 4 Å molecular sieves in dry CH2Cl2 (10 mL) was stirred at room temperature for 1 h. The reaction was cooled to −40° C., boron trifluoride ethyl etherate (12 μL, 0.109 mmol) was then added slowly and the resulting reaction mixture was stirred for 2 h. The reaction was quenched by adding Et3N, diluted with CH2Cl2, filtered through Celite and concentrated in vacuo. The residue was purified by flash column chromatography (0%→15% EA in toluene) to afford S9a (0.310 g, 70%) as white foam. TLC (ethyl acetate:toluene=2/8, v/v): Rf=0.46; 1H NMR (600 MHz, CDCl3): δ 7.84-7.65 (m, 8H, Ar—H), 7.38-7.31 (m, 2H, Ar—H), 7.30-7.18 (m, 28H, Ar—H), 6.98-6.90 (m, 7H, Ar—H), 6.75-6.71 (m, 3H, Ar—H), 5.45 (s, 1H, Ph-CH, benzylidene), 5.43-5.43 (d, J=3.4 Hz, 1H, H-2d), 5.34 (d, J=3.1 Hz, 1H, H-2c), 5.21 (d, J=8.1 Hz, 1H, H-1a), 5.19 (d, J=2.1 Hz, 1H, H-1d), 4.90 (d, J=8.1 Hz, 1H, H-1a), 4.83-4.81 (m, 3H), 4.67 (s, 1H), 4.67-4.61 (m, 2H), 4.53-4.43 (m, 7H), 4.38-4.23 (q, 2H), 4.22-4.16 (m, 1H), 4.13-4.06 (m, 6H), 3.87-3.75 (m, 6H), 3.66-3.60 (m, 3H), 3.53-3.45 (m, 3H), 3.38 (dd, J=4.2 & 12.0 Hz, 1H), 3.26-3.17 (m, 3H), 3.09-3.07 (m, 1H), 2.87-2.82 (m, 2H), 2.06 (s, 3H, —C(O)CH3), 2.03 (s, 3H, —C(O)CH3), 1.35-1.23 (m, 4H, —CCH2C—, linker), 1.07-1.01 (m, 2H, —CCH2C—, linker); 13C NMR (150 MHz, CDCl3): δ 169.87, 168.75, 167.83, 138.97, 138.47, 138.17, 137.36, 134.30, 134.10, 131.72, 129.12, 128.90, 128.64, 128.55, 128.51, 128.32, 128.23, 128.09, 127.84, 127.46, 128.14, 126.24, 123.40, 101.44, 99.38, 98.90, 98.37 (C-1d, 1 J C,H=172 Hz), 97.31, 79.05, 78.84, 77.89, 76.14, 75.02, 74.78, 73.70, 73.40, 73.06, 73.04, 72.37, 72.03, 71.00, 69.11, 69.85, 69.11, 68.85, 68.59, 68.50, 67.84, 66.70, 56.85, 55.99, 51.38, 28.95, 28.55, 23.28, 21.33, 21.16;

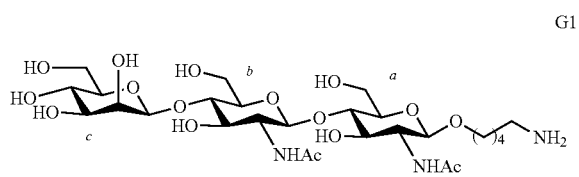

G1

5-Aminopentyl-β-D-mannopyranosyl-(1→4)-2-acetamido-2-deoxy-β-D-glucopyranosyl-(1→4)-2-acetamido-2-deoxy-β-D-glucopyranoside (G1): Compound 14 (0.150 g, ESI-MS: m/z calcd for C, 105; H, 107; N, 5; O, 25: 1838.7180; found 1861.7223 (M+Na)+.

5-Azidopentyl-O-(2-O-acetyl-3,4,6-tri-O-benzyl-α-D-mannopyranosyl-(1→3)-2-O-acetyl-β-D-mannopyranosyl- S9b

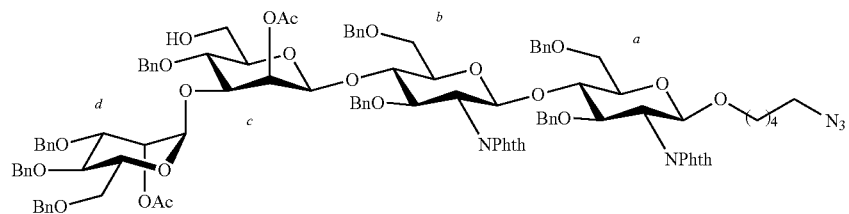

5-Azidopentyl-O-(2-O-acetyl-3,4,6-tri-O-benzyl-α-D-mannopyranosyl-(1→3)-2-O-acetyl-4-O-benzyl-β-D-mannopyranosyl-(1→4)-O-(3,6-di-O-benzyl-2-deoxy-2-phthalimido-β-D-glucopyranosyl)-(1→4)-O-3,6-di-O-benzyl-2-deoxy-2-phthalimido-β-D-glucopyranoside (S9b): A mixture of tetrasaccharide S9a (0.280 g, 0.152 mmol) and 4 Å activated molecular sieves in CH2Cl2 (10 mL) was stirred at room temperature for 1 h. Reaction was cooled to −78° C., triethyl silane (73 μL, 0.456 mmol) and dichlorophenyl borane (69 μL, 0.532 mmol) were added and stirred for 1 h. The reaction was quenched by adding Et3N, filtered through Celite and concentrated in vacuo. The residue was co-distilled with methanol 2-3 times before being purified by flash column chromatography (0%→15% EA in toluene) to afford 6"-OH S9b (0.230 g, 82%). TLC: (ethyl acetate: toluene=2/8, v/v): Rf=0.36; 1H NMR (600 MHz, CDCl3): δ 7.85-7.52 (m, 8H, Ar—H), 7.52-7.12 (m, 29H, Ar—H), 7.00-6.88 (m, 9H, Ar—H), 6.74-6.70 (m, 3H, Ar—H), 5.39 (d, J=1.8 Hz, 1H, H-2d), 5.32 (d, J=3.6 Hz, 1H, H-2c), 5.21 (d, J=8.4 Hz, 1H, H-1a), 5.10 (s, 1H, H-1d), 4.90-4.81 (m, 4H), 4.67-4.61 (m, 2H, overlapped H-2b), 4.59 (s, 1H, H-1c), 4.59-4.44 (m, 9H), 4.37 (d, J=12 Hz, 2H), 4.24-4.12 (m, 3H), 4.10-4.05 (m, 3H), 3.90-3.77 (m, 4H), 3.69-3.58 (m, 7H), 3.49 (t, J=11.5 Hz, 2H), 3.41-3.36 (dd, J=6.1, 11.2 Hz, 2H), 3.26 (dd, J=6.0, 9.2 Hz, 1H), 3.26-3.18 (m, 2H), 3.06-2.98 (m, 1H), 2.88-2.81 (m, 2H, linker), 2.06 (s, 3H, —C(O)CH3), 2.04 (s, 3H, —C(O)CH3), 1.37-1.22 (m, 4H, linker), 1.07-1.00 (m, 2H, linker); 13C NMR (150 MHz, CDCl3): δ 170.45, 169.88, 168.78, 168.24, 167.86, 138.95, 138.92, 138.77, 138.58, 138.21, 138.11, 137.95, 137.37, 134.35, 134.16, 133.89, 132.09, 131.70, 128.90, 128.76, 128.71, 128.64, 128.58, 128.51, 128.41, 128.31, 128.08, 127.96, 127.81, 127.64, 127.13, 123.97, 123.46, 100.14, 98.40, 98.36, 97.36, 76.24, 75.52, 75.30, 74.96, 74.71, 74.51, 74.29, 73.41, 73.09, 72.55, 72.12, 69.41, 69.20, 68.85, 68.48, 67.93, 67.71, 61.87, 56.78, 56.00, 51.38, 28.96, 28.55, 23.28, 21.37; ESI-MS: m/z calcd for C, 105; H, 109; N, 5; O25: 1840.7337; found 1863.7383 (M+Na)+.

(1→4)-O-(3,6-di-O-benzyl-2-deoxy-2-phthalimido-β-D-glucopyranosyl)-(1→4)-O-3,6-di-O-benzyl-2-deoxy-2-phthalimido-β-D-glucopyranoside (S9c): p-Toluenesulfonic acid monohydrate (0.045 g, 0.239 mmol) was added to a stirred solution of tetrasaccharide S9a (0.220 g, 0.119 mmol) in acetonitrile (10 mL) at room temperature. After 8 h, the reaction mixture was quenched with Et3N and concentrated in vacuo. The residue was purified by flash column chromatography (0%→15% EA in toluene) to give the title diol S9c (0.140 g, 66%) as white solid. TLC: (ethyl acetate: toluene=2/8, v/v): Rf=0.26; 1H NMR (600 MHz, CDCl3): δ 7.85-7.52 (m, 8H, Ar—H), 7.32-7.17 (m, 25H, Ar—H), 6.98-6.91 (m, 7H, Ar—H), 6.75-6.71 (m, 3H, Ar—H), 5.30 (d, J=3.6 Hz, 1H,), 5.21 (d, J=8.6 Hz, 1H, H-1a), 5.20 (s, 2H, overlapped H-1d), 4.89 (d, J=8.4 Hz, 1H, H-1b), 4.85-4.82 (m, 3H), 4.64-4.60 (m, 3H), 4.54-4.46 (m, 7H), 4.38 (d, J=12.0 Hz, 1H), 4.34 (d, J=12.2 Hz, 1H), 4.21-4.04 (m, 5H), 3.92 (m, 1H), 3.87-3.79 (m, 3H), 3.70-3.59 (m, 5H), 3.52-3.43 (m, 4H), 3.39 (dd, J=3.2, 8.3 Hz, 1H), 3.28 (dd, J=3.2, 8.2 Hz, 1H), 3.29-3.19 (m, 2H), 2.29 (m, 1H), 2.86-2.83 (m, 3H), 2.11 (s, 3H, —C(O)CH3), 2.03 (s, 3H, —C(O)CH3), 1.35-1.23 (m, 4H, —CCH2C—, linker), 1.06-1.01 (m, 2H, —CCH2C—, linker); 13C NMR (150 MHz, CDCl3): δ 170.76, 169.88, 138.92, 138.70, 138.62, 138.52, 138.12, 138.06, 134.27, 134.07, 133.81, 131.95, 131.64, 128.82, 128.64, 128.59, 128.52, 128.50, 128.39, 138.33, 128.20, 128.09, 128.06, 128.03, 128.01, 127.94, 127.81, 127.75, 127.54, 127.42, 127.29, 127.06, 123.90, 123.36, 98.51, 98.30, 98.24 (C-1d, 1 J, C,H=173 Hz), 97.30, 79.07, 78.38, 77.60, 76.10, 75.52, 75.03, 74.79, 74.71, 74.59, 74.51, 73.39, 73.03, 72.07, 72.01, 71.30, 69.53, 69.27, 69.05, 68.44, 67.70, 67.17, 62.44, 56.74, 55.94, 51.32, 28.89, 28.49, 23.22, 21.31, 21.22; ESI-MS: m/z calcd for C, 98; H, 103; N, 5; O, 25: 1750.6868; found 1773.6913 (M+Na)+.

S9c

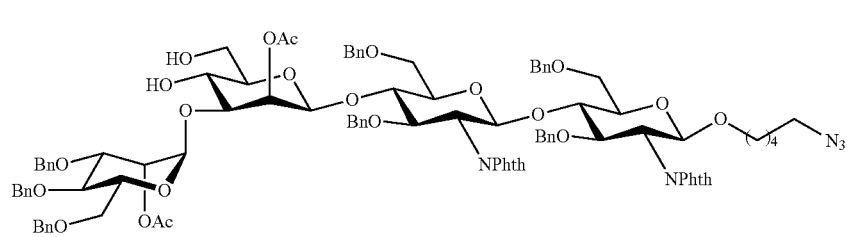

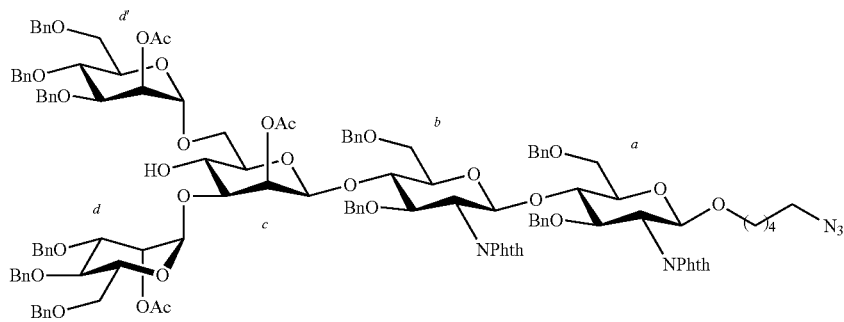

S9d

5-Azidopentyl-O-di-(2-O-acetyl-3,4,6-tri-O-benzyl-α-D-mannopyranosyl-(1→3), (1→6)-2-O-acetyl-4-O-benzyl-β-D-mannopyranosyl-(1→4)-O-(3,6-di-O-benzyl-2-deoxy-2-phthalimido-β-D-glucopyranosyl)-(1→4)-O-3,6-di-O-benzyl-2-deoxy-2-phthalimido-β-D-glucopyranoside (S9d): A mixture of donor 1 (0.113 g, 0.178 mmol), acceptor S9b (0.220 g, 0.119 mmol) and activated 4 Å molecular sieves in dry CH2Cl2 (10 mL) was stirred at room temperature for 1 h. The reaction was cooled to −60° C., boron trifluoride ethyl etherate (12 μL, 0.109 mmol) was added slowly and the resulting reaction mixture was stirred for 2 h at −20° C. The reaction was quenched by adding Et3N, diluted with CH2Cl2, filtered through Celite and concentrated in vacuo. The residue was purified by flash column chromatography (0%→20% EA in hexane) to afford S9d (0.170 g, 60%) as colorless foam. TLC: (ethyl acetate:hexane=3/7, v/v): Rf=0.46; 1H NMR (600 MHz, CDCl3): δ 7.77-7.59 (m, 8H, Ar—H), 7.32-7.16 (m, 43H, Ar—H), 7.14-7.08 (m, 2H, Ar—H), 6.91-6.89 (m, 4H, Ar—H), 6.73-6.67 (m, 6H, Ar—H), 5.45 (s, 1H, H-2d), 5.34 (d, J=3.1 Hz, 1H, H-2c), 5.32 (s, 1H, H-2d'), 5.17 (d, J=8.4 Hz, 1H, H-1a), 5.09 (s, 1H, H-1d), 5.0 (s, 1H, H-1d'), 4.87 (d, J=8.4 Hz, 1H, H-1b), 4.83-4.78 (q, 2H), 4.74-4.71 (q, 2H), 4.65-4.61 (m, 4H), 4.56-4.42 (m, 15H), 4.31 (d, J=9.2 Hz, 1H), 4.12-4.03 (m, 5H), 4.03-3.76 (m, 9H), 3.68-3.43 (m, 9H), 3.30 (dd, J=3.2, 9.1 Hz, 1H), 3.21-3.15 (m, 2H), 3.13 (d, J=9.2 Hz, 1H), 3.09 (d, J=8.4 Hz, 1H), 2.89-2.79 (m, 2H, —CH2N3-, linker), 2.12 (s, 3H, —C(O)CH3), 2.07 (s, 3H, —C(O)CH3), 1.69 (s, 3H, —C(O)CH3), 1.37-1.12 (m, 4H, —CCH2C—, linker), 1.07-1.01 (m, 2H, —CCH2C—, linker); 13C NMR (150 MHz, CDCl3): δ 170.45, 170.22, 170.18, 168.21, 167.71, 138.93, 138.72, 138.68, 138.50, 138.24, 138.22, 138.07, 133.83, 133.75, 128.87, 128.79, 128.67, 128.63, 128.58, 128.42, 128.21, 128.06, 127.99, 127.96, 127.81, 127.76, 127.70, 127.46, 127.08, 123.36, 100.13 (C-1a, 1 J C,H=159.3 Hz), 99.39 (C-1d', 1 J C,H=171.5 Hz), 98.35 (C-1b, 1 J C,H=162.3 Hz), 98.31 (C-1d, 1 J C,H=170 Hz), 97.16, 76.20, 76.05, 75.58, 75.21, 74.97, 74.89, 74.70, 74.47, 74.28, 73.94, 73.72, 73.00, 72.25, 72.20, 71.70, 71.50, 69.15, 69.07, 69.04, 68.99, 68.50, 68.45, 67.80, 65.45, 56.83, 51.37, 29.94, 23.27, 21.31, 21.28, 20.83; ESI-MS: m/z calcd for C, 134; H, 139; N, 5; O, 31: 2314.9379; found 2337.9461 (M+Na)+.

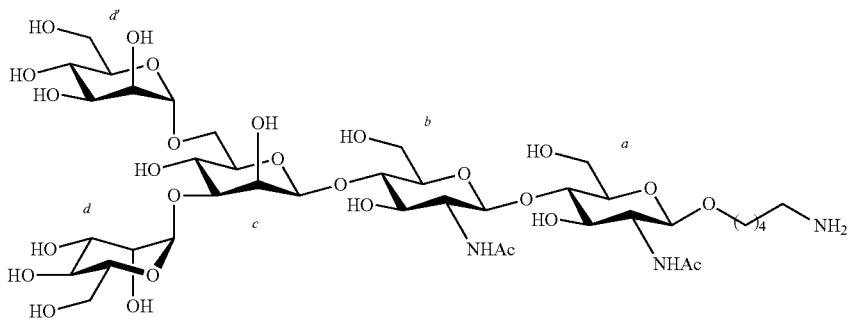

G2

5-Aminopentyl-di-(α-D-mannopyranosyl)-(1→3), (1→6)-β-D-mannopyranosyl-(1→4)-2-acetamido-2-deoxy-β-D-glucopyranosyl-(1→4)-2-acetamido-2-deoxy-β-D-glucopyranoside (G2): Pentasaccharide S9d (0.090 g, 0.038 mmol) was deprotected by following the general procedure 2 (Method 1) to afford compound G2 (0.020 g, 52%) as a white powder. 1H NMR (600 MHz, D2O): δ 5.10 (d, J=1.3 Hz, 1H, H-1d), 5.09 (d, J=1.5 Hz, 1H, H-1d'), 4.78 (s, 1H, overlapped with D2O, H-1c), 4.59 (d, J=8.4 Hz, 1H, H-1a), 4.49 (d, J=7.8 Hz, 1H, H-1b), 4.25 (s, 1H), 4.01 (d, J=1.5 Hz, 1H), 4.00 (d, J=1.3 Hz, 1H), 3.97-3.77 (m, 8H), 3.75-3.65 (m, 20H), 3.52-3.48 (m, 2H), 2.98 (t, J=11.2 Hz, 2H), 2.06 (s, 3H), 2.02 (s, 3H), 1.68-1.65 (m, 2H), 1.60-1.57 (m, 2H), 1.49-1.40 (m, 2H); 13C NMR (150 MHz, D2O): δ 181.17, 174.69, 174.42, 102.51 (C-1d, 1 J C,H=171.5 Hz), 101.34, 101.04, 100.35 (C-1d', 1 J C,H=173.5 Hz), 99.60, 80.48, 79.61, 79.30, 74.49, 74.36, 74.16, 73.43, 72.66, 72.37, 71.93, 70.39, 70.31, 70.13, 70.09, 69.98, 69.85, 66.84, 66.76, 65.80, 61.12, 90.93, 60.07, 59.97, 54.97, 54.85, 39.30, 28.03, 26.35, 23.07, 22.17, 22.07; ESI-MS: m/z calcd for C, 39; H, 69; N, 3; O, 26: 995.4067; found 1018.4106 (M+Na)+.

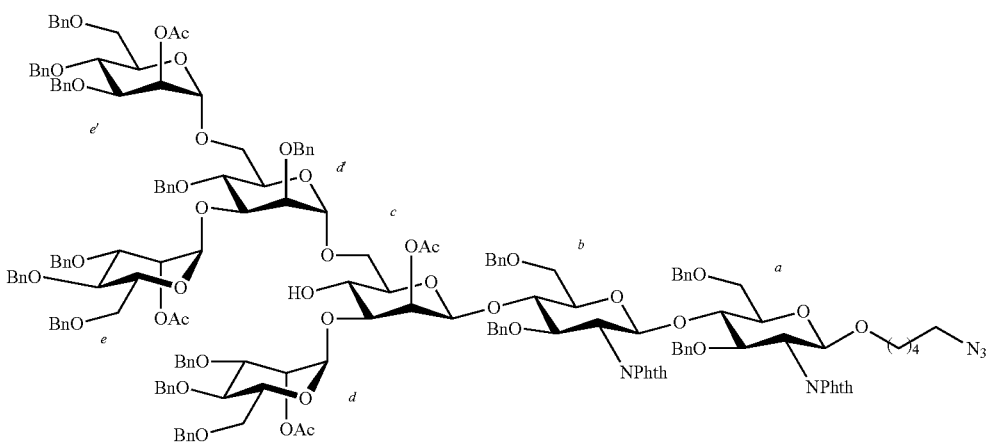

S9e

5-Azidopentyl-O-(2-O-acetyl-3,4,6-tri-O-benzyl-α-D-mannopyranosyl-(1→3)-{2-O-acetyl3,4,6-tri-O-benzyl-α-D-mannopyranosyl-(1→3)}-[2-O-acetyl-3,4,6-tri-O-benzyl-α-D-mannopyranosyl-(1→6)]-2,4-di-O-benzyl-α-D-mannopyranosyl-(1→6)}-2-O-acetyl-β-D-mannopyranosyl-(1→4)-O-(3,6-di-O-benzyl-2-deoxy-2-phthalimido-β-D-glucopyranosyl)(1→4)-O-3,6-di-O-benzyl-2-deoxy-2-phthalimido-β-D-glucopyranoside (S9e): A mixture of Silver triflate (0.127 g, 0.497 mmol), Bis(cyclopentadienyl) hafnium dichloride (0.121 g, 0.319 mmol) and 4 Å activated molecular sieves in dry toluene (10 mL) was stirred at room temperature for 1 h. The reaction mixture was then cooled to −40° C., a solution of donor 4 (0.103 g, 0.085 mmol) and acceptor S9c (0.125 g, 0.071 mmol) in 5 mL toluene was added. The mixture was stirred for 2 h, quenched with Et3N, diluted with CH2Cl2 and filtered through celite. The filtrate was washed with aqueous NaHCO3 (2×50 mL), and a brine (50 mL) solution. The organic layer was dried over Na2SO4 and concentrated in vacuo. The residue was purified by flash column chromatography (0%→15% EA in toluene) to afford S9e (0.110 g, 52%) as colorless foam. TLC: (acetone:toluene=2/8, v/v): Rf=0.36; 1H NMR (600 MHz, CDCl3): δ 7.77-7.40 (m, 8H, Ar—H), 7.32-7.07 (m, 85H, Ar—H), 6.99-6.88 (m, 4H, Ar—H), 6.79-6.68 (m, 6H, Ar—H), 5.44 (s, 1H, H-2d), 5.43 (s, 1H, H-2e), 5.41 (s, 1H, H-2e'), 5.29 (d, J=3.4 Hz, 1H, H-2c), 5.18 (s, 2H, H-1d,d'), 5.16 (s, 1H, H-1e), 5.09 (s, 1H, H-1e'), 4.92 (s, 1H, H-1c), 4.91 (d, J=8.5 Hz, 1H, H-1a), 4.83-4.78 (q, 1H), 4.84-4.73 (m, 6H), 4.65-4.61 (m, 2H), 4.60-4.57 (m, 5H), 4.52-4.35 (m, 17H), 4.27 (d, J=12.3 Hz, 1H), 4.20-4.19 (m, 1H), 4.10-3.99 (m, 6H), 3.97-3.70 (m, 13H), 3.69-3.57 (m, 8H), 3.56-3.31 (m, 6H), 3.30 (dd, J=3.2, 9.2 Hz, 1H), 3.30-3.18 (m, 5H), 2.97-2.96 (m, 1H), 2.89-2.79 (m, 2H, —CCH2C—, linker), 2.12 (s, 3H, —C(O)CH3), 2.07 (s, 3H, —C(O)CH3), 2.01 (s, 6H, —C(O)CH3), 1.33-1.23 (m, 4H, —CCH2C—, linker), 1.06-0.99 (m, 2H, —CCH2C—, linker); 13C NMR (150 MHz, CDCl3): δ 170.56, 170.42, 170.26, 170.02, 168.45, 168.69, 138.95, 138.93, 138.72, 138.68, 138.58, 138.24, 138.22, 138.07, 133.83, 132.09, 131.76, 128.87, 128.79, 128.67, 128.63, 128.61, 128.58, 128.52, 128.42, 128.13, 128.06, 127.99, 127.92, 127.81, 127.76, 127.74, 127.46, 127.08, 123.71, 123.36, 100.13 (C-1e,e', 1 J C,H=169.2 Hz), 99.39 (C-1b, 1 J C,H=162.2 Hz), 98.35 (C-1d, 1 J C,H=171.5 Hz), 98.31 (C-1a, 1 J C,H=160.2 Hz), 97.16 (C-1d', 1 J C,H=170.5 Hz), 76.20, 76.05, 75.42, 74.97, 74.89, 74.80, 74.70, 74.65, 74.47, 74.28, 73.94, 73.68, 73.26, 72.60, 72.25, 72.20, 71.70, 71.50, 69.15, 69.07, 69.04, 68.99, 68.50, 68.45, 67.80, 65.54, 56.73, 55.90, 51.29, 31.14, 29.91, 28.87, 28.47, 23.19, 21.33, 21.27, 21.191; HRMS (MALDI-TOF): m/z calcd for C, 176; H, 185; N, 5; O, 42: 3042.2400; found 3065.2210 (M+Na)+.

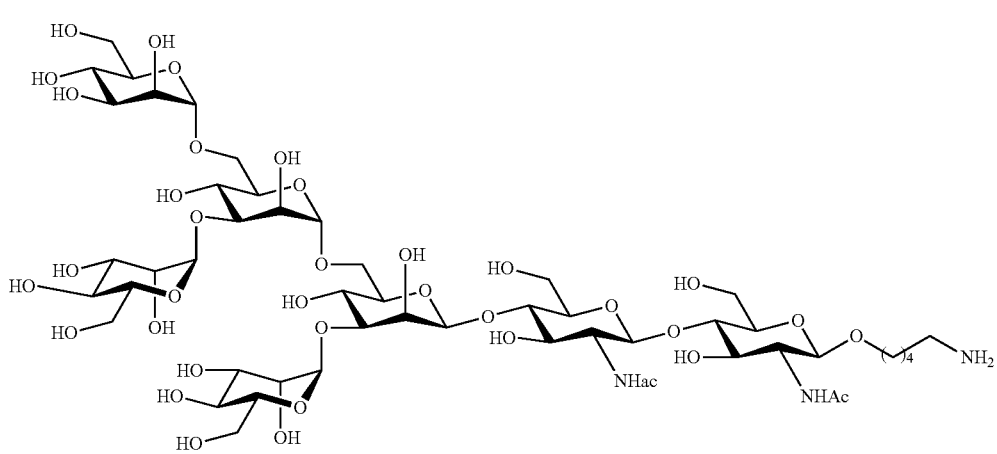

G4

5-Aminopentyl-α-D-mannopyranosyl(1→3),[di-(α-D-mannopyranosyl)-(1→3), (1→6)-α-D-mannopyranosyl](1→6)-β-D-mannopyranosyl-(1→4)-2-acetamido-2-deoxy-β-D-glucopyranosyl-(1→4)-2-acetamido-2-deoxy-β-D-glucopyranoside (G4): Heptasaccharide S9e (0.140 g, 0.024 mmoles), was deprotected by following the general procedure 2 (Method 1) to obtain title compound G4 (0.039 g, 29%) as a white solid. 1H NMR (600 MHz, D2O): δ 5.09 (s, 1H, H-1d), 4.89 (s, 1H, H-1d'), 4.86 (d, J=1.5 Hz, 1H, H-1e), 4.75 (d, J=1.5 Hz, 1H, H-1e'), 4.76 (s, 1H, overlapped with D2O, H-1c), 4.50 (d, J=7.8 Hz, 1H, H-1a), 4.35 (d, J=7.9 Hz, 1H, H-1b), 4.17 (d, J=1.7 Hz, 1H), 4.07-4.05 (m, 1H), 4.00-3.97 (m, 2H), 3.94-3.37 (m, 40H), 2.90-2.85 (m, 2H, —CH2N linker), 1.98 (s, 3H, —C(O)CH3), 1.94 (s, 3H, —C(O)CH3), 1.61-1.46 (m, 4H, —CCH2C—, linker), 1.35-1.26 (m, 2H, —CCH2C—, linker); 13C NMR (150 MHz, D2O): δ 177.2, 172.3, 102.44, 101.44, 101.01, 100.37, 99.85, 99.25, 80.54, 79.49, 79.28, 78.58, 74.45, 74.43, 72.50, 71.93, 70.64, 70.24, 70.15, 70.04, 70.01, 69.87, 69.46, 69.39, 66.69, 66.66, 65.94, 65.91, 65.56, 65.13, 65.12, 60.93, 60.91, 60.43, 60.13, 60.04, 59.97, 54.90, 54.86, 39.28, 27.98, 26.48, 22.08, 22.02, 21.99; ESI-MS: m/z calcd for C, 51; H, 89; N, 3; O, 36: 1319.5123; found 1342.5165 (M+Na)+.

cooled to 40° C., a solution of donor 2 (0.383 g, 0.282 mmol) and acceptor 14 (0.350 g, 0.256 mmol) in 5 mL toluene was added. The mixture was stirred for 2 h, quenched with Et3N, diluted with CH2Cl2 and filtered through Celite. The filtrate was washed with aqueous NaHCO3 (2×50 mL), and a brine (50 mL) solution. The organic layer was dried over Na2SO4 and concentrated in vacuo. The residue was purified by flash column chromatography (0%→15% EA in toluene) to afford S10a (0.405 g, 58%) as colorless foam. TLC: (ethyl acetate: toluene=2/8, v/v): Rf=0.46; 1H NMR (600 MHz, CDCl3): δ 7.89-7.35 (m, 8H, Ar—H), 7.38-7.12 (m, 56H, Ar—H), 7.12-7.08 (m, 3H, Ar—H), 7.03-6.88 (m, 7H, Ar—H), 6.78-6.69 (m, 4H, Ar—H), 5.50 (s, 1H, H-1f), 5.37 (d, J=1.4 Hz, 1H, H-2c), 5.25 (s, 1H, Ph-CH—, benzylidene), 5.23-5.17 (m, 3H, overlapped, H-1d,e,f), 4.98 (s, 1H, H-1c), 4.95 (d, J=7.5 Hz, 1H, H-1a), 4.91-4.53 (m, 5H), 4.69-4.58 (m, 3H), 4.55-4.28 (m, 16H), 4.25-4.00 (m, 13H), 3.95-3.91 (m, 1H), 3.91-3.60 (m, 14H), 3.58 (d, J=12 Hz, 1H), 3.51-3.45 (m, 4H), 3.42-3.38 (m, 3H), 3.29-3.10 (m, 3H), 2.98-2.78 (m, 3H), 2.08 (s, 3H, —C(O)CH3), 1.99 (s, 3H, —C(O)CH3), 1.35-1.23 (m, 4H, —CCH2C—, linker), 1.07-1.00 (m, 2H, —CCH2C—, linker); 13C NMR (150 MHz,

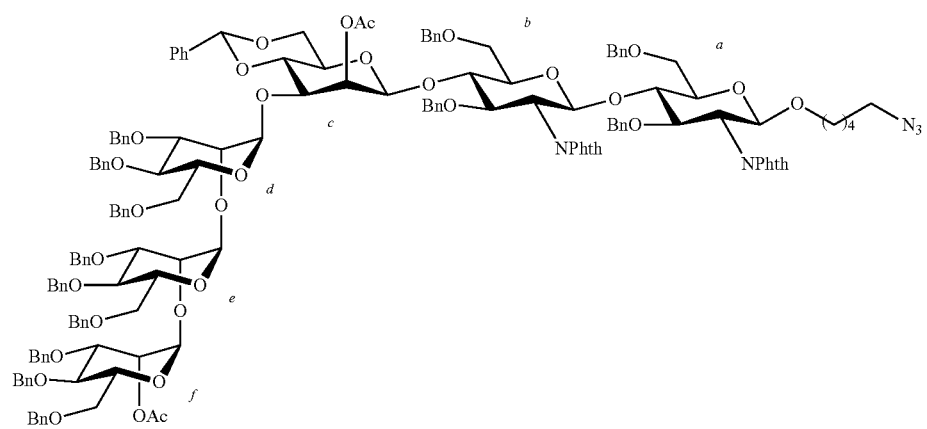

S10a

5-Azidopentyl-O-(2-O-acetyl-3,4,6-tri-O-benzyl-α-D-mannopyranosyl-(1→2)-3,4,6-tri-O-benzyl-α-D-mannopyranosyl-(1→2)-3,4,6-tri-O-benzyl-α-D-mannopyranosyl-(1→3)-2-O-acetyl-4,6-O-benzylidene-β-D-mannopyranosyl-(1→4)-O-(3,6-di-O-benzyl-2-deoxy-2-phthalimido-β-D-glucopyranosyl)-(1→4)-O-3,6-di-O-benzyl-2-deoxy-2-phthalimido-β-D-glucopyranoside (S10a): A mixture of Silver triflate (0.328 g, 1.28 mmol), Bis(cyclopentadienyl) hafnium dichloride (0.340 g, 0.897 mmol) and 4 Å activated molecular sieves in dry toluene (10 mL) was stirred at rt for 1 h. The reaction mixture was then CDCl3): δ 170.38, 169.81, 168.76, 168.26, 139.06, 138.95, 138.92, 138.87, 138.60, 137.36, 128.85, 128.66, 128.64, 128.58, 128.55, 128.48, 128.43, 128.39, 128.35, 128.26, 128.10, 128.02, 127.82, 127.71, 101.48, 100.08, 99.75, 99.39, 98.36, 97.27, 77.80, 78.75, 76.10, 75.38, 74.93, 74.82, 74.70, 73.58, 73.28, 73.21, 73.06, 72.79, 72.65, 72.57, 72.17, 71.01, 69.60, 69.10, 68.96, 68.63, 66.74, 56.85, 55.97, 51.37, 28.95, 28.54, 23.27, 21.43, 21.09; ESI-MS: m/z calcd for C, 159; H, 163; N, 5; O, 35: 2703.1054; found 2726.1214 (M+Na)+.

G5

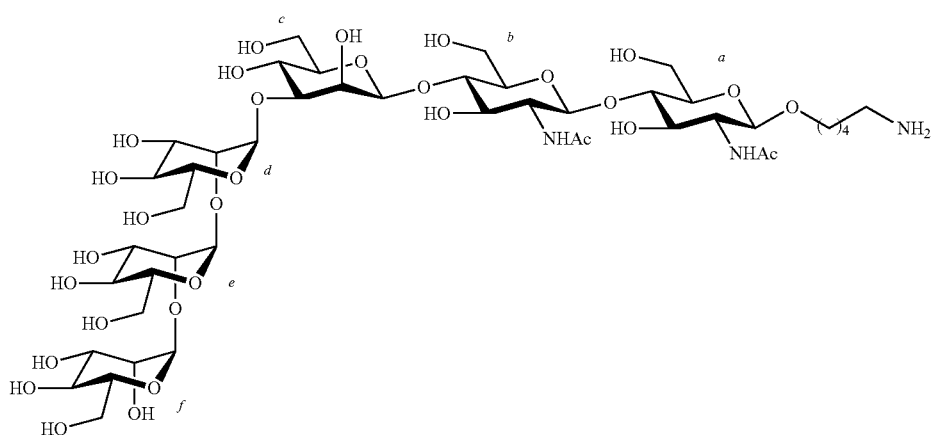

5-Aminopentyl-α-D-mannopyranosyl-(1→2)-α-D-mannopyranosyl-(1→2)-α-D-mannopyranosyl-(1→3)-β-D-mannopyranosyl-(1→4)-2-acetamido-2-deoxy-β-D-glucopyranosyl-(1→4)-2-acetamido-2-deoxy-β-D-glucopyranoside (G5): Hexasaccharide S10a (0.140 g, 0.051 mmoles), was deprotected by following general procedure 2 (Method 1) to obtain the title compound G5 (0.025 g, 42%) as white solid. 1H NMR (600 MHz, D2O): δ 5.32 (s, 1H, H-1d), 5.27 (s, 1H, H-1e), 5.01 (s, 1H, H-1f), 4.74 (s, 1H, H-1c), 4.56 (d, J=7.8 Hz, 1H, H-1a), 4.63 (d, J=7.8 Hz, 1H, H-1b), 4.18 (d, J=3.3 Hz, 1H), 4.07 (s, 1H), 4.04 (d, J=3.2 Hz, 1H), 4.03 (d, J=3.1 Hz, 1H), 3.32-3.33 (m, 35H), 2.05 (t, J=11.2 Hz, 2H, —CH2NH2, linker), 2.03 (s, 3H, —C(O)CH3), 2.00 (s, 3H, —C(O)CH3), 1.64 (m, 2H, —CCH2C—, linker), 1.50 (m, 2H, —CCH2C—, linker), 1.36 (m, 2H, —CCH2C—, linker); 13C NMR (150 MHz, D2O): δ 174.54, 174.38, 102.17 (C-1e, 1 J C,H=170.2 Hz), 101.34 (C-1b, 1 J C,H=161.2 Hz), 101.014 (C-1d, 1 J C,H=169.8 Hz), 100.70 (C-1f, 1 J C,H=172.2 Hz), 100.56 (C-1a, 1 J C,H=160.2 Hz), 99.85, 80.50, 79.25, 78.66, 78.55, 78.47, 76.12, 74.48, 73.37, 73.13, 72.33, 71.88, 70.24, 70.17, 70.05, 69.95, 69.89, 66.95, 66.81, 66.71, 65.81, 61.01, 60.97, 60.88, 60.76, 60.02, 59.92, 54.92, 39.25, 27.99, 26.32, 23.19, 22.06, 22.04; ESI-MS: m/z calcd for C, 45; H, 79; N, 3; O, 31: 1157.4590; found 1180.4591 (M+Na)+.

5-Azidopentyl-O-(2-O-acetyl-3,4,6-tri-O-benzyl-α-D-mannopyranosyl-(1→2)-3,4,6-tri-O-benzyl-α-D-mannopyranosyl-(1→2)-3,4,6-tri-O-benzyl-α-D-mannopyranosyl-(1→3)-2-O-acetyl-β-D-mannopyranosyl-(1→4)-O-(3,6-di-O-benzyl-2-deoxy-2-phthalimido-β-D-glucopyranosyl)-(1→4)-O-3,6-di-O-benzyl-2-deoxy-2-phthalimido-β-D-glucopyranoside (S10b): To a solution of S10a (0.205 g, 0.075 mmol) in 10 mL acetonitrile was added p-toluene sulfonic acid monohydrate (0.020 g, 0.113 mmol), stirred at room temperature for 9 h. The reaction was quenched with Et3N and concentrated in vacuo. The residue was purified by flash column chromatography (0%→20% EA in toluene) to give diol S10b (0.120 g, 60%). TLC: (acetone:toluene=2/8, v/v): Rf=0.26; 1H NMR (600 MHz, CDCl3): δ 7.83-7.62 (m, 8H, Ar—H), 7.41-7.06 (m, 57H, Ar—H), 6.95-6.89 (m, 6H, Ar—H), 6.73-6.71 (m, 2H, Ar—H), 5.50 (d, J=4.8 Hz, 1H, H-2f), 5.23 (d, J=1.8 Hz, 1H, H-1d), 5.22 (d, J=3.8 Hz, 1H, H-1c), 5.19 (d, J=3.2 Hz, 1H, H-1e), 5.18 (s, 1H, H-1f), 5.03 (d, J=7.8 Hz, 1H, H-1a), 4.88 (t, J=7.8 Hz, 1H), 4.82-4.74 (m, 5H), 4.68-4.38 (m, 21H), 4.33 (d, J=7.8 Hz, 1H), 4.29 (d, J=7.9 Hz, 1H), 4.20-4.00 (m, 8H), 3.95-3.71 (m, 9H), 3.69-3.53 (m, 6H), 3.52-3.33 (m, 8H), 3.29-3.15 (m, 5H), 2.90-2.79 (m, 2H), 2.08 (s, 3H, —C(O)CH3), 1.92 (s, 3H, —C(O)CH3), 1.35-1.20 (m, 4H, —CCH2C—, linker), 1.08-1.01 (m, 2H, —CCH2C—, linker); 13C NMR S10b

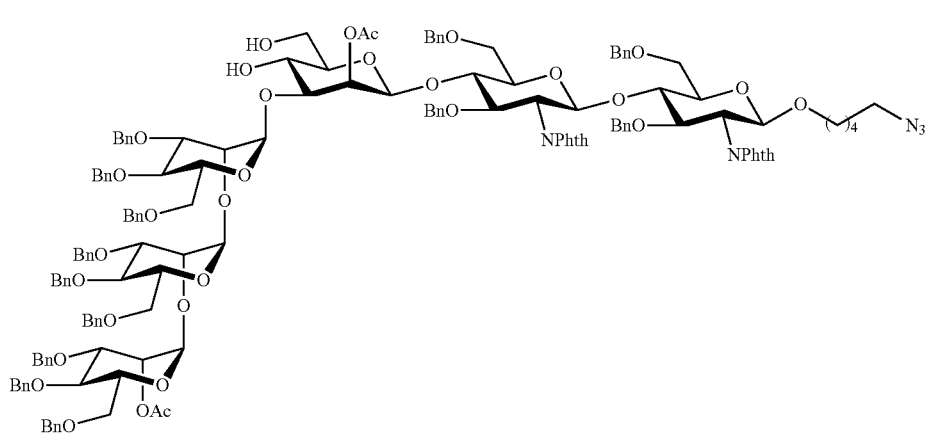

(150 MHz, CDCl3): δ 170.40, 169.88, 168.68, 138.20, 138.94, 138.78, 138.71, 138.56, 138.48, 138.38, 138.21, 138.02, 134.30, 133.84, 132.02, 128.78, 128.65, 128.63, 128.43, 128.40, 128.38, 128.25, 128.15, 128.06, 127.94, 127.88, 127.84, 127.77, 127.69, 127.65, 127.56, 127.10, 123.90, 123.41, 100.98, 99.83, 98.34, 97.32, 78.31, 78.17, 78.11, 78.00, 76.22, 75.52, 75.28, 75.05, 74.82, 74.40, 73.98, 73.67, 73.58, 73.36, 73.06, 72.59, 72.48, 72.42, 72.09, 71.32, 70.52, 69.46, 69.09, 68.83, 68.72, 68.42, 68.20, 67.61, 62.57, 56.77, 55.98, 51.37, 29.99, 29.65, 28.94, 28.54, 23.27, 21.44, 21.13, 14.41; ESI-MS: m/z calcd for C, 152; H, 159; N, 5; O, 35: 1615.0741; found 2638.0754 (M+Na)+.

at rte for 6 h. TLC (ethyl acetate:toluene, 2/8) indicated formation of product with consumption of starting material, reaction was quenched by Et3N. The reaction mixture was diluted with CH2Cl2 and filtered through Celite. The filtrate was washed with aqueous NaHCO3 (2×50 mL), and a brine (50 mL) solution. The organic layer was dried over Na2SO4 and concentrated in vacuo. The residue was purified by flash column chromatography (0%→10% EA in toluene) to afford S10c (0.095 g, 52%) as colorless foam. TLC: (acetone: toluene=2/8, v/v): Rf=0.41; 1H NMR (600 MHz, CDCl3): δ 7.77-7.50 (m, 8H, Ar—H), 7.29-6.98 (m, 126H, Ar—H), 6.95-6.89 (m, 4H, Ar—H), 6.746.64 (m, 5H, Ar—H), 5.56

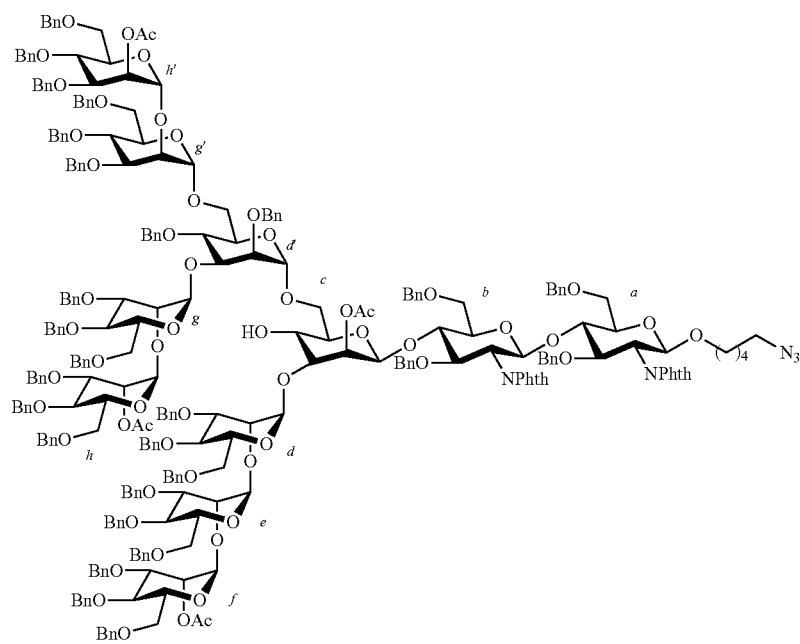

S10c

5-Azidopentyl-O-(2-O-acetyl-3,4,6-tri-O-benzyl-α-D-mannopyranosyl-(1→2)-3,4,6-tri-O-benzyl-α-D-mannopyranosyl-(1→2)-3,4,6-tri-O-benzyl-α-D-mannopyranosyl-(1→3)-{2-O-acetyl-3,4,6-tri-O-benzyl-α-D-mannopyranosyl-(1→2)-3,4,6-tri-O-benzyl-α-D-mannopyranosyl-(1→3)-[2-O-acetyl-3,4,6-tri-O-benzyl-α-D-mannopyranosyl-(1→2)-3,4,6-tri-O-benzyl-α-D-mannopyranosyl-(1→6)]-2,4-di-O-benzyl-α-D-mannopyranosyl-(1→6)}-2-O-acetyl-β-D-mannopyranosyl-(1→4)-O-(3,6-di-O-benzyl-2-deoxy-2-phthalimido-β-D-glucopyranosyl)-(1→4)-O-3,6-di-O-benzyl-2-deoxy-2-phthalimido-β-D-glucopyranoside (S10c): A mixture of hexasaccharide acceptor S10a (0.1 g, 0.038 mmol), thiomannoside donor 5 (0.104 g, 0.045 mmol) and activated 4 Å molecular sieves (0.5 g) in CH3CN (10 mL) was stirred at rt for 1 h. The resulting mixture was cooled to −10° C., tris(4-bromophenyl)aminium hexachloroantimonate (0.096 g, 0.114 mmol) was added and stirred (s, 1H, H-2f), 5.53 (s, 1H, H-2h), 5.51 (s, 1Hh'), 5.34 (s, 1H, H-2c), 5.32 (d, J=12.2 Hz, 2H), 5.18 (d, J=7.8 Hz, 1H), 5.12 (s, 1H), 5.08 (s, 1H), 5.04 (s, 2H), 4.59-3.75 (m, 116H), 3.26-3.16 (m, 4H), 3.08-3.02 (m, 2H), 2.93-2.83 (m, 2H), 2.12 (s, 3H), 2.06 (s, 3H), 2.06 (s, 3H), 1.97 (s, 3H), 1.39-1.26 (m, 4H), 1.07-1.05 (m, 2H); 13C NMR (150 MHz, CDCl3): δ 170.12, 170.03, 169.76, 168.14, 167.36, 138.64, 138.54, 138.45, 138.41, 138.27, 138.07, 133.68, 133.57, 131.74, 129.05, 128.62, 128.57, 128.51, 128.33, 128.23, 128.14, 128.06, 127.99, 127.94, 127.81, 127.78, 127.73, 127.45, 101.24, 99.81, 99.59, 99.48, 99.34, 99.24, 99.05, 98.02, 96.95, 79.82, 79.23, 78.33, 78.24, 78.14, 75.86, 75.22, 75.12, 75.02, 74.93, 74.77, 74.57, 74.47, 74.38, 74.30, 74.17, 73.29, 73.11, 72.50, 72.20, 71.94, 71.35, 71.25, 69.13, 69.03, 68.79, 68.53, 68.48, 68.35, 68.17, 67.40, 56.56, 55.69, 51.09, 28.66, 28.26, 22.99, 21.17, 21.12; HRMS (MALDI-TOF): m/z calcd for C, 284; H, 297; N, 5; O, 62: 4772.0232; found 4794.9783 (M+Na)+.

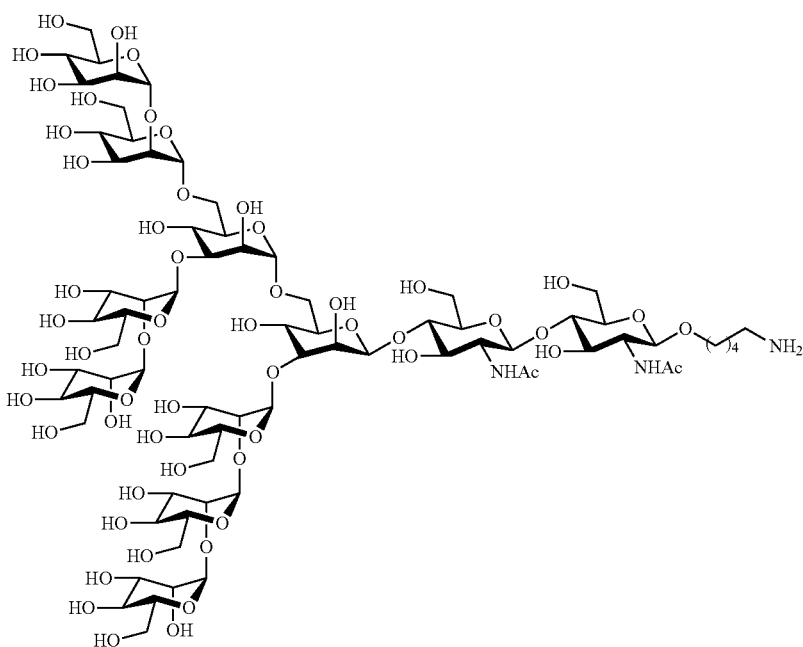

G6

5-Aminopentyl-α-D-mannopyranosyl-(1→2)-α-D-mannopyranosyl-(1→2)-α-D-mannopyranosyl-(1→3)-{α-D-mannopyranosyl-(1→2)-α-D-mannopyranosyl-(1→3)-[α-D-mannopyranosyl-(1→2)-α-D-mannopyranosyl-(1→6)]-α-D-mannopyranosyl-(1→6)}-β-D-mannopyranosyl-(1→4)-2-acetamido-2-deoxy-β-D-glucopyranosyl-(1→4)-2-acetamido-2-deoxy-β-D-glucopyranoside (G6): Compound S10c (0.120 g, 0.024 mmoles) was deprotected by following general procedure 2 (Method 1) to get Man9GlcNAc2 G6 (0.012 g, 26%) as a white solid. 1H NMR (600 MHz, D2O): δ 5.40 (s, 1H, H-1d), 5.33 (s, 1H, H-1d'), 5.30 (s, 1H, H-1e), 5.14 (s, 1H, H-1), 5.05 (s, 1H, H-1), 5.03 (d, J=2.4 Hz, 2H, H-1), 4.86 (s, 1H, H-1), 4.58 (d, J=7.8 Hz, 1H, H-1a), 4.48 (d, J=7.8 Hz, 1H, H-1b), 4.22 (d, J=2.4 Hz, 1H), 4.14 (s, 1H), 4.14 3.95 (m, 12H), 3.94-3.59 (m, 54H), 3.50-3.48 (m, 1H), 3.02 (t, J=9.2 Hz, 2H), 2.06 (s, 3H, —C(O)CH3), 2.02 (s, 3H, —C(O)CH3), 1.68-1.63 (m, 2H, —CCH2C—, linker), 1.59-1.56 (m, 2H, —CCH2C—, linker), 1.41-1.37 (m, 2H, —CCH2C—, linker); 13C NMR (150 MHz, D2O): δ 174.47, 171.01, 102.24 (C-1d, 1 J C,H=171.8 Hz), 102.21 (C-1d', 1 J C,H=169.0 Hz), 102.19 (C-1e, 1 J C,H=173.8 Hz), 101.43, 101.03, 100.82, 100.59 (C-1a, 1 J C,H=162.8 Hz), 100.21, 99.61, 97.97 (C-1b, 1 J C,H=159.8 Hz), 81.86, 79.32, 78.88, 78.63, 78.45, 74.50, 74.48, 74.14, 73.39, 73.27, 73.20, 73.17, 72.69, 72.36, 71.90, 71.61, 70.21, 70.03, 69.93, 69.37, 67.01, 66.94, 66.90, 66.85, 66.81, 66.76, 65.42, 65.40, 65.07, 64.90, 61.11, 61.06, 61.01, 60.91, 60.06, 59.94, 54.95, 39.29, 38.61, 28.02, 26.34, 22.16, 22.10, 22.06; ESI-MS: m/z calcd for C, 75; H, 129; N, 3; O, 56: 1967.7231; found 1990.7279 (M+Na)+.

Synthesis of hybrid type oligosaccharides (G7-G14) as shown in FIG. 74 depicts the structures of hybrid type glycans and their fragments.

Figure 75A:
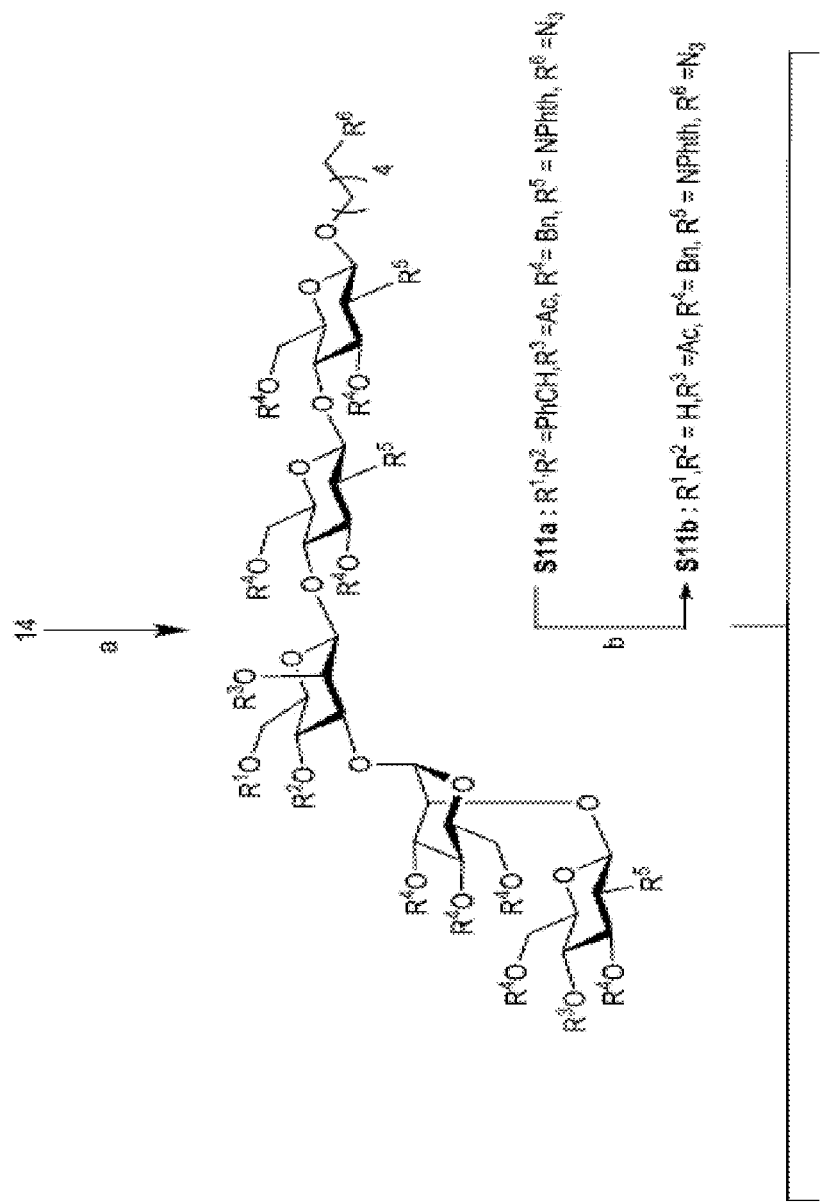
FIGS. 75A and 75B.
Figure 75B:
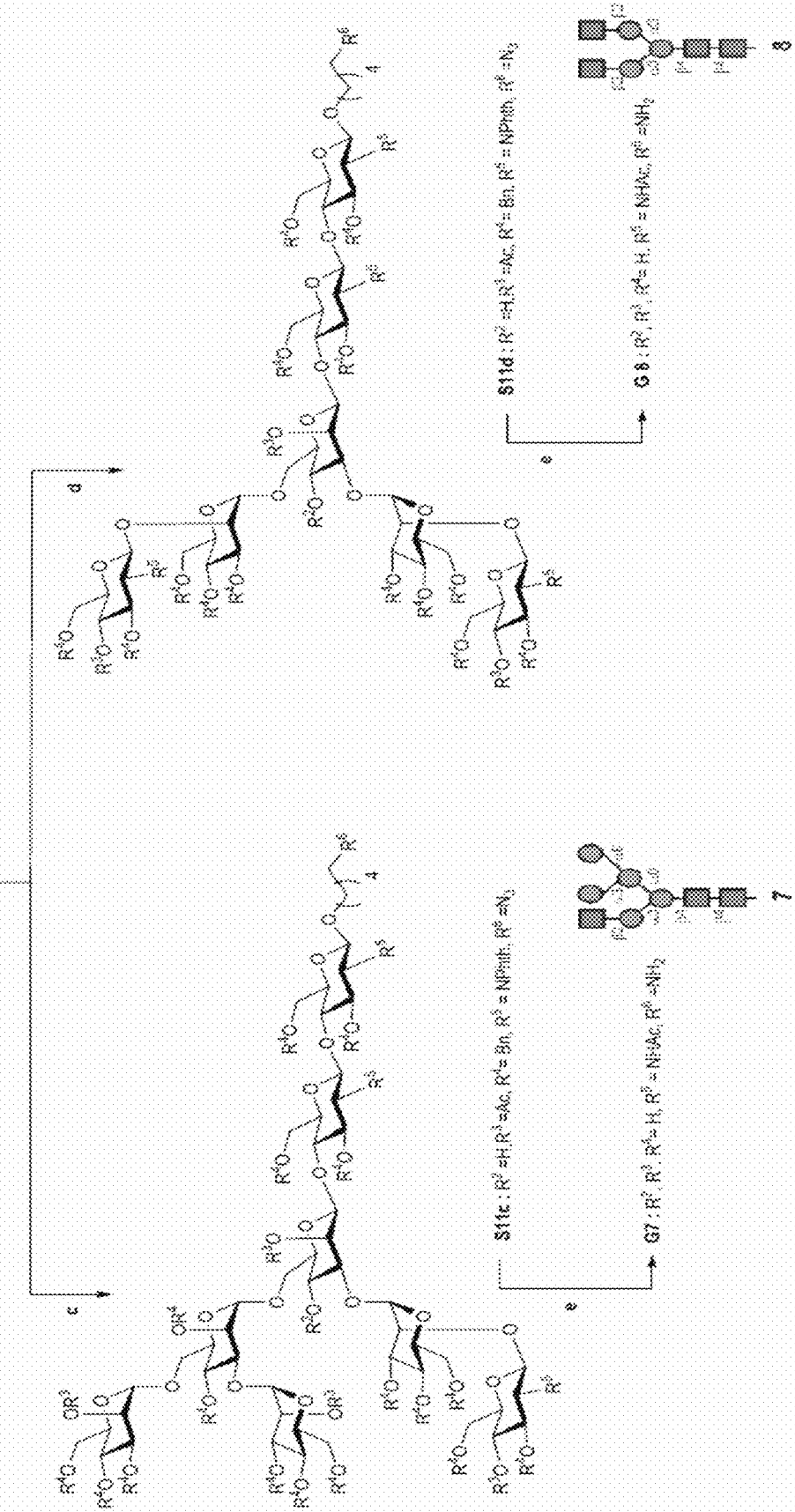
Figure 76:
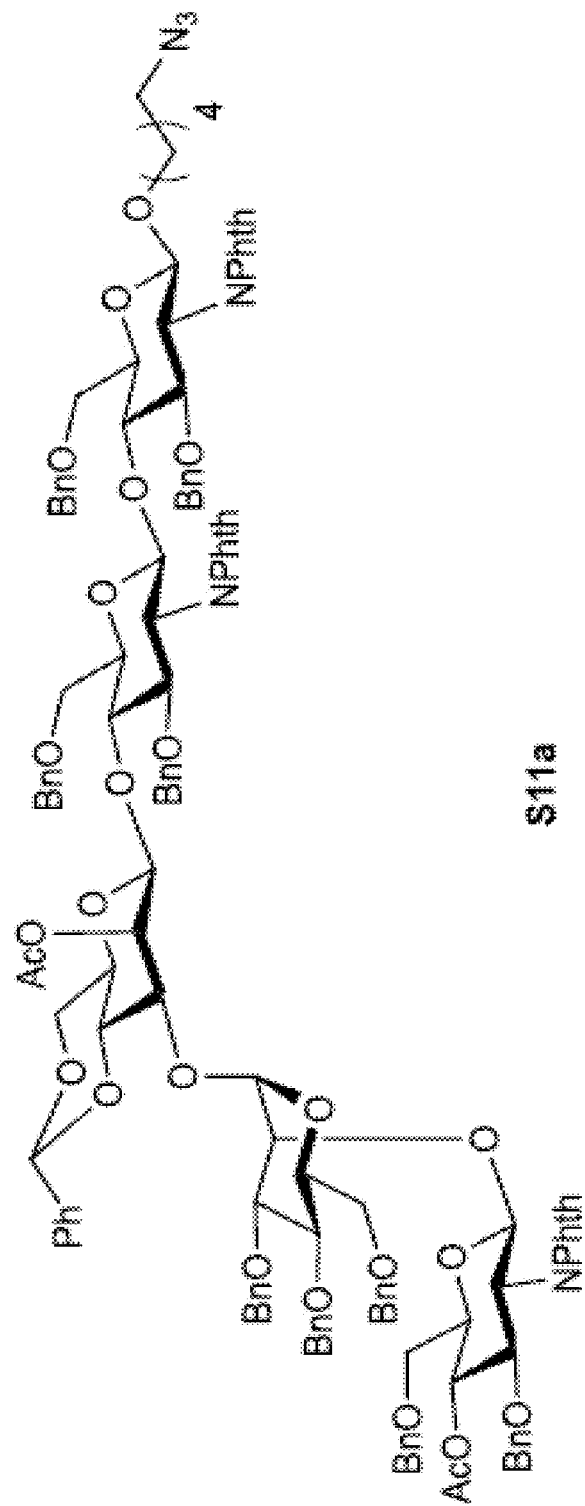
FIG. 76 Exemplary structure embodiments and synthetic scheme embodiments of the present disclosure.
Figure 77:
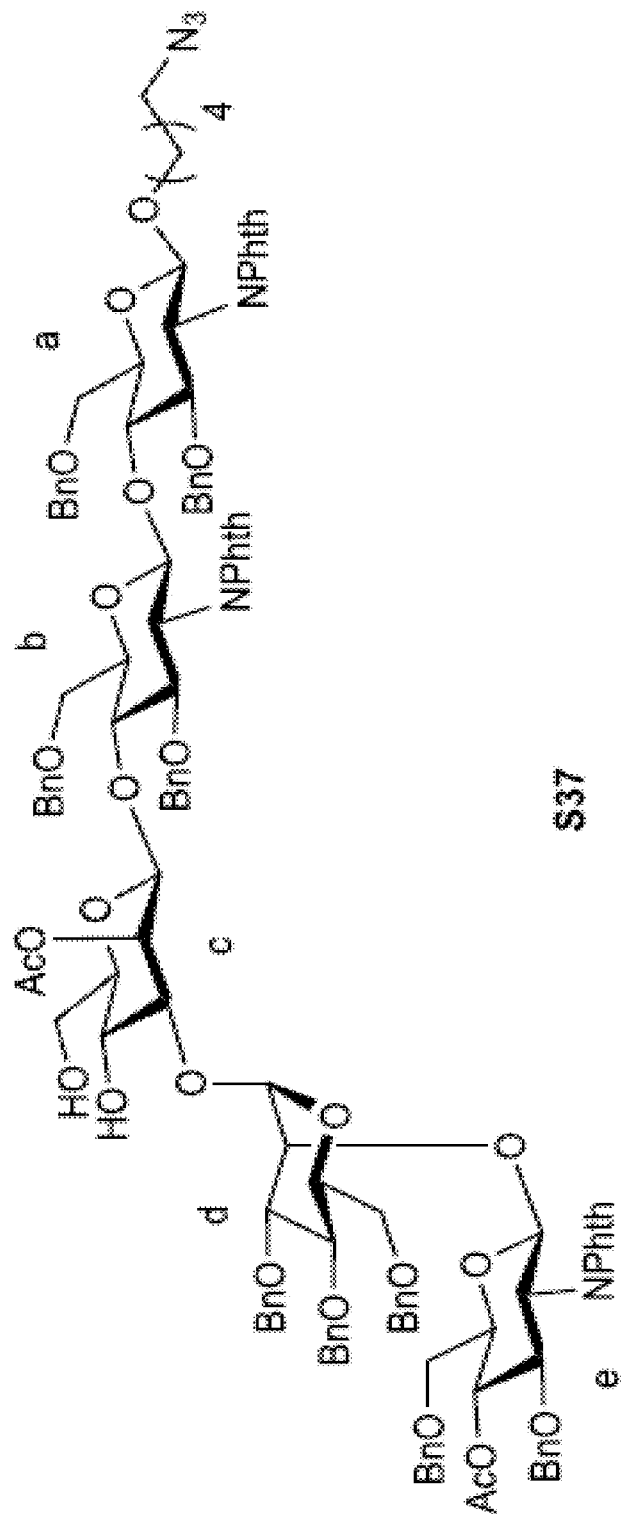
FIG. 77 Exemplary structure embodiments and synthetic scheme embodiments of the present disclosure.
Figure 78:
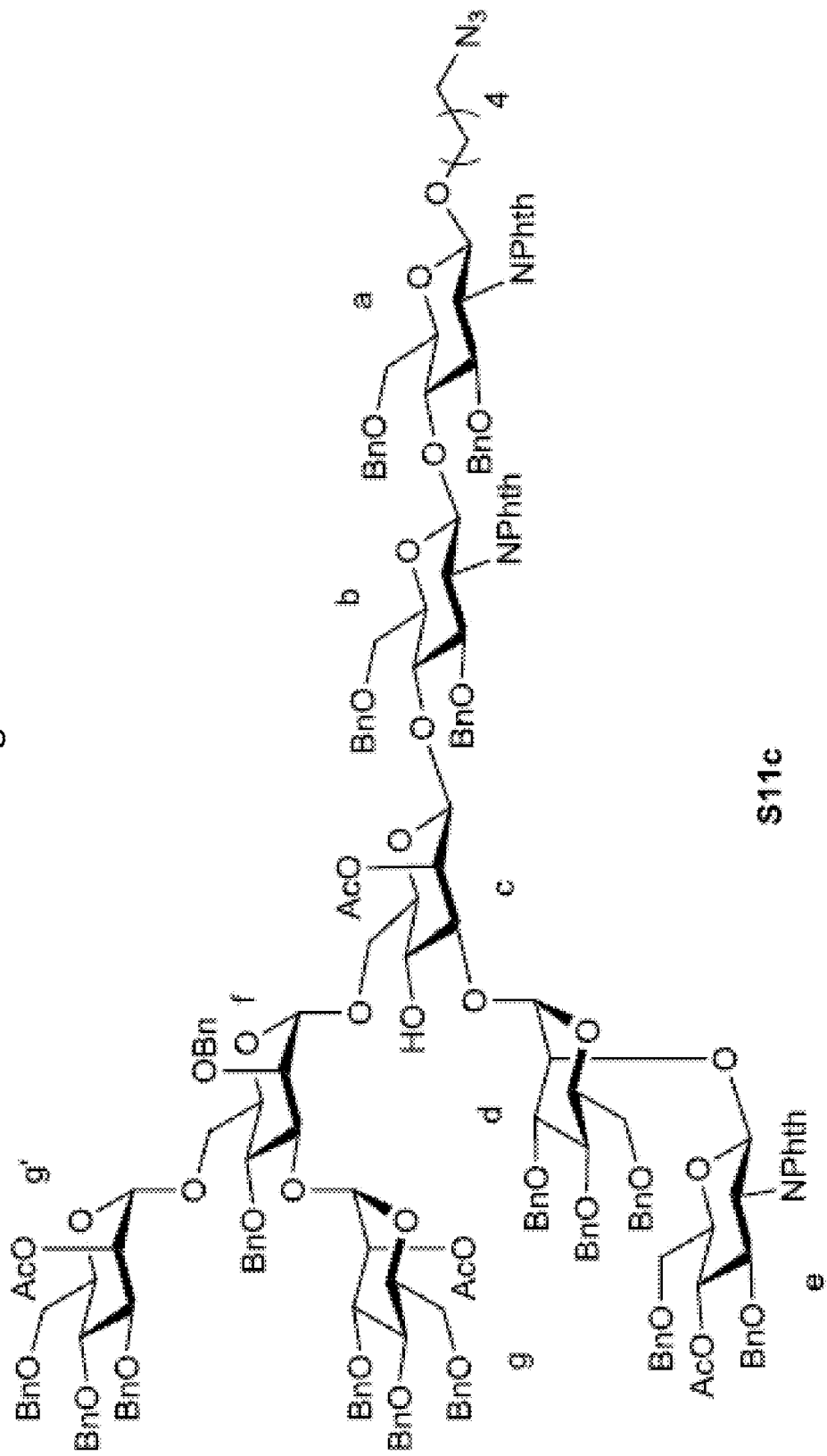
FIG. 78 Exemplary structure embodiments and synthetic scheme embodiments of the present disclosure.
Figure 79:
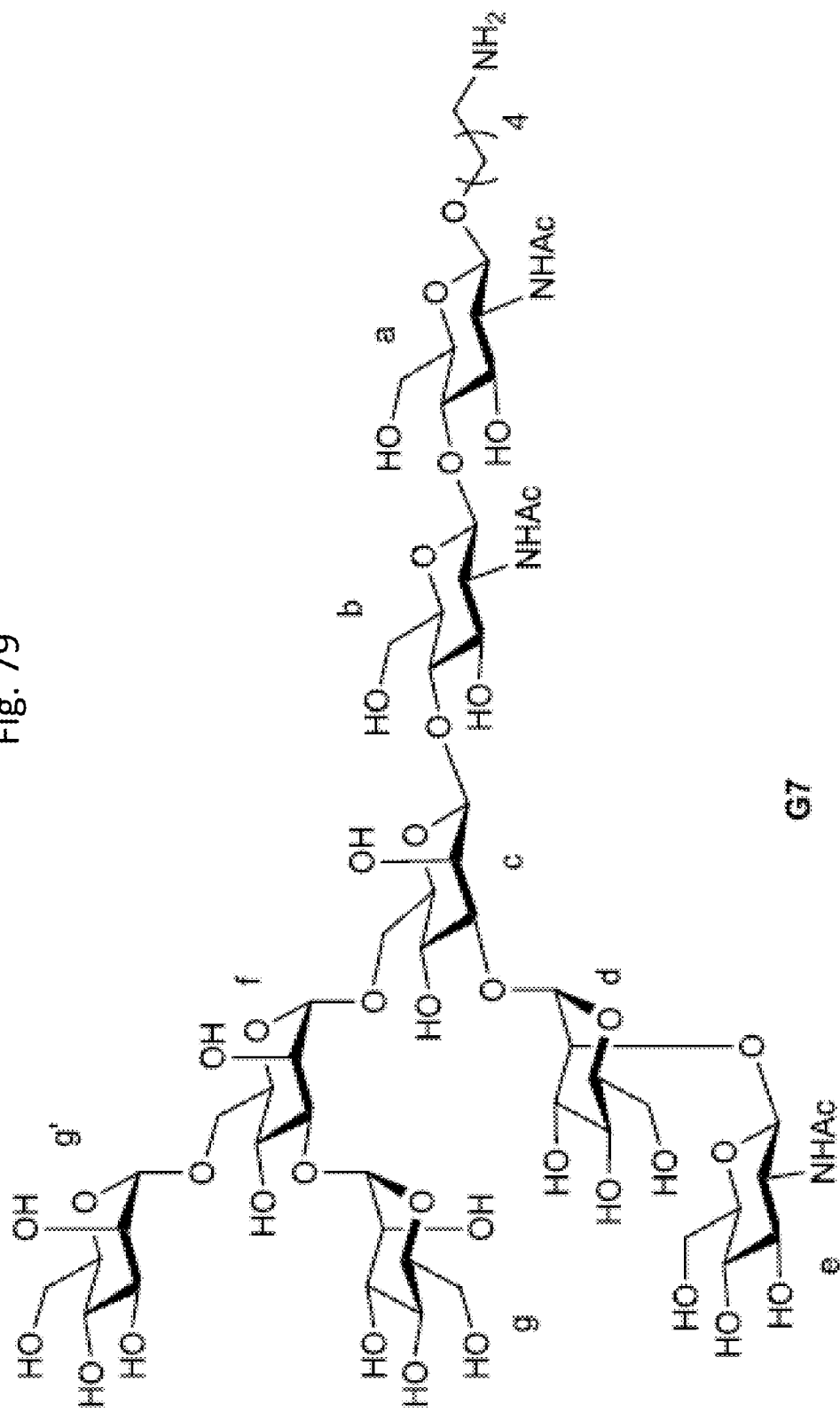
FIG. 79 Exemplary structure embodiments and synthetic scheme embodiments of the present disclosure.
Figure 80:
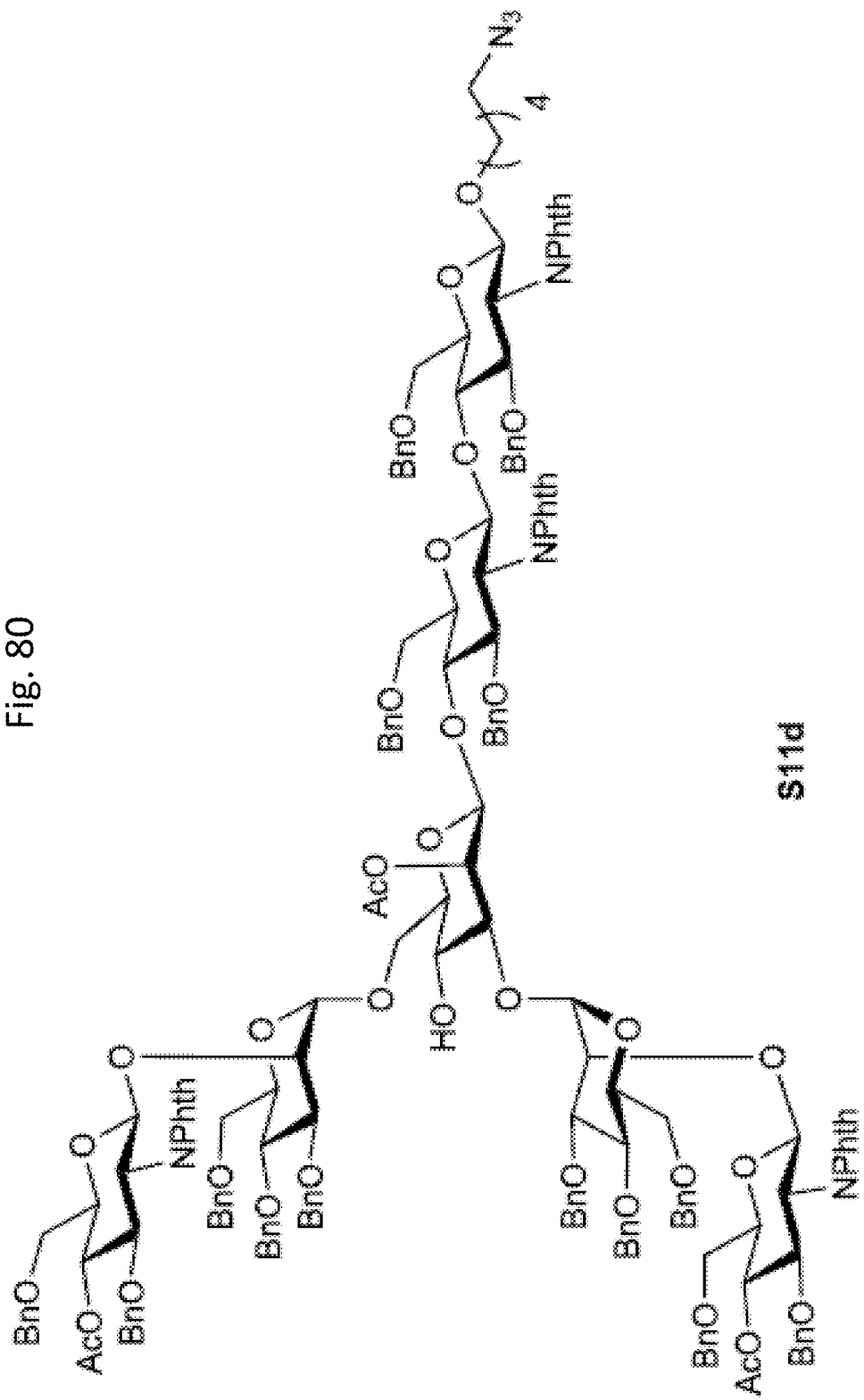
FIG. 80 Exemplary structure embodiments and synthetic scheme embodiments of the present disclosure.
Figure 81:
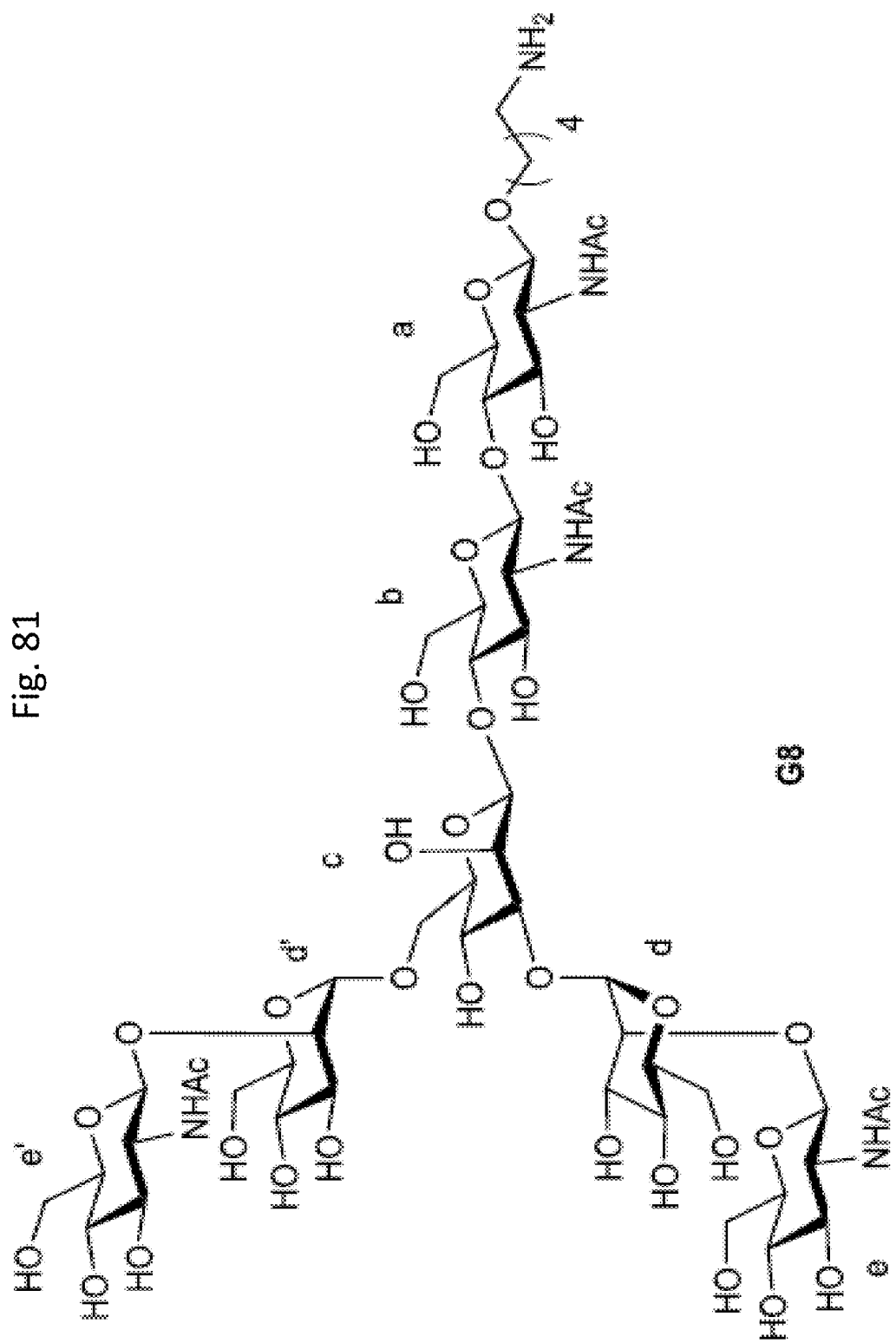
FIG. 81 Exemplary structure embodiments and synthetic scheme embodiments of the present disclosure.
Figure 82A:
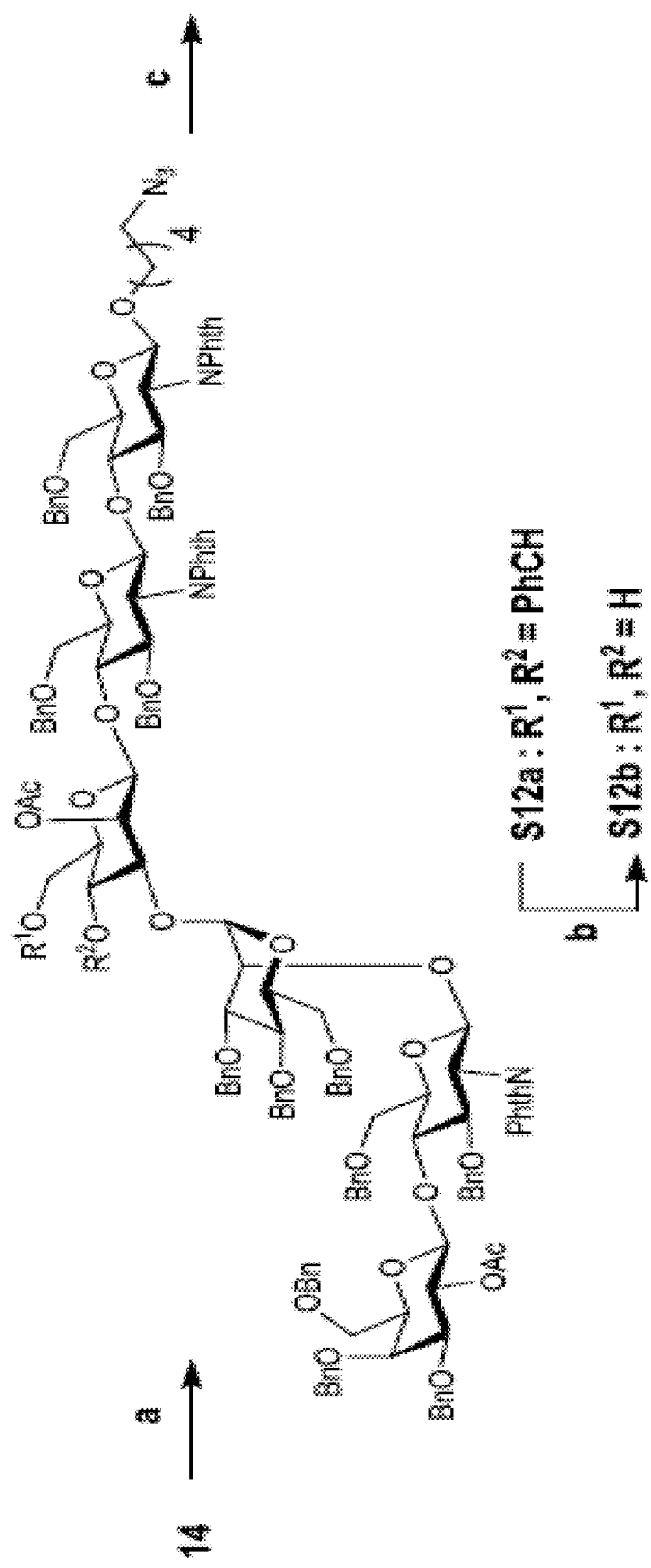
FIGS. 82A, 82B, 82C, and 82D.
Figure 82B:
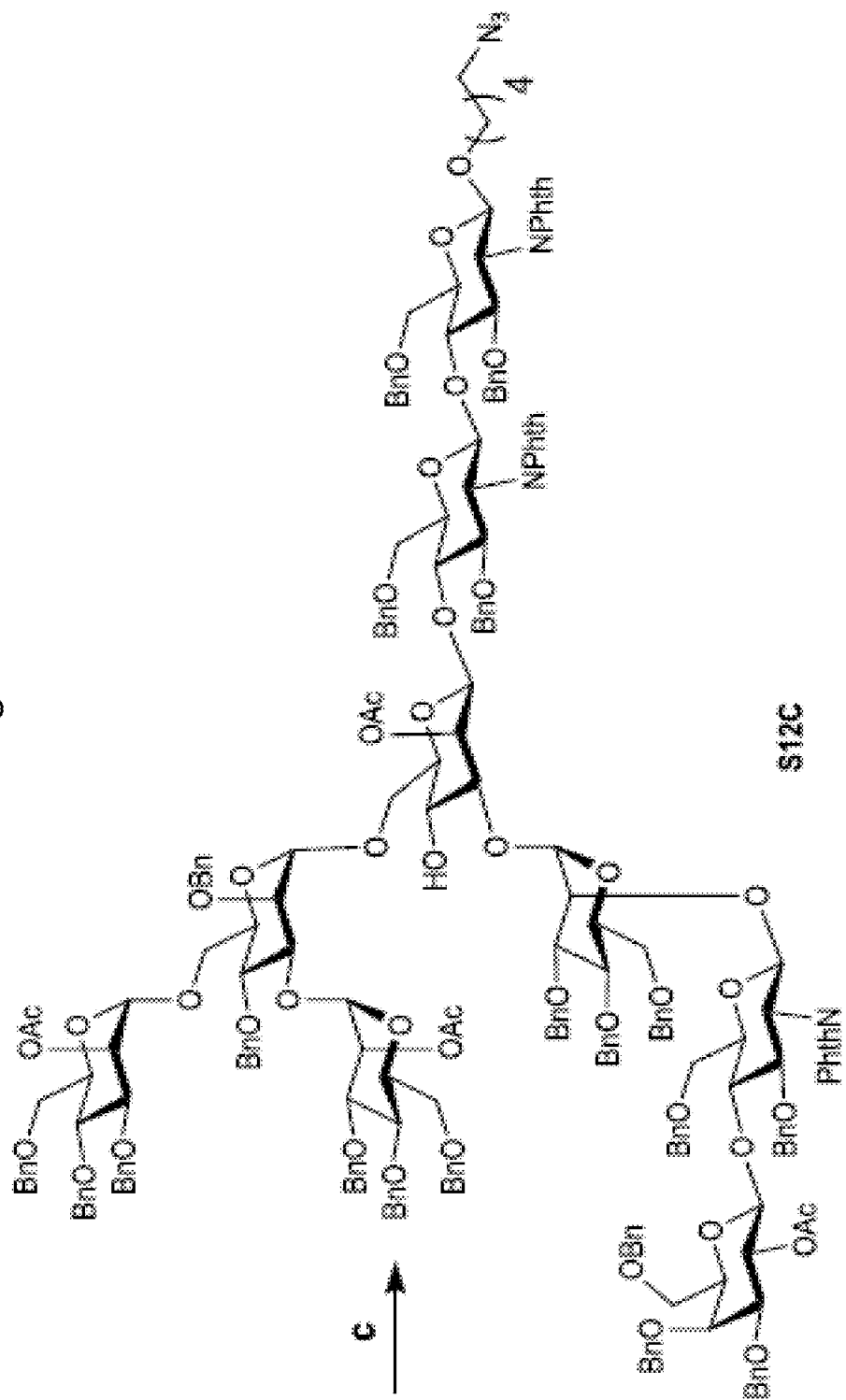
Figure 82C:
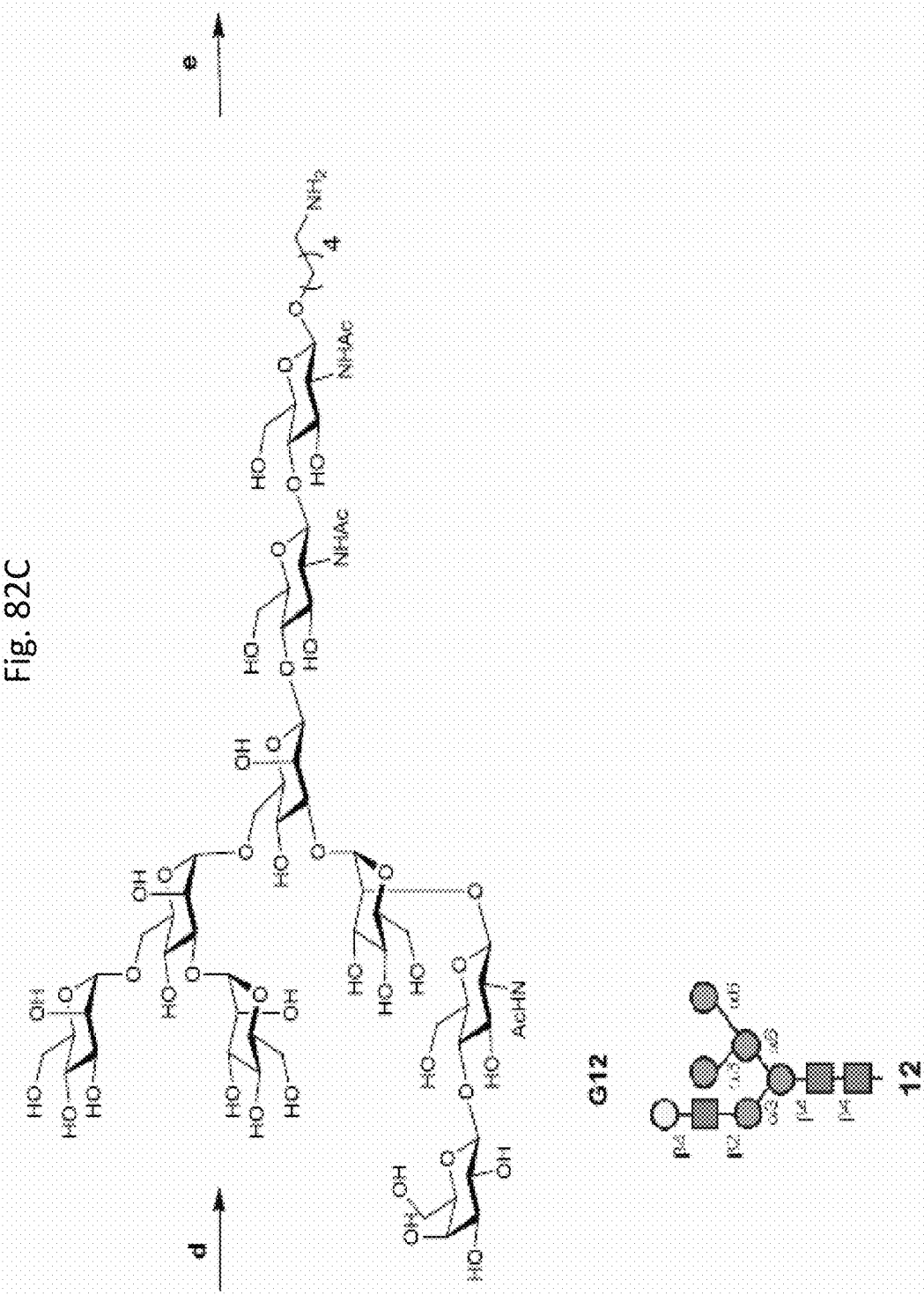
Figure 82D:
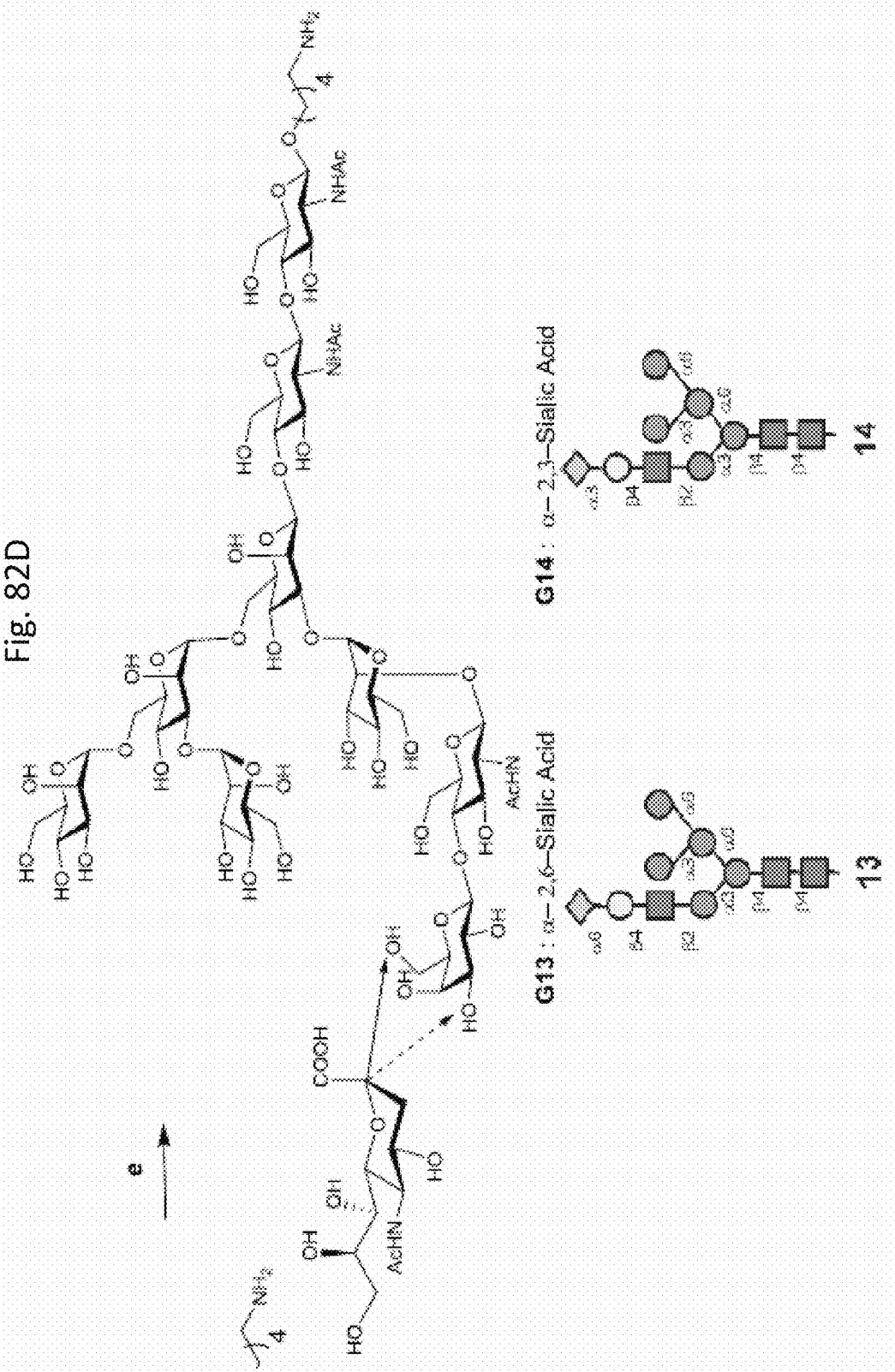
Figure 83:
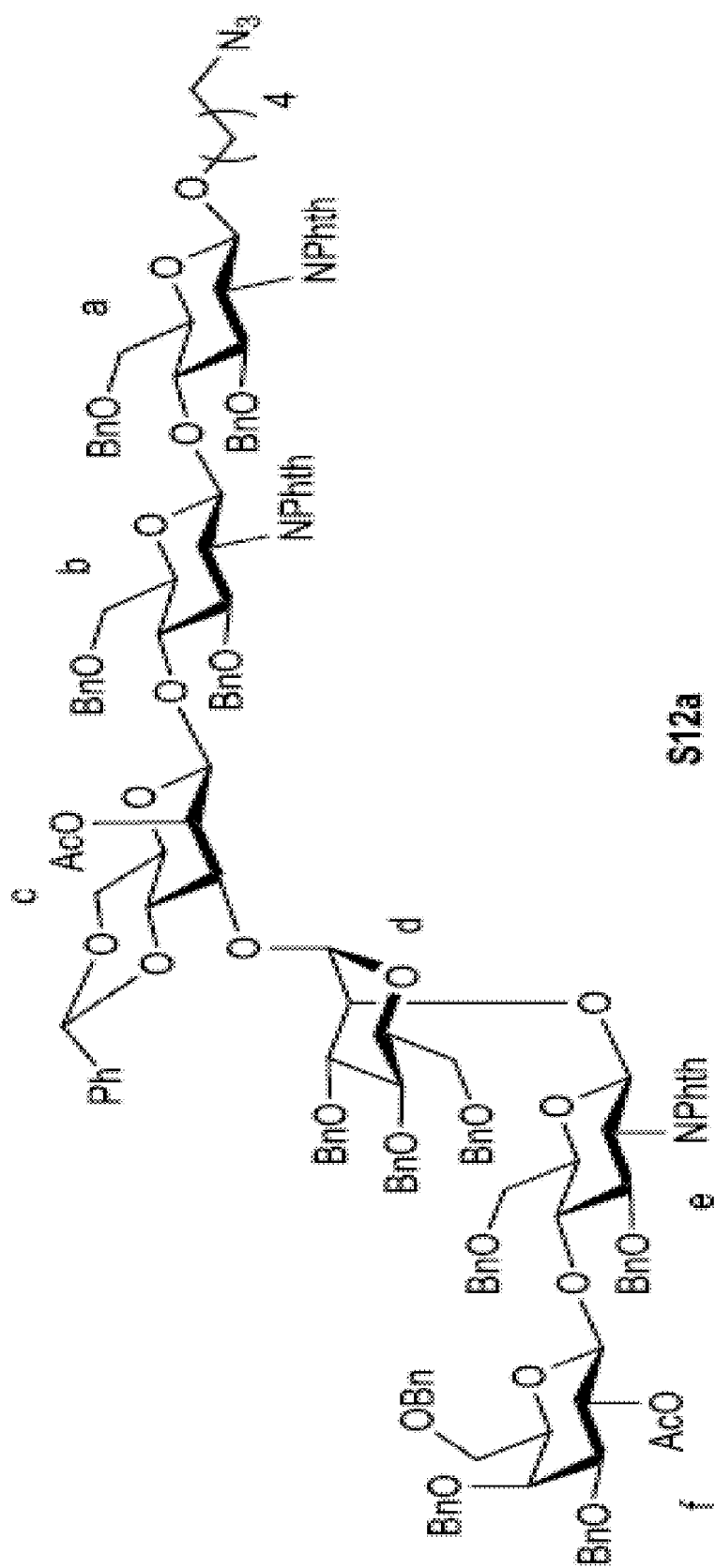
FIG. 83 Exemplary structure embodiments and synthetic scheme embodiments of the present disclosure.
Figure 84:
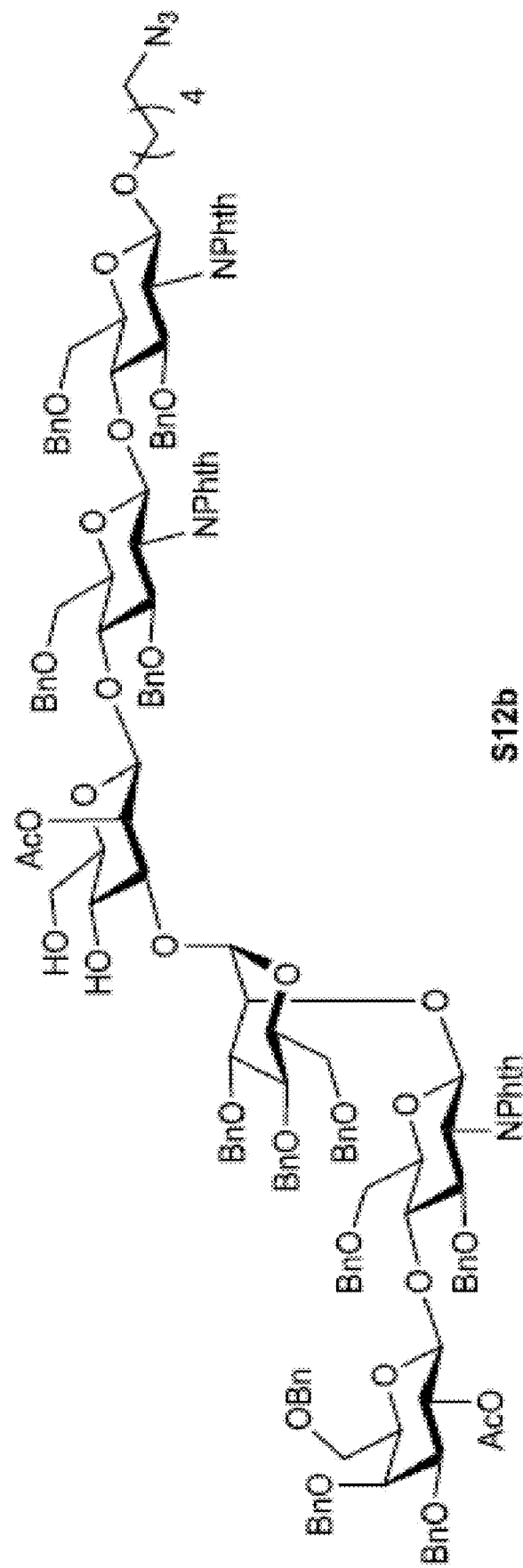
FIG. 84 Exemplary structure embodiments and synthetic scheme embodiments of the present disclosure.
Figure 85:
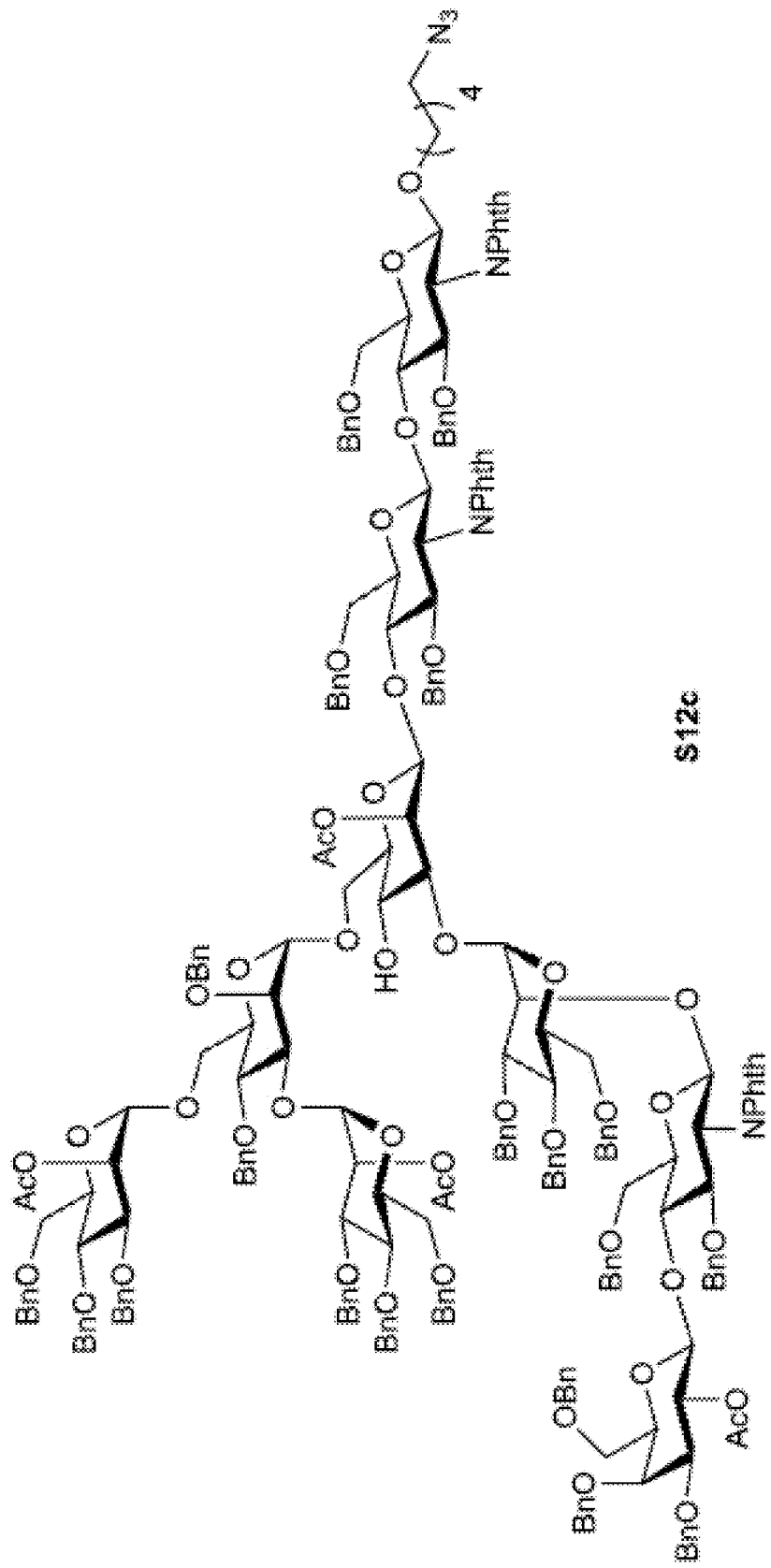
FIG. 85 Exemplary structure embodiments and synthetic scheme embodiments of the present disclosure.
Figure 86:
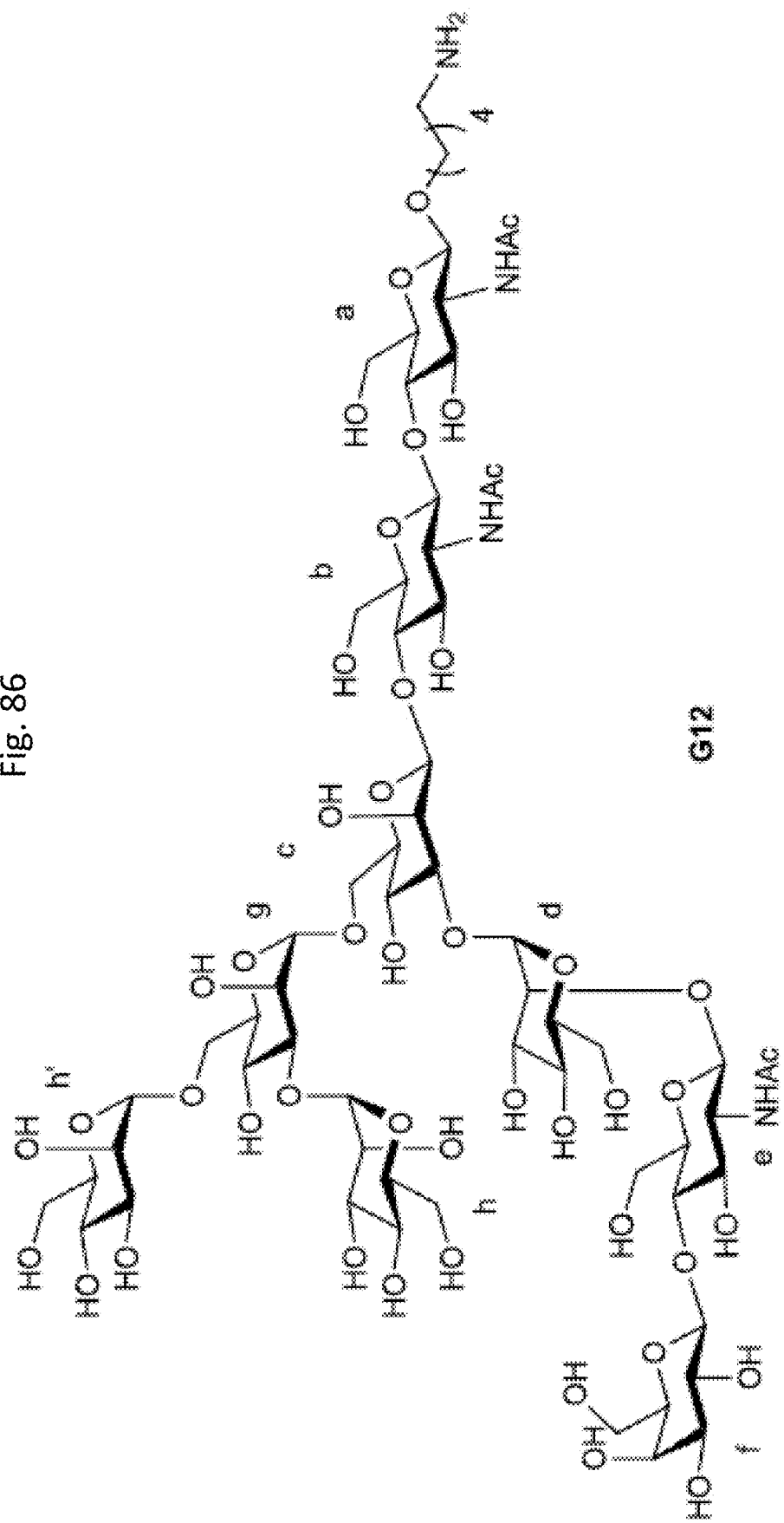
FIG. 86 Exemplary structure embodiments and synthetic scheme embodiments of the present disclosure.
Figure 87:
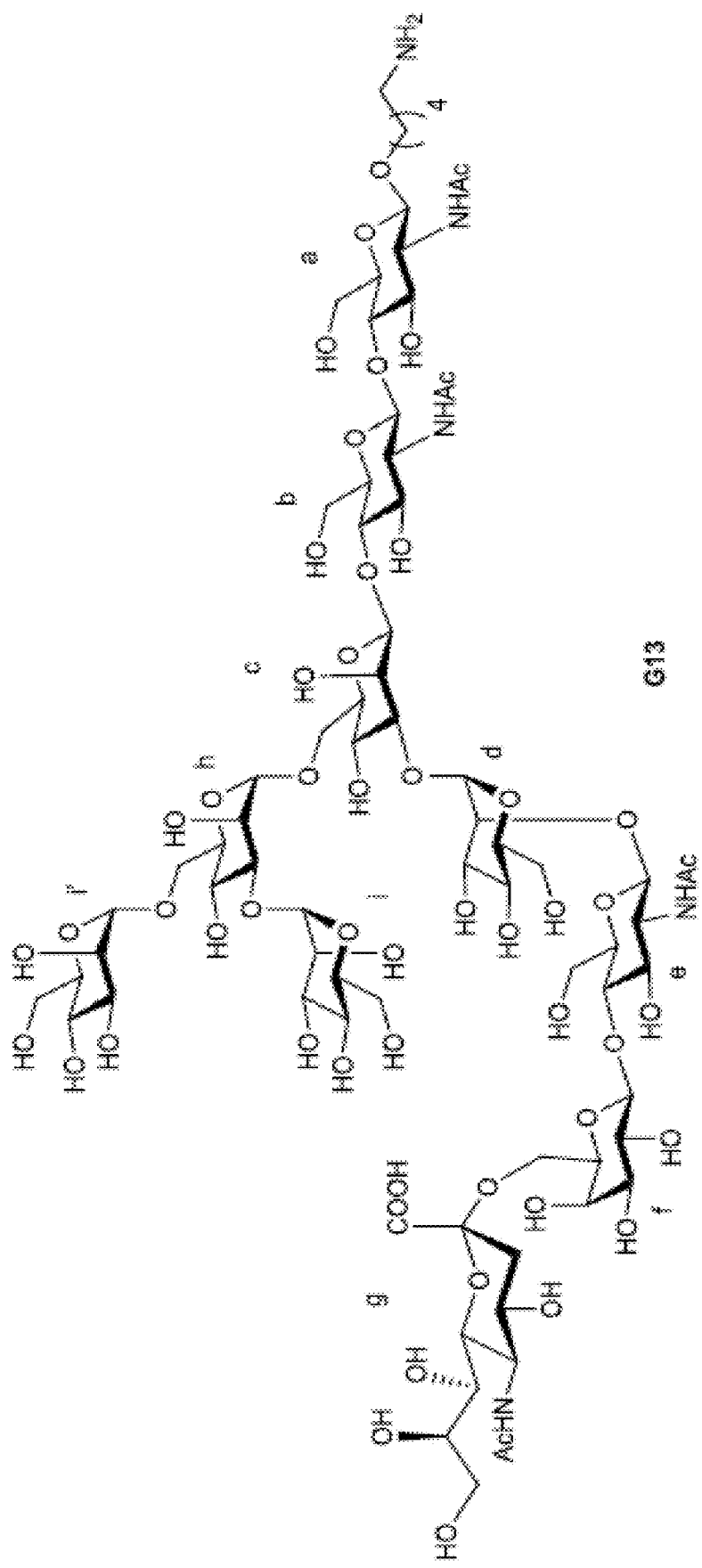
FIG. 87 Exemplary structure embodiments and synthetic scheme embodiments of the present disclosure.
Figure 88:
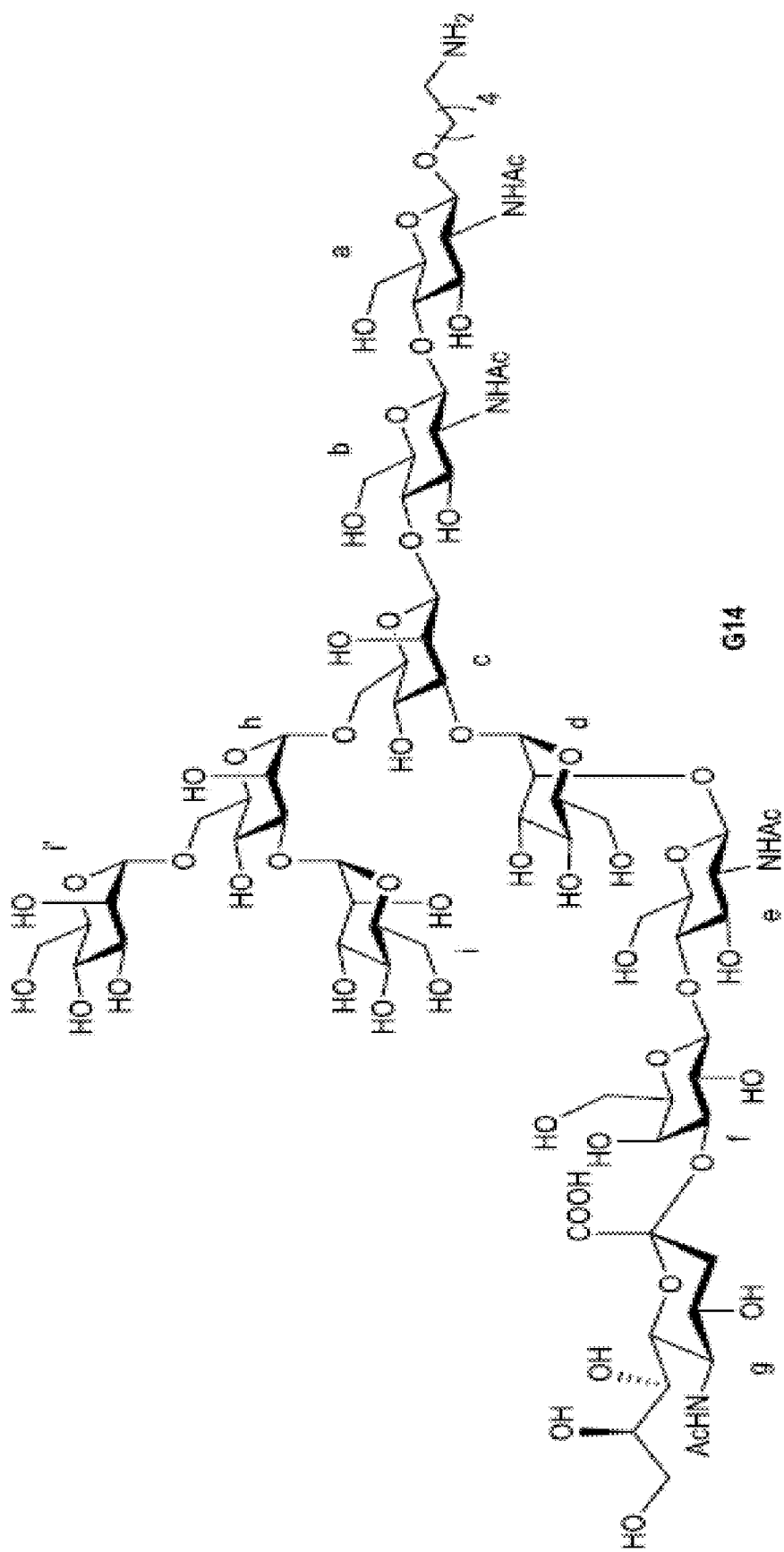
FIG. 88 Exemplary structure embodiments and synthetic scheme embodiments of the present disclosure.

Synthesis of hybrid type sugars commenced with condensation of 14 with 6 catalyzed by AgOTf/Cp2HfCl2 to give pentasaccharide S11a in 63% yield (Scheme S11 as shown in FIGS. 75A and 75B). Reductive benzilidine opening resulted in diol S11b, which was further glycosylated at 6"-O with trimannosyl thioglycoside 3 to afford S11c in 55% yield. Cp2HfCl2/AgOTf mediated condensation of acceptor S11b with 6 resulted in the formation of S11d in 58% yield.

Scheme S11 as shown in FIGS. 75A and 75B depicts the preparation of octasaccharide G7 and heptasaccharide G8. a, 6, AgOTf, Cp2HfCl2, Toluene, 4 Å MS, −40° C., 4 h, 63%; b, pTsOH, CH3CN, 5 h, 78%; c, 3, (BrC6H4)3NSbCl6, CH3CN, 4 Å MS, −10° C. to RT, 4 h, 55%; d, 6, AgOTf, Cp2HfCl2, Toluene, 4 Å MS, −40° C., 4 h, 58%; e, (1) NH2CH2CH2NH2, nBuOH, 90° C., overnight; (2) Ac2O, pyridine, overnight; (3) NaOMe, MeOH, overnight; (4) Pd(OH)2, MeOH:H2O:HCOOH (5:3:2), H2; G7:26%, G8:32%.

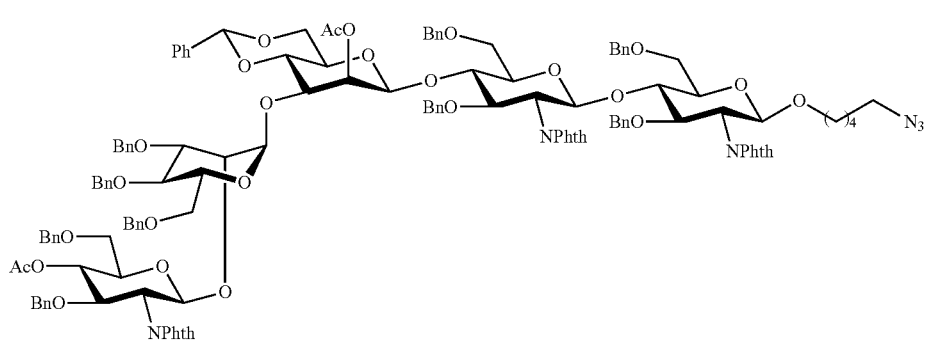

S11a

5-Azidopentyl-O-2-O-acetyl-3,6-O-di-benzyl-2-deoxy-2-phthalimido-β-D-glucopyranosyl-(1→2)-O-(3,4,6-tri-O-benzyl-α-D-mannopyranosyl-(1→3)-2-O-acetyl-4,6-O-benzylidine-β-D-mannopyranosyl-(1→4)-O-(3,6-di-O-benzyl-2-deoxy-2-phthalimido-β-D-glucopyranosyl)-(1→4)-O-3,6-di-O-benzyl-2-deoxy-2-phthalimido-β-D-glucopyranoside (S11a): A mixture of trichloroacetimidate donor 6 (0.341 g, 0.308 mmol), chitobiose acceptor 14 (0.350 g, 0.256 mmol) and activated 4 Å molecular sieves in dry CH2Cl2 (10 mL) was stirred at rt for 1 h. The reaction was cooled to −40° C., boron trifluoride ethyl etherate (14.8 µL, 0.129 mmol) was then added slowly and the resulting reaction mixture was stirred for 2 h. The reaction was quenched by adding Et3N, diluted with CH2Cl2, filtered through Celite and concentrated in vacuo. The residue was purified by flash column chromatography (0%→10% EA in toluene) to afford S11a (0.360 g, 63%) as white foam. TLC: (ethyl acetate:toluene=2/8, v/v): Rf=0.56; 1H NMR (600 MHz, CDCl3): δ 7.84-7.55 (m, 12H, Ar—H), 7.45-7.10 (m, 28H, Ar—H), 7.06-6.90 (n, 18H, Ar—H), 6.75-6.71 (m, 4H, Ar—H), 5.37 (d, J=8.4 Hz, 1H, H-1), 5.21 (d, J=8.4 Hz, 1H, H-1), 5.19 (s, 1H, Ph-CH, benzylidene), 5.09 (t, J=9.0 Hz, 1H), 4.93-4.76 (m, 6H), 4.57 (s, 1H), 4.54 (d, J=12.0 Hz, 1H), 4.45-4.07 (m, 20H), 3.69-3.15 (m, 22H), 3.02-3.00 (m, 1H), 2.86-2.81 (m, 2H, linker), 2.25 (s, 3H, —C(O)CH3), 1.84 (s, 3H, —C(O)CH3), 1.35-1.23 (m, 4H, —CCH2C—, linker), 1.07-1.02 (m, 2H, —CCH2C—, linker); 13C NMR (150 MHz, CDCl3): δ 170.68, 170.05, 167.88, 138.98, 138.89, 138.85, 138.71, 138.63, 138.14, 138.07, 137.78, 134.08, 133.90, 133.46, 132.06, 131.81, 129.32, 128.90, 128.83, 128.67, 128.55, 128.50, 128.34, 128.27, 127.95, 127.79, 127.70, 127.60, 101.00, 99.41, 98.38, 97.91, 97.29, 80.38, 79.02, 76.82, 76.76, 76.52, 76.14, 75.25, 74.90, 74.83, 74.67, 74.51, 74.44, 73.68, 73.52, 73.38, 73.06, 73.02, 72.93, 71.46, 70.65, 70.40, 70.03, 69.66, 69.14, 68.52, 67.56, 56.83, 55.98, 55.85, 51.37, 29.99, 28.95, 28.55, 23.28, 21.67, 21.19; ESI-MS: m/z calcd for C, 133; H, 132; N, 6; O, 31: 2309.8862; found 2332.8861 (M+Na)+.

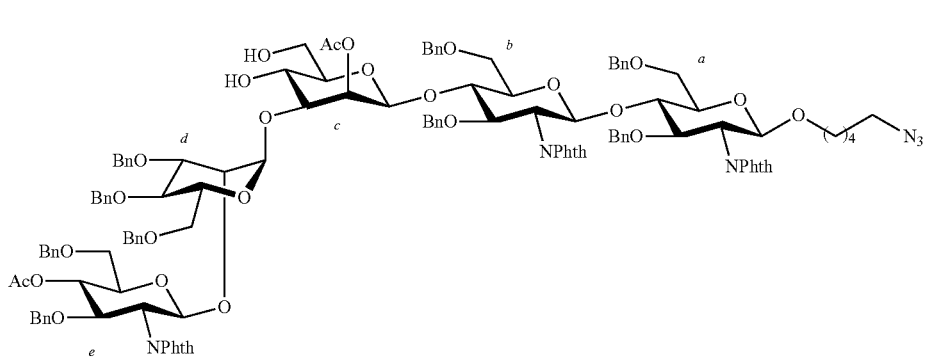

S37

5-Azidopentyl-O-2-O-acetyl-3,6-O-di-benzyl-2-deoxy-2-phthalimido-β-D-glucopyranosyl(1→2)-O-(3,4,6-tri-O-benzyl-α-D-mannopyranosyl-(1→3)-2-O-acetyl-β-D-mannopyranosyl-(1→4)-O-(3,6-di-O-benzyl-2-deoxy-2-phthalinmido-β-D-glucopyranosyl)-(1→4)-O-3,6-di-O-benzyl-2-deoxy-2-phthalimido-β-D-glucopyranoside (S11b): p-Toluene sulfonic acid monohydrate (0.020 g, 0.143 mmol) was added to a solution of S11a (0.220 g, 0.095 mmol) in acetonitrile (20 mL) and the resulting reaction mixture was stirred at rt for 5 h. The reaction was quenched by adding Et3N and concentrated in vacuo. The residue was purified by flash column chromatography (0%→15% EA in toluene) to give diol S11b (0.165 g, 78%). TLC: (ethyl acetate:toluene=2/8, v/v): Rf=0.32; 1H NMR (600 MHz, CDCl3): δ 7.89-7.43 (m, 12H, Ar—H), 7.35-7.16 (m, 28H, Ar—H), 7.09-7.05 (m, 5H, Ar—H), 7.03-6.89 (m, 9H, Ar—H), 6.75-6.72 (m, 3H, Ar—H), 5.30 (d, J=8.4 Hz, 1H, H-1a), 5.23 (d, J=8.4 Hz, 1H, H-1b), 5.12 (d, J=9.0 Hz, 1H), 5.09 (t, J=9.8 Hz, 1H), 4.95 (d, J=12.0 Hz, 1H), 4.90 (d, J=8.4 Hz, 1H, H-1e), 4.87-4.80 (m, 2H), 4.58-4.55 (m, 2H), 4.50-4.41 (m, 10H, overlapped, H-1d), 4.37-4.34 (m, 3H), 4.27-4.24 (m, 2H), 4.18-4.15 (m, 2H), 4.10-3.92 (m, 5H), 3.73-3.70 (m, 2H), 3.65-3.61 (m, 2H), 3.59-3.51 (m, 5H), 3.47-3.38 (m, 6H), 3.23-3.17 (m, 4H), 3.04 (dd, J=3.6, 9.0 Hz, 1H), 3.01-3.98 (m, 1H), 2.83-2.78 (m, 3H), 2.38 (s, 3H, —C(O)CH3), 1.90 (s, 3H, —C(O)CH3), 1.36-1.22 (m, 4H, —CCH2C—, linker), 1.06-1.01 (m, 2H, —CCH2C—, linker); 13C NMR (150 MHz, CDCl3): δ 170.93, 170.05, 168.77, 167.86, 167.69, 138.90, 138.83, 138.65, 138.47, 138.23, 138.14, 138.07, 138.04, 134.35, 134.13, 133.91, 132.04, 131.84, 131.72, 128.81, 128.65, 128.64, 128.62, 128.54, 128.53, 128.48, 128.46, 128.36, 128.17, 128.09, 128.02, 127.99, 127.97, 127.92, 127.91, 127.83, 127.77, 127.74, 127.63, 127.13, 124.73, 123.97, 123.43, 123.08, 118.73, 100.25 (C-1e), 98.37 (C-1d), 98.21 (C-1c), 97.86 (C-1b), 97.30 (C-1a), 82.86, 80.05, 78.38, 76.92, 76.15, 75.72, 75.60, 75.45, 74.86, 74.83, 74.70, 74.42, 74.24, 73.75, 73.42, 73.38, 72.82, 70.81, 70.60, 70.27, 69.99, 69.50, 69.15, 69.13, 68.53, 67.88, 66.28, 62.98, 56.78, 55.99, 55.88, 51.37, 32.21, 29.98, 28.94, 28.54, 23.27, 21.69, 21.18; ESI-MS: m/z calcd for C, 126; H, 128; N, 6; O, 31: 2221.8549; found 2244.8529 (M+Na)+.

for 4 h. TLC (ethyl acetate:toluene, 2/8) indicated formation of product with consumption of starting material, the reaction was quenched by Et3N. The reaction mixture was diluted with CH2Cl2 and filtered through Celite. The filtrate was washed with aqueous NaHCO3 (2×50 mL), and a brine (50 mL) solution. The organic layer was dried over Na2SO4 and concentrated in vacuo. The residue was purified by flash column chromatography (0%→10% EA in toluene) to afford S11c (0.130 g, 55%) as colorless foam. TLC: (ethyl acetate:toluene=1/9, v/v): Rf=0.42; 1H NMR (600 MHz, CDCl3): δ 7.71-7.30 (m, 8H, Ar—H), 7.28-7.10 (m, 70H, Ar—H), 7.97-6.86 (m, 12H, Ar—H), 6.69 (m, 7H, Ar—H), 5.47 (d, J=8.4 Hz, 2H), 5.44 (s, 1H), 5.32 (d, J=8.4 Hz, 1H, H-1a), 5.15 (d, J=8.4 Hz, 1H, H-1b), 5.13-5.10 (m, 2H), 5.00 (s, 1H,

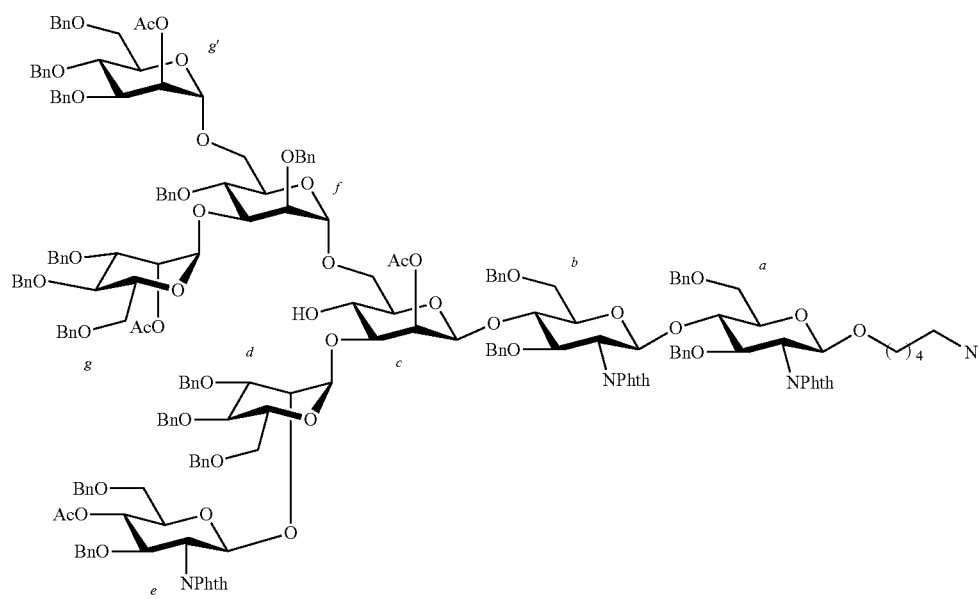

S11c

5-Azidopentyl-O-{4-O-acetyl-3,6-O-di-benzyl-2-deoxy-2-phthalimido-β-D-glucopyranosyl-(1→2)}-O-{3,4,6-tri-O-benzyl-α-D-mannopyranosyl-(1→3)-{2-O-acetyl-3,4,6-tri-O-benzyl-α-D-mannopyranosyl-(1→3)}-[2-O-acetyl-3,4,6-tri-O-benzyl-α-D-mannopyranosyl(1→6)]-2,4-di-O-benzyl-α-D-mannopyranosyl-(1→6))}-2-O-acetyl-β-D-mannopyranosyl-(1→4)-O-(3,6-di-O-benzyl-2-deoxy-2-phthalimido-β-D-glucopyranosyl)-(1→4)-O-3,6-di-O-benzyl-2-deoxy-2-phthalimido-β-D-glucopyranoside (S11c): A mixture of pentasaccharide acceptor S11b (0.150 g, 0.067 mmol), thiomannoside donor 3 (0.110 g, 0.080 mmol) and activated 4 Å molecular sieves (0.500 g) in CH3CN (10 mL) was stirred at rt for 1 h. The resulting mixture was cooled to −10° C., tris (4-bromophenyl) aminium hexachloroantimonate (0.170 g, 0.201 mmol) was added and resulting reaction was stirred at room temperature H-1d), 4.95 (s, 1H, H-1f), 4.91 (s, 2H, H-1g, H-1g'), 4.87-4.73 (m, 8H), 4.62 (d, J=8.7 Hz, 1H), 4.57-4.28 (m, 26H), 4.15-3.70 (m, 20H), 3.68-3.40 (m, 15H), 3.38-3.25 (m, 6H), 3.24-3.09 (m, 5H), 2.98 (dd, J=2.3, 7.8 Hz, 1H), 2.89-2.79 (m, 2H), 2.73-2.71 (m, 1H), 2.27 (s, 3H, —C(O)CH3), 2.05 (s, 3H, —C(O)CH3), 1.99 (s, 3H, —C(O)CH3), 1.88 (s, 3H, —C(O)CH3), 1.32-1.28 (m, 4H, —CCH2C—, linker), 1.07-0.98 (m, 2H, —CCH2C—, linker); 13C NMR (150 MHz, CDCl3): δ 170.26, 168.89, 138.38, 128.47, 128.37, 128.32, 128.30, 128.26, 128.24, 128.19, 128.08, 128.04, 127.91, 127.86, 127.73, 127.56, 127.49, 127.39, 127.26, 100.35, 100.23, 99.89, 99.56, 99.23, 98.54, 98.33, 98.23, 78.43, 76.09, 75.37, 75.07, 74.08, 74.44, 74.04, 73.47, 73.31, 72.63, 68.81, 51.08, 29.71, 29.37, 28.66, 28.25, 22.98; HRMS (MALDI-TOF): m/z calcd for C, 204; H, 210; N, 6; O, 48; 3513.4134 found 3536.4050 (M+Na)+.

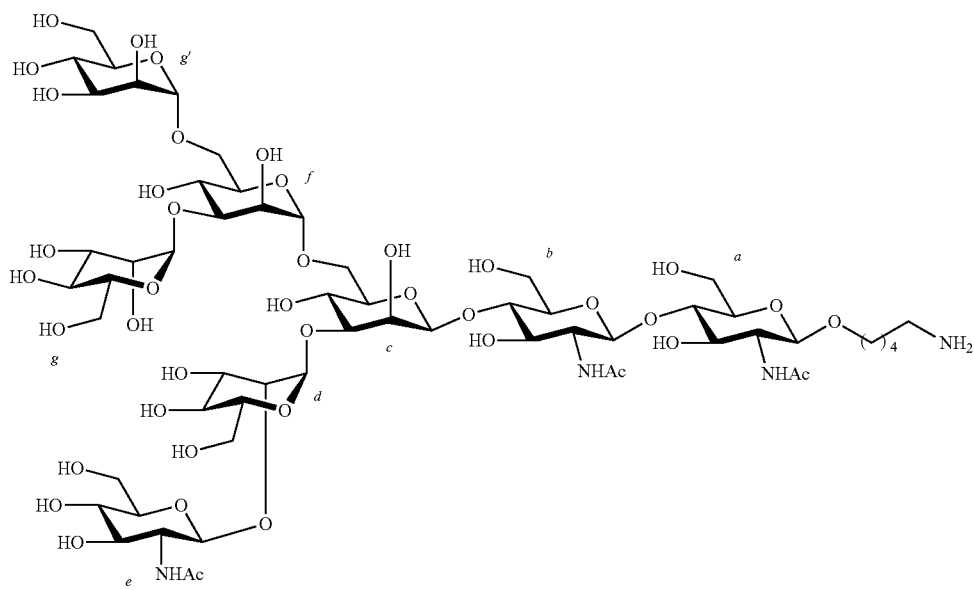

G7

5-Aminopentyl-2-acetamido-2-deoxy-β-D-glucopyranosyl-(1→2)-α-D-mannopyranosyl-(1→3),[di-(α-D-mannopyranosyl)-(1→3),(1→6)-α-D-mannopyranosyl](1→6)-β-D-mannopyranosyl-(1→4)-2-acetamido-2-deoxy-β-D-glucopyranosyl-(1→4)-2-acetamido-2-deoxy-β-D-glucopyranoside (G7): Compound S11c (0.105 g, 0.030 mmole) was deprotected by following general procedure 2 (Method 1) to get the title compound G7 (0.012 g, 26%) as a white solid. 1H NMR (600 MHz, D2O): δ 5.09 (d, J=1.2 Hz, 1H, H-1d), 5.02 (d, J=8.4 Hz, 1H, H-1a), 4.95 (s, 1H, H-1f), 4.91 (s, 1H, H-1g), 4.85 (s, 1H, H-1g'), 4.78 (S, 1H, H-1c), 4.61 (d, J=7.8 Hz, 1H, H-1e), 4.51 (d, J=7.8 Hz, 1H, H-1b), 4.22 (t, J=10.2 Hz, 2H), 4.18 (dd, J=1.8, 3.0 Hz, 1H), 4.00 (dd, J=1.8, 3.1 Hz, 1H), 4.08-3.38 (m, 47H), 3.03 (t, J=8.2 Hz, 2H, —NCH2-, linker), 2.09 (s, 3H, —C(O)CH3), 2.08 (s, 3H, —C(O)CH3), 2.01 (s, 3H, —C(O)CH3), 1.71-1.66 (m, 2H, —CCH2C—, linker), 1.62-1.59 (m, 2H, —CCH2C—, linker), 1.44-1.40 (m, 2H, —CCH2C—, linker); 13C NMR (150 MHz, D2O): δ 174.91, 174.42, 171.02, 110.64 (C-1d, 1 J C,H=174 Hz), 102.32, 101.48, 100.51 (C-1a, 1 J C,H=161 Hz), 100.44, 100.15, 99.26, 97.58 (C-1g, 1 J C,H=169.6 Hz), 79.48, 78.86, 78.72, 76.64, 76.04, 75.72, 74.65, 74.51, 74.42, 73.31, 72.69, 72.35, 72.09, 71.96, 70.86, 70.57, 70.34, 70.12, 70.09, 69.94, 69.42, 67.39, 66.70, 66.36, 65.54, 65.14, 61.68, 61.02, 60.93, 39.31, 38.62, 28.03, 26.39, 22.58, 22.20, 22.11, 22.08, 21.82; ESI-MS: m/z calcd for C, 59; H, 102; N, 4; O, 41; 1522.6092 found 1523.6148 (M+H)+.

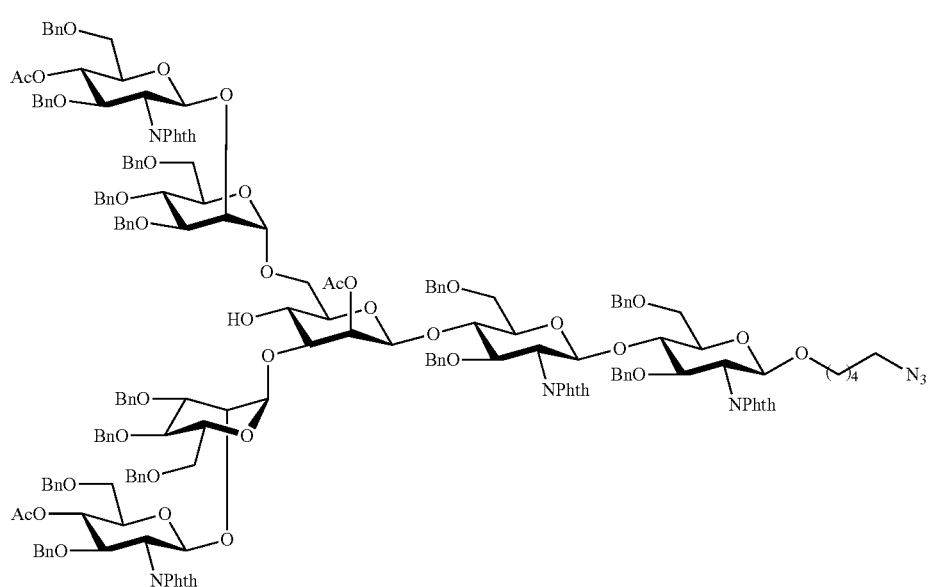

S11d

5-Azidopentyl-O-di-[{4-O-acetyl-3,6-O-di-benzyl-2-deoxy-2-phthalimido-β-D-gluco-pyranosy-(1→2)}-O-{3,4,6-tri-O-benzyl-α-D-mannopyranosyl}]-(1→3),(1→6)-2-O-acetyl-β-D-mannopyranosyl-(1→4)-O-(3,6-di-O-benzyl-2-deoxy-2-phthalimido-β-D-glucopyranosyl)-(1→4)-O-3,6-di-O-benzyl-2-deoxy-2-phthalimido-β-D-glucopyranoside (S11 d): A mixture of Silver triflate (0.080 g, 0.315 mmol), Bis(cyclopentadienyl)hafnium dichloride (0.084 g, 0.220 mmol) and 4 Å activated molecular sieves in dry toluene (10 mL) was stirred at rt for 1 h. The reaction mixture was then cooled to −40° C., a solution of donor 6 (0.091 g, 0.094 mmol) and acceptor S11b (0.140 g, 0.063 mmol) in 5 mL toluene was added. The mixture was stirred for 4 h, quenched with Et3N, diluted with CH2Cl2 and filtered through Celite. The filtrate was washed with aqueous NaHCO3 (2×50 mL), and a brine (50 mL) solution. The organic layer was dried over Na2SO4 and concentrated in vacuo. The residue was purified by flash column chromatography (0%→15% EA in toluene) to afford S11d (0.110 g, 58%) as colorless foam. TLC: (acetone:toluene=2/8, v/v): Rf=0.39; 1H NMR (600 MHz, CDCl3): δ 7.62-7.32 (m, 16H, Ar—H), 7.27-6.87 (m, 41H, Ar—H), 6.85-6.59 (m, 29H, Ar—H), 5.27 (d, J=8.4 Hz, 1H), 5.16 (s, 1H), 5.14 (d, J=3.6 Hz, 1H), 5.10 (d, J=1.8 Hz, 1H), 4.98 (d, J=3.6 Hz, 1H), 4.89-4.68 (m, 10H), 4.59-4.21 (m, 21H), 4.19-3.87 (m, 7H), 3.80 (dd, J=3.2, 1.8 Hz, 1H), 3.70-3.52 (m, 7H), 3.51-3.28 (m, 8H), 3.27-3.18 (m, 5H), 3.15-3.03 (m, 3H), 3.01 (dd, J=3.2, 1.8 Hz, 1H), 2.91-2.75 (m, 5H), 2.73-2.69 (m, 1H), 2.27 (s, 3H), 1.98 (s, 3H), 1.86 (s, 3H), 1.32-1.23 (m, 4H), 1.03-0.99 (m, 2H); 13C NMR (150 MHz, CDCl3): δ 171.09, 171.04, 170094, 167.91, 167.57, 139.19, 138.86, 138.63, 138.54, 138.42, 138.31, 138.21, 138.14, 137.93, 133.84, 133.71, 132.04, 131.80, 131.69, 128.80, 128.64, 128.39, 128.32, 128.13, 128.08, 127.79, 127.70, 127.60, 100.18, 100.00, 98.36, 97.88, 97.61, 97.30, 97.22, 80.14, 79.97, 79.31, 75.85, 75.56, 75.39, 75.30, 75.04, 74.71, 74.59, 73.95, 73.64, 73.24, 72.86, 72.14, 71.55, 71.37, 71.04, 70.53, 70.40, 70.15, 69.71, 69.12, 68.12, 65.40, 63.29, 56.34, 55.92, 51.45, 51.37, 51.27, 28.95, 28.54, 23.26, 21.13, 21.02; HRMS (MALDI-TOF): m/z calcd for C, 183; H, 183; N, 7; O, 43; 3168.2306 found 3191.2375 (M+Na)+.

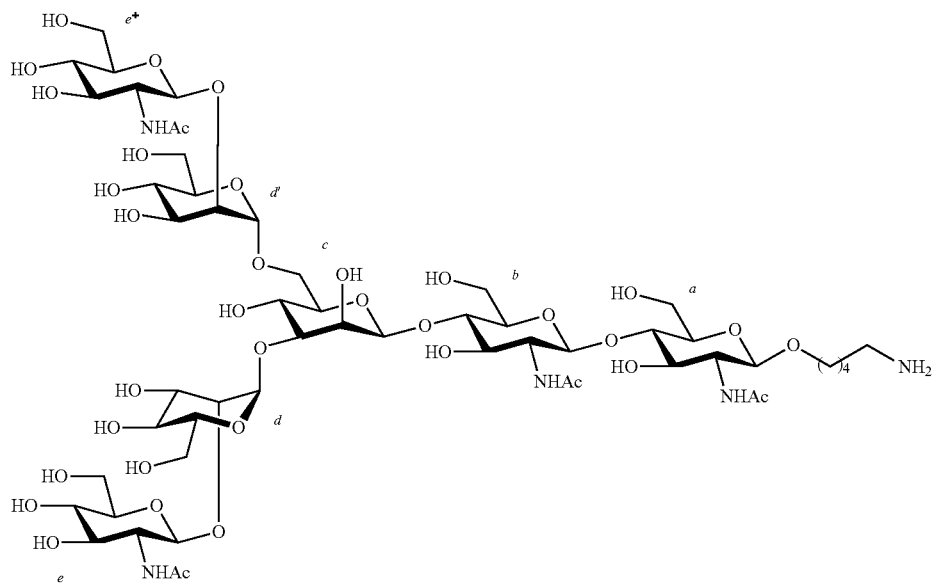

G8

5-Aminopentyl-di-[2-acetamido-2-deoxy-β-D-glucopyranosyl-(1→2)-α-D-mannopyranosyl]-(1→3),(1→6)-β-D-mannopyranosyl-(1→4)-2-acetamido-2-deoxy-β-D-glucopyranosyl-(1→4)-2-acetamido-2-deoxy-β-D-glucopyranoside (G8): Compound S11d (0.130 g, 0.041 mmol) was deprotected by following general procedure 2 (Method 1) to get the desired heptasaccharide G8 (0.015 g, 29%) as a white solid. 1H NMR (600 MHz, D2O): δ 5.99 (d, J=8.5 Hz, 1H, H-1a), 4.93 (s, 1H, H-1d), 4.83 (s, 1H, H-1d'), 4.76 (s, 1H, H-1c), 4.60 (d, J=7.8 Hz, 1H, H-1b), 4.56 (d, J=7.9 Hz, 1H, H-1e), 4.49 (d, J=7.9 Hz, 1H, H-1e'), 4.27 (s, 2H), 4.11 (d, J=1.8 Hz, 1H), 3.96-3.41 (m, 41H), 2.98 (t, J=8.9 Hz, 2H, —NCH2-, linker), 2.13 (s, 3H, C(O)CH3), 2.09 (s, 3H, —C(O)CH3), 2.06 (s, 3H, —C(O)CH3), 2.01 (s, 3H, —C(O)CH3), 1.69-1.64 (n, 2H, —CCH2C—, linker), 1.60-1.57 (m, 2H, —CCH2C—, linker), 1.42-1.38 (m, 2H, —CCH2C—, linker); 13C NMR (150 MHz, D2O): δ 174.88, 174.78, 174.65, 174.42, 171.0, 101.39, 101.05, 100.61 (C-1c), 100.39 (C-1a), 99.55 (C-1e'), 97.60 (C-1d'), 97.20 (C-1d), 79.41, 79.28, 78.92, 76.63, 76.25, 75.79, 74.50, 73.64, 72.84, 71.95, 70.09, 69.89, 69.48, 67.39, 67.35, 66.20, 65.39, 61.66, 61.61, 60.75, 60.61, 59.96, 55.68, 54.98, 54.94, 39.30, 28.04, 26.35, 22.55, 22.31, 22.21, 22.12, 22.08; ESI-MS: m/z calcd for C, 55; H, 95; N, 5; O, 36; 1402.5830; found 1403.5862 (M+H)+.

Preparation of glycans G12-G14

Stereoselective installation of trisaccharide antenna 7 at the 3-O position of the core trisaccharide acceptor 14 was performed under the promotion of Cp2HfCl2/AgOTf to afford hexasaccharide S12a. The p-toluene sulfonic acid-mediated reductive ring opening of S12a provided diol S12b. Considering the higher reactivity of the primary hydroxyl, S12b was further glycosylated at the 6-O position with trimannosyl thioglycoside 3 and, then, activated by the stable radical cation tris(4-bromophenyl) ammoniumyl hexachloroantimonate in a one electron transfer reaction to afford nonasaccharide S12c. With compound S12c in hand, a series of functional group transformations were carried out to afford the desired fully deprotected glycan G12. The precursor oligosaccharide G12, is an appropriate starting material for sialylation by α-2,6 or 2,3 sialyltransferase derived from marine bacteria, known for their broader acceptor specificity and no intrinsic sialidase activity. Sialyl transferase (SiaT)-mediated enzymatic terminal sialylation1-4 of G12 efficiently permitted access to α-2,6 and α-2,3 sialylated glycans G13 and G14, respectively (Scheme S12 as shown in FIGS. 82A, 82B, 82C and 82D).

Scheme S12 as shown in FIGS. 82A, 82B, 82C and 82D depicts the preparation of G12-G14. i) 7, Cp2HfCl2, AgOTf, 4 Å MS, −40° C., 2 h, 63%; ii) p-TsOH, CH3CN, 5 h, 78%; iii) 3, (BrC6H4)3NSbCl6, CH3CN, 4 Å MS, −10° C. to RT, 4 h, 55%; iv) (1) NH2CH2CH2NH2, n-BuOH, 90° C., overnight; (2) Ac2O, pyridine, overnight; (3) NaOMe, MeOH, overnight; (4) Pd(OH)2, MeOH:H2O:HCOOH (5:3:2), H2; 62%; v) CMP-β-D-Sialic acid, α-2,6- or 2,3-sialyl-transferase, G13: 60%; G14: 56%; Cp2HfCl2: Bis(cyclopentadienyl) hafnium dichloride; AgOTf: Silver trifluromethanesulfonate; (BrC6H4)3NSbCl6: Tris (4-bromophenyl) ammoniumyl hexachloroantimonate.

benzylidine-β-D-mannopyranosyl-(1→4)-O-(3,6-di-O-benzyl-2-deoxy-2-phthalimido-β-D-glucopyranosyl)-(1→4)-O-3,6-di-O-benzyl-2-deoxy-2-phthalimido-β-D-glucopyranoside (S12a): A mixture of silver triflate (0.327 g, 1.28 mmol), bis (cyclopentadienyl) hafnium dichloride (0.339 g, 0.896 mmol) and 4 Å activated molecular sieves in dry toluene (10 mL) was stirred at rt for 1 h. The reaction mixture was then cooled to −40° C., a solution of donor 7 (0.430 g, 0.307 mmol) and acceptor chitobiose trisaccharide 14 (0.35 g, 0.256 mmol) in 5 mL toluene was added. The mixture was stirred for 2 h, quenched with Et3N, diluted with EtOAc and filtered through Celite. The filtrate was washed with aqueous NaHCO3 (2×50 mL), and a brine (50 mL) solution. The organic layer was dried over Na2SO4 and concentrated in vacuo. The residue was purified by flash column chromatography (0%→15% EA in toluene) to afford S12a (0.500 g, 71%) as white foam. TLC: (ethyl acetate: toluene=2/8, v/v): Rf=0.62; 1H NMR (600 MHz, CDCl3): δ 7.85-7.49 (m, 8H, Ar—H), 7.02-7.39 (m, 44H, Ar—H), 7.19-7.02 (m, 11H, Ar—H), 6.99-6.90 (m, 6H, Ar—H), 6.83-6.78 (m, 3H, Ar—H), 6.75-6.70 (m, 5H, Ar—H), 5.310 (t, J=7.5 Hz, 1H, H-2f), 5.27 (d, J=8.1 Hz, 1H, H-1a), 5.25 (d, J=8.4 Hz, 1H, H-1e), 5.15 (d, J=2.3 Hz, 1H), 5.01 (s, 1H, Ph-CH, benzylidene), 4.90-4.80 (m, 7H), 4.62 (d, J=8.5 Hz, 1H), 4.58-4.53 (m, 3H), 4.52-4.38 (m, 10H), 4.32-4.13 (m, 11H), 4.12-4.05 (m, 5H), 4.02 (m, 1H), 3.89 (d, J=3.2 Hz, 1H), 3.75-3.73 (m, 2H), 3.72-3.49 (m, 8H), 3.48-3.37 (m, 5H), 3.34-3.29 (m, 4H), 3.29-3.18 (m, 4H), 2.98 (m, 1H), 2.89-2.79 (m, 2H, linker), 2.29 (s, 3H, —C(O)CH3), 1.99 (s, 3H, —C(O)CH3), 1.49-1.30 (m, 4H, —CCH2C—), 1.10-1.00 (m, 2H, —CCH2C—); 13C NMR (150 MHz, CDCl3): δ 170.8, 169.4, 168.7, 167.7, 139.1, 139.9, 138.9, 138.8, 138.8, 138.5, 138.2, 138.2, 138.1, 137.9, 137.6, 134.2, 133.8, 133.1, 131.9, 131.8, 131.6, 129.1, 128.8, 128.6, 128.5, 128.4, 128.4, 128.4, 128.3, 128.3, 128.2, 128.1, 128.0, 128.0, 127.9, 127.8, 127.8, 127.7, 127.7, 127.5, 127.5, 127.4, 127.3, 127.0, 126.7, 126.1, 123.8, 123.3, 122.8, 100.88, 100.83, 99.94, 99.38, 98.43, 98.30, 97.26, 80.31, 79.00, 78.05, 77.61, 76.42, 76.31, 76.1, 75.1, 74.8, 74.7, 74.6, 74.6, 74.4, 74.4, 74.2, 73.6, 73.4, 73.3, 72.9, 72.8,

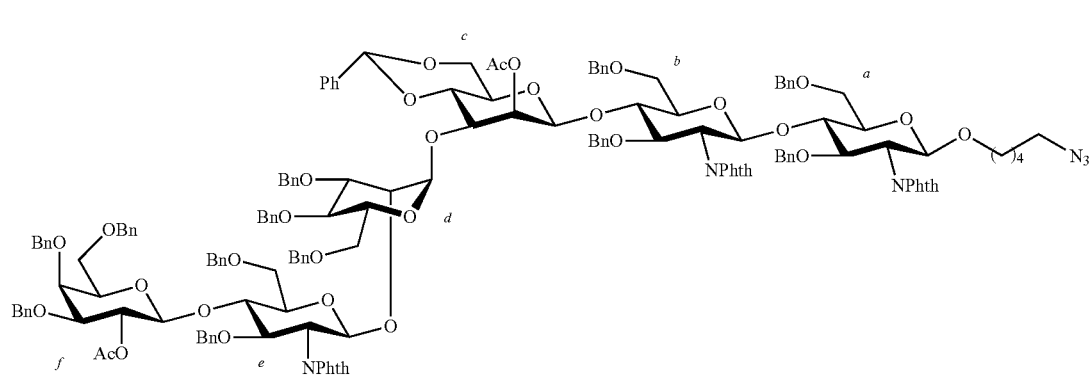

S12a

5-Azidopentyl-O-2-O-acetyl-3,4,6-O-tri-benzyl-β-D-galactopyranosyl-(1→4)-O-3,6-O-di-benzyl-2-deoxy-2-phthalimido-β-D-glucopyranosyl-(1→2)-O-(3,4,6-tri-O-benzyl-α-D-mannopyranosyl-(1→3)-2-O-acetyl-4,6-O-

72.2, 71.8, 71.7, 70.4, 70.0, 69.8, 69.0, 68.8, 68.4, 68.2, 67.7, 67.6, 56.7 56.0, 55.9, 51.3, 28.8, 28.4, 23.2, 21.7, 21.2; ESI-MS: m/z calcd for C, 160; H, 160; N, 6; O, 36; 2742.0799 found 2765.0952 (M+Na)+.

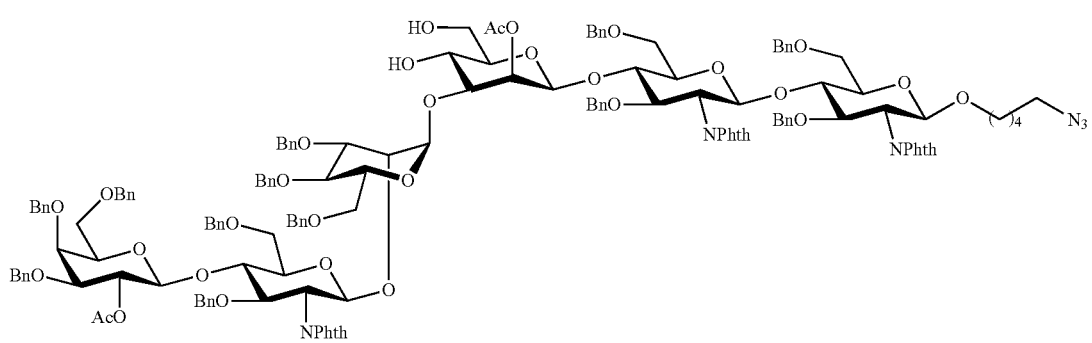

S12b

5-Azidopentyl-O-2-O-acetyl-3,4,6-O-tri-benzyl-β-D-galactopyranosyl-(1→4)-O-3,6-O-di-benzyl-2-deoxy-2-phthalimido-β-D-glucopyranosyl-(1→2)-O-(3,4,6-tri-O-benzyl-α-D-mannopyranosyl-(1→3)-2-O-acetyl-β-D-mannopyranosyl-(1→4)-O-(3,6-di-O-benzyl-2-deoxy-2-phthalimido-β-D-glucopyranosyl)-(1→4)-O-3,6-di-O-benzyl-2-deoxy-2-phthalimido-β-D-glucopyranoside (S12b): To a solution of S12a (0.601 g, 0.219 mmol) in acetonitrile (10 mL) was added p-toluene sulfonic acid monohydrate (0.046 g, 0.328 mmol), stirred at rt for 2 h. The reaction was quenched with Et3N and concentrated in vacuo. The residue was purified by flash column chromatography (0%→15% EA in toluene) to afford diol S12b (0.460 g, 78%). TLC: (acetone:toluene=2/8, v/v): Rf=0.32; 1H NMR (600 MHz, CDCl3): δ 7.91-7.42 (m, 12H, Ar—H), 7.39-7.12 (m, 41H, Ar—H), 7.10-6.93 (m, 13H, Ar—H), 6.85-6.81 (m, 3H, Ar—H), 6.78-6.73 (m, 3H, Ar—H), 5.33 (t, J=7.8 Hz, 1H, H-2f), 5.23 (t, J=8.4 Hz, 2H, H-1), 5.08 (d, J=6.2 Hz, 1H), 4.97 (d, J=8.9 Hz, 1H, H-1), 4.94-4.80 (m, 5H), 4.64-4.60 (m, 2H), 4.49-4.21 (m, 21H), 4.19-4.15 (m, 2H), 4.15-3.89 (m, 8H), 3.89 (d, J=6.2 Hz, 1H), 3.78 (d, J=5.8 Hz, 1H), 3.69 (dd, J=6.3, 12.1 Hz, 1H), 3.65-3.64 (m, 1H), 3.56-3.32 (m, 15H), 3.29 (dd, J=6.6, 12.5 Hz, 1H), 3.29-3.23 (m, 3H), 3.00-2.99 (m, 2H), 2.87-2.82 (m, 2H), 2.74 (t, J=9.5 Hz, 1H), 2.28 (s, 3H, —C(O)CH3), 1.98 (s, 3H, —C(O)CH3), 1.37-1.22 (m, 4H, —CCH2C—), 1.07-1.00 (m, 2H, —CCH2C—); 13C NMR (150 MHz, CDCl3): δ 171.29, 169.57, 168.78, 168.58, 168.03, 167.90, 139.01, 138.92, 138.84, 138.68, 138.45, 138.39, 138.36, 138.22, 138.14, 137.98, 134.35, 134.15, 134.02, 133.89, 132.04, 131.95, 131.68, 130.10, 129.54, 129.46, 128.80, 128.70, 128.66, 128.62, 128.60, 128.52, 128.47, 128.46, 128.39, 128.30, 128.15, 128.07, 128.01, 127.98, 127.94, 127.91, 127.83, 127.72, 127.60, 127.39, 127.20, 126.96, 123.90, 123.46, 122.88, 101.11, 100.87, 98.87, 98.33, 83.75, 80.57, 80.14, 78.58, 78.29, 76.15, 75.78, 75.45, 74.11, 74.96, 74.83, 74.70, 74.61, 74.44, 74.10, 73.77, 73.73, 73.59, 73.43, 73.38, 73.03, 72.30, 71.97, 70.61, 70.29, 69.82, 69.14, 69.08, 68.54, 68.38, 67.94, 66.94, 66.47, 63.21, 56.80, 56.09, 56.01, 51.37, 31.71, 31.21, 30.97, 30.59, 29.99, 29.65, 28.55, 27.87, 27.29, 26.96, 26.24, 25.59, 25.36, 24.26, 23.27, 22.98, 21.86, 21.32, 20.80, 20.49, 18.94, 16.76, 15.95, 15.44, 15.10, 14.40, 14.07, 13.67, 13.47; ESI-MS: m/z calcd for C, 153; H, 156; N, 6; O, 36; 1327.0189; found 1350.0207 (M+Na)+.

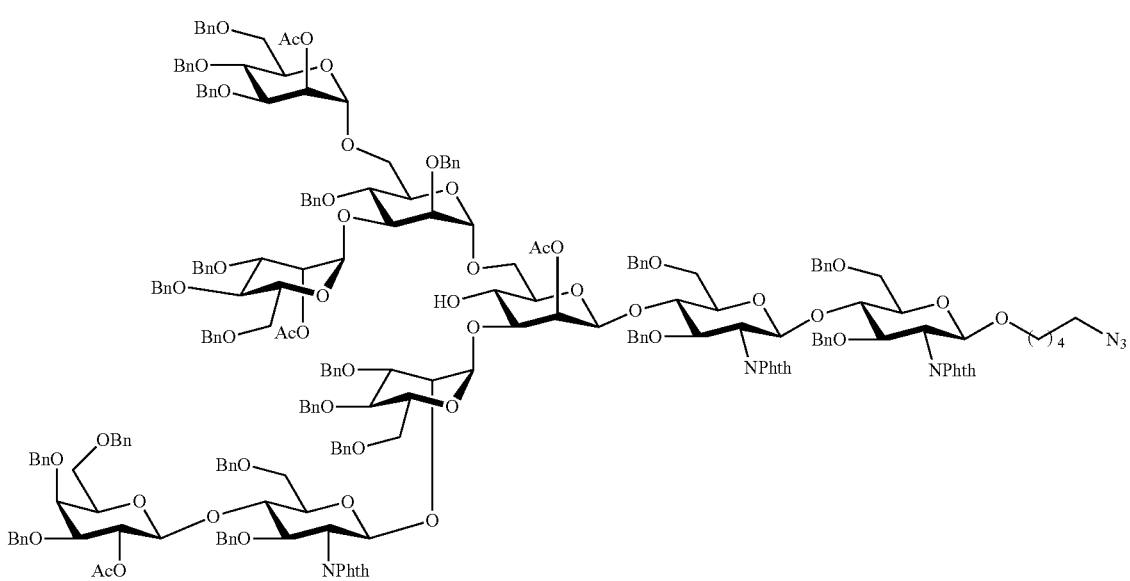

S12c

5-Azidopentyl-O-{2-O-acetyl-3,4,6-O-tri-benzyl-β-D-galactopyranosyl-(1→4)}-O-{3,6-O-di-benzyl-2-deoxy-2-phthalimido-β-D-glucopyranosyl-(1→2)}-O-{3,4,6-tri-O- benzyl-α-D-mannopyranosyl-(1→3)-{2-O-acetyl-3,4,6-tri-O-benzyl-α-D-mannopyranosyl-(1→3)})-[2-O-acetyl-3,4,6-tri-O-benzyl-α-D-mannopyranosyl-(1→6)]-2,4-di-O-benzyl-α-D-mannopyranosyl-(1→6)})-2-O-acetyl-β-D-mannopyranosyl-(1→4)-O-(3,6-di-O-benzyl-2-deoxy-2-phthalimido-β-D-glucopyranosyl)-(1→4)-O-3,6-di-O-benzyl-2-deoxy-2-phthalimido-β-D-glucopyranoside (S12c): A mixture of hexasaccharide acceptor S12b (0.40 g, 0.15 mmol), thiomannoside donor 3 (0.229 g, 0.226 mmol) and activated 4 Å molecular sieves (0.50 g) in CH3CN (10 mL) was stirred at rt for 1 h. The resulting mixture was cooled to −10° C., tris (4-bromophenyl)aminium hexachloroantimonate (0.254 g, 0.30 mmol) was added and stirred at rt for 3 h. TLC indicated formation of product with consumption of starting material, the reaction was then quenched by Et3N. The reaction mixture was diluted with CH2Cl2 and filtered through celite. The filtrate was washed with aqueous NaHCO3 (2×50 mL), and a brine (50 mL) solution. The organic layer was dried over Na2SO4 and concentrated in vacuo. The residue was purified by flash column chromatography (0%→10% EA in toluene) to afford S12c (0.335 g, 55%) as colorless foam and acceptor 9 (0.103 g). TLC: (ethyl acetate:toluene=1/9, v/v): Rf=0.46; 1H NMR (600 MHz, CDCl3): δ 7.72-7.45 (m, 11H, Ar—H), 7.37-7.28 (m, 5H, Ar—H), 7.28-7.12 (m, 67H, Ar—H), 7.09-7.02 (m, 12H, Ar—H), 6.94-6.90 (m, 7H, Ar—H), 6.80-6.78 (m, 4H, Ar—H), 6.696.68 (m, 3H, Ar—H), 6.62-6.61 (m, 3H, Ar—H), 5.49 (s, 1H), 5.48 (s, 1H), 5.35 (t, J=8.4 Hz, 1H), 5.28 (d, J=8.4 Hz, 1H, H-1), 5.17 (d, J=8.4 Hz, 1H, H-1), 5.09 (d, J=6.2 Hz, 1H), 5.00 (s, 1H, H-1), 4.92 (d, J=3.1 Hz, 1H), 4.90-4.72 (m, 12H), 4.69-4.72 (m, 23H), 4.26-4.17 (m, 5H), 4.133.97 (m, 12H), 3.89-3.82 (m, 12H), 3.72 (t, 1H), 3.68-3.62 (m, 1H), 3.65-3.55 (m, 7H), 3.54-3.45 (m, 4H), 3.43-3.40 (m, 4H), 3.40-3.29 (m, 9H), 3.23-3.19 (m, 3H), 3.17-3.09 (m, 2H), 2.91-2.79 (m, 3H), 2.68 (s, 1H), 2.28 (s, 3H, —C(O)CH3), 2.05 (s, 3H, —C(O)CH3), 2.01 (s, 3H, —C(O)CH3), 1.99 (s, 3H, —C(O)CH3), 1.34-1.22 (m, 4H, linker), 1.06-1.00 (m, 2H, linker); 13C NMR (150 MHz, CDCl3): δ 171.37, 170.38, 170.29, 169.54, 168.49, 168.23, 167.97, 167.53, 139.28, 139.11, 139.03, 138.97, 138.94, 138.67, 138.63, 138.58, 138.53, 138.41, 138.38, 138.25, 138.10, 128.74, 128.70, 128.67, 128.63, 128.58, 128.55, 128.53, 128.51, 128.48, 128.44, 128.40, 128.37, 128.34, 128.30, 128.15, 128.03, 128.00, 127.95, 127.92, 127.84, 127.77, 127.75, 127.70, 127.64, 127.61, 101.17, 100.92, 98.84, 98.28, 97.71, 97.45, 75.49, 75.36, 75.26, 75.17, 75.06, 74.96, 74.82, 74.75, 74.65, 74.60, 74.38, 74.30, 73.99, 73.77, 73.73, 73.59, 73.25, 73.25, 73.06, 72.99, 72.91, 72.26, 72.18, 71.98, 71.82, 71.57, 71.45, 70.52, 70.03, 69.92, 69.56, 69.10, 68.90, 68.85, 68.57, 68.48, 68.37, 66.64, 66.06, 56.75, 56.09, 55.99, 51.37, 34.25, 29.99, 28.94, 28.54, 25.90, 23.27, 21.86, 21.42, 21.33; HRMS (MALDI-TOF): m/z calcd for C, 231; H, 238; N, 6; O, 53; 3945.6071; found 3968.6006 (M+Na)+.

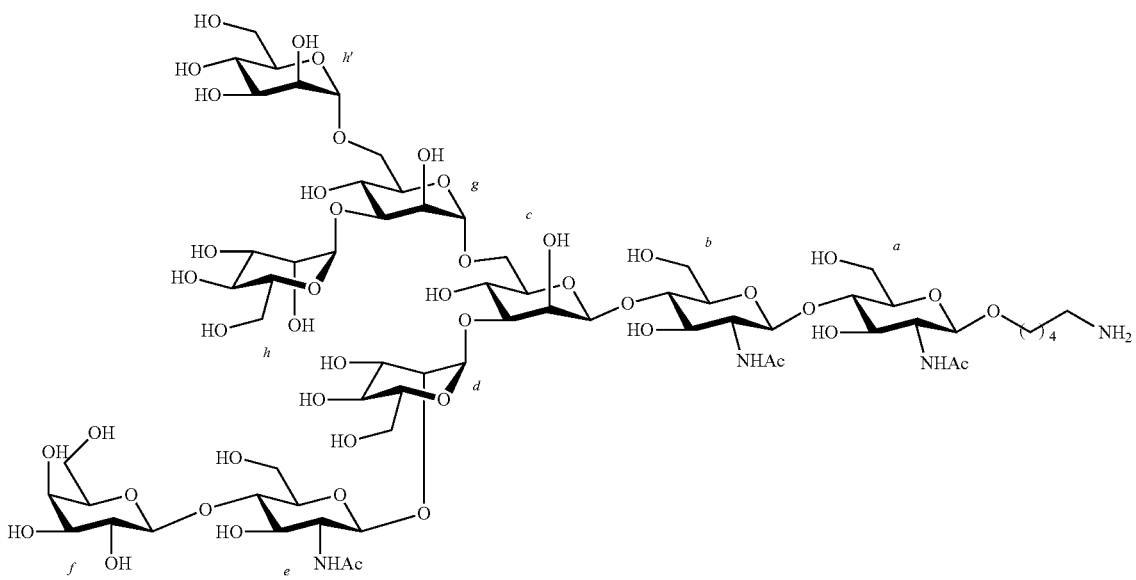

G12

5-Aminopentyl-β-D-galactopyranosyl-(1→4)-[2-acetamido-2-deoxy-β-D-glucopyranosyl-(1→2)-α-D-mannopyranosyl-(1→3)],[di-(α-D-mannopyranosyl)-(1→3),(1→6)-α-D-mannopyranosyl](1→6)-β-D-mannopyranosyl-(1→4)-2-acetamido-2-deoxy-β-D-glucopyranosyl-(1→4)-2-acetamido-2-deoxy-β-D-glucopyranoside (G12): Compound S12c (0.16 g, 0.048 mmol) was deprotected by following general procedure 2 (Method 1) to afford desired the nonasaccharide G12 (0.052 g, 62%). 1H NMR (600 MHz, D2O): δ 5.10 (s, 1H, H-1d), 5.07 (d, J=9.5 Hz, 1H, H-1a), 4.91 (s, 2H, H-1h,h'), 4.84 (s, 1H, H-1f), 4.61 (s, 1H, H-1c), 4.50 (d, J=9.2 Hz, 1H, H-1b), 4.49 (d, J=8.1 Hz, 1H, H-1e), 4.31 (s, 2H), 4.19 (bs, 1H), 4.07 (bs, 1H), 4.023.51 (m, 53H), 3.40-3.30 (m, 2H) 2.99 (t, J=11.2 Hz, 2H, —NCH2-, linker), 2.08 (s, 3H, —C(O)CH3), 2.07 (s, 3H, —C(O)CH3), 2.04 (s, 3H, —C(O)CH3), 1.70-1.65 (m, 2H, —CCH2C—, linker), 1.62-1.58 (m, 2H, —CCH2C—, linker), 1.48-1.38 (m, 2H, —CCH2C—, linker); 13C NMR (150 MHz, D2O): δ 177.60, 177.17, 105.68 (C-1b), 105.05 (C-1d), 104.23, 104.04, 103.79, 103.37, 103.18, 102.88, 102.23 (C-1h'), 102.03 (C-1h), 100.24 (C-1g), 82.20, 82.06, 82.01, 81.58, 81.51, 81.40, 79.38, 78.70, 78.08, 77.43, 77.37, 77.18, 77.03, 76.07, 75.66, 75.43, 75.23, 75.11, 75.06, 74.96, 74.83, 74.71, 73.72, 73.65, 73.33, 73.20, 73.11, 72.95, 72.89, 72.84, 72.69, 72.18, 71.28, 70.15, 68.50, 69.46, 69.36, 69.01, 68.31, 67.90, 67.86, 64.45, 63.75, 63.69, 63.61, 62.87, 62.82, 62.75, 57.94, 57.72, 42.06, 30.78, 29.10, 25.35, 25.30, 24.96, 24.87, 24.83; ESI-MS: m/z calcd for C, 65; H, 112; N, 4; O, 46; 1684.6620 found 1685.6968 (M+H)+.

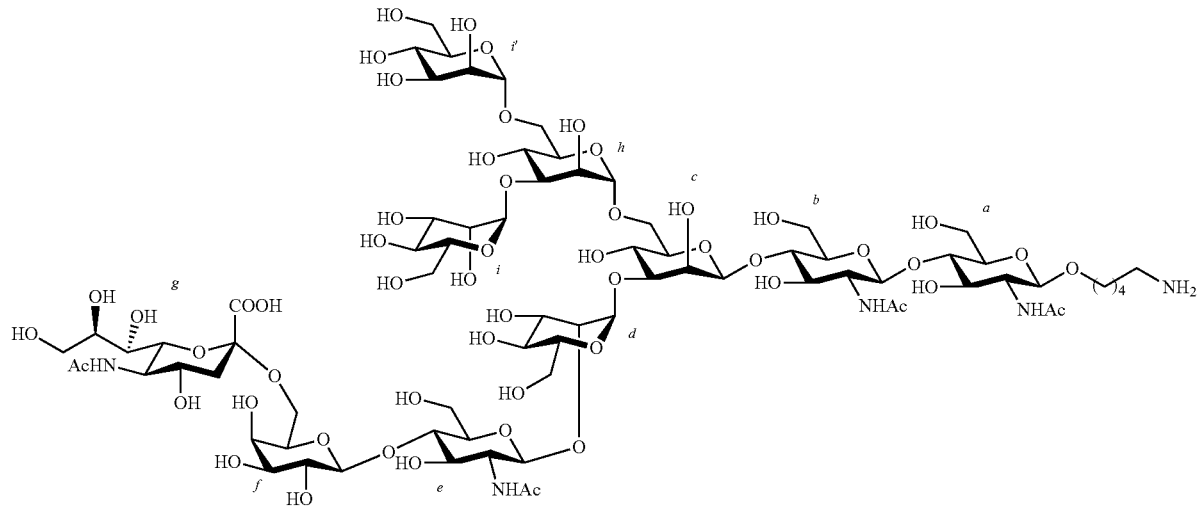

G13

5-Aminopentyl-5-Acetamido-3,5-dideoxy-D-glycero-α-D-galacto-2-nonulopyrano-sylonate-(2→6)-β-D-galactopyranosyl-(1→4)-[2-acetamido-2-deoxy-β-D-glucopyranosyl-(1→2)-α-D-mannopyranosyl-(1→3)],[di-(α-D-mannopyranosyl)-(1→3),(1→6)-α-D-mannopyranosyl](1→6)-β-D-mannopyranosyl-(1→4)-2-acetamido-2-deoxy-β-D-glucopyranosyl-(1→4)-2-acetamido-2-deoxy-β-D-glucopyranoside (G13): Compound G12 (5 mg, 0.0029 mmol) was sialylated with α-2,6-sialyltransferase for 2 days by following general procedure 3 to get the desired title compound G13 (3.5 mg, 60%) as white solid. 1H NMR (600 MHz, D2O): δ 5.07 (s, 1H, H-1d), 5.06 (d, J=8.5 Hz, 1H, H-1a), 4.92 (s, 1H, H-1h), 4.90 (s, 1H1), 4.89 (s, 1H, H-1i'), 4.78 (s, 1H, H-1c), 4.58 (d, J=7.2 Hz, 1H, H-1f), 4.46 (d, J=7.8 Hz, 1H, H-1b), 4.41 (d, J=8.4 Hz, 1H, H-1e), 4.25-4.24 (m, 2H), 4.12 (s, 1H), 4.04 (d, J=4.7 Hz, 1H), 4.04-3.42 (m, 61H), 3.40 (t, J=10.8 Hz, 1H), 3.39-3.35 (m, 1H), 2.95 (t, J=10.9 Hz, 2H), 2.64 (dd, J=4.2, 12.2 Hz, 1H, H-3equi. g), 2.04 (s, 3H, —C(O)CH3), 2.04 (s, 3H, —C(O)CH3), 2.00 (s, 3H, —C(O)CH3), 2.00 (s, 3H, —C(O)CH3), 1.71-1.61 (m, 3H, —CCH2C—, linker and H-3axial g), 1.58-1.54 (m, 2H, —CCH2C—, linker), 1.39-1.35 (m, 2H, —CCH2C—, linker); 13C NMR (150 MHz, D2O): δ 174.90, 174.79, 174.38, 173.47, 103.42, 102.29 (C-1d, 1 J C,H=170.9 Hz), 101.48, 101.01, 100.41, 100.18 (C-1a, 1 J C,H=162.9 Hz), 100.15, 99.24 ((C-1h, 1 J C,H=171.3 Hz)), 97.87, 97.27, 80.78, 79.59, 79.20, 78.72, 78.36, 76.61, 75.81, 74.79, 74.48, 74.36, 73.63, 73.28, 72.63, 72.52, 72.35, 72.30, 72.09, 71.94, 71.65, 70.82, 70.69, 70.53, 70.31, 70.12, 70.05, 69.89, 69.41, 68.33, 68.17, 67.32, 67.17, 66.66, 65.47, 65.09, 63.30, 62.62, 61.66, 60.98, 60.89, 60.32, 60.02, 59.94, 57.95, 54.91, 51.81, 40.01, 39.27, 28.00, 26.37, 23.62, 23.19, 22.59, 22.17, 22.05, 22.00; ESI-MS (negative mode): m/z calcd for C, 76; H, 129; N, 5; O, 54; 1975.7418 found 1974.7600 (M−H)−.

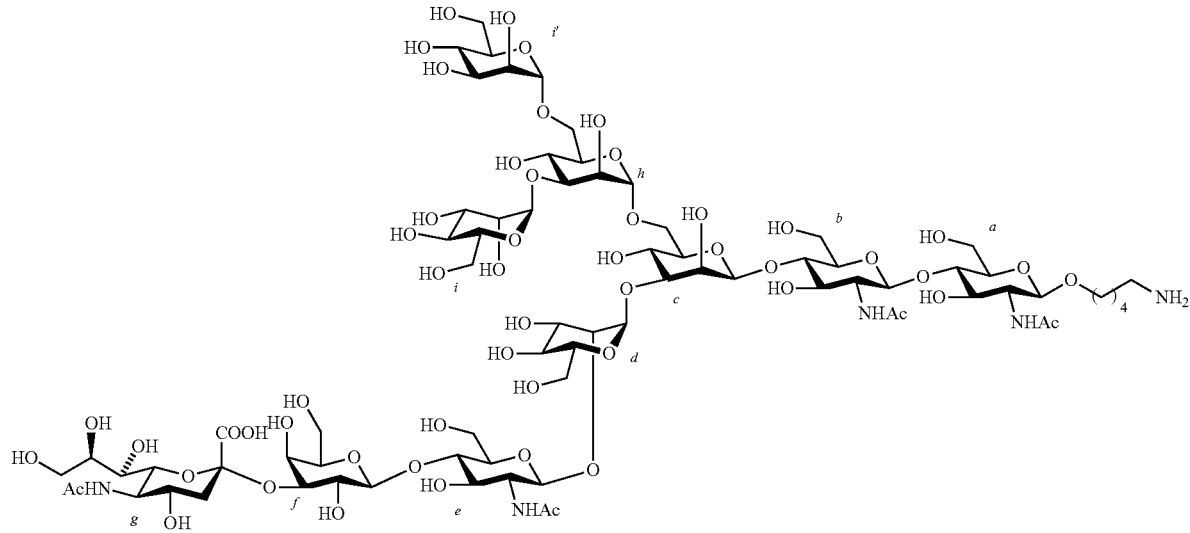

G14

5-Aminopentyl-5-Acetamido-3,5-dideoxy-D-glycero-α-D-galacto-2-nonulopyrano-sylonate-(2→3)-β-D-galactopyranosyl-(1→4)-[2-acetamido-2-deoxy β-D-glucopyranosyl-(1→2)-α-D-mannopyranosyl-(1→3)],[di-(α-D-mannopyranosyl)-(1→3),(1→6)-α-D-mannopyranosyl](1→6)-β-D-mannopyranosyl-(1→4)-2-acetamido-2-deoxy-β-D-glucopyranosyl-(1→4)-2-acetamido-2-deoxy-β-D-glucopyranoside (G14): Compound G12 (5 mg, 0.0029 mmol) was sialylated with α-2,3-sialyltransferase for 8 d by following general procedure 3 to get the desired title compound G14 (3.1 mg, 56%) as white solid. 1H NMR (600 MHz, D2O): δ 5.01 (s, 1H, H-1d), 4.97 (dd, J=3.2, 7.2 Hz, 1H, H-1a), 4.84 (s, 1H, H-1h), 4.81 (s, 1H, H-1i), 4.75 (s, 1H, H-1i'), 4.62 (s, 1H, H-1c), 4.52 (d, J=7.8 Hz, 1H, H-1f), 4.97 (d, J=9.2 Hz, 1H, H-1b), 4.42 (d, J=8.3 Hz, 1H, H-1e), 4.39 (d, J=8.3 Hz, 1H), 4.22 (t, J=7.8 Hz, 2H), 4.09 (s, 1H), 4.06 (d, J=7.4 Hz, 1H), 4.03 (d, J=7.3 Hz, 1H), 4.00 (d, J=3.2 Hz, 1H), 3.96-3.85 (m, 10H), 3.85-3.71 (m, 19H), 3.72-3.52 (m, 26H), 3.51-3.48 (m, 2H,), 3.38-3.370 (m, 2H), 2.90 (t, J=7.9 Hz, 2H, —NCH2-, linker), 2.68 (dd, J=4.8, 12.0 Hz, 1H, H-3 equi. g), 2.01 (s, 3H, —C(O)CH3), 1.99 (s, 3H, —C(O)CH3), 1.96 (s, 3H, —C(O)CH3), 1.95 (s, 3H, —C(O)CH3), 1.73 (t, J=8.6 Hz, 1H, H-3 axial g), 1.61-1.56 (m, 2H, —CCH2C—, linker), 1.54-1.46 (m, 2H, —CCH2C—, linker), 1.34-1.33 (m, 2H, —CCH2C—, linker); 13C NMR (150 MHz, D2O): δ 171.94, 171.81, 171.37, 170.80, 113.44, 99.86, 99.53, 99.27, 98.42, 97.99, 97.38, 97.08, 96.74, 96.21, 75.74, 75.66, 75.52, 73.56, 72.85, 72.41, 72.10, 71.62, 71.45, 71.36, 70.27, 69.81, 69.62, 69.28, 69.14, 69.02, 68.90, 68.69, 67.91, 67.82, 67.50, 67.20, 67.08, 66.87, 66.36, 65.46, 65.29, 65.01, 64.39, 64.32, 63.68, 62.47, 62.09, 61.02, 59.50, 59.39, 58.64, 57.96, 57.87, 57.10, 56.91, 52.12, 51.91, 48.60, 42.85, 40.32, 36.54, 36.25, 35.04, 25.27, 24.98, 23.34, 20.60, 19.53, 19.13, 19.03, 18.95, 13.70; ESI-MS (negative mode): m/z calcd for C, 76; H, 129; N, 5; O, 54; 1975.7418 found 1974.7671 (M−H)−.

Figure 89A:
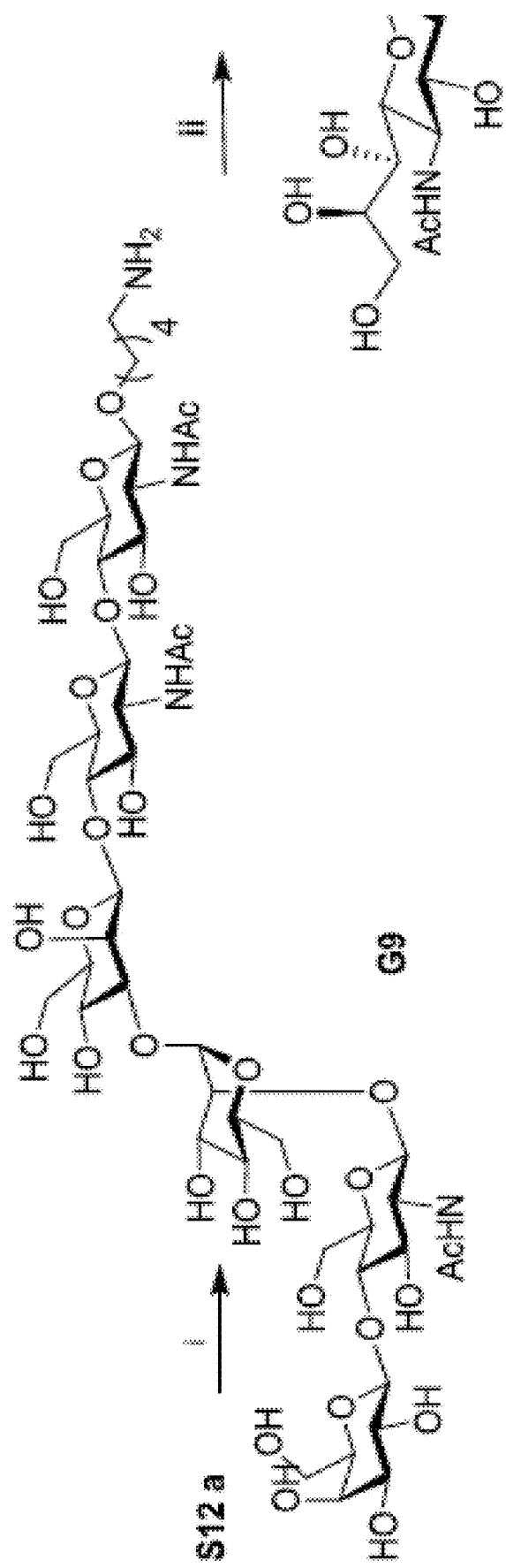
FIGS. 89A and 89B.
Figure 89B:
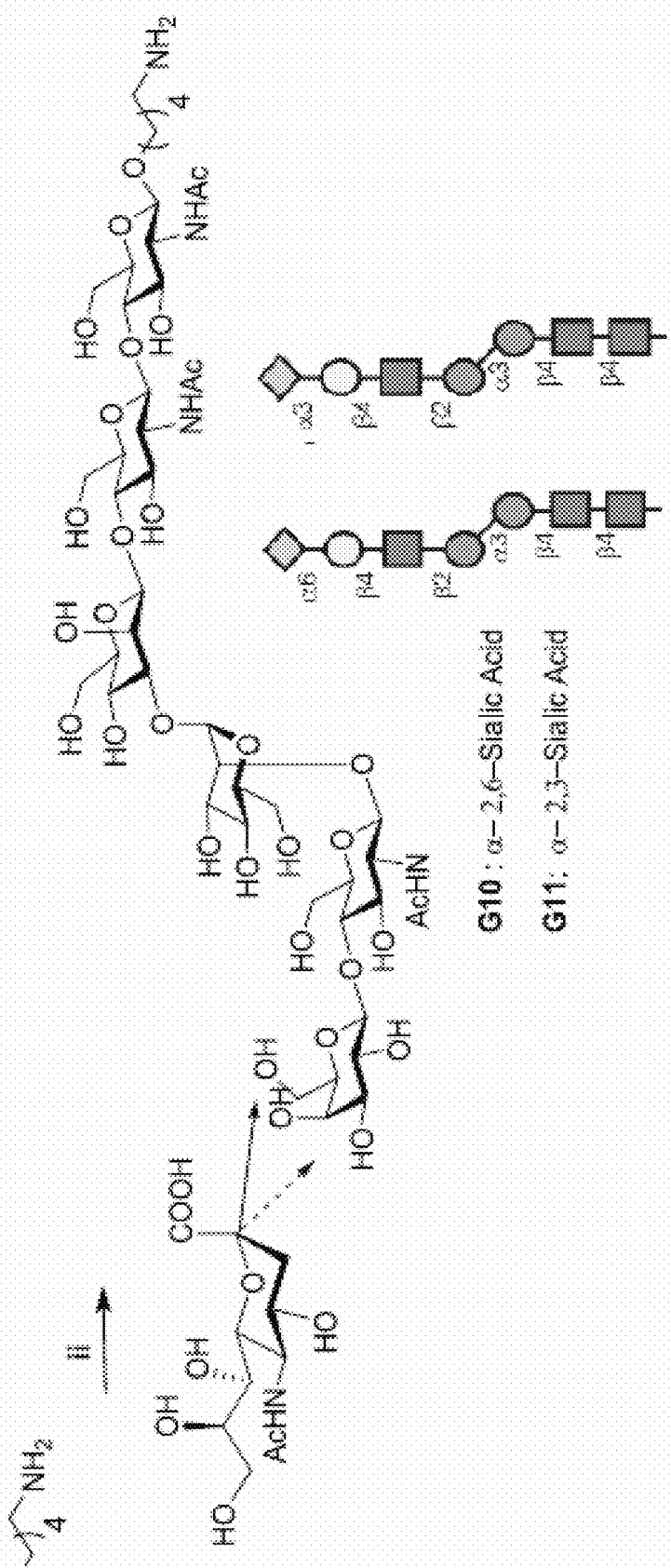
Figure 90:
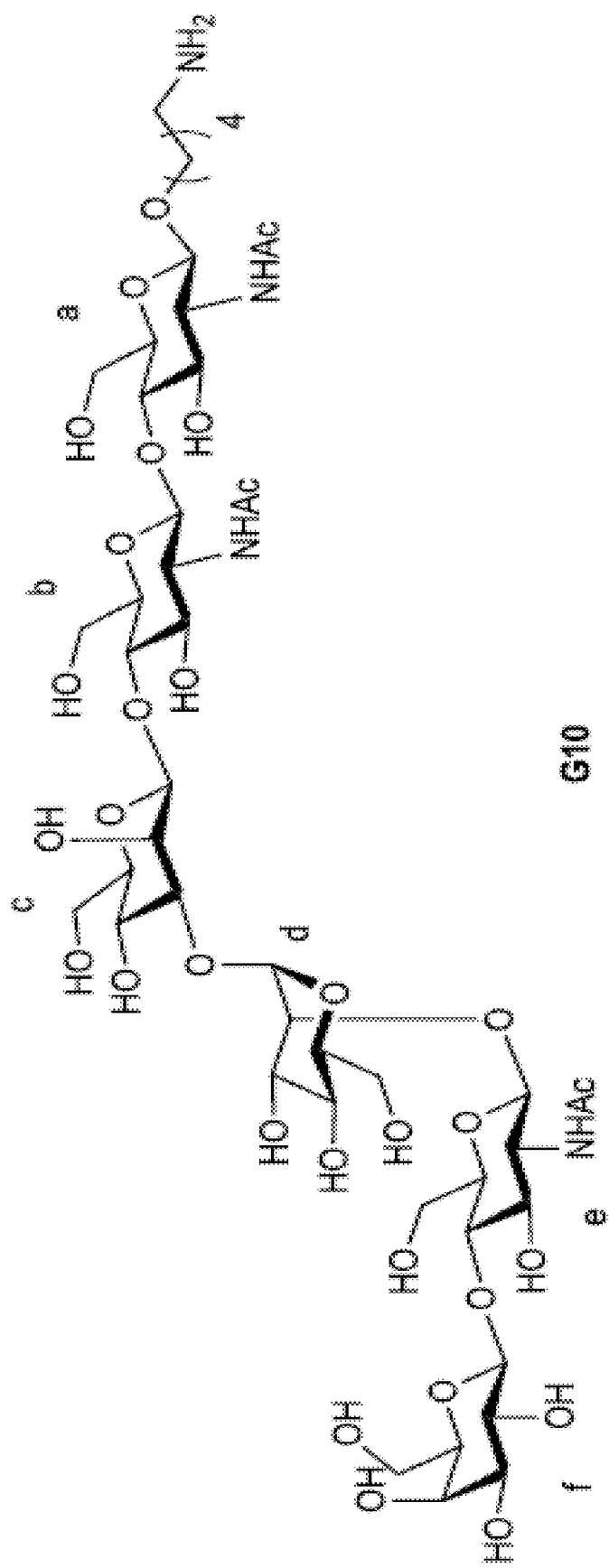
FIG. 90 Exemplary structure embodiments and synthetic scheme embodiments of the present disclosure.
Figure 91:
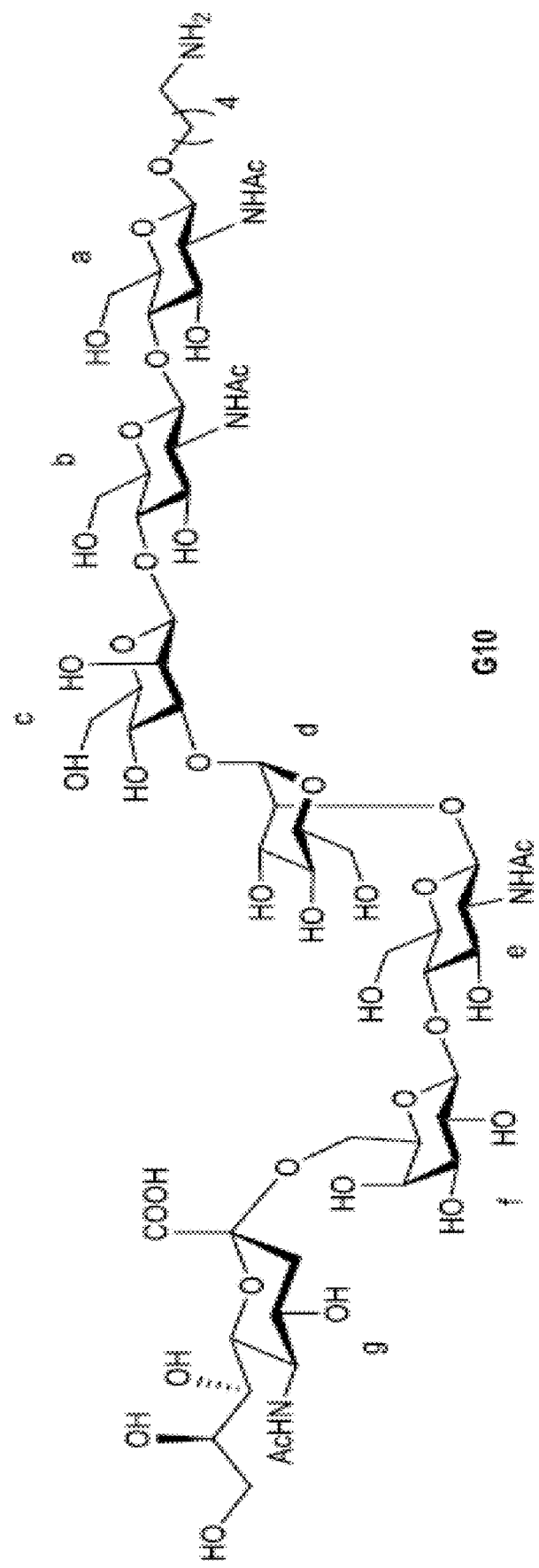
FIG. 91 Exemplary structure embodiments and synthetic scheme embodiments of the present disclosure.
Figure 92:
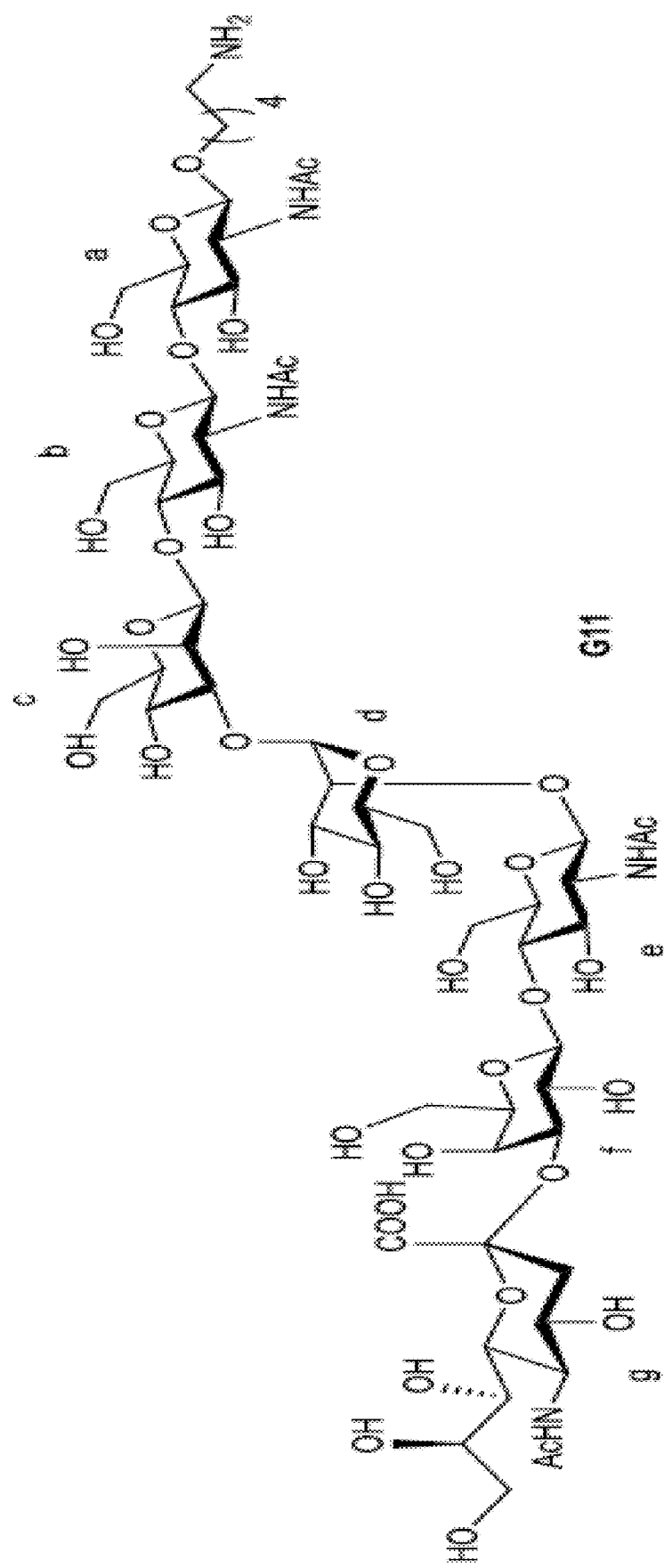
FIG. 92 Exemplary structure embodiments and synthetic scheme embodiments of the present disclosure.

Scheme S13 as shown in FIGS. 89A and 89B depicts the preparation of G9-G11. i) (1) NH2CH2CH2NH2, n-BuOH, 90° C., overnight; (2) Ac2O, pyridine, overnight; (3) NaOMe, MeOH, overnight; (4) Pd(OH)2, MeOH:H2O:HCOOH (5:3:2), H2; 51%; ii) CMP-β-D-Sialic acid, α-2,6/2,3-sialyltransferase, G10: 77%; G11: 52%

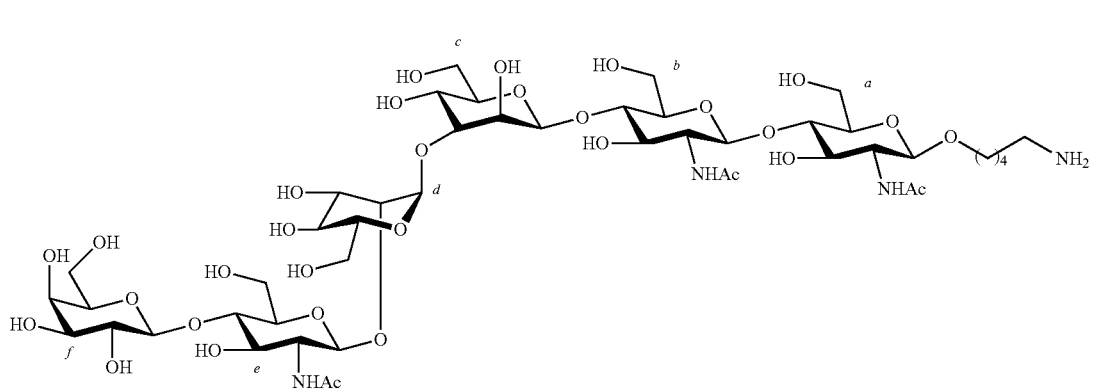

G10

5-Aminopentyl-β-D-galactopyranosyl-(1→4)-2-acetamido-2-deoxy-β-D-glucopyranosyl (1→2)-α-D-mannopyranosyl]-(1→3)-β-D-mannopyranosyl-(1→4)-2-acetamido-2-deoxy-βD-glucopyranosyl-(1→4)-2-acetamido-2-deoxy-β-D-glucopyranoside (G10): Hexasaccharide S12a (0.110 g, 0.041 mmol) was deprotected following general procedure 2 (Method 1) to get the desired compound G10 (0.025 g, 51%) as white solid. 1H NMR (600 MHz, D2O): δ 5.04 (d, J=8.4 Hz, 1H, H-1a), 4.84 (s, 1H, H-1d), 4.78 (s, 1H, H-1c), 4.60 (d, J=8.2 Hz, 1H, H-1e), 4.51 (d, J=8.1 Hz, 1H, H-1b), 4.46 (d, J=7.8 Hz, 1H, H-1f), 4.28 (d, J=3.3 Hz, 1H), 4.26 (d, J=3.6 Hz, 1H), 4.10-3.82 (m, 9H), 3.82-3.56 (m, 23H), 3.52-3.38 (m, 5H), 2.97 (t, J=7.8 Hz, 2H, —NCH2-, linker), 2.07 (s, 3H, —C(O)CH3), 2.05 (s, 3H, —C(O)CH3), 2.03 (s, 3H, —C(O)CH3), 1.701.65 (m, 2H, —CCH2C—, linker), 1.62-1.58 (m, 2H, —CCH2C—, linker), 1.48-1.41 (m, 2H, —CCH2C—, linker); 13C NMR (150 MHz, D2O): δ 177.64, 177.32, 177.17, 173.74, 105.65, 104.13, 103.80, 103.18, 102.70, 100.08, 82.05, 81.50, 81.37, 79.38, 79.04, 78.85, 78.09, 77.42, 77.28, 77.24, 75.23, 75.13, 75.06, 74.80, 74.67, 73.69, 72.84, 71.27, 70.14, 70.07, 68.12, 64.43, 63.74, 63.61, 62.85, 62.82, 62.75, 57.91, 57.78, 57.73, 42.05, 30.78, 29.10, 25.27, 24.87, 24.85, 24.83; ESI-MS: m/z calcd for C, 47; H, 82; N, 4; O, 3; 1198.4855 found 1221.5223 (M+Na)+.

G10

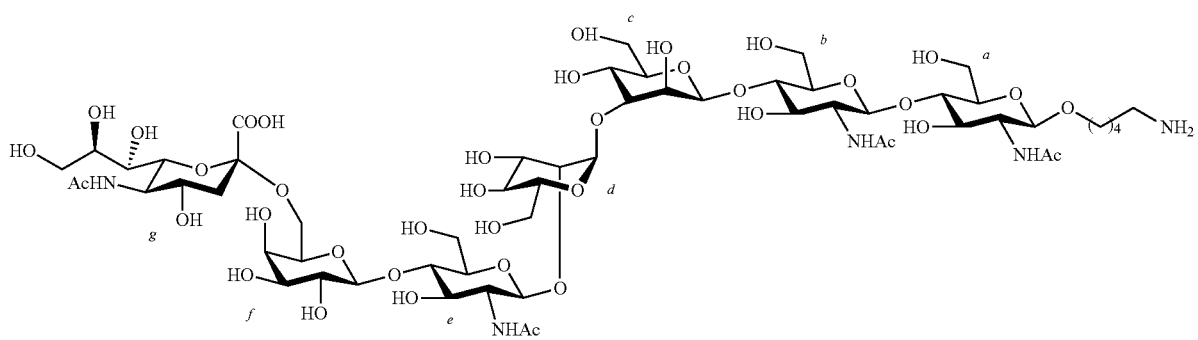

5-Aminopentyl-[5-Acetamido-3,5-dideoxy-D-glycero-α-D-galacto-2-nonulopyrano-sylonate-(2→6)-β-D-galactopyranosyl-(1→4)-2-acetamido-2-deoxy-β-D-glucopyranosyl-(1→2)-α-D-mannopyranosyl]-(1→3)-β-D-mannopyranosyl-(1→4)-2-acetamido-2-deoxy-β-D-glucopyranosyl-(1→4)-2-acetamido-2-deoxy-β-D-glucopyranoside (G10): Compound G9 (10 mg, 0.0083 mmol) was sialylated with α-2,6-sialyltransferase for 2 days by following general procedure 3 to get the desired title compound G10 (9.5 mg, 77%) as white solid. 1H NMR (600 MHz, D2O): δ 5.06 (d, J=7.8 Hz, 1H, H-1a), 4.80 (s, 1H, H-1d), 4.78 (s, 1H, H-1c), 4.60 (d, J=7.8 Hz, 1H, H-1e), 4.49 (d, J=7.8 Hz, 1H, H-1b), 4.43 (d, J=7.8 Hz, 1H, H-1f), 4.27 (d, J=3.6 Hz, 1H), 4.25 (d, J=3.6 Hz, 1H), 4.08-3.38 (m, 45H), 2.98 (t, J=11.2 Hz, 2H, —NCH2-, linker), 2.60 (dd, J=4.8, 12.0 Hz, 1H, H-3 equi. g), 2.08 (s, 6H, —C(O)CH3) 2.05 (s, 3H, —C(O)CH3), 2.03 (s, 3H, —C(O)CH3, 1.71 (t, J=7.8 Hz, 1H, H-3 axial g), 1.69-1.69 (m, 2H, —CCH2C—, linker), 1.611.56 (m, 2H, —CCH2C—, linker), 1.41-1.37 (m, 2H, —CCH2C—, linker); 13C NMR (150 MHz, D2O): δ 174.94, 174.83, 174.56, 174.40, 103.50, 101,37, 101.03, 100.31, 100.12, 99.92, 97.31, 80.99, 79.28, 78.63, 78.59, 76.61, 76.32, 76.07, 74.51, 74.48, 74.38, 73.67, 72.52, 72.38, 72.36, 72.08, 71.90, 71.66, 70.70, 70.06, 68.37, 68.34, 67.33, 63.35, 62.63, 61.67, 60.88, 60.09, 59.98, 54.99, 54.87, 51.85, 40.02, 39.30, 28.01, 26.36, 22.56, 22.10, 22.08, 21.99; ESI-MS (negative mode): m/z calcd for C, 58; H, 99; N, 5; O, 39; 1489.5833 found 1488.5949 (M–H)–.

noside (G11): Compound G9 (7 mg, 0.0058 mmol) was sialylated with α-2,3-sialyltransferase for 4 days by following general procedure 3 to get desired the title compound G11 (4.6 mg, 52%) as white solid. 1H NMR (600 MHz, D2O): δ 5.06 (d, J=8.4 Hz, 1H, H-1a), 4.79 (s, 1H, H-1d), 4.75 (s, 1H, H-1c), 4.62 (d, J=6.6 Hz, 1H, H-1e), 4.56 (d, J=7.8 Hz, 1H, H-1b), 4.51 (d, J=7.8 Hz, 1H, H-1f), 4.28 (d, J=8.4 Hz, 2H), 4.13 (d, J=9.6 Hz, 1H), 3.99-3.83 (m, 12H), 3.82-3.57 (m, 27H), 3.53-3.39 (m, 4H), 2.99 (t, J=7.8 Hz, 2H), 2.77 (dd, J=4.8, 2.0 Hz, 1H, H-3 equi. g), 2.12 (s, 3H, —C(O)CH3) 2.09 (s, 3H, —C(O)CH3), 2.05 (s, 3H, —C(O)CH3), 2.03 (s, 3H, —C(O)CH3), 1.80 (t, J=7.8 Hz, 1H, H-3 axial g), 1.71-1.66 (m, 2H, —CCH2C—, linker), 1.62-1.59 (m, 2H, —CCH2C—, linker), 1.44-1.41 (m, 2H, —CCH2C—, linker); 13C NMR (150 MHz, D2O): δ 174.88, 174.53, 174.46, 174.40, 102.50, 102,37, 101.65, 101.31, 100.12, 99.86, 98.31, 80.32, 79.67, 78.78, 78.56, 76.66, 75.32, 75.07, 74.51, 74.48, 74.38, 73.67, 72.52, 72.38, 72.36, 72.08, 71.90, 71.66, 70.70, 70.06, 68.37, 68.34, 67.33, 63.35, 62.63, 61.67, 60.88, 60.09, 59.98, 54.99, 54.87, 51.85, 40.02, 39.30, 28.01, 26.36, 22.56, 22.10, 22.08, 21.27 20.27; ESI-MS (negative mode): m/z calcd for C, 58; H, 99; N, 5; O, 39; 1489.5833 found 1488.5944 (M–H)–.

Synthesis of complex type oligosaccharides as shown in 93A, 93B and 93C depicts the structures of complex type gylcans.

Previously, we have developed an efficient chemo-enzymatic strategy for the rapid production of bi-(G15, G16, and G17), tri-(G20-G22, G23, G25 and G26) and tetraantennary (G28, G32 and G33) complex type N-glycans, with and without terminal N-acetylneuraminic acid residues connected via the α-2,6 or α-2,3 linkages. In addition, we have developed a total chemical synthesis strategy which utilized a modular set of glycosyl donors (1-13) for stereo- and

G11

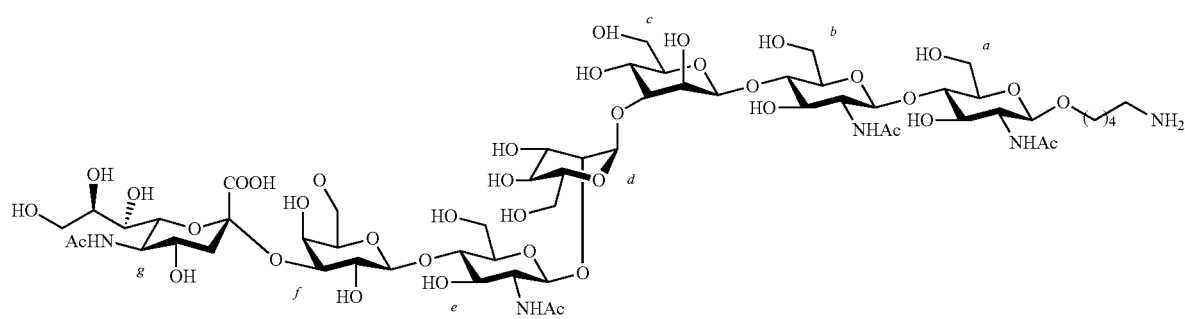

5-Aminopentyl-[5-Acetamido-3,5-dideoxy-D-glycero-α-D-galacto-2-nonulopyrano-sylonate-(2→3)-β-D-galactopyranosyl-(1→4)-2-acetamido-2-deoxy-β-D-glucopyranosyl-(1→2)-α-D-mannopyranosyl]-(1→3)-β-D-mannopyranosyl-(1→4)-2-acetamido-2-deoxy-β-D-glucopyranosyl-(1→4)-2-acetamido-2-deoxy-β-D-glucopyraregion-selective glycosylation to core trisaccharide 15. However, the synthesis of assymetrically sialylated glycans by enzyme is complicated by their specificity. For this reason, we demonstrated the utility of glycosyl fluoride to prepare assymetric complex type glycans. Initially, we started with pthallamide protections at $C_{2-8}$mine of all glucosamine residues of both antennae and core trisaccharides (14), however, in presence of preinstalled sialic acid, the process of global deprotection was found to be complicated. To overcome this difficulty, the pthallamide protections at C2-amine of all glucosamine residues were replaced with trichloroethyl carbonate (troc).

Synthesis of glycan G18.

Glycosylation of sialylated antenne 9 with core 15 at 3-O site provided desired heptasaccharide S14a in 63% yield. Benzylidene was removed in the presence of p-TSA to get 4,6-diol S14b, which was further alpha glycosylated at 6-O position with 8 to afford desired S14c as mixture of α and β forms (7/3 isolated yield). The major α isomer was isolated by column chromatography and finally deprotected to get G18 as a white solid.

Figure 94:
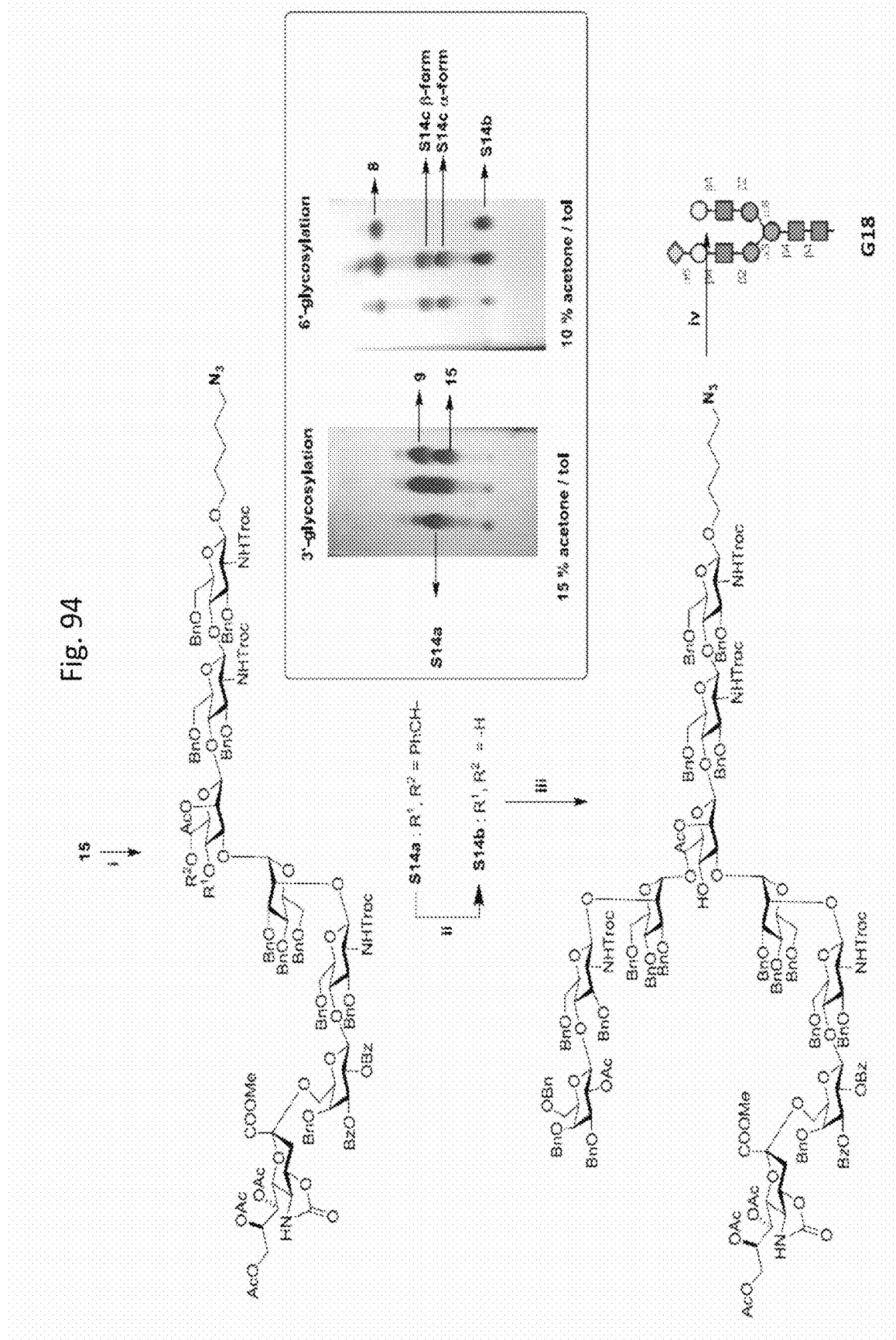
FIG. 94 Exemplary structure embodiments and synthetic scheme embodiments of the present disclosure.
Figure 95:
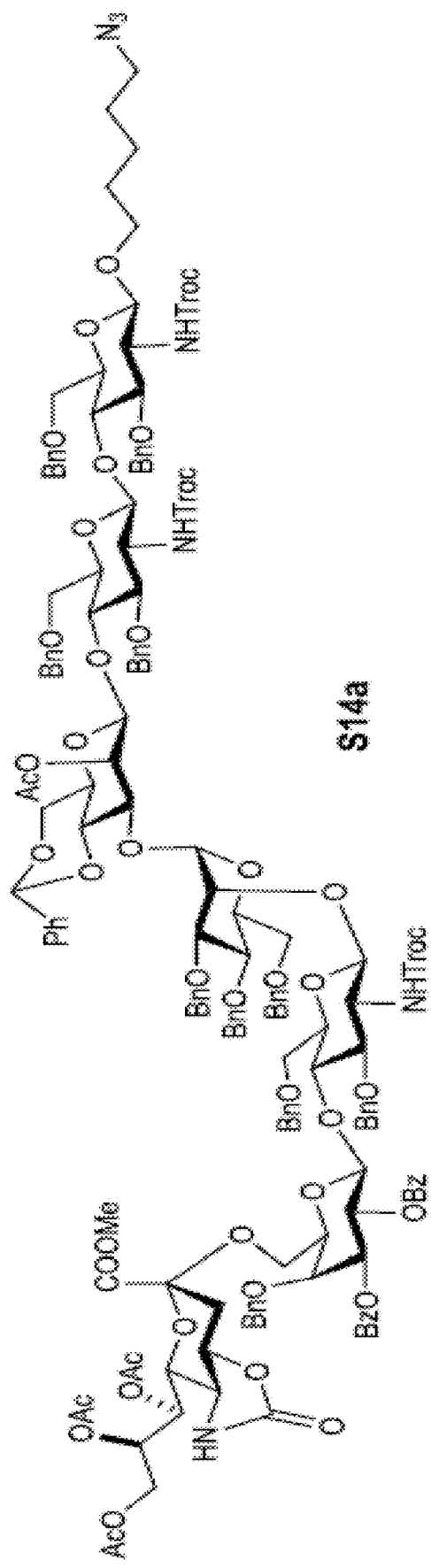
FIG. 95 Exemplary structure embodiments and synthetic scheme embodiments of the present disclosure.
Figure 96:
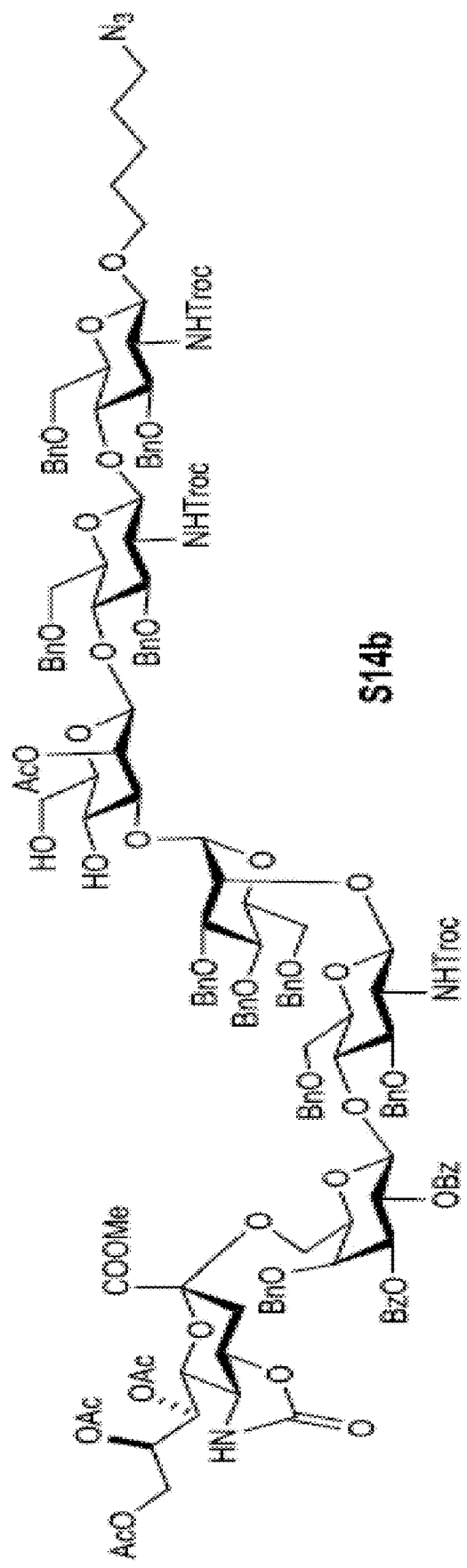
FIG. 96 Exemplary structure embodiments and synthetic scheme embodiments of the present disclosure.
Figure 97:
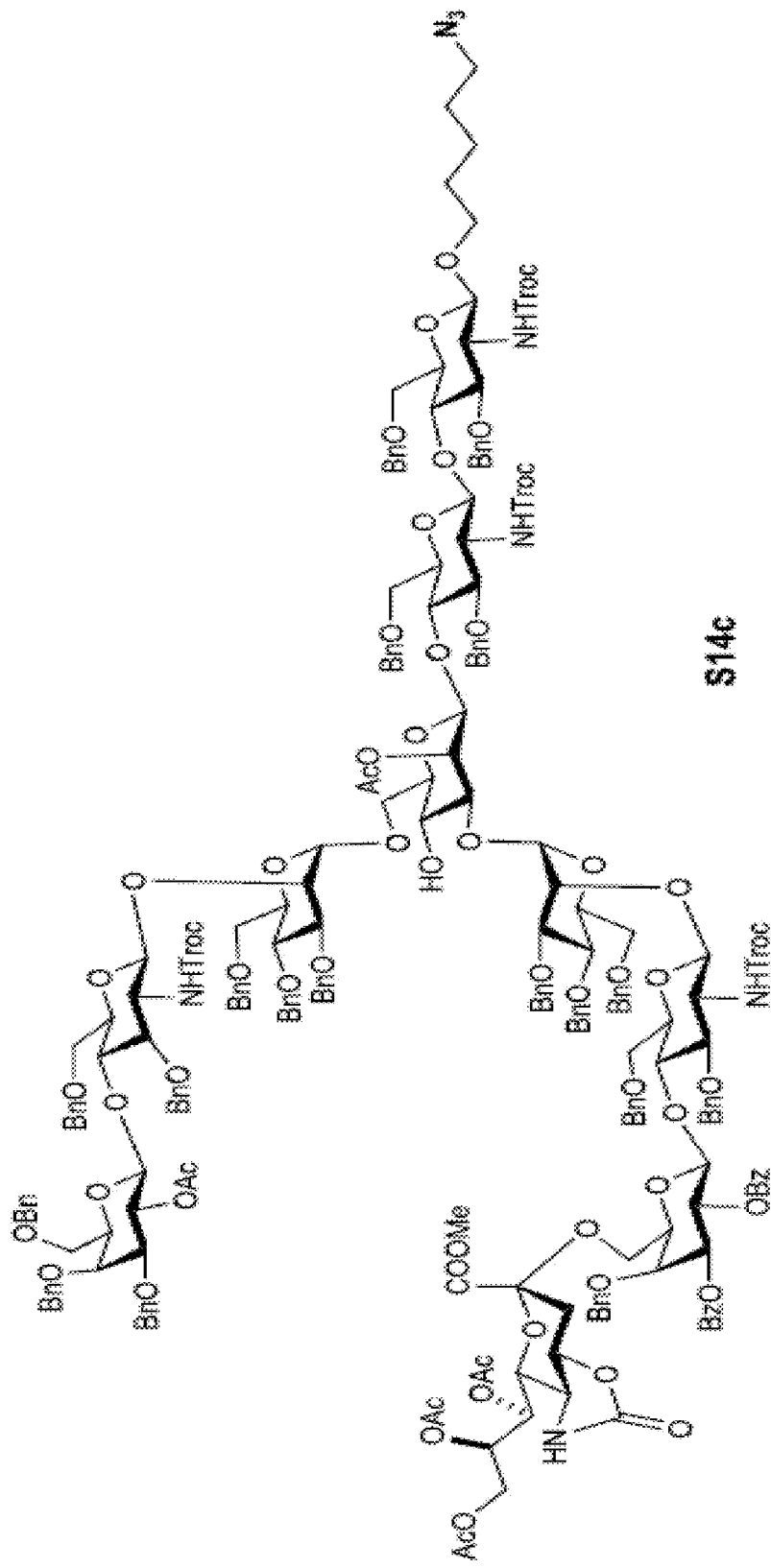
FIG. 97 Exemplary structure embodiments and synthetic scheme embodiments of the present disclosure.
Figure 98:
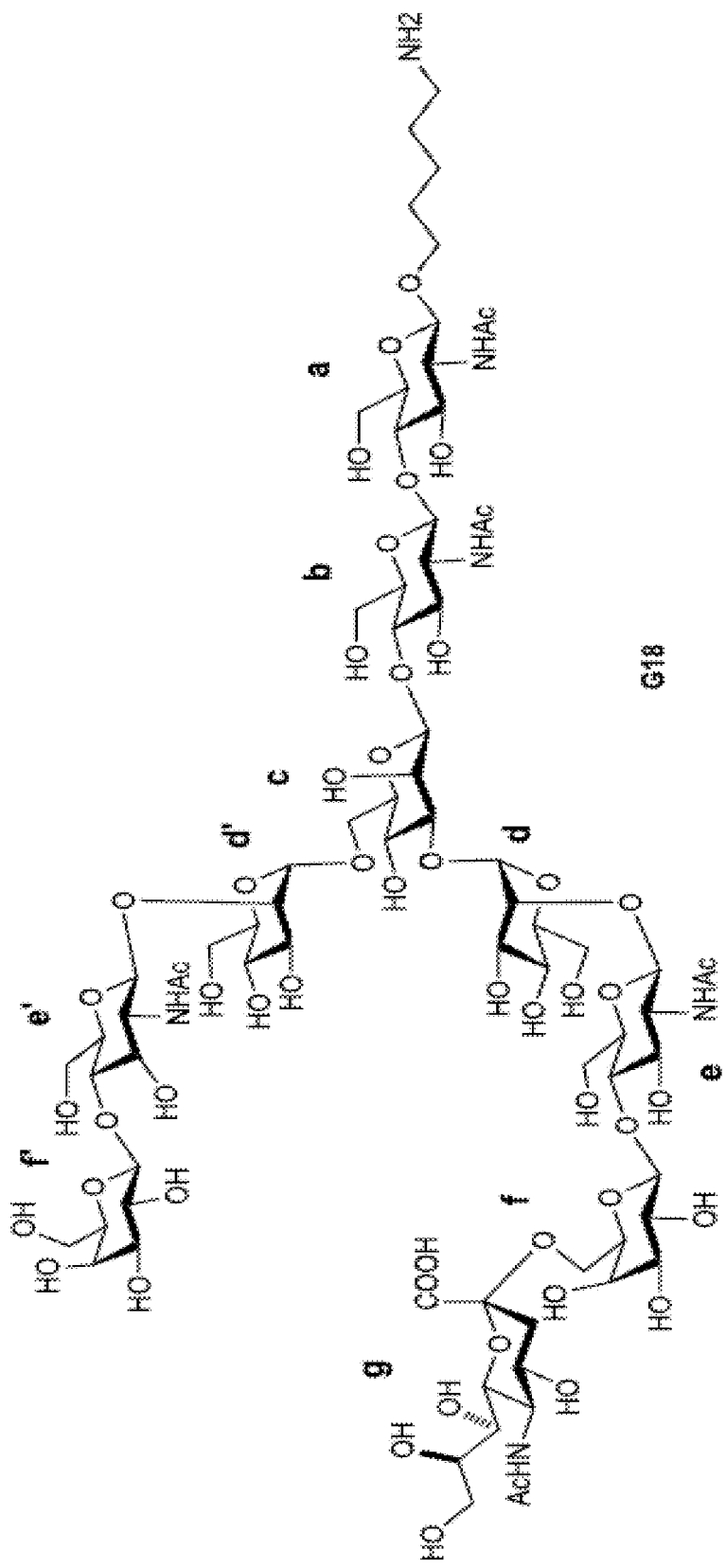
FIG. 98 Exemplary structure embodiments and synthetic scheme embodiments of the present disclosure.

Scheme S14 as shown in FIG. 94 depicts the preparation of G18. i, 9, AgOTf, Cp2HfCl2, toluene, −20° C. to 0° C., 63%; ii, pTSA, acetonitrile, 59%; iii, 8, AgOTf, Cp2HfCl2, toluene, −40° C. to −20° C., 58%; iv, (1) LiOH, 1,4-dioxane: H2O, 90° C., (2) Ac2O, pyridine, (3) NaOMe, MeOH, (4) Pd(OH)2, MeOH:H2O, H2, 25%.

Compound S14a: A mixture of silver triflate (0.087 g, 0.34 mmol), bis (cyclopentadienyl) hafnium dichloride (0.090 g, 0.23 mmol) and 4 Å activated molecular sieves in dry toluene (10 mL) was stirred at rt for 1 h. The reaction mixture was then cooled to −20° C., a solution of donor 9 (0.153 g, 0.082 mmol) and acceptor chitobiose trisaccharide 15 (0.100 g, 0.068 mmol) in 5 mL toluene was added. The mixture was stirred for 2 h at 0° C., quenched with Et3N, diluted with EtOAc and filtered through Celite. The filtrate was washed with aqueous NaHCO3 (2×50 mL), and a brine (50 mL) solution. The organic layer was dried over Na2SO4 and concentrated in vacuo. The residue was purified by flash column chromatography (0%→10% acetone in toluene) to afford S14a (0.140 g, 63%) as white foam. TLC: (acetone: toluene=1.5/8.5, v/v): Rf=0.52; 1H NMR (600 MHz, CDCl3): δ 7.89 (d, J=7.8 Hz, 4H), 7.49-7.46 (m, 2H), 7.37-7.06 (m, 59H), 5.77 (t, J=10.8 Hz, 1H), 5.35-5.37 (m, 2H), 5.26 (s, 1H), 5.18 (dd, J=3.8 & 7.7 Hz, 1H), 5.08 (d, J=3.2 Hz, 1H), 5.07 (dd, J=3.2 & 8.4 Hz, 1H), 4.97 (d, J=8.4 Hz, 1H), 4.91 (d, J=9.1 Hz, 1H), 4.86 (d, J=8.7 Hz, 3H), 4.73-4.13 (m, 32H), 4.02-3.30 (m, 29H), 3.20 (t, J=10.8 Hz, 2H), 3.10 (d, J=8.7 Hz, 1H), 2.98 (t, J=9.2 Hz, 1H), 2.87-2.85 (m, 1H), 2.80 (dd, J=3.2 & 7.8 Hz, 1H), 2.10 (s, 6H), 2.08 (t, J=9.3 Hz, 1H), 2.00 (s, 6H), 1.40-1.17 (m, 4H), 0.87-0.82 (m, 2H); 13C NMR (150 MHz, CDCl3): δ 171.9, 170.8, 170.2, 170.0, 167.9, 166.1, 165.5, 159.5, 154.5, 154.3, 154.1, 138.2, 130.1, 129.8, 129.6, 129.4, 128.9, 128.8, 128.7, 128.6, 128.5, 128.4, 128.3, 128.2, 128.1, 127.9, 127.8, 127.6, 127.0, 100.8, 100.5, 98.0, 95.8, 76.8, 76.7, 75.5, 74.8, 74.6, 74.4, 74.3, 74.1, 73.8, 73.7, 73.4, 73.2, 69.9, 69.7, 69.5, 68.7, 67.5, 66.7, 61.9, 58.9, 57.6, 53.4, 37.4, 29.9, 29.2, 28.8, 23.4, 21.3, 21.2, 21.0, 20.9, 14.3; ESI-MS: m/z calcd for C, 160; H, 172; C, 19; N, 7; O, 48; 3278.8343 found 3278.8127.

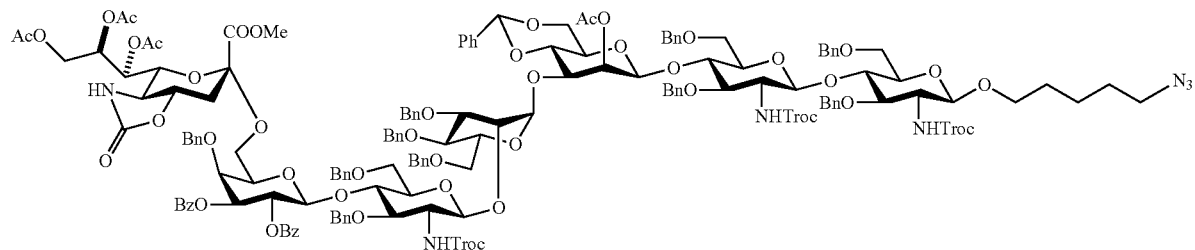

S14a

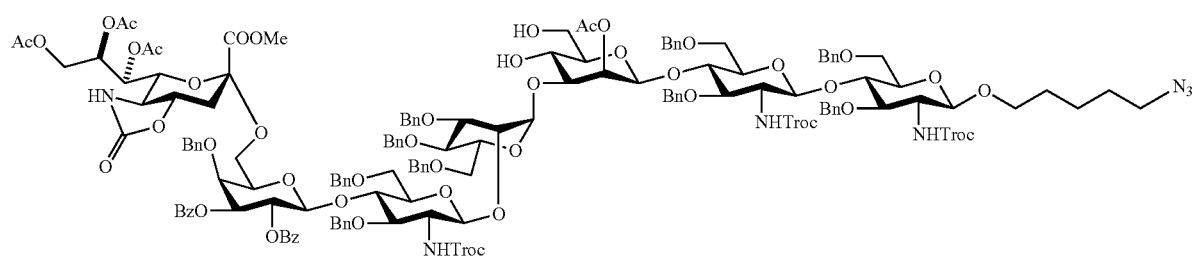

S14b

Compound S14b: p-Toluene sulfonic acid monohydrate (0.004 g, 0.022 mmol) was added to a solution of S14a (0.150 g, 0.045 mmol) in acetonitrile (20 mL) and the resulting reaction mixture was stirred at room temperature for 5h. The reaction was quenched by adding Et3N and concentrated in vacuo. The residue was purified by flash column chromatography (0%→15% EA in toluene) to give diol S14b (0.085 g, 59%). TLC: (acetone:toluene=2/8, v/v): Rf=0.32 NMR (600 MHz, CDCl3): δ 7.89-7.86 (m, 4H), 7.49-7.37 (m, 2H), 7.30-7.09 (m, 54H), 5.78 (t, J=10.2 Hz, 1H), 5.51 (d, J=7.8 Hz, 1H), 5.37 (dt, J=2.4 & 7.2 Hz, 1H), 5.26 (s, 1H), 5.19 (dd, J=2.4 & 10.8 Hz, 1H), 5.12 (d, J=3.6 Hz, 1H), 4.95-4.85 (m, 5H), 4.75-4.12 (m, 25H), 4.08-4.03 (m, 3H), 3.96-3.89 (m, 7H), 3.74-3.67 (m, 8H), 3.63-3.30 (m, 20H), 3.20 (t, J=10.2 Hz, 2H), 3.10 (d, J=8.9 Hz, 2H), 2,89 (s, 1H), 2.76 (dd, J=3.6 & 7.9 Hz, 1H), 2.08 (s, 3H), 2.05 (s, 3H), 1.99 (s, 3H), 1.95 (s, 3H), 1.41-1.31 (m, 5H), 1.27-1.17 (m, 2H); 13C NMR (150 MHz, CDCl3): δ 172.4, 172.3, 171.3, 171.2, 170.7, 170.3, 170.0, 168.4, 168.3, 166.1, 165.5, 154.5, 154.3, 154.1, 153.9, 138.5, 138.4, 138.1, 138.0, 133.7, 133.3, 130.1, 129.8, 129.7, 129.5, 129.3, 128.9, 128.8, 128.7, 128.6, 128.6, 128.5, 128.4, 128.3, 128.2, 128.1, 128.0, 127.9, 101.1, 100.8, 100.6, 100.4, 99.7, 99.2, 96.0, 95.8, 76.3, 76.1, 75.7, 75.5, 74.9, 74.8, 74.5, 74.3, 74.0, 73.7, 73.4, 73.3, 73.2, 73.1, 73.0, 72.6, 72.3, 72.1, 71.3, 71.0, 69.9, 69.6, 69.4, 69.3, 68.4, 67.8, 66.1, 66.2, 62.8, 62.2, 59.2, 57.7, 53.4, 51.5, 36.9, 29.9, 29.2, 28.8, 25.0, 23.4, 21.4, 21.3, 21.2, 21.1, 15.5, 14.4; ESI-MS (negative mode): m/z calcd for C, 153; H, 168; C, 19; N, 7; O, 48; 3191.8105 found 3236.8033 (M+2Na)−.

Compound S14c: A mixture of silver triflate (0.067 g, 0.27 mmol). bis (cyclopentadienyl) hafnium dichloride (0.071 g, 0.18 mmol) and 4 Å activated molecular sieves in dry toluene (10 mL) was stirred at rt for 1 h. The reaction mixture was then cooled to −40° C., a solution of donor 8 (0.097 g, 0.068 mmol) and acceptor S14b (0.175 g, 0.054 mmol) in 5 mL toluene was added. The mixture was stirred for 2 h at −20° C., quenched with Et3N, diluted with EtOAc and filtered through Celite. The filtrate was washed with aqueous NaHCO3 (2×50 mL), and a brine (50 mL) solution. The organic layer was dried over Na2SO4 and concentrated in vacuo. The residue was purified by flash column chromatography (0%→10% acetone in toluene) to separate mixture of α and β isomers to afford S14c (0.149 g, 58%) as white foam. TLC: (acetone:toluene=1.5/8.5, v/v): Rf=0.52; 1H NMR (600 MHz, CDCl3): δ 7.90 (d, J=7.2 Hz, 2H), 7.83 (d, J=7.8 Hz, 2H), 7.51-7.41 (m, 4H), 7.34-7.06 (m, 92H), 5.83 (t, J=10.2 Hz, 1H), 5.48-5.03 (m, 3H), 5.00-4.75 (m, 13H), 4.60-4.08 (m, 41H), 3.99-3.07 (m, 53H), 2.96 (t, J=10.2 Hz, 2H), 2.80 (dd, J=3.8 & 7.9 Hz, 1H), 2.15 (s, 3H), 2.10 (s, 3H), 2.07 (s, 3H), 2.00 (s, 3H), 1.93 (s, 3H), 1.40-1.17 (m, 5H), 0.91-0.81 (m, 2H); 13C NMR (150 MHz, CDCl3): δ 170.9, 170.6, 170.4, 169.9, 169.4, 166.5, 159.5, 154.7, 154.4, 139.8, 138.8, 138.7, 138.6, 138.4, 138.2, 133.7, 130.9, 130.7, 129.7, 129.6, 129.4, 129.2, 129.0, 128.7, 128.6, 128.6, 128.4, 128.3, 128.2, 127.9, 127.6, 127.3, 100.4, 100.2, 99.8, 99.4, 74.9, 74.7, 74.5, 73.3, 73.2, 66.1, 60.6, 51.5321, 32.1, 29.8, 29.7, 29.6, 29.3, 28.7, 23.7, 22.8, 22.4, 22.0, 21.6, 21.4, 21.2, 20.9, 15.4, 14.3, 14.2, 14.0, 11.3, 10.2; ESI-MS: m/z calcd for C, 232; H, 250; Cl, 12; N, 8; O, 65; 4607.2765 found 2330.6261 (M+Na)2+.

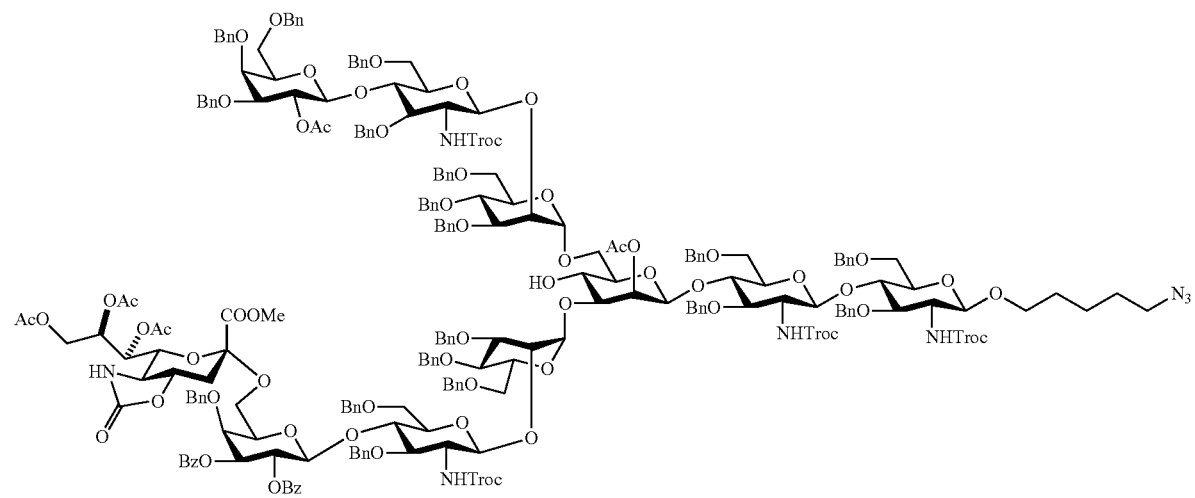

S14c

G18

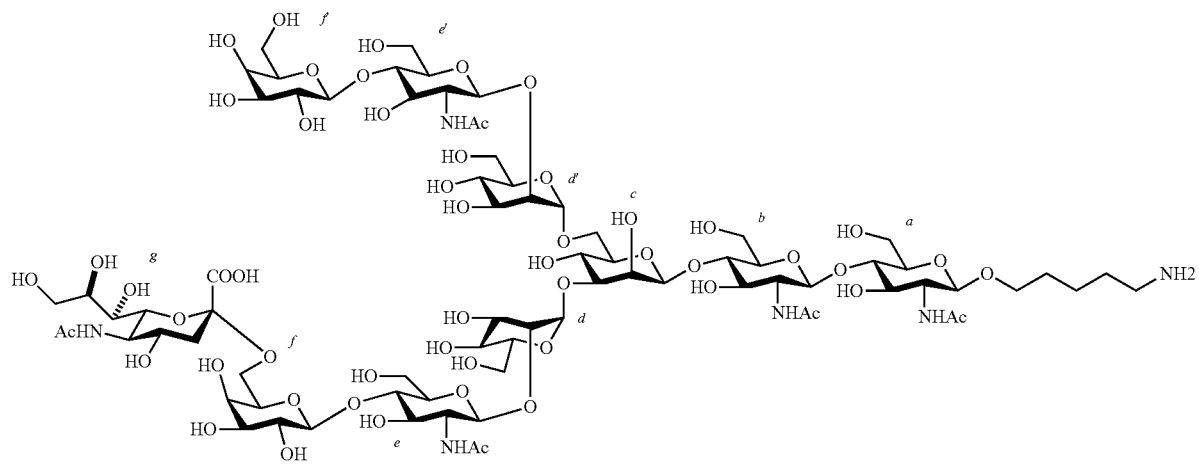

5-Aminopentyl-[5-Acetamido-3,5-dideoxy-D-glycero-α-D-galacto-2-nonulpyranosylonate-(2→6)-β-D-galactopyranosyl-(1→4)-2-acetamido-2-deoxy-β-D-glucopyranosyl-(1→2)-α-D-mannopyranosyl]-(1→3),-[β-D-galactopyranosyl-(1→4)-2-acetamido-2-deoxy-β-D-glucopyranosyl-(1→2)-α-D-mannopyranosyl]-(1→6)-β-D-mannopyranosyl-(1→4)-2-acetamido-2-deoxy-β-D-glucopyranosyl-(1→4)-2-acetamido-2-deoxy-β-D-glucopyranoside G18: Compound S14c (0.135 g, 0.029 mmol) was deprotected by following general procedure 2 (method 2) to afford the desired glycan G18 (0.015 g, 25%). 1H NMR (600 MHz, D2O): 5.11 (s, 1H, H-1d), 4.89 (s, 1H, H-1d'), 4.73 (s, 1H, H-1c), 4.57 (dt, J=10.2 Hz, 2H, H-1f,f'), 4.47 (d, J=7.8 Hz, 2H, H-1a,b), 4.47 (d, J=8.4 Hz, 2H, H-1e,e'), 4.23 (s, 1H), 4.17 (s, 1H), 4.09 (d, J=1.3 Hz, 1H), 4.03-3.48 (m, 61H), 2.98 (t, J=10.2 Hz, 2H, —CH2- linker), 2.65 (dd, J=4.8 & 12.6 Hz, 1H, H-3equi. g), 2.10 (s, 3H), 2.09 (s, 3H), 2.07 (s, 3H), 2.02 (s, 6H), 1.72-1.64 (m, 3H, H-3axial g, linker —CH2-), 1.63-1.54 (m, 2H), 1.39-1.35 (m, 2H); 13C NMR (150 MHz, D2O): δ 177.7, 177.5, 177.4, 177.1, 176.2, 176.1, 106.2, 106.1, 104.1, 103.7, 103.5, 103.1, 102.9, 102.9, 99.5, 83.6, 83.1, 82.2, 82.1, 81.7, 79.4, 79.1, 78.9, 77.3, 77.2, 76.8, 76.4, 75.3, 75.1, 74.8, 74.5, 73.5, 73.4, 72.8, 71.2, 70.9, 70.0, 67.6, 66.0, 65.6, 65.4, 64.5, 62.8, 57.7, 57.3, 55.0, 54.6, 54.0, 42.8, 42.3, 42.0, 41.78, 30.7, 30.5; ESI-MS (negative mode): m/z calcd for C, 78; H, 132; N, 6; O, 54 2016.7767; found 1007.3799 (M−H)2−.

Synthesis of glycan G24.

Compound S14b acts as common acceptor for both G18 and G24. Glycosylation of S14b at 6-O site provided the desired S15a with 10% acceptor recovery. At last, global deprotection yielded the desired glycan G24.

Figure 99:
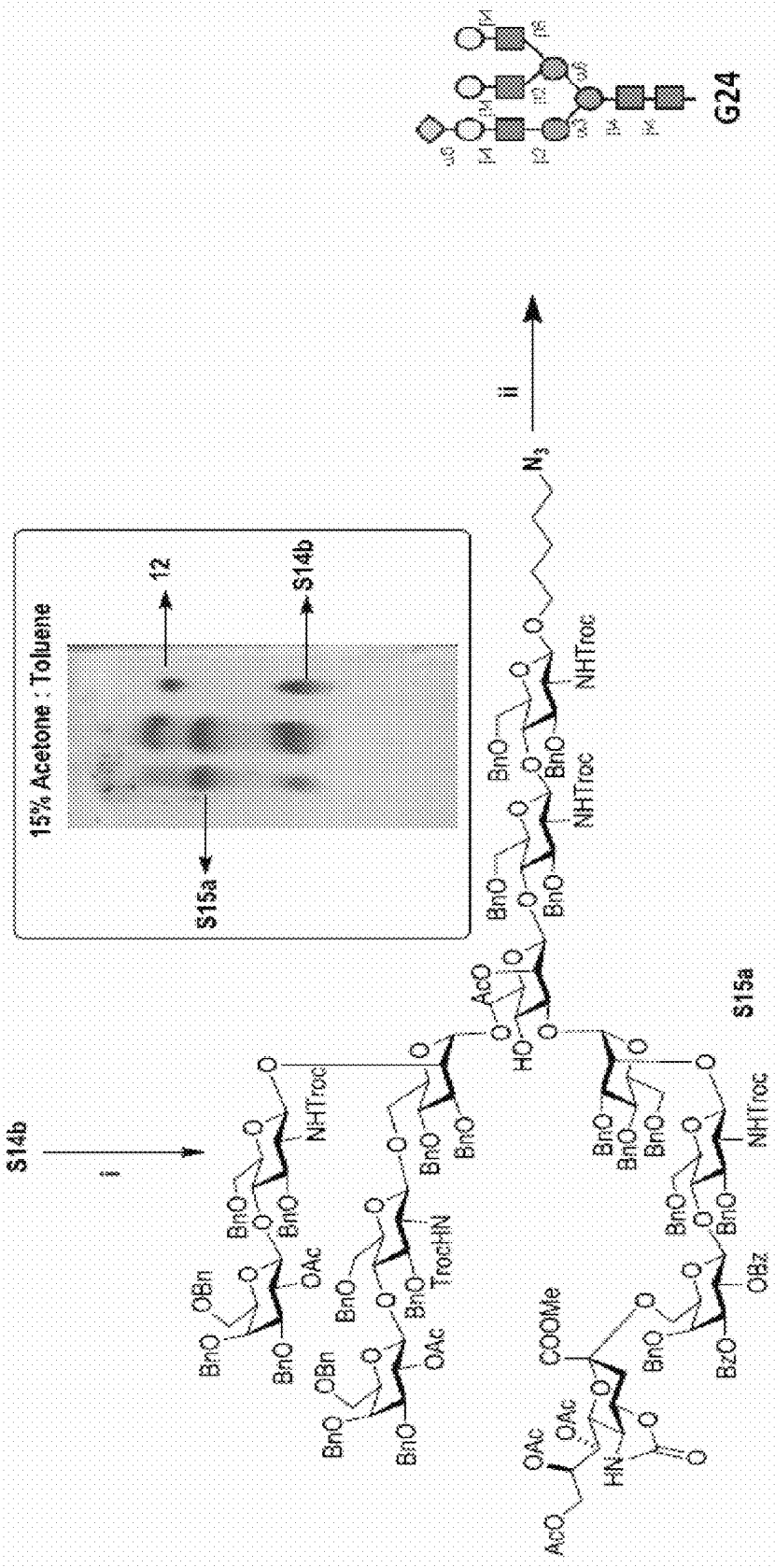
FIG. 99 Exemplary structure embodiments and synthetic scheme embodiments of the present disclosure.
Figure 100:
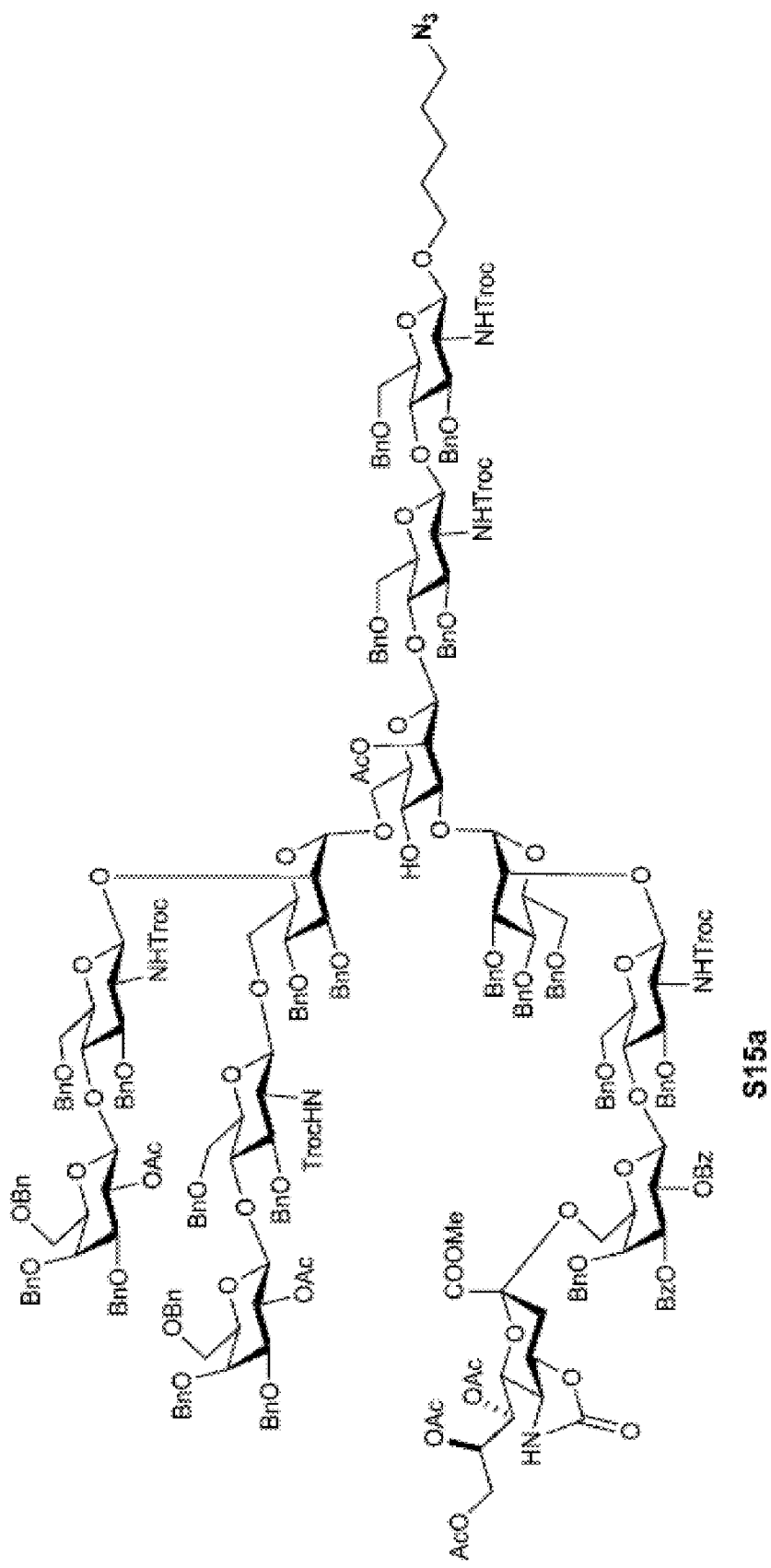
FIG. 100 Exemplary structure embodiments and synthetic scheme embodiments of the present disclosure.
Figure 101:
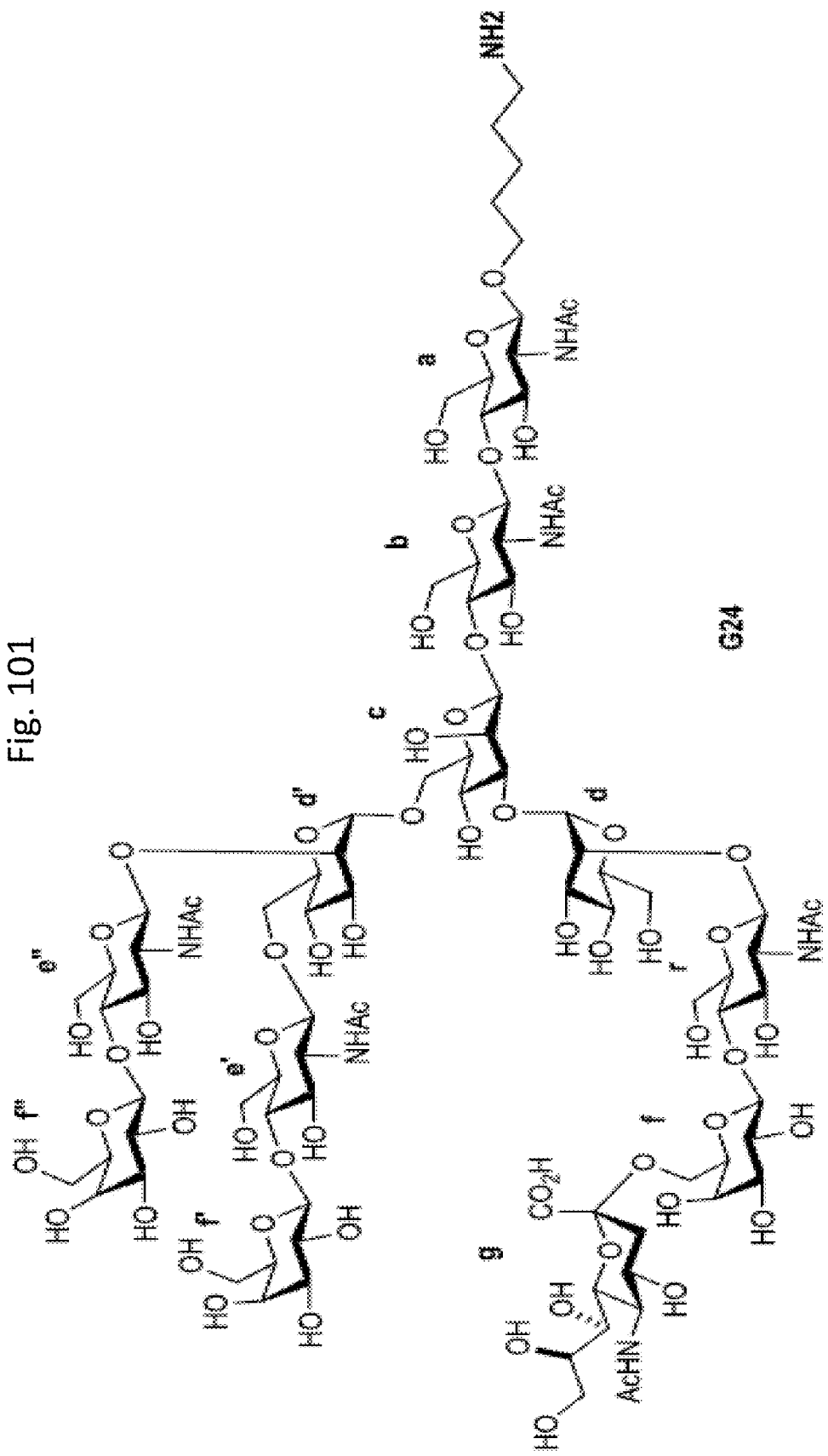
FIG. 101 Exemplary structure embodiments and synthetic scheme embodiments of the present disclosure.

Scheme S15 as shown in FIG. 99 depicts the preparation of G24. i, 12, AgOTf, Cp2HfCl2, toluene, −40° C., 63%; ii, (1) LiOH, 1,4-dioxane, 90° C., (2) Ac2O, pyridine, (3) NaOMe, MeOH, (4) Pd(OH)2, MeOH:H2O, H2, 42%.

S15a

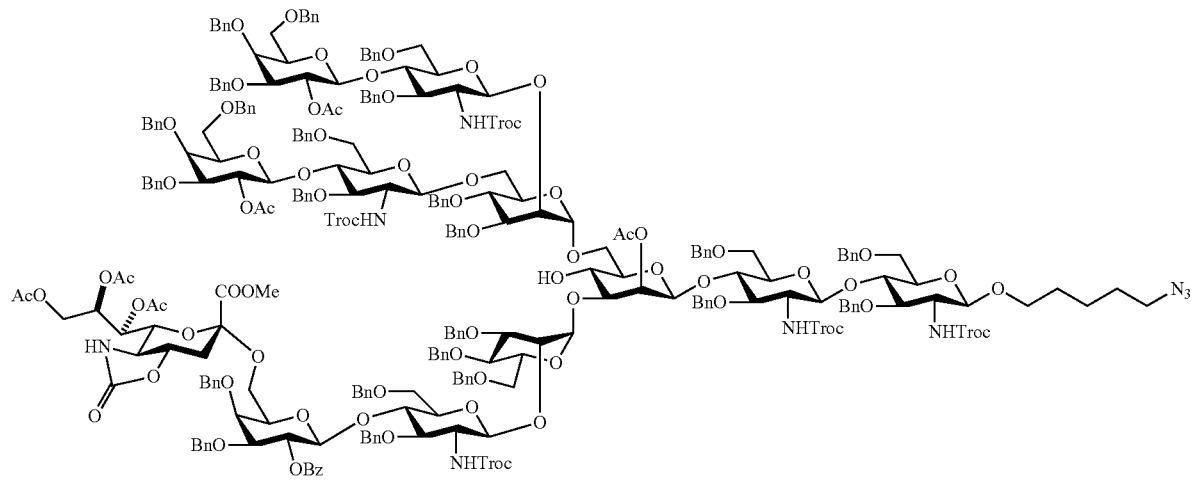

Compound S15a of FIG. 99: A mixture of silver triflate (0.058 g, 0.23 mmol), bis (cyclopentadienyl) hafnium dichloride (0.061 g, 0.23 mmol) and 4 Å activated molecular sieves in dry toluene (10 mL) was stirred at rt for 1 h. The reaction mixture was then cooled to −40° C., a solution of donor 12 (0.135 g, 0.056 mmol) and acceptor S14b (0.150 g, 0.046 mmol) in 5 mL toluene was added. The mixture was stirred for 2 h at −20° C., quenched with Et3N, diluted with EtOAc and filtered through Celite. The filtrate was washed with aqueous NaHCO3 (2×50 mL), and a brine (50 mL) solution. The organic layer was dried over Na2SO4 and concentrated in vacuo. The residue was purified by flash column chromatography (0%→10% acetone in toluene) to afford S15a (0.165 g, 63%) as white foam. TLC: (acetone:toluene=1.5/8.5, v/v): Rf=0.58; 1H NMR (600 MHz, CDCl3): δ 8.00-7.80 (m, 4H), 7.50-6.80 (m, 116H), 5.80 (t, J=10.2 Hz, 1H), 5.40-5.30 (m, 7H), 5.10-4.08 (m, 65H), 4.00-3.05 (m, 65H), 2.98 (dd, J=3.2 & 8.5 Hz, 1H), 2.15 (s, 6H), 2.10 (s, 6H), 2.00 (s, 6H), 1.37-1.17 (m, 5H), 0.87-0.84 (m, 2H); 13C NMR (150 MHz, CDCl3): δ 170.8, 167.9 154.1, 139.1, 139.0, 138.9, 138.8, 138.6, 138.3, 138.1, 138.0, 129.8, 129.6, 129.3, 128.9, 128.8, 128.7, 128.7, 128.6, 128.5, 128.4, 128.2, 128.0, 127.7, 127.4, 127.3, 127.2, 127.1, 127.0, 100.8, 100.0, 74.9, 74.8, 74.5, 74.4, 73.6, 73.3, 72.6, 53.5, 29.9, 29.2, 23.4, 21.3, 21.2, 21.0, 20.9, 15.5, 14.4; ESI-MS (negative mode): m/z calcd for C, 277; H, 298; C, 115; N, 9; O, 77; 5517.1670 found 2803.7442 (M+2Na)2−.

glucopyranoside G24: Compound S15a (0.090 g, 0.016 mmol) was deprotected by following general procedure 2 (method 2) to afford desired glycan G24 (0.016 g, 42%) as a white solid. 1H NMR (600 MHz, D2O): δ 5.14 (s, 1H, H-1d), 4.88 (s, 1H, H-1d'), 4.60 (t, J=10.2 Hz, 3H, H-1e,f,e'), 4.55 (d, J=8.4 Hz, 1H), 4.48 (dd, J=3.2 & 8.6 Hz, 4H), 4.45 (d, J=7.8 Hz, 1H), 4.26 (s, 1H), 4.20 (s, 1H), 4.09 (s, 1H), 4.01-3.50 (m, 71H), 2.97 (t, J=10.2 Hz, 2H, linker —CH2-), 2.68 (dd, J=3.8 & 8.3 Hz, 1H, H-3equi. g), 2.08 (s, 3H, —C(O)CH3), 2.07 (s, 3H, —C(O)CH3), 2.04 (s, 3H, —C(O)CH3), 2.03 (s, 6H, —C(O)CH3), 1.72 (t, J=10.2 Hz, 1H, H-3axial g), 1.67-1.65 (m, 2H), 1.60-1.56 (m, 2H, linker —CH2-), 1.40-1.39 (m, 2H, linker —CH2-); 13C NMR (150 MHz, D2O): δ 174.9, 174.7, 174.6, 174.5, 174.4, 174.1, 173.5, 103.6, 103.5, 102.9, 102.8, 101.5, 101.4, 101.0, 100.3, 100.1, 99.5, 99.3, 80.7, 80.4, 79.5, 79.3, 79.2, 78.5, 76.5, 75.4, 75.2, 74.7, 74.5, 74.4, 74.3, 73.7, 73.4, 72.5, 72.4, 72.3, 72.1, 71.9, 71.6, 71.3, 70.9, 70.8, 70.5, 70.3, 69.5, 69.4, 68.5, 68.3, 68.2, 67.5, 67.3, 65.4, 63.3, 62.5, 61.7, 61.0, 60.2, 60.1, 59.8, 55.08, 54.9, 54.8, 54.6, 51.0, 40.9, 39.4, 28.0, 26.7, 22.5, 22.4, 22.3, 22.2, 22.1, 22.0, 21.09; ESI-MS (negative mode): m/z calcd for C, 92; H, 155; N, 7; O, 64; 2383.2370 found 1213.4483 (M+Na)2−.

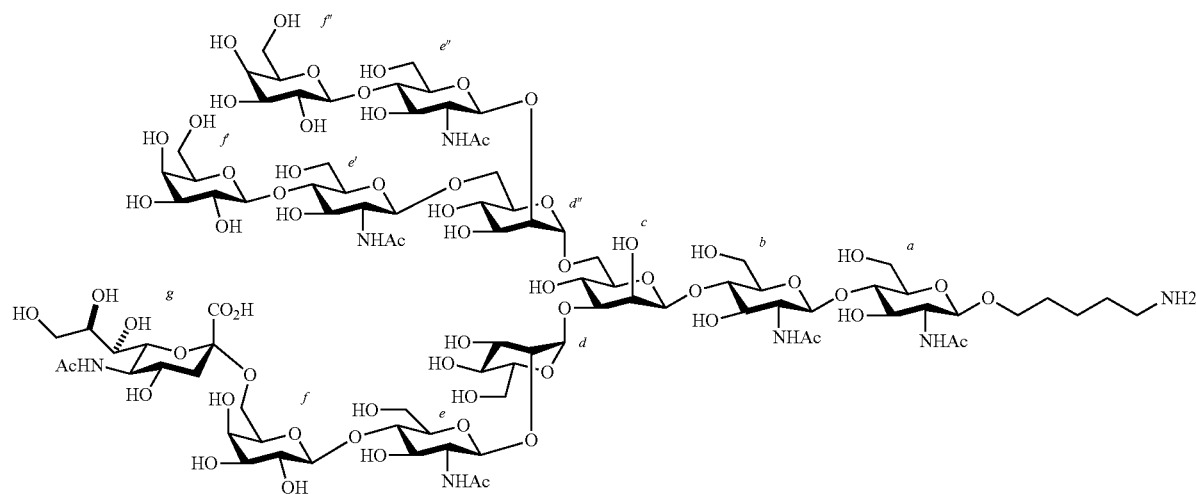

G24

5-Aminopentyl-[5-Acetamido-3,5-dideoxy-D-glycero-α-D-galacto-2-nonulopyrano-sylonate-(2→6)-β-D-galactopyranosyl-(1→4)-2-acetamido-2-deoxy-β-D-glucopyranosyl-(1→2)-α-D-mannopyranosyl]-(1→3),-[β-D-galactopyranosyl-(1→4)-2-acetamido-2-deoxy-β-D-glucopyranosyl-(1→2), (1→6)-α-D-mannopyranosyl]-(1→6)-β-D-mannopyranosyl-(1→4)2-acetamido-2-deoxy-β-D-glucopyranosyl-(1→4)-2-acetamido-2-deoxy-β-D-

Figure 102A:
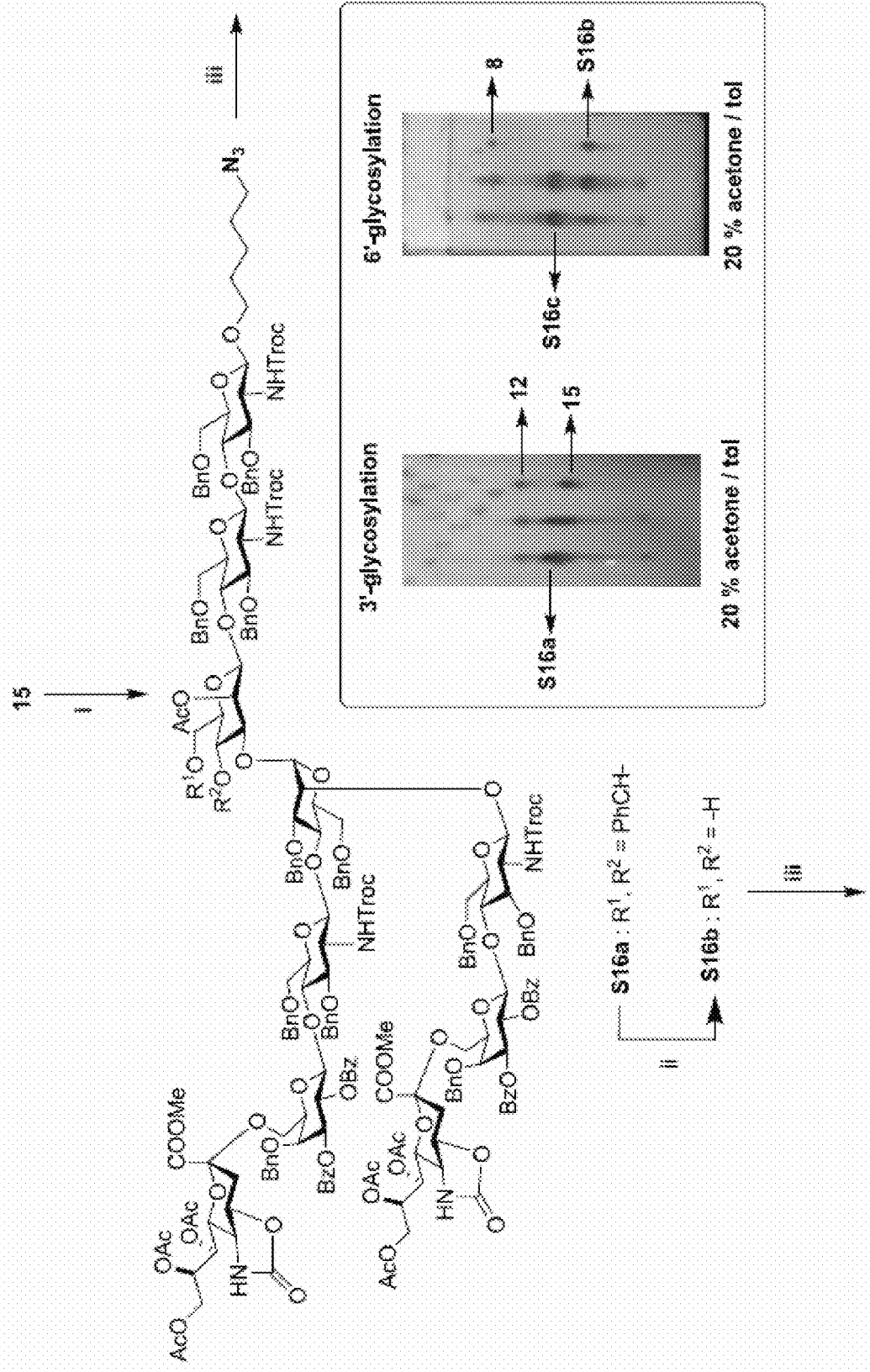
FIGS. 102A and 102B.
Figure 102B:
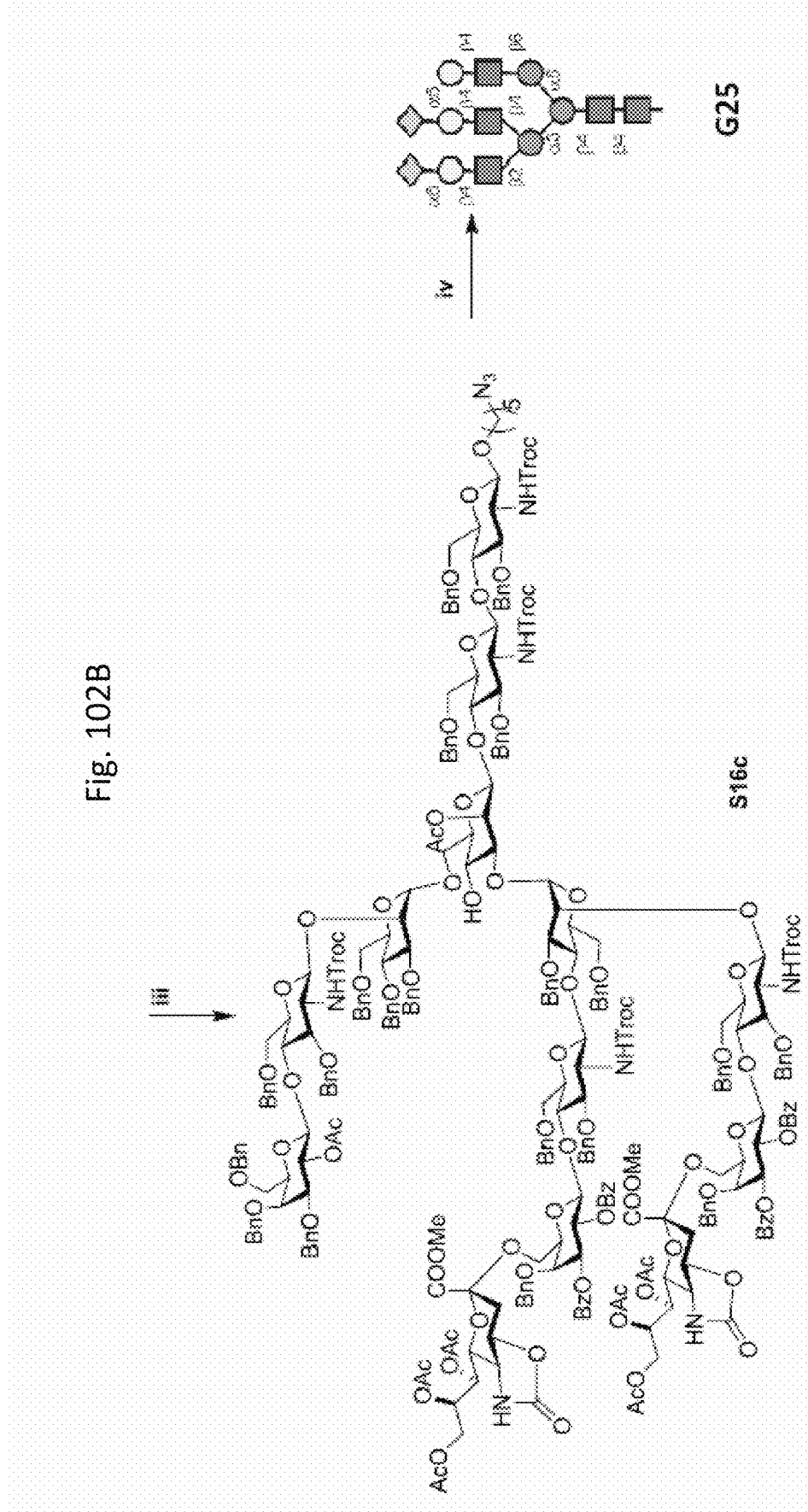
Figure 103:
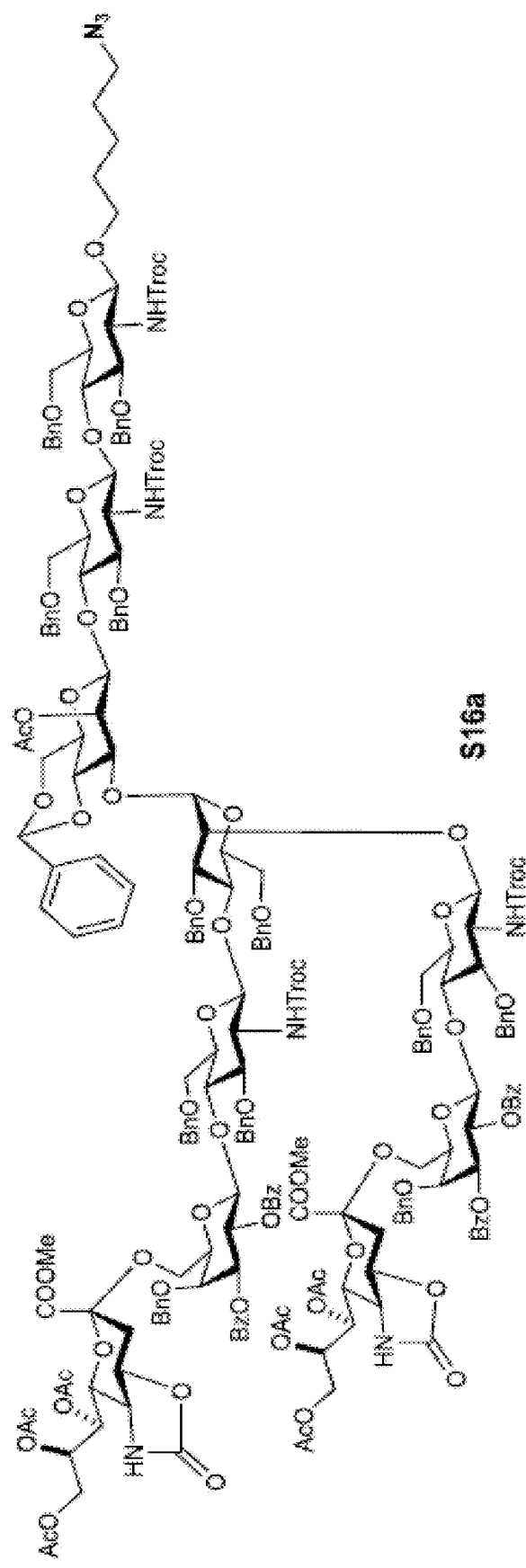
FIG. 103 Exemplary structure embodiments and synthetic scheme embodiments of the present disclosure.
Figure 104:
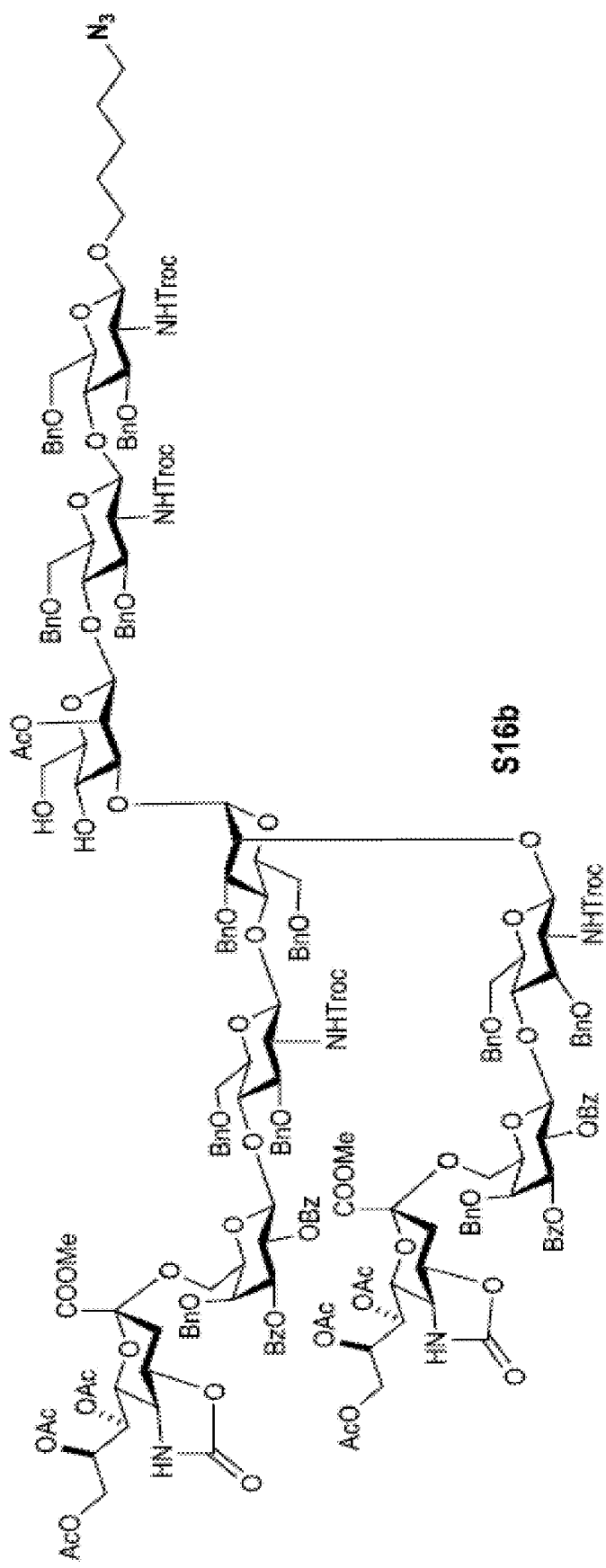
FIG. 104 Exemplary structure embodiments and synthetic scheme embodiments of the present disclosure.
Figure 105:
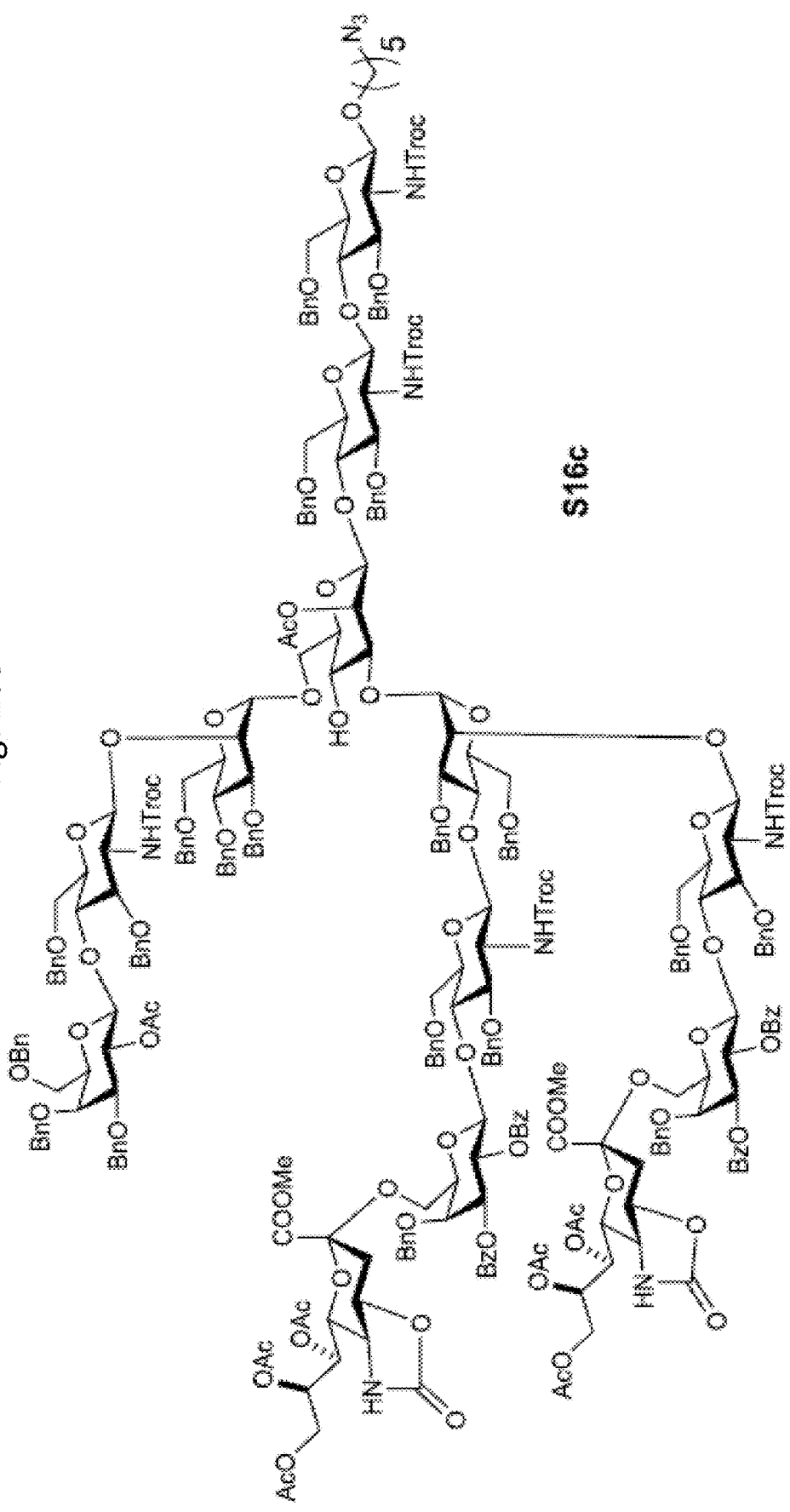
FIG. 105 Exemplary structure embodiments and synthetic scheme embodiments of the present disclosure.
Figure 106:
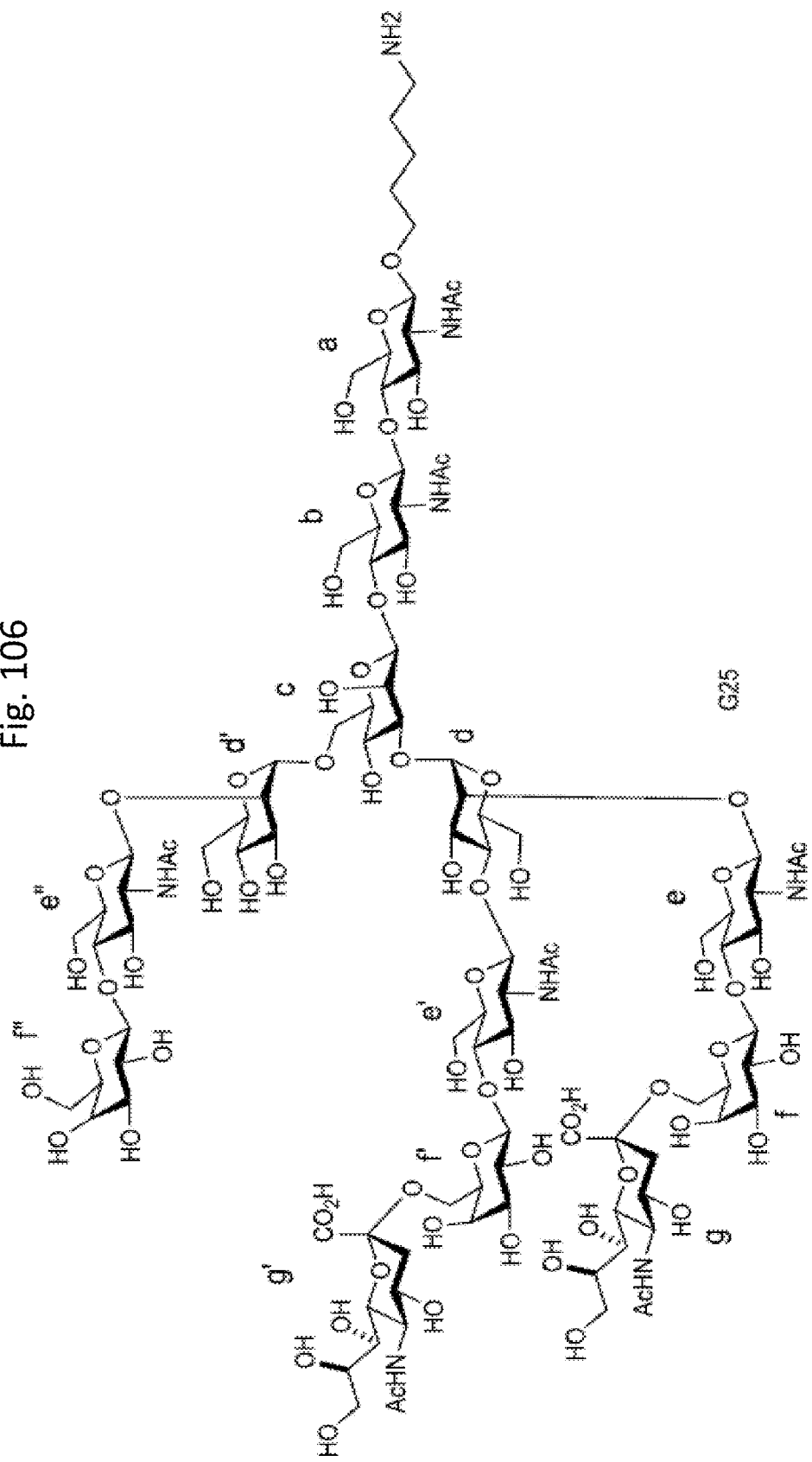
FIG. 106 Exemplary structure embodiments and synthetic scheme embodiments of the present disclosure.

Synthesis of glycan G25 as shown in FIGS. 102A and 102B.

Scheme S16 as shown in FIGS. 102A and 102B depicts the preparation of G25. i, 12, AgOTf, Cp2HfCl2, toluene, −40° C., 64%; ii, pTSA, acetonitrile, 56%; iii, 8, AgOTf, Cp2HfCl2, toluene, −78° C., 49%; iv, (1) LiOH, 1,4-dioxane, 90° C., (2) Ac2O, pyridine, (3) NaOMe, MeOH, (4) Pd(OH)2, MeOH:H2O, H2, 38%.

S16a

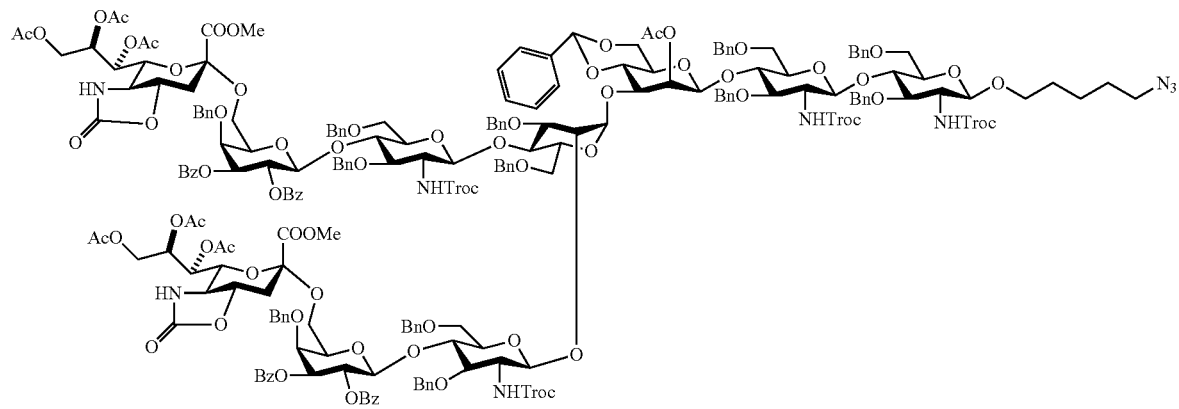

Compound 16a: A mixture of silver triflate (0.087 g, 0.34 mmol), bis (cyclopentadienyl) hafnium dichloride (0.090 g, 0.23 mmol) and 4 Å activated molecular sieves in dry toluene (10 mL) was stirred at rt for 1 h. The reaction mixture was then cooled to −40° C., a solution of donor 12 (0.259 g, 0.082 mmol) and acceptor 15 (0.100 g, 0.068 mmol) in 5 mL toluene was added. The mixture was stirred for 3 h at −10° C., quenched with Et3N, diluted with EtOAc and filtered through Celite. The filtrate was washed with aqueous NaHCO3 (2×50 mL), and a brine (50 mL) solution. The organic layer was dried over Na2SO4 and concentrated in vacuo. The residue was purified by flash column chromatography (0%→20% acetone in toluene) to afford S16a (0.201 g, 64%) as white foam. TLC: (acetone:toluene=2.5/7.5, v/v): Rf=0.50; 1H NMR (600 MHz, CDCl3): δ 7.92-7.83 (m, 9H), 7.69-7.67 (m, 2H), 7.52-7.44 (m, 6H), 7.37-6.96 (m, 63H), 5.34-5.32 (m, 2H), 5.26-5.24 (m, 4H), 5.20-5.10 (m, 3H), 5.08 (d, J=9.8 Hz, 3H), 4.59-4.40 (m, 8H), 4.75-4.50 (m, 20H), 4.49-4.00 (m, 20H), 3.98-3.60 (m, 16H), 3.48-3.06 (m, 16H), 2.98 (t, J=10.7 Hz, 2H), 2.76 (dd, J=3.8 & 7.8 Hz, 2H), 2.08 (s, 3H), 2.07 (s, 3H), 2.06 (s, 6H), 1.99 (s, 9H), 1.37-1.17 (m, 6H), 0.89-0.84 (m, 2H); 13C NMR (150 MHz, CDCl3): δ 171.8, 171.7, 171.6, 169.8, 169.4, 168.0, 167.6, 166.6, 166.4, 166.2, 165.4, 165.3, 159.7, 159.4, 154.3, 154.2, 139.8, 139.7, 139.6, 139.4, 139.2, 138.7, 138.6, 138.5, 138.4, 138.3, 138.2, 133.9, 132.7, 131.9, 131.2, 130.6, 129.8, 129.6, 129.4, 129.3, 129.2, 129.0, 128.8, 128.7, 128.6, 128.6, 128.4, 128.2, 128.1, 128.0, 127.9, 127.8, 127.7, 127.6, 127.5, 127.4, 127.3, 127.2, 127.0, 102.7, 102.4, 101.9, 101.8, 100.8, 100.7, 100.4, 100.2, 100.0, 99.2, 99.4, 98.4, 96.5, 95.9, 74.3, 74.1, 74.0, 73.8, 73.7, 73.5, 73.4, 73.2, 73.1, 72.7, 72.5, 72.1, 71.3, 70.9, 70.4, 69.5, 69.4, 68.5, 68.4, 68.3, 68.1, 67.9, 67.4, 53.4, 51.6, 37.5, 33.9, 32.2, 31.8, 29.9, 28.8, 26.5, 23.4, 22.9, 21.2, 21.0, 20.0, 14.6, 14.3; ESI-MS: m/z calcd for C, 220; H, 235; C, 112; N, 9; O, 72; 4582.6910 found 915.6684 (M+H)5+.

S16b

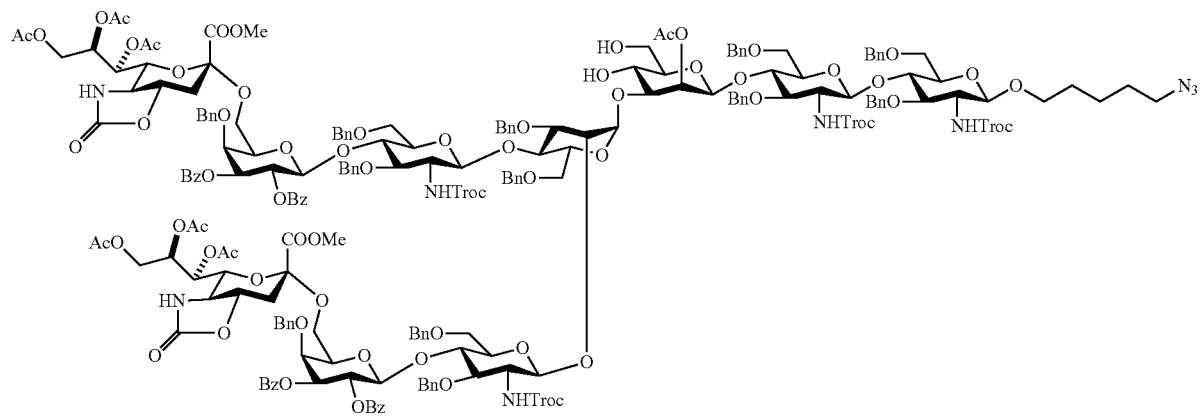

Compound 16b: p-Toluene sulfonic acid monohydrate (0.002 g, 0.008 mmol) was added to a solution of S14a (0.200 g, 0.043 mmol) in acetonitrile (10 mL) and resulting reaction mixture was stirred at rt for overnight. Reaction was quenched by adding Et3N and concentrated in vacuo. The residue was purified by flash column chromatography (0%→20% acetone in toluene) to give diol S16b (0.110 g, 56%). TLC: (acetone:toluene=2.5/7.5, v/v): Rf=0.32; 1H NMR (600 MHz, CDCl3): δ 7.90-7.80 (m, 7H), 7.79 (d, J=8.4 Hz, 2H), 7.69-7.46 (m, 5H), 7.41-7.04 (m, 65H), 5.78 (t, J=10.1 Hz, 1H), 5.73 (t, J=10.7 Hz, 1H), 5.35-5.25 (m, 7H), 5.20 (dd, J=3.2 & 7.9 Hz, 1H), 5.15 (dd, J=3.8 & 8.4 Hz, 1H), 5.08 (t, J=10.8 Hz, 2H), 4.90-4.80 (m, 5H), 4.794.50 (m, 15H), 4.48-4.30 (m, 8H), 4.20-4.10 (m, 15H), 3.92-3.20 (m, 35H), 3.2 (t, J=8.8 Hz, 2H), 3.18-3.05 (m, 3H), 3.0-2.95 (m, 3H), 2.81-2.70 (m, 3H), 2.08 (s, 6H), 2.07 (s, 6H), 2.03 (s, 6H), 1.92 (s, 6H), 1.32-1.17 (m, 6H), 0.89-0.83 (m, 2H); 13C NMR (150 MHz, CDCl3): δ 171.8, 170.7, 168.0, 166.1, 159.6, 138.1, 133.7, 132.7, 131.1, 130.1, 129.9, 129.7, 129.4, 128.9, 128.8, 128.7, 128.6, 128.4, 128.3, 128.2, 127.8, 127.7, 127.6, 74.9, 74.7, 74.6, 73.9, 68.8, 66.1, 53.4, 51.6, 37.3, 32.4, 31.4, 29.9, 29.8, 29.7, 28.7, 28.4, 23.4, 22.3, 20.9, 20.7, 20.4, 15.5, 14.6, 14.2; ESI-MS: m/z calcd for C, 213; H, 231; C, 112; N, 9; O, 72; 4494.5820 found 681.2953 (M+K)7+.

for 3 h at −20° C., quenched with Et3N, diluted with EtOAc and filtered through Celite. The filtrate was washed with aqueous NaHCO3 (2×50 mL), and a brine (50 mL) solution. The organic layer was dried over Na2SO4 and concentrated in vacuo. The residue was purified by flash column chromatography (0%→20% acetone in toluene) to afford S16c (0.148 g, 49%) as white foam. TLC: (acetone:toluene=2.5/7.5, v/v): Rf=0.50; 1H NMR (600 MHz, CDCl3): δ 7.90 (m, 10H), 7.52-6.80 (m, 110H), 5.79 (t, J=10.2 Hz, 2H), 5.48 (dd, J=4.2 & 8.7 Hz, 2H), 5.34-5.14 (m, 10H), 4.98-3.10 (m, 129H), 2.85 (t, J=10.2 Hz, 2H), 2.30 (dd, J=3.4 & 8.2 Hz, 2H), 2.01 (s, 3H), 2.00 (s, 6H), 1.95 (s, 6H), 1.94 (s, 6H), 1.91 (s, 3H), 1.39-1.29 (m, 6H), 1.26-1.91 (m, 2H); 13C NMR (150 MHz, CDCl3): δ 172.1, 170.8, 170.3, 170.1, 170.0, 169.3, 169.2, 168.0, 167.3, 166.5, 165.8, 165.1, 165.0, 154.0, 153.8, 153.7, 153.7, 139.0, 138.9, 138.8, 138.7, 138.6, 138.3, 138.2, 138.1, 137.9, 137.4, 133.4, 133.2, 132.0, 130.3, 129.8, 129.7, 129.4, 129.3, 129.2, 129.1, 128.9, 128.8, 128.5, 128.3, 128.2, 128.1, 128.0, 127.9, 100.4, 100.2, 99.3, 75.8, 75.6, 75.4, 75.3, 75.2, 75.1, 74.8, 74.7, 74.6, 74.5, 74.4, 74.3, 74.2, 74.2, 74.1, 73.5, 73.4,

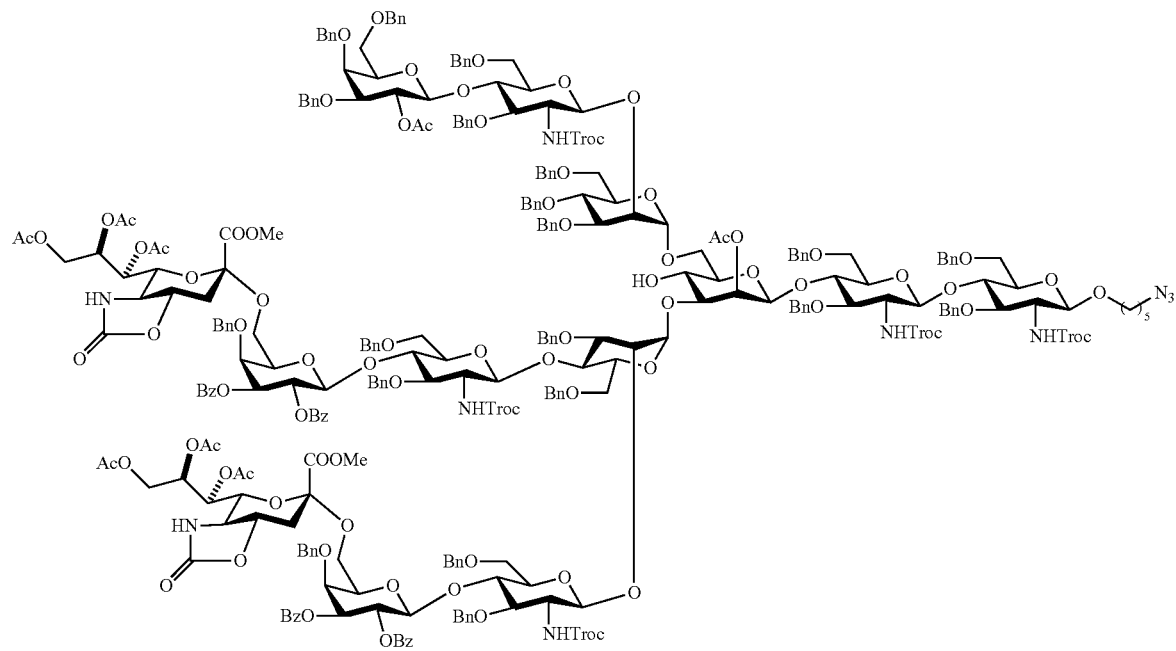

S16c

Compound 16c: A mixture of silver triflate (0.068 g, 0.34 mmol), bis (cyclopentadienyl) hafnium dichloride (0.065 g, 0.17 mmol) and 4 Å activated molecular sieves in dry toluene (10 mL) was stirred at rt for 1 h. The reaction mixture was then cooled to −78° C., a solution of donor 8 (0.109 g, 0.076 mmol) and acceptor 16b (0.230 g, 0.051 mmol) in 5 mL toluene was added. The mixture was stirred 73.3, 73.2, 73.1, 73.0, 72.9, 72.6, 72.2, 71.9, 71.7, 71.6, 71.3, 71.1, 70.1, 69.9, 69.8, 68.5, 68.3, 68.2, 63.4, 58.8, 58.3, 58.0, 53.4, 51.3, 31.9, 30.3, 30.0, 29.8, 29.7, 29.5, 28.7, 28.5, 28.3, 27.1, 24.5, 24.1, 23.8, 22.7, 22.1, 21.7, 20.9, 20.7, 20.6, 14.1, 14.0, 10.9; ESI-MS (negative mode): m/z calcd for C, 292; H, 313; Cl, 15; N, 10; O, 89; 5918.4470 found 1486.4746 (M+6H)4+.

G25

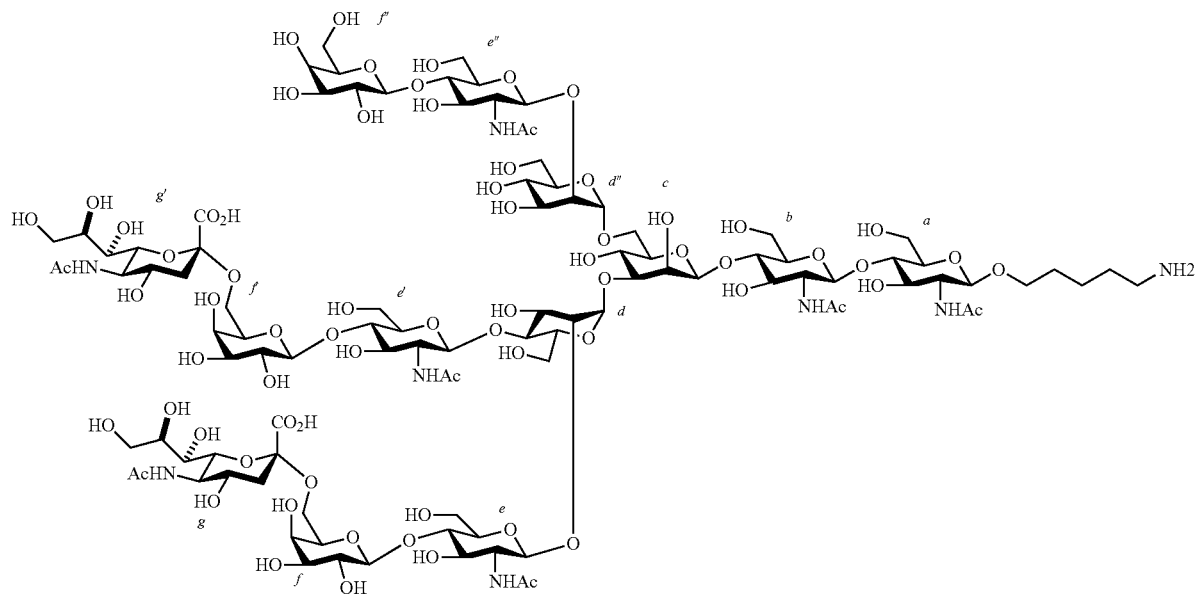

5-Aminopentyl-di-[5-Acetamido-3,5-dideoxy-D-glycero-α-D-galacto-2-nonulopyrano-sylonate-(2→6)-β-D-galactopyranosyl-(1→4)-2-acetamido-2-deoxy-β-D-glucopyranosyl-(1→2),(1→4)-α-D-mannopyranosyl]-(1→3),-[β-D-galactopyranosyl-(1→4)-2-acetamido-2-deoxy-β-D-glucopyranosyl-(1→2)-α-D-mannopyranosyl]-(1→6)-β-D-mannopyranosyl-(1→4)-2-acetamido-2-deoxy-β-D-glucopyranosyl-(1→4)-2-acetamido-2-deoxy-β-D-glucopyranoside G25: Compound S16c (0.115 g, 0.019 mmol) was deprotected by following general procedure 2 (method 2) to afford the desired glycan G25 (0.020 g, 38%). 1H NMR (600 MHz, D2O): δ 5.15 (d, 1H, H-1d), 4.94 (s, 1H, H-1d'), 4.63 (d, J=8.4 Hz, 2H, H-1a,b), 4.58 (d, J=7.8 Hz, 2H, H-1e,e'), 4.52 (d, J=7.8 Hz, 2H, H-1e'',f'), 4.50 (s, 1H, H-1c), 4.42 (dd, J=3.2 & 10.2 Hz, 2H, H-1f,f''), 4.23 (s, 2H), 4.08 (s, 1H), 3.92 (dd, J=3.2 & 7.8 Hz, 2H), 3.90-3.45 (m, 75H), 3.01 (t, J=10.2 Hz, 2H, linker CH2), 2.69 (dd, J=3.6 & 12.1 Hz, 2H, H-3equi.g,g'), 2.12 (s, 3H), 2.10 (s, 3H), 2.09 (s, 3H), 2.07 (s, 3H), 2.05 (s, 9H), 1.77-1.66 (m, 4H, H-3axial.g,g' and linker CH2), 1.62-1.60 (m, 2H), 1.42-1.40 (m, 2H); 13C NMR (150 MHz, D2O): δ 177.6, 177.4, 177.3, 177.1, 176.1, 106.3, 105.6, 104.2, 104.1, 103.7, 103.1, 102.8, 102.1, 101.8, 99.8, 78.7, 78.0, 77.4, 77.2, 77.1 76.4, 75.5, 75.2, 75.1, 75.0, 74.8, 74.4, 74.0, 73.7, 73.4, 73.0, 72.8, 72.1, 71.5, 70.9, 70.8, 70.0, 68.4, 66.0, 65.4, 64.3, 64.0, 63.7, 63.1, 63.8, 62.6, 57.7, 57.6, 57.5, 57.3, 54.6, 42.7, 42.0, 30.7, 29.0, 25.3, 25.0, 24.9, 24.8, 24.7; ESI-MS (negative mode): m/z calcd for C, 103; H, 172; N, 8; O, 72; 2674.4930 found 1335.9948 (M−2H)2−.

Figure 107:
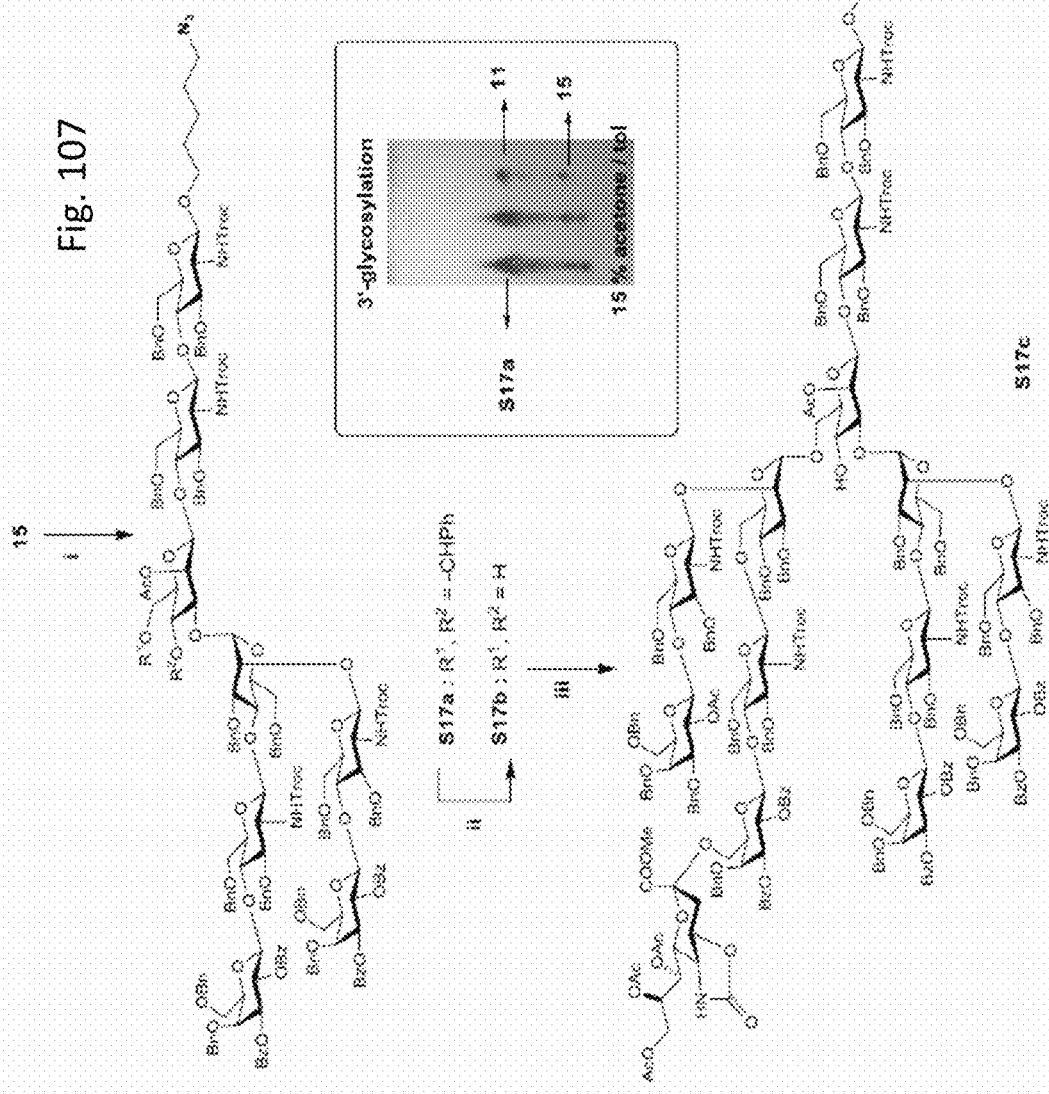
FIG. 107 Exemplary structure embodiments and synthetic scheme embodiments of the present disclosure.
Figure 108:
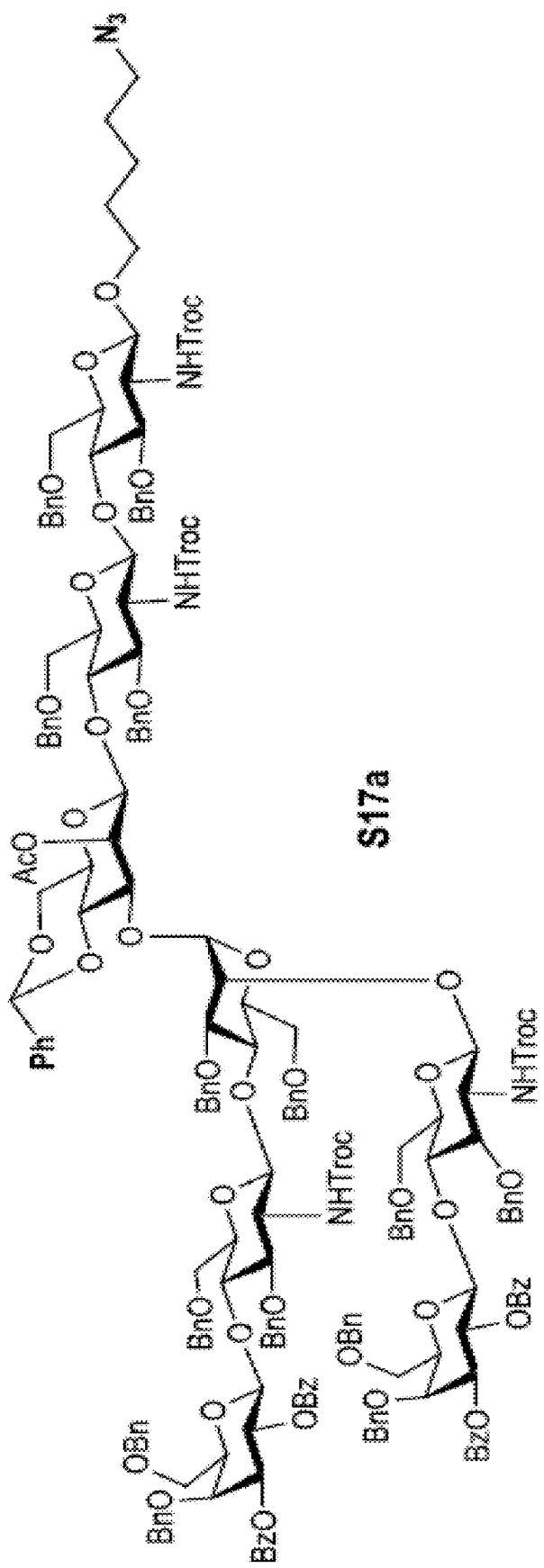
FIG. 108 Exemplary structure embodiments and synthetic scheme embodiments of the present disclosure.
Figure 109:
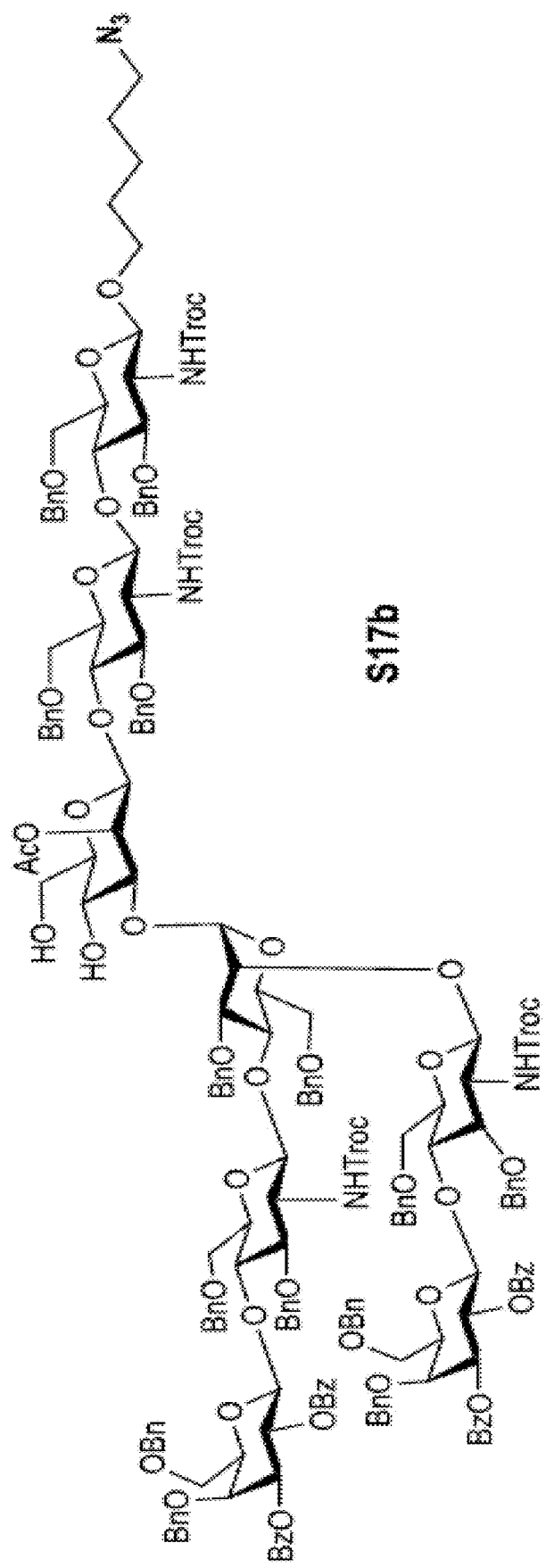
FIG. 109 Exemplary structure embodiments and synthetic scheme embodiments of the present disclosure.
Figure 110:
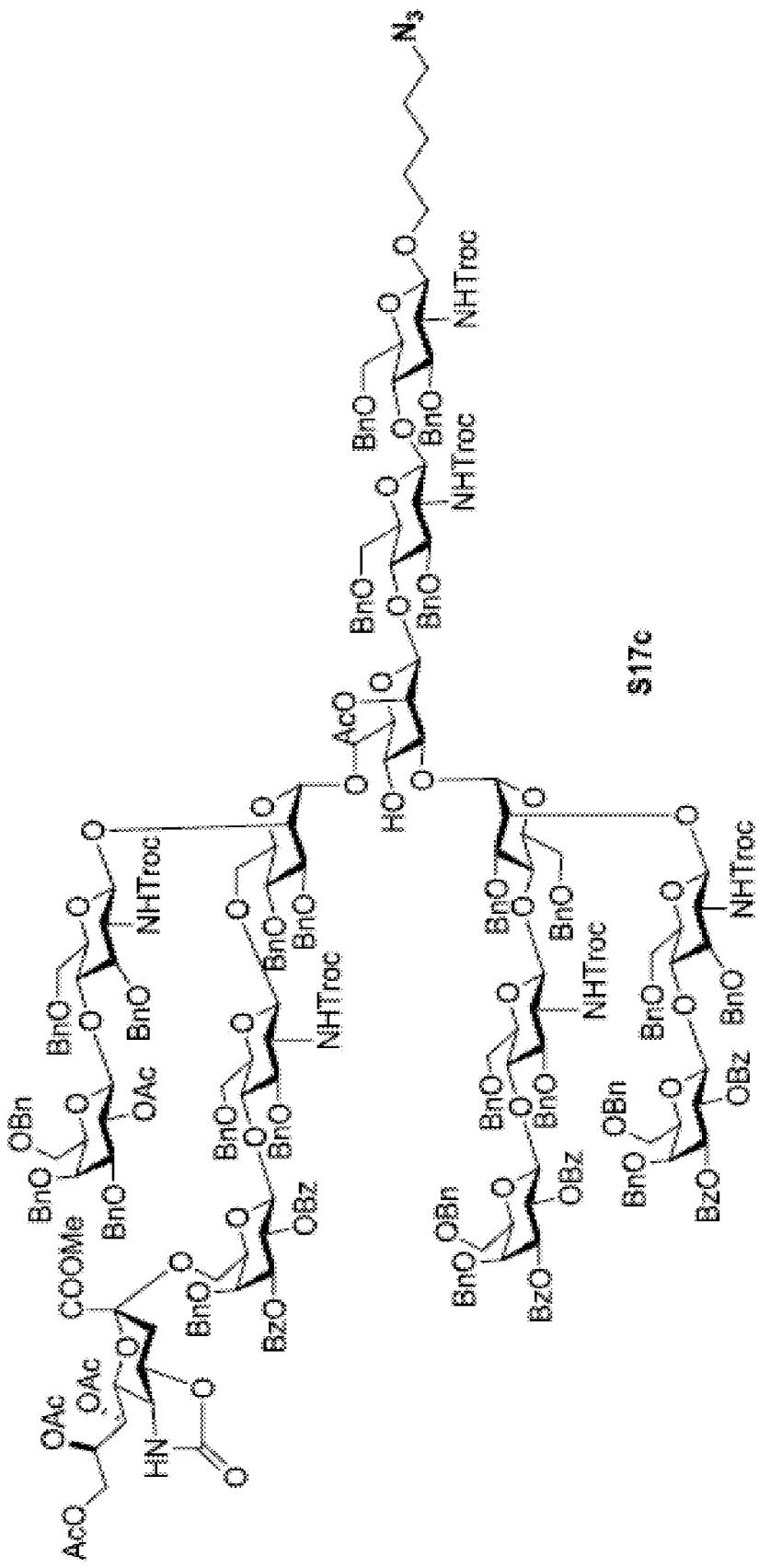
FIG. 110 Exemplary structure embodiments and synthetic scheme embodiments of the present disclosure.
Figure 111:
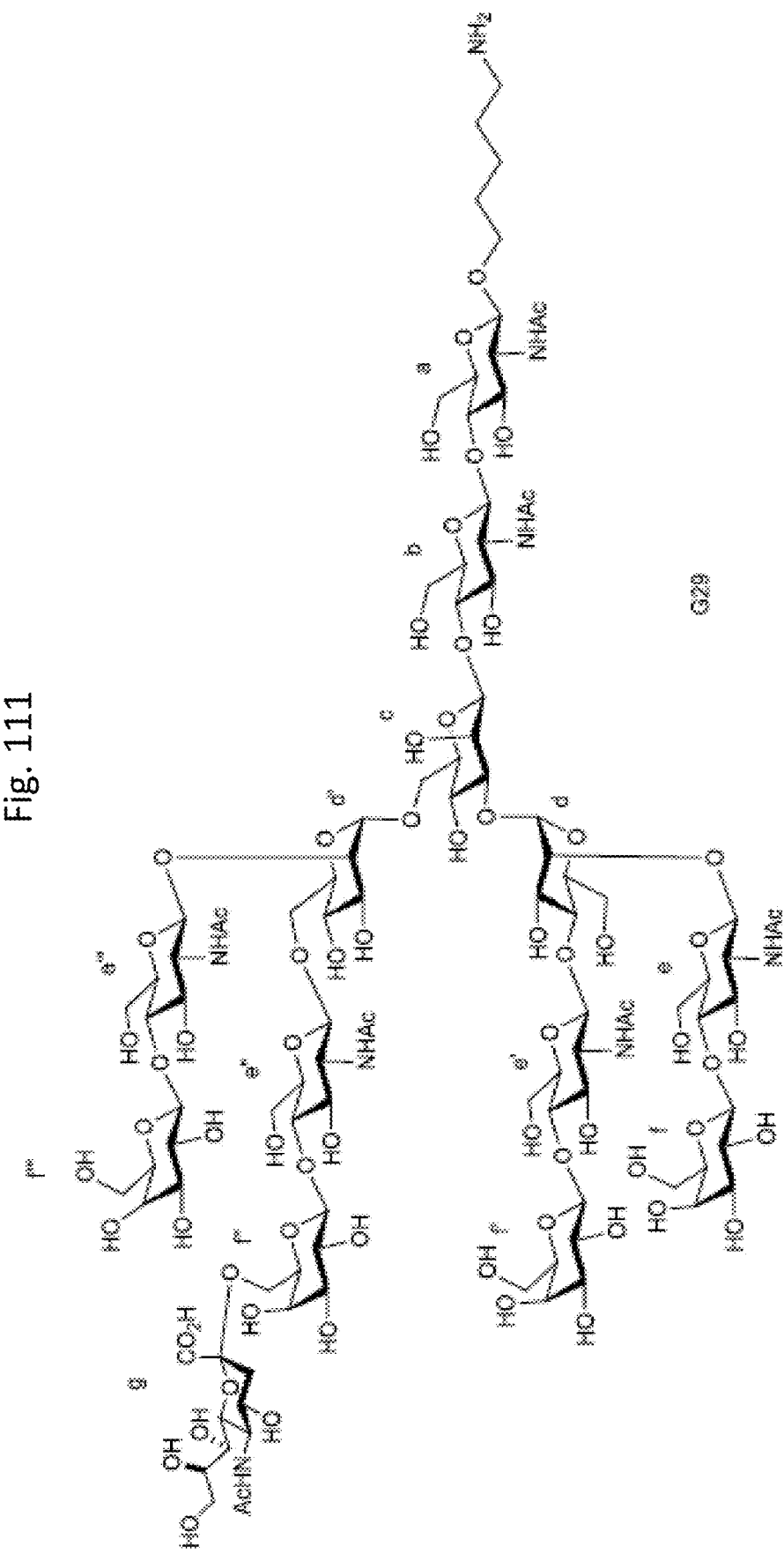
FIG. 111 Exemplary structure embodiments and synthetic scheme embodiments of the present disclosure.

Synthesis of glycan G29 as Shown in FIG. 107.

Glycan G29 is mono sialylated tetraantennary complex type structure. The synthesis began with construction of D1 arm by glycosylation of donor 11 at 3-O position of 15 to afford compound S17a. The reaction was progress was checked by TLC as shown in Scheme S17 as shown in FIG. 107. Removal benzyledene followed by 6-O glycosylation afforded desired tetra-decasaccharide S17c. Finally, global deprotection provided desired glycan G29.

Scheme S17 as shown in FIG. 107 depicts the preparation of G29. i, 11, AgOTf, Cp2HfCl2, toluene, −40° C., 77%; ii, pTSA, acetonitrile, 73%; iii, 13, AgOTf, Cp2HfCl2, toluene, −40° C., 57%; iv, (1) LiOH, 1,4-dioxane, 90° C., (2) Ac2O, pyridine, (3) NaOMe, MeOH, (4) Pd(OH)2, MeOH:H2O, H2, 34%.

S17a

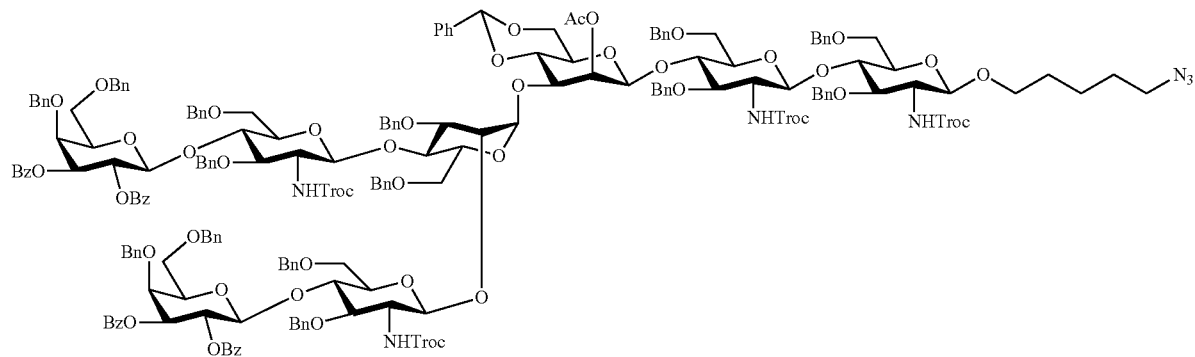

Compound S17a: A mixture of silver triflate (0.173 g, 0.675 mmol), bis (cyclopentadienyl) hafnium dichloride (0.177 g, 0.469 mmol) and 4 Å activated molecular sieves in dry toluene (10 mL) was stirred at room temperature for 1 h. The reaction mixture was then cooled to −50° C., a solution of donor 11 (0.345 g, 0.470 mmol) and acceptor 15 (0.195 g, 0.134 mmol) in 5 mL toluene was added. The mixture was stirred for 2 h at −10° C., quenched with Et3N, diluted with EtOAc and filtered through Celite. The filtrate was washed with aqueous NaHCO3 (2×50 mL), and a brine (50 mL) solution. The organic layer was dried over Na2SO4 and concentrated in vacuo. The residue was purified by flash column chromatography (0%→10% acetone in toluene) to afford S17a (0.380 g, 77%) as white foam. TLC: (acetone:toluene=1/9, v/v): Rf=0.60 NMR (600 MHz, CDCl3): δ 7.30-7.12 (m, 60H), 7.08-6.72 (m, 25H), 5.39 (t, J=10.2 Hz, 1H), 5.29 (t, J=10.3 Hz, 1H'), 5.16 (d, J=4.2 Hz, 1H), 5.09 (d, J=8.4 Hz, 1H), 4.91-4.72 (n, 18H, overlapped), 4.63-4.56 (m, 5H), 4.01-4.80 (m, 30H), 3.80-3.95 (m, 10H), 3.60-3.75 (m, 4H), 3.52-3.48 (m, 6H), 3.41-3.15 (m, 20H), 2.98 (d, J=9.6 Hz, 1H), 2.90-2.76 (m, 3H), 2.662.62 (m, 1H), 1.95 (s, 3H), 1.93 (s, 3H), 1.87 (s, 3H), 1.38-1.23 (m, 4H, —CCH2C—), 1.08-1.01 (m, 2H, —CCH2C—); 13C NMR (150 MHz, CDCl3): δ 172.1, 171.9, 170.5, 156.7, 156.6, 142.0, 141.8, 141.6, 141.5, 141.4, 141.3, 141.3, 141.1, 140.8, 140.6, 140.5, 139.8, 135.2, 133.6, 133.2, 131.8, 131.5, 131.3, 131.1, 130.6, 130.5, 130.2, 130.1, 129.8, 129.0, 127.3, 104.8, 104.8, 103.2, 102.9, 77.7, 77.5, 77.3, 77.2, 77.1, 76.9, 76.2, 76.1, 76.0, 75.9, 75.5, 75.4, 74.8, 74.6, 74.5, 74.4, 74.3, 71.0, 70.8, 70.6, 54.0, 31.7, 31.3, 25.9, 23.9, 23.8, 23.7, 23.6, 17.2, 17.1, 16.8, 16.7, 13.7, 13.6; HRMS (negative mode): m/z calcd for C, 190; H, 205; Cl, 12; N, 7; O, 48; 3778.9981 found 3824.9969 (M+2Na)−.

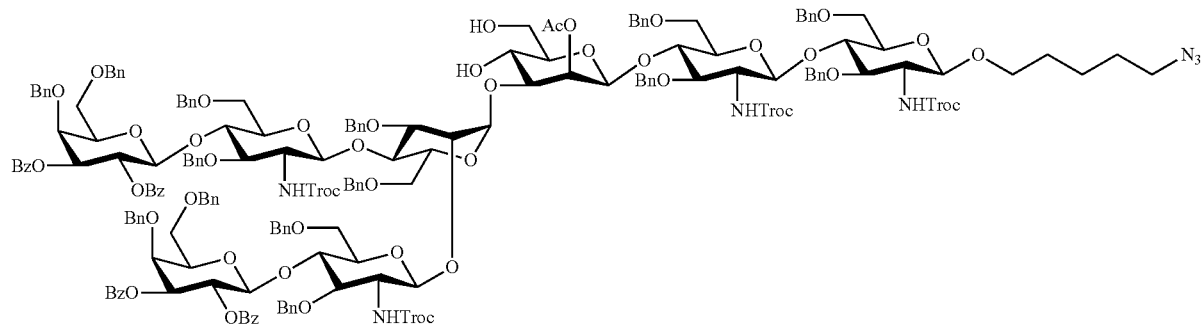

S17b

Compound S17b: p-Toluene sulfonic acid monohydrate (0.004 g, 0.02 mmol) was added to a solution of S17a (0.377 g, 0.102 mmol) in acetonitrile (10 mL) and the resulting reaction mixture was stirred at rt for overnight. The reaction was quenched by adding Et3N and concentrated in vacuo. The residue was purified by flash column chromatography (0%→10% acetone in toluene) to give diol S17b (0.270 g, 73%). TLC: (acetone:toluene=1.5/8.5, v/v): Rf=0.32; 1H NMR (600 MHz, CDCl3): δ 7.34-7.11 (m, 80H), 5.37 (s, 1H), 5.29 (t, J=10.2 Hz, 1H), 5.22 (t, J=9.8 Hz, 1H), 5.02 (d, J=3.6 Hz, 2H), 4.92-4.74 (m, 7H), 4.70-4.21 (m, 34H), 3.93-3.51 (m, 17H), 3.65-3.20 (m, 30H), 3.20 (t, J=10.2 Hz, 4H), 2.98 (d, J=3.8 Hz, 2H), 2.89 (s, 1H), 2.11 (s, 3H), 1.94 (s, 3H), 1.90 (s, 3H), 1.40-1.17 (m, 4H), 091-0.84 (m, 2H); 13C NMR (150 MHz, CDCl3): δ 170.1, 170.0, 169.6, 168.0, 154.3, 154.1, 139.6, 139.1, 139.0, 138.9, 138.7, 138.5, 138.3, 138.1, 138.0, 132.7, 131.1, 129.6, 129.4, 129.3, 129.0, 128.7, 128.6, 128.5, 128.4, 128.3, 128.2, 128.1, 128.0, 127.9, 127.6, 127.5, 127.3, 127.1, 127.0, 100.9, 100.6, 100.5, 98.6, 95.9, 95.8, 76.75, 76.3, 75.6, 74.8, 74.6, 74.5, 74.3, 74.2, 73.8, 73.7, 73.5, 73.2, 72.8, 72.5, 72.1, 69.6, 68.8, 68.5, 68.4, 68.2, 68.1, 62.8, 62.1, 57.6, 39.0, 37.3, 33.7, 32.5, 31.4, 30.6, 29.9, 29.2, 28.8, 26.6, 24.0, 23.4, 23.2, 22.9, 21.5, 21.3, 20.1, 15.5, 14.6, 14.4, 14.3, 11.2; HRMS (negative mode): m/z calcd for C, 183; H, 201; Cl, 12; N, 7; O48; 3692.0222 found 3737.9645 (M+2Na)2−.

S17c

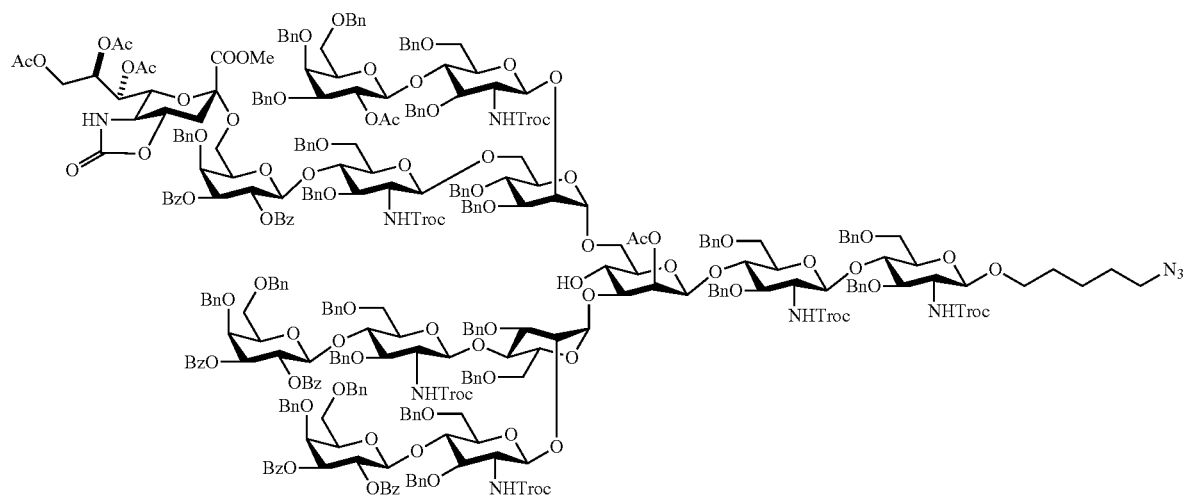

Compound S17c: A mixture of silver triflate (0.046 g, 0.180 mmol), bis (cyclopentadienyl) hafnium dichloride (0.048 g, 0.126 mmol) and 4 Å activated molecular sieves in dry toluene (5 mL) was stirred at rt for 1 h. The reaction mixture was then cooled to −50° C., a solution of donor 13 (0.100 g, 0.36 mmol) and acceptor S17 b (0.118 g, 0.032 mmol) in 5 mL toluene was added. The mixture was stirred for 3 h at −10° C., quenched with Et3 N, diluted with EtOAc and filtered through Celite. The filtrate was washed with aqueous NaHCO3 (2×50 mL), and a brine (50 mL) solution. The organic layer was dried over Na2SO4 and concentrated in vacuo. The residue was purified by flash column chromatography (0%→10% actone in toluene) to afford S17c (0.120 g, 57%) as white foam. TLC: (acetone:toluene=1/9, v/v): Rf=0.60; 1H NMR (600 MHz, CDCl3): δ 7.58-7.54 (m, 6H), 7.50-6.98 (m, 134H), 5.57 (t, J=10.3 Hz, 4H), 5.42-5.30 (m, 24H), 5.01-4.70 (m, 35H), 4.65-4.10 (m, 50H), 4.0-2.90 (m, 52H), 2.80 (d, J=9.8 Hz, 2H), 2.15 (s, 3H), 2.09 (s, 3H), 2.07 (s, 3H), 1.96 (s, 3H), 1.93 (s, 3H), 1.88 (s, 3H), 1.86 (s, 3H), 1.34-1.17 (m, 5 H), 0.89-0.81 (m, 2H); 13C NMR (150 MHz, CDCl3): δ 139.1, 139.0, 138.3, 138.2, 138.1, 130.1, 129.9, 129.1, 129.0, 128.9, 128.8, 128.7, 128.6, 128.4, 128.3, 128.1, 128.0, 127.9, 127.8, 127.6, 127.4, 74.8, 74.6, 73.7, 73.6, 71.9; HRMS (negative mode): m/z calcd for C, 322; H, 346; Cl, 18 ; N, 10; O, 89; 6418.3910 found 3253.3555 (M+2Na)2−.

G29

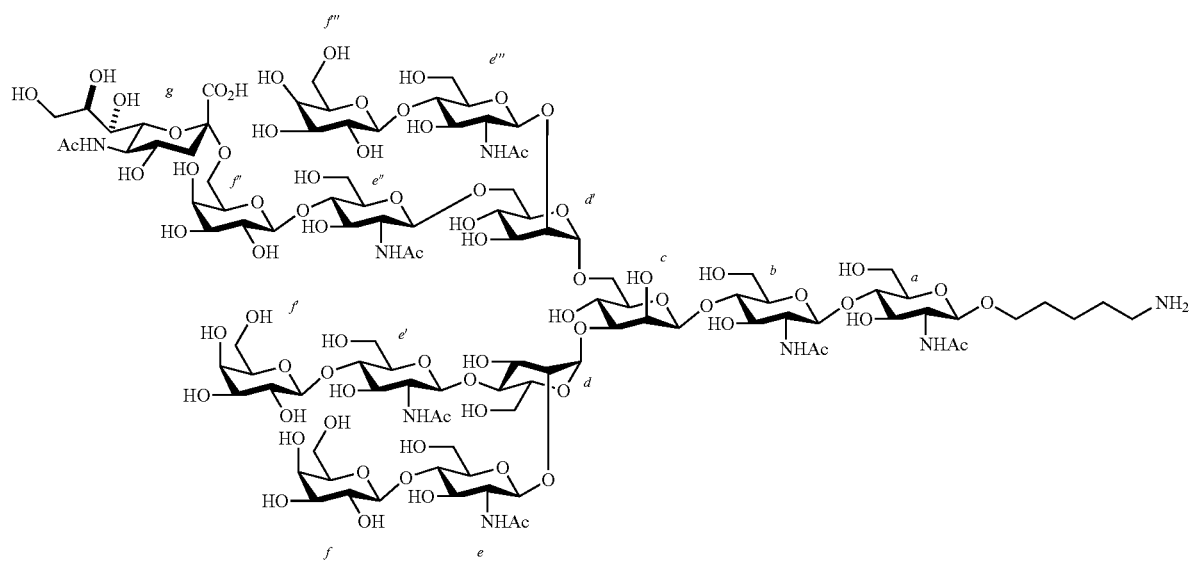

5-Aminopentyl-di-[β-D-galactopyranosyl-(1→4)-2-acetamido-2-deoxy-β-D-glucopyranosyl-(1→2),(1→4)-α-D-mannopyranosyl]-(1→3),-[5-Acetamido-3,5-dideoxy-D-glycero-α-D-galacto-2-nonulopyrano-sylonate-(2→6)-β-D- galactopyranosyl-(1→4)-2-acetamido-2-deoxy-β-D-glucopyranosyl-(1→6)-β-D-galactopyranosyl-(1→4)-2-acetamido-2-deoxy-β-D-glucopyranosyl-(1→2)-α-D-mannopyranosyl]-(1→6)-β-D-mannopyranosyl-(1→4)-2-acetamido-2-deoxy-β-D-glucopyranosyl-(1→4)-2-acetamido-2-deoxy-β-D-glucopyranoside G29: Compound S17c (0.095 g, 0.015 mmol) was deprotected by following general procedure 2 (method 2) to afford desired glycan G29 (0.014 g, 34%) as a white powder. 1H NMR (600 MHz, D2O): δ 4.99 (s, 1H, H-1d), 4.75 (s, 1H, H-1d'), 4.72 (d, J=8.4 Hz, 1H, H-1e), 4.62 (d, 1H, J=7.8 Hz, 1H, H-1e'), 4.63 (s, 1H, H-1c), 4.45 (dd, J=3.6 & 7.8 Hz, 4H, H-1e",e''', f,f'), 4.36-4.31 (m, 4H), 4.09 (s, 3H), 3.98-3.04 (m, 85H), 2.83 (t, J=10.2 Hz, 2H, linker), 2.56 (dd, J=3.2 & 8.4 Hz, 1H, H-3equi. g'), 1.95 (s, 3H, —C(O)CH3), 1.94 (s, 3H, —C(O)CH3), 1.93 (s, 3H, —C(O)CH3), 1.92 (s, 3H, —C(O)CH3), 1.92 (s, 3H, —C(O)CH3), 1.90 (s, 3H, —C(O)CH3), 1.89 (s, 3H, —C(O)CH3), 1.61-1.42 (m, 5H, H-3axial g' and linker CH2), 1.30-1.24 (m, 2H, linker); 13C NMR (150 MHz, D2O): δ 186.6, 174.7, 174.3, 174.2, 103.3, 102.7, 101.8, 100.8, 99.9, 98.5, 97.3, 78.9, 78.1, 77.8, 75.1, 74.4, 74.2, 74.1, 72.2, 71.7, 71.5, 70.7, 69.8, 68.3, 68.1, 63.1, 62.4, 60.8, 60.2, 59.7, 54.9, 54.6, 51.6, 39.9, 39.1, 27.8, 26.1, 22.2, 21.8, 17.6; ESI-MS (negative mode): m/z calcd for C, 106; H, 178; N, 8; O, 74; 2747.0411 found 1396.0177 (M+Na)2−.

Figure 112:
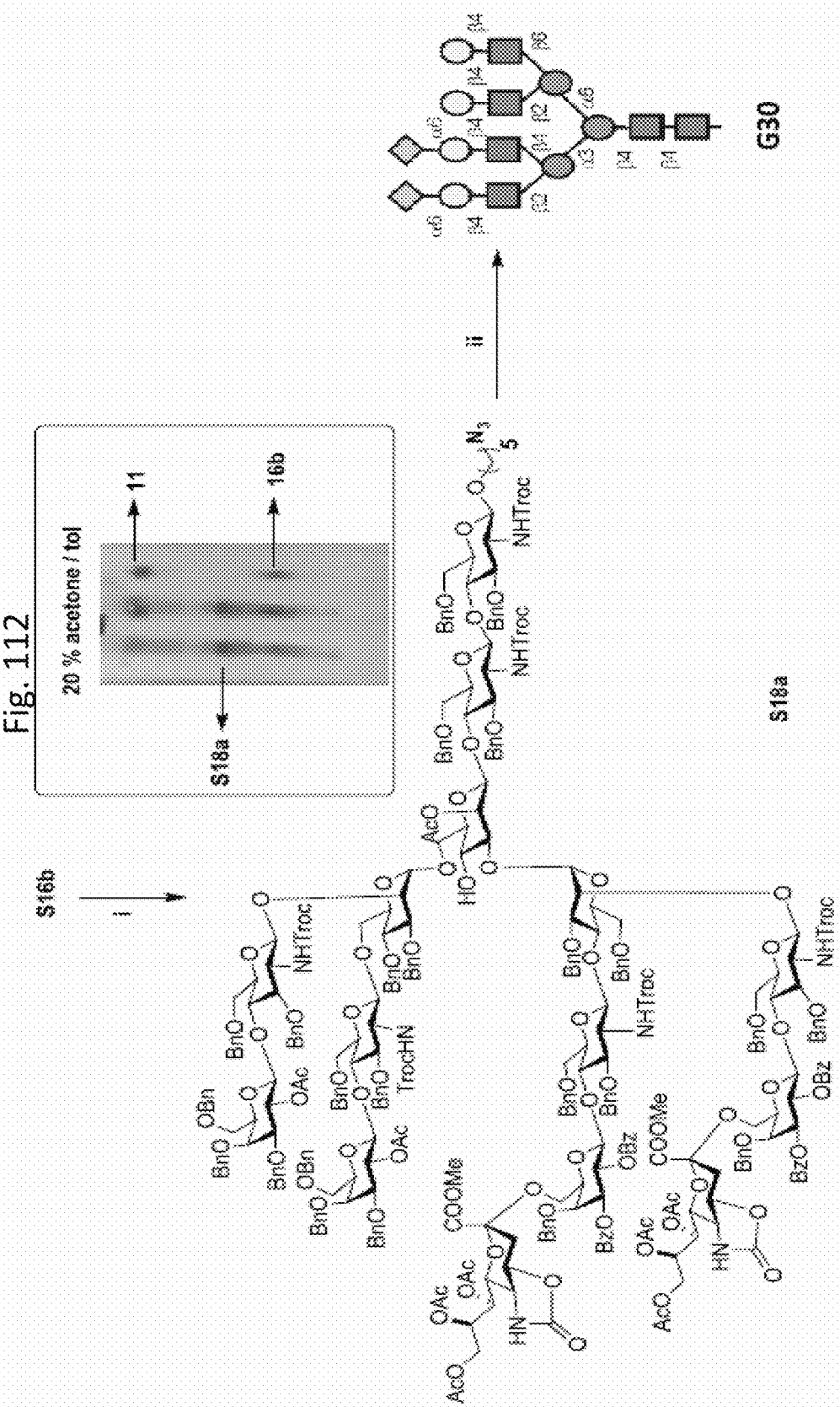
FIG. 112 Exemplary structure embodiments and synthetic scheme embodiments of the present disclosure.
Figure 113:
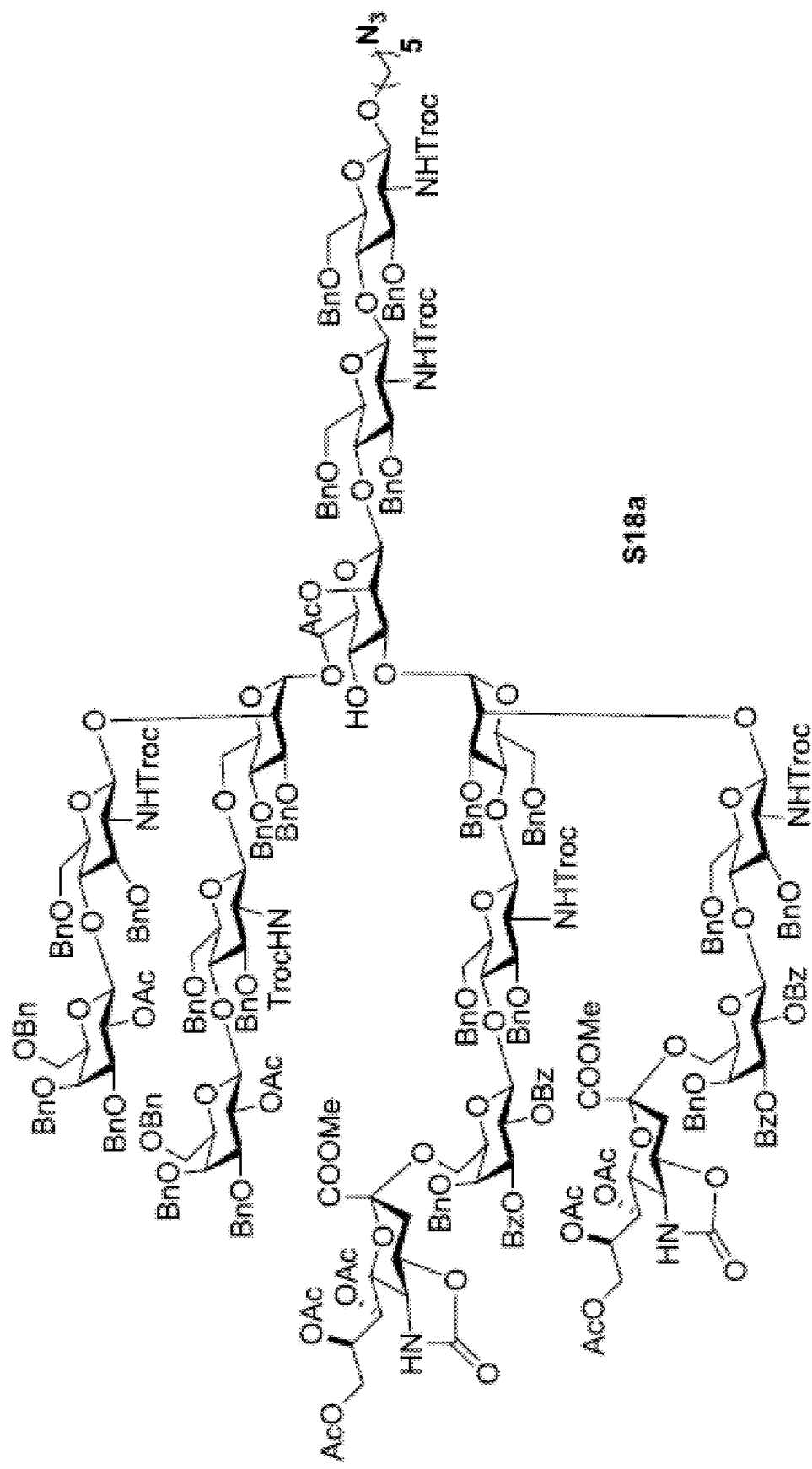
FIG. 113 Exemplary structure embodiments and synthetic scheme embodiments of the present disclosure.
Figure 114:
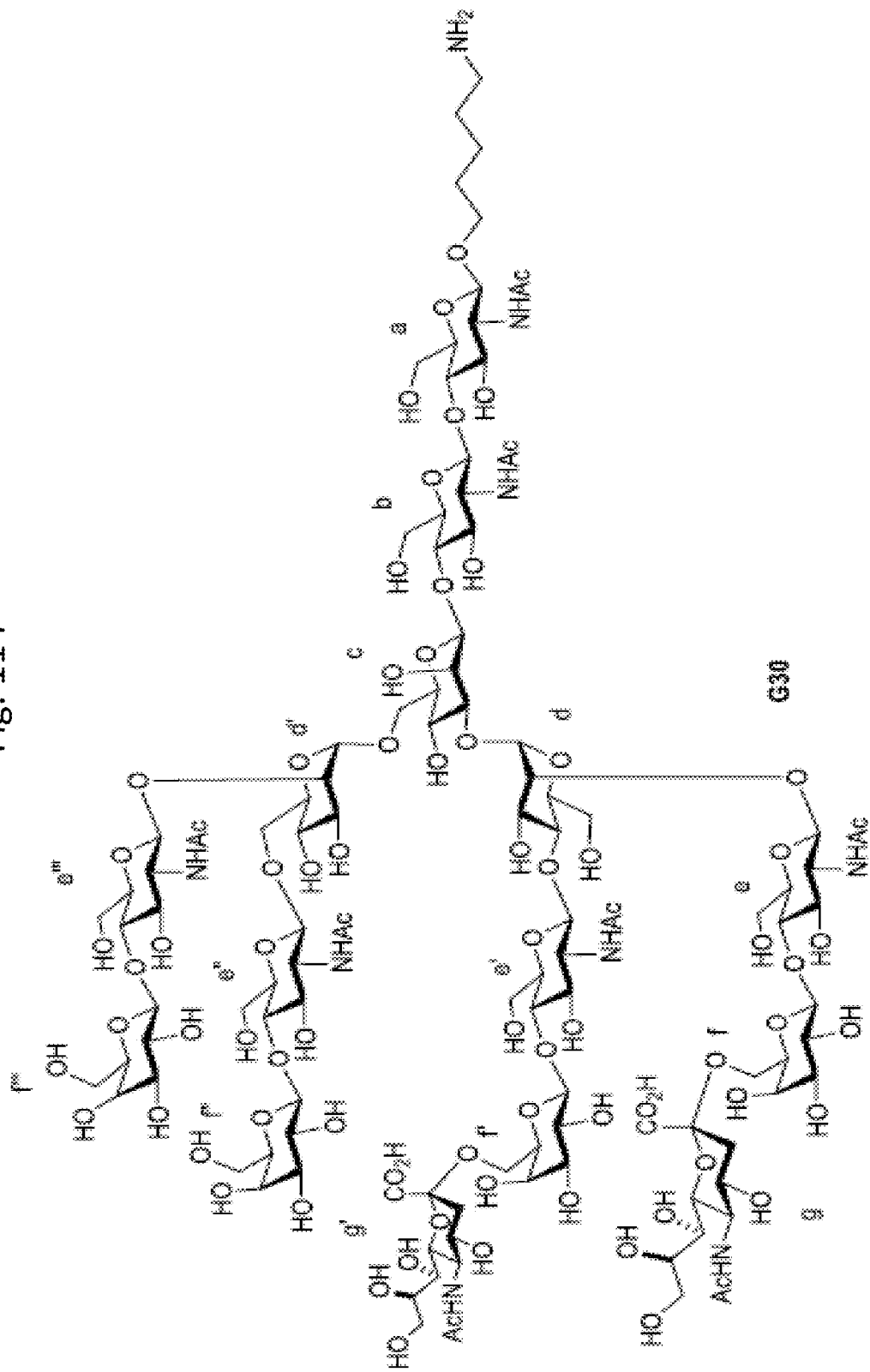
FIG. 114 Exemplary structure embodiments and synthetic scheme embodiments of the present disclosure.

Synthesis of glycan G30 as Shown in FIG. 112.

Depicted in Scheme S18 as shown in FIG. 112, precursor S16b from scheme S16 shown in FIGS. 102A and 102B was used as acceptor for 6-O glycosylation with donor 11 under the promotion of silver triflate and hafnocene dichloride to obtain the desired S18a. The final deprotection provided the disialylated tetra-antennary complex glycan G30.

Scheme S18 as shown in FIG. 112 the preparation of G30. i, 11, AgOTf, Cp2HfCl2, toluene, −40° C., 37%; ii, (1) LiOH, 1, 4-dioxane, 90° C., (2) Ac2O, pyridine, (3) NaOMe, MeOH, (4) Pd(OH)2, MeOH:H2O, H2, 45%.

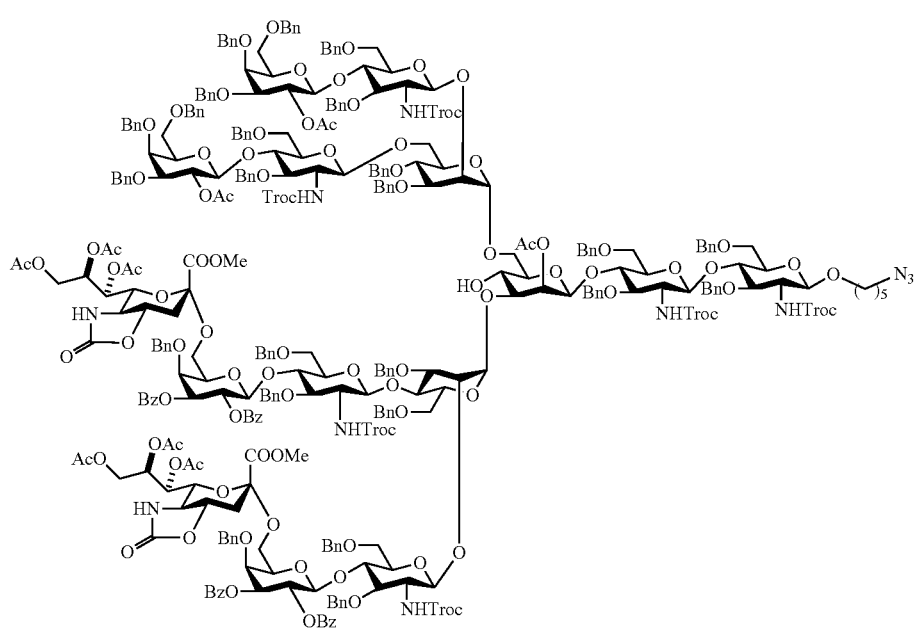

S16a

Compound S18a: A mixture of silver triflate (0.051 g, 0.200 mmol), bis (cyclopentadienyl) hafnium dichloride (0.053 g, 0.140 mmol) and 4 Å activated molecular sieves in dry toluene (5 mL) was stirred at room temperature for 1 h. The reaction mixture was then cooled to −50° C., a solution of donor 11 (0.144 g, 0.060 mmol) and acceptor S16b (0.180 g,0.040 mmol) in 5 mL toluene was added. The mixture was stirred for 3 h at −10° C., quenched with Et3N, diluted with EtOAc and filtered through Celite. The filtrate was washed with aqueous NaHCO3 (2×50 mL), and a brine (50 mL) solution. The organic layer was dried over Na2SO4 and concentrated in vacuo. The residue was purified by flash column chromatography (0%→10% acetone in toluene) to afford S18a (0.103 g, 37%) as white foam. TLC: (acetone: toluene=2/8, v/v): Rf=0.53; 1H NMR (600 MHz, CDCl3): δ 7.69-7.52 (m, 20H), 7.33-7.06(m, 130H), 5.60 (m, 17H), 4.80-4.30 (m, 40H), 4.20-4.00 (m, 50H), 3.99-3.02 (m, 25H), 2.08 (s, 9H), 2.07 (s, 6H), 2.05 (s, 6H), 2.02 (s, 6H), 1.78-1.74 (m, 6H), 0.91-0.84 (m, 2H); 13C NMR (150 MHz, CDCl3): δ 170.9, 170.4, 170.2, 169.8, 169.4, 169.3, 132.7, 131.1, 129.0, 128.7, 128.4, 128.3, 128.2, 128.0, 127.8, 127.7, 127.6, 127.5, 68.8, 68.4, 39.0, 37.3, 33.7, 31.4, 30.6, 29.9, 29.2, 26.6, 26.0, 24.0, 23.2, 22.9, 20.1, 14.6, 14.2, 11.40; ESI-MS (negative mode): m/z calcd for C, 337; H, 361; Cl, 18; N, 11; O, 101; 6806.6710 found 723.5969 (M+K)10−.

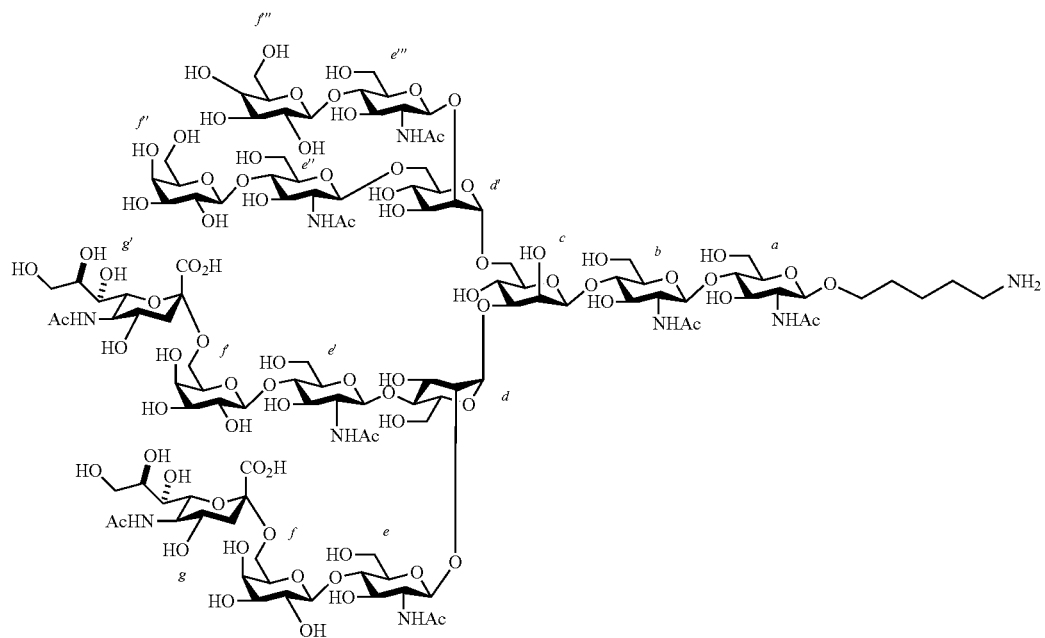

G30

5-Aminopentyl-di-[5-Acetamido-3,5-dideoxy-D-glycero-α-D-galacto-2-nonulopyrano-sylonate-(2→6)-β-D-galacto-pyranosyl-(1→4)-2-acetamido-2-deoxy-β-D-glucopyrano-syl-(1→2),(1→4)-α-D-mannopyranosyl]-(1→3),-di-[-β-D-galactopyranosyl-(1→4)-2-acetamido-2-deoxy-β-D-glucopyranosyl-(1→6),(1→2)-α-D-mannopyranosyl]-(1→6)-β-D-mannopyranosyl-(1→4)-2-acetamido-2-deoxy-β-D-glucopyranosyl-(1→4)-2-acetamido-2-deoxy-β-D-glucopyranoside G30: Compound S18a (0.075 g, 0.010 mmol) was deprotected by following general procedure 2 (method 2) to afford desired glycan G30 (0.015 mg, 45%). 1H NMR (600 MHz, D2O): δ 5.12 (s, 1H, H-1d), 4.86-4.74 (m, 3H, H-1d', c, b, overlapped with D2O), 4.59-4.55 (m, 5H, H-1e,e',e",e"',a), 1.48-4.42 (m, 4H, H-1f,f',f",f'"), 4.21-4.06 (m, 5H), 3.98-3.3.20 (m, 91H), 2.98 (t, J=10.7 Hz, 2H, linker CH2), 2.66 (dd, J=3.7 & 10.1 Hz, 2H, 2×H-3equi.g, g'), 2.12 (s, 3H), 2.09 (s, 3H, —C(O)CH3), 2.06 (s, 3H, —C(O)CH3), 2.05 (s, 3H, —C(O)CH3), 2.03 (s, 12H, —C(O)CH3), 1.75-1.54 (m, 6H, 2×H-3axial. g,g' and linker CH2), 1.42-1.36 (m, 2H, linker); 13C NMR (150 MHz, D2O): δ 174.7, 174.2, 174.1, 103.4, 102.7, 101.3, 101.2, 101.0, 100.8, 100.6, 99.9, 98.9, 97.9, 78.1, 75.1, 74.3, 73.4, 72.3, 72.1, 71.7, 70.7, 70.4, 69.8, 68.3, 68.0, 59.9, 59.7, 54.7, 51.6, 39.9, 27.8, 22.7, 22.0, 21.9, 21.8; ESI-MS (negative mode): m/z calcd for C, 117; H, 195; N, 9; O, 82; 3039.8280 found 1518.5585 (M−H)2−.

Figure 115:
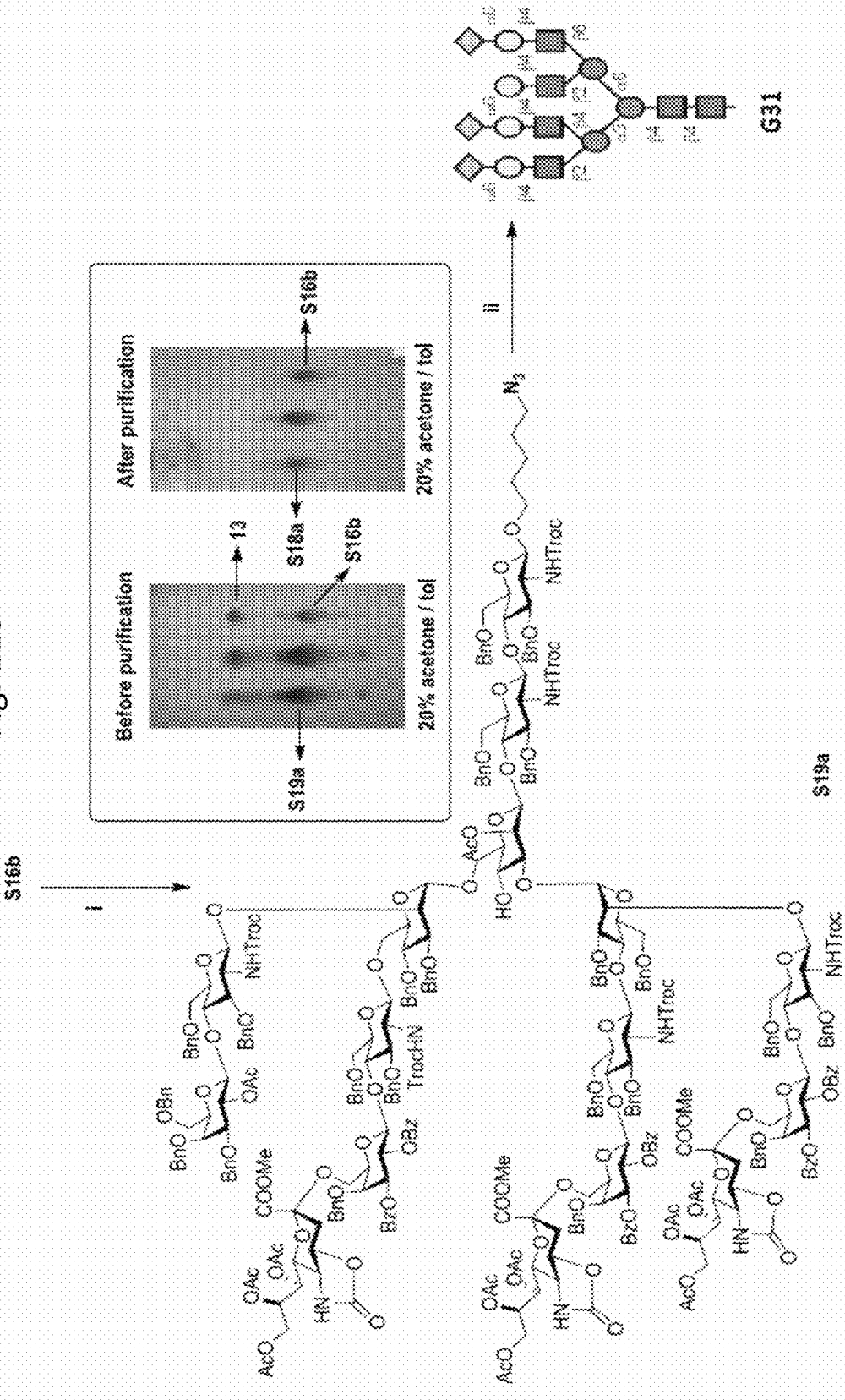
FIG. 115 Exemplary structure embodiments and synthetic scheme embodiments of the present disclosure.
Figure 116:
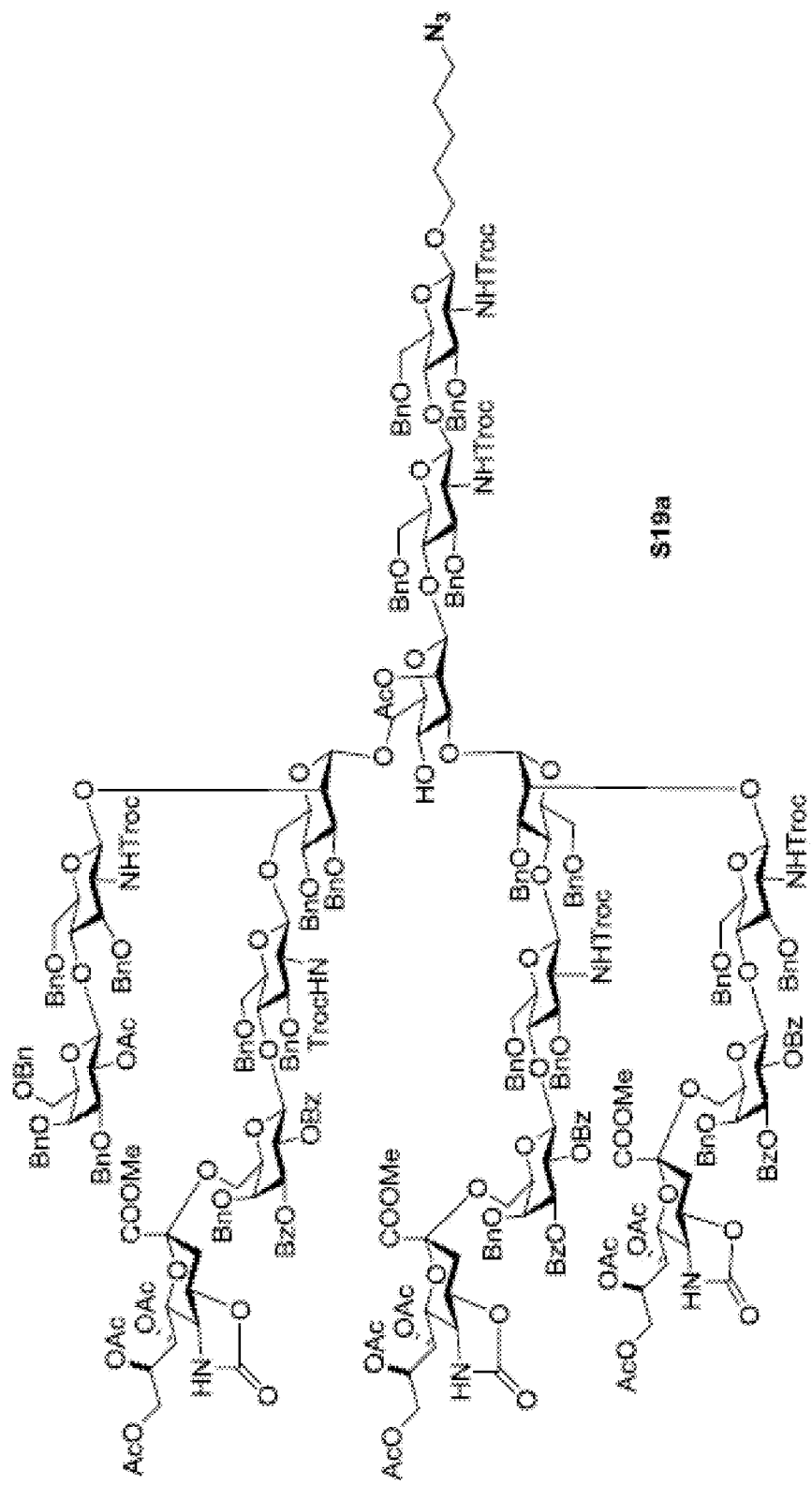
FIG. 116 Exemplary structure embodiments and synthetic scheme embodiments of the present disclosure.
Figure 117:
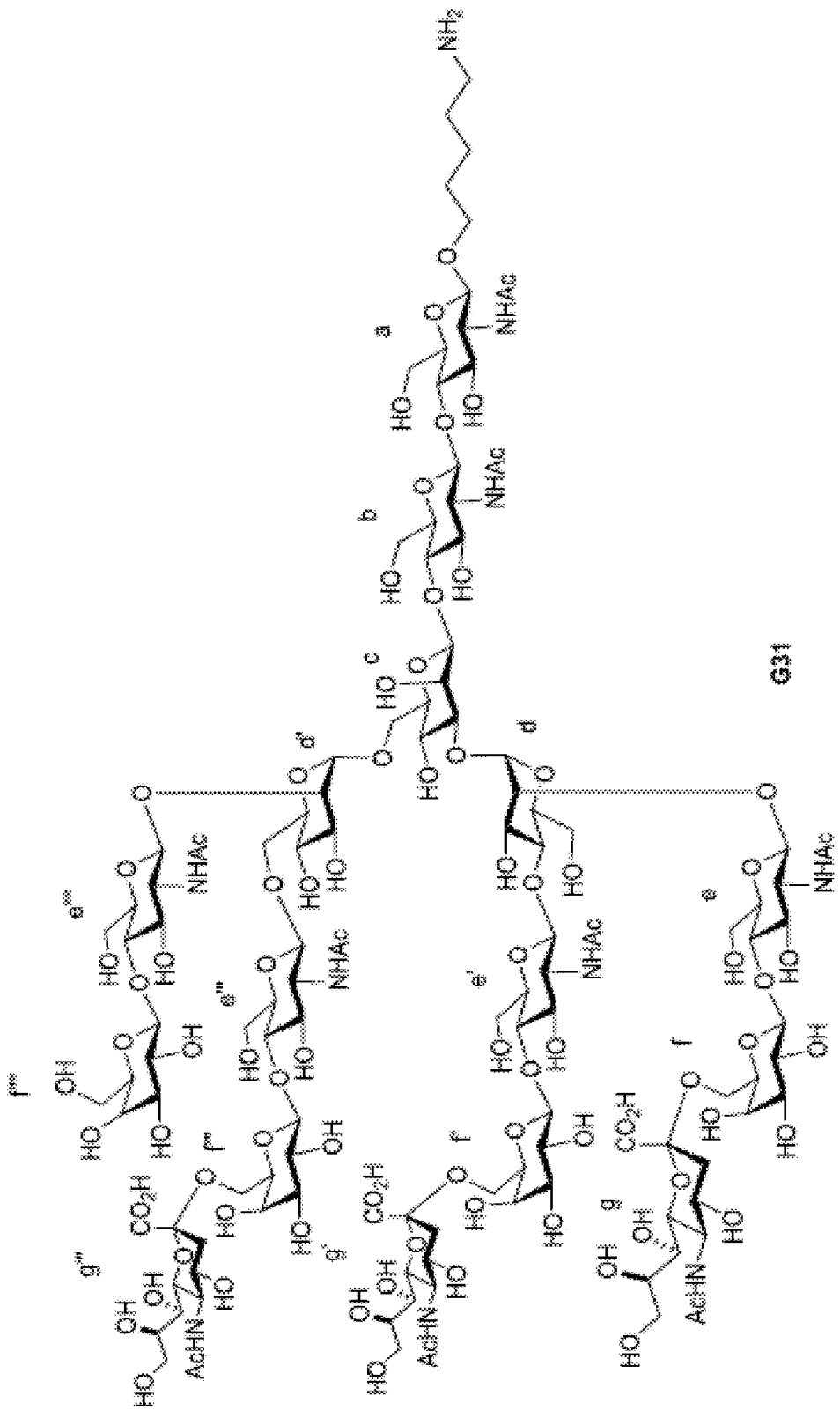
FIG. 117 Exemplary structure embodiments and synthetic scheme embodiments of the present disclosure.

Synthesis of glycan G31 as shown in FIG. 115.

Intermediate S16b derived from scheme S16 as shown in FIGS. 102A and 102B was used for α-selective glycosylation using donor 13 in presence of AgOTf/Cp2HfCl2 to get S19a in 74% yield. However, the newly formed product was overlapped with acceptor on TLC (Scheme S19 as shown in FIG. 115). S19a was then further deprotected to furnish glycan G31.

Scheme S19 as shown in FIG. 115 depicts the preparation of G31. i, 13, AgOTf, Cp2HfCl2, toluene, −50° C., 74%; ii, (1) LiOH, 1,4-dioxane, 90° C., (2) Ac2O, pyridine, (3) NaOMe, MeOH, (4) Pd(OH)2, MeOH:H2O, H2, 47%.

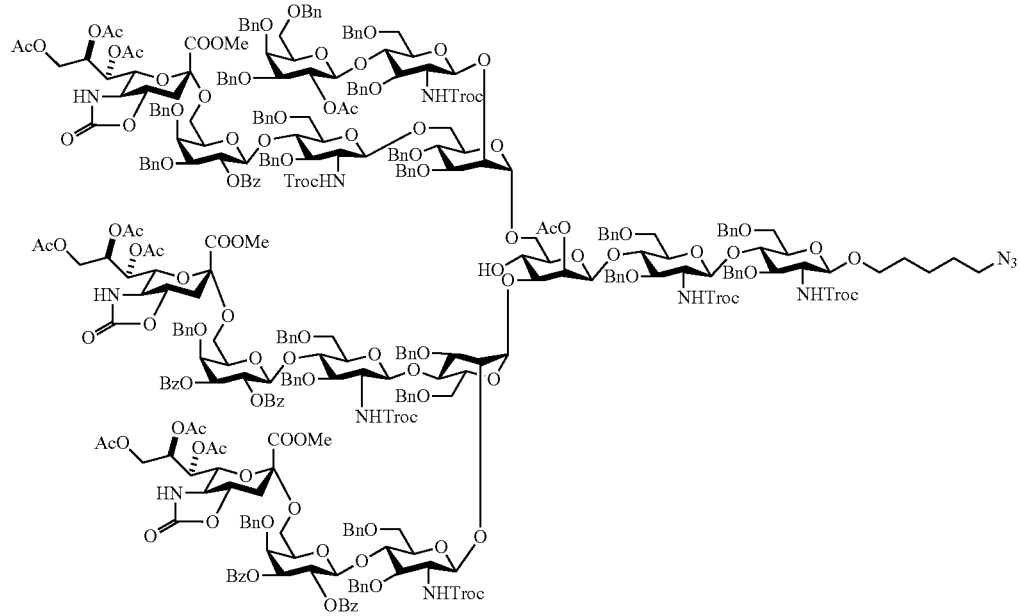

S19a

Compound S19a: A mixture of silver triflate (0.042 g, 0.165 mmol), bis (cyclopentadienyl) hafnium dichloride (0.043 g, 0.115 mmol) and 4 Å activated molecular sieves in dry toluene (5 mL) was stirred at rt for 1 h. The reaction mixture was then cooled to −50° C., a solution of donor 13 (0.100g, 0.036 mmol) and acceptor S16b (0.150 g, 0.033 mmol) in 5 mL toluene was added. The reaction mixture was stirred for 2 h at −20° C., quenched with Et3N, diluted with EtOAc and filtered through Celite. The filtrate was washed with aqueous NaHCO3 (2×50 mL), and a brine (50 mL) solution. The organic layer was dried over Na2SO4 and concentrated in vacuo. The residue was purified by flash column chromatography (0%→15% acetone in toluene) to afford S19a (0.183 g, 74%) as white foam. TLC: (acetone: toluene=2/8, v/v): Rf=0.50; 1H NMR (600 MHz, CDCl3): δ 7.90-7.83 (m, 9H), 7.69-7.67 (m, 3H), 7.57-7.50 (m, 3H), 7.38-7.04 (m, 125H), 5.77 (t, J=10.2 Hz, 4H), 5.54-5.40 (m, 20H), 5.39 (t, J=8.4 Hz, 4H), 5.08 (t, J=7.8 Hz, 4H), 4.98-4.60 (m, 25H), 4.53-4.42 (m, 31H), 4.30-4.10 (m, 35H), 4.00-3.80 (m, 42H), 3.21-3.18 (m, 64H), 2.93-2.78 (m, 4H), 2.08 (s, 6H), 2.07 (s, 6H), 2.05 (s, 3H), 2.02 (s, 3H), 1.98 (s, 6H), 1.94 (s, 6H), 1.74-1.18 (m, 7H), 0.91-0.84 (m, 2H); 13C NMR (150 MHz, CDCl3): δ 171.8, 171.7, 170.8, 169.9, 169.8, 168.5, 168.0, 166.1, 165.4, 159.5, 132.7, 131.7, 130.1, 129.9, 129.2, 128.9, 128.8, 128.7, 128.6, 128.4, 128.3, 128.2, 128.1, 128.0, 127.9, 127.8, 127.7, 127.6, 127.5, 100.7, 100.6, 100.4, 95.8, 74.9, 74.6, 74.2, 73.9, 73.7, 73.6, 73.2, 72.9, 72.2, 71.9, 71.0, 70.5, 69.3, 68.5, 68.3, 68.0, 67.3, 66.1, 65.3, 62.3, 61.2, 53.4, 51.5, 39.0, 37.3, 33.7, 32.4, 32.2, 30.6, 29.9, 29.6, 29.4, 29.3, 28.8, 26.6, 24.0, 23.9, 23.5, 23.4, 23.1, 21.2, 20.1, 15.5, 14.6, 14.4, 14.3, 11.2; HRMS (negative mode): m/z calcd for C, 352; H, 376; Cl, 18; N, 12; O, 113; 7220.9510 found 3654.9220 (M+2Na)2−.

G31

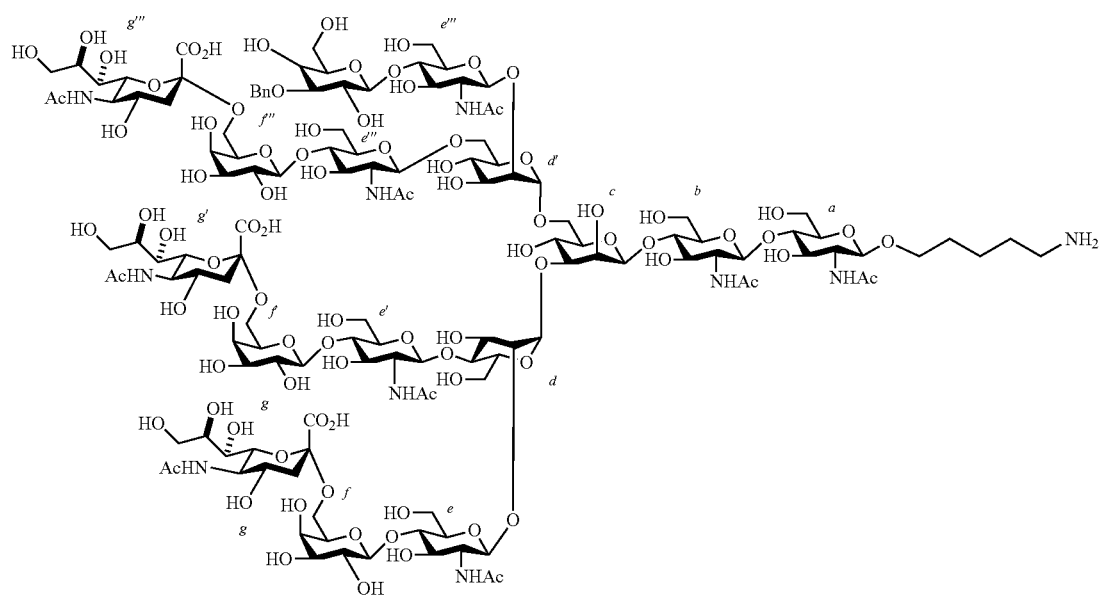

5-Aminopentyl-di-[5-Acetamido-3,5-dideoxy-D-glycero-α-D-galacto-2-nonulopyrano-sylonate-(2→6)-β-D-galactopyranosyl-(1→4)-2-acetamido-2-deoxy-β-D-glucopyranosyl-(1→2),(1→4)-α-D-mannopyranosyl]-(1→3),-[5-Acetamido-3,5-dideoxy-D-glycero-α-D-galacto-2-nonulopyrano-sylonate-(2→6)-β-D-galactopyranosyl-(1→4)-2-acetamido-2-deoxy-β-D-glucopyranosyl-(1→6)-β-D-galactopyranosyl-(1→4)-2-acetamido-2-deoxy-β-D-glucopyranosyl-(1→2)-α-D-mannopyranosyl]-(1→6)-β-D-mannopyranosyl-(1→4)-2-acetamido-2-deoxy-β-D-glucopyranosyl-(1→4)-2-acetamido-2-deoxy-β-D-glucopyranoside G31: Compound S19a (0.180 g, 0.024 mmol) was deprotected by following general procedure 2 (method 2) to afford desired glycan G31 (0.039 g, 47%). 1H NMR (600 MHz, D2O): δ 5.12 (s, 1H, H-1d), 4.87 (s, 2H, H-1d',c), 4.75 (d, J=8.4 Hz, 2H, H-1b, e), 5.59-4.55 (m, 5H, overlapped H-1a, e', e''', e'''', f), 4.49-4.42 (m, 5H, overlapped H-1f'-f''''), 4.21-4.19 (m, 4H), 4.06-3.54 (m, 95H), 2.97 (t, J=10.2 Hz, 2H, linker —CH2), 2.66 (dd, J=3.2 & 7.8 Hz, 3H, H-3g,g',g'''equi), 2.09 (s, 3H), 2.06 (s, 9H), 2.04 (s, 3H), 2.02 (s, 12H), 1.74 (m, 2H, linker), 1.64 (t, J=10.2 Hz, 3H, H-3g,g',g'''axial), 1.59-1.57 (m, 2H, linker), 1.39-1.37 (m, 2H, linker); 13C NMR (150 MHz, D2O): δ 174.8, 174.7, 174.5, 174.4, 174.3, 174.1, 173.3, 103.5, 102.9, 101.7, 101.4, 101.2, 100.2, 100.0, 99.8, 99.6, 99.3, 80.8, 80.6, 80.3, 79.3, 78.4, 78.3, 76.7, 75.3, 74.3, 74.2, 74.1, 74.0, 73.8, 72.9, 72.8, 72.6, 72.4, 72.3, 72.2, 72.1, 72.0, 71.9, 71.7, 71.3, 70.8, 70.4, 70.3, 70.2, 68.4, 68.4, 63.4, 62.9, 60.4, 60.3, 60.2, 59.8, 54.8, 54.3, 54.2, 51.8, 51.0, 43.7, 43.3, 39.8, 39.5, 34.4, 27.5, 26.3, 22.6, 22.4, 22.4, 22.2, 22.0, 21.9; ESI-MS (negative mode): m/z calcd for C, 128; H, 212; N, 10; O, 90; 3331.0840 found 1664.1108 (M−H)2−.

Synthesis of core fucosylated glycans G3 and G19 as shown in FIGS. 127 and 128.

The pauci mannose type structure bearing core fucose G312 was assembled from the reducing end disaccharide S20k through fucosylation of diol acceptor S20j by donor S20i (Scheme S20). The α-selectivity was enhanced by in situ anomarization protocol (CuBr2, tetrabutyl ammonium bromide), which was first developed by Lemieux and co-workers14, to get disaccharide S20k in 67% yield with its regio- and stereo-chemistry confirmed by NMR analysis. The formation of the key f-mannosyl linkage using sulfoxide donor S20a13 and acceptor S20b was performed using DTBP and Tf2O to get disaccharide S20c in 67% yield with α/β ratio of 1:7. The p-methoxy benzyl ether protection at 3″ was removed by using DDQ to afford 3″-OH S20d, which was further subjected to 3″-O α-mannosylation by using imidate 1 under the promotion of BF3.OEt2 to obtained trisaccharide S20e. Selective benzylidene opening of S20e produced S20f, which further underwent a-mannosylation at 6″-position to get tetrasaccharide S20g. Compound S20g was then converted into glycosyl imidate S20h by treatment with PdCl2 and then trichloroacetimidate and DBU. Finally the condensation of imidate S20h and disaccharide S20k12 in the presence of BF3.OEt2 provided desired hexasaccharide S20i. The global deprotection afforded the paucimannose type oligosaccharide G3.

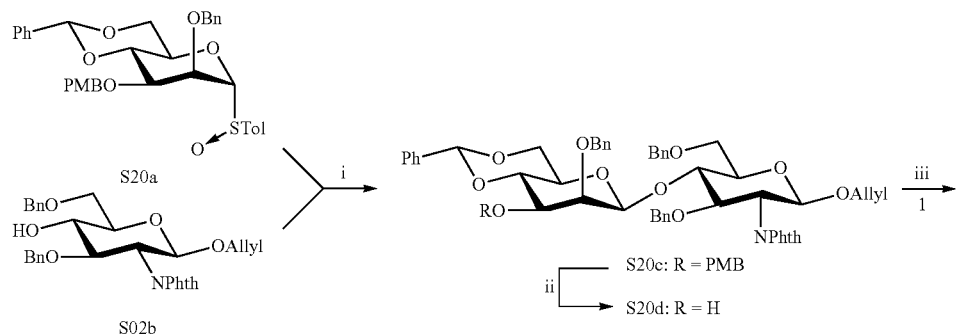
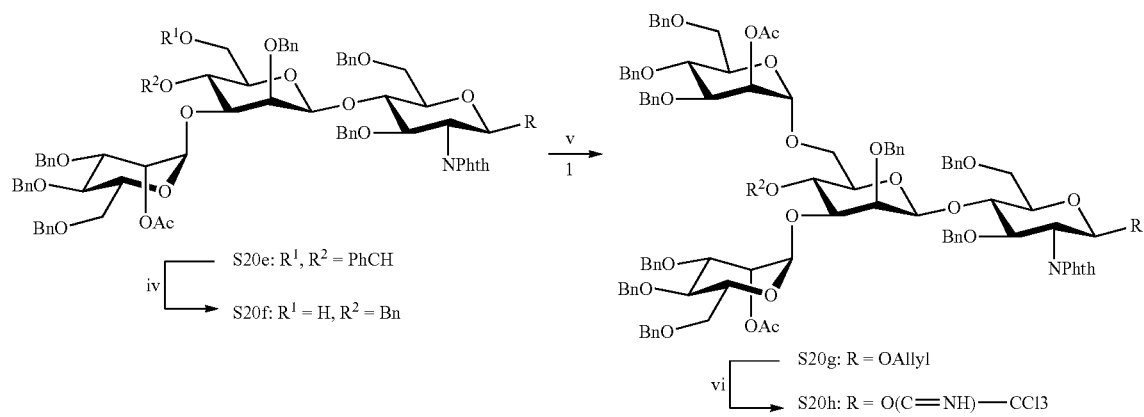
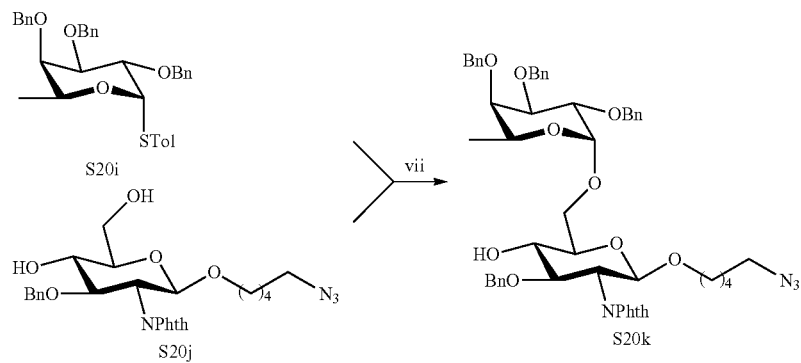
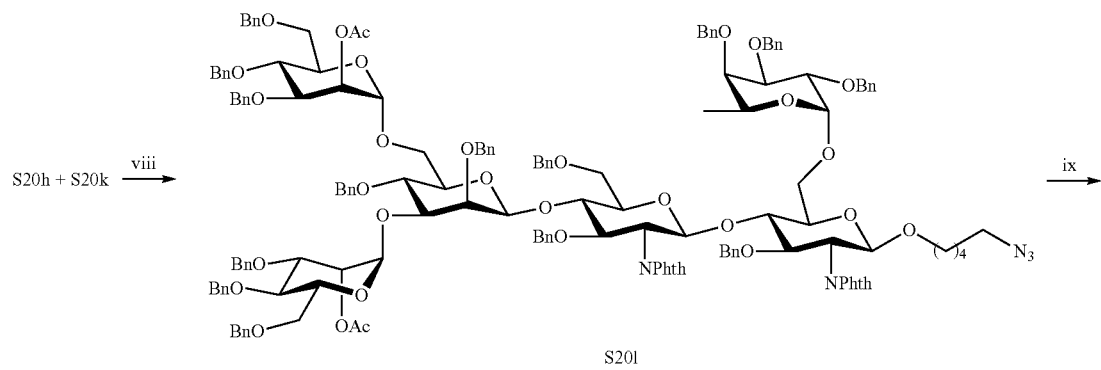

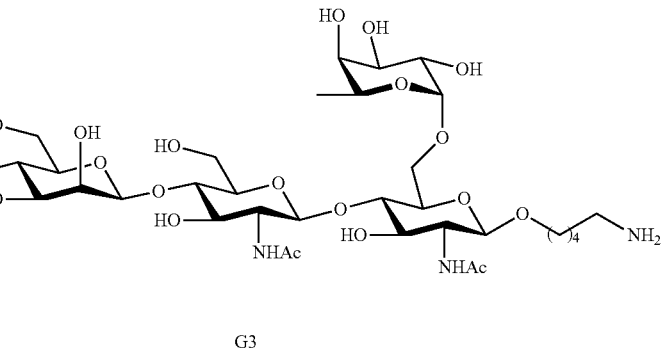

G3

Scheme S20 as shown in 118A, 118B and 118C depicts the preparation of glycan G3. i, DTBP, Tf2O, CH2Cl2, −60° C., 3 h, 67% (α/β 1:7); ii. DDQ, CH2Cl2:H2O=10/1, 3 h, 70%; iii, 1, BF3.OEt2, CH2Cl2, 4 Å MS, −40° C., 1 h 81%; iv, Triethyl silane, PhBCl2, CH2Cl2, 1 h, 73%; v, BF3.OEt2, CH2Cl2, 4 Å MS, −20° C., 2 h, 65%; vi, (i) PdCl2, MeOH:CH2Cl2, RT, 6 h, (ii) DBU, trichloroacenitrile, CH2Cl2, 63% over 2 steps; vii, Cu(II)Br, TBAB, DMF:CH2Cl2, 4 Å Ms, 0° C. to RT, overnight, 76%; viii, BF3.OEt2 CH2Cl2, 4 Å Ms, −70° C., 2 h, 45%; ix, (i) NH2CH2CH2NH2, nBuOH, 100° C.; (ii) Ac2O, pyridine, 0° C. to Rt; (iii) NaOMe, MeOH; (iv) Pd(OH)2, MeOH:H2O:HCOOH (5:3:2), H2, 22% over 4 steps. TBAB=Tetrabutyl ammonium bromide.

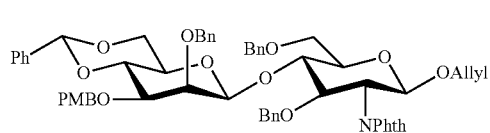
S20c

Allyl-O-2-O-benzyl-3-O-p-methoxy-benzyl-4,6-O-benzylidine-β-D-mannopyranosyl-(1→4)-O-(3,6-di-O-benzyl-2-deoxy-2-phthalimido-β-D-glucopyranoside (S20c): A mixture of donor S20a (0.272 g, 0.483 mmol) and activated 4 Å molecular sieves (0.5 g) in CH2Cl2 (10 mL) was stirred at rt for 1 h. The reaction mixture was cooled to −60° C., 2,6-di-ter-butyl pyridine (268 µL, 1.24 mmol) followed by Tf2O (79 jµL, 0.483 mmol) was added and stirred for 40 minutes. A solution of acceptor S20b (0.2 g, 0.378 mmol) in CH2Cl2 (5 mL) was added slowly and the resulting reaction mixture was stirred for 1 h until TLC (ethyl acetate:toluene, 1/9) indicated formation of a product with consumption of the starting material. The reaction mixture was quenched with Et3N, diluted with CH2Cl2, filtered through Celite and concentrated in vacuo. The residue was purified by flash column chromatography (0%→10% EA in toluene) to afford S20c (0.230 g, 67%) as white solid. TLC: (ethyl acetate:toluene=1/9, v/v): Rf=0.52; 1H NMR (600 MHz, CDCl3): δ 7.65-7.45 (m, 8H, Ar—H), 7.35-7.21 (m, 13H, Ar—H), 6.91-6.90 (m, 2H, Ar—H), 6.90-6.81 (m, 5H, Ar—H), 5.67-5.65 (m, 1H, allyl), 5.49 (s, 1H, Ph-CH, benzylidene), 5.13 (d, J=8.4 Hz, 1H, H-1a), 5.07 (d, J=8.8 Hz, 1H), 4.99 (d, J=10.4 Hz, 1H), 4.87-4.82 (m, 3H), 4.65 (d, J=5.4 Hz, 1H), 4.63 (d, J=5.4 Hz, 1H), 4.53 (s, 1H), 4.50 (d, J=12.0 Hz, 1H), 4.41 (d, J=6.0 Hz, 1H), 4.39 (d, J=6.0 Hz, 1H), 4.24-4.21 (m, 2H), 4.05-3.96 (m, 3H), 3.81 (s, 3H, OMe of PMB), 3.71 (d, J=3.0 Hz, 1H), 3.64 (d, J=10.8 Hz, 1H), 3.56-3.52 (m, 2H), 3.45-3.47 (d, J=10.0 Hz, 1H), 3.40 (dd, J=3.0, 6.6 Hz, 1H), 3.13-3.12 (m, 1H); 13C NMR (150 MHz, CDCl3): δ 159.46, 139.08, 138.99, 138.12, 138.00, 134.05, 130.93, 129.37, 129.22, 128.84, 128.60, 128.54, 128.47, 128.45, 128.26, 128.12, 128.09, 128.07, 127.83, 127.21, 126.41, 117.60, 114.04, 102.28, 101.63, 97.70, 79.85, 78.99, 78.33, 77.44, 75.29, 75.03, 74.95, 73.86, 72.61, 69.99, 68.86, 68.84, 67.66, 55.96, 55.58; ESI-MS: m/z calcd for C, 59; H, 59; NO, 13: 989.3879; found 1012.3888 (M+Na)+.

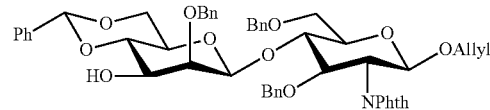
S20d

Allyl-O-2-O-benzyl-4,6-O-benzylidine-β-D-mannopyranosyl-(1→4)-O-(3,6-di-O-benzyl-2-deoxy-2-phthalimido-β-D-glucopyranoside (S20d): To a solution of S20c (0.5 g, 0.505 mmol) in 10 mL CH2Cl2:H2O (10:1) was added DDQ (0.219g, 1.01 mmol) at 0° C. and the resulting reaction mixture was stirred for 3 h. The reaction mixture was then filtered, organic layer washed with H2O (2×30 mL). The aqueous layer was further extracted with CH2Cl2 (2×50 mL). The combined organic layers were washed with brine solution (40 mL), dried over Na2SO4 and concentrated in vacuo. The residue was purified by flash column chromatography (0%→10% EA in toluene) to afford S20d (0.308 g, 70%) as colorless foam. TLC: (ethyl acetate:toluene=2/8, v/v): Rf=0.42; 1H NMR (600 MHz, CDCl3): δ 7.65-7.44 (m, 6H, Ar—H), 7.43-7.28 (m, 13H, Ar—H), 6.92-6.90 (m, 2H, Ar—H), 6.83-6.81 (m, 3H, Ar—H), 5.68-5.64 (m, 1H, Allyl), 5.42 (s, 1H, Ph-CH, benzylidene), 5.14 (d, J=8.4 Hz, 1H, H-1a), 5.08 (d, J=12.8 Hz, 1H), 5.01-4.98 (m, 2H), 4.85 (d, J=12.6 Hz, 1H), 4.74 (d, J=12.0 Hz, 1H), 4.65 (d, J=12.0 Hz, 1H), 4.62 (s, 1H, H-1b), 4.84 (d, J=12.0 Hz, 1H), 4.40 (d, J=12.0 Hz, 1H), 4.25-4.16 (t, J=9.6 Hz, 1H), 3.99 (dd, J=13.0 & 6.3 Hz, 1H), 3.73-3.65 (m, 4H), 3.54-3.47 (m, 3H), 3.13-3.09 (m, 1H); 13C NMR (150 MHz, CDCl3): 138.97, 138.44, 137.93, 137.56, 133.98, 129.37, 128.92, 128.79, 128.53, 128.43, 128.35, 128.26, 128.21, 128.10, 127.99, 127.27, 126.58, 117.64, 102.33, 102.25, 97.66, 79.91, 79.42, 79.15, 77.43, 76.00, 75.03, 74.89, 74.01, 71.24, 69.99, 68.78, 68.67, 67.17, 55.90; ESI-MS: m/z calcd for C, 51; H, 51; NO, 12: 869.3303; found 892.3314 (M+Na)+.

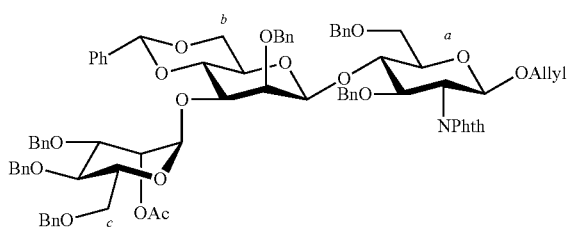

S20e

Ally-O-(2-O-acetyl-3,4,6-tri-O-benzyl-α-D-mannopyranosyl-(1→3)-2-O-benzyl-4,6-O-benzylidine-β-D-mannopyranosyl-(1→4)-O-(3,6-di-O-benzyl-2-deoxy-2-phthalimido-β-D-glucopyranoside (S20e): A mixture of donor 1 (0.537 g, 0.863 mmol), acceptor S20d (0.50 g, 0.574 mmol) and activated 4 Å molecular sieves in dry CH2Cl2 (10 mL) was stirred at rt for 30 minutes. The reaction was cooled to −40° C., boron trifluoride ethyl etherate (32 µL, 0.288 mmol) was then added slowly and the resulting reaction mixture was stirred for 1 h. The reaction was quenched by adding Et3N, diluted with CH2Cl2, filtered through Celite and concentrated in vacuo. The residue was purified by flash column chromatography (0%→20% EA in hexane) to afford S20e (0.630 g, 81%) as colorless oil. TLC: (ethyl acetate:hexane=3/7, v/v): Rf=0.62; 1H NMR (600 MHz, CDCl3): δ 7.41-7.39 (m, 4H, Ar—H), 7.39-7.25 (m, 30H, Ar—H), 7.16-6.82 (m, 5H, Ar—H), 5.57-5.57 (m, 1H, Allyl), 5.59 (d, J=3.0 Hz, 1H), 5.47 (s, 1H, Ph-CH, benzylidene), 5.29 (d, J=2.1 Hz, 1H, H-1c), 5.13 (d, J=8.4 Hz, 1H, H-1a), 5.08 (dd, J=6.0 & 12.2 Hz, 1H), 5.00 (dd, J=6.0, 10.2 Hz, 1H), 4.87-4.82 (m, 2H), 4.79-4.78 (m, 2H), 4.66-4.59 (m, 3H), 4.54 (s, 1H, H-1b), 4.46-4.44 (m, 3H), 4.22-4.20 (m, 2H), 4.17-4.14 (m, 2H), 4.03-3.93 (m, 4H), 3.82-3.71 (m, 5H), 3.64-3.62 (m, 2H), 3.60-3.52 (m, 2H), 3.50 (d, J=8.2 Hz, 1H), 3.19 (m, 1H), 2.34 (s, 3H, —C(O)CH3); 13C NMR (150 MHz, CDCl3): δ 170.26, 163.58, 162.83, 138.98, 138.77, 138.60, 138.40, 138.09, 138.04, 137.58, 133.97, 131.97, 129.01, 128.79, 128.71, 128.64, 128.62, 128.56, 128.52, 128.38, 128.32, 128.24, 128.12, 128.05, 127.97, 127.94, 127.84, 127.18, 126.26, 123.57, 117.58, 101.76, 101.35, 98.96, 97.63, 79.24, 78.91, 78.56, 78.22, 75.76, 75.62, 75.03, 74.77, 74.44, 73.75, 72.55, 71.83, 69.94, 69.32, 68.64, 68.54, 68.39, 67.16, 55.88, 36.75, 31.70, 21.27; ESI-MS: m/z calcd for C, 80; H, 81; NO, 18: 1343.5346; found 1366.5369 (M+Na)+.

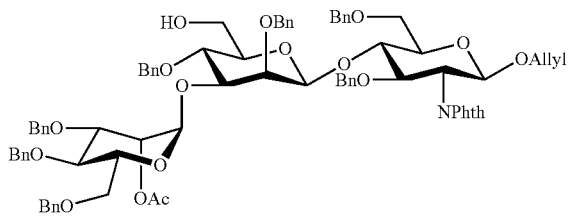

S20f

Ally-O-(2-O-acetyl-3,4,6-tri-O-benzyl-α-D-mannopyranosyl-(1→3)-2,4-O-di-benzyl-β-D-mannopyranosyl-(1→4)-O-(3,6-di-O-benzyl-2-deoxy-2-phthalimido-β-D-glucopyranoside (S20f): A mixture of compound S20e (0.630 g, 0.468 mmol) and activated 4 Å molecular sieves in 20 mL CH2Cl2 was stirred for 1 h at rt. The reaction mixture was cooled to −78° C., triethyl silane (148 µL, 0.946 mmol) followed by dichlorophenyl borane (146 µL, 1.18 mmol) was added and stirred for 1 h. The reaction was quenched by Et3N, methanol, filtered through Celite and concentrated in vacuo. The residue was co-distilled with methanol 2-3 times before being purified by flash column chromatography (0%→10% EA in toluene) to give alcohol S20f (0.460 g, 73%). TLC: (ethyl acetate:toluene=2/8, v/v): Rf=0.42; 1H NMR (600 MHz, CDCl3): δ 7.73-7.57 (m, 4H, Ar—H), 7.50-7.08 (m, 31H, Ar—H), 6.83-6.81 (m, 4H, Ar—H), 5.76-5.69 (m, 1H, Allyl), 5.44 (t, J=3.0 Hz, 1H), 5.13 (s, 1H, H-1c), 5.12 (s, 1H), 5.08 (d, J=7.8 Hz, 1H, H-1a), 5.01 (d, J=11 Hz, 1H), 4.93 (d, J=11.0 Hz, 1H), 4.87 (d, J=8.6 Hz, 1H), 4.83 (d, J=8.0 Hz, 1H), 4.76 (d, J=12.0 Hz, 1H), 4.69 (d, J=11.0 Hz, 1H), 4.62 (t, J=8.6 Hz, 1H), 4.57 (t, J=7.8 Hz, 2H), 4.50 (d, J=10.8 Hz, 1H), 4.44 (d, J=2.5 Hz, 1H), 4.42 (s, 1H), 4.40 (d, J=8.0 Hz, 1H), 4.35 (d, J=12.0 Hz, 1H), 4.22-4.181 (m, 3H), 4.00-3.99 (m, 2H), 4.90-3.91 (s, 1H), 3.83-3.82 (m, 1H), 3.83 (d, J=2.4 Hz, 1H), 3.77-3.78 (m, 2H), 3.64-3.54 (m, 6H), 3.41-3.39 (m, 2H), 3.19-3.18 (m, 1H), 2.08 (s, 3H); 13C NMR (150 MHz, CDCl3): δ 170.34, 138.90, 138.77, 138.73, 138.36, 138.14, 138.07, 138.03, 135.91, 134.50, 134.03, 133.86, 132.97, 131.94, 131.40, 129.31, 128.86, 128.68, 128.66, 128.61, 128.57, 128.50, 128.45, 128.38, 128.26, 128.20, 128.12, 128.11, 128.03, 127.97, 127.94, 127.79, 127.76, 127.72, 127.47, 127.35, 123.50, 117.59, 101.04, 99.89, 97.61, 80.92, 78.64, 78.48, 78.41, 78.21, 75.93, 75.26, 75.20, 75.19, 75.16, 74.82, 74.59, 74.52, 73.78, 73.75, 72.61, 72.11, 69.91, 69.50, 68.99, 68.43, 62.25, 55.86, 21.29; ESI-MS: m/z calcd for C, 80; H, 83; NO, 18: 1345.5502; found 1368.5527 (M+Na)+.

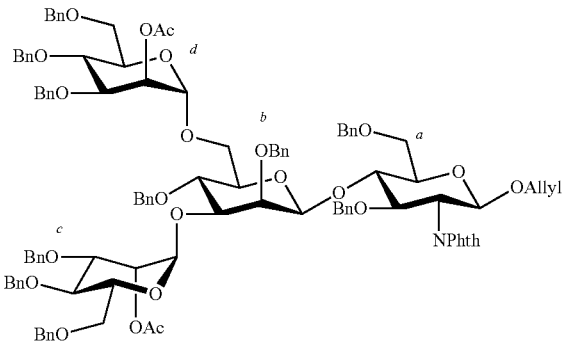

S20g

Allyl-O-di-(2-O-acetyl-3,4,6-tri-O-benzyl-α-D-mannopyranosyl-(1→3),(1→6)-2,4-O-di-benzyl-β-D-mannopyranosyl-(1→4)-O-(3,6-di-O-benzyl-2-deoxy-2-phthalimido-β-D-glucopyranoside (S20g): A mixture of donor 1 (0.429 g, 0.690 mmol), acceptor S20f (0.460 g, 0.345 mmol) and activated 4 Å molecular sieves in dry CH2Cl2 (10 mL) was stirred at rt for 30 minutes. The reaction was cooled to −20° C., boron trifluoride ethyl etherate (19 μL, 0.173 mmol) was then added slowly and the resulting reaction mixture was stirred for 2 h. The reaction was quenched by adding Et3N, diluted with CH2Cl2, filtered through Celite and concentrated in vacuo. The residue was purified by flash column chromatography (0%→20% EA in hexane) to afford S57 (0.380 g, 65%) as colorless foam. TLC: (ethyl acetate:hexane=3/7, v/v): Rf=0.56; 1H NMR (600 MHz, CDCl3):δ 7.60-7.29 (m, 4H, Ar—H), 7.28-7.08 (m, 37H, AR-H), 7.07-7.08 (m, 8H, Ar—H), 7.07-6.93 (d, J=8.0 Hz, 1H, Ar—H), 6.82-6.59 (m, 3H, Ar—H), 5.61-5.59 (m, 1H, Allyl), 5.43 (d, J=6.0 Hz, 1H, H-2c), 5.31 (d, J=6.0 Hz, 1H, H-2d), 5.10 (d, J=3.0 Hz, 1H, H-1c), 5.06 (d, J=8.0 Hz, 1H, H-1a), 4.99 (d, J=10.0 Hz, 1H), 4.85 (d, J=8.0 Hz, 1H), 4.83 (s, 1H, H-1d), 4.67 (d, J=8.0 Hz, 1H), 4.64-4.62 (q, 4H), 4.56 (d, J=3.0 Hz, 1H, H-1b), 4.55-4.45 (m, 8H), 4.45-4.39 (m, 9H), 4.38 (d, J=10.0 Hz, 1H), 4.21 (d, J=9.0 Hz, 1H), 4.19-4.10 (m, 2H), 4.08-3.70 (m, 10H), 3.69-3.49 (m, 7H), 3.39 (d, J=9.1 Hz, 1H), 3.19 (d, J=9.1 Hz, 1H), 2.07 (s, 3H, —C(O)CH3), 1.82 (s, 3H, —C(O)CH3); 13C NMR (150 MHz, CDCl3): δ 170.31, 170.11, 163.43, 139.07, 138.93, 138.83, 138.80, 138.65, 138.35, 138.32, 138.21, 138.09, 134.08, 133.77, 132.00, 128.87, 128.76, 128.66, 128.56, 128.43, 128.37, 128.16, 127.99, 127.91, 127.82, 127.73, 127.13, 123.46, 117.45, 102.07, 99.92, 99.74, 98.62, 97.55, 81.40, 79.81, 78.31, 78.23, 76.84, 75.87, 75.77, 75.66, 74.87, 74.65, 74.44, 74.38, 31.21, 21.29, 21.23; ESI-MS: m/z calcd for C, 109; H, 113; NO, 24: 1820.7578; found 1843.7676 (M+Na)+.

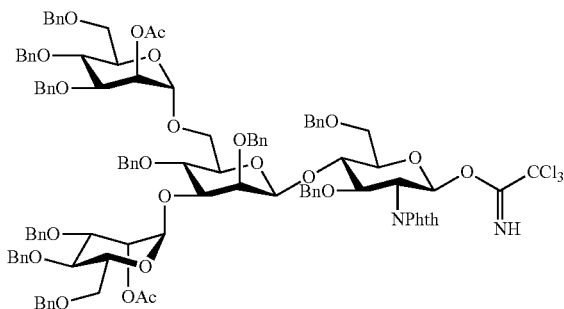

Di-(2-O-acetyl-3,4,6-tri-O-benzyl-α-D-mannopyranosyl-(1→3),(1→6)-2,4-O-di-benzyl-β-D-mannopyranosyl-(1→4)-O-(3,6-di-O-benzyl-2-deoxy-2-phthalimido-β-D-glucopyranosyl trichloroacetimidate (S20h): To a solution of S20g (0.2 g, 0.109 mmol) in 10 mL CH2Cl2:MeOH (1/1) was added PdCl2 (20 mg) and stirred at room temperature for 6 h until TLC (ethyl acetate:toluene, 2/8) indicated formation of a product with consumption of the starting material. The reaction mixture was then concentrated in vacuo. The residue was purified by flash column chromatography (0%→10% EA in toluene) to afford alcohol (0.140 g, 60%) as colorless foam. To a solution of alcohol (0.150 g, 0.084 mmol) in CH2Cl2 (10 mL) was added trichloroacetamidate (33 μL, 0.336 mmol) followed by DBU (12 μL, 0.033 mmol) at 0° C. and stirred at rt for 8 h. The reaction was quenched with Et3N and concentrated in vacuo. The residue was purified by flash column chromatography (0%→10% EA in toluene) to afford S20h (0.121 g, 67%) as colorless oil. TLC: (ethyl acetate:toluene=2/8, v/v): Rf=0.47; 1H NMR (600 MHz, CDCl3): δ 8.51 (s, 1H, C=NH), 7.53-7.42 (m, 4H, Ar—H), 7.40-7.00 (m, 49H, Ar—H), 6.58 (d, J=6.6 Hz, 2H, Ar—H), 6.52-6.50 (m, 3H, Ar—H), 5.43 (s, 1H, H-1a), 5.32 (s, 1H, H-1c), 5.03 (s, 1H), 5.01 (t, J=7.8 Hz, 1H), 4.90-4.78 (m, 6H), 4.67-4.45 (m, 7H), 4.43-4.30 (m, 9H), 4.28-4.20 (m, 2H), 4.10 (t, J=7.8 Hz, 1H), 3.39-3.42 (m, 18H), 3.19 (d, J=9.3 Hz, 1H), 2.09 (s, 3H, —C(O)CH3), 1.83 (s, 3H, —C(O)CH3).

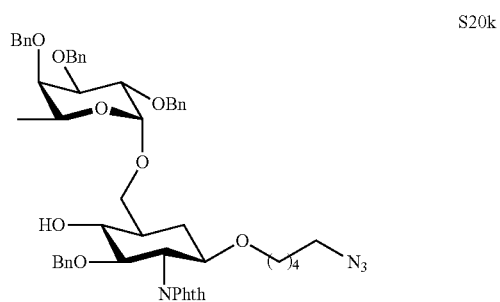

5-Azidopentyl-O-2,3,4-tri-O-benzyl-α-L-fucopyranosyl-(1→6)-3-O-benzyl-2-deoxy-2-phthalimido-β-D-glucopyranoside (S20k): A mixture of CuBr2 (0.450 g, 2.01 mmol), Bu4NBr (0.655 g, 2.03 mmol) and activated 4 Å molecular sieves in 10 mL of CH2Cl2:DMF (2/1) was stirred and cooled over an ice water bath. A solution of donor S20i (0.5 g, 0.925 mmol) and acceptor S20j (0.450 g, 0.882 mmol) in CH2Cl2 (10 mL) was added drop wise and the resulting reaction mixture was stirred at rt for overnight. TLC (ethyl acetate:hexane, 4/6) indicated formation of a product with consumption of the starting material. The reaction was quenched with aq. NaHCO3, diluted with ethyl acetate (50 mL) and filtered through Celite. The filtrate was washed with aq.NaHCO3, brine (50 mL), dried over sodium sulfate. The organic layer was concentrated in vacuo. The residue was purified by flash column chromatography (0%→30% EA in hexane) to afford S20k (0.604 g, 76%) as colorless oil. TLC: (ethyl acetate:hexane=4/6, v/v): Rf=0.47; 1H NMR (600 MHz, CDCl3): δ 7.80-7.64 (m, 4H, Ar—H), 7.41-7.23 (m, 15H, Ar—H), 7.00-6.98 (m, 2H, Ar—H), 6.90-6.87 (m, 3H, Ar—H), 5.06 (d, J=8.4 Hz, 1H, H-1a), 4.96 (d, J=11.4 Hz, 1H), 4.86 (d, J=11.4 Hz, 1H), 4.82-4.72 (m, 4H), 4.67 (d, J=12.0 Hz, 1H), 4.64 (d, J=12.0 Hz, 1H), 4.48 (d, J=12.6 Hz, 1H), 4.16-4.13 (m, 1H), 4.08-4.05 (m, 2H), 3.39-3.95 (m, 2H), 3.90-3.83 (m, 3H), 3.78 (m, 1H), 3.73-3.69 (m, 2H), 3.56-3.53 (m, 1H), 3.35-3.21 (m, 1H), 2.00-2.03 (m, 2H, —CCH2C—, linker), 1.38-1.30 (m, 4H, —CCH2C—, linker), 1.12 (d, J=8.4 Hz, 3H, Me of Fucose), 1.00-0.96 (m, 2H, —CCH2C—, linker); 13C NMR (150, MHz, CDCl3): δ 138.83, 138.77, 138.36, 134.13, 128.90, 128.77, 128.67, 128.60, 128.52, 128.31, 128.26, 128.17, 127.93, 127.88, 127.52, 123.64, 98.81, 98.59, 79.60, 78.07, 77.77, 76.67, 75.22, 74.54, 74.51, 74.24, 73.35, 73.20, 69.37, 68.79, 67.15, 55.88, 51.39, 29.00, 28.58, 23.30, 16.89; ESI-MS: m/z calcd for C, 53; H, 58; N, 4; O, 11: 926.3994; found 949.3998 (M+Na)+.

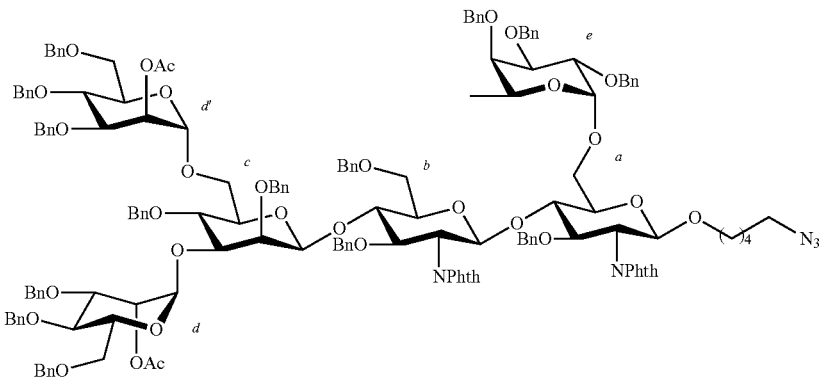

5-Azidopentyl-O-2-O-acetyl-3,4,6-tri-O-benzyl-α-D-mannopyranosyl-(1→6)-(2-O-acetyl-3,4,6-tri-O-benzyl-α-D-mannopyranosyl-(1→3))-2,4-di-O-benzyl-β-mannopyranosyl-(1→4)-O-3,6-di-O-benzyl-2-deoxy-2-phthalimido-β-D-glucopyranosyl-(1→4)-(2,3,4-tri-O-benzyl-α-L-fuco pyranosyl-(1→6))-3-O-benzyl-2-deoxy-2-phthalimido-β-D-glucopyranoside (S20l): A mixture of donor S20h (0.050 g, 0.025 mmol), acceptor S20k (0.028 g, 0.031 mmol) and activated 4 Å molecular sieves in dry CH2Cl2 (10 mL) was stirred at rt for 30 minutes. The reaction was cooled to −70° C., boron trifluoride ethyl etherate (0.725 μL, 0.0062 mmol) was then added slowly and the resulting reaction mixture was stirred for 2 h. The reaction was quenched by adding Et3N, diluted with CH2Cl2, filtered through Celite and concentrated in vacuo. The residue was purified by flash column chromatography (0%→20% EA in hexane) to afford S20l (0.027 g, 45%) as a white foam. TLC: (ethyl acetate: hexane=3/7, v/v): Rf=0.50; 1H NMR (600 MHz, CDCl3): δ 7.83-7.62 (m, 7H, Ar—H), 7.49-7.30 (m, 8H, Ar—H), 7.30-7.10 (m, 47H, Ar—H), 7.09-7.03 (m, 10H, AR-H), 7.03-6.99 (m, 1H, Ar—H), 6.93 (d, J=8.9 Hz, 2H, AR-H), 6.79-6.63 (m, 6H, AR-H), 6.55 (t, J=7.8 Hz, 2H, H-2d,d'), 5.40 (s, 1H, H-1d), 5.29-5.29 (m, 1H), 5.09 (d, J=1.3 Hz, 1H, H1d'), 4.88-4.76 (m, 13H), 4.67-4.65 (m, 2H), 4.58-5.48 (m, 9H), 4.42-4.40 (m, 3H), 4.36-4.30 (m, 5H), 4.20-4.10 (m, 5H), 4.05-4.00 (m, 2H), 3.92-3.80 (m, 7H), 3.79-3.60 (m, 7H), 3.62-3.41 (m, 10H), 3.25 (dd, J=3.2, 8.2 Hz, 1H), 3.18-3.17 (m, 2H), 2.85-2.79 (m, 2H), 2.06 (s, 3H, —C(O) CH3), 1.76 (s, 3H, —C(O)CH3, 1.42-1.34 (m, 4H, —CCH2C—, linker), 1.03-0.99 (m, 5H, —CCH2C—, linker and CH3 of Fucose); 13C NMR (150 MHz, CDCl3): δ 170.30, 169.91, 168.15, 167.76, 139.16, 138.99, 138.88, 138.82, 138.77, 138.54, 138.28, 138.21, 138.10, 138.08, 138.05, 133.86, 132.02, 131.72, 128.80, 128.62, 128.60, 128.57, 128.55, 128.33, 128.23, 128.40, 127.98, 127.92, 127.70, 127.55, 127.26, 127.06, 123.33, 101.97, 99.62, 98.41, 97.95, 97.09, 97.05, 81.42, 79.71, 78.36, 74.98, 74.75, 74.68, 73.65, 72.57, 72.51, 72.03, 71.38, 68.93, 68.86, 68.12, 66.63, 66.12, 56.76, 56.01, 51.26, 28.82, 28.56, 23.20, 21.23, 20.91; ESI-MS: m/z calcd for C, 159; H, 165; N, 5; O, 34: 2689.1261; found 2712.1338 (M+Na)+.

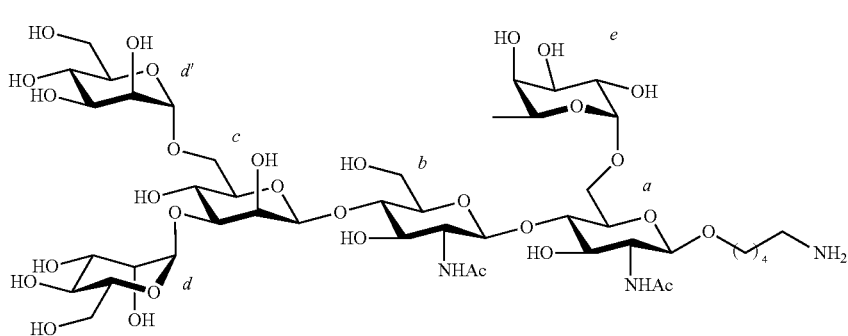

G3

5-Aminopentyl-di-(α-D-mannopyranosyl)-(1→3), (1→6)-β-D-mannopyranosyl-(1→4)-2-acetamido-2-deoxy-β-D-glucopyranosyl-(1→4)-(α-L-fucopyranosyl-(1→6)-2-acetamido-2-deoxy-β-D-glucopyranoside (G3): Compound S20h (0.030 g, 0.011 mmol) was deprotected by following general procedure 2 (method 1) to obtain the title compound G3 (0.007 g, 22%) as a white powder. 1H NMR (600 MHz, D2O): δ 5.09 (s, 1H, H-1d), 4.91 (s, 1H, H-1d'), 4.89 (d, J=3.2 Hz, 1H, H-1e), 4.78 (s, 1H, H-1c), 4.65 (d, J=7.8 HZ, 1H, H-1a), 4.49 (d, J=7.8 Hz, 1H, H-1b), 4.25 (s, 1H), 4.15-4.10 (m, 1H), 4.05 (s, 1H), 3.95 (s, 1H), 3.95-3.80 (m, 8H), 3.80-3.50 (m, 23H), 3.00 (m, 2H), 2.10 (s, 3H, —C(O) CH3), 2.09 (s, 3H, —C(O)CH3, 1.67-1.60 (m, 2H, —CCH2C—), 1.60-1.57 (m, 2H, —CCH2C—), 1.41-1.37 (m, 2H, —CCH2C—), 1.25 (d, J=7.8 Hz, 3H, —CH3 of Fucose); 13C NMR (150 MHz, D2O): δ 174.67, 174.39, 170.97, 102.51, 101.10, 101.04, 100.38, 99.60, 99.39, 80.46, 79.72, 78.60, 74.33, 74.15, 73.42, 72.65, 72.30, 71.95, 71.85, 70.29, 70.12, 70.00, 69.97, 69.85, 69.45, 68.15, 66.77, 66.14, 65.85, 65.80, 61.11, 60.92, 59.97, 55.05, 54.86, 46.66, 39.28, 38.61, 28.05, 26.36, 22.27, 22.15, 21.08, 21.50, 15.37, 15.34; ESI-MS: m/z calcd for C, 45; H, 80; N, 3; O, 30; 1141.4821; found 1142.4827 (M+H)+.

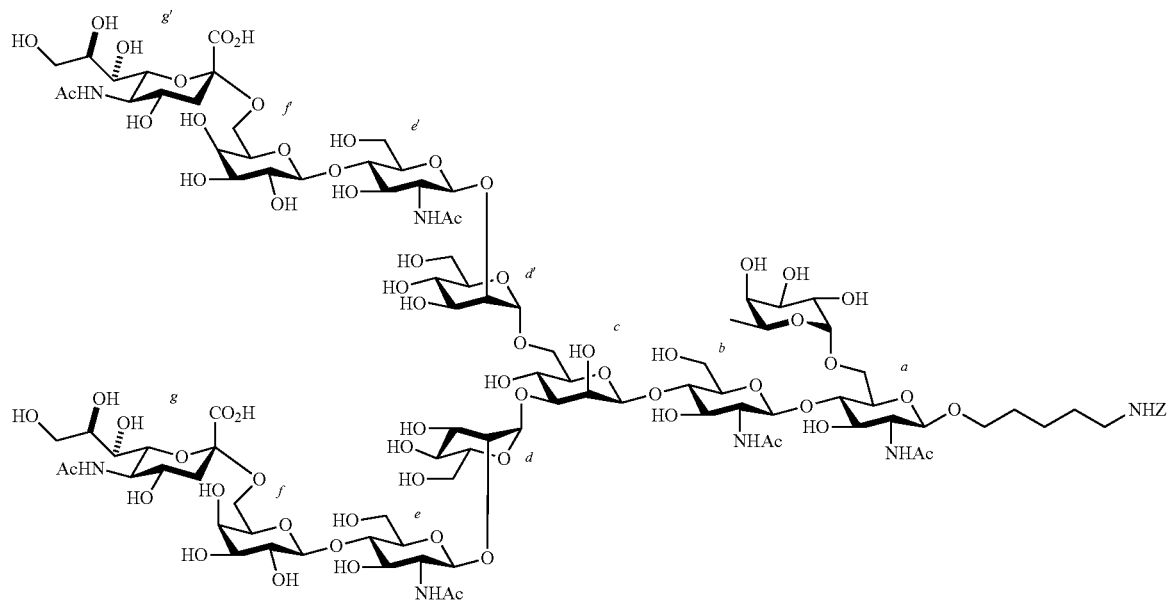

G19

5-Aminopentyl-di-[5-Acetamido-3,5-dideoxy-D-glycero-α-D-galacto-2-nonulopyrano-sylonate-(2→6)-β-D-galacto-pyranosyl-(1→4)-2-acetamido-2-deoxy-β-D-glucopyrano-syl-(1→2)-α-D-mannopyranosyl]-(1→3),(1→6)-β-D-mannopyranosyl-(1→4)-2-acetamido-2-deoxy-β-D-glucopyranosyl-(1→4)-(α-L-fucopyranosyl-(1→6)-2-acetamido-2-deoxy-β-D-glucopyranoside (G19): Sialylated biantennary with core fucose glycan G19 was prepared by using reported procedure 11,12. 1H NMR (600 MHz, D2O): δ 4.90 (s, 1H, H-1d), 4.72 (s, 1H, H-1d'), 4.66 (d, J=3.6 Hz, 1H, H-1c), 4.56 (s, 1H), 4.43 (d, J=7.2 Hz, 1H, H-1b), 4.37 (d, J=7.2 Hz, 2H, H-1e,e'), 4.25 (d, J=7.8 Hz, 1H, H-1a), 4.21 (d, J=7.8 Hz, 2H, H-1f), 4.04 (s, 1H), 3.97 (s, 1H), 3.90 (t, J=10.1 Hz, 2H), 3.76-3.25 (m, 65H), 2.74 (t, J=7.8 Hz, 2H, linker), 2.43 (dd, J=3.8 & 7.2 Hz, 1H, H-3equi. g, g'), 1.87 (s, 3H), 1.84 (s, 3H, —C(O)CH3), 1.83 (s, 3H, —C(O)CH3), 1.80 (s, 6H, —C(O)CH3), 1.51 (t, J=12H, 2H, H-3axial g,g'), 1.46-1.41 (m, 2H), 1.37-1.34 (m, 2H), 1.18-1.15 (m, 2H), 1.00 (d, J=6.6 Hz, 3H, —CH3 of Fucose); 13C NMR (150 MHz, D2O): δ 174.5, 174.3, 174.1, 173.3, 103.3, 100.9, 100.7, 100.2, 99.7, 99.6, 99.3, 99.1, 98.9, 96.5, 80.2, 79.5, 77.8, 75.9, 75.6, 74.0, 73.3, 73.2, 73.1, 72.4, 72.2, 71.8, 71.7, 71.3, 70.3, 69.9, 69.7, 69.3, 69.1, 68.0, 67.9, 67.0, 66.9, 66.5, 65.7, 65.4, 63.0, 62.2, 61.4, 61.3, 59.8, 59.4, 54.7, 54.4, 54.2, 51.5, 39.7, 38.9, 27.7, 26.1, 22.1, 22.0, 22.0, 21.8, 21.7, 15.1; ESI-MS: m/z calcd for C, 95; H, 159; N, 7; O, 66; 2451.9121; found 1226.4513 (M−H)2−.

Synthesis of glycans with phosphonic acid tails.

General procedure: To a solution of sugars with amine tail (3-5 μmol) in DMF (400 μL) was added linker [2(2(2(bis(benzyloxy)phosphoryl)ethoxyethoxy)ethyl(2,5-dioxopyrrolidin-1-yl)carbonate] (15-25 μmol), and the resulting reaction mixture was stirred at rt for 5 h. DMF was removed by using high vacuum and the product was purified by using Bio-Gel P-2 chromatography (eluent H2O). The solid was dissolved in 2 mL of H2O, added Pd(OH)2 (50% by weight) and hydrogenated for overnight. The reaction mixture was filtered through Celite and concentrated in vacuo. The residue was purified by Bio-Gel P-2 (BIO-RAD) column chromatography using water as eluent. The product was the lypholysed to obtain the desired sugar with phosphonic acid tail as white color powder.

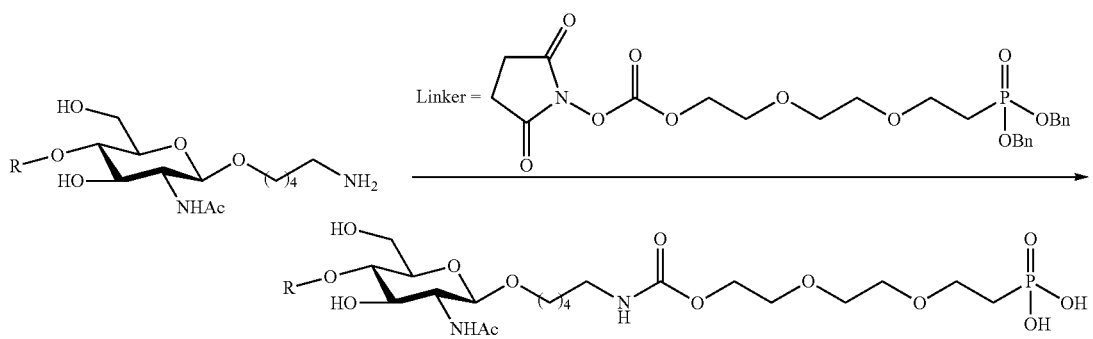

Scheme S21 as shown in FIG. 129 depicts the preparation of sugars with phosphonic acid linker. i, (1) Linker, DMF, RT, 5 h; (2) Pd(OH)2, H2O, H2, RT, overnight.

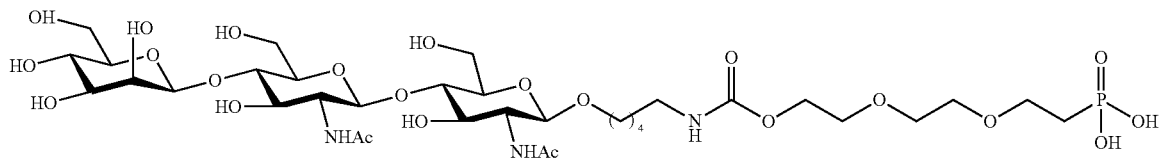

I

β-D-mannopyranosyl-(1→4)-2-acetamido-2-deoxy-β-D-glucopyranosyl-(1→4)-2-acetamido-2-deoxy-β-D-glucopyranoside (I): Compound S23 (3.5 mg, 5.4 μmol) was modified by above general procedure to afford compound I (2.2 mg, 61%), as white solid. TLC (MeOH:EA:AcOH:H2O, 7/1/1/1, v/v). 1H NMR (600 MHz, D2O): δ 4.60 (d, J=8.4 Hz, 1H), 4.48 (d, J=7.8 Hz, 1H), 4.19 (s, 2H), 4.05 (d, J=3.2 Hz, 1H), 3.93-3.49 (m, 33H), 1.75 (t, J=7.8 Hz, 2H), 2.06 (s, 3H), 1.95 (s, 3H), 1.95-1.92 (m, 2H), 1.58-1.54 (m, 2H), 1.50-1.47 (m, 2H), 1.33-1.30 (m, 2H). HRMS (MALDI-TOF): m/z calcd for C, 34; H, 59; N, 3; O, 23P; 908.3067 found 954.3099 (M+2Na)+.

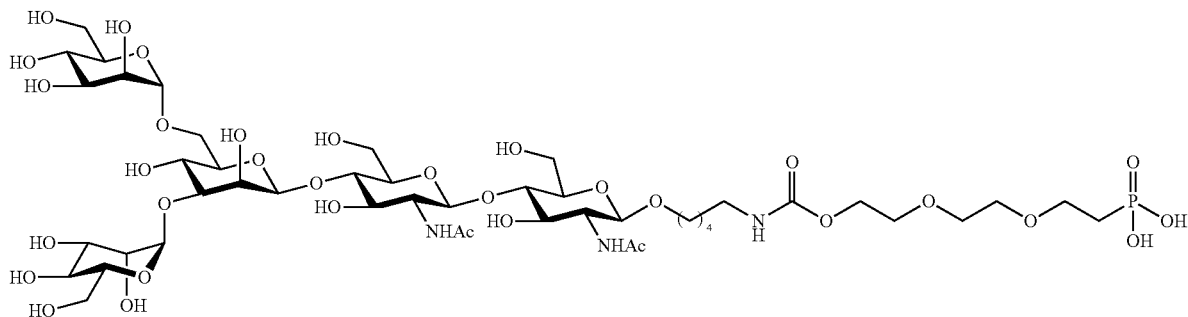

II (Phosphonate-tri-(ethyleneglycol)-carbonylamino)-pentyl-α-D-mannopyranosyl(1→3)-α-D-mannopyranosyl]-(1→6)-β-D-mannopyranosyl-(1→4)-2-acetamido-2-deoxy-β-D-glucopyranosyl-(1→4)-2-acetamido-2-deoxy-β-D-glucopyranoside (II): Glycan G2 (4 mg, 2.3 μmol) was modified by above general procedure to afford compound II (3.2 mg, 71%), as white solid. TLC (MeOH:EA:AcOH:H2O, 7/1/1/1, v/v). 1H NMR (600 MHz, D2O): δ 5.01 (s, 1H), 4.83 (s, 1H), 4.51 (d, J=6.1 Hz, 1H), 4.40 (d, J=6.2 Hz, 1H), 4.17 (s, 1H), 4.11 (s, 2H), 3.98 (s, 1H), 3.88-3.39 (m, 52H), 3.03 (t, J=7.8 Hz, 2H), 1.99 (s, 3H), 1.95 (s, 3H), 1.95-1.91 (m, 2H), 1.50-1.45 (m, 2H), 1.42-1.38 (m, 2H), 1.26-1.22 (m, 2H). HRMS (MALDI-TOF) Negative mode: m/z calcd for C, 58; H, 102; N, 3; O, 43P; 1234.4484 found 1278.5001 (M+2Na−2H)−.

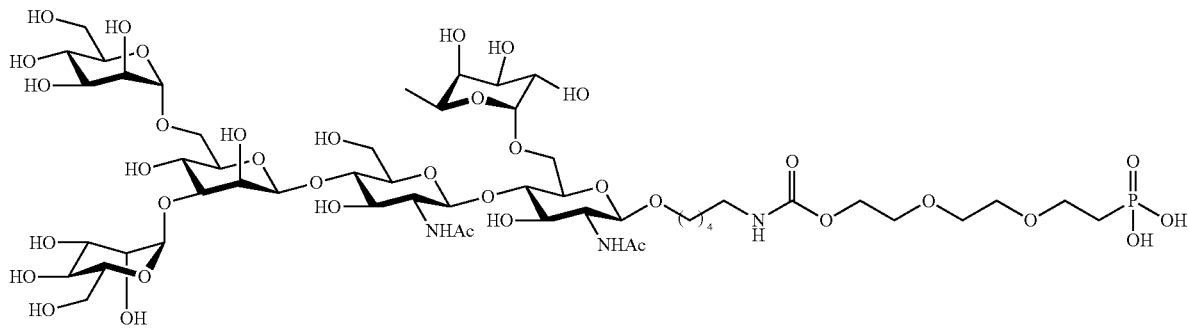

III (Phosphonate-tri-(ethyleneglycol)-carbonylamino)-pentyl-α-D-mannopyranosyl(1→3)-α-D-mannopyranosyl]-(1→6)-)-D-mannopyranosyl-(1→4)-2-acetamido-2-deoxy-β-D-glucopyranosyl-(1→4)-)-(α-L-fucopyranosyl-(1→6)-2-acetamido-2-deoxy-β-D-glucopyranoside) (III): Glycan G3 (1.2 mg, 1.0 μmol) was modified by above general procedure to afford compound III (1.0 mg, 91%), as white solid. TLC (MeOH:EA:AcOH:H2O, 7/1/1/1, v/v). 1H NMR (600 MHz, D2O): δ 5.09 (s, 1H), 4.90 (s, 1H), 4.88 (d, J=7.4 Hz, 1H), 4.66 (d, J=7.5 Hz, 1H), 4.48 (d, J=7.2 Hz, 1H), 4.25 (s, 1H), 4.19 (s, 2H), 4.12-4.10 (m, 1H), 4.06 (s, 1H), 3.95 (s, 1H), 3.92-3.84 (m, 10H), 3.79-3.69 (m, 31H), 3.11-3.09 (m, 2H), 2.08 (s, 3H), 2.02 (s, 3H), 1.99-1.93 (m, 2H), 1.58-1.53 (m, 2H), 1.49-1.47 (m, 2H), 1.34-1.30 (m, 2H), 1.22 (d, 3H). HRMS (MALDI-TOF): m/z calcd for C, 34; H, 59; N, 3; O, 23P; 1381.5709.3067 found 1450.5709 (M+3Na)+.

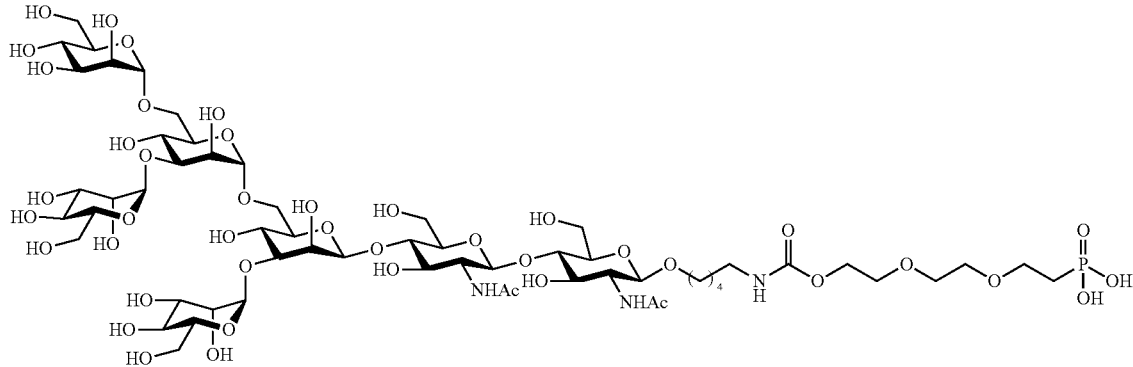

IV (Phosphonate-tri-(ethyleneglycol)-carbonylamino)-pentyl-α-D-mannopyranosyl(1→3),[di-(α-D-mannopyranosyl)-(1→3),(1→6)-α-D-mannopyranosyl]-(1→6)-β-D-mannopyranosyl-(1→4)-2-acetamido-2-deoxy-β-D-glucopyranosyl-(1→4)-2-acetamido-2-deoxy-β-D-glucopyranoside (IV): Glycan G4 (4 mg, 3.1 μmol) was modified by above general procedure to afford compound IV (3.7 mg, 78%), as white solid. TLC (MeOH:EA:AcOH:H2O, 7/1/1/1, v/v). 1H NMR (600 MHz, D2O): δ 5.10 (d, J=9.6 Hz, 2H), 4.93 (s, 1H), 4.70 (s, 1H), 4.57 (d, J=7.2 Hz, 1H), 4.48 (d, J=7.8 Hz, 1H), 4.24 (d, J=3.2 Hz, 2H), 4.19-4.13 (m, 4H), 4.06-4.04 (m, 3H), 3.95-3.40 (m, 45H), 3.38-3.37 (m, 1H), 2.10 (t, J=7.8 Hz, 2H), 2.07 (s, 6H), 2.02 (s, 6H), 1.98-1.93 (m, 2H), 1.58-1.47 (m, 2H), 1.34-1.29 (m, 2H), 1.27-1.25 (m, 2H); HRMS (MALDI-TOF): m/z calcd for C, 58; H, 102; N, 3; O, 43P; 1560.3985 found 1607.0452 (M+2Na+H)+.

V

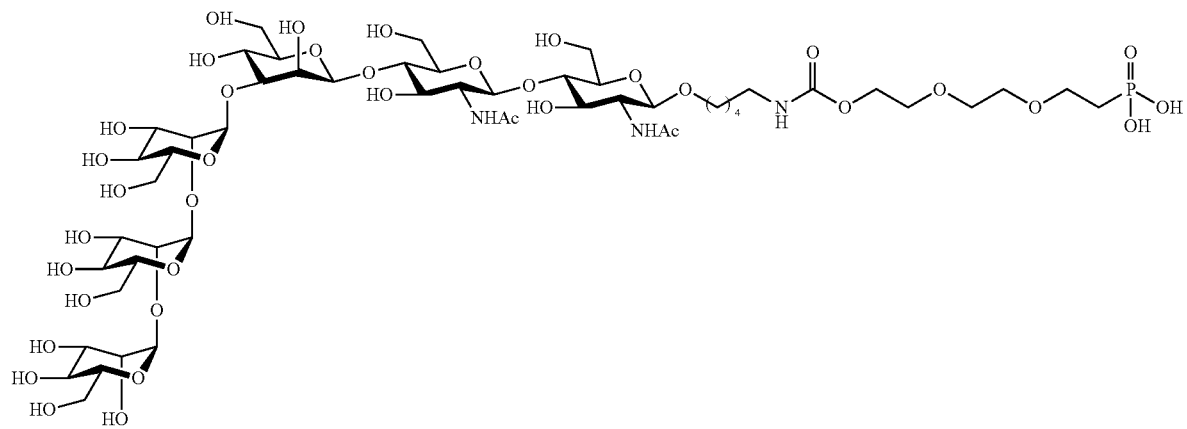

(Phosphonate-tri-(ethylene glycol)-carbonylamino)-pentyl-α-D-mannopyranosyl-(1→2)-α-D-mannopyranosyl-(1→2)-α-D-mannopyranosyl-(1→3)-β-D-mannopyranosyl-(1→4)-2-acetamido-2-deoxy-β-D-glucopyranosyl-(1→4)-2-acetamido-2-deoxy-β-D-glucopyranoside (V): Glycan G5 (5 mg, 4.4 μmol) was modified by above general procedure to afford compound V (3.5 mg, 58%), as white solid. TLC (MeOH:EA:AcOH:H2O, 7/1/1/1, v/v). 1H NMR (600 MHz, D2O): δ 5.34 (s, 1H), 5.29 (s, 1H), 5.03 (s, 1H), 4.58 (d, J=7.8 Hz, 1H), 4.47 (d, J=7.8 Hz, 1H), 4.20 (bs, 3H), 4.09-4.05 (m, 3H), 3.90-3.20 (m, 41H), 3.10 (t, J=7.8 Hz, 2H), 2.05 (s, 3H), 2.01 (s, 3H), 2.00-1.92 (m, 2H), 1.56-1.53 (m, 2H), 1.49-1.46 (m, 2H), 1.33-1.30 (m, 2H); HRMS (MALDI-TOF): m/z calcd for C, 52; H, 92; N, 3; O, 38P; 1398.2579 found 1444.5470 (M+2Na)+.

VI

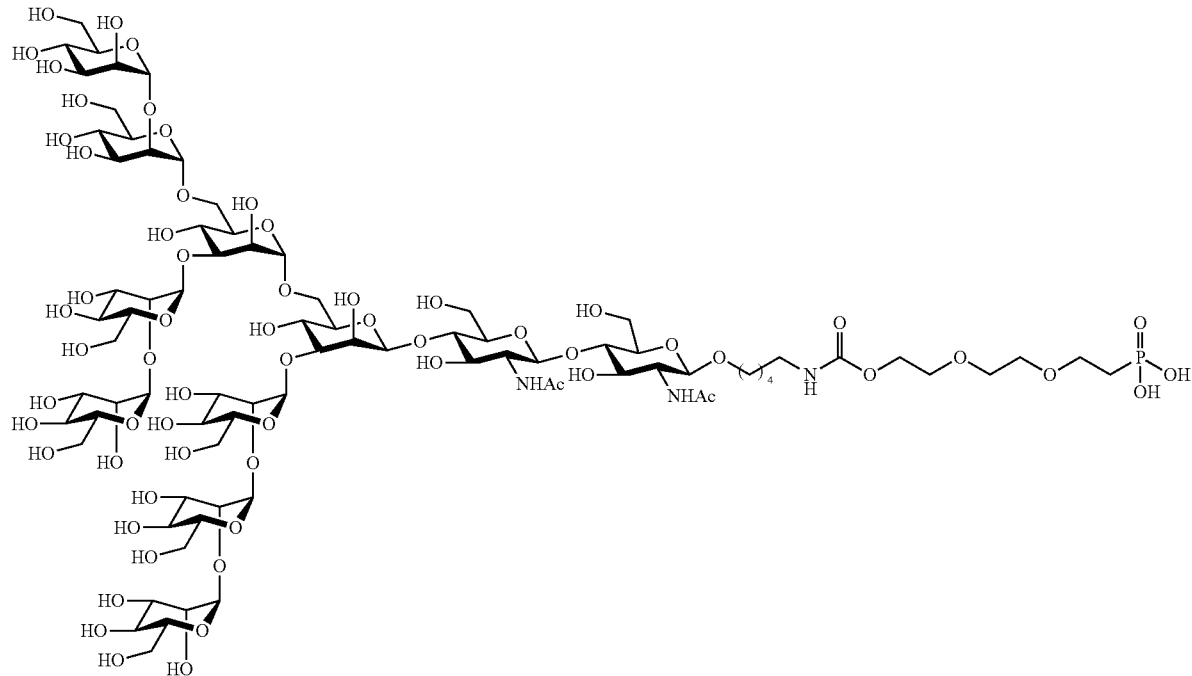

(Phosphonate-tri-(ethyleneglycol)-carbonylamino)-pentyl-α-D-mannopyranosyl-(1→2)-α-D-mannopyranosyl-(1→2)-α-D-mannopyranosyl-(1→3)-{α-D-mannopyranosyl-(1→2)-α-D-mannopyranosyl-(1→3)-[α-D-mannopyranosyl-(1→2)-α-D-mannopyranosyl-(1→6)]-α-D-mannopyranosyl-(1→6)}-β-D-mannopyranosyl-(1→4)-2-acetamido-2-deoxy-β-D-glucopyranosyl-(1→4)-2-acetamido-2-deoxy-β-D-glucopyranoside (VI): Glycan G6 (4 mg, 2.0 μmol) was modified by above general procedure to afford compound VI (3.7 mg, 66%), as white solid. TLC (MeOH:EA:AcOH:H2O, 7/1/1/1, v/v). 1H NMR (600 MHz, D2O): δ 5.53 (s, 1H), 5.39 (d, J=10.2 Hz, 1H), 5.26 (d, J=9.8 Hz, 1H), 5.23 (s, 1H), 5.16 (d, J=4.8 Hz, 1H), 5.08-5.05 (m, 5H), 4.60 (d, J=7.8 Hz, 1H), 4.50 (d, J=7.8 Hz, 1H), 2.08 (s, 3H), 2.02 (s, 3H), 1.38-1.03 (m, 2H), 1.58-1.56 (m, 2H), 1.52-1.48 (m, 2H), 1.35-1.32 (m, 2H); HRMS (MALDI-TOF): m/z calcd for C, 82; H, 142; N, 3; O, 63P; 2209.0310 found 2257.0812 (M+2Na)+.

VII

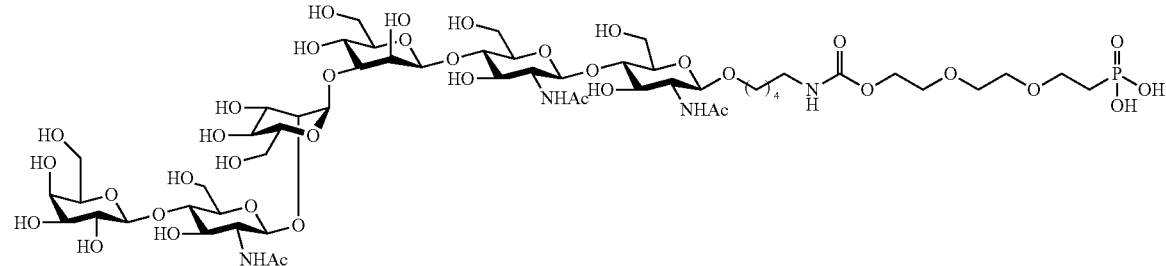

(Phosphonate-tri-(ethyleneglycol)-carbonylamino)-pentyl-β-D-galactopyranosyl-(1→4)-2-acetamido-2-deoxy-β-D-glucopyranosyl-(1→2)-α-D-mannopyranosyl]-(1→3)-β-D-mannopyranosyl-(1→4)-2-acetamido-2-deoxy-β-D-glucopyranosyl-(1→4)-2-acetamido-2-deoxy-β-D-glucopyranoside (VII): Glycan G9 (6.0 mg, 5.1 μmol) was modified by above general procedure to afford compound VII (3.5 mg, 50%), as white solid. TLC (MeOH:EA:AcOH:H2O, 7/1/1/1, v/v). 1H NMR (600 MHz, D2O): δ 5.03 (d, J=8.4 Hz, 2H), 4.58 (d, J=7.2 Hz, 1H), 4.48 (d, J=7.2 Hz, 1H), 4.45 (d, J=7.8 Hz, 1H), 4.26 (dd, J=3.0 & 9.2 Hz, 2H), 4.19 (bs, 2H), 4.00-3.38 (m, 48H), 3.11 (t, J=7.8 Hz, 2H), 2.06 (s, 3H), 2.05 (s, 3H), 2.02 (s, 3H), 1.99-1.93 (m, 2H), 1.56-1.54 (m, 2H), 1.50-1.48 (m, 2H), 1.31-1.27 (m, 2H); HRMS (MALDI-TOF): m/z calcd for C, 54; H, 92; N, 4; O, 38P; 1435.4917 found 1481.5069 (M+2Na)+.

Phosphonate-tri-(ethyleneglycol)-carbonylamino)-pentyl-[5-Acetamido-3,5-dideoxy-D-glycero-α-D-galacto-2-nonulopyrano-sylonate-(2→6)-β-D-galactopyranosyl-(1→4)-2-acetamido-2-deoxy-β-D-glucopyranosyl-(1→2)-α-D-mannopyranosyl]-(1→3)-β-D-mannopyranosyl-(1→4)-2-acetamido-2-deoxy-β-D-glucopyranosyl-(1→4)-2-acetamido-2-deoxy-β-D-glucopyranoside (IX): Glycan G10 (5.0 mg, 2.5 μmol) was modified by above general procedure to afford compound IX (3.8 mg, 63%), as white

VIII

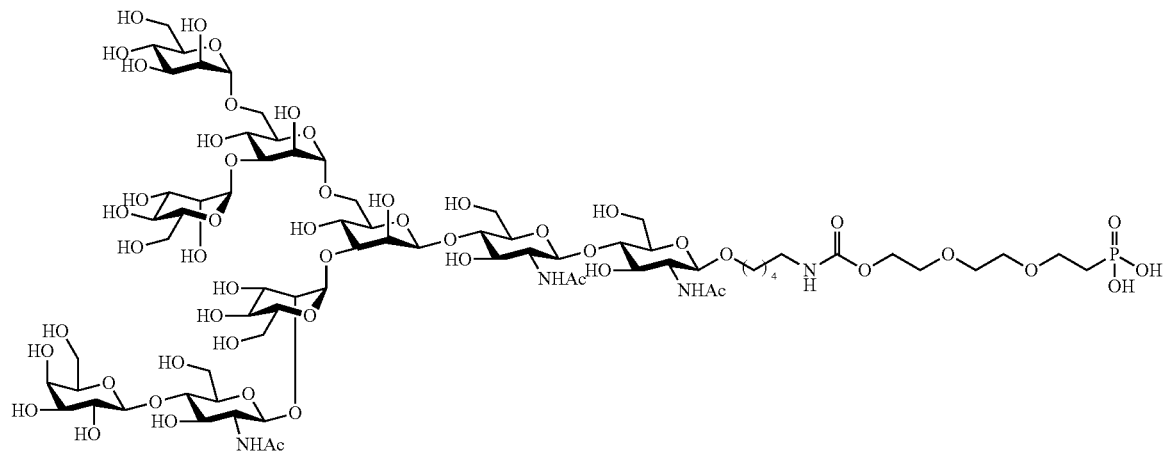

(Phosphonate-tri-(ethyleneglycol)-carbonylamino)-pentyl-β-D-galactopyranosyl-(1→4)-[2-acetamido-2-deoxy-β-D-glucopyranosyl-(1→2)-α-D-mannopyranosyl-(1→3),[di-(α-D-mannopyranosyl)-(1→3),(1→6)-α-D-mannopyranosyl](1→6)-β-D-mannopyranosyl-(1→4)-2-acetamido-2-deoxy-β-D-glucopyranosyl-(1→4)-2-acetamido-2-deoxy-β-D-glucopyranoside (VIII): Glycan G12 (5.0 mg, 3.0 μmol) was modified by above general procedure to afford compound VIII (3.1 mg, 54%), as white solid. TLC (MeOH:EA:AcOH:H2O, 7/1/1/1, v/v). 1H NMR (600 MHz, D2O): δ 5.11 (s, 2H), 5.02 (d, J=7.8 Hz, 2H), 4.68 (d, J=3.2 Hz, 2H), 4.48 (d, J=7.2 Hz, 1H), 4.45 (d, J=7.2 Hz, 1H), 4.27 (s, 2H), 4.22 (s, 2H), 4.15 (s, 1H), 4.08 (s, 2H), 4.00-3.30 (m, 60H), 3.10 (t, J=7.8 Hz, 2H), 2.08 (s, 3H), 2.05 (s, 3H), 2.02 (s, 3H), 1.93-1.87 (m, 2H), 1.56-1.54 (m, 2H), 1.51-1.47 (m, 2H), 1.33-1.30 (m, 2H); HRMS (MALDI-TOF): m/z calcd for C, 72; H, 122; N, 4; O, 53P; 1921.6502 found 1967.6622 (M+2Na)+.

solid. TLC (MeOH:EA:AcOH:H2O, 7/1/1/1, v/v). 1H NMR (600 MHz, D2O): δ 5.08 (d, J=8.4 Hz, 2H), 4.93 (s, 1H), 4.62 (d, J=7.2 Hz, 1H), 4.51 (d, J=7.8 Hz, 1H), 4.45 (d, J=7.8 Hz, 1H), 4.30 (d, J=3.2 Hz, 1H), 4.28 (s, 1H), 4.22 (s, 2H), 4.02-3.30 (m, 53H), 3.13 (t, J=7.8 Hz, 2H), 2.68 (dd, J=3.2, 7.8 Hz, 1H), 2.09 (s, 6H), 2.05 (s, 6H), 2.01-1.93 (m, 2H), 1.74 (t, J=12.1 Hz, 1H), 1.60-1.57 (m, 2H), 1.54-1.51 (m, 2H), 1.35-1.32 (m, 2H); HRMS (MALDI-TOF): m/z calcd for C, 65; H, 109; N, 5; O, 46P; 1726.5871 found 1772.5817 (M+2Na)+.

IX

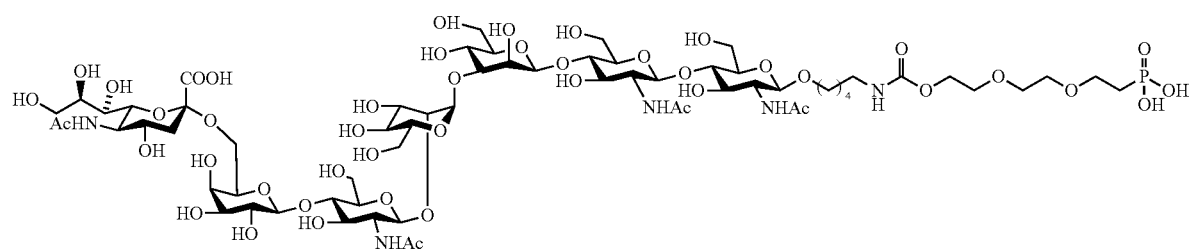

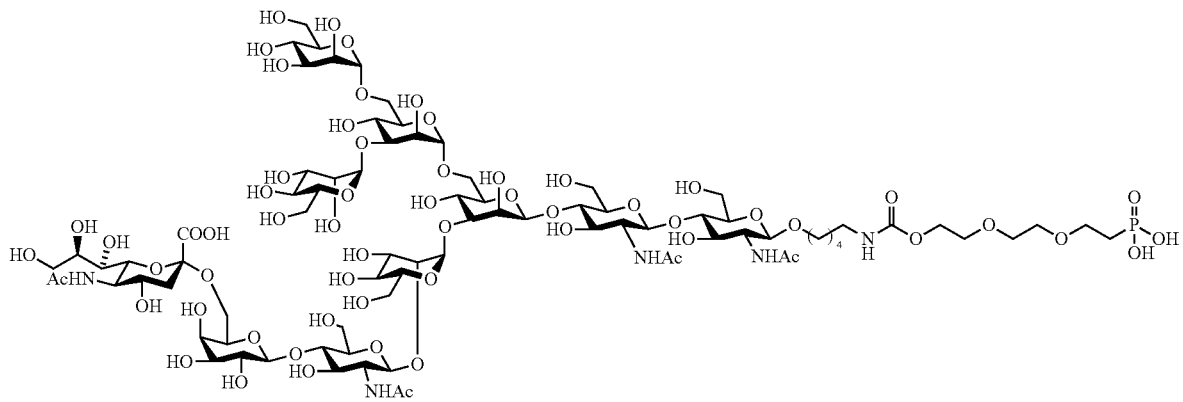

X (Phosphonate-tri-(ethyleneglycol)-carbonylamino)-pentyl-5-Acetamido-3,5-dideoxy-D-glycero-α-D-galacto-2-nonulopyrano-sylonate-(2→6)-β-D-galactopyranosyl-(1→4)-[2-acetamido-2-deoxy-β-D-glucopyranosyl-(1→2)-α-D-mannopyranosyl-(1→3),[di-(α-D-mannopyranosyl)-(1→3),(1→6)-α-D-mannopyranosyl](1→6)-β-D-mannopyranosyl-(1→4)-2-acetamido-2-deoxy-β-D-glucopyranosyl-(1→4)-2-acetamido-2-deoxy-β-D-glucopyranoside (X): Glycan G13 (4.0 mg, 2.3 μmol) was modified by above general procedure to afford compound X (3.2 mg, 71%), as white solid. TLC (MeOH:EA:AcOH: H2O, 7/1/1/1, v/v). 1H NMR (600 MHz, D2O): δ 5.08 (d, J=10.2 Hz, 1H), 5.03 (s, 1H), 4.94 (s, 2H), 4.91 (s, 1H), 4.62 (s, 1H), 4.51 (d, J=6.6 Hz, 1H), 4.46 (d, J=7.8 Hz, 1H), 4.30 (s, 2H), 4.25 (s, 2H), 4.17 (s, 1H), 4.06 (s, 1H), 4.00-3.20 (m, 70H), 2.70 (dd, J=3.2, 7.8 Hz, 1H), 2.11 (s, 6H), 2.05 (s, 6H), 2.03-1.97 (m, 2H), 1.14 (t, J=12.6 Hz, 1H), 1.58-1.51 (m, 4H), 1.36-1.31 (m, 2H). HRMS (MALDI-TOF): m/z calcd for C, 83; H, 144; N, 5; O, 61P; 1102.2301 found 1148.2946 (M+2Na)2−.

nonulopyrano-sylonate-(2→6)-β-D-galactopyranosyl-(1→4)-2-acetamido-2-deoxy-β-D-glucopyranosyl-(1→2)-α-D-mannopyranosyl]-(1→3),(1→6)-β-D-mannopyranosyl-(1→4)-2-acetamido-2-deoxy-β-D-glucopyranosyl-(1→4)-2-acetamido-2-deoxy-β-D-glucopyranoside (XI): Glycan G16 (3.5 mg, 1.5 μmol) was modified by above general procedure to afford compound XI (2.6 mg, 69%) as a white solid. TLC (MeOH:AcOH:H2O, 8/1/1, v/v). 1H NMR (600 MHz, D2O): δ 5.05 (d, J=8.4 Hz, 1H), 4.63 (d, J=6.6 Hz, 1H), 4.51 (s, 1H), 4.46 (t, J=7.8 Hz, 2H), 4.32 (s, 1H), 4.29 (s, 2H), 4.22 (s, 2H), 4.09-3.48 (m, 79H), 3.13 (t, J=7.8 Hz, 2H), 2.74-2.68 (m, 2H), 2.10 (s, 9H), 2.05 (s, 9H), 2.12-2.00 (m, 2H), 1.76-1.73 (m, 2H), 1.58-1.55 (m, 2H), 1.51-1.50 (m, 2H), 1.35-1.29 (m, 2H); HRMS (MALDI-TOF negative mode): m/z calcd for C, 96; H, 162; N, 7; O, 69P; 2547.9096 found 1294.9685 (M+Na) 2−.

Chemo-enzymatic synthesis of D1 and D2/D3 arm modules S

Our chemo-enzymatic strategy commensed with preparation of acceptor substrates 16-20. As depicted in scheme S22

XI

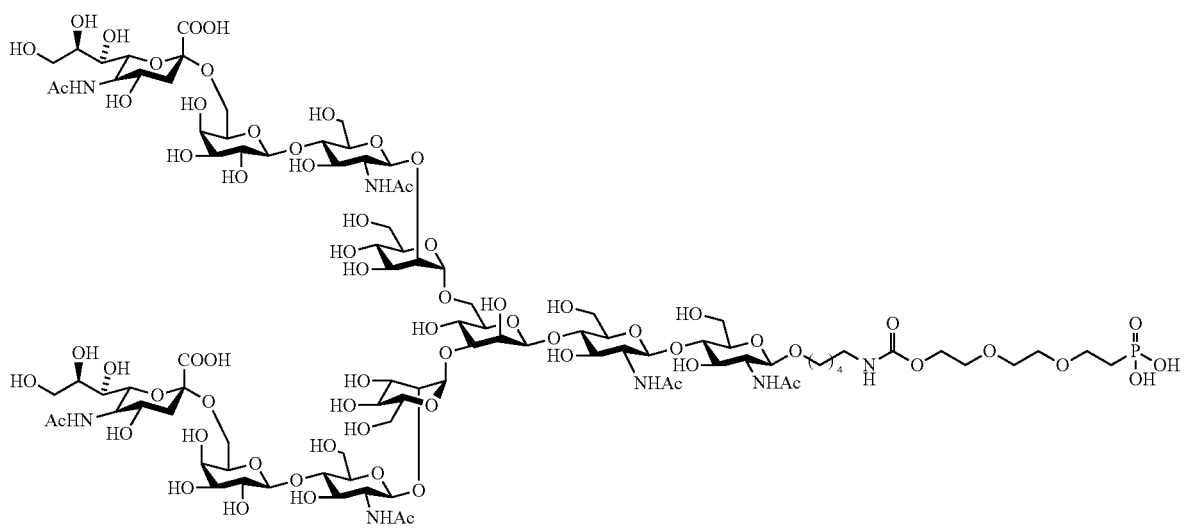

Phosphonate-tri-(ethyleneglycol)-carbonylamino)-pentyl-di-[5-Acetamido-3,5-dideoxy-D-glycero-α-D-galacto-2- in FIG. 141, mannosyl acceptor S22b was glycosylated with donor S22a in the presence of NIS/TfOH to afford the disaccharide S22c in 60% yield. Benzyledine ring of S22c was opened both at 4-OH, S22d or 6-OH, S22g under different reaction conditions. Donor S22e was installed separately at 4-O and 6-O positions of S22d and S22g respectively. Finally, global deprotection of intermediates S22c, S22f and S22h was performed. In case of compounds S22j and S22l, the GlcNAc residues at Man 4 and 6-O positions were differentiated from 2-O GlcNAc through acetylation of 4-OH, for preparation of assymetric modules.

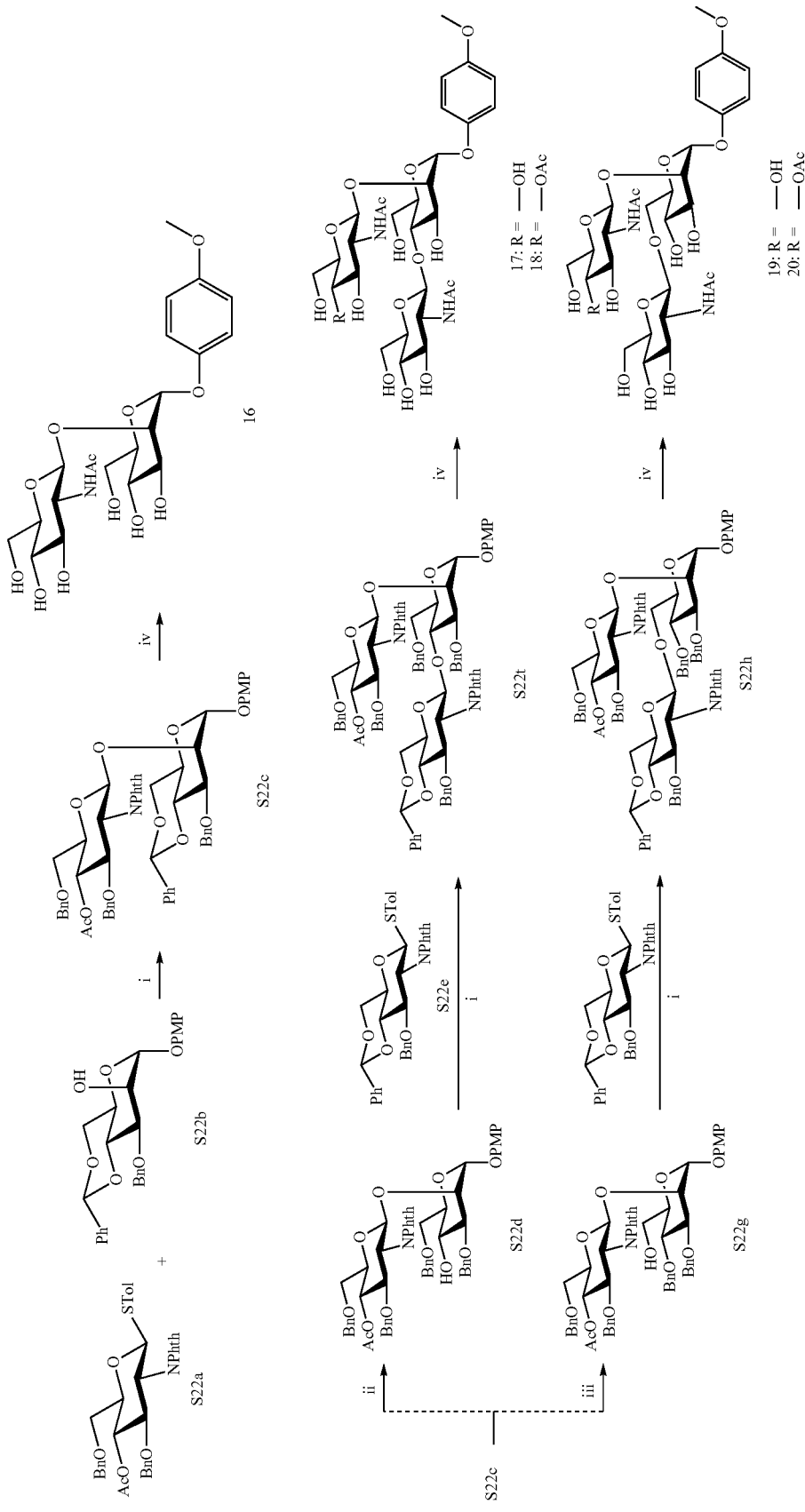

Scheme S22 as shown in FIG. 141 depicts the preparation of acceptor substrates. i, NIS, TfOH, CH2Cl2, −50° C., 3 h; ii, Triethyl silane, TFA, 4 Å MS, CH2Cl2, 0° C., 2 h, 58%; iii, BH3.THF, Bu2BOTf, CH2Cl2, 4 Å MS, −10° C., 1 h, 71%; iv, (1)NH2CH2CH2NH2, nBuOH, 100° C.; (2) Ac2O, pyridine, 0° C. to RT; (3) Pd(OH)2, MeOH:H2O:HCOOH (5:3:2), H2;

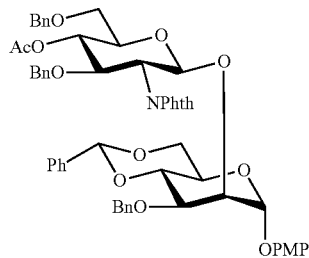

S22c p-methoxyphenyl-O-[4-O-acetyl-3,6-O-di-benzyl-2-de-oxy-2-phthalimido-β-D-glucopyranosyl-(1→2)-O-4,6-O-benzylidene-3-O-benzyl-α-D-mannopyranoside (S22c): Activated 4 Å molecular sieves (1 g) were added to a solution of acceptor S22b (0.250 g, 0.536 mmol) and donor S22a (0.410 g, 0.643 mmol) in anhydrous CH2Cl2 (10 mL). The reaction mixture was stirred for 1 h at rt then cooled to −50° C. NIS (0.241 g, 1.07 mmol) and TfOH (11.8 μL, 0.134 mmol) were added slowly, and the resulting reaction mixture was stirred for 1 h. When TLC (ethyl acetate:toluene, 2/8) indicated formation of product with consumption of starting material, the reaction was quenched by adding Et3N then filtered through Celite. The filtrate was washed with aqueous NaHCO3 (2×50 mL), aqueous Na2S2O3 (2×50 mL), and brine (50 mL) solution. The organic layer was dried over Na2SO4 and concentrated in vacuo. The residue was purified by flash column chromatography (0%→10% EA in toluene) to afford S22c (0.403 g, 76%) as a white foam. TLC (ethyl acetate:toluene=2/8, v/v); Rf=0.49; 1H NMR (400 MHz, CDCl3): δ 7.69-3.56 (m, 4H), 7.36-7.22 (m, 15H), 7.20-6.96 (m, 5H), 6.53 (d, J=8.4 Hz, 2H), 6.50 (d, J=8.2 Hz, 2H), 5.41 (s, 1H), 5.24 (d, J=7.8 Hz, 1H), 5.10 (t, 1H), 4.93 (s, 1H), 4.73-4.43 (m, 10H), 4.00-3.20 (m, 5H), 1.98 (s, 3H); 13C NMR (150 MHz, CHCl3): δ 169.2, 152.3, 135.1, 134.9, 133.9, 128.7, 128.6, 128.4, 128.1, 128.1, 128.0, 127.7, 127.6, 127.5, 117.8, 114.7, 97.1, 96.3, 74.0, 73.9, 73.1, 72.9, 72.8, 72.8, 72.5, 72.2, 71.4, 65.7, 55.4, 54.2, 22.5; ESI-MS: m/z calcd for C, 57; H, 55; NO, 14; 977.3623 found 1000.3490 (M+Na)+.

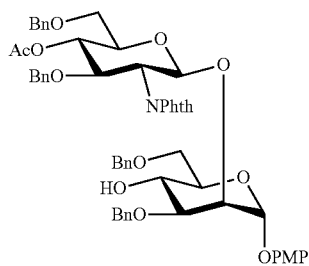

S22d p-methoxyphenyl-O-[4-O-acetyl-3,6-O-di-benzyl-2-de-oxy-2-phthalimido-β-D-glucopyranosyl-(1→2)-O-3,6-O-dibenzyl-α-D-mannopyranoside (S22d): To a solution of S22c (1.01 g, 1.02 mmol) in anhydrous CH2Cl2 (10 mL) was added triethyl silane (1.63 mL, 10.2 mmol) followed by trifluoroacetic acid (0.758 mL, 10.2 mmol) at 0° C. The resulting reaction mixture was stirred for 3 h. After 3 h, TLC (ethyl acetate:toluene, 1.5/8.5 v/v) indicated product formation with consumption of starting material. The reaction mixture was washed with sat. NaHCO3 (2×50 mL). The aqueous layer was further extracted with CH2Cl2 (3×30 mL), and the combined organic layer were washed with brine solution (100 mL), dried over MgSO4, filtered and concentrated in vacuo. The residue was purified by flash column chromatography (0%→10% EA in toluene) to afford S22d (0.580 g, 65%) as clear oil. TLC (ethyl acetate:toluene=1.5/8.5, v/v): Rf=0.35; 1H NMR (400 MHz, CDCl3): δ 7.63-7.35 (m, 4H), 7.30-7.10 (m, 14H), 7.02-6.97 (m, 3H), 6.93-6.86 (m, 3H), 6.72-6.66 (m, 4H), 5.27 (d, J=8.4 Hz, 1H), 5.11 (t, J=10.2 Hz, 1H), 5.02 (d, J=2.8 Hz, 1H), 4.88 (s, 2H), 4.80 (s, 1H), 4.60 (d, J=10.2 Hz, 2H), 4.58-4.24 (m, 6H), 4.01 (s, 2H), 3.79-3.74 (m, 2H), 3.72 (s, 3H), 3.64-3.56 (m, 3H), 3.35 (dd, J=2.8 & 8 Hz, 1H), 2.93 (dd, J=2.3 & 7.8 Hz, 1H), 1.94 (s, 3H); 13C NMR (150 MHz, CHCl3): δ 150.33, 138.18, 137.98, 133.96, 128.70, 128.65, 128.42, 128.18, 128.12, 128.02, 127.76, 127.62, 127.52, 117.89, 114.71, 97.19, 96.33, 74.08, 73.96, 73.10, 72.95, 72.80, 71.86, 70.96, 70.75, 70.48, 67.72, 55.89, 55.69, 21.21; ESI-MS: m/z calcd for C, 57; H, 57; NO, 14; 979.3779 found 1002.3660 (M+Na)+.

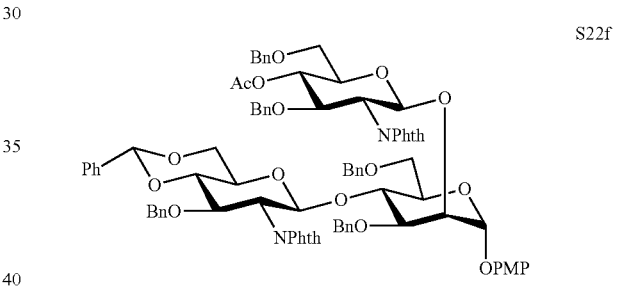

S22f p-methoxyphenyl-O-4-O-acetyl-3,6-O-di-benzyl-2-de-oxy-2-phthalimido-β-D-glucopyranosyl-(1→2)-[-O-4,6-O-benzylidene-3-O-benzyl-2-deoxy-2-phthalimido-β-D-glu-copyranosyl-(1→4)]-3,6-O-di-benzyl-α-D-mannopyranoside (S33f): Activated 4 Å molecular sieves (1 g) were added to a solution of acceptor S22d (0.580 g, 0.590 mmol) and donor S22e (0.525 g, 0.880 mmol) in anhydrous CH2Cl2 (10 mL). The reaction mixture was stirred for 1 h at rt then cooled to −50° C. NIS (0.265 g, 1.14 mmol) and TfOH (13 μL, 0.147 mmol) were added slowly, and the resulting reaction mixture was stirred for 2 h. When TLC (ethyl acetate:toluene, 1.5/8.5) indicated formation of product with consumption of starting material, the reaction was quenched by adding Et3N then filtered through Celite. The filtrate was washed with aqueous NaHCO3 (2×50 mL), aqueous Na2S2O3 (2×50 mL), and brine (50 mL) solution. The organic layer was dried over Na2SO4 and concentrated in vacuo. The residue was purified by flash column chromatography (0%→10% EA in toluene) to afford S22f (0.730 g, 85%) as a pale yellow solid. TLC (ethyl acetate:toluene=1.5/8.5, v/v): Rf=0.60; 1H NMR (400 MHz, CDCl3): δ 7.69-6.67 (m, 8H), 7.59-7.18 (m, 20H), 6.96-6.75 (m, 10H), 6.57-6.52 (m, 4H), 5.44 (s, 1H), 5.27 (d, J=8.4 Hz, 1H), 5.21 (d, J=8.8 Hz, 1H), 5.11 (t, J=10.7 Hz, 1H), 3.29-3.24 (m, 1H), 4.94 (d, J=8.4 Hz, 1H), 4.76-4.69 (m, 2H), 4.57 (d, J=7.8 Hz, 1H), 4.53 (d, J=7.2 Hz, 1H), 4.45-4.19 (m, 9H), 4.10-4.06 (m, 2H), 3.99-3.94 (m, 2H), 3.63 (s, 3H), 3.56-3.48 (m, 8H), 3.00 (dd, J=2.3 and 7.8 Hz, 2H), 1.99 (s, 3H); 13C NMR (150 MHz, CHCl3): δ 169.98, 168.04, 138.94, 138.46, 138.14, 137.96, 133.90, 131.78, 129.24, 128.69, 128.52, 128.34, 128.25, 128.18, 128.08, 127.72, 127.33, 126.38, 123.56, 117.90, 114.47, 101.43, 99.38, 83.11, 78.85, 74.79, 74.27, 73.94, 73.76, 72.80, 72.34, 71.43, 70.26, 69.23, 68.90, 66.00, 56.49, 55.85, 55.70, 21.70; ESI-MS: m/z calcd for C, 85; H, 80; N, 2; O, 20; 1448.5153 found 1471.5156 (M+Na)+.

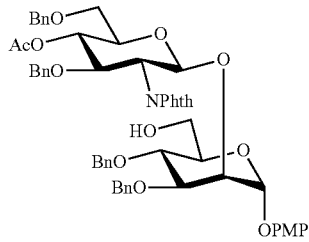

S22g p-methoxyphenyl-O-[4-O-acetyl-3,6-O-di-benzyl-2-de-oxy-2-phthalimido-β-D-glucopyranosyl-(1→2)-O-3,4-O-dibenzyl-α-D-mannopyranoside (S22g): To a mixture of compound S22c (0.800 g, 0.816 mmol) and activated molecular sieves (1 g) in anhydrous CH2Cl2 (10 mL) was added borane. THF complex (0.781 mL of a 1M solution in THF, 8.15 mmol) and Bu2BOTf (0.351 mL of a 1M solution in CH2Cl2, 1.63 mmol) were added at 0° C. The reaction mixture was allowed to stirred at room temperature for 3 h. TLC (acetone:toluene, 1/9) indicated formation of a product with consumption of the starting material. Triethyl amine was added to the reaction mixture followed by slow addition of methanol at 0° C. When no more hydrogen was produced, the reaction mixture was filtered through Celite, The filtrate was washed with aqueous NaHCO3 (2×50 mL), and brine (50 mL) solution. The organic layer was dried over Na2SO4 and concentrated in vacuo. The residue was purified by flash column chromatography (0%→10% EA in toluene) to afford S22g (0.500 g, 62%) as clear foam. TLC (acetone:toluene=2/8, v/v): Rf=0.41; 1H NMR (400 MHz, CDCl3): δ 7.84-7.55 (m, 4H), 7.40-6.90 (m, 10H), 6.87-6.80 (m, 7H), 6.93-6.86 (m, 3H), 6.72-6.66 (m, 4H), 5.27 (d, J=8.4 Hz, 1H), 5.11 (t, J=10.2 Hz, 1H), 5.02 (d, J=2.8 Hz, 1H), 4.88 (s, 2H), 4.80 (s, 1H), 4.60 (d, J=10.2 Hz, 2H), 4.58-4.24 (m, 6H), 4.01 (s, 2H), 3.79-3.74 (m, 2H), 3.72 (s, 3H), 3.64-3.56 (m, 3H), 3.35 (dd, J=2.8 & 8 Hz, 1H), 2.93 (dd, J=2.3 & 7.8 Hz, 1H), 1.94 (s, 3H); 13C NMR (150 MHz, CHCl3): δ 154.2, 138.6, 136.5, 133.5, 128.0, 127.5 127.4, 128.18, 127.1, 127.0, 126.7, 126.6, 126.5, 117.89, 114.71, 97.19, 96.33, 74.08, 73.96, 73.10, 72.9, 72.8, 72.5, 72.6, 71.9, 71.4, 65.7, 56.8, 56.6, 21.9; ESI-MS: m/z calcd for C, 57; H, 57; NO, 14; 979.2640; found 979.2012.

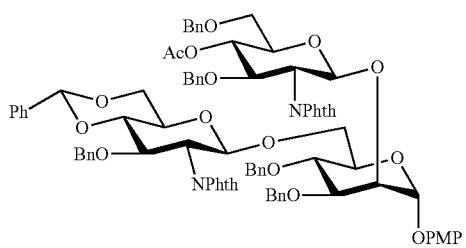

S22h p-methoxyphenyl-O-4-O-acetyl-3,6-O-di-benzyl-2-de-oxy-2-phthalimido-β-D-glucopyranosyl-(1→2)-[-O-4,6-O-benzylidene-3-O-benzyl-2-deoxy-2-phthalimido-β-D-glu-copyranosyl-(1→6)]-3,6-O-di-benzyl-α-D-mannopyranoside (S22h): Activated 4 Å molecular sieves (1 g) were added to a solution of acceptor S22g (0.500 g, 0.509 mmol) and donor S22e (0.452 g, 0.763 mmol) in anhydrous CH2Cl2 (10 mL). The reaction mixture was stirred for 1 h at room temperature then cooled to −50° C. NIS (0.229 g, 1.01 mmol) and TfOH (22 µL, 0.250 mmol) were added slowly, and the resulting reaction mixture was stirred for 1 h. When TLC (ethyl acetate:toluene, 1/9) indicated formation of product with consumption of starting material, the reaction was quenched by adding Et3N then filtered through Celite. The filtrate was washed with aqueous NaHCO3 (2×50 mL), aqueous Na2S2O3 (2×50 mL), and brine (50 mL) solution. The organic layer was dried over Na2SO4 and concentrated in vacuo. The residue was purified by flash column chromatography (0%→10% EA in toluene) to afford S22h (0.610 g, 82%) as a pale yellow solid. TLC (ethyl acetate:toluene=1/9, v/v): 1H NMR (400 MHz, CDCl3): δ 7.75-7.50 (m, 8H), 7.47-7.05 (m, 25H), 7.02-6.82 (m, 10H), 6.66 (d, J=8.5 Hz, 2H), 6.48 (d, J=8.6 Hz, 2H), 5.38 (s, 1H), 5.17 (d, J=8.4 Hz, 1H), 5.21 (t, J=10.3 Hz, 1H), 4.85 (d, J=8.6 Hz, 1H), 3.29-3.24 (m, 1H), 4.94 (d, J=8.4 Hz, 1H), 4.76-4.69 (m, 2H), 4.57 (d, J=7.8 Hz, 1H), 4.53 (d, J=7.2 Hz, 1H), 4.45-4.19 (m, 9H), 4.10-4.06 (m, 2H), 3.99-3.94 (m, 2H), 3.63 (s, 3H), 3.56-3.55 (m, 6H), 3.44-3.25 (m, 2H), 3.00 (t, J=10.3 Hz, 2H), 1.99 (s, 3H); 13C NMR (150 MHz, CHCl3): δ 170.0, 154.9, 150.7, 146.8, 138.6, 137.9, 137.4, 137.1, 136.9, 133.9, 132.7, 129.24, 128.69, 128.52, 128.34, 128.25, 127.9, 127.72, 127.33, 126.38, 123.56, 117.90, 114.47, 101.43, 99.38, 83.11, 78.85, 74.79, 74.27, 73.94, 73.76, 72.80, 72.34, 71.43, 70.26, 69.23, 68.90, 66.00, 58.49, 56.8, 56.7, 55.90, 55.8, 21.8; ESI-MS: m/z calcd for C, 85; H, 80; N, 2; O, 20; 1448.5153 found 1449.5678 (M+H)+.

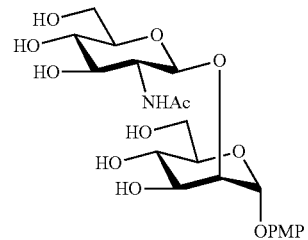

16 p-methoxyphenyl-O-2-acetamido-2-deoxy-β-D-glucopy-ranosyl-(1→2)-α-D-mannopyranoside (16): Compound S22c (0.105 g, 0.107 mmole) was deprotected by following general procedure 2 (method 1) to get the title compound 16 (0.035 g, 66%) as a white solid. 1H NMR (400 MHz, D2O): δ 7.08 (d, J=9.6 Hz, 2H), 6.92 (d, J=9.1 Hz, 2H), 5.43 (s, 1H), 4.60 (d, J=8.4 Hz, 1H), 4.25 (t, J=2.3 Hz, 1H), 4.01 (dd, J=3.2 & 10.1 Hz, 1H), 3.87 (dd, J=3.1 & 12.2 Hz, 1H), 3.80 (dd, J=3.0 & 12.8 Hz, 1H), 3.78 (s, 3H), 3.72-3.67 (m, 3H), 3.61-3.52 (m, 3H), 3.46-3.40 (m, 2H), 1.99 (s, 3H), 13C NMR (150 MHz, D2O): δ 174.64, 170.85, 154.46, 149.57, 118.60, 114.83, 99.57, 96.50, 76.24, 75.67, 73.35, 73.10, 69.67, 69.28, 66.90, 61.14, 60.40, 55.55, 55.20; ESI-MS: m/z calcd for C, 21; H, 31; NO, 1; 489.1738 found 512.1715 (M+Na)+.

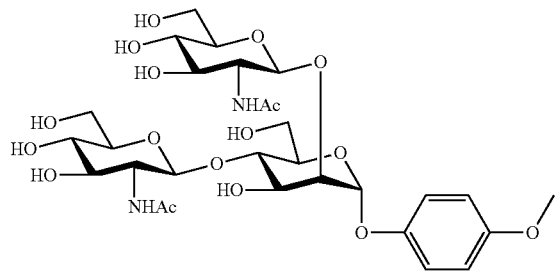

17

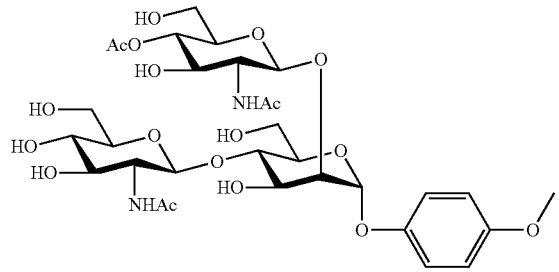

19 p-methoxyphenyl-O-di-(2-acetamido-2-deoxy-β-D-glucopyranosyl)-(1→2),(1→4)-α-D-mannopyranoside (17): Compound S22f (0.125 g, 0.086 mmole) was deprotected by following general procedure 2 (method 1) to get the title compound 17 (0.42 g, 66%) as a white solid. 1H NMR (400 MHz, D2O): δ 7.10 (d, J=8.8 Hz, 2H), 7.08 (d, J=8.2 Hz, 2H), 5.39 (s, 1H), 4.53 (d, J=8.2 Hz, 1H), 4.50 (d, J=7.8 Hz, 1H), 4.25 (s, 1H), 4.20 (d, J=7.8 Hz, 1H), 4.00 (dd, J=3.2 and 7.2 Hz, 1H), 3.71 (s, 3H), 3.67-3.74 (m, 9H), 2.02 (s, 3H), 1.91 (s, 3H); 13C NMR (150 MHz, D2O): δ 174.48, 147.04, 154.49, 149.86, 118.53, 114.97, 100.80, 99.64, 96.55, 76.40, 75.71, 75.66, 73.74, 73.01, 72.63, 69.74, 69.27, 69.19, 67.32, 60.72, 60.60, 60.45, 59.05, 55.62, 55.34, 55.22, 22.24, 22.01; ESI-MS: m/z calcd for C, 29; H, 44; N, 2; O, 17; 693.2713 found 693.2688 (M+H)+.

18

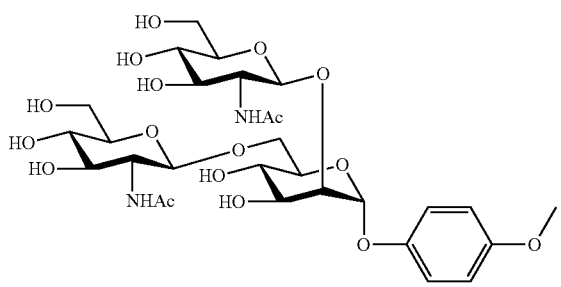

p-methoxyphenyl-O-di-(2-acetamido-2-deoxy-β-D-glucopyranosyl)-(1→2),(1→6)-α-D-mannopyranoside (18): Compound S22h (0.200 g, 0.138 mmole) was deprotected by following general procedure 2 (method 1) to get the title compound 18 (0.60 g, 63%) as a white solid. 1H NMR (400 MHz, D2O): δ 7.10 (d, J=8.8 Hz, 2H), 6.96 (d, J=8.2 Hz, 2H), 5.44 (s, 1H), 4.60 (d, J=7.5 Hz, 1H), 4.52 (d, J=7.3 Hz, 1H), 4.31 (s, 1H), 4.18 (d, J=2.8 Hz, 1H), 3.90 (t, J=10.7 Hz, 2H), 3.80 (s, 3H), 3.77-3.70 (m, 7H), 3.56-3.44 (m, 8H), 2.02 (s, 6H); 13C NMR (150 MHz, CHCl3): δ 172.7, 171.9, 157.9, 150.3, 118.5, 114.9, 100.2, 99.4, 99.0, 75.74, 74.2, 73.9, 72.1, 70.3, 68.7, 68.3, 68.2, 55.9, 55.6, 55.1, 20.1; ESI-MS: m/z calcd for C, 29; H, 44; N, 2; O, 17; 692.2532 found 715.2518 (M+Na)+.

p-methoxyphenyl-O-(4-O-acetyl-2-acetamido-2-deoxy-β-D-glucopyranosyl)-(1→2)-O-(2-acetamido-2-deoxy-β-D-glucopyranosyl)-(1→4)-α-D-mannopyranoside (19): A mixture of S22f (0.610 g, 0.421 mmol) and 10 mL of ethylene diamine:nBuOH (1:4) was stirred at 90° C. for overnight. Volatiles were then evaporated and the crude product was reacted with 10 mL Ac2O/pyridine (1:2) for overnight. The solvents were removed using high vacuum and product was purified by flash column chromatography (acetone:toluene, 2/8, v/v). The product was dissolved in 10 mL MeOH:H2O:HCOOH (6:3:1), Pd(OH)2 (50% by weight) was added and the reaction mixture was hydrogenated for overnight. The reaction mixture was filtered through Celite and concentrated in vacuo. The residue was purified by Bio-Gel P-2 (BIO-RAD) column chromatography using water as eluent, and the product was the lyophilized to get 19 (0.210 g, 67%) as a white color powder. 1H NMR (400 MHz, D2O): δ 7.01 (d, J=9.2 Hz, 2H), 6.90 (d, J=9.8 Hz, 2H), 5.40 (s, 1H), 4.61 (d, J=8.0 Hz, 1H), 4.52 (d, J=8.4 Hz, 1H), 4.25 (d, J=2.1 Hz, 1H), 4.73 (dd, J=1.2 & 7.2 Hz, 1H), 3.92 (d, J=12.3 Hz, 1H), 3.74 (s, 3H), 3.72-3.67 (m, 8H), 3.60-3.41 (m, 7H), 2.12 (s, 3H), 2.03 (s, 6H); 13C NMR (150 MHz, D2O): δ 174.67, 174.17, 172.91, 154.43, 149.58, 118.53, 114.81, 101.48, 99.70, 96.04, 77.51, 76.00, 75.75, 73.50, 73.39, 71.74, 71.06, 70.93, 69.57, 69.34, 68.04, 60.58, 60.47, 60.00, 55.55, 55.39, 55.13, 22.24, 21.95, 20.17, 20.03; ESI-MS: m/z calcd for C, 31; H, 46; N, 2; O, 18; 735.2818 found 735.2780 (M+H)+.

20

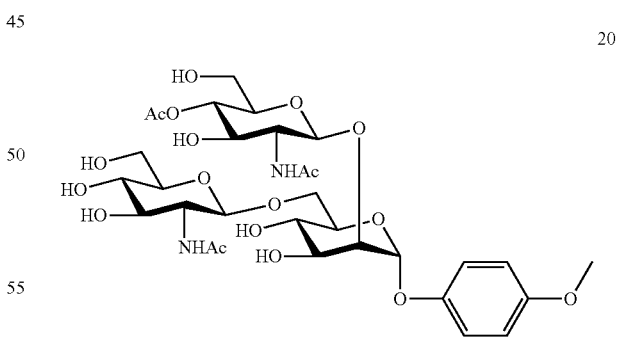

p-methoxyphenyl-O-(4-O-acetyl-2-acetamido-2-deoxy-2-D-glucopyranosyl)-(1→2)-O-(2-acetamido-2-deoxy-β-D-glucopyranosyl)-(1→6)-α-D-mannopyranoside (20): A mixture of S22h (0.350 g, 0.241 mmol) and 10 mL of ethylene diamine:nBuOH (1:4) was stirred at 90° C. for overnight. Volatiles were then evaporated and the crude product was reacted with 10 mL Ac2O/pyridine (1:2) for overnight. The solvents were removed using high vacuum and product was purified by flash column chromatography (acetone:toluene, 2/8, v/v). The product was dissolved in 10 mL MeOH:H2O:HCOOH (6:3:1), Pd(OH)2 (50% by weight) was added and the reaction mixture was hydrogenated for overnight. The reaction mixture was filtered through Celite and concentrated in vacuo. The residue was purified by Bio-Gel P-2 (BIO-RAD) column chromatography using water as eluent, and the product was the lyophilized to get 20 (0.120 g, 70%) as a white color powder. 1H NMR (400 MHz, D2O): δ 7.08 (d, J=8.4 Hz, 2H), 6.91 (d, J=8.2 Hz, 2H), 5.38 (s, 1H), 4.66 (d, J=8.0 Hz, 1H), 4.48 (d, J=8.2 Hz, 1H), 4.38-4.27 (m, 2H), 4.19 (t, J=2.8 Hz, 1H), 4.09 (d, J=12.2 Hz, 1H), 3.98 (dd, J=2.8 and 7.8 Hz, 1H), 3.84 (d, J=12.3 Hz, 2H), 3.75 (s, 3H), 3.67-3.33 (m, 11H), 1.93 (s, 3H), 1.91 (s, 3H), 1.78 (s, 3H); 13C NMR (150 MHz, D2O): δ 174.41, 173.93, 173.75, 154.47, 149.86, 118.53, 118.48, 114.93, 100.84, 99.71, 96.50, 76.76, 75.66, 73.75, 73.27, 72.74, 72.60, 69.76, 69.47, 69.24, 69.12, 67.28, 62.94, 60.62, 55.60, 55.32, 55.22, 22.30, 22.06, 20.03; ESI-MS: m/z calcd for C, 31; H, 46; N, 2; O, 18; 735.2818 found 735.2769 (M+H)+.

Preparation of Linear Module. As depicted in scheme S23 in FIG. 152, the preparation of linear modules was commensed with enzymatic β-1,4-galactosylation of GlcNAc residue of acceptor 16 to form LacNAc moiety 21. Modules 21 was then underwent action of α-1,3-fucosyltransferase, α-2,6-sialyltransferase, α-2,3-sialyltransferase, and α-1,3-fucosyltransferase to obtain modules 22, 23, 24, and 25 respectively. Presence of α-1,3 fucose residue on GlcNAc restrict addition of sialic acid on adjacent galactose at both 3 and 6 positions. Interestingly, α-2,3-sialylated LacNAc 24 was found to be the substrate of α-1,3-fucosyltransferase to get 25, but not the α-2,6-sialylated LacNAc 23. More striking to us was the α-1,2-fucosylated LacNAc 26 was the substrate of α-2,6-sialyltransferase, but not of α-2,3-sialyltransferase. Unique substrate specificities of FucTs and SiaTs allowed us to establish a rapid access to more diverse type of modules for N-glycan synthesis.

Scheme S23 as shown in FIG. 152 depicts the preparation of linear modules. i, UDP-galactose, β1,4-GalT; ii, GDP-fucose, α1,3-FucT; iii, CMP-Neu5Ac, α2,6-SiaT; iv, CMP-Neu5Ac, α2,3-SiaT; v, GDP-fucose, α1,2-FucT.

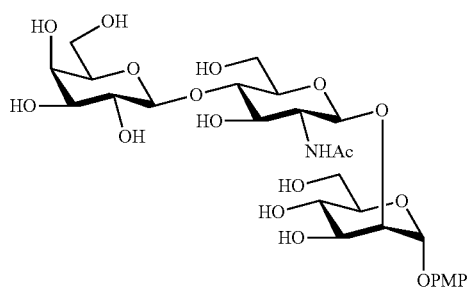

21 p-methoxyphenyl-O-β-D-galactopyranosyl-(1→4)-2-acetamido-2-deoxy-β-D-glucopyranosyl-(1→2)-α-D-mannopyranoside (21): Compound 16 (100 mg, 0.204 mmol) was galactosylated by using general procedure 4 to get 21 (115 mg, 86%) as amorphous white solids. 1H NMR (400 MHz, D2O): δ 7.10 (d, J=8.8 Hz, 2H), 6.96 (d, J=8.1 Hz, 2H), 5.44 (s, 1H), 4.59 (d, J=8.4 Hz, 1H), 4.49 (d, J=8.2 Hz, 1H), 4.45 (s, 1H), 4.00-3.75 (m, 17H), 3.60 (s, 3H), 2.01 (s, 3H); ESI-MS: m/z calcd for C, 27; H, 41; NO, 17; 652.2447 found 674.2262 (M+H)+.

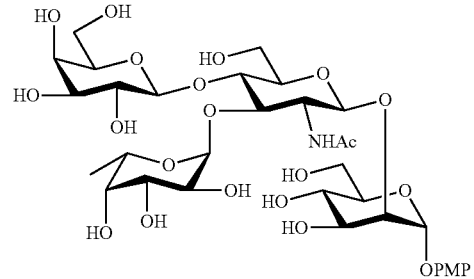

22 p-methoxyphenyl-O-β-D-galactopyranosyl-(1→4)-[α-L-fucopyranosyl-(1→3)-2-acetamido-2-deoxy-β-D-glucopyranosyl]-(1→2)-α-D-mannopyranoside (22): Compound 21 (80 mg, 0.122 mmol) was fucosylated by using general procedure 5 to afford 22 (82 mg, 84%) as white solid after lyophilization. 1H NMR (400 MHz, D2O): δ 7.15 (d, J=9.2 Hz, 2H), 7.00 (d, J=9.1 Hz, 2H), 5.45 (s, 1H), 5.12 (d, J=4.1 Hz, 1H), 4.67 (d, J=7.8 Hz, 2H), 4.44 (d, J=8.4 Hz, 1H), 4.05 (s, 1H), 4.01 (dd, J=3.2 and 7.8 Hz, 1H), 3.98 (t, J=10.2 Hz, 2H), 3.80-3.70 (m, 6H), 3.79 (s, 3H), 3.70-3.40 (m, 11H), 2.06 (s, 3H), 1.18 (d, J=6.4 Hz, 3H); ESI-MS: m/z calcd for C, 33; H, 51; NO, 21; 797.7570 found 820.2837 (M+Na)+.

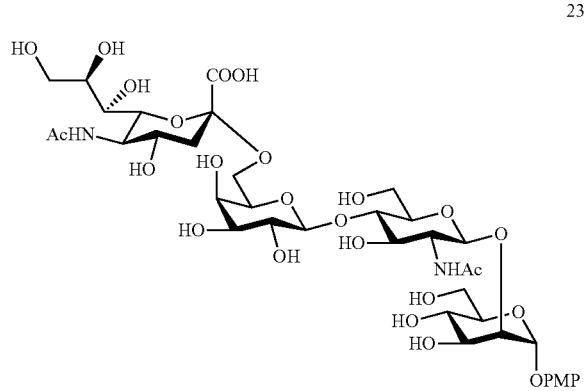

23 p-methoxyphenyl-O-[5-Acetamido-3,5-dideoxy-D-glycero-α-D-galacto-2-nonulopyrano-sylonate-(2→6)-β-D-galactopyranosyl-(1→4)-2-acetamido-2-deoxy-β-D-glucopyranosyl-(1→2)-α-D-mannopyranoside (23): Compound 21 (150 mg, 0.184 mmol) was α2,6-sialylated by using general procedure 3 to afford 23 (169 mg, 90%) as white solid after lyophilization. 1H NMR (400 MHz, D2O): δ 7.10 (d, J=9.2 Hz, 2H), 7.08 (d, J=9.1 Hz, 2H), 5.49 (s, 1H), 4.64 (d, J=8.1 Hz), 1H), 4.40 (d, J=8.2 Hz, 1H), 4.26 (t, J=2.1 Hz, 1H), 4.01-3.80 (m, 7H), 3.74 (s, 3H), 3.66-3.58 (m, 20H), 2.63 (dd, J=4.4 and 12.8 Hz, 1H), 2.07 (s, 3H), 1.97 (s, 3H), 1.68 (t, 1H); ESI-MS: m/z calcd for C, 38; H, 58; N, 2; O, 25; 942.3245 found 941.3269 (M–H)–.

24

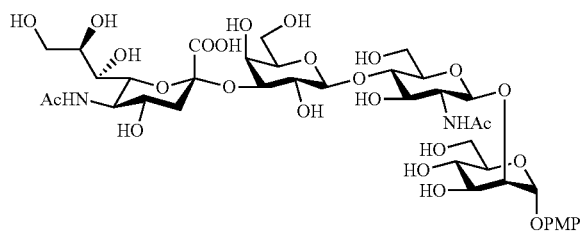

p-methoxyphenyl-O-[5-Acetamido-3,5-dideoxy-D-glycero-α-D-galacto-2-nonulopyrano-sylonate-(2→3)-β-D-galactopyranosyl-(1→4)-2-acetamido-2-deoxy-β-D-glucopyranosyl-(1→2)-α-D-mannopyranoside (24): Compound 21 (10 mg, 15.3 μmol) was α2,3-sialylated by using general procedure 3 to afford 24 (11.5 mg, 80%) as white solid after lyophilization. 1H NMR (400 MHz, D2O): δ 7.16 (d, J=9.2 Hz, 2H), 7.03 (d, J=9.5 Hz, 2H), 5.49 (s, 1H), 4.67 (d, J=8.4 Hz, 1H), 4.56 (d, J=8.4 Hz, 1H), 4.32 (t, J=2.1 Hz, 1H), 4.15 (dd, J=3.2 & 7.5 Hz, 1H), 4.10-3.98 (m, 4H), 3.95-3.85 (m, 6H), 3.84 (s, 3H), 3.80-3.50 (m, 13H), 2.79 (dd, J=4.8 and 12.1 Hz, 1H), 2.09 (s, 3H), 2.07 (s, 3H), 1.85 (t, 1H); ESI-MS: m/z calcd for C, 38; H, 58; N, 2; O, 25; 942.3245 found 941.3312 (M−H)−.

25

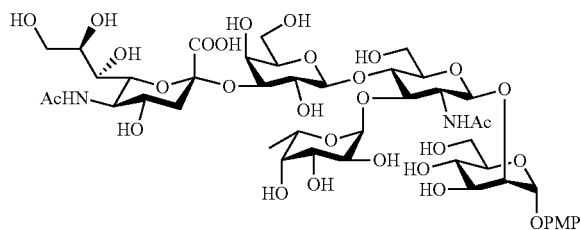

p-methoxyphenyl-O-[5-Acetamido-3,5-dideoxy-D-glycero-α-D-galacto-2-nonulopyrano-sylonate-(2→3)-β-D-galactopyranosyl-(1→4)-[α-L-fucopyranosyl-(1→3)-2-acetamido-2-deoxy-β-D-glucopyranosyl]-(1→2)-α-D-mannopyranoside (25): Compound 24 (8 mg, 8.5 μmol) was fucosylated by using general procedure 5 to afford 25 (6.5 mg, 70%) as white solid after lyophilization. 1H NMR (400 MHz, D2O): δ 7.14 (d, J=6.8 Hz, 2H), 6.98 (d, J=7.2 Hz, 2H), 5.46 (s, 1H), 5.12 (d, J=4.2 Hz, 1H), 4.67 (d, J=8.4 Hz, 1H), 4.30 (t, J=2.3 Hz, 1H), 4.10 (dd, J=3.0 & 7.8 Hz, 1H), 4.00-3.80 (m, 14H), 3.79 (s, 3H), 3.75-3.50 (m, 13H), 2.75 (dd, J=4.0 and 12.0 Hz, 1H), 2.03 (s, 3H), 2.01 (s, 3H), 1.76 (t, 1H), 1.17 (d, 3H, Fuc-Me); ESI-MS: m/z calcd for C, 44; H, 68; N, 2; O, 2 9; 1088.3857 found 1087.3850 (M−H)−.

26

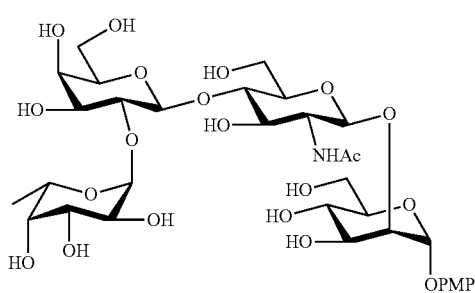

p-methoxyphenyl-O-[α-L-fucopyranosyl-(1→2)-β-D-galactopyranosyl]-(1→4)-2-acetamido-2-deoxy-β-D-glucopyranosyl]-(1→2)-α-D-mannopyranoside (26): Compound 21 (3 mg, 4.6 μmol) was fucosylated by using general procedure 5 to afford 26 (2.1 mg, 53%) as white solid after lyophilization. 1H NMR (400 MHz, D2O): δ 7.17 (d, J=7.2 Hz, 2H), 7.01 (d, J=10.1 Hz, 2H), 5.49 (s, 1H), 5.33 (s, 1H), 4.67 (d, J=8.2 Hz, 1H), 4.56 (d, J=8.2 Hz, 1H), 4.33 (m, 1H), 4.25 (q, 1H), 3.98 (dd, J=3.1 and 7.2 Hz, 1H), 3.96 (dd, J=1.8 and 7.2 Hz, 1H), 3.85-3.50 (m, 20H), 3.40 (m, 1H), 1.97 (s, 3H), 1.14 (d, J=6.4 Hz, 3H); ESI-MS: m/z calcd for C, 33; H, 51; NO, 21; 797.2954 found 820.2922 (M+Na)+.

27

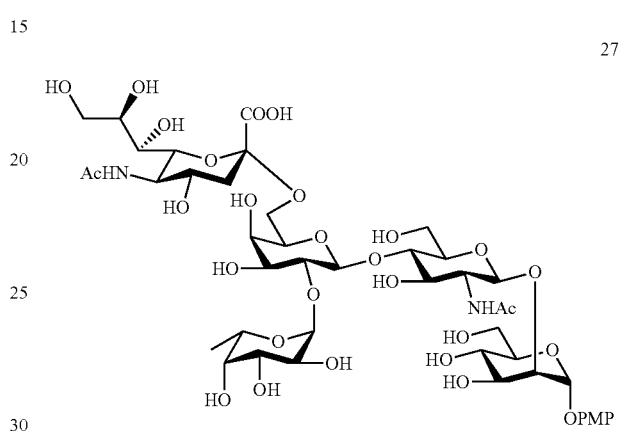

p-methoxyphenyl-O-[5-Acetamido-3,5-dideoxy-D-glycero-α-D-galacto-2-nonulopyrano-sylonate-(2→6)-[α-L-fucopyranosyl-(1→2)-β-D-galactopyranosyl]-(1→4)-2-acetamido-2-deoxy-β-D-glucopyranosyl]-(1→2)-α-D-mannopyranoside (27): Compound 26 (2.0 mg, 2.7 μmol) was α2,6-sialylated by using general procedure 3 to afford 27 (1.8 mg, 66%) as white solid after lyophilization. 1H NMR (400 MHz, D2O): δ 7.08 (d, J=9.5 Hz, 2H), 6.91 (d, J=9.2 Hz, 2H), 5.49 (s, 1H), 5.27 (s, 1H), 4.59 (d, J=8.2 Hz, 1H), 4.47 (d, J=8.1 Hz, 1H), 4.22 (bs, 1H), 4.12 (d, J=6.8 Hz, 1H), 4.00-3.49 (m, 30H), 2.63 (dd, J=3.2 and 12.0 Hz, 1H), 2.01 (s, 3H), 1.97 (s, 3H), 1.67 (t, 1H), 1.19 (d, 3H, Fuc-Me); ESI-MS: m/z calcd for C, 44; H, 68; N, 2; O, 29; 1088.3857 found 1087.3814 (M−H)−.

Preparation of symmetrically branched modules as shown in FIG. 160.

i, β-1,4 GalT, UDP-Gal; ii, α1,3-fucosyltransferase, GDP-fucose; iii, α2,6-sialyltransferase, CMP-β-D-Sialic acid.

28

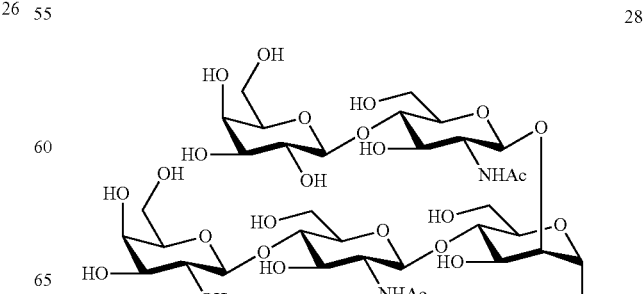

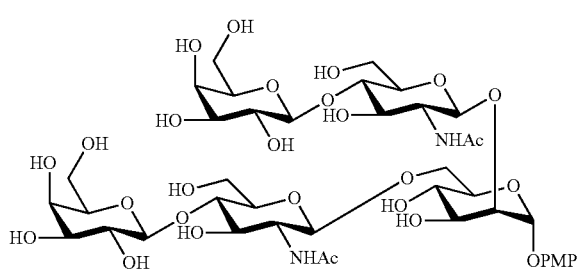

29

Compound 28 and 29: Compound 17 (10 mg, 14.3 μmol) and 18 (10 mg, 14.3 μmol) were galactosylated by using general procedure 4 to get 28 (10 mg, 71%) and 29 (9 mg, 61%) as amorphous white solids.

p-methoxyphenyl-O-di-[β-D-galactopyranosyl-(1→4)-2-acetamido-2-deoxy-β-D-glucopyranosyl]-(1→2), (1→4)-α-D-mannopyranoside (28): 1H NMR (400 MHz, D2O): δ 7.11 (d, J=9.2 Hz, 2H), 6.95 (d, J=8.5 Hz, 2H), 5.44 (s, 1H), 4.65 (d, J=8.9 Hz, 1H), 4.58 (d, J=9.2 Hz, 1H), 4.45 (dd, J=3.8 & 9.2 Hz, 2H), 4.30 (t, J=2.1 & 6.5 Hz, 1H), 4.18 (dd, J=3.2 & 7.8 Hz, 1H), 4.00 (t, J=10.8 Hz, 2H), 3.90 (d, J=8.2 Hz, 2H), 3.78 (s, 3H), 3.75-3.64 (m, 20H), 3.58-3.49 (m, 4H), 2.02 (s, 3H), 2.01 (s, 3H); ESI-MS: m/z calcd for C, 41; H, 64; N, 2; O, 27; 1016.9564 found 1039.3607 (M+Na)+.

p-methoxyphenyl-O-di-[β-D-galactopyranosyl-(1→4)-2-acetamido-2-deoxy-β-D-glucopyranosyl]-(1→2),(1→6)-α-D-mannopyranoside (29): 1H NMR (400 MHz, D2O): δ 7.02 (d, J=9.0 Hz, 2H), 6.92 (d, J=9.0 Hz, 2H), 5.32 (s, 1H), 4.55 (d, J=4.3 Hz, 1H), 4.41 (d, J=8.2 Hz, 1H), 4.34 (dd, J=13.1, 7.9 Hz, 2H), 4.16 (s, 1H), 4.00 (d, J=11.0 Hz, 1H), 3.84-3.95 (m, 2H), 3.70-3.81 (m, 9H), 3.49-3.68 (m, 16H), 3.37-3.44 (m, 4H), 1.94 (s, 3H), 1.82 (s, 3H); ESI-MS: m/z calcd for C, 41; H, 64; N, 2; NaO, 27; 1039.3594 found 1039.3551.

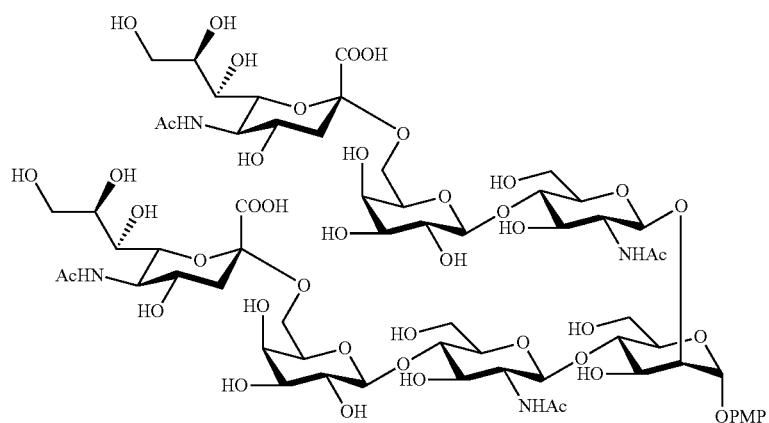

30

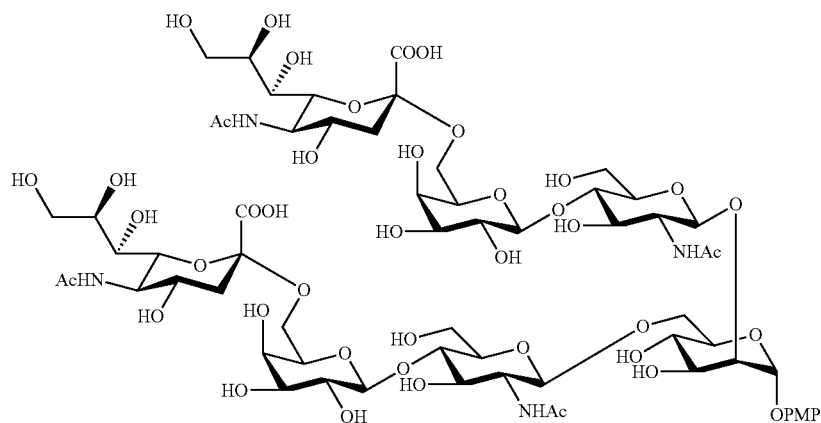

31

Compound 30 and 31: Compound 28 (8 mg, 7.3 μmol) and 29 (8 mg, 7.3 μmol) were sialylated by using general procedure 3 to afford 30 (9 mg, 78%) and 31 (7.5 mg, 65%) as a white solid after lyophilization.

p-methoxyphenyl-O-di-[5-Acetamido-3,5-dideoxy-D-glycero-α-D-galacto-2-nonulopyrano-sylonate-(2→6)-β-D-galactopyranosyl-(1→4)-2-acetamido-2-deoxy-β-D-glucopyranosyl]-(1→2),(1→4)-α-D-mannopyranoside (30): 1H NMR (400 MHz, D2O): δ 7.12 (d, J=9.8 Hz, 2H), 6.98 (d, J=9.3 Hz, 2H), 5.46 (s, 1H), 4.63 (d, J=8.4 Hz, 1H), 4.58 (d, J=8.2 Hz, 1H), 4.42 (d, J=7.8 Hz, 2H), 4.32 (t, J=3.2 Hz, 1H), 4.20 (dd, J=3.2 & 7.2 Hz, 1H, 4.03-3.85 (m, 4H), 3.82-3.40 (m, 43H), 2.58 (dd, 2H, J=3.2 & 10.3 Hz), 2.05 (s, 3H), 2.04 (s, 3H), 2.02 (s, 3H), 2.00 (s, 3H), 1.53 (m, 2H); ESI-MS: m/z calcd for C, 63; H, 98; N, 4; O, 43; 1599.4620 found 798.2775 (M−H)2−.

p-methoxyphenyl-O-di-[5-Acetamido-3,5-dideoxy-D-glycero-α-D-galacto-2-nonulopyrano-sylonate-(2→6)-β-D-galactopyranosyl-(1→4)-2-acetamido-2-deoxy-β-D-glucopyranosyl]-(1→2), (1→5)-α-D-mannopyranoside (31): 1H NMR (600 MHz, D2O): δ 7.05 (d, J=9.2 Hz, 2H), 6.95 (d, J=9.2 Hz, 2H), 5.36 (d, J=1.6 Hz, 1H), 4.59 (d, J=8.2 Hz, 1H), 4.46 (d, J=8.1 Hz, 1H), 4.36 (d, J=7.9 Hz, 1H), 4.32 (d, J=7.9 Hz, 1H), 4.20 (dd, J=3.4, 1.8 Hz, 1H), 4.06 (d, J=10.3 Hz, 1H), 3.86-3.98 (m, 4H), 3.64-3.86 (m, 19H), 3.53-3.62 (m, 13H), 3.37-3.50 (m, 9H), 2.58 (ddd, J=12.0, 4.4, 2.1 Hz, 2H), 1.98 (s, 3H), 1.94 (s, 3H), 1.94 (s, 3H), 1.87 (s, 3H), 1.63 (td, J=12.2, 8.6 Hz, 2H); ESI-MS: m/z calcd for C, 63; H, 98; N, 4; NaO, 43; 1621.5479 found 1621.5473.

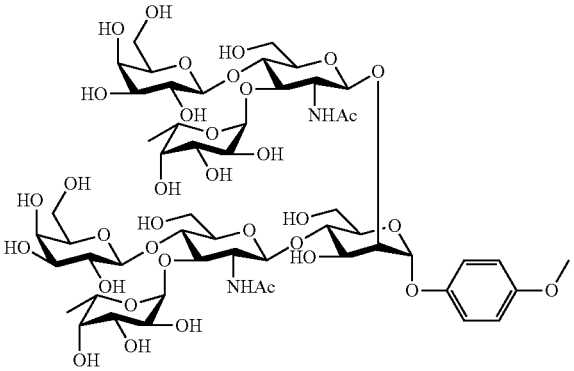

32 p-methoxyphenyl-O-di-{β-D-galactopyranosyl-(1→4)-[α-L-fucopyranosyl-(1→3)-2-acetamido-2-deoxy-β-D-glucopyranosyl]}-(1→2),(1→4)-α-D-mannopyranoside (32): Compound 28 (15 mg, 14.7 μmol) was fucosylated by using general procedure 5 to get 32 (14 mg, 73%) as amorphous white solids. 1H NMR (400 MHz, D2O): δ 7.13 (d, J=9.2 Hz, 2H), 6.99 (d, J=9.0 Hz, 2H), 5.44 (d, J=3.2 Hz, 1H), 5.12 (d, J=4.1 Hz, 1H), 5.10 (d, J=4.0 Hz, 1H), 4.81 (d, J=8.4 Hz, 2H), 4.68 (d, J=7.4 Hz, 1H), 4.58 (d, J=7.2 Hz, 1H), 4.45 (dd, J=3.2 & 8.4 Hz, 2H), 4.31 (t, J=3.2 Hz, 1H), 4.20 (dd, J=3.2 & 8.4 Hz, 1H), 4.09-3.84 (m, 14H), 3.82 (s, 3H), 3.80-3.40 (m, 14H), 2.06 (s, 6H), 1.17 (d, J=6.4 Hz, 6H); ESI-MS: m/z calcd for C, 53; H, 84; N, 2; O, 35; 1308.4855 found 1309.4911 (M+H)+.

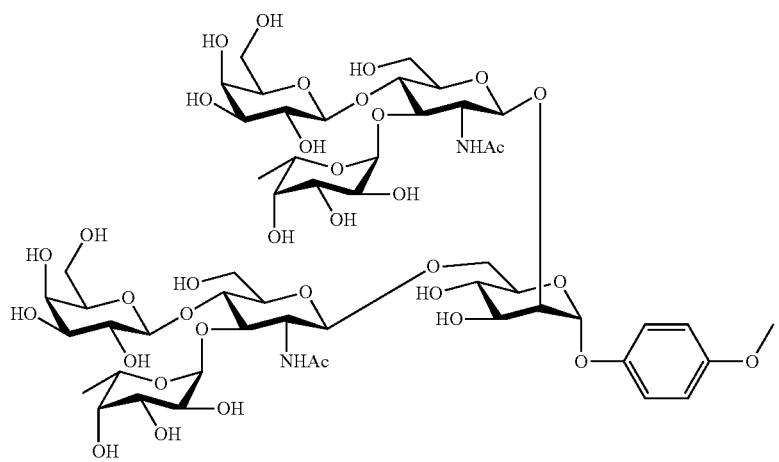

33 p-methoxyphenyl-O-di-{β-D-galactopyranosyl-(1→4)-[α-L-fucopyranosyl-(1→3)-2-acetamido-2-deoxy-β-D-glucopyranosyl]}-(1→2),(1→6)-α-D-mannopyranoside (33): Compound 29 (15 mg, 14.7 μmol) was fucosylated by using general procedure 5 to get 33 (15.5 mg, 81%) as amorphous white solids. 1H NMR (400 MHz, D2O): δ 7.17 (d, J=8.2 Hz, 2H), 7.06 (d, J=8.0 Hz, 2H), 5.42 (s, 1H), 5.14 (d, J=4.0 Hz, 1H), 5.09 (d, J=4.0 Hz, 1H), 4.87-4.85 (m, 2H), 4.60 (d, J=7.2 Hz, 1H), 4.56 (q, 2H), 4.30 (m, 1H), 4.15 (d, J=12.2 Hz, 1H), 4.06 (dd, J=3.2 & 7.8 Hz, 1H), 4.00-3.45 (m, 37), 2.06 (s, 3H), 1.95 (s, 3H), 1.19 (d, J=6.5 Hz, 6H); ESI-MS: m/z calcd for C, 53; H, 84; N, 2; O, 35; 1308.4855 found 1331.3561 (M+Na)+.

Preparation of asymmetrically branched module.

Scheme S25 as shown in FIG. 165 depicts the preparation of assymetric module. UDP-galactose, β1,4-GaT; ii, GDP-fucose α1,3-FucT; iii, CMP-Neu5Ac, α2,6-SiaT; vi, NaOH.

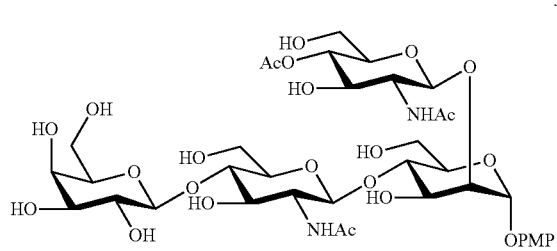

34 p-methoxyphenyl-O-(4-O-acetyl-2-acetamido-2-deoxy-β-D-glucopyranosyl)-(1→2)-O-(β-D-galactopyranosyl-(1→4)-O-2-acetamido-2-deoxy-β-D-glucopyranosyl)-(1→4)-α-D-mannopyranoside (34): Compound 19 (15 mg, 20.4 μmol) was galactosyalated using general procedure 4 to afford the 34 (12.5 mg, 68%) as amorphous white solids. 1H NMR (600 MHz, D2O) δ 7.01 (d, J=9.2 Hz, 2H), 6.88 (d, J=9.2 Hz, 1H), 5.34 (d, J=1.8 Hz, 1H), 4.56 (d, J=8.5 Hz, 1H), 4.45 (d, J=8.1 Hz, 1H), 4.37 (d, J=7.7 Hz, 1H), 4.20-4.33 (m, 2H), 4.16-4.20 (m, 1H), 4.07 (dd, J=8.7, 3.0 Hz, 1H), 3.86-3.94 (m, 1H), 3.81 (d, J=3.4 Hz, 1H), 3.31-3.78 (m, 21H), 2.03 (s, 3H), 1.93 (s, 3H), 1.92 (s, 3H); ESI-MS: m/z calcd for C, 37; H, 56; N, 2; NaO, 23; 919.9166 found 919.3156.

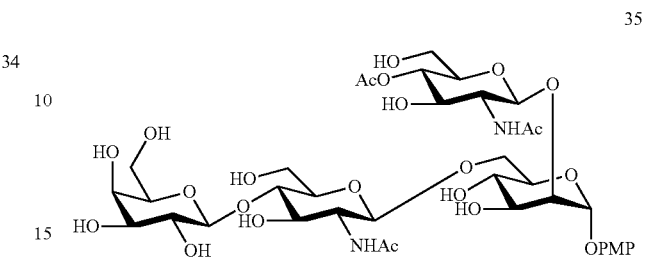

35 p-methoxyphenyl-O-(4-O-acetyl-2-acetamido-2-deoxy-β-D-glucopyranosyl)-(1→2)-O-(β-D-galactopyranosyl-(1→4)-O-2-acetamido-2-deoxy-β-D-glucopyranosyl)-(1→6)-α-D-mannopyranoside (S27a): Compound 20 (8 mg, 10.9 μmol) was galactosylated by using general procedure 4 to give the 35 (5 mg, 75%) as amorphous white solids. 1H NMR (600 MHz, D2O): δ 7.12 (d, J=9.1 Hz, 2H), 7.01 (d, J=9.8 Hz, 2H), 5.40 (s, 1H), 4.67 (d, J=8.4 Hz, 1H), 4.49 (d, J=8.4 Hz, 1H), 4.40 (d, J=8.3 Hz, 2H), 4.31 (dd, J=3.1 & 7.8 Hz, 1H), 4.21 (t, J=3.1 Hz, 1H), 4.08 (d, J=12.3 Hz, 2H), 4.00 (dd, J=3.2 & 8.1 Hz, 1H), 3.90-3.48 (m, 3H), 3.80 (s, 3H), 3.75-3.47 (m, 16H), 2.15 (s, 3H), 2.0 (s, 3H), 1.98 (s, 3H); ESI-MS: m/z calcd for C, 37; H, 56; N, 2; O, 23; 896.3162 found 919.3164 (M+Na)+.

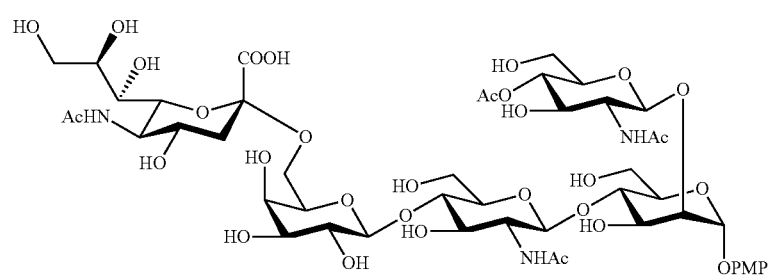

36 p-methoxyphenyl-O-(4-O-acetyl-2-acetamido-2-deoxy-β-D-glucopyranosyl)-(1→2)-O-(5-Acetamido-3,5-dideoxy-D-glycero-α-D-galacto-2-nonulopyrano-sylonate-(2→6)-β-D-galactopyranosyl-(1→4)-O-2-acetamido-2-deoxy-β-D-glucopyranosyl)-(1→4)-α-D-mannopyranoside (36): Compound 34 (10 mg, 11.1 μmol) was α2,6-sialylated by using general procedure 3 to afford 36 (11.2 mg, 84%) as white solid after lyophilization. 1H NMR (600 MHz, D2O): δ 7.02 (d, J=9.2 Hz, 2H), 6.89 (d, J=9.2 Hz, 2H), 5.35 (d, J=2.0 Hz, 1H), 4.55 (dd, J=18.4, 8.4 Hz, 1H), 4.48 (d, J=7.9 Hz, 1H), 4.17-4.37 (m, 4H), 4.05-4.12 (m, 1H), 3.29-3.97 (m, 36H), 2.56 (dd, J=12.4, 4.7 Hz, 1H), 2.04 (s, 3H), 1.96 (s, 3H), 1.92 (s, 3H), 1.92 (s, 3H), 1.60 (t, J=12.2 Hz, 1H); ESI-MS: m/z calcd for C, 48; H, 72; N, 3; O, 31; 1186.4155 found 1186.4175.

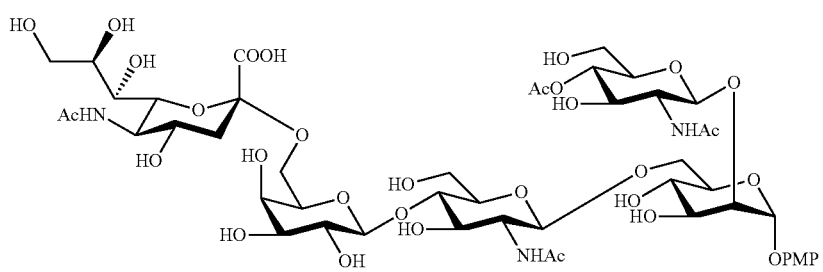

37 p-methoxyphenyl-O-(4-O-acetyl-2-acetamido-2-deoxy-β-D-glucopyranosyl)-(1→2)-O-(5-Acetamido-3,5-dideoxy-D-glycero-α-D-galacto-2-nonulopyrano-sylonate-(2→6)-β-D-galactopyranosyl-(1→4)-O-2-acetamido-2-deoxy-β-D-glucopyranosyl)-(1→6)-α-D-mannopyranoside (37): Compound 35 was α2,6-sialylated by using general procedure 3 to afford 37 (5.1 mg, 77%) as white solid after lyophilization. 1H NMR (600 MHz, D2O): δ 7.11 (d, J=9.1 Hz, 2H), 7.00 (d, J=9.2 Hz, 2H), 5.38 (s, 1H), 4.50 (d, J=8.4 Hz, 1H), 4.36 (d, J=8.2 Hz, 1H), 4.22 (t, J=2.1 Hz, 1H), 4.10 (dd, J=3.1 & 7.8 Hz, 1H), 3.97-3.85 (m, 4H), 3.77 (s, 3H), 3.73-3.46 (m, 25H), 2.63 (dd, J=3.2 and 7.8 Hz, 1H), 2.09 (s, 3H), 2.01 (s, 3H), 1.99 (s, 3H), 1.94 (s, 3H), 1.65 (t, 1H); ESI-MS: m/z calcd for C, 48; H, 73; N, 3; O, 31; 1187.4144 found 1186.4133 (M–H)–.

μmol) and stirred for 4 h. Reaction was neutralized and product was purified by Bio-Gel P-2 chromatography (eluent H2O) to afford 38 (6.1 mg, 89%) as white solid after lyophilization. Compound 38 (6 mg, 5.3 μmol) and UDP galactose (6.4 mg, 10.6 μmol) were dissolved in Tris buffer (25 mM, pH 7.5) and MnCl2 (20 mM). GalT-1 (150 units) were added to achieve a final concentration of glycan to 5 mM. The resulting reaction mixture was incubated at 37° C. for 48 h. The reaction mixture was centrifuged and the supernatant subjected to gel filtration over P2-Biogel (eluent water). Fractions containing the product were combined and lyophilized to give the 40 (5 mg, 73%) as amorphous white solids. 1H NMR (400 MHz, D2O) δ 7.02 (d, J=9.2 Hz, 2H),

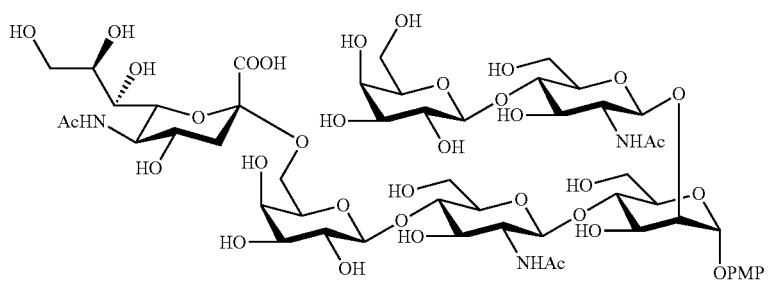

40 p-methoxyphenyl-O-(β-D-galactopyranosyl-(1→4)-O-2-acetamido-2-deoxy-β-D-glucopyranosyl)-(1→2)-O-(5-Acetamido-3,5-dideoxy-D-glycero-α-D-galacto-2-nonulopyrano-sylonate-(2→6)-β-D-galactopyranosyl-(1→4)-O-2-acetamido-2-deoxy-β-D-glucopyranosyl)-(1→4)-α-D-mannopyranoside (40): To a solution of compound 36 (7 mg, 5.8 μmol) in 0.5 mL H2O was added NaOH (9.4 mg, 23.6

6.88 (d, J=9.2 Hz, 2H), 5.35 (d, J=1.8 Hz, 1H), 4.56 (d, J=7.9 Hz, 1H), 4.48 (d, J=7.9 Hz, 1H), 4.35 (dd, J=9.6, 7.7 Hz, 2H), 4.27-4.30 (m, 2H), 4.21-4.24 (m, 1H), 4.02-4.20 (m, 6H), 3.87-3.92 (m, 3H), 3.39-3.85 (m, 28H), 2.56 (dd, J=12.4, 4.6 Hz, 1H), 1.96 (s, 3H), 1.93 (s, 3H), 1.92 (s, 3H), 1.60 (t, J=12.2 Hz, 1H); ESI-MS: m/z calcd for C, 52; H, 80; N, 3; O, 35; 1306.4578 found 1306.4617.

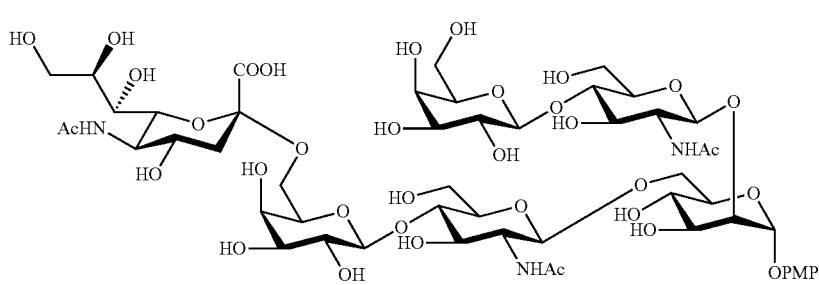

41 p-methoxyphenyl-O-(β-D-galactopyranosyl-(1→4)-O-2-acetamido-2-deoxy-β-D-glucopyranosyl)-(1→2)-O-(5-Acetamido-3,5-dideoxy-D-glycero-α-D-galacto-2-nonulopyrano-sylonate-(2→6)-β-D-galactopyranosyl-(1→6)-O-2-acetamido-2-deoxy-β-D-glucopyranosyl)-(1→4)-α-D-mannopyranoside (41): To a solution of compound 37 (5 mg, 4.2 µmol) in 0.5 mL H2O was added NaOH (6.7 mg, 16.8 µmol) and stirred for 4 h. Reaction was neutralized and product was purified by Bio-Gel P-2 chromatography (eluent H2O) to afford 39 (3.8 mg, 79%) as white solid after lyophilization. Compound 39 (3.5 mg, 3.0 µmol) and UDP galactose (3.9 mg, 6.1 µmol) were dissolved in Tris buffer (25 mM, pH 7.5) and MnCl2 (20 mM). GalT-1 (150 units) were added to achieve a final concentration of glycan to 5 mM. The resulting reaction mixture was incubated at 37° C. for 48 h. The reaction mixture was centrifuged and the supernatant subjected to gel filtration over P2-Biogel (eluent water). Fractions containing the product were combined and lyophilized to give the 41 (3.3 mg, 75%) as amorphous white solids. 1H NMR (400 MHz, D2O): δ 7.11 (d, J=9.1 Hz, 2H), 7.00 (d, J=9.2 Hz, 2H), 5.38 (s, 1H), 4.64 (d, J=8.1 Hz, 1H), 4.50 (d, J=8.2 Hz, 1H), 4.23 (d, J=8.3 Hz, 1H), 4.38 (d, J=8.0 Hz, 1H), 4.22 (t, J=2.1 Hz, 1H), 4.10 (d, J=12.2 Hz, 1H), 4.01-3.95 (m, 4H), 3.87-3.63 (m, 26H), 3.52-3.45 (m, 8H), 2.63 (dd, J=2.1 and 7.8 Hz, 1H), 2.63 (dd, J=3.2 and 7.8 Hz, 1H), 2.01 (s, 3H), 1.99 (s, 3H), 1.93 (s, 3H), 1.67 (t, 1H); ESI-MS: m/z calcd for C, 52; H, 81; N, 3; O, 35; 1307.4567 found 1306.4609 (M−H)−.

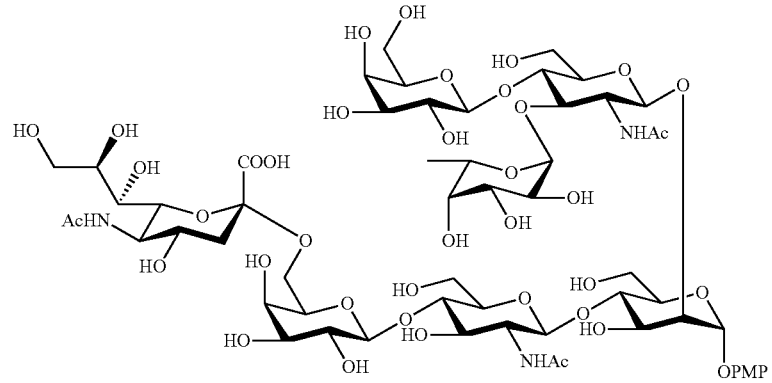

42 p-methoxyphenyl-O-(β-D-galactopyranosyl-(1→4)-O-[α-L-fucopyranosyl-(1→3)-2-acetamido-2-deoxy-β-D-glucopyranosyl]-(1→2)-O-(5-Acetamido-3,5-dideoxy-D-glycero-α-D-galacto-2-nonulopyrano-sylonate-(2→6)-β-D-galactopyranosyl-(1→4)-O-2-acetamido-2-deoxy-β-D-glucopyranosyl)-(1→4)-α-D-mannopyranoside (42): Compound 40 (2 mg, 1.52 µmol) was α1,3-fucosylated by using general procedure 5 to get 42 (2 mg, 85%) as amorphous white solids. 1H NMR (400 MHz, D2O): δ 7.16 (d, J=8.8 Hz, 2H), 7.06 (d, J=8.1 Hz, 2H), 5.45 (s, 1H), 5.08 (d, J=4.1 Hz, 1H), 4.60 (d, J=4.2 Hz, 1H), 4.44 (dd, J=3.5 & 7.9 Hz, 2H), 4.30 (bs, 1H), 4.15 (d, J=8.4 Hz, 1H), 4.09-3.40 (m, 40H), 2.70 (d, J=11.2 Hz, 1H), 2.08 (s, 3H), 2.05 (s, 3H), 1.93 (s, 3H), 1.74 (t, 1H), 1.20 (d, J=6.4 Hz, 3H); ESI-MS: m/z calcd for C, 58; H, 91; N, 3; O, 39; 1453.5245 found 1452.5157 (M−H)−.

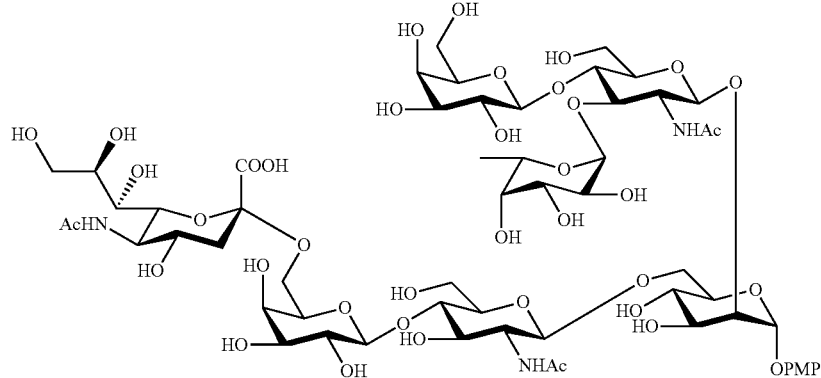

43 p-methoxyphenyl-O-(β-D-galactopyranosyl-(1→4)-O-[α-L-fucopyranosyl-(1→3)-2-acetamido-2-deoxy-β-D-glucopyranosyl]-(1→2)-O-(5-Acetamido-3,5-dideoxy-D-glycero-α-D-galacto-2-nonulopyrano-sylonate-(2→6)-β-D-galactopyranosyl-(1→4)-O-2-acetamido-2-deoxy-β-D-glucopyranosyl)-(1→6)-α-D-mannopyranoside (43): Compound 41 (4 mg, 3.05 µmol) was α1,3-fucosylated by using general procedure 5 to get 43 (3.2 mg, 72%) as amorphous white solids. 1H NMR (400 MHz, D2O): δ 7.21 (d, J=8.2 Hz, 2H), 7.06 (d, J=8.0 Hz, 2H), 5.74 (s, 1H), 5.72 (d, J=8.1 Hz, 2H), 5.52 (dd, J=3.1 & 7.2 Hz, 1H), 5.40 (s, 1H), 5.01 (d, J=4.2 Hz, 1H), 4.50-3.25 (m, 42H), 2.50 (dd, J=3.1 & 7.2 Hz, 1H), 2.01 (s, 3H), 1.99 (s, 6H), 1.56 (t, 1H), 1.05 (d, 3H, Fuc-Me); ESI-MS: m/z calcd for C, 58; H, 91; N, 3; O, 39; 1453.5245 found 1452.5445 (M−H)−.

44

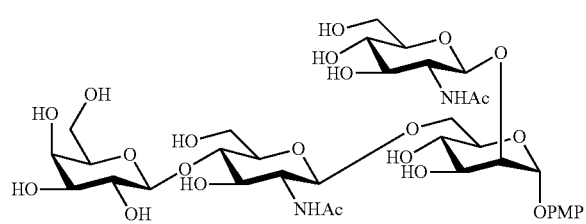

p-methoxyphenyl-O-(2-acetamido-2-deoxy-β-D-glucopyranosyl)-(1→2)-O-(β-D-galactopyranosyl-(1→4)-O-2-acetamido-2-deoxy-β-D-glucopyranosyl)-(1→6)-α-D-mannopyranoside (44): To a solution of compound 35 (20 mg, 22.3 µmol) in 0.5 mL H2O was added NaOH (3.57 mg, 89.2 iµmol) and stirred for 4 h. Reaction was neutralized and product was purified by Bio-Gel P-2 chromatography (eluent H2O) to afford 44 (15.3 mg, 80%) as white solid after lyophilization. 1H NMR (400 MHz, D2O): δ 7.15 (d, J=9.2 Hz, 2H), 7.06 (d, J=9.8 Hz, 2H), 5.42 (s, 1H), 4.67 (d, J=8.2 Hz, 1H), 4.54 (d, J=8.0 Hz, 1H), 4.47 (d, J=8.2 Hz, 1H), 4.32 (t, J=2.1 Hz, 1H), 4.10 (d, J=12.2 Hz, 1H), 4.09 (dd, J=3.2 & 8.2 Hz, 1H), 4.01-3.91 (m, 4H), 3.85 (s, 3H), 3.80-3.40 (m, 21H), 2.03 (s, 3H), 1.98 (s, 3H); ESI-MS: m/z calcd for C, 35; H, 54; N, 2; O, 22; 854.3125 found 877.3062 (M+Na)+.

45

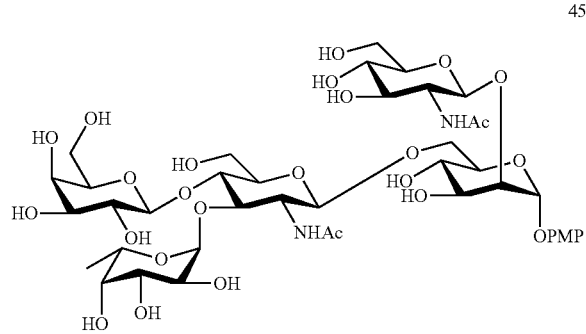

p-methoxyphenyl-O-(2-acetamido-2-deoxy-β-D-glucopyranosyl)-(1→2)-O-(β-D-galactopyranosyl-(1→4)-O-[α-L-fucopyranosyl-(1→3)-2-acetamido-2-deoxy-β-D-glucopyranosyl]-(1→6)-α-D-mannopyranoside (45): Compound 44 (8 mg, 9.3 µmol) was α1,3-fucosylated by using general procedure 5 to afford 45 (6 mg, 66%) as white solid after lyophilization. 1H NMR (400 MHz, D2O): δ 7.14 (d, J=8.2 Hz, 2H), 7.02 (d, J=8.1 Hz, 2H), 5.41 (s, 1H), 5.07 (d, J=4.0 Hz, 1H), 4.64 (d, J=8.2 Hz, 2H), 4.58 (d, J=7.4 Hz, 1H), 4.44 (d, J=8.5 Hz, 1H), 4.28 (t, J=2.1 Hz, 1H), 4.10 (d, J=12.2 Hz, 1H), 4.05 (dd, J=3.1 & 7.2 Hz, 1H), 3.95-3.85 (m, 8H), 3.82 (s, 3H), 3.80-3.33 (m, 17H), 2.04 (s, 3H), 1.93 (s, 3H), 1.17 (d, J=6.8 Hz, 3H); ESI-MS: m/z calcd for C, 41; H, 64; N, 2; O, 26; 1000.2356 found 1023.3599 (M+Na)+.

46

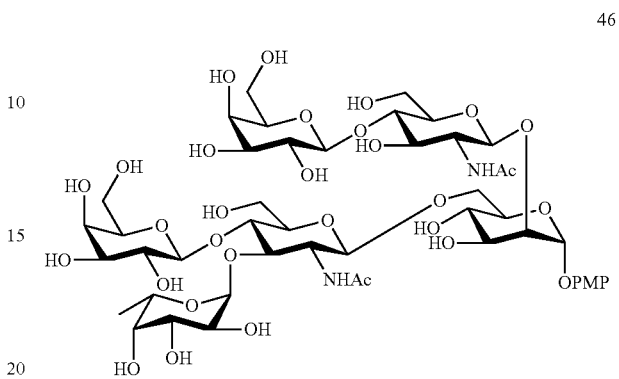

p-methoxyphenyl-O-(β-D-galactopyranosyl-(1→4)-2-acetamido-2-deoxy-β-D-glucopyranosyl)-(1→2)-O-(β-D-galactopyranosyl-(1→4)-O-[α-L-fucopyranosyl-(1→3)-2-acetamido-2-deoxy-β-D-glucopyranosyl]-(1→6)-α-D-mannopyranoside (46): Compound 45 (7 mg, 7.2 µmol) was β1,4-galactosylated by using general procedure 4 to give the 46 (6.5 mg, 80%) as amorphous white solids. 1H NMR (400 MHz, D2O): δ 7.16 (d, J=9.4 Hz, 2H), 7.05 (d, J=9.3 Hz, 2H), 5.43 (s, 1H), 5.09 (d, J=4.2 Hz, 1H), 4.83 (d, J=7.5 Hz, 1H), 4.78 (d, J=7.2 Hz, 1H), 4.58 (d, J=8.2 Hz, 1H), 4.48 (d, J=9.5 Hz, 1H), 4.42 (d, J=8.5 Hz, 1H), 4.30 (dd, J=2.1 & 3.4 Hz, 1H), 4.14 (s, 1H), 4.09-3.92 (m, 14H), 3.85 (s, 3H), 3.84-3.50 (m, 17H), 2.06 (s, 3H), 1.95 (s, 3H), 1.20 (d, J=6.5 Hz, 3H); ESI-MS: m/z calcd for C, 47; H, 74; N, 2; O, 31; 1162.4309 found 1185.4076 (M+Na)+.

47

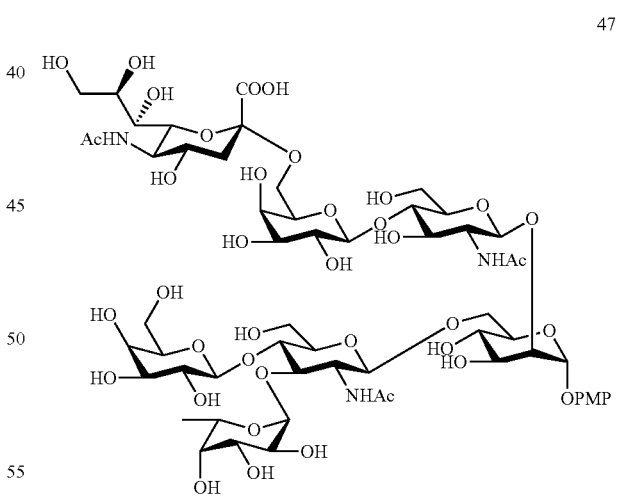

p-methoxyphenyl-O-(β-D-galactopyranosyl-(1→4)-O-[α-L-fucopyranosyl-(1→3)-2-acetamido-2-deoxy-β-D-glucopyranosyl]-(1→6)-O-(5-Acetamido-3,5-dideoxy-D-glycero-α-D-galacto-2-nonulopyrano-sylonate-(2→6)-β-D-galactopyranosyl-(1→4)-O-2-acetamido-2-deoxy-β-D-glucopyranosyl)-(1→2)-α-D-mannopyranoside (47): Compound 46 (5 mg, 4.31 µmol) was α2,6-sialylated by using general procedure 3 to get 47 (5.2 mg, 83%) as amorphous white solids. 1H NMR (400 MHz, D2O): δ 7.08 (d, J=8.1 Hz, 2H), 6.97 (d, J=8.0 Hz, 2H), 5.48 (s, 1H), 5.10

(d, J=5.1 Hz, 1H), 4.50 (d, J=7.2 Hz, 1H), 4.43 (dd, J=3.1 & 8.2 Hz, 2H), 4.32 (bs, 1H), 4.08 (d, J=8.1 Hz, 1H), 4.09-3.40 (m, 41H), 2.60 (dd, J=3.2 & 9.2 Hz, 1H), 1.97 (s, 3H), 1.95 (s, 3H), 1.90 (s, 3H), 1.54 (t, 1H), 1.18 (d, J=6.4 Hz, 3H); ESI-MS: m/z calcd for C, 58; H, 91; N, 3; O, 39; 1453.5245 found 1452.5101 (M−H)−.

Chemical derivatization of chemo-enzymatically prepared modules. The modules 21 and 22 generated by chemo-enzymatic way were then peracetylated in presence of Ac2O/pyridine. The reducing end p-methoxy phenyl ether protection was then cleaved using cerium ammonium nitrate and free hydroxyl was changed to fluoride to obtained donors 50 and 51 (Scheme S28 as shown in FIG. 188).

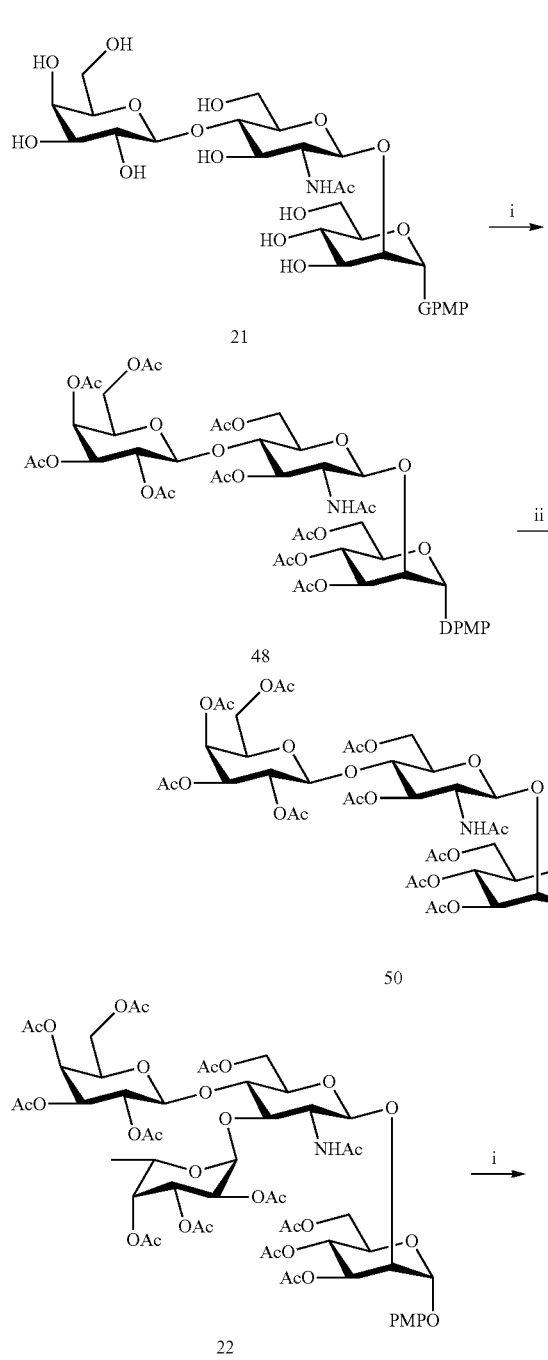

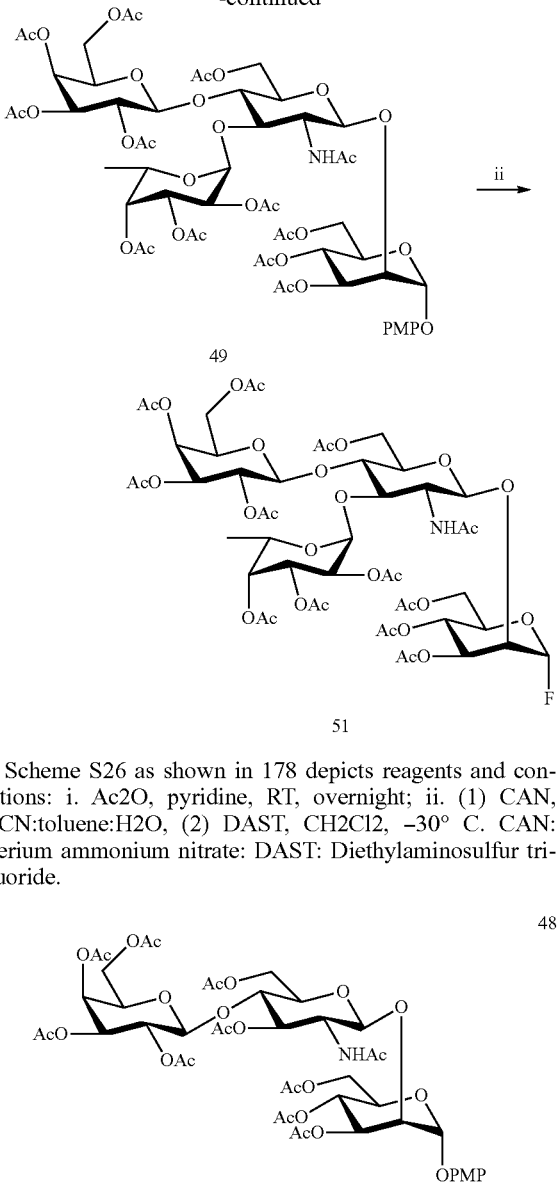

Scheme S26 as shown in 178 depicts reagents and conditions: i. Ac2O, pyridine, RT, overnight; ii. (1) CAN, ACN:toluene:H2O, (2) DAST, CH2Cl2, −30° C. CAN: Cerium ammonium nitrate: DAST: Diethylaminosulfur trifluoride.

p-methoxyphenyl-O-[2,3,4,6-O-tetraacetyl-β-D-galactopyranosyl]-(1→4)-[3,6-O-diacetyl-2-acetamido-2-deoxy-β-D-glucopyranosyl]-(1→2)-3,4,6-O-triacetyl-α-D-mannopyranoside (48): To a solution of 21 (0.230depicts reagents and conditions: in 10 mL pyridine at 0° C. was added acetic anhydride (6 mL) and stirred at RT for overnight. Reaction mixture was then concentrated, diluted with 50 mL of CH2Cl2 and extracted with sat. NaHCO3. Combined organic layers were evaporated and product was purified by silica gel column chromotography (0%→20% acetone in toluene) to afford desired 48 (0.260 g, 72%). TLC (acetone:toluene=3/7, v/v), Rf=0.34; 1H NMR (400 MHz, CHCl3): δ 7.00 (d, J=9.1 Hz, 2H), 6.82 (d, J=9.1 Hz, 2H), 5.74 (d, J=8.7 Hz, 1H), 5.33-5.35 (m, 2H), 5.27-5.30 (m, 2H), 5.22 (dd, J=9.6, 8.2 Hz, 1H), 5.10 (dd, J=10.5, 7.9 Hz, 1H), 4.96 (dd, J=10.5, 3.4 Hz, 1H), 4.72 (d, J=7.5 Hz, 1H), 4.47 (d, J=7.9 Hz, 1H), 4.41 (dd, J=11.8, 2.7 Hz, 1H), 4.31 (t, J=2.2 Hz, 1H), 3.98-4.21 (m, 6H), 3.81-3.91 (m, 2H), 3.72-3.79 (m, 4H), 3.63 (ddd, J=8.6, 5.6, 2.7 Hz, 1H), 2.14 (s, 3H), 2.11 (s, 3H), 2.08 (s, 3H), 2.06 (s, 2H), 2.03 (s, 3H), 2.03 (s, 6H), 2.02 (s, 3H), 1.96 (s, 6H); ESI-MS: m/z calcd for C, 45; H, 59; NO, 26; 1029.9480 found 1030.4587 (M+H)+.

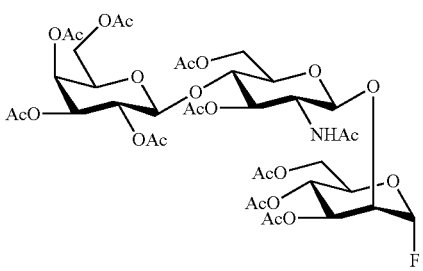

[2,3,4,6-O-tetraacetyl-β-D-galactopyranosyl]-(1→4)-[3,6-O-diacetyl-2-acetamido-2-deoxy-β-D-glucopyranosyl]-(1→2)-3,4,6-O-triacetyl-α-D-mannopyranosyl fluoride (50): Cerium ammonium nitrate (0.2 g, 0.554 mmol) was added to a solution of compound 48 (0.200 g, 0.203 mmol) in 10 mL of acetonitrile:toluene:H2O (4:2:1). The resulting reaction mixture was stirred at RT for 3 h. The reaction was diluted with EtOAc (50 mL) and washed with H2O (30×2 mL) and brine (30 mL). The organic layer was dried over Na2SO4 and concentrated in vacuo. The product was purified by flash column chromatography (0%→25% acetone in toluene) to afford —OH compound (0.120 g) as a foam. The residue (0.120 g, 0.130 mmol) was dissolved in CH2Cl2 (10 mL) at −30° C. Then, DAST (34 μL, 0.260 mmol) was added slowly, and the resulting reaction mixture was stirred for 1 h. When TLC (acetone:toluene, 3/7) indicated formation of product with consumption of starting material, the reaction was quenched with aq. NaHCO3. The filtrate was washed with aqueous NaHCO3 (2×30 mL) and brine (20 mL) solution. The organic layer was dried over Na2SO4 and concentrated in vacuo. The residue was purified by silica gel column chromatography (0%→20% acetone in toluene) to afford 50 (0.080 g, 51% over 2 steps) as white solid. TLC (acetone:toluene=3/7, v/v), Rf=0.34; 1H NMR (600 MHz, CHCl3): δ 5.50 (d, J=49.6 Hz, 1H), 5.30 (d, J=3.8 Hz, 1H), 2.26 (t, J=7.8 Hz, 1H), 5.05-4.89 (m, 4H), 4.55 (d, J=8.4 Hz, 1H), 4.40 (d, J=8.2 Hz, 1H), 4.32 (s, 2H), 4.18 (dd, J=3.2 and 7.8 Hz, 1H), 4.05-4.01 (m, 6H), 3.81 (t, J=7.8 Hz, 1H), 3.71 (t, J=7.1 Hz, 1H), 3.50 (t, J=3.1 Hz, 1H), 2.29 (s, 3H), 2.08 (s, 3H), 2.07 (s, 3H), 2.06 (s, 3H), 2.02 (s, 3H), 1.99 (s, 3H), 1.98 (s, 3H), 1.96 (s, 3H), 1.91 (s, 3H), 1.82 (s, 3H), 13C NMR (150 MHz, CHCl3): 171.29, 171.10, 170.66, 170.56, 170.35, 170.30, 169.50, 129.21, 128.40, 125.47, 106.54, 104.31, 101.05, 100.31, 76.07, 72.82, 72.64, 72.36, 71.16, 70.95, 70.71, 69.41, 69.28, 66.86, 64.92, 62.38, 62.13, 61.04, 53.12, 23.13, 21.64, 21.22, 20.95, 20.87, 20.77, 20.68, 20.62; ESI-MS: m/z calcd for C, 38; H, 52; FNO, 24; 925.8145 found 925.8354 (M+H)+.

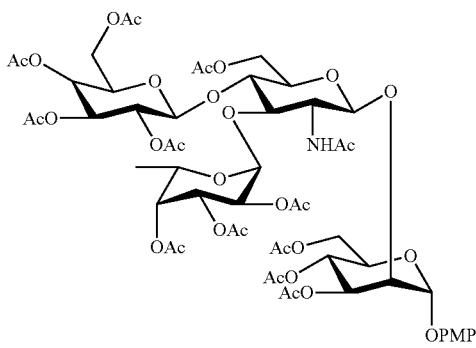

p-methoxyphenyl-O-[2,3,4,6-O-tetraacetyl-β-D-galactopyranosyl]-(1→4)-[2,3,4-O-triacetyl-α-L-fucopyranosyl-(1→3)-3,6-O-diacetyl-2-acetamido-2-deoxy-β-D-glucopyranosyl]-(1→2)-3,4,6-O-triacetyl-α-D-mannopyranoside (49): To a solution of 22 (0.100 g, 0.125 mmol) in 6 mL pyridine at 0° C. was added acetic anhydride (4 mL) and stirred at rt for overnight. Reaction mixture was then concentrated, diluted with 50 mL of CH2Cl2 and extracted with sat. NaHCO3. Combined organic layers were evaporated and product was purified by silica gel column chromatography (0%→10% acetone in CH2Cl2) to afford desired 49 (0.135 g, 85%). TLC (acetone:CH2Cl2=1/9, v/v), Rf=0.31; 1H NMR (400 MHz, CHCl3): δ 7.00 (d, J=6.8 Hz, 2H), 6.83 (d, J=6.8 Hz, 2H), 5.43 (d, J=3.2 Hz, 1H), 4.42 (d, J=3.2 Hz, 1H), 3.98 (d, J=2.1 Hz, 2H), 5.25 (dd, J=3.2 & 8.2 Hz, 2H), 5.19 (dd, J=3.8 & 8.5 Hz, 2H), 5.10 (t, J=9.8 Hz, 2H), 4.89 (d, J=6.3 Hz, 1H), 4.85 (d, J=2.2 Hz, 1H), 4.70 (d, J=9.8 Hz, 2H), 4.61 (d, J=1.2 Hz, 1H), 4.40 (dd, J=3.2 & 7.2 Hz, 1H), 4.31 (m, 3H), 4.22-3.89 (m, 6H), 3.80 (m, 2H), 3.78 (s, 3H), 3.60 (m, 1H), 2.10 (s, 3H), 2.08 (s, 3H), 2.08 (s, 3H), 2.02 (s, 3H), 2.00 (s, 3H), 1.99 (s, 3H), 1.98 (s, 3H), 1.96 (s, 3H), 1.93 (s, 3H), 1.90 (s, 3H), 1.89 (s, 3H), 1.88 (s, 3H), 1.11 (d, 3H); ESI-MS: m/z calcd for C, 55; H, 73; NO, 32; 1259.4116 found 1282.3974 (M+Na)+.

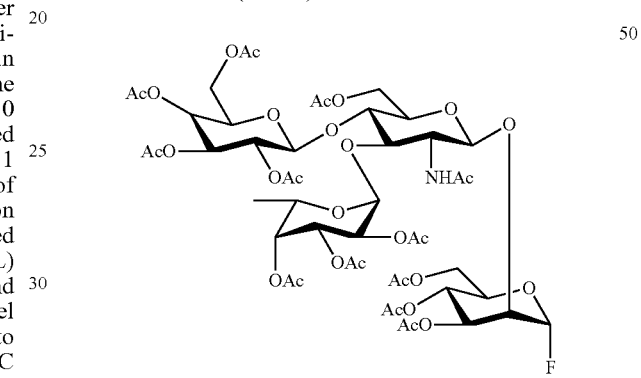

[2,3,4,6-O-tetraacetyl-1-β-D-galactopyranosyl]-(1→4)-[2,3,4-O-triacetyl-α-L-fucopyranosyl-(1→3)-3,6-O-diacetyl-2-acetamido-2-deoxy-β-D-glucopyranosyl]-(1→2)-3,4,6-O-triacetyl-α-D-mannopyranosyl fluoride (50): Cerium ammonium nitrate (0.121 g, 0.142 mmol) was added to a solution of compound 49 (0.090 g, 0.071 mmol) in 7 mL of acetonitrile:toluene:H2O (4:2:1). The resulting reaction mixture was stirred at rt for 3 h. The reaction was diluted with EtOAc (40 mL) and washed with H2O (10×2 mL) and brine (10 mL). The organic layer was dried over Na2SO4 and concentrated in vacuo. The product was purified by flash column chromatography (0%→15% acetone in CH2Cl2) to afford —OH compound (0.065 g) as a foam. The residue (0.060 g, 0.052 mmol) was dissolved in CH2Cl2 (5 mL) at −30° C. Then, DAST (11.6 L, 0.104 mmol) was added slowly, and the resulting reaction mixture was stirred for 1 h. When TLC (acetone:CH2Cl2, 1/9) indicated formation of product with consumption of starting material, the reaction was quenched with aq. NaHCO3. The filtrate was washed with aqueous NaHCO3 (2×10 mL) and brine (10 mL) solution. The organic layer was dried over Na2SO4 and concentrated in vacuo. The residue was purified by silica gel column chromatography (0%→10% acetone in CH2Cl2) to afford 51 (0.055 g, 67% over 2 steps) as white solid. TLC (acetone:CH2Cl2=1/9, v/v), Rf=0.44; 1H NMR (400 MHz, CHCl3): δ 5.55 (d, J=52.1 Hz, 1H), 5.40 (dt, J=3.2 & 7.8 Hz, 3H), 5.21 (dd, J=2.1 & 8.2 Hz, 2H), 5.18-5.04 (m, 3H), 5.0 (bs, 1H), 4.60 (s, 2H), 4.40 (dd, J=5.6 & 8.5 Hz, 1H), 4.38-4.00 (m, 7H), 3.80 (m, 2H), 3.60 (m, 1H), 2.16 (s, 3H), 2.14 (s, 3H), 2.13 (s, 3H), 2.10 (s, 3H), 2.09 (s, 3H), 2.07 (s, 3H), 2.06 (s, 3H), 2.06 (s, 3H), 2.05 (s, 3H), 2.04 (s, 3H), 2.00 (s, 3H), 1.95 (s, 3H), 1.94 (s, 3H), 1.17 (d, J=6.4 Hz, 3H); ESI-MS: m/z calcd for C, 48; H, 66; FNO, 30; 1155.0314 found 1178.3491 (M+Na)+.

Chemical glycosylation to core trisaccharide: At this stage we are in position to investigate the coupling efficiency of fluoride donors 50 and 51 to core trisaccharide 15. Depicted in Scheme S29, stereo-selective conjugation of 50 to 3-O position of core in presence of AgOTf/Cp2HfCl2 provided expected hexasaccharide 52 in 56% yield. The reductive cleavage of benzylidine ring using catalytic p-toluene sulfonic acid provided 4, 6-diol 53. Taking advantage of its reactivity, primary hydroxyl group of 53 was then selectively glycosylated with 51 to afford fully protected decasaccharide 54 in moderate yield. At last, the global deprotection afforded the desired selectively fucosylated bi-antennary complex type glycan 55.

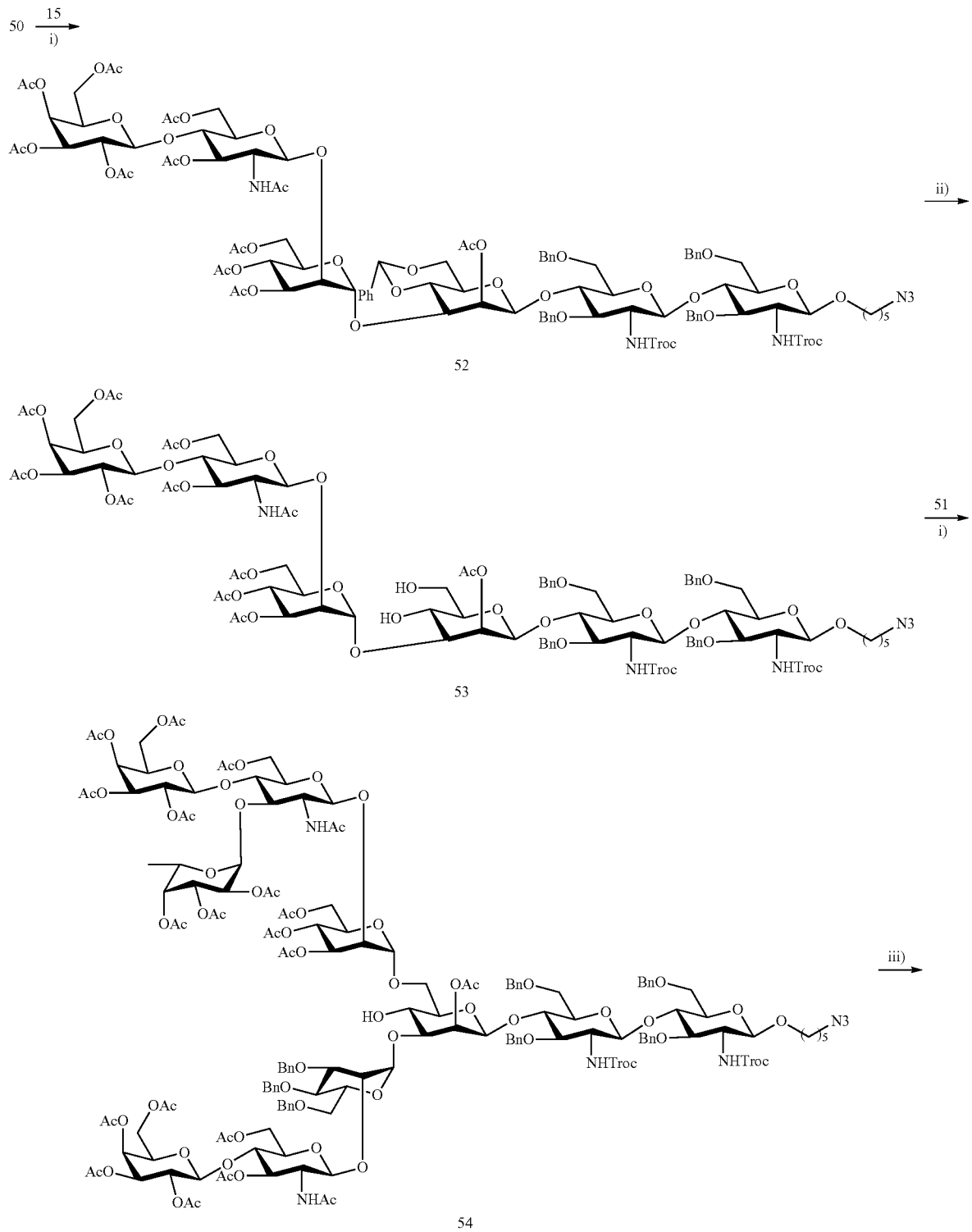

-continued

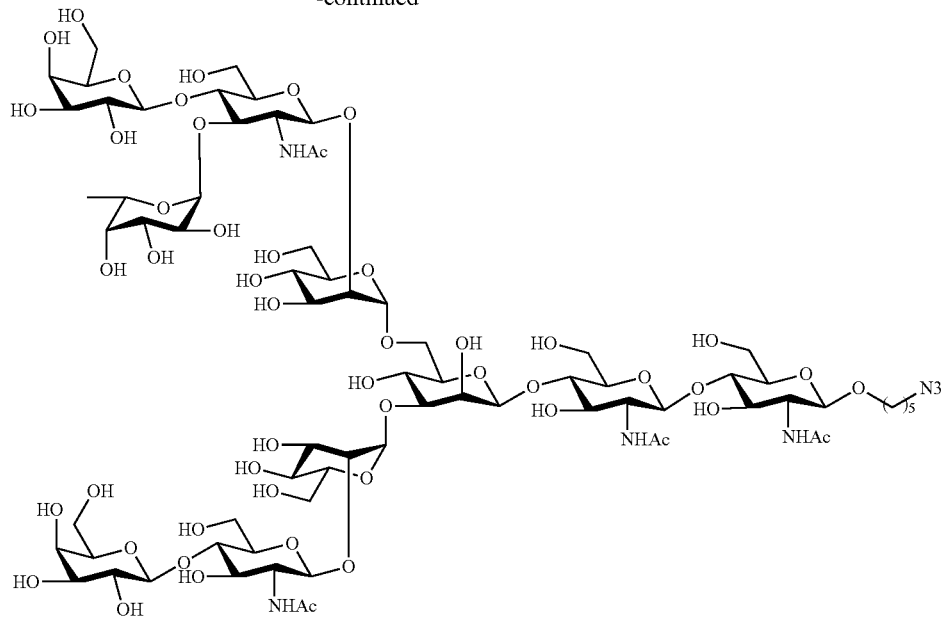

55

Scheme S27 as shown in 183A and 183B depicts reagents and conditions: i, AgOTf, Cp2HfCl2, toluene, 4 Å MS, 0° C. to RT; ii, p-TSA, acetonitrile, RT; iii, (1) LiOH, 1,4-dioxane: H2O; 90° C., overnight; (2) Ac2O, pyridine, overnight; (3) NaOMe, MeOH, overnight; (4) Pd(OH)2, MeOH:H2O: HCOOH (5:3:2), H2.

AgOTf: Silver trifluromethanesulfonate; Cp2HfCl2: Bis (cyclopentadienyl)hafnium dichloride, MS: molecular sieves.

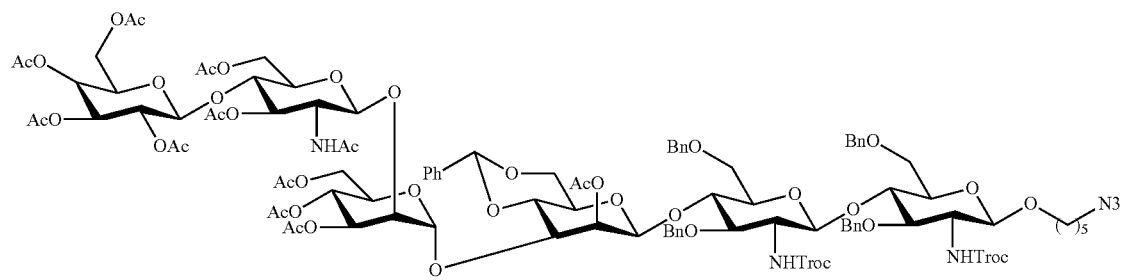

52

5-Azidopentyl-O-{[2,3,4,6-O-tetraacetyl-β-D-galactopyranosyl]-(1→4)-[3,6-O-diacetyl-2-acetamido-2-deoxy-β-D-glucopyranosyl]-(1→2)-[3,4,6-O-triacetyl-α-D-mannopyranosyl]}-(1→3)-[2-O-acetyl-4,6-O-benzylidine-β-D-mannopyranosyl-(1→4)-O-(3,6-di-O-benzyl-2-deoxy-2-(2,2,2-trichloroethoxy)carbonylamino-β-D-glucopyranosyl)-(1→4)-O-3,6-di-O-benzyl-2-deoxy-2-(2,2,2-trichloroethoxy)carbonylamino-β-D-glucopyranoside (52). A mixture of Silver triflate (0.039 g, 0.155 mmol), Bis (cyclopentadienyl) hafnium dichloride (0.041 g, 0.108 mmol) and 4 Å activated molecular sieves in dry toluene (3 mL) was stirred at RT for 1 h. The reaction mixture was then cooled to 0° C., a solution of donor 50 (0.043 g, 0.046 mmol) and acceptor 15 (0.045 g, 0.031 mmol) in 3 mL toluene was added. The mixture was stirred at RT for 3 h, quenched with Et3N, diluted with CH2Cl2 and filtered through Celite. The filtrate was washed with aqueous NaHCO3 (2×20 mL), and a brine (20 mL) solution. The organic layer was dried over Na2SO4 and concentrated in vacuo. The residue was purified by flash column chromatography (0%→10% acetone in CH2Cl2) to afford 52 (0.051 g, 70%) as colorless foam. TLC: (acetone:CH2Cl2=1.5/8.5, v/v): Rf=0.46; 1H NMR (400 MHz, CHCl3): δ 7.46-7.16 (m, 25H), 5.41 (s, 1H), 5.32 (d, J=9.8 Hz, 1H), 5.29 (d, J=7.2 Hz, 1H), 5.20 (t, J=10.2 Hz, 1H), 5.09 (t, J=10.3 Hz, 1H), 4.93-4.87 (m, 5H), 4.82-4.57 (m, 5H), 4.50 (d, J=12.2 Hz, 2H), 4.41-4.22 (m, 4H), 4.13-3.56 (m, 8H), 3.43-3.36 (m, 4H), 3.20 (t, J=10.3 Hz, 4H), 3.19 (t, J=10.2 Hz, 1H), 2.20 (s, 3H), 2.18 (s, 3H), 2.13 (s, 3H), 2.06 (s, 3H), 2.05 (s, 3H), 2.04 (s, 3H), 2.03 (s, 3H), 1.98 (s, 3H), 1.96 (s, 3H), 1.90 (s, 3H), 1.81 (s, 3H), 1.58-1.51 (m, 4H), 1.40-1.34 (m, 2H); 13C NMR (150 MHz, CHCl3): δ 171.28, 170.80, 170.69, 170.49, 170.43, 170.36, 169.97, 169.68, 169.41, 154.30, 154.13, 138.83, 138.18, 137.44, 131.28, 129.25, 129.11, 128.91, 128.63, 128.54, 128.37, 128.18, 128.10, 128.00, 127.79, 127.71, 126.47, 102.55, 101.37, 100.84, 100.44, 98.60, 95.82, 76.07, 74.74, 74.61, 74.51, 74.19, 73.83, 73.59, 72.35, 71.24, 70.95, 70.79, 70.03, 69.62, 69.52, 69.37, 68.66, 68.42, 66.92, 66.41, 65.51, 62.42, 62.02, 61.15, 57.88, 57.23, 53.60, 51.58, 29.27, 28.82, 23.46, 23.29, 21.10, 20.96, 20.82; ESI-MS: m/z calcd for C, 104; H, 126; C, 16; N, 6; O, 41; 2360.8510 found 2361.6131 (M+H)+.

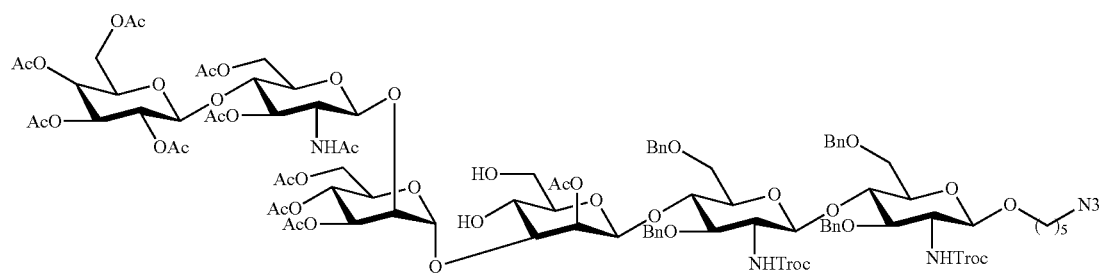

53

5-Azidopentyl-O-{[2,3,4,6-O-tetraacetyl-β-D-galactopyranosyl]-(1→4)-[3,6-O-diacetyl-2-acetamido-2-deoxy-β-D-glucopyranosyl]-(1→2)-[3,4,6-O-triacetyl-α-D-mannopyranosyl]}-(1→3)-[2-O-acetyl-β-D-mannopyranosyl-(1→4)-O-(3,6-di-O-benzyl-2-deoxy-2-(2,2,2-trichloroethoxy)carbonylamino-β-D-glucopyranosyl)-(1→4)-O-3,6-di-O-benzyl-2-deoxy-2-(2,2,2-trichloroethoxy)carbonylamino-β-D-glucopyranoside (53): p-Toluene sulfonic acid monohydrate (0.001 g, 0.008 mmol) was added to a solution of 52 (0.040 g, 0.016 mmol) in acetonitrile:MeOH 2/1 (3 mL) and the resulting reaction mixture was stirred at RT for 5 h. The reaction was quenched by adding Et3N and concentrated in vacuo. The residue was purified by flash column chromatography (0%→15% acetone in CH2Cl2) to give diol 53 (0.022 g, 57%). TLC: (acetone:CH2Cl2=1.5/8.5, v/v): Rf=0.32; 1H NMR (400 MHz, CDCl3): δ 7.43-7.17 (m, 20H), 5.33 (d, J=3.2 Hz, 1H), 5.25 (d, J=3.2 Hz, 1H), 5.19-5.04 (m, 4H), 4.98 (d, J=3.2 Hz, 1H), 4.95 (d, J=3.1 Hz, 1H), 4.94-4.89 (m, 2H), 4.72-4.55 (m, 8H), 4.50-4.28 (m, 9H), 4.20-3.30 (m, 30H), 3.20 (t, 5H), 2.15 (s, 3H), 2.14 (s, 3H), 2.12 (s, 3H), 2.09 (s, 3H), 2.07 (s, 3H), 2.06 (s, 3H), 2.04 (s, 3H), 2.03 (s, 3H), 2.02 (s, 3H), 2.01 (s, 3H), 2.00 (s, 3H), 1.95 (s, 3H), 1.94 (s, 3H), 1.56-1.51 (m, 4H), 1.40-1.34 (m, 2H); ESI-MS: m/z calcd for C, 97; H, 122; Cl, 6; N, 6; O, 43; 2272.7420 found 2295.5522 (M+Na)+.

5-Azidopentyl-O-{[2,3,4,6-O-tetraacetyl-β-D-galactopyranosyl]-(1→4)-[3,6-O-diacetyl-2-acetamido-2-deoxy-β-D-glucopyranosyl]-(1→2)-[3,4,6-O-triacetyl-α-D-mannopyranosyl]}-(1→3)-{2,3,4,6-O-tetraacetyl-β-D-galactopyranosyl]-(1→4)-[2,3,4-O-triacetyl-α-L-fucopyranosyl-(1→3)-3,6-O-diacetyl-2-acetamido-2-deoxy-β-D-glucopyranosyl]-(1→2)-3,4,6-O-triacetyl-α-D-mannopyranosyl}-(1→6)-[2-O-acetyl-β-D-mannopyranosyl-(1→4)-O-(3,6-di-O-benzyl-2-deoxy-2-(2,2,2-trichloroethoxy)carbonylamino-β-D-glucopyranosyl)-(1→4)-O-3,6-di-O-benzyl-2-deoxy-2-(2,2,2-trichloroethoxy)carbonylamino-β-D-glucopyranoside (53): A mixture of Silver triflate (0.011 g, 44.1 μmol), Bis (cyclopentadienyl) hafnium dichloride (0.012 g, 30.8 μmol) and 4 Å activated molecular sieves in dry toluene (3 mL) was stirred at RT for 1 h. The reaction mixture was then cooled to 0° C., a solution of donor 50 (0.015 g, 13.2 μmol) and acceptor 15 (0.020 g, 8.80 μmol) in 2 mL toluene was added. The mixture was stirred at RT for 5 h, quenched with Et3N, diluted with CH2Cl2 and filtered through Celite. The filtrate was washed with aqueous NaHCO3 (2×10 mL), and a brine (20 mL) solution. The organic layer was dried over Na2SO4 and concentrated in vacuo. The residue was purified by flash column chromatography (0%→15% acetone in CH2Cl2) to afford 52 (0.010 g, 34%) as colorless foam. TLC: (acetone:CH2Cl2=1.5/8.5, v/v): Rf=0.41; 1H NMR

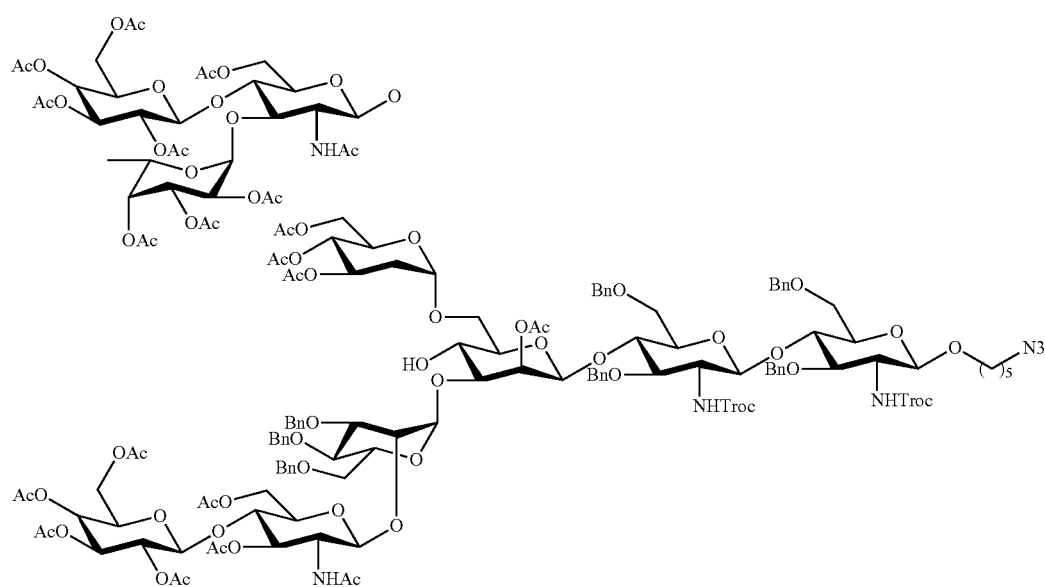

54

(400 MHz, CHCl3): δ 7.48-7.20 (m, 20H), 5.40-4.51 (m, 24H), 4.50-4.00 (m, 10H), 3.98-3.50 (m, 30H), 3.49-3.10 (m, 20H), 2.18 (s, 3H), 2.16 (s, 3H), 2.15 (s, 3H), 2.14 (s, 3H), 2.13 (s, 3H), 2.12 (s, 3H), 2.11 (s, 3H), 2.10 (s, 3H), 2.09 (s, 3H), 2.07 (s, 3H), 2.06 (s, 3H), 2.05 (s, 3H), 2.04 (s, 3H), 2.03 (s, 3H), 2.02 (s, 3H), 2.01 (s, 3H), 2.00 (s, 3H), 1.99 (s, 3H), 1.97 (s, 3H), 1.95 (s, 3H), 1.94 (s, 3H), 1.93 (s, 3H), 1.33-1.23 (m, 4H), 1.20-1.15 (m, 2H); ESI-MS: m/z calcd for C, 145; H, 187; C, 16; N, 7; O, 73; 3408.7670 found 1176.3855 (M+K)3+.

residue was purified by Bio-Gel P-2 (BIO-RAD) column chromatography using water as eluent. The product was lyophilized to get desired oligosaccharides 55 (0.002 g, 36%) as a white color powder. TLC:(n-BuOH:AcOH: H2O=1/1/1, v/v): Rf=0.32; 1H NMR (400 MHz, D2O): δ 5.15 (d, J=4.2 Hz, 1H), 4.94 (s, 1H), 4.60 (m, 3H), 4.45 (q, 3H), 4.30 (s, 1H), 4.21 (d, J=2.1 Hz, 1H), 4.13 (d, J=2.0 Hz, 1H), 4.05-3.40 (m, 58H), 3.01 (t, 2H, linker), 2.10 (s, 3H, —Ac), 2.07 (s, 3H, —Ac), 2.06 (s, 3H, —Ac), 2.05 (s, 3H, —Ac), 1.76-1.58 (m, 4H, liner), 1.45-1.36 (m, 2H, linker),

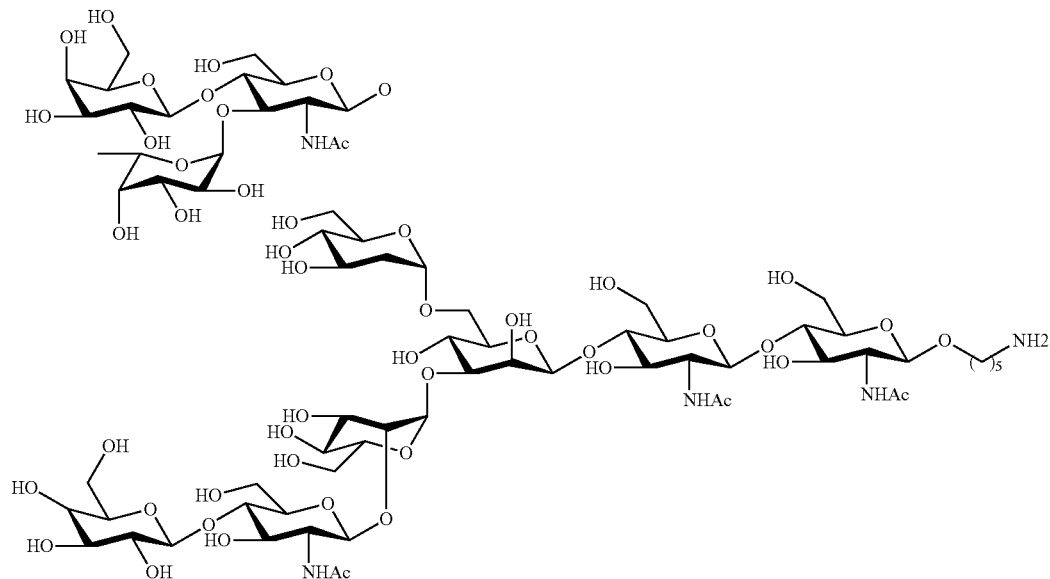

55

5-Aminopentyl-β-D-galactopyranosyl-(1→4)-2-acetamido-2-deoxy-β-D-glucopyranosyl-(1→2)-α-D-mannopyranosyl]-(1→3),-[β-D-galactopyranosyl-(1→4)-(α-L-fucopyranosyl-(1→3)-2-2-acetamido-2-deoxy-β-D-glucopyranosyl)-(1→2)-α-D-mannopyranosyl]-(1→6)-β-D-mannopyranosyl-(1→4)-2-acetamido-2-deoxy-β-D-glucopyranosyl-(1→4)-2-acetamido-2-deoxy-β-D-glucopyranoside (55): A mixture of 54 (0.010 g, 2.9 µmol) and lithium hydroxide (0.005 g, 50% by wt) in 2 mL of 1,4 dioxane:H2O (4:1) was stirred at 90° C. for overnight. Volatiles were then evaporated and the crude product was reacted with 3 mL Ac2O:pyridine (1:2) for overnight. The solvents were removed using high vacuum and product was purified by C18 gel column chromatography (MeOH:H2O as an eluent). The product was de-acetylated using sodium methoxide in MeOH (3 mL) for overnight. The reaction mixture was neutralized by using IR-120, filtered and concentrated in vacuo. The residue was purified by C18 gel column chromatography (MeOH:H2O as an eluent). The product was dissolved in 3 mL MeOH:H2O:HCOOH (6:3: 1), Pd(OH)2 (50% by weight) was added and the mixture was hydrogenated for overnight. The reaction mixture was filtered through Celite and concentrated in vacuo. The 1.21 (d, J=6.5 Hz, 3H, Fuc-Me); 13C NMR (100 MHz, CHCl3): δ 174.6, 174.4, 102.9, 101.8, 101.0, 99.4, 99.1, 98.5, 96.8, 80.3, 79.6, 79.3, 78.4, 76.4, 75.3, 75.2, 74.7, 74.6, 74.5, 74.3, 73.5, 72.8, 72.4, 71.9, 71.0, 70.9, 70.0, 69.5, 69.4, 69.1, 68.5, 68.3, 67.7, 67.2, 66.7, 65.8, 61.4, 60.9, 59.6, 59.5, 55.6, 54.9, 54.8, 39.3, 28.0, 26.3, 22.3, 22.2, 22.0, 15.3; ESI-MS: m/z calcd for C, 73; H, 125; N, 5; O, 50; 1871.7545 found 1872.7477 (M+H)+.

Chemical derivatization of sialylated module. Preparation of sialylated antennae is of particular importance due to the complexity associated with sialic acid chemistry. Having established the synthetic protocol for non-sialylated modules (Scheme S28 as shown in FIG. 188), we turned our attention to sialylated module 22. The carboxylic acid functionality was esterified in presence of trimethylsilyl diazomethane without affecting free hydroxyl groups. Next, the peracetylation was performed using acetic anhydride and pyridine to afford S30a. The peracetylation step allows for purification of the oligosaccharide material before the removal of anomeric groups. At last, reducing end transformation was done to form anomeric fluoride donor S30b.

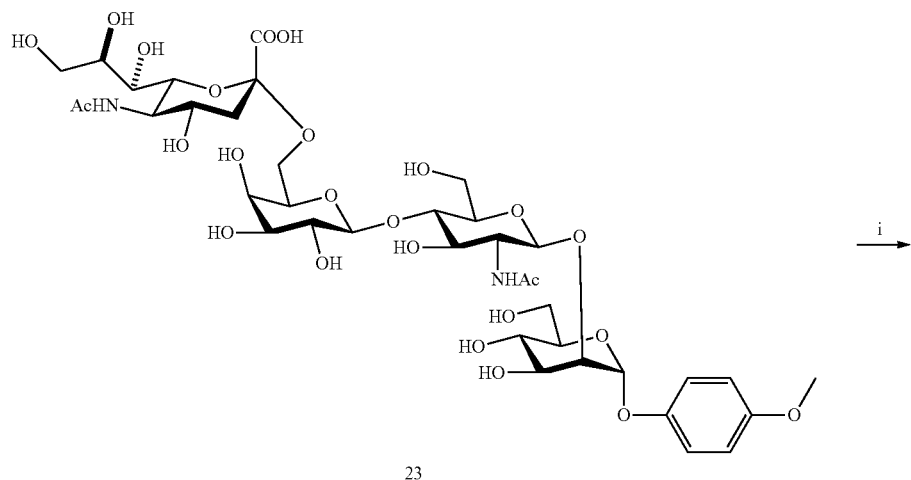
23
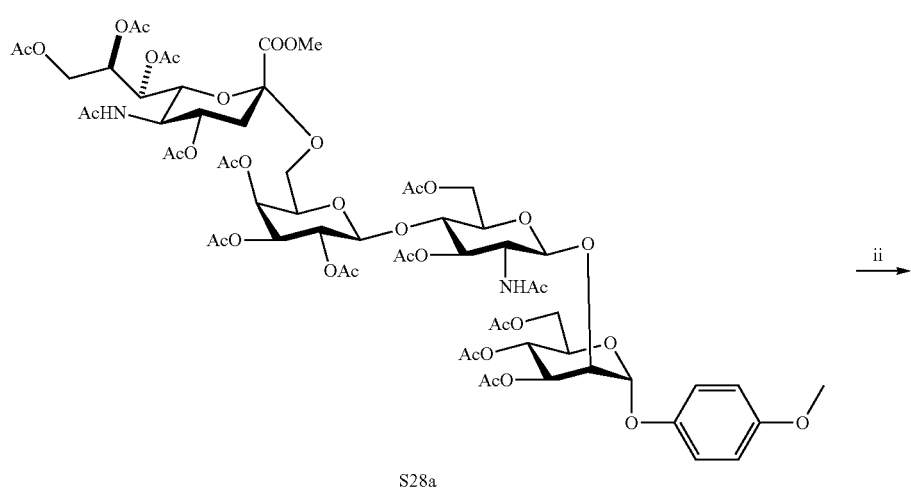
S28a
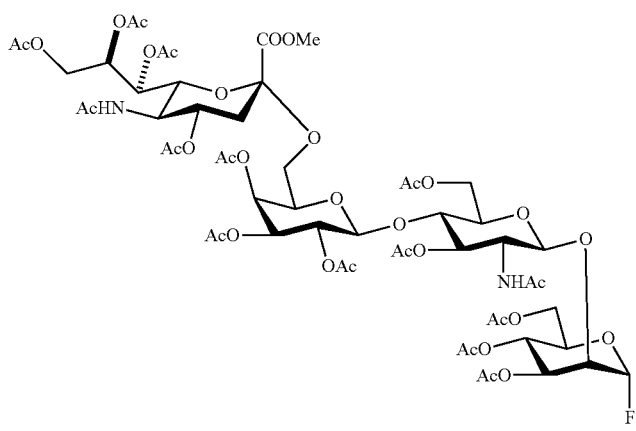
S28b
Scheme S28 as shown in FIG. 188 depicts reagents and Conditions: i, (1) Trimethylsilyl diazomethane, MeOH; (2) Ac2O, pyridine, RT, overnight; ii, (1) CAN, ACN:toluene: H2O, (2) DAST, CH2Cl2, −30° C., 34% over 2 steps.

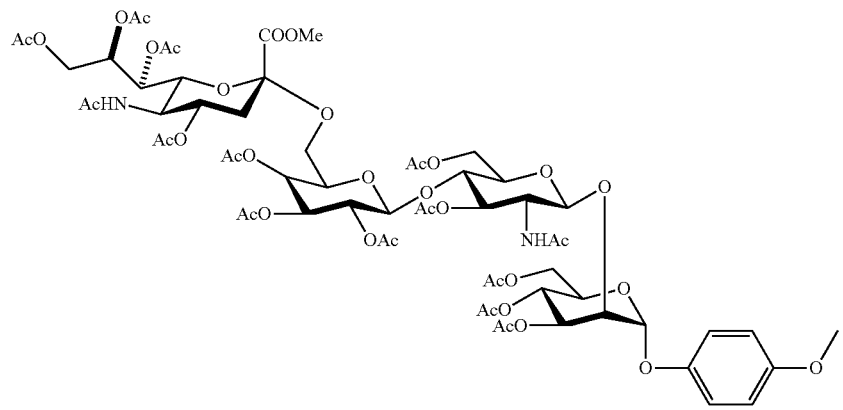

p-methoxyphenyl-O-[3,7,8,9-O-tetraacetyl-5-Acetamido-3,5-dideoxy-D-glycero-α-D-galacto-2-nonulopyrano-sylonate]-(2→6)-O-[2,3,4,6-O-tetraacetyl-β-D-galactopyranosyl]-(1→4)-[3,6-O-diacetyl-2-acetamido-2-deoxy-β-D-glucopyranosyl]-(1→2)-3,4,6-O-triacetyl-α-D-mannopyranoside (S28a): To a solution of compound 23 (30 mg, 0.031 mmol) in MeOH (3 mL) was added trimethylsilyl diazomethane (1M solution in hexane, 0.046 mL, 0.31 mmol). The resulting reaction mixture was stirred at RT for overnight. Complete consumption of starting material was confirmed by NMR and mass. The reaction mixture was concentrated to dryness and purified by C18 (eluent MeOH:H2O). TLC: (n-butanol:H2O:acetic acid=2/1/1, v/v): Rf=0.45; 1H NMR (400 MHz, MeOD): δ 7.14 (d, J=9.5 Hz, 2H), 6.97 (d, J=9.8 Hz, 2H), 5.50 (s, 1H), 4.68 (d, J=8.5 Hz), 1H, 4.45 (d, J=8.0 Hz, 1H), 4.36 (s, 1H), 4.20-3.90 (m, 10H), 3.84 (s, 3H), 3.76-3.58 (m, 17H), 3.51 (s, 3H), 2.66 (dd, J=3.8 and 11.5 Hz, 1H), 2.00 (s, 3H), 1.96 (s, 3H), 1.60 (t, 1H); ESI-MS: m/z calcd for C, 39; H, 60; N, 2; O, 25; 942.3245 found 987.3033 (M+Na)+.

A solution of methyl ester (0.025 mg, 0.025 mmol) in pyridine (2 mL) and acetic anhydride (1.5 mL) was stirred at rt for overnight. Reaction was then concentrated to dryness, dissolved in dicloromethane, extracted with saturated NaHCO3 solution, dried and concentrated. Product was purified by C18 column (MeOH:water eluent) to afford S28a (0.030 mg, 74%) as a white solid. TLC: (acetone:CH2Cl2 4/6, v/v): Rf=0.42; 1H NMR (400 MHz, MeOD): δ 7.07 (d, J=8.5 Hz, 2H), 6.88 (d, J=8.9 Hz, 2H), 5.45 (s, 1H), 5.40 (d, J=7.2 Hz, 1H), 5.36 (t, J=10.3 Hz, 1H), 5.30 (d, J=7.5 Hz, 1H), 5.28 (d, J=7.0 Hz, 1H), 5.26 (s, 1H), 5.23 (s, 1H), 5.19 (d, J=8.6 Hz, 1H), 5.17 (t, J=10.3 Hz, 1H), 5.11-5.07 (m, 5H), 5.00-4.95 (m, 3H), 4.70 (dd, J=4.2 & 7.8 Hz, 2H), 4.46-4.35 (m, 4H), 4.30-4.13 (m, 3H), 4.08-3.97 (m, 8H), 3.76 (s, 3H), 3.75 (s, 3H), 3.60-3.56 (m, 3H), 2.58 (dd, J=4.2 & 8.5 Hz, 1H), 2.13 (s, 3H), 2.12 (s, 3H), 2.11 (s, 3H), 2.10 (s, 6H), 2.07 (s, 3H), 2.05 (s, 6H), 2.02 (s, 6H), 1.99 (s, 3H), 1.98 (s, 3H), 1.91 (s, 6H), 1.84 (t, J=10.2 Hz, 1H); ESI-MS: m/z calcd for C, 63; H, 84; N, 2; O, 37; 1461.3420 found 1486.4864 (M+2H+Na)+.

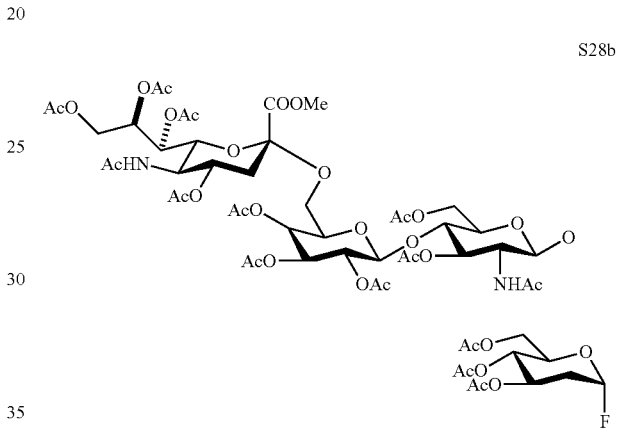

p-methoxyphenyl-O-[3,7,8,9-O-tetraacetyl-5-Acetamido-3,5-dideoxy-D-glycero-α-D-galacto-2-nonulopyrano-sylonate]-(2→6)-O-[2,3,4,6-O-tetraacetyl-β-D-galactopyranosyl]-(1→4)-[3,6-O-diacetyl-2-acetamido-2-deoxy-β-D-glucopyranosyl]-(1→2)-3,4,6-O-triacetyl-α-D-mannopyranosyl fluoride (S28b): Cerium ammonium nitrate (0.037 g, 0.065 mmol) was added to a solution of compound S28a (0.020 mg, 0.013 mmol) in 2 mL of acetonitrile:toluene:H2O (4:2:1). The resulting reaction mixture was stirred at RT for 3 h. The reaction was diluted with EtOAc (10 mL) and washed with H2O (10×2 mL) and brine (10 mL). The organic layer was dried over Na2SO4 and concentrated in vacuo. The product was purified by C18 column chromatography (MeOH:H2O eluent) to afford 1 —OH compound (11 mg). The residue (10 mg, 0.007 mmol) was dissolved in CH2Cl2 (5 mL) at −30° C. Then, DAST (3 μL, 0.021 mmol) was added slowly, and the resulting reaction mixture was stirred for 1 h. When TLC (acetone:CH2Cl2, 4/6) indicated formation of product with consumption of starting material, the reaction was quenched with aq. NaHCO3. The filtrate was washed with aqueous NaHCO3 (2×5 mL) and brine (5 mL) solution. The organic layer was dried over Na2SO4 and concentrated in vacuo. The residue was purified by C18 column chromatography (MeOH:H2O eluent) to afford S30b (0.007 g, 38% over 2 steps). TLC (acetone:CH2Cl2=6/6, v/v), Rf=0.24; 1H NMR (400 MHz, CHCl3): δ 5.99 (d, J=10.2 Hz, 1H), 5.50 (d, J=52.2 Hz, 1H), 5.39 (d, J=10.3 Hz, 1H), 5.33-5.17 (m, 7H), 4.87-4.81 (m, 2H), 4.61 (d, J=10.2 Hz, 1H), 4.52 (d, J=10.3 Hz, 1H), 4.40-4026 (m, 5H), 4.21-3.83 (m, 4H), 3.70 (s, 3H), 3.49-

3.47 (m, 2H), 2.54 (dd, J=3.8 & 8.1 Hz, 1H), 2.19 (s, 6H), 2.17 (s, 6H), 2.14 (s, 6H), 2.10 (s, 3H), 2.05 (s, 6H), 2.02 (s, 6H), 1.98 (s, 3H), 1.97 (s, 6H), 1.23 (t, J=10.1 Hz, 1H); ESI-MS: m/z calcd for C, 56; H, 77; FN, 2; O, 35; 1357.2094 found 1339.3978 (M+Na)+.

Glycan Array Analysis

Microarray Fabrication a) Fabrication of N-hydroxy succinimide-coated glass slide: All monovalent glycans (G1-33) were prepared in 10 mM concentration individually and served as mother solutions which are to be diluted with printing buffer to prepare a working solution. Microarrays were printed (BioDot Cartesian Technologies) by robotic pin (SMP3: TeleChem International) deposition of ~0.6 nL of 100 µM concentration of amine-containing glycans in printing buffer from a 384 well plate onto NHS-coated glass slides. The printed slides were allowed to react in an atmosphere of 80% humidity for an hour followed by desiccation overnight. These slides were designed for 16 grids in one slide, and stored at room temperature in a desiccator prior to use. Before the binding assay, these slides were blocked with blocking solution for 3 h. The slides were then washed with PBST-BSA buffer prior to use. Unless otherwise stated, reagents were obtained from commercial suppliers and used without purification. All aqueous solutions were prepared from distilled de-ionized water filtered with a Milli-Q purification system and sterile filtered through a 0.2 µm filter. Buffers used in the experiment include the printing buffer (pH 8.5, 300 mM phosphate buffer containing 0.05% (v/v) Tween-20), the blocking buffer (superblock blocking buffer in PBS, Pierce), the washing buffer (PBST buffer; PBS and 0.05% Tween-20) and the binding buffer (PBST-BSA Buffer; PBST buffer and 3% BSA). Printing buffer, blocking buffer, and binding buffer were prepared freshly before use.

b) Fabrication of aluminum oxide coated glass slide. The aluminum oxide glass substrate provides advantages for being able to be assessed by both mass spectrometry and fluorescence scanning. In addition, the fluorescence intensity of sugar-protein binding on the substrates was found to be more sensitive than that on transparent glass slide15. There are many reports describing the surface of micron to nano pore structures of anodized aluminum oxide. However, only a few articles have mentioned the initial planar layer of aluminum oxide16 during the treatment of surface anodization. In the development of AAO glass substrate, a computer experimental design program (Design Expert 8.0) has been used to optimize the planar layer of surface anodized aluminum oxide to be best used in glycan microarray 17.

As shown in FIG. 191, which depicts a schematic drawing of the fabrication of anodized aluminum oxide (AAO) glass-substrate, approximately a larger of 300 nm aluminum coated on glass slide (1×75.5×24.5 mm) was fabricated using E-Beam VDP coater by The Thin Film Technology Division, Instrument Technology Research Center at National Applied Research Laboratories, (Hsinchu Science Park, Hsinchu, Taiwan, R.O.C.). The slide after Al-coating was immediately packed (one slide per container) and vacuum sealed in air-tight laminated foil pouches until the moment for surface anodization. Surface anodization of the aluminum coated glass slide has been conducted in-house via electrochemical reaction in a 0.3 M oxalic acid aqueous solution in a 4° C. chamber. The anodization reaction was controlled by voltage and reaction time. Under proper reaction conditions, a layer of approximately 50 to 65 nm (in thickness) of smooth anodized aluminum oxide (AAO) can be grown consistently on top of aluminum coated glass slide. Unlike the conventional anodic aluminum oxide surface with pores, as the AFM picture shown in FIG. 192A, we have developed a smooth AAO glass substrate with Rsm surface roughness (2.3 nm) similar to the surface of glass slide (<3 nm). The cross section picture of a typical AAO glass substrate is shown in FIG. 192B. To obtain the optimized AAO glass substrate with its physical properties shown in FIGS. 192A and 192B, the detail experiment using computer program generated factorial design and response surface methodology has been conducted and will be reported in a separate article. FIG. 192A depicts an AFM picture—Roughness Analysis of the surface. Img. Rms (Rq) 2.319 nm and FIG. 192B depicts a cross Section SEM picture of the AAO Glass Substrate.

Surface Comparison of AAO Glass Substrate vs. NHS-Activated Glass Slide

NHS-glass slide has been widely used for glycan microarray in our and other groups. The amide formation of the NHS functional group with the amine of sugar derivative was taken place on the surface. Its first chemical reaction was to covalently bond to the carboxyl group of the functionalized glass surface. The AAO glass substrate contains a layer of stable polymer network of amorphous aluminum oxide on the surface which is ready for the chemical reaction with the phosphonic acid tail of glycan derivative to form a phosphonate. Interface reaction of phosphonic acid on metal oxides, either aluminum oxide or titanium oxide, is spontaneous and the resulting array is more homogeneous, and density and distribution can be easily controlled compared to the reactions on NHS slide. To identify the reactive site available for interface covalent bonding, Cy5-phosphonic acid and Cy5-amine have been used for microarray on the surfaces directly. These dyes (FIG. 193) have been synthesized in-house starting from Cy5-NHS ester (Lumiprobe Corp. Item No. 63020). FIG. 193 depicts structures of Cy5-phosphonic acid linker and Cy5-amine linker The dyes, Cy5-phosphonic acid and Cy5-amine, were dissolved in a 7:3 ratio of ethylene glycol/water mixtures (1 mM) with pH adjustment to 6 and 8.5 respectively. The arrayed slides were washed thoroughly with a mixture of 5% methanol in water, spin-dried before subjecting for GenePix (4300A) Scanning. FIGS. 195A, 195B and 195C show the microarray pictures of Cy5-phosphonic acid on AAO glass substrate (FIG. 195A), Cy5-amine on NHS-glass slide (FIG. 195B) and their 20 spots average fluorescence intensity (FIG. 195C). The representative confocal microscope pictures of these arrayed spots are given in FIG. 194. Higher loading capacity and more uniformly distributed Cy5-molecules have been observed similarly to those which have been seen usually in the glycan microarray and sugar/protein binding. FIGS. 195A, 195B and 195C depict a genePix Scanning (at PMT 450) of 1 mM of (FIG. 195A) Cy5-phosphonic Acid on AAO glass substrate (FIG. 195B) Cy5-Amine on NHS glass slide, and (FIG. 195C) their averaged 20 spots fluorescence intensity. FIG. 194 depicts a representative Confocal Microscopes pictures Cy5-phosphonic Acid, and Cy5-Amine on AAO glass substrate and NHS glass slide. Selective 900 µm2 area within the spots.

Surface uniformity comparison of ACG and NHS slide using confocal microscope

To evaluate the density and uniformity of glycan array on ACG and NHS activated glass slide, we used the mannose monosaccharide formed glycan array as a model. A mannose solution of 100 µM was used in arraying, and a solution of ConA488 of 50 µg/mL was used in sugar/protein binding. The images of ConA488/mannose binding observed from confocal microscope further confirmed that the AAO glass substrate has denser and more uniformly distributed covalently bonded sugars. FIG. 196 shows the images observed from Confocal Microscope (Leica SP5) of ConA488/mannose binding on AAO Glass Substrate vs. NHS Glass Slide. FIG. 196 depicts a confocal Microscope of ConA488/Mannose binding on AAO glass Substrate vs. NHS-Glass Slide.

Atomic force microscopy image of sugar distribution on aluminum-oxide coated glass slide, and NHS coated glass slide suggest that the AAO glass substrate (FIG. 197A) provides more uniform distribution of covalently bonded sugars than that of NHS glass slide (FIG. 197B). Particle counts of these images were obtained by counting the particles over the height of one half width distribution of the maximum numbers of particle height. Mannose derivatives can only covalently bond on the slides where the activated functional groups were available on the surface. Regardless of differences in Rms of the glass base materials, the AAO glass substrate provides more homogeneous distribution than that of NHS glass slide. FIGS. 197A and 197B depicts atomic force microscopy image showing sugar distribution on a) aluminum-oxide coated glass slide, and b) NHS coated glass slide Antibody binding assay Antibodies PG9, PG16 and PGTs 141-145 were diluted by binding buffer to 100 µg/mL prior to use. DyLight649-conjugated Donkey Anti-Human IgG antibody was then pre-complexed with primary antibodies. The final concentration of the precomplexed solution was adjusted to 50 µg/mL with binding buffer. The printed glass slide was assembled into FAST® frame slide holder (Whatman®), 80 µL of precomplexed antibody solution were then applied to each well accordingly. The antibodies binding process was maintained in 4° C. with gentle shaking and then antibody solutions were carefully pipetted out after 6 hours incubation. The glass slide was gently washed by 100 µL PBST washing buffer and then spin-dried for 3 minutes.

Image Processing and Data Analysis

The slide was scanned at 635 nm with a microarray fluorescence chip reader (GenePix® 4300A, Molecular Devices Corporation). Scanned images were analyzed with GenePix Pro 6.0 analysis software (Molecular Devices Corporation,). The image resolution was set to 5 µm per pixel. Spots were defined as circular features with defined diameter of 100 µm. The values of total intensity were chosen for data processing, performed with Graphpad Prism® 6.0. The intensities was calculated and averaged. Error bars represent the standard deviation for all data points reported.

Analyzing glycan binding specificity of HIV-1 bNAbs on NHS-coated glass slide

The slide for the study of PG9, PG16 and PGTs141-145 was prepared by printing glycans G1-33 (FIG. 198) on the N-hydroxysuccinimide coated surface through covalent bond formation. Slide images obtained by fluorescent scan after secondary antibody incubation. FIG. 198 depicts a schematic representation of N-glycans printed on NHS coated glass slide.

Having incorporated diverse HIV-1 gp120 related N-glycans in our array, we next proceed to characterize binding behavior of PG16 to those glycans. Our results are consistent with our previously reported data, where, the PG16 binding is proportional to a 2,6-Neu5Ac count at the termini (FIG. 199). A short conclusion from our study is presence of di-sialylated antennae in defined orientation is deterministic of binding in PG16 binding pocket. FIG. 199 depicts binding behavior of PG16 using NHS-coated glass slide. Bindings of PG16 to panel of N-glycans represented in bar chart.

Binding of defined set of glycans binding to antibodies PG9 and PGTs141-45. We screened PG9 and PGTs141-145 on our NHS-coated glass slide array.

FIG. 203 depicts the binding behavior of PG9 using NHS-coated glass slide.

FIGS. 204A, 204B and 204C depict binding behavior of PGTs 141-143 using NHS-coated glass slide. Antibody concentrations used here are 25 µg/mL.

FIGS. 205A and 205B. Binding behavior of PGTs14-145 using NHS-coated glass slide. Antibody concentrations used here are 25 µg/mL.

We observed a low level binding for antibodies PG9 (FIG. 203) and PGTs 141-145 (FIGS. 204A, 204B, 204C, 205A and 205B) towards any of the glycans printed on array.

Analyzing glycan binding specificity of HIV-1 bNAbs on ACG slide.

Having demonstrated the applicability of ACG slide over NHS-coated slide in terms of glycan density and enhancement in signal intensity, we printed glycan glycans I-XI on ACG array using phosphonate chemistry (FIG. 200). The binding specificities of PGTs141-144 are shown in FIG. 200. FIG. 200 represents glycans printed on ACG array. The structure of linker is shown on the upper left corner.

The binding specificities of PGTs141-144 are shown in FIGS. 201A and 201B. However, we could not find the binding for PGT145 on ACG array, most probably because of its weak glycan binding affinity. FIGS. 201A and 201B depict bindings of PGTs 141-144 towards panel of N-glycans on ACG array is shown in bar chart.

Determination of surface dissociation constants (KD.surf) on ACG slide

The aluminum oxide coated glass slides for the determination of dissociation constants were spotted with 100 and 50 µM concentrations of glycans Man5GlcNAc2 (V), hybrid type (XI), bi-antennary complex type (XII), V+XI (1:1 mole ratio), V+XII, and XI+XII. Antibody PG16 was serially diluted to 3.32, 1.66, 0.833, 0.415, 0.207, 0.103, 0.051 and 0.025 µM with 3% BSA-PBST buffer. DyLight649-conjugated Donkey Anti-Human IgG antibody was pre-complexed with primary antibody PG16 (1:1 by weight). The pre-complexed solution (100 µL) was applied to each well and incubated at 4° C. for 6 h in the dark. Finally, slides were washed with PBST, spin dried and scanned at 450 nm with a microarray fluorescence chip reader. Scanned images were analyzed with GenePix Pro 6.0 analysis software. The signal intensities for binding of PG16 to Man5GlcNAc2 (V) and mixture of V+XI (1:1 mole ratio) were too weak to determine the KD. The binding curves for the rest of samples printed on array are shown in FIGS. 202A and 202B and KD values are summarized in Table S2.

In the case of PG9, because of its very weak glycan binding affinity, we were not able to achieve the signal saturation to measure the binding constants, however, increasing PG9 concentration to 700 µg/mL resulted in a precipitation on array surface. FIGS. 202A and 202B depict antibody PG16 binding curves observed for glycans X, XI and mixtures V+XI and X+XII at 100 µM concentration. The curves were obtained by using DyLight649-conjugated donkey anti-Human IgG secondary antibody.

TABLE S2

KD, surf (μM) values of antibody PG16 and glycans X, XI and mixtures V + XI and X + XI.

| Glycan no. | $K_{D,surf}$ (μM) ± SD (μM) |
|---|---|
| X | 0.935 ± 0.026 μM |
| XI | 0.320 ± 0.125 μM |
| V + XI | 0.827 ± 0.200 μM |
| X + XI | 0.988 ± 0.223 μM |

ADDITIONAL EXAMPLES

Additional Examples are attached as a separate document, labeled P3-1 through P3-7.

Additional Examples: (P3-1)

Compound 42, is a Transformer of Mixed Compound 4 and Compound 20, Therein, it is Also Recognized and Bound by Anti HIV-1 Broadly Neutralizing Monoclonal Antibodies (bnMAb) with Binding and Recognition the Mixture of Compound 4 and Compound 20, e.g. PG9 and PG16

Additional Examples: (P3-2)

Schematic Representation of N-glycans Printed on NHS Coated Glass Slide

Additional Examples: (P3-3)

Synthesis of Compound 42

Additional Examples: (P3-4)

General Exemplary Procedures for the Synthesis of Hybrid Glycans with Man3/Man5 Glycan at the 3-Arm and Complexed Glycan at the 6-Arm

Additional Examples: (P3-5)

General Exemplary Procedures for the Synthesis of Hybrid Glycans with Man3/Man5 Glycan at the 6-Arm and Complexed Glycan at the 3-Arm

Additional Examples: (P3-6)

Exemplary Hybrid Glycans Via Synthesis

Additional Examples: (P3-7)

Exemplary Hybrid Glycans Via Synthesis

REFERENCES

1. Barouch, D. H. Challenges in the development of an HIV-1 vaccine. Nature 455, 613-619, (2008).
2. Gaschen, B. et al. AIDS—Diversity considerations in HIV-1 vaccine selection. Science
3. 296, 2354-2360, (2002).
4. Astronomo, R D. & Burton, D. R Carbohydrate vaccines: developing sweet solutions to sticky situations? Nat. Rev. Drug. Discov. 9, 308-324, (2010).
5. Craigo, J. K., Montelaro, R. C. Lessons in AIDS vaccine development learned from studies of equine infectious, anemia virus infection and immunity. Viruses 5, 2963-76, (2013)
6. Scanlan, C. N., Offer, J., Zitzmann, N. & Dwek, R. A. Exploiting the defensive sugars of HIV-1 for drug and vaccine design. Nature 446, 1038-1045, (2007).
7. Kwong, P. D., Mascola, J. R. & Nabel, G. J. Rational Design of Vaccines to Elicit Broadly Neutralizing Antibodies to HIV-1. Cold Spring Harb Perspect. Med. 1, (2011).
8. Burton, D. R., Mascola, J. R. Antibody responses to envelope glycoproteins in HIV-1 infection. Nature Immunol. 16, 571-6, (2015).
9. Pritchard, L. K., Harvey, D. J., Bonomelli, C., Crispin, M., Doores, K. J. Cell- and Protein-Directed Glycosylation of Native Cleaved HIV-1 Envelope. J. Virol. 89, 8932-44, (2015).
10. Pritchard, L. K. et al. Structural Constraints Determine the Glycosylation of HIV-1 Envelope Trimers. Cell Rep. 11, 1604-13, (2015).
11. Doores, K. J. et al. Envelope glycans of immunodeficiency virions are almost entirely oligomannose antigens. Proc. Natl. Acad. Sci. U.S.A 107, 13800-13805, (2010).
12. Pabst, M., Chang, M., Stadlmann, J. & Altmann, F. Glycan profiles of the 27 N-glycosylation sites of the HIV envelope protein CN54gp140. Biol. Chem. 393, 719-730, (2012).
13. Go, E. P. et al. Comparative Analysis of the Glycosylation Profiles of Membrane-Anchored HIV-1 Envelope Glycoprotein Trimers and Soluble gp140. J. Virol. 89, 8245-57, (2015).
14. Wang, W. et al. A systematic study of the N-glycosylation sites of HIV-1 envelope protein on infectivity and antibody-mediated neutralization. Retrovirology, 10, 14, (2014).
15. Calarese, D. A. et al. Antibody domain exchange is an immunological solution to carbohydrate cluster recognition. Science 300, 2065-2071, (2003).
16. Wang, L. X. Carbohydrate-based vaccines against HIV/AIDS. Acs Sym. Ser. 932, 133-160 (2006).
17. Joyce, J. G. et al. An oligosaccharide-based HIV-1 2G12 mimotope vaccine induces carbohydrate-specific antibodies that fail to neutralize HIV-1 virions. Proc. Natl. Acad. Sci. U.S.A 105, 15684-15689, (2008).
18. Wang, L. X. Synthetic carbohydrate antigens for HIV vaccine design. Curr. Opin. Chem. Biol. 17, 997-1005, (2013).
19. Horiya, S., MacPherson, I. S., Krauss, I. J. Recent strategies targeting HIV glycans in vaccine design. Nat. Chem. Biol. 10, 990-999, (2014).
20. Fernandez-Tejada, A., Haynes, B. F., Danishefsky, S. J. Designing synthetic vaccines for HIV. Expert Rev. Vaccines 14, 815-31, 2015.
21. Walker, L. M. et al. Broad neutralization coverage of HIV by multiple highly potent antibodies. Nature 477, 466-470, (2011).
22. Sok, D., Moldt, B., Burton, D. R. SnapShot: broadly neutralizing antibodies. Cell 155, 728-728, (2013).
23. Garces, F. et al. Structural evolution of glycan recognition by a family of potent HIV antibodies. Cell 159, 69-79, (2014).
24. Wu, X. et al. Rational design of envelope identifies broadly neutralizing human monoclonal antibodies to HIV-1. Science 329, 856-861, (2010).
25. Pancera, M. et al. Crystal structure of PG16 and chimeric dissection with somatically related PG9: structure-function analysis of two quaternary-specific antibodies that effectively neutralize HIV-1. J. Virol. 84, 8098-8110, (2010).

26. Doores, K. J. & Burton, D. R. Variable Loop Glycan Dependency of the Broad and Potent HIV-1-Neutralizing Antibodies PG9 and PG16. J. Virol. 84, 10510-10521, (2010).
27. McLellan, J. S. et al. Structure of HIV-1 gp120 V1/V2 domain with broadly neutralizing antibody PG9. Nature 480, 336-343, (2011).
28. Pejchal, R. et al. A potent and broad neutralizing antibody recognizes and penetrates the HIV glycan shield. Science 334, 1097-1103, (2011).
29. Mouquet, H. et al. Complex-type N-glycan recognition by potent broadly neutralizing HIV antibodies. Proc. Natl. Acad. Sci. U.S.A 109, E3268-E3277, (2012).
30. Falkowska, E. et al. Broadly neutralizing HIV antibodies define a glycan-dependent epitope on the prefusion conformation of gp41 on cleaved envelope trimers. Immunity 40, 657-68, 2014.
31. Pancera, M. et al. Structural basis for diverse N-glycan recognition by HIV-1-neutralizing V1-V2-directed antibody PG16. Nat. Struct. Mol. Biol. 20, 804-813, (2013).
32. Amin, M. N. et al. Synthetic glycopeptides reveal the glycan specificity of HIV-neutralizing antibodies. Nat. Chem. Biol. 9, 521-526, (2013).
33. Murphy, C. I. et al. Enhanced expression, secretion, and large-scale purification of recombinant HIV-1 gp120 in insect cell using the baculovirus egt and p67 signal peptides. Protein Expres. Purif. 4, 349-357 (1993).
34. Kong, L. et al. Expression-system-dependent modulation of HIV-1 envelope glycoprotein antigenicity and immunogenicity. J. Mol. Biol. 403, 131-147, (2010).
35. Go, E. P. et al. Characterization of glycosylation profiles of HIV-1 transmitted/founder envelopes by mass spectrometry. J. Virol. 85, 8270-8284, (2011).
36. Eggink, D. et al. Lack of complex N-glycans on HIV-1 envelope glycoproteins preserves protein conformation and entry function. Virology 401, 236-247, (2010).
37. Zhu, X., Borchers, C., Bienstock, R. J. & Tomer, K. B. Mass spectrometric characterization of the glycosylation pattern of HIV-gp120 expressed in CHO cells. Biochemistry 39, 11194-11204 (2000).
38. Raska, M. et al. Glycosylation patterns of HIV-1 gp120 depend on the type of expressing cells and affect antibody recognition. J. Biol. Chem. 285, 20860-20869, (2010).
39. De Paz, J. L., Horlacher, T. & Seeberger, P. H. Oligosaccharide microarrays to map interactions of carbohydrates in biological systems. Methods Enzymol. 415, 269-292, (2006).
40. Oyelaran, O. & Gildersleeve, J. C. Glycan arrays: recent advances and future challenges. Curr. Opin. Chem. Biol. 13, 406-413, (2009).
41. Rillahan, C. D. & Paulson, J. C. Glycan microarrays for decoding the glycome. Annu Rev. Biochem. 80, 797-823, (2011).
42. Blixt, O. et al. Printed covalent glycan array for ligand profiling of diverse glycan binding proteins. Proc. Natl. Acad. Sci. U.S.A 101, 17033-17038, (2004).
43. Fukui, S., Feizi, T., Galustian, C., Lawson, A. M. & Chai, W. Oligosaccharide microarrays for high-throughput detection and specificity assignments of carbohydrate-protein interactions. Nat. Biotechnol. 20, 1011-1017, (2002).
44. Wang, D., Liu, S., Trummer, B. J., Deng, C. & Wang, A. Carbohydrate microarrays for the recognition of cross-reactive molecular markers of microbes and host cells. Nat. Biotechnol. 20, 275-281, (2002).
45. Fazio, F., Bryan, M. C., Blixt, O., Paulson, J. C. & Wong, C.-H. Synthesis of sugar arrays in microtiter plate. J. Am. Chem. Soc. 124, 14397-14402, (2002).
46. Paulson, J. C., Blixt, O. & Collins, B. E. Sweet spots in functional glycomics. Nat. Chem. Biol. 2, 238-248, (2006).
47. Scurr, D. J. et al. Surface characterization of carbohydrate microarrays. Langmuir 26, 17143-17155, (2010).
48. Chang, S. H. et al. Glycan array on aluminum oxide-coated glass slides through phosphonate chemistry. J. Am. Chem. Soc. 132, 13371-13380, (2010).
49. Tseng, S. Y. et al. Glycan arrays on aluminum-coated glass slides. Chem.-Asian J. 3, 1395-1405, (2008).
50. Wang, Z. et al. A general strategy for the chemoenzymatic synthesis of asymmetrically branched N-glycans. Science 341, 379-383, (2013).
51. Shivatare, S. S. et al. Efficient convergent synthesis of bi-, tri-, and tetra-antennary complex type N-glycans and their HIV-1 antigenicity. J. Am. Chem. Soc. 135, 15382-15391, (2013).
52. Li, L. et al. Efficient chemoenzymatic synthesis of an N-glycan isomer library. Chem. Sci. 6, 5652-5661 (2015).
53. Takakura, Y., Tsukamoto, H. & Yamamoto, T. Molecular cloning, expression and properties of an alpha/beta-Galactoside alpha 2,3-sialyltransferase from Vibrio sp. JT-FAJ-16. J. Biochem. 142, 403-412, (2007).
54. Tsukamoto, H., Takakura, Y., Mine, T. & Yamamoto, T. Photobacterium sp. JT-ISH-224 produces two sialyltransferases, alpha-/beta-galactoside alpha2,3-sialyltransferase and beta-galactoside alpha2,6-sialyltransferase. J. Biochem. 143, 187-197, (2008).
55. Toshima, K. Glycosyl fluorides in glycosidations. Carbohydr. Res. 327, 15-26 (2000).
56. Rabbani, S., Schwardt, O. & Ernst, B. Glycosyltransferases: An efficient tool for the enzymatic synthesis of oligosaccharides and derivatives as well as mimetics thereof. Chimia 60, 23-27, (2006).
57. Muthana, S., Yu, H., Huang, S., and Chen, X. Chemoenzymatic synthesis of size-defined polysaccharides by sialyltransferase-catalyzed block transfer of oligosaccharides. J. Am. Chem. Soc. 129, 11918-11919, (2007).
58. Lau, K. et al. Highly efficient chemoenzymatic synthesis of β1-4-linked galactosides with promiscuous bacterial β1-4-galactosyltransferases. Chem. Commun. 46, 6066-6068, (2010).
59. Soriano del Amo, D. et al. Chemoenzymatic synthesis of the sialyl Lewis X glycan and its derivatives. Carbohydr. Res. 345, 1107-13, (2010).
60. Liang, P. H., Wang, S. K. & Wong, C.-H. Quantitative analysis of carbohydrate-protein interactions using glycan microarrays: Determination of surface and solution dissociation constants. J. Am. Chem. Soc. 129, 11177-11184, (2007).
61. Takakura, Y., Tsukamoto, H. & Yamamoto, T. Molecular cloning, expression and properties of an alpha/beta-Galactoside alpha2,3-sialyltransferase from Vibrio sp. JT-FAJ-16. *J. Biochem.* 142, 403-412, (2007).
62. Tsukamoto, H., Takakura, Y., Mine, T. & Yamamoto, T. *Photobacterium* sp. JT-ISH-224 produces two sialyltransferases, alpha-/beta-galactoside alpha2,3-sialyltransferase and beta-galactoside alpha2,6-sialyltransferase. *J. Biochem.* 143, 187-197, (2008).
63. Shivatare, S. S. et al. Efficient convergent synthesis of bi-, tri-, and tetra-antennary complex type N-glycans and their HIV-1 antigenicity. *J. Am. Chem. Soc.* 135(41), 15382-15391, (2013).

64. TSai, T. I. et al. Effective sugar nucleotide regeneration for the large-scale enzymatic synthesis of Globo H and SSEA4. *J. Am. Chem. Soc.* 135(39), 14831-9, (2013).
65. Doores K J, et al. A nonself sugar mimic of the HIV glycan shield shows enhanced antigenicity. *Proc. Natl. Acad. Sci. U.S.A.* 107(40), 17107-17112, (2010).
66. Mandal, M., Dudkin, V. Y., Geng, X. & Danishefsky, S. J. In pursuit of carbohydrate-based HIV vaccines, part 1: The total synthesis of hybrid-type gp120 fragments. *Angew. Chem. Int. Ed.* 43, 2557-2561, (2004).
67. Lee, H. K. et al. Reactivity-based one-pot synthesis of oligomannoses: defining antigens recognized by 2G12, a broadly neutralizing anti-HIV-1 antibody. *Angew. Chem. Int. Ed.* 43, 1000-1003, (2004).
68. John, F. & Hendrickson, T. L. Synthesis of Truncated Analogues for Studying the Process of Glycosyl Phosphatidylinositol Modification. *Org. Lett.* 12, 2080-2083, (2010).
69. Pratt, M. R. & Bertozzi, C. R. Chemoselective ligation applied to the synthesis of a biantennary N-linked glycoform of CD52. *J. Am. Chem. Soc.* 125, 6149-6159, (2003).
70. Hsu, C, H. et al. Highly alpha-selective sialyl phosphate donors for efficient preparation of natural sialosides. *Chem. Eur. J.* 16-6, 1754-1760, (2010).
71. Sema, S., Etxebarria, J., Ruiz, N., Martin-Lomas, M. & Reichardt, N. C. Construction of N-Glycan Microarrays by Using Modular Synthesis and On-Chip Nanoscale Enzymatic Glycosylation. *Chem. Eur. J.* 16, 13163-13175, (2010).
72. Sun, B., Srinibasan, B., Huang, X., Pre-activation-based one-pot synthesis of an alpha-(2,3)-sialylated core-fucosylated complex type bi-antennary N-glycan dodecasaccharide. *Chem. Eur. J.* 14 (23), 7072-81, (2008).
73. Kanie, O., Ito, Y. & Ogawa, T. Orthogonal glycosylation strategy in synthesis of extended blood group B determinant. *Tetrahedron Lett.* 37, 4551-4554 (1996).
74. Lemieux, R. U., Hendriks, K. B., Stick, R. V., James, K. Halide ion catalyzed glycosidation reactions. Syntheses of a-linked disaccharides. *J. Am. Chem. Soc.* 97(14), 4056-62, (1975).
75. S. Y. Tseng, C.-C. Wang, C.-W. Lin, C.-L. Chen, W.-Y. Yu, C.-H. Chen, C.-Y. Wu, C.-H. Wong "Glycan Arrays on Aluminum Coated Glass Slides". *Chem. Asian J.* 2008, 3, 1395-1405
76. Z. Su, G. Hahner, W. Zhou "Investigation of the pore formation in anodic aluminum oxide" *J. Mater. Chem.* 2008, 18 5787-5795.
77. K. Rana, G. Kucukayan-Dogu, E. Bengu "Growth of vertically aligned carbon nanotubes over self-ordered nano-porous alumina films and their surface properties" *Applied Surface Science,* 2012, 258 7112-7117.

We claim:
1. A method of preparation of a compound having the general formula:

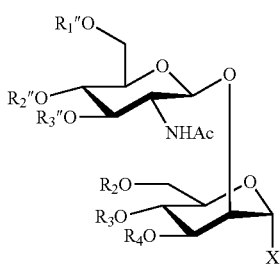

wherein, each of $R^2$, $R^3$, $R^4$, $R^{1\prime\prime\prime}$, $R^{2\prime\prime\prime}$, and $R^{3\prime\prime\prime}$ is independently selected from —H, benzyl (Bn), acetyl (Ac), benzoyl (Bz), or independently selected from a sugar moiety selected from:

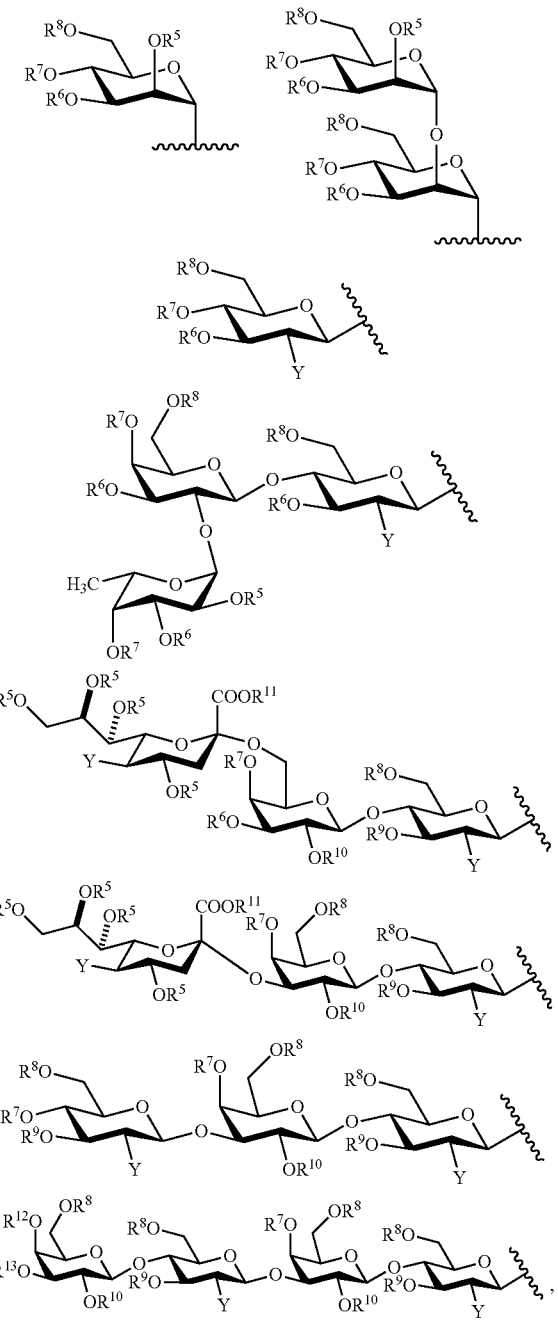

wherein at least one of $R^2$, $R^3$, $R^4$, $R^{1\prime\prime\prime}$, $R^{2\prime\prime\prime}$, and $R^{3\prime\prime\prime}$ is one of said sugar moieties, wherein, each of $R^5$, $R^6$, $R^7$, $R^8$, $R^9$ $R^{10}$, and $R^{12}$ is independently selected from —H, benzyl (Bn), acetyl (Ac), or benzoyl (Bz);

$R^{11}$ is selected from —H, Me (methyl) or Et (ethyl);

$R^{13}$ is selected from —H, benzyl (Bn), acetyl (Ac), benzoyl (Bz), or:

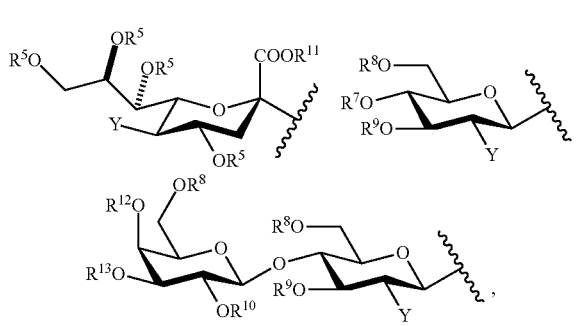

X is —OR$^{14}$ or an anomeric leaving group;
wherein, R$^{14}$ is selected from H, alkyl, alkenyl, alkynyl, aryl, unsubstituted aryl, substituted aryl; benzyl (Bn), para-methoxy benzyl ether (PMB), methoxy phenyl ether (PMP), or allyl ether (allyl);
Y is —NHR$^{16}$; and R$^{16}$ is acetyl (Ac),
wherein the method comprises the stepwise enzymatic extension on a hydroxyl group of a compound having the structure of formula (III):

I.

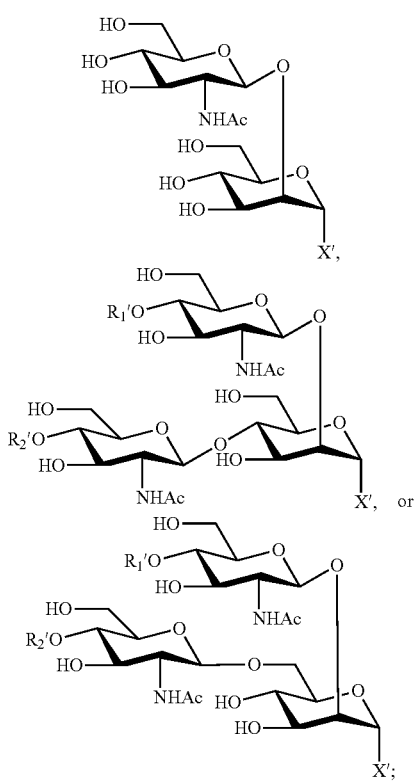

wherein,
each of R$^{1\prime}$ and R$^{2\prime}$ is independently selected from —H, acetyl (Ac), or benzoyl (Bz);
X' is —OR$^{3\prime}$ and R$^{3\prime}$ is selected from —H, benzyl (Bn), para-methoxy benzyl ether (PMB), methoxy phenyl ether (PMP), or allyl ether (allyl);
wherein the enzymes to enzymatically extend the compounds of formula (III) are independently selected from the group consisting of α (1→2) Fucosyltransferase, β (1→3) N-acetyl glucosamine transferase, and α (2→3) sialyltransferase.

2. A method of generating a glycan, the method comprising:
(a) performing an enzymatic extension on a free hydroxyl group of a compound of any of the compounds of formula (III)

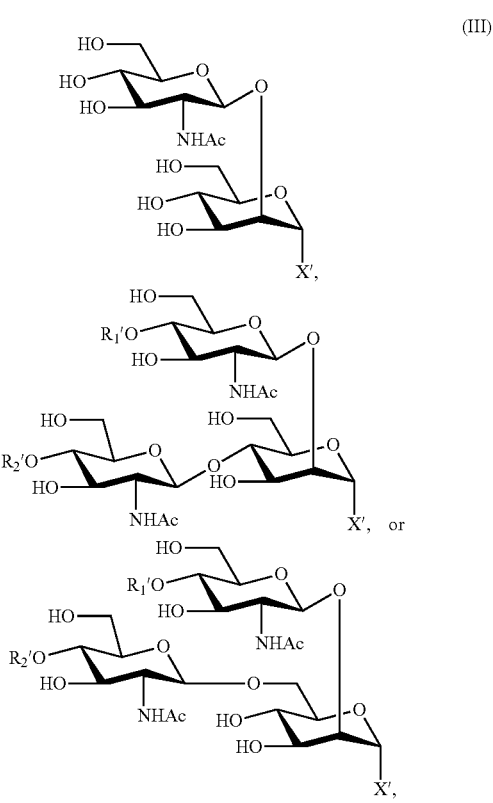

wherein,
each of R$^{1\prime}$ and R$^{2\prime}$ is independently selected from —H, acetyl (Ac), or benzoyl (Bz);
X' is —OR$^{3\prime}$ and R$^{3\prime}$ is selected from benzyl (Bn), 2-naphthylmethyl (Nap), 1-naphthylmethyl (1-Nap), para-methoxy benzyl ether (PMB), methoxy phenyl ether (PMP), or allyl ether (allyl),
to form a compound having the formula,

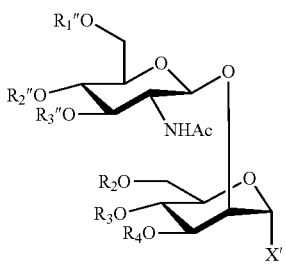

wherein, each of R$^2$, R$^3$, R$^4$, R$^{1\prime\prime}$, R$^{2\prime\prime}$, and R$^{3\prime\prime}$ is independently selected from —H, benzyl (Bn), acetyl (Ac), benzoyl (Bz), or independently selected from a sugar moiety selected from:

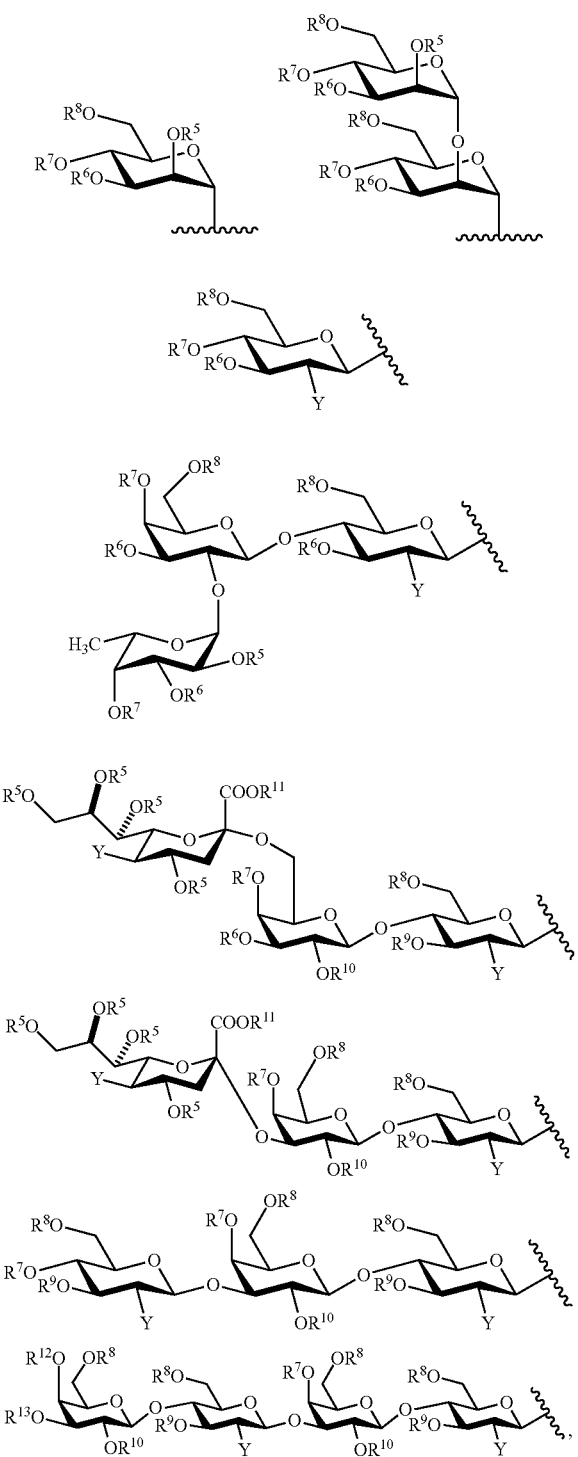

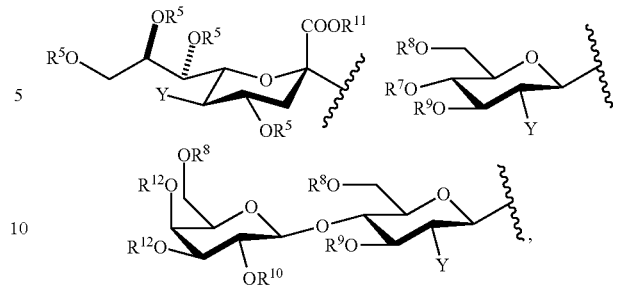

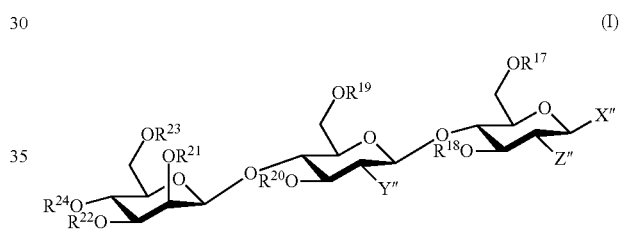

wherein at least one of $R^2$, $R^3$, $R^4$, $R^{1''}$, $R^{2''}$, and $R^{3''}$ is one of said sugar moieties, wherein, each of $R^5$, $R^6$, $R^7$, $R^8$, $R^9$, $R^{10}$, and $R^{12}$ is independently selected from —H, benzyl (Bn), acetyl (Ac), or benzoyl (Bz);

$R^{11}$ is selected from —H, Me (methyl) or Et (ethyl);

$R^{13}$ is selected from —H, benzyl (Bn), acetyl (Ac), benzoyl (Bz), or:

X' is —$OR^{14}$ or —$SR^{15}$ or an anomeric leaving group;

wherein, $R^{14}$ is selected from H, alkyl, alkenyl, alkynyl, substituted aryl, unsubstituted aryl; para-methoxy benzyl ether (PMB), methoxy phenyl ether (PMP), or allyl ether (allyl);

Y is —$NHR^{16}$; and $R^{16}$ is acetyl (Ac);

(b) converting X' to a leaving group to form a leaving-group containing compound;

(c) performing stereo- and regioselective glycosylations on the 3-O and/or 6-O positions of the compound of formula (I) with said leaving-group containing compound to form an extended trisaccharide, wherein formula (I) has the following structure:

(I)

wherein each of $R^{17}$, $R^{18}$, $R^{19}$, $R^{20}$, $R^{21}$, and $R^{22}$ is independently selected from the group consisting of hydrogen, benzyl (Bn), acetyl (Ac), para-methoxy benzyl ether (PMB), methoxy phenyl ether (PMP), levulinoyl (Lev), benzoyl (Bz), allyl ether (allyl), and silyl ether;

$R^{23}$ and $R^{24}$ are independently selected from the group consisting of hydrogen, para-methoxy benzyl ether (PMB), methoxy phenyl ether (PMP), levulinoyl (Lev), benzoyl (Bz), allyl ether (allyl), and silyl ether or are alternatively together fused to form a benzylidene ring;

X" is —$OR^{25}$ ; wherein $R^{25}$ is selected from —H or optionally substituted $C_3$-$C_{10}$ alkyl chains terminated with —$N_3$ or —$NHR^{26}$; and $R^{26}$ is selected from —H, benzyl (Bn), or carbobenzoyl (Cbz);

Y" and Z" are —$NHR^{27}$; and $R^{27}$ is selected from the group consisting of 9-fluorenylmethoxycarbonyl (Fmoc), allyloxycarbonyl (alloc), [2,2,2-trichloroethoxycarbonyl](troc), acetyl (Ac), phthalimido (Phth), carbobenzyloxy (Cbz) and tert-butoxycarbonyl (Boc), wherein at least one of $R^{22}$ or $R^{23}$ is H; and (d) removing one or a plurality of protecting groups on the extended trisaccharide to form a glycan;

wherein the enzymes to enzymatically extend the compounds of formula (III) are independently selected from the group consisting of α (1→2) Fucosyltransferase, β(1→3) N-acetyl glucosamine transferase, and α (2→3) sialyltransferase.

3. The method of claim 2, wherein when $R^{23}$ and $R^{24}$ are fused to form a benzylidene ring, said benzylidene ring is cleaved to form a glycan structure comprising 4-OH, 6-OH, or both 4-OH and 6-OH functional groups.

4. The method of claim 2, wherein the silyl ether is selected from: thexyldimethylsilyl (TDS), t-butyldimethylsilyl (TBS), t-butyldiphenyl silyl (TBDPS), triisopropylsilyl (TIPS), trimethylsilyl (TMS), or triethylsilyl (TES).

5. The method of claim 2, wherein the anomeric leaving group is selected from trichloroacetimidate —C(NH)—CCl$_3$, phenyltrifluoroacetimidate —C(NPh)—CF$_3$, trifluoroacetimidate —C(NH)—CF$_3$; thioalkyl, thiophenyl, and fluoride.

6. The method of any of claims 1, or 2, wherein when the enzyme is α (2→3) sialyltransferase, the cofactor is regenerated.

* * * * *